US011873520B2

(12) United States Patent
Sillers et al.

(10) Patent No.: US 11,873,520 B2
(45) **Date of Patent: *Jan. 16, 2024**

(54) PRODUCTION OF MALONYL-COA DERIVED PRODUCTS VIA ANAEROBIC PATHWAYS

(71) Applicant: Lallemand Hungary Liquidity Management LLC, Budapest (HU)

(72) Inventors: William Ryan Sillers, Lebanon, NH (US); Shital A. Tripathi, Berkeley, CA (US); Arthur J. Shaw, IV, Grantham, NH (US); Aaron Argyros, White River Junction, VT (US); David A. Hogsett, Grantham, NH (US)

(73) Assignee: Lallemand Hungary Liquidity Management LLC, Budapest (HU)

(*) Notice: Subject to any disclaimer, the term of this patent is extended or adjusted under 35 U.S.C. 154(b) by 0 days.

This patent is subject to a terminal disclaimer.

(21) Appl. No.: 17/491,268

(22) Filed: Sep. 30, 2021

(65) Prior Publication Data

US 2022/0267816 A1 Aug. 25, 2022

Related U.S. Application Data

(63) Continuation of application No. 16/166,274, filed on Oct. 22, 2018, now Pat. No. 11,162,125, which is a continuation of application No. 13/814,616, filed as application No. PCT/US2011/046869 on Aug. 5, 2011, now Pat. No. 10,138,504.

(60) Provisional application No. 61/371,582, filed on Aug. 6, 2010.

(51) Int. Cl.

| | |
|---|---|
| ***C12P 17/18*** | (2006.01) |
| ***C12N 1/22*** | (2006.01) |
| ***C12N 9/10*** | (2006.01) |
| ***C12N 9/88*** | (2006.01) |
| ***C12P 7/6409*** | (2022.01) |

(52) U.S. Cl.

CPC .............. *C12P 17/182* (2013.01); *C12N 1/22* (2013.01); *C12N 9/1018* (2013.01); *C12N 9/88* (2013.01); *C12P 7/6409* (2013.01); *G01N 2333/91034* (2013.01)

(58) Field of Classification Search

CPC ........ C12P 17/182; C12P 7/6409; C12N 1/22; C12N 9/1018; C12N 9/88; G01N 2333/91034

See application file for complete search history.

(56) References Cited

U.S. PATENT DOCUMENTS

| | | | |
|---|---|---|---|
| 5,252,466 A | 10/1993 | Cronan, Jr. | |
| 5,487,987 A | 1/1996 | Frost et al. | |
| 5,616,496 A | 4/1997 | Frost et al. | |
| 6,852,517 B1 | 2/2005 | Suthers et al. | |
| 7,011,959 B1 | 3/2006 | Santi et al. | |
| 7,186,541 B2 | 3/2007 | Gokarn et al. | |
| 7,393,676 B2 | 7/2008 | Gokarn et al. | |
| 7,638,316 B2 | 12/2009 | Gokarn et al. | |
| 7,799,545 B2 | 9/2010 | Burgard et al. | |
| 7,846,712 B2 | 12/2010 | Zhang et al. | |
| 8,034,591 B2 | 10/2011 | Winkler et al. | |
| 8,048,654 B2 | 11/2011 | Berry et al. | |
| 8,048,976 B2 | 11/2011 | McPhee | |
| 8,062,871 B2 | 11/2011 | Burgard et al. | |
| 8,076,120 B2 | 12/2011 | Gokarn et al. | |
| 8,088,607 B2 | 1/2012 | Burgard et al. | |
| 8,097,439 B2 | 1/2012 | Alibhai et al. | |
| 8,217,128 B2 | 7/2012 | McPhee | |
| 8,247,201 B2 | 8/2012 | Tajima et al. | |
| 9,029,124 B2 | 5/2015 | Robertson et al. | |
| 9,410,131 B2 | 8/2016 | Milo et al. | |
| 10,138,504 B2 * | 11/2018 | Sillers | C12N 9/88 |
| 11,162,125 B2 * | 11/2021 | Sillers | C12N 9/1018 |

(Continued)

FOREIGN PATENT DOCUMENTS

| | | |
|---|---|---|
| WO | 95/07996 A1 | 3/1995 |
| WO | 01/16346 A1 | 3/2001 |

(Continued)

OTHER PUBLICATIONS

Liang, S.-T., et al., "Activities of constitutive promoters in *Escherichia coli*," J. Mol. Bio. vol. 292, Issue 1, Sep. 10, 1999, pp. 19-37.
Liu, X., et al., "Two novel metal-independent long-chain alkyl alcohol dehydrogenases from Geobacillus thermodenitrificans NG80-2," Microbiology. Jun. 2009;155(Pt 6):2078-85.
Magnuson, K. et al., "Regulation of fatty acid biosynthesis in *Escherichia coli*," Microbiol Rev. Sep. 1993; 57(3):522-542.
Matte, A., et al., "Structure and mechanism of phosphoenolpyruvate carboxykinase," J Biol Chem. Mar. 28, 1997;272(13):8105-8.

(Continued)

*Primary Examiner* — Ganapathirama Raghu
(74) *Attorney, Agent, or Firm* — Sterne, Kessler, Goldstein & Fox P.L.L.C.

(57) ABSTRACT

The present invention provides for novel metabolic pathways to convert biomass and other carbohydrate sources to malonyl-CoA derived products, such as hydrocarbons and other bioproducts, under anaerobic conditions and with the net production of ATP. More specifically, the invention provides for a recombinant microorganism comprising one or more native and/or heterologous enzymes that function in one or more engineered metabolic pathways to achieve conversion of a carbohydrate source to, e.g., long-chain hydrocarbons and hydrocarbon derivatives, wherein the one or more native and/or heterologous enzymes is activated, upregulated, downregulated, or deleted. The invention also provides for processes to convert biomass to malonyl-CoA derived products which comprise contacting a carbohydrate source with a recombinant microorganism of the invention.

27 Claims, 72 Drawing Sheets

Specification includes a Sequence Listing.

(56) References Cited

U.S. PATENT DOCUMENTS

| | | | |
|---|---|---|---|
| 2004/0076982 | A1 | 4/2004 | Gokarn et al. |
| 2007/0184524 | A1 | 8/2007 | Gokarn et al. |
| 2008/0076167 | A1 | 3/2008 | Gokarn et al. |
| 2008/0092829 | A1 | 4/2008 | Renninger et al. |
| 2008/0261287 | A1 | 10/2008 | Winkler et al. |
| 2008/0293060 | A1 | 11/2008 | Schirmer et al. |
| 2009/0053783 | A1 | 2/2009 | Gokarn et al. |
| 2009/0275097 | A1 | 11/2009 | Sun et al. |
| 2009/0305364 | A1 | 12/2009 | Burgard et al. |
| 2010/0056714 | A1 | 3/2010 | McPhee |
| 2010/0056743 | A1 | 3/2010 | McPhee |
| 2010/0068773 | A1 | 3/2010 | Marx et al. |
| 2010/0071259 | A1 | 3/2010 | Hu et al. |
| 2010/0105955 | A1 | 4/2010 | Alibhai et al. |
| 2010/0105963 | A1 | 4/2010 | Hu |
| 2010/0297716 | A1 | 11/2010 | Tajima et al. |
| 2010/0317822 | A1 | 12/2010 | Boussie et al. |
| 2010/0317823 | A1 | 12/2010 | Boussie et al. |
| 2010/0317825 | A1 | 12/2010 | Boussie et al. |
| 2010/0330626 | A1 | 12/2010 | Burgard et al. |
| 2011/0059485 | A1 | 3/2011 | Caiazza et al. |
| 2011/0125118 | A1 | 5/2011 | Lynch |
| 2011/0144377 | A1 | 6/2011 | Eliot et al. |
| 2011/0195466 | A1 | 8/2011 | Burgard et al. |
| 2011/0218318 | A1 | 9/2011 | Boussie et al. |
| 2011/0306790 | A1 | 12/2011 | Murphy et al. |
| 2012/0135481 | A1 | 5/2012 | Jessen et al. |
| 2013/0323766 | A1 | 12/2013 | Sillers et al. |

FOREIGN PATENT DOCUMENTS

| | | | |
|---|---|---|---|
| WO | 02/42418 | A2 | 5/2002 |
| WO | 2006/009434 | A1 | 1/2006 |
| WO | 2009/035595 | A1 | 3/2009 |
| WO | 2009/072562 | A1 | 6/2009 |
| WO | 2009/151728 | A2 | 12/2009 |
| WO | 2010/144862 | A2 | 12/2010 |
| WO | 2011/003034 | A2 | 1/2011 |
| WO | 2011/063055 | A2 | 5/2011 |
| WO | 2011/094457 | A1 | 8/2011 |
| WO | 2011/140386 | A2 | 11/2011 |
| WO | 2012/019175 | A2 | 2/2012 |

OTHER PUBLICATIONS

Millard, et al., Enhanced production of succinic acid by overexpression of phosphoenolpyruvate carboxlase in *Escherichia coli*, Appl. Environ. Microbiol., vol. 62(5), pp. 18108-18110 (1996).

Mota, L. J., et al., "Control of the Arabinose Regulon in Bacillus subtilis by AraR In Vivo: Crucial Roles of Operators, Cooperativity, and DNA Looping," J. Bacteriol. 183(14):4190-201, American Society for Microbiology, United States (2001).

Mota, L. J., et al., "Mode of action of AraR, the key regulator of L-arabinose metabolism in Bacillus subtilis," Mol. Microbial. 33(3):476-89, Blackwell Science Ltd., England (1999).

Murtif et al., Mutagenesis affecting carboxyl terminus of the biotinyl subunit of transcarboxylase, J. Biol. Chem., vol. 262(24), pp. 11813-11816 (1987).

Nackley, et al., Human Caechol-O-Methytransferase haplotypes modulate protein expression by altering mRNA secondary structure, Science, vol. 314, pp. 1930-1933 (2006).

Nakamura, Y., et al. "Codon usage tabulated from international DNA sequence databases: status for the year 2000," Nucl. Acids Res. 28(1):292, Oxford University Press, England (2000).

National Microbial Pathogen Data Resource, SEED Subsystem: L-Arabinose_utilization, accessed at http://www .nmpdr.org/FIG/subsys.cgi?user=&ssa _name= L-Arabinose utilization&reQuest= show ssa, accessed on Jun. 11, 2013.

Neumann, G., et al.., "Prediction of the Adaptability of Pseudomonas putida DOT-T1E to a Second Phase of a Solvent for Economically Sound Two-Phase Biotransformations," Appl. Environ. Microbial 71(11):6606-12, American Society for Microbiol., United States (2005).

Pelletier, E., et al., "Candidatus Cloacamonas Acidaminovorans": Genome Sequence Reconstruction Provides a First Glimpse of a New Bacterial Division, J Bacteriol. Apr. 2008; 190(7): 2572-2579.

Peralta-Yahya, P. P. and Keasling, J.D., "Advanced biofuel production in microbes," Biotechnol. J 5:147-62, Wiley-VCH Verlag GmbH & Co. KGaA, Germany (Feb. 2010).

Picataggio, S., et at., "Metabolic Engineering of Candida tropicalis for the Production of Long-Chain Dicarboxylic Acids," Biotechnology 10:894-98, Nature Pub. Co., United States (1992).

Rathnasingh, C., et al., "Development and Evaluation of Efficient Recombinant *Escherichia coli* Strains for the Production of 3-Hydroxypropionic Acid From Glycerol," Biotech. Bioeng 104(4):729-39, Wiley Periodicals, Inc., United States (2009).

Rathnasingh, C., et al., "Production of 3-hydroxypropionic acid via malonyl-CoA pathway using recombinant *Escherichia coli* strains," J Biotech. 157:633-40, Elsevier B.V. Netherlands (2012) Epub Jun. 23, 2011.

Reiser, S. and Somerville, C., "Isolation of Mutants of Acinetobacter calcoaceticus Deficient in Wax Ester Synthesis and Complementation of One Mutation with a Gene Encoding a Fatty Acyl Coenzyme A Reductase," J. Bacteriol. 179(9):2969-75; 1997.

Rodolfi, L., et al., "Microalgae for Oil: Strain Selection, Induction of Lipid Synthesis and Outdoor Mass Cultivation in a Low-Cost Photobioreactor," Biotech. Bioeng. 102(1):100-12, Wiley Periodicals, Inc., United States (2009).

Sauer, U., "Evolutionary Engineering of Industrially Important Microbial Phenotypes," Advances in Biochemical Engineering/Biotechnology 73:129-69, Springer-Verlag, Germany (2001).

Sauna, et al., Silent polymorhisms speak: How they affect pharmacogenomics and the treatment of cancer, Cancer Res., vol. 67(20), pp. 9609-9612 (2007).

Schleif, R., "Regulation of the L-arabinose operon of *Escherichia coli*," Trends Genet. 16(12):559-65, Elsevier Science Ltd., England (2000).

Seffernick, et al., Melamine deaminase and Atrazine chlorohydrolase: 98 percent identical but functionally different. J. Bacteriol., vol. 183(8), pp. 2405-2410 (2001).

Sen, et al., Developments in directed evolution for improving enzyme functions, Appl. Biochem. Biotechnol., vol. 143, pp. 212-223 (2007).

Shanks, R.M.Q et al., "*Saccharomyces cerevisiae*-based Molecular Tool Kit for Manipulation of Genes from Gram-Negative Bacteria," Appl. Environ. Microbiol., 2006, 72(7): 5027-5036.

Shaw, A.J. et al., "Natural Competence in *Thermoanaerobacter* and *Thermoanaerobacterium* Species," Appl. Environ. Microbiol., 2010, 76(14):4713-4719.

Shenoy, et al., Effect of mutations at Met-88 and Met-90 on the biotination of apo 1.3S subunit of transcarboxylase. FASEB J., vol. 2, pp. 2505-2511 (1988).

Steen, E., et al., Microbial production of fatty-acid-derived fuels and chemicals from plant biomass, Nature, vol. 463. No. 7280, pp. 559-562 (Jan. 28, 2010).

Sukovich, D. J., et al., "Widespread Head-to-Head Hydrocarbon Biosynthesis in Bacteria and Role of OleA," Appl Environ Microbiol. Jun. 2010; 76(12): 3850-3862.

Suwannakham, S., et al., Enhanced proprionic acid fermentation byPropionibacterium acidipropionici mutant obtained by adaptation in a firbrous-bed bioreactor, Biotechnology and BioEngineering, vol. 91, pp. 325-337 (Jun. 23, 2005).

Sá-Nogueira, I., et al., "The Bacillus subtilis L-arabinose (ara) operon: nucleotide sequence, genetic organization and expression," Microbiology, 143:957-969, Society for General Microbiology, Great Britain (1997).

Tsuruta, H., et al., "High-level production of amorpha-4,11-diene, a precursor of the antimalarial agent artemisinin, in *Escherichia coli*," Plos ONE. 2009; 4(2): e4489.

Van Beilen, J.B., et al., "Analysis of Pseudomonas putida alkane-degradation gene clusters and flanking insertion sequences: evolution and regulation of the alk genes," Microbiology, Jun. 2001 147: 1621-1630.

(56) References Cited

OTHER PUBLICATIONS

Van Walsum, G.P., et al., "Allocation of ATP to synthesis of cells and hydrolytic enzymes in cellulolytic fermentative microorganisms: Bioenergetics, kinetics, and bioprocessing," Biotech. Bioeng., 58:316-320, (1998).
Vanhanen, S., et al., "A consensus sequence for long-chain fatty-acid alcohol oxidases from Candida identifies a family of genes involved in lipid omega-oxidation in yeast with homologues in plants and bacteria," J Biol Chem. Feb. 11, 2000,275(6):4445-52.
Wahlen, B. D., et al., "Purification, Characterization, and Potential Bacterial Wax Production Role of an NADPH-Dependent Fatty Aldehyde Reductase from Marinobacter aquaeolei VT8," Appl Environ Microbiol. May 2009; 75(9): 2758-2764.
Wang, L., et al., "Isolation and characterization of a novel thermophilic Bacillus strain degrading long-chain n-alkanes," Extremophiles. Aug. 2006;10(4):347-56. Epub Apr. 8, 2006.
Watanabe, S., et al., "Cloning, Expression, and Characterization of Bacterial L-Arabinose 1-Dehydrogenase Involved in an Alternative Pathway of L-Arabinose Metabolism," J. Biol. Chem., 281(5):2612-2623, American Society for Biochemistry and Molecular Biology, United States (2006).
Whisstock, et al., Prediction of protein function from protein sequence; Q. Rev. Biophysics, vol. 36 (3), pp. 307-340 (2003).
Whited, G. M., et al., "Development of a gas-phase bioprocess for isoprene-monomer production using metabolic pathway engineering," Industrial Biotechnol. vol. 6 Issue 3: Jun. 23, 2010.
Wishart, et al., A single mutation converts a novel phosphotyrosine binding domain into a dual-specificity phosphatase, J. Viol. Chem., vol. 270 (45), pp. 26782-26785 (1995).
Witkowsi, et al., Conversion of b-ketoacyl synthase to a Malonyl Decarboxylase by replacement of the active cystein with glutamine; Biochemistry, vol. 38, pp. 11643-11650 (1999).
Wood, H. G., et al., "Transcarboxylase, II. Purification and properties of methylmalonyl-oxaloacetic franscarboxylase," Proc Natl Acad Sci U S A. Mar. 1961; 47(3): 289-303.
Yan, Y. and Liao, J. C., "Engineering metabolic systems for production of advanced fuels," of advanced I fuels.
Zelle Rintz, M., et al., Phosphoenolpyruvate Carboxykinase as the Sole Anaplerotic Enzyme in *Saccharomyces cerevisiae*, Applied and Environmental Microbiology, vol. 76, No. 16, pp. 5383-5389 (Aug. 1, 2020).
Zhang, X., et al., Metabolic evolution of energy-conserving pathways for succinate production in *Escherichia coli*, Proceedings of the National Academy of Sciences, vol. 106, No. 48, pp. 20180-20185 (Dec. 1, 2009).
[No Author Listed] Accession No. AAS20429, NCBI Database, Bugler, M. and Fuchs, G., accessed at www.ncbi.nlm.nih.gov/protein/AAS20429, accessed on Jun. 11, 2013; 2 pages.
[No Author Listed] Accession No. U00096.2, NCBI Database, Blattner, F. R., et al., accessed at www.ncbi.nlm nih.gov/nuccore/U00096, accessed on Jun. 11, 2013; 119 pages.
[No Author Listed] Accession No. YP 001277512, NCBI Database, Copeland, A., et al., accessed at www.ncbi.nlm.nih.gov/protein/YP_001277512, accessed on Jun. 11, 2013; 3 pages.
[No Author Listed] Accession No. YP 001433009, NCBI Database, Copeland, A., et al.., accessed at www.ncbi.nlm.nih.gov/protein/YP _001433009, accessed on Jun. 11, 2013; 3 pages.
[No Author Listed] Accession No. YP 002570540, NCBI Database, Lucas, S., et al., accessed at www.ncbi.nlm.nih.gov/protein/YP 002570540, accessed on Jun. 11, 2013; 3 pages.
[No Author Listed] Accession No. YP_001636209.1, NCBI Database, Copeland, A., et al., accessed at www.ncbi.nlm.nih.gov/proteinNP _001636209.1, accessed on Jun. 11, 2013; 3 pages.
[No Author Listed] Accession No. YP_002462600, NCBI Database, Lucas, S et al., accessed at www.ncbi.nlm.nih.gov/protein/YP_002462600, accessed on Jun. 11, 2013; 3 pages.
[No Author Listed] Accession No. ZP 01039179.1, NCBI Database, Falkowski, P., et al.., accessed at www.ncbi.nlm.nih/gov/protein/ZP 01039179.1 ?report=genpept, accessed on Jun. 11, 2013; 2 pages.
[No Author Listed] Accession No. ZP_07684596.1, NCBI Database, Kuznetsov, B. B. and Beletsky, A. V., accessed at www.ncbi.nlm.nih.gov/protein/ZP 07684596.1 ?report=genpept, accessed on Jun. 11, 2013; 2 pages.
[No Author Listed] Accession No. ZP_04957196.1, NCBI Database, Amann, R., et al., accessed at www.ncbi.nlm.nih.gov/protein/ZP_04957196.1?report=genpept, accessed on Jun. 11, 2013; 2 pages.
Aklujkar, M., et al., "The Genome of Geobacter bemidjiensis, exemplar for the subsurface clade of Geobacter species that predominate in FE(III)-reducing subsurface environments," BMC Genomics 11:490, BioMed Central, England (Sep. 2010); (18 pages).
Aldai, N., et al., "Gas-liquid chromatographic method for analysing complex mixtures of fatty acids including conjugated linoleic acids (cis9trans11 and trans10cis12 isomers) and long-chain (n-3 or n-6) polyunsaturated fatty acids: Application to the intramuscular fat of beef meat," Journal of Chromatography A 1110:133-39, Elsevier B.V., Netgherlands (2006).
An, J.H., et al., "A gene cluster encoding malonyl-CoA decarboxylase (MatA), malonyl-CoA synthetase (MatB) and a putative dicarboxylate carrier protein (MatC) in Rhizobium trifolii--cloning, sequencing, and expression of the enzymes in *Escherichia coli*," Eur J Biochem. Oct. 15, 1998,257(2):395-402.
Bar-Even, et al., Design and analysis of synthetic carbon fixation pathways, PNAS, vol. 107 (19), pp. 8889-8894 (2010).
Beller, H.R., et al., "Genes Involved in Long-Chain Alkene Biosynthesis in Micrococcus luteus," Appl Environ Microbiol. Feb. 2010; 76(4): 1212-1223; published ahead of print on Dec. 28, 2009.
Berrios-Rivera, S. J., et al., "Metabolic Engineering of Escherichia coli : Increase of NADH Availability by Overexpressing an NADp-Dependent Formate Dehydrogenase," Metabolic Engineering 4, 217-229 (2002).
Black, P. N., et al., "Transmembrane Movement of Exogenous Long-Chain Fatty Acids: Proteins, Enzymes, and Vectorial Esterification," Microbiol Mol Biol Rev. Sep. 2003; 67(3): 454-472.
Broun, et al., Catalytic plasticity of fatty acid modification enzymes underlying chemical diversity of plant lipids; Science, vol. 282, pp. 1315-1317 (1998).
Burgard, A. P., "OptKnock: A Bilevel Programming Framework for Identifying Gene Knockout Strategies for Microbial Strain Optimization," Biotech. Bioeng. 84(6): 647-57, Wiley Periodicals, Inc. US (2003).
Carey, P. R., et al., "Transcarboxylase: one of nature's early nanomachines," IUBMB Life. Oct. 2004;56(10):575-83.
Chica, et al., Semi-rational approaches to engineering enzyme activity: combining the benefits of directed evolution and rational design, Curr. Opi. Biotechnol, vol. 16, pp. 378-384 (2005).
Davis, M. S., et al., "Inhibition of *Escherichia coli* acetyl coenzyme A carboxylase by acyl-acyl carrier protein," J Bacteriol. Feb. 2001;183(4):1499-503.
Davis, M., et al., Overproduction of Acetyl-CoA Carboxylase Activitiy Increases the Rate of Fatty Acid Biosynthesis n *Escherichia coli*, Journal of Biological Chemistry, vol. 275, pp. 28593-28598 (Sep. 8, 2000).
Deok, et al., Influence of gluconeogenic phosphoenolpyruvate carboxykinase (PCK) expression on succinic acid fermentation in *Escherichia coli* under high bicarbonate condition, J. Microbiol. Biotechnol., vol. 16(9), pp. 1448-1452 (2006).
Devos, et al., Practical limits of function prediction; Proteins: Structure, Function and Genetics, vol. 41, pp. 98-107 (2000).
[No Author Listed] Enzyme Entry 2.1.3.1; one page downloaded from <http://enzyme.expasy.org/> on Sep. 10, 2016.
Falentin, H., et al., The Complete Genome of Propionibacterium freudenreichii CIRM-BIAI, a Hard Actinobacterium with Food and Probiotic Applications, Plos One, vol. 5, No. 7, pp. 1-12 (Jan. 1, 2010).
Heath, R. J., et al., "Regulation of fatty acid elongation and initiation by acyl-acyl carrier protein in *Escherichia coli*," J Biol Chem. Jan. 26, 1996;271(4):1833-6.
Hopner, T., et al., "Determination with Formate Dehydrogenase," in Bergmeyer H.U. ed, Methods of Enzymatic Analysis, Ed 2, vol. 3, pp. 1551-1555, Academic Press, New York (1974).

(56) References Cited

OTHER PUBLICATIONS

Houwen, et al., Enzymatic evidence for involvement of methylmalonyl-CoA pathway in propionate oxidation by Syntrophobacter wolinil. Arch Microbiol., vol. 155, pp. 52-55 (1990).
Hugler, M., et al., "Malonyl-Coenzyme A Reductase from Chloroflexus aurantiacus, a Key Enzyme of the 3-Hydroxypropionate Cycle for Autotrophic CO2 Fixation," J Bacteriol. May 2002; 184(9): 2404-2410.
International Search Report and Written Opinion dated Dec. 5, 2011 Appl. No. PCT/US2011/046869.
Inui, H., et al., "Fatty acid synthesis in mitochondria of Euglena gracilis," Eur. J. Biochem. 142:121-26, FEBS, England (1984).
Inui, H., et al., "Wax ester fermentation in Euglena gracilis," FEBS Lett., 150(1): 89-93, Elsevier Biomedical Press, Netherlands (1982).
Jenke-Kodama, H., et al., "Evolutionary implications of bacterial polyketide synthases," Mol Biol Evol. Oct. 2005,22(10):2027-39. Oxford University Press, England.
Jeppson, M., et al., "Reduced oxidative pentose phosphate pathway flux in recombinant xylose-utilizing *Saccharomyces cerevisiae* strains improves the ethanol yield from xylose," Appl Environ Microbiol. Apr. 2002;68(4):1604-9.
Kalscheuer, R., et al., "A novel bifunctional wax ester synthase/acyl-CoA:diacylglycerol acyltransferase mediates wax ester and triacylglycerol biosynthesis in Acinetobacter calcoaceticus ADP1," J Biol Chem. Mar. 7, 2003;278(10):8075-82.
Kalscheuer, R., et al., "Microdiesel: *Escherichia coli* engineered for fuel production," Microbiology. Sep. 2006;152(Pt 9):2529-36.
Karhumaa, K., et al., "Comparison of the xylose reductase-xylitol dehydrogenase and the xylose isomerase pathways for xylose fermentation by recombinant *Saccharomyces cerevisiae*," Microb Cell Fact. Feb. 5, 2007;6:5.
Kieboom, J., et al., "Identification and molecular characterization of an efflux pump involved in Pseudomonas putida S12 solvent tolerance," J Biol Chem. Jan. 2, 1998; 273(1):85-91.
Kim, Y., et al., "Construction of an *Escherichia coli* K-12 mutant for homoethanologenic fermentation of glucose or kylose without foreign genes," Appl Environ Microbiol. Mar. 2007;73(6): 1766-71; published ahead of print Jan. 26, 2007.
Kimchi-Sarfaty, et al., A "Silent" polymorphism in the MDR1 gene changes substrate specificity, Science, vol. 315, pp. 525-528 (2007).
Kisselev, L., Polypeptide release factors in prokaryotes and eukaryotes: same function, different structure, Structure, vol. 10, pp. 8-9 (2002).
Kosaka, T., et al., "The genome of Pelotomaculum thermopropionicum reveals niche-associated evolution in anaerobic microbiota," Genome Res. Mar. 2008; 18(3):442-8. Epub Jan. 24, 2008.
Kuyper, M., et al., "Evolutionary engineering of mixed-sugar utilization by a xylose-fermenting *Saccharomyces cerevisiae* strain," FEMS Yeast Res. Jul. 2005;5(10):925-34.
Kuyper, M., et al., "Metabolic engineering of a xylose-isomerase-expressing *Saccharomyces cerevisiae* strain for rapid anaerobic xylose fermentation," FEMS Yeast Res. Feb. 2005;5(4-5):399-409.
Kuyper, M., et al., "Minimal metabolic engineering of *Saccharomyces cerevisiae* for efficient anaerobic xylose fermentation: a proof of principle," FEMS Yeast Res. Mar. 2004;4(6):655-64.
Leal, T.F. and De Sá-Nogueira, I., "Purification, characterization and functional analysis of an endo-arabinose (AbnA) from Bacillus subtilis," FEMS Microbiol. Let., 241:41-48, Elsevier, B.V., Netherlands (2004).
Li, N., et al., "Conversion of fatty aldehydes to alka(e)nes and formate by a cyanobacterial aldehyde decarbonylase: cryptic redox by an unusual dimetal oxygenase," J Am Chem Soc. Apr. 27, 2011;133(16):6158-61.
Li, S-J., et al., "Growth rate regulation of *Escherichia coli* acetyl coenzyme A carboxylase, which catalyzes the first committed step of lipid biosynthesis," J Bacteriol. Jan. 1993;175(2):332-40.

* cited by examiner

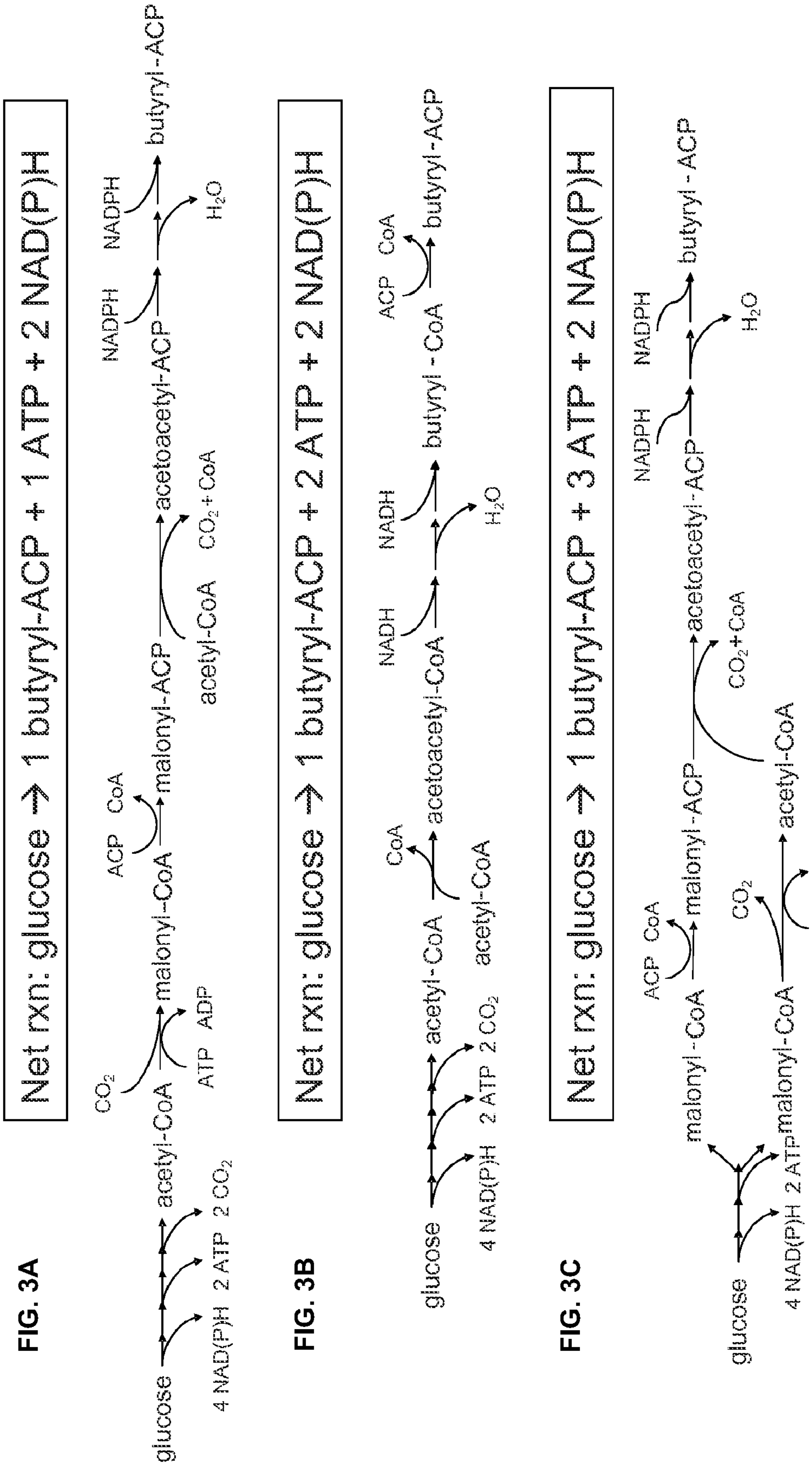
FIG. 3A
Net rxn: glucose → 1 butyryl-ACP + 1 ATP + 2 NAD(P)H
glucose
4 NAD(P)H
2 ATP
2 CO2
acetyl-CoA
CO2
ATP
ADP
malonyl-CoA
ACP
CoA
malonyl-ACP
acetyl-CoA
CO2 + CoA
acetoacetyl-ACP
NADPH
NADPH
H2O
butyryl-ACP
FIG. 3B
Net rxn: glucose → 1 butyryl-ACP + 2 ATP + 2 NAD(P)H
glucose
4 NAD(P)H
2 ATP
2 CO2
acetyl-CoA
acetyl-CoA
CoA
acetoacetyl-CoA
NADH
NADH
H2O
butyryl-CoA
ACP
CoA
butyryl-ACP
FIG. 3C
Net rxn: glucose → 1 butyryl-ACP + 3 ATP + 2 NAD(P)H
glucose
4 NAD(P)H
2 ATP
malonyl-CoA
malonyl-CoA
ACP
CoA
malonyl-ACP
CO2
ADP
ATP
acetyl-CoA
CO2 + CoA
acetoacetyl-ACP
NADPH
NADPH
H2O
butyryl-ACP

FIG. 7A

Transcarboxylase 5S subunit

```
                                        1                                                50
SEQ. ID NO. 11:      Pfreud 5S     (1)  MSPREIEVSEPREVGITELVLRDAHQSLMATRMAMEDMVGACADIDAAGY
SEQ. ID NO. 18:      Pacnes 5S     (1)  --------MSPRKIGVTELVLRDAHQSLLATRMAMEDMVDACADIDAAGF
SEQ. ID NO. 25:      Cthe_0701     (1)  ----------MAKVKITETALRDAHQSLIATRMRIEEMLPIIDKLDEIGY
SEQ. ID NO. 33: Tsacch or1888      (1)  ----------MSKIKITETVLRDAHQSLLATRMSTDEMLPILEKLDESGF
                                        51                                              100
SEQ. ID NO. 11:      Pfreud 5S    (51)  WSVECWGGATYDSCIRFLNEDPWERLRTFRKLMPNSRLQMLLRGQNLLGY
SEQ. ID NO. 18:      Pacnes 5S    (43)  WSVECWGGATFDSCIRFLNEDPWERLRTFRKLLPNSRLQMLLRGQNLLGY
SEQ. ID NO. 25:      Cthe_0701    (41)  HSLEVWGGATFDACLRFLNEDPWERLRIIKEHCKETPLQMLLRGQNLLGY
SEQ. ID NO. 33: Tsacch or1888     (41)  FSLEFWGGATFDACMRFLNEDPWERLRLIKKAIKETPLQMLLRGQNLLGY
                                        101                                             150
SEQ. ID NO. 11:      Pfreud 5S   (101)  RHYNDEVVDRFVDKSVENGMDVFRVFDAMNDPRNMAHAMAAVKKAGKHAQ
SEQ. ID NO. 18:      Pacnes 5S    (93)  RHYNDEVVDKFVEKSVENGMDVFRVFDALNDPRNLEHAMAAVKKCGKHAQ
SEQ. ID NO. 25:      Cthe_0701    (91)  KHYADDVVEYFVKKSVANGIDIIRIFDALNDVRNIETAIKACKKEGGHAQ
SEQ. ID NO. 33: Tsacch or1888     (91)  KHYPDDVVEKFIIKSVENGIDIIRIFDALNDVRNLEVPIKSAKKAGAHVQ
                                        151                                             200
SEQ. ID NO. 11:      Pfreud 5S   (151)  GTICYTISPVHTVEGYVKLAGQLLDMGADSIALKDMAALLKPQPAYDIIK
SEQ. ID NO. 18:      Pacnes 5S   (143)  GTICYTTSPIHTPESFVKQAERLIDMGADSIAIKDMAALLKPQPAYDIIK
SEQ. ID NO. 25:      Cthe_0701   (141)  GTVCYTISPVHTLESLFVKDAKTLVEMGADSICVKDMAGLLLPYVAYDLIK
SEQ. ID NO. 33: Tsacch or1888    (141)  AEIVYTVSPVHTLDHYLKVAKSLQDMGADSICIKDMSGILKPYVAYDLIK
                                        201                                             250
SEQ. ID NO. 11:      Pfreud 5S   (201)  AIKDEYGQKVQINLHCHSTTGVTEVSLMKAIEAGVDVVDTAISSMSLGPG
SEQ. ID NO. 18:      Pacnes 5S   (193)  GIKENH-PEVQINLHCHSTTGVTLVTLQKAIEAGVDVVDTAISSMSLGPG
SEQ. ID NO. 25:      Cthe_0701   (191)  ALKENV--KVPIQLHTHYTSGVASMTYLKAIEAGCDVVDCAISSMSMGTS
SEQ. ID NO. 33: Tsacch or1888    (191)  SLKEAL--YEPIQLHSHYTTGLASMTYLKAIEAGVDGVDTAISSLALGTS
                                        251                                             300
SEQ. ID NO. 11:      Pfreud 5S   (251)  ENPTESVVEMLEGTGYTTNLDYDRLHKIRDHFKAIRPKYKKFESKTLVDT
SEQ. ID NO. 18:      Pacnes 5S   (242)  ENPTESLVEMLEGTEYITGLDMDRLLKIRDHFKKVRPKYKKFESKTLVNT
SEQ. ID NO. 25:      Cthe_0701   (239)  QPPTESLVATLKGTPYDTGLDLDKLSEIADYFRPLKEKYIESEGLLDVKVM
SEQ. ID NO. 33: Tsacch or1888    (239)  QPATESIVAALKETEYDTGLDLELLAEIAEHFVVKQEHKEDEMSLLMS
                                        301                                             350
SEQ. ID NO. 11:      Pfreud 5S   (301)  ---S-IEKSQIPGGMLSNMESQLRAQGAEDKMDEVMAEVPRVRKAAGFPP
SEQ. ID NO. 18:      Pacnes 5S   (292)  ---N-IEKSQIPGGMLSNMESQLKAQGAGDRMDEVMKEVPRVRKDAGYPP
SEQ. ID NO. 25:      Cthe_0701   (289)  GVDVNTLKYQVPGGMLSNLVSQLKQQNAVDKAEEVLKEVPRVRKDFGYPP
SEQ. ID NO. 33: Tsacch or1888    (289)  -VDVKALEKSQIPGGMLSNLVSQLKQQNALEKYEDVLKEVPRVRKDLGYPP
                                        351                                             400
SEQ. ID NO. 11:      Pfreud 5S   (347)  LVTPSSQIVGTQAVLNVMMG--EYKRMTGEFADIMLGYYGASPADRNPKV
SEQ. ID NO. 18:      Pacnes 5S   (338)  LVTPSSQIVGTQAVLNVLMGNGSYKNLTAEFADLMLGYYGKPIGELNPEI
SEQ. ID NO. 25:      Cthe_0701   (339)  LVTPTSQIVGTQAVLNVVTG-ERYKMVTKESKALIKGEYGRIPAPVNPEV
SEQ. ID NO. 33: Tsacch or1888    (338)  LVTPMSQMVGTQAVLNVITG-ERYKIVTKEIKDYVKGLYGMPPAPIQDEI
                                        401                                             450
SEQ. ID NO. 11:      Pfreud 5S   (395)  VKLAEGQSGKEPITQRPADLLPPEWEEQSKEAAALKGFNGTDEDVLTYAL
SEQ. ID NO. 18:      Pacnes 5S   (388)  VEMAKKQTGKEPIDCRPADLLEPEWDKLVEQAKSLEGFDGSDEDVLTNAL
SEQ. ID NO. 25:      Cthe_0701   (388)  QKKILK--GEEPITVRPADLIEPELDKIRN---EMKEYLEQDEDVLSYAL
SEQ. ID NO. 33: Tsacch or1888    (387)  RKKIIG--KEEVISKRPADLLEPELDEKKN---EIKEFIEQDEDVLSYAL
                                        451                                             500
SEQ. ID NO. 11:      Pfreud 5S   (445)  FPQVAPVFFEHRAEGPHSVALTDAQLKAEAEGDEKSLAVAGPVTYNVNVG
SEQ. ID NO. 18:      Pacnes 5S   (438)  FPGVAPKFLKERAQGPKSVAMTEAQLKAEKVG-TGAAGIAGPVNYNVTVG
SEQ. ID NO. 25:      Cthe_0701   (433)  FPQVAEKFFKYRKAQKYGIEPDMGNYINRVHPV-----------------
SEQ. ID NO. 33: Tsacch or1888    (432)  FPQVARKFFEYRQAKKYRIDSTLLNIGERVHPI-----------------
                                        501       511
SEQ. ID NO. 11:      Pfreud 5S   (495)  GTVREVTVQQA
SEQ. ID NO. 18:      Pacnes 5S   (487)  GNSHQVTVEPA
SEQ. ID NO. 25:      Cthe_0701   (466)  -----------
SEQ. ID NO. 33: Tsacch or1888    (465)  -----------
```

FIG. 7B

Transcarboxylase 1.3S subunit

```
                                          1                                                50
SEQ. ID NO.  8:    Pfreud 1.3S      (1)   -MKLKVTVNGTAYDVDVDVDKSHENPMGTILFGGG GGAPAPRAA GAG-
SEQ. ID NO. 19:    Pacnes 1.3S      (1)   -MKLKVTVN VAYDVDVDVDKTANAPMAPILFGGGAG--- PMKASGGG-
SEQ. ID NO. 23:      Cthe_0700      (1)   MKK LI VNGNQYEVEVEEIR GASAPQVTLSTP AAPAPSPAPA E KT
SEQ. ID NO. 31: Tsacch or0947      (1)   MKK IVTVNGKKYDVEVEEVK  VA EKKAKE TAAKNA  ASVKSK---
                                          51                                              100
SEQ. ID NO.  8:    Pfreud 1.3S     (49)   -------AGKAGEGEIPAPLAGTVSKILV  GDTVKAGQ VLVLEAMKME
SEQ. ID NO. 19:    Pacnes 1.3S     (46)   -------AGKAGEGEVPAPLAGTVAKILVA GD VKAGQVLLTLEAMKME
SEQ. ID NO. 23:      Cthe_0700     (51)   AAPKKDS VPAGATAIKAPMPGTIL IRV QGDTVKKGQVLLILEAMKME
SEQ. ID NO. 31: Tsacch or0947     (48)   QVEVKN--EVK GF INAPMPGTIL VKISQG IVRRG VLLILEAMKME
                                          101                            132
SEQ. ID NO.  8:    Pfreud 1.3S     (92)   TEINAPTDG VE VLV  RDAVQGGQGLI IG
SEQ. ID NO. 19:    Pacnes 1.3S     (89)   TEINAPADGTVK ILVAVGDAVQGGQGLVALG
SEQ. ID NO. 23:      Cthe_0700    (101)    EIVAPNDGTVASINVSKGASVNVG VLVSLK
SEQ. ID NO. 31: Tsacch or0947     (96)    EI SPYDGTIISINVSKGASVNTG VLLYLK
```

FIG. 7C

Transcarboxylase 12S subunit (N-terminus)

```
                                               1                                                50
SEQ. ID NO. 14:   Pfreud 12S-N     (1)   MAENNNLKLASTMEGRVEQLAE RQVIEAGGGE RVEKQH  GKQTARER
SEQ. ID NO. 17:    Pacnes 12S      (1)   MAEKKPIKLADTMAGRIEQLAD RH VELGGGEDRL KQ DRGKQTARER
SEQ. ID NO. 21:     Cthe_0699      (1)   ----------MDKV KIGLLREKLAQVEQGGGAEKIAKQ DAGKMTARER
SEQ. ID NO. 29:  Tsacch or0945     (1)   ----------MSID RIE LL RREMVLEGGGLDKVEKQ  KGKLTARER
                                         51                                              100
SEQ. ID NO. 14:   Pfreud 12S-N    (51)   LNNLLDPHSFDEVGAFRKHRTTLFGMDKAVVPADGVVTGRGTILGRPVH
SEQ. ID NO. 17:    Pacnes 12S     (51)   I NLVDAYSFDEVGAFRKHRTTLFGMDKA VPADGVVTGRATI GRPVHI
SEQ. ID NO. 21:     Cthe_0699     (41)   IQALLDE SFVEI  FV TRSIDF M KKKVPGDGVVTGYGSIDGRLV V
SEQ. ID NO. 29:  Tsacch or0945    (41)   IY LLDE SFVEI AYV HRCIDFGMEKQRIPGEGVVTGYGTIDGRLVYV
                                         101                                             150
SEQ. ID NO. 14:   Pfreud 12S-N   (101)   ASQDFTVMGGSAGETQSTKVV IMEQALLTGTPFLFFYDSGGARIQEGID
SEQ. ID NO. 17:    Pacnes 12S    (101)   ASQDFTVMGGSAGETQSTKVV IMEQSLLTGTPFLFFYDSGGARIQEGID
SEQ. ID NO. 21:     Cthe_0699     (91)   AAQDFTVIGGSLGEM A KI K MDMAMKMG PFIS NDSGGARI EGID
SEQ. ID NO. 29:  Tsacch or0945    (91)   YAQDFTVLGGSLGEY A KI KIMDMALKMG P IG NDSGGARIQEGVD
                                         151                                             200
SEQ. ID NO. 14:   Pfreud 12S-N   (151)   SLSGYGKMFFANVKLSGVVPQIAIIAGPCAGGASYSPALTDFIIM -K A
SEQ. ID NO. 17:    Pacnes 12S    (151)   SLSGYGKMFYANVKLSGVVPQIAIIAGPCAGGASYSPALTDFIIM -K A
SEQ. ID NO. 21:     Cthe_0699    (141)   AL GFG IFYRN LASGVIPQISVIMGPCAGGAVYSPAITDFI MVDKTS
SEQ. ID NO. 29:  Tsacch or0945   (141)   ALSGYG IFFRN LASGVIPQISVIMGP AGGAVYSPALTDFI MVDKTS
                                         201                                             250
SEQ. ID NO. 14:   Pfreud 12S-N   (200)    MFITGPQVIKSVTGEDVTADELGGAE HMAISGNIHFVAEDDDA ELIA
SEQ. ID NO. 17:    Pacnes 12S    (200)    MFITGPGVIKSVTGEEVTADDLGGAD HMSTSGNIHFVAEDDDA VLIA
SEQ. ID NO. 21:     Cthe_0699    (191)   QMFITGPQVIKSVTGEDVTFE LGGAETHNSISGVAHFRS  E ECIEQI
SEQ. ID NO. 29:  Tsacch or0945   (191)   QMFITGPQVIKAVTGEDVSAEELGGSITHSTKSGVAHFRAE DEECLKM
                                         251                                             300
SEQ. ID NO. 14:   Pfreud 12S-N   (250)   KKLLSFLPQNNTEEA  VN N DVSPNTE-LRDIVPIDG KGYDVRDVIA
SEQ. ID NO. 17:    Pacnes 12S    (250)    KLLSFLPQNNTEDAQISN NDDVSPQ E-LRDIVPLDG KGYDVRDVIS
SEQ. ID NO. 21:     Cthe_0699    (241)   NKLLSYLP NNL D PIVPTQDDI RITDNLVDIIPQD NKPYDMMEIIT
SEQ. ID NO. 29:  Tsacch or0945   (241)   RKLLSYLP NNLEDPPQLAT DDI RFSDRLIEIIPD PNKPYDMKEVIS
                                         301                                             350
SEQ. ID NO. 14:   Pfreud 12S-N   (299)   KIVDWGDYLEV AGYAINLVTAFARVNGRSVGIVANQP VMSGCLDINAS
SEQ. ID NO. 17:    Pacnes 12S    (299)   KIVDWGDYLEV AGWAINIVTAFARVNGRTVGIVANQPKVMSGCLDINAS
SEQ. ID NO. 21:     Cthe_0699    (291)    VVDNGDF EIQK FA NIIIGFGRMNGGTVGIVANQPKVAAGVLDVNSS
SEQ. ID NO. 29:  Tsacch or0945   (291)    IVDEGVY ESQAMYAQNIITAFARLNGRTVGIIANQPKVLAGCLDINAS
                                         351                                             400
SEQ. ID NO. 14:   Pfreud 12S-N   (349)   DKAA FV FCDSFNIPLVQLVDVPGFLPGVQQEYGGIIRHGAKMLYAYSE
SEQ. ID NO. 17:    Pacnes 12S    (349)   DKAA FITFCDSFNIPLVQLVDVPGFLPGVQQEYGGIIRHGAKMLYAYSE
SEQ. ID NO. 21:     Cthe_0699    (341)   DKAARFVRFCDAFNIPIIT  DVPGYLPGVGQEH GVIRHGAKLLYAFSE
SEQ. ID NO. 29:  Tsacch or0945   (341)   DKASRFIRFCDAFNIPLLNIVDVPGFLPG NQEYGGIIRHGAKMLYAYSE
                                         401                                             450
SEQ. ID NO. 14:   Pfreud 12S-N   (399)   ATVPKITVVLRKAYGGSYLAMC RDLGADAVYAWPSAEIAVMGAEGAANV
SEQ. ID NO. 17:    Pacnes 12S    (399)   ATVPKITVVLRKAYGGSYLAMC RDLGADAVYAWPSAEIAVMGADGAANV
SEQ. ID NO. 21:     Cthe_0699    (391)   ATVPKI VIVRKAYGGAYIAMNSK LGADMVFAWPSAEIAVMGPEGAANI
SEQ. ID NO. 29:  Tsacch or0945   (391)   ATVPKVTLIVRKAYGGAYLAMCSKILGADFVLAWPTAEIAVMGPDGAANI
                                         451                                             500
SEQ. ID NO. 14:   Pfreud 12S-N   (449)   IFRKEIKAADDPDAMRAEKIEEY NAFNTPYVAAARGQVDDVIDPADTRR
SEQ. ID NO. 17:    Pacnes 12S    (449)   IFRR IKDSEDP ATRAAKIEEYRNAFNTPYVAAARGQVDDVIDPADTRR
SEQ. ID NO. 21:     Cthe_0699    (441)   IFKKDIAAADDPMETRK LIEEYR KF  PYVAASRGYVDDVIDPATTRI
SEQ. ID NO. 29:  Tsacch or0945   (441)   VFK EIKSSDDPVA RNEKI EYR NFA PYRAAARGYVDDVVLPQETRP
                                         501                      526
SEQ. ID NO. 14:   Pfreud 12S-N   (499)   KIASALEMYATKRQTRPAKKHGNFPC
SEQ. ID NO. 17:    Pacnes 12S    (499)   KITAALETYATKRQSRPAKKHGV PC
SEQ. ID NO. 21:     Cthe_0699    (491)   RLISALEMLASKR  RPAKKHGN PL
SEQ. ID NO. 29:  Tsacch or0945   (491)   RLISA DMLMSKR SRPSKKHGNFPV
```

FIG. 13
BTE acyl-ACP thioesterase
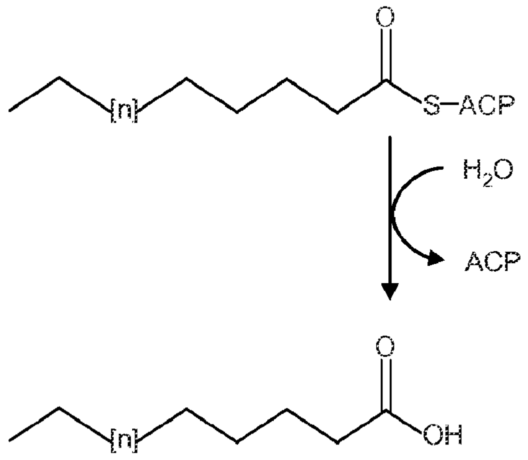
"free" fatty acid
AAR acyl-ACP reductase &
ADH alcohol dehydrogenase
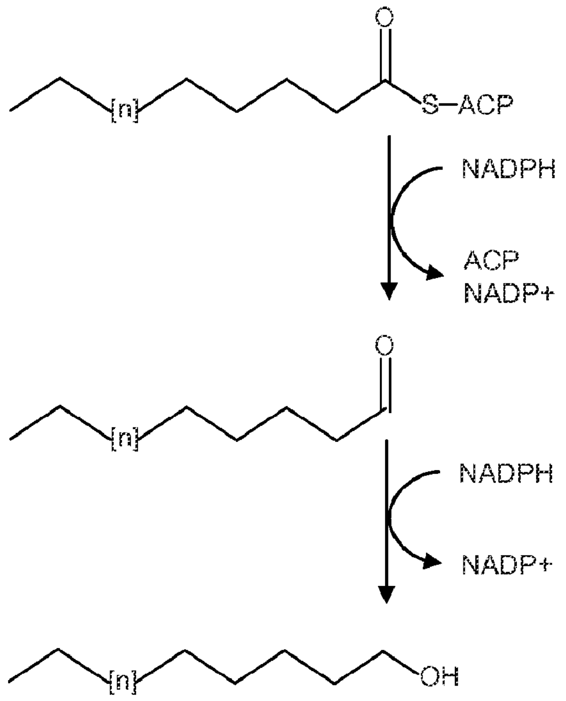
"free" fatty alcohol

FIG. 22A

| | pMU690 | pMU3061 | pMU3062 | pMU3063 | pMU3064 |
|---|---|---|---|---|---|
| **Sum** | 45 | 154 | 201 | 39 | 54 |
| **12:0** | 0.00 | 49.53 | 2.82 | 0.25 | 0.25 |
| **14:0** | 1.94 | 1.88 | 70.37 | 3.57 | 1.76 |
| **14:1** | 0.00 | 15.92 | 2.56 | 0.16 | 0.14 |
| **15:0** | 0.00 | 0.00 | 0.43 | 0.14 | 0.00 |
| **15:1** | 0.00 | 0.00 | 0.00 | 0.00 | 0.00 |
| **16:0** | 21.87 | 5.39 | 19.30 | 12.41 | 20.21 |
| **16:1w5** | 0.00 | 0.00 | 0.00 | 0.00 | 0.00 |
| **16:1w7** | 5.74 | 4.01 | 75.74 | 6.28 | 5.57 |
| **17:0** | 0.49 | 0.38 | 0.52 | 0.37 | 0.34 |
| **17:1** | 5.76 | 1.85 | 3.21 | 4.93 | 5.72 |
| **18:0** | 1.76 | 1.94 | 1.72 | 1.37 | 2.19 |
| **18:1w9** | 0.37 | 0.54 | 0.16 | 0.14 | 0.17 |
| **18:1w7** | 5.73 | 10.16 | 7.53 | 5.36 | 12.13 |
| **18:2w6** | 0.00 | 0.36 | 7.65 | 0.34 | 0.35 |
| **20:0** | 0.00 | 0.00 | 0.00 | 0.00 | 0.00 |
| **20:1w9** | 0.00 | 0.00 | 0.49 | 0.00 | 0.27 |
| **20:2w6** | 0.00 | 0.00 | 3.64 | 0.00 | 0.00 |
| **20:3w6** | 0.00 | 0.00 | 1.33 | 0.00 | 0.00 |
| **20:5w3** | 0.00 | 0.00 | 1.05 | 0.00 | 0.00 |
| **22:0** | 0.00 | 0.00 | 0.00 | 0.00 | 0.00 |
| **22:1w9** | 0.30 | 0.13 | 0.29 | 0.23 | 0.22 |
| **24:0** | 0.00 | 0.00 | 0.00 | 0.00 | 0.00 |
| **other** | 0.57 | 61.53 | 2.05 | 3.72 | 4.42 |

FIG. 26B cont.
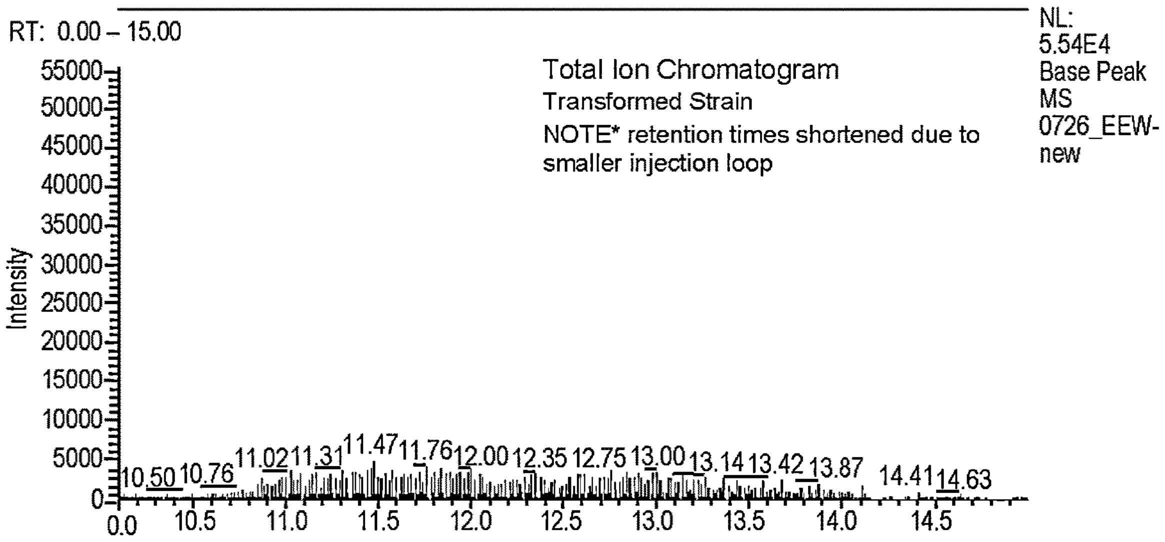
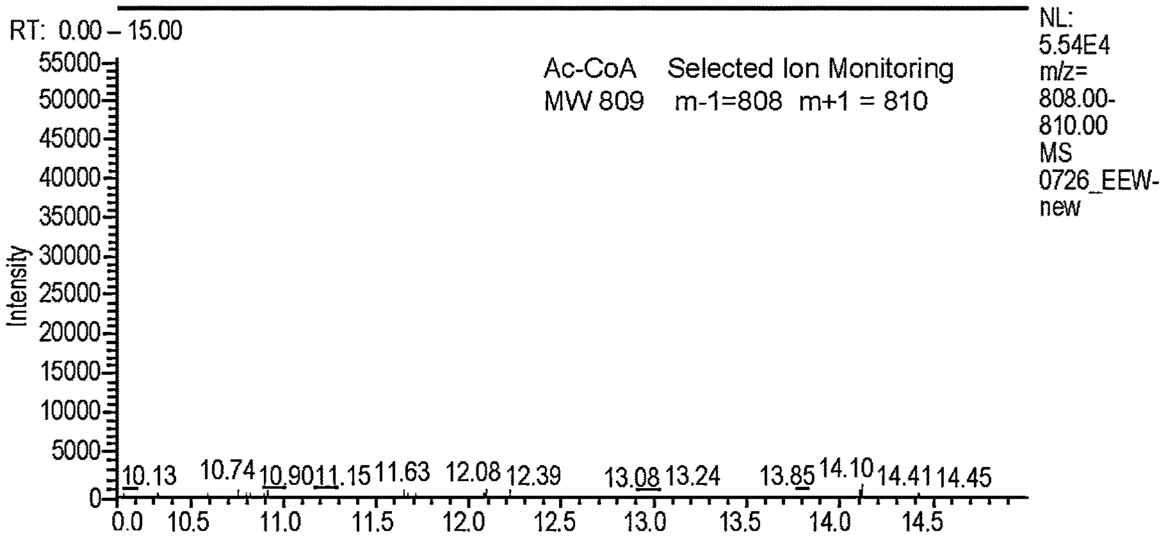
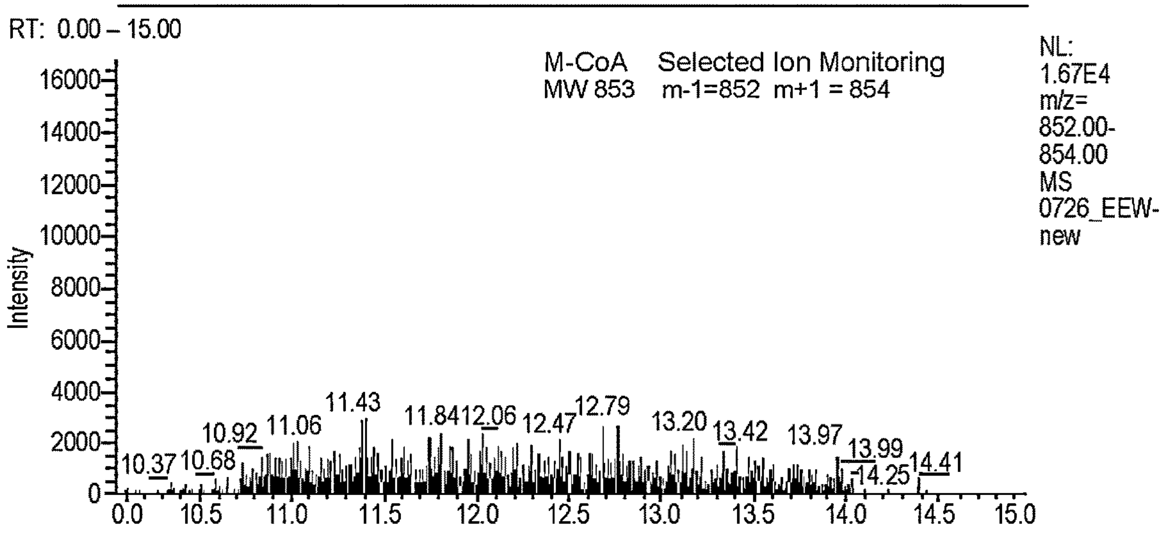

| | μmax | SD |
|---|---|---|
| M2767 | 0.005 | 0.00 |
| M2767-T3 | 0.24 | 0.00 |

| | μmax | SD |
|---|---|---|
| M2772 | 0.01 | 0.00 |
| M2772-T3 | 0.18 | 0.00 |

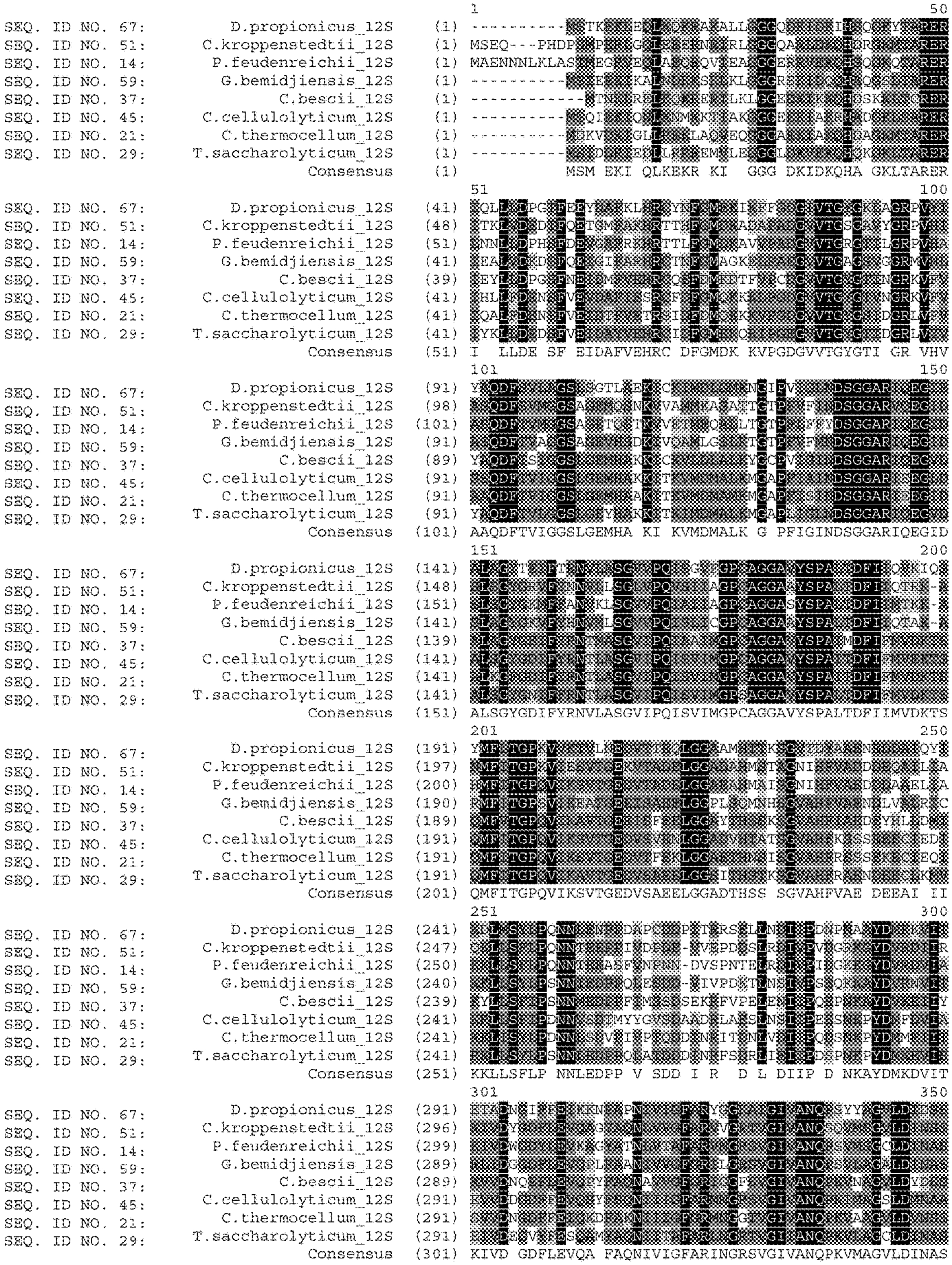

FIG. 31

12S subunits

```
                                                     1                                                  50
SEQ. ID NO. 67:   D.propionicus_12S      (1)   ----------MTK  ED  A ALL  GG Q      I  Q YT  RER
SEQ. ID NO. 51:   C.kroppenstedtii_12S   (1)   MSEQ---PHDP  P   G    N  RL  GGQA     DR    RER
SEQ. ID NO. 14:   P.feudenreichii_12S    (1)   MAENNNLKLAS  EG   E   A  QV EA  GGE   E  Q  Q  RER
SEQ. ID NO. 59:   G.bemidjiensis_12S     (1)   ----------  E  KA   N  KL   GRE          R   RER
SEQ. ID NO. 37:   C.bescii_12S           (1)   ----------NTN RE   Q  LKL GE    K   SK    RER
SEQ. ID NO. 45:   C.cellulolyticum_12S   (1)   ----------  QI   Q  NM KT AK GG E  A  K D    RER
SEQ. ID NO. 21:   C.thermocellum_12S     (1)   ----------  KV  GL   LAQ EQ GG A  A  A      RER
SEQ. ID NO. 29:   T.saccharolyticum_12S  (1)   ----------  D   E  L R  EM LE  GL          K RER
                  Consensus              (1)              MSM EKI QLKEKR KI  GGG DKIDQHA GKLTARER

                                                     51                                                100
SEQ. ID NO. 67:   D.propionicus_12S      (41)  QL   PG   EY   KL  Y    I  PF  G   VTG  K  GRPV
SEQ. ID NO. 51:   C.kroppenstedtii_12S   (48)  TK   D D   Q TGM AN  RTTL    AD   G   VTG A Y GRPV
SEQ. ID NO. 14:   P.feudenreichii_12S    (51)  NNM  D  DP  G  RK  RTTL  M  AV  E G VTGR   LGRPV A
SEQ. ID NO. 59:   G.bemidjiensis_12S     (41)  EA   D   D QE  GI R    M AGKE      VTGA G  GRM
SEQ. ID NO. 37:   C.bescii_12S           (39)  EY  D PG   N    R Q  Y  T    C G VTGC    GRKV
SEQ. ID NO. 45:   C.cellulolyticum_12S   (41)  HL   D N  V   S  F  MQ KK     C G VTG C  NGRKV
SEQ. ID NO. 21:   C.thermocellum_12S     (41)  QA  D N  V      T SI  Y K      G VTG C  DGRLV
SEQ. ID NO. 29:   T.saccharolyticum_12S  (41)  YK  D D  VB    RI  M       C G VTG C  DGRLV
                  Consensus              (51)  I   LLDE SF EIDAFVEHRC DFGMDK KVPGDGVVTGYGTI GR VHV

                                                     101                                               150
SEQ. ID NO. 67:   D.propionicus_12S      (91)  Y QDF   GS  SGTL K  C         N  EV    DSGGAR   EG
SEQ. ID NO. 51:   C.kroppenstedtii_12S   (98)   QDF   GS A  N   VA  A A TGT F   DSGGAR   EG
SEQ. ID NO. 14:   P.feudenreichii_12S    (101) QDF   AG S   T   VE  Q  LT TP  FY DSGGAP   EG
SEQ. ID NO. 59:   G.bemidjiensis_12S     (91)   QDF  A   GS A  DK VA LG   T  F   DSGGAR   EG
SEQ. ID NO. 37:   C.bescii_12S           (89)  Y QDF  S  GS    K C      C P V   DSGGAR   GRM
SEQ. ID NO. 45:   C.cellulolyticum_12S   (91)   QDF   GS    K  T       MCAP   DSGGAR   EG
SEQ. ID NO. 21:   C.thermocellum_12S     (91)   QDF   GS    AK T       MCAP   DSGGAR   EG
SEQ. ID NO. 29:   T.saccharolyticum_12S  (91)  Y AQDF   GS   Y  K T    GCAPL   DSGGAR   EG
                  Consensus              (101) AAQDFTVIGGSLGEMHA KI KVMDMALK G PFIGINDSGGARIQEGID

                                                     151                                               200
SEQ. ID NO. 67:   D.propionicus_12S      (141)  L  T  T  N   SG  PQ  G GP AGGA YSPA  DFI  M KIQ
SEQ. ID NO. 51:   C.kroppenstedtii_12S   (148) I C    N  LSG  PQ   AGP AGGA YSPA  DFI  TH  -
SEQ. ID NO. 14:   P.feudenreichii_12S    (151) I    AN KL SG  PQ    AGP AGGA YSPA  DFI  K  -
SEQ. ID NO. 59:   G.bemidjiensis_12S     (141) I C   NN  LSG  PQ     GP AGGA YSPA  DFI QTA  -
SEQ. ID NO. 37:   C.bescii_12S           (139) I       N    SG  PQ    GP AGGA YSPA MDFI
SEQ. ID NO. 45:   C.cellulolyticum_12S   (141) I    N    SG  PQ     GP AGGA YSPA  DFI
SEQ. ID NO. 21:   C.thermocellum_12S     (141) I    N    SG  PQ     GP AGGA YSPA  DFI
SEQ. ID NO. 29:   T.saccharolyticum_12S  (141) I       N    SG  PQ    GP AGGA YSPA  DFI
                  Consensus              (151) ALSGYGDIFYRNVLASGVIPQISVIMGPCAGGAVYSPALTDFI IMVDKTS

                                                     201                                               250
SEQ. ID NO. 67:   D.propionicus_12S      (191) Y MF TGP V   LK     LGG AM   KG   TA     QY
SEQ. ID NO. 51:   C.kroppenstedtii_12S   (197)   MF TGP V   E       LGG A  MT NI   D  C L  A
SEQ. ID NO. 14:   P.feudenreichii_12S    (200) RM MF TGP V  TA    E  LGG A  MK NI    A ELA
SEQ. ID NO. 59:   G.bemidjiensis_12S     (190)   MF TGP V      E   LGG PL QMNH  Y    NL V R C
SEQ. ID NO. 37:   C.bescii_12S           (189)   MF TGP V      E  F LGG  A       D  YH LD
SEQ. ID NO. 45:   C.cellulolyticum_12S   (191)   MF TGP V      E   V LGG V A T  YA K    S   ED
SEQ. ID NO. 21:   C.thermocellum_12S     (191)   MF TGP V      E  F LGG  NGI       R SS  K  EQ
SEQ. ID NO. 29:   T.saccharolyticum_12S  (191)   MF TGP V IKS V E   LGG I    K  R    N   K
                  Consensus              (201) QMFITGPQVIKSVTGEDVSAEELGGADTHSS SGVAHPVAE DEEAI II

                                                     251                                               300
SEQ. ID NO. 67:   D.propionicus_12S      (241)     S  PQNN  N   DAPC  P T RS L N    DP A  VD   R
SEQ. ID NO. 51:   C.kroppenstedtii_12S   (247)   L S  PQNN   IDEP  - VEPD  R    VG   VD     R
SEQ. ID NO. 14:   P.feudenreichii_12S    (250)   L S  PDNN   A F NENN -DVSPNTE  K  NS  P    VD    I
SEQ. ID NO. 59:   G.bemidjiensis_12S     (240)   L S  P NN   QE  N  IVPD T NS  E    QK N  VD  I T
SEQ. ID NO. 37:   C.bescii_12S           (239) Y L S  PS NN   F M  S SEK FVPE LN  E  PK    VD    Y
SEQ. ID NO. 45:   C.cellulolyticum_12S   (241)   L S  PDNN   MYYGV S AAD LA  SNN  PE S  PVD F
SEQ. ID NO. 21:   C.thermocellum_12S     (241)   L S  PDNN   V  PT D N  ITNV    Q S  PYD   M
SEQ. ID NO. 29:   T.saccharolyticum_12S  (241)   L S  SNN   Q A  D NRFSK  L    DP   YD
                  Consensus              (251) KKLLSFLP NNLEDPP V SDD I R  D L DIIP D NKAYDMKDVIT

                                                     301                                               350
SEQ. ID NO. 67:   D.propionicus_12S      (291)    D  I   KN   P    YG   GI ANQ SYY  GLD
SEQ. ID NO. 51:   C.kroppenstedtii_12S   (296)    V  E        L   V    GI ANQ      C  LD
SEQ. ID NO. 14:   P.feudenreichii_12S    (299)    V  E    A N    P RLG   GI ANQ    C LD
SEQ. ID NO. 59:   G.bemidjiensis_12S     (289)         E     T     P  G    GI ANQ  S  QK  LD
SEQ. ID NO. 37:   C.bescii_12S           (289)    NQ        TY  A   P G   GI ANQ     G LD
SEQ. ID NO. 45:   C.cellulolyticum_12S   (291)     D  H   Y        G   GI ANQ   G S LD K
SEQ. ID NO. 21:   C.thermocellum_12S     (291)    QN  Y            G   GI ANQ    A C LD
SEQ. ID NO. 29:   T.saccharolyticum_12S  (291)    PV  ES M      ER   G   GI ANQ    C  LD
                  Consensus              (301) KIVD GDFLEVQA FAQNIVIGFARINGRSVGIVANQPKVMAGVLDINAS
```

FIG. 31 (cont.)

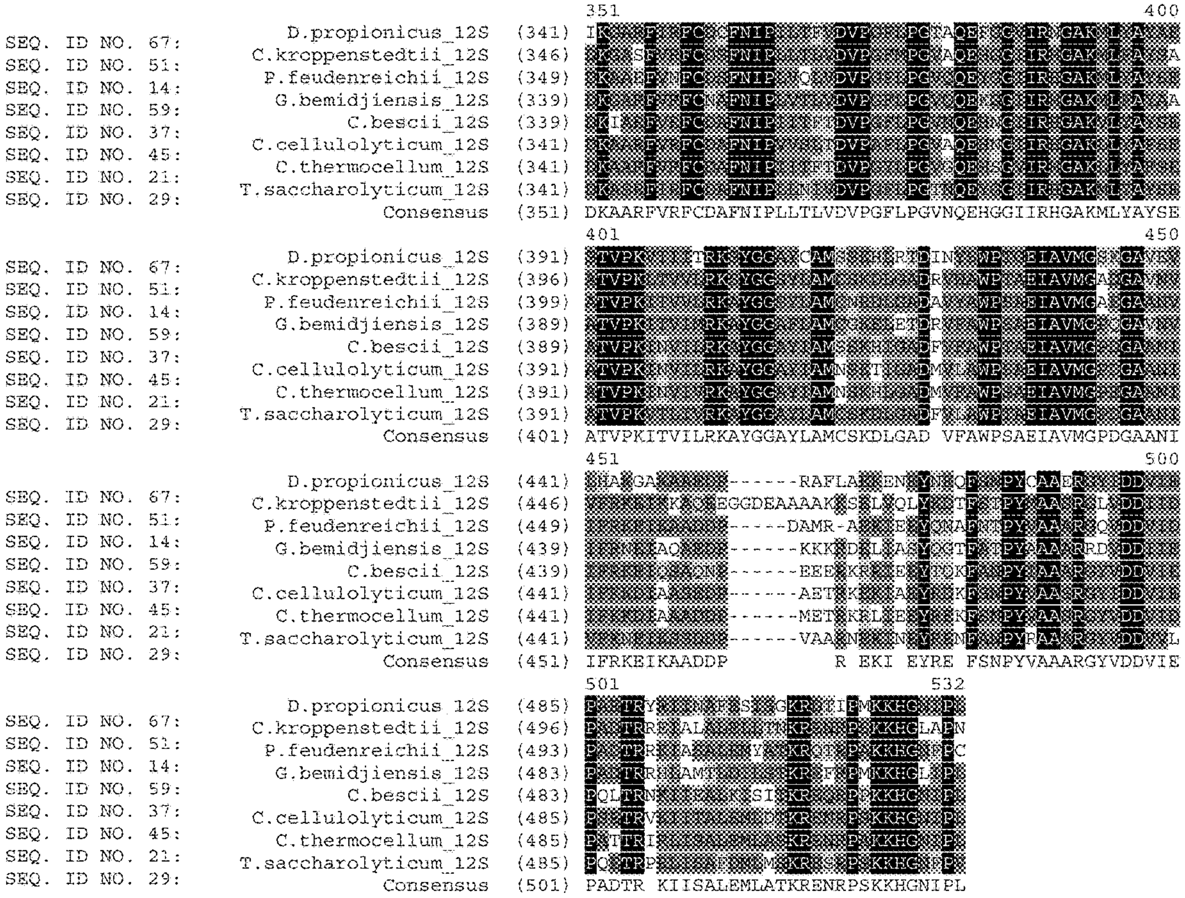

5S subunits

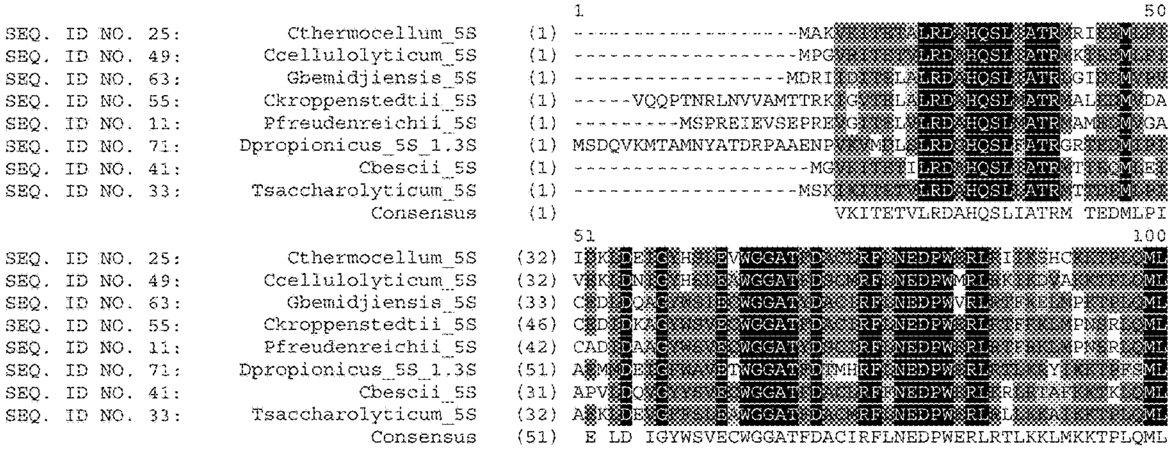

[Sequence alignment figure showing 12S subunits (positions 351-532) and 5S subunits (positions 1-100) for multiple organisms including D.propionicus, C.kroppenstedtii, P.freudenreichii, G.bemidjiensis, C.bescii, C.cellulolyticum, C.thermocellum, and T.saccharolyticum, with SEQ ID NOs. 67, 51, 14, 59, 37, 45, 21, 29 for 12S subunits and SEQ ID NOs. 25, 49, 63, 55, 11, 71, 41, 33 for 5S subunits.]

12S Consensus (351): DKAARFVRFCDAFNIPLLTLVDVPGFLPGVNQEHGGIIRHGAKMLYAYSE
12S Consensus (401): ATVPKITVILRKAYGGAYLAMCSKDLGAD VFAWPSAEIAVMGPDGAANI
12S Consensus (451): IFRKEIKAADDP R EKI EYRE FSNPYVAAARGYVDDVIE
12S Consensus (501): PADTR KIISALEMLATKRENRPSKKHGNIPL

5S subunits

5S Consensus (1): VKITETVLRDAHQSLIATRM TEDMLPI
5S Consensus (51): E LD IGYWSVECWGGATFDACIRFLNEDPWERLRTLKKLMKKTPLQML

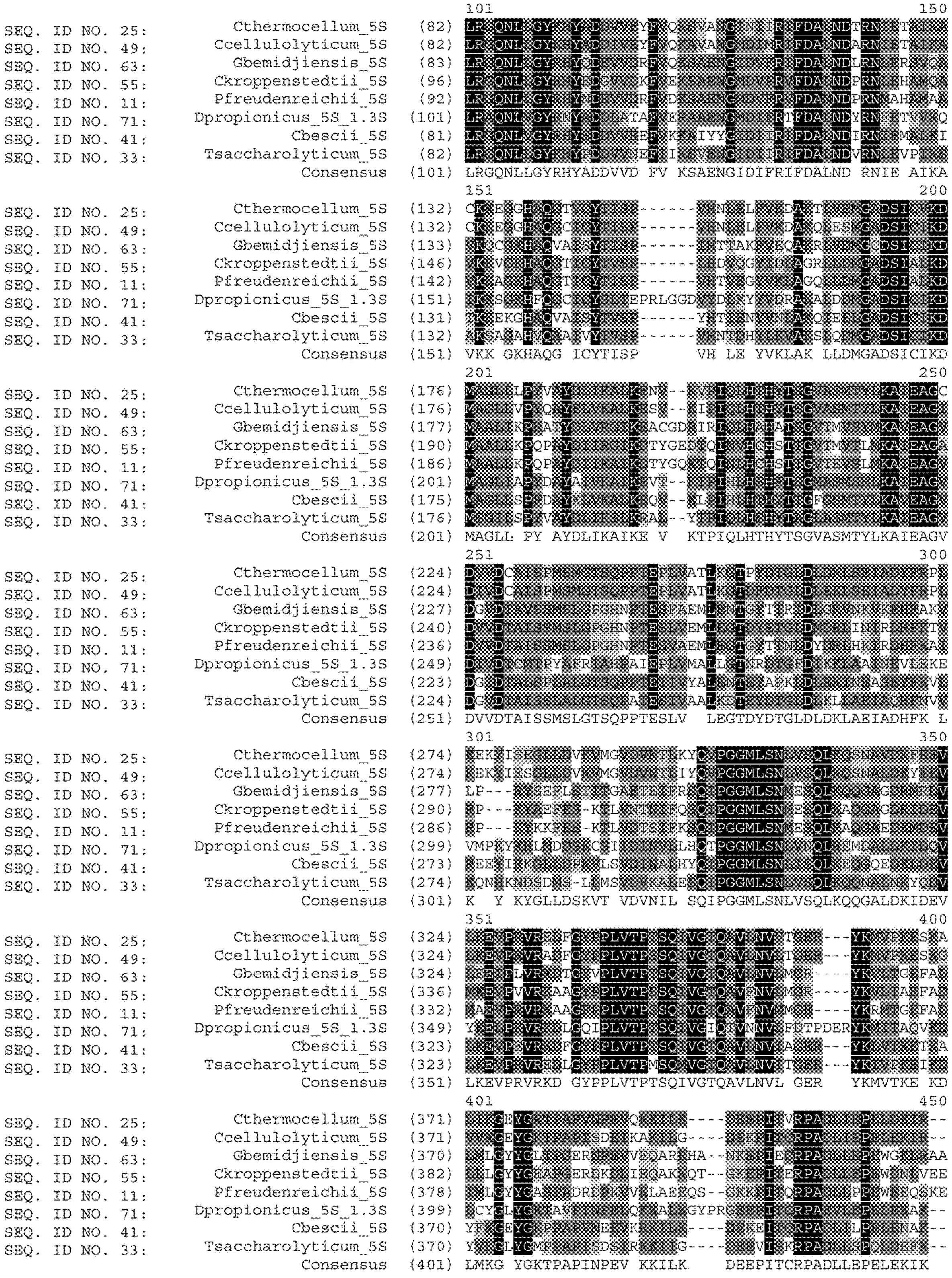

FIG. 31 (cont.)

```
                                                  101                                               150
SEQ. ID NO. 25:     Cthermocellum_5S    (82)   LRQNL GY Y  Y Q  VA    R FDA ND RN    T
SEQ. ID NO. 49:     Ccellulolyticum_5S  (82)   LRQNL GY Y  Y Q  VA    R FDA ND RN    T
SEQ. ID NO. 63:     Gbemidjiensis_5S    (83)   LRQNL GY Y  Y Q        R FDA ND RN
SEQ. ID NO. 55:     Ckroppenstedtii_5S  (96)   LRQNL GY Y  Y          R FDA ND PRN
SEQ. ID NO. 11:     Pfreudenreichii_5S  (92)   LRQNL GY Y  Y  R  A  G R FDA ND PRN AH  A
SEQ. ID NO. 71:     Dpropionicus_5S_1.3S (101)  LP QNL GY Y  D ATA  E    RT FDA ND YRN  TV  Q
SEQ. ID NO. 41:     Cbescii_5S          (81)   LR QNL GY Y  D  E  K  IYY  R FDA ND RN    I
SEQ. ID NO. 33:     Tsaccharolyticum_5S (82)              E          IR FDA ND VRN  VP
                    Consensus          (101)   LRGQNLLGYRHYADDVVD FV KSAENGIDIFRIFDALND RNIE AIKA
                                                  151                                               200
SEQ. ID NO. 25:     Cthermocellum_5S   (132)   C  E G  Q T  Y       ------  N L  DA T    C DSI   KD
SEQ. ID NO. 49:     Ccellulolyticum_5S (132)   C  E G  Q C  Y       ------  N L  DA  ES   C DSI   KD
SEQ. ID NO. 63:     Gbemidjiensis_5S   (133)    G   QVAL  Y         ------  TTAK VEQAR    C DSI A KD
SEQ. ID NO. 55:     Ckroppenstedtii_5S (146)    GV      T  Y        ------  D   G   AGPL  C DSI A KD
SEQ. ID NO. 11:     Pfreudenreichii_5S (142)    CA     T  Y         ------  T G    AGQ    C DSI A KD
SEQ. ID NO. 71:     Dpropionicus_5S_1.3S (151)   C    Q C          EPRLGGD  D NY  DR A D  C DSI  KD
SEQ. ID NO. 41:     Cbescii_5S         (131)    EKG  QVA   Y        ------  Y T N  K A E   C DSI  KD
SEQ. ID NO. 33:     Tsaccharolyticum_5S (132)   A AA  A   V         ------  N  H  A S Q E  C DSI  KD
                    Consensus          (151)   VKK GKHAQG ICYTISP      VH LE YVKLAK LLDMGADSICIKD
                                                  201                                               250
SEQ. ID NO. 25:     Cthermocellum_5S   (176)      L V        N  --  V   H T C      KA EAC C
SEQ. ID NO. 49:     Ccellulolyticum_5S (176)      VD C       S  --I    H T C      KA EAC
SEQ. ID NO. 63:     Gbemidjiensis_5S   (177)      K  ATT     KA ACGD IR   A  C      KA EAC
SEQ. ID NO. 55:     Ckroppenstedtii_5S (190)        QP Y     TYGE  Q   H ST C  TM L KA EAC
SEQ. ID NO. 11:     Pfreudenreichii_5S (186)       KQP Y     TYGQ     H T  C       L KA EAC
SEQ. ID NO. 71:     Dpropionicus_5S_1.3S (201)    A  DYA     V  --   H T C        KA EAC
SEQ. ID NO. 41:     Cbescii_5S         (175)      S  Y      KQ  -- L  H T CF      KA EAC
SEQ. ID NO. 33:     Tsaccharolyticum_5S (176)      S V  Y    RA  --Y    H T C      KA EAGV
                    Consensus          (201)   MAGLL PY AYDLIKAIKE V KTPIQLHTHYTSGVASMTYLKAIEAGV
                                                  251                                               300
SEQ. ID NO. 25:     Cthermocellum_5S   (224)   D  C      P     E  AT K P       D                P
SEQ. ID NO. 49:     Ccellulolyticum_5S (224)   D  C   A  P     E P AT K        D
SEQ. ID NO. 63:     Gbemidjiensis_5S   (227)   DG D         PGHN  E  FKEM   T TP D   NK K  AK
SEQ. ID NO. 55:     Ckroppenstedtii_5S (240)   D  D A      A   E   AEM  T TN    D    IN R   T
SEQ. ID NO. 11:     Pfreudenreichii_5S (236)       D        PGHN  E     M  T TN    D   HK R   A
SEQ. ID NO. 71:     Dpropionicus_5S_1.3S (249)  D  DC   PY  R  A IE MA  G  R D  K A  VLEKE
SEQ. ID NO. 41:     Cbescii_5S         (223)   DG D         A   E  YA  S  AFK D    A    V
SEQ. ID NO. 33:     Tsaccharolyticum_5S (224)   DG          AS E AA  K    D  KL A  Q  KV
                    Consensus          (251)   DVVDTAISSMSLGTSQPPTESLV LEGTDYDTGLDLDKLAEIADHFK L
                                                  301                                               350
SEQ. ID NO. 25:     Cthermocellum_5S   (274)    EK IE      V  MG     KY C PGGMLSN  QL           
SEQ. ID NO. 49:     Ccellulolyticum_5S (274)    EK IE      V  MG     IY C PGGMLSN  QL        Y
SEQ. ID NO. 63:     Gbemidjiensis_5S   (277)   LP---     EPL   GA   PR Q PGGMLSN  EQI          V
SEQ. ID NO. 55:     Ckroppenstedtii_5S (290)    P---     E   -K L T    Q PGGMLSN  QL A         E
SEQ. ID NO. 11:     Pfreudenreichii_5S (286)    P---    KK  -K    T    Q PGGMLSN  QL           E
SEQ. ID NO. 71:     Dpropionicus_5S_1.3S (299)  VMP Y    L D  C      LH  T PGGMLSN  QL  M       GV
SEQ. ID NO. 41:     Cbescii_5S         (273)    EE IK     E    LS   HY C PGGMLSN  QL  E QE     V
SEQ. ID NO. 33:     Tsaccharolyticum_5S (274)    QN KN  D  S -L MS   KA E C PGGMLSN  QL         Y V
                    Consensus          (301)   K Y KYGLLDSKVT VDVNIL SQIPGGMLSNLVSQLKQQGALDKIDEV
                                                  351                                               400
SEQ. ID NO. 25:     Cthermocellum_5S   (324)    E PVR  FG  PLVTP SQ VG Q V NV T       YK  S  A
SEQ. ID NO. 49:     Ccellulolyticum_5S (324)    E PVRA FC  PLVTP SQ VG Q V NV T       YK  S  
SEQ. ID NO. 63:     Gbemidjiensis_5S   (324)    E PVR  TG VPLVTP SQ VG Q V NV M       YK  G FA
SEQ. ID NO. 55:     Ckroppenstedtii_5S (336)    E PVR AAG   PLVTP SQ VG Q V NV  ----   YK  A FA
SEQ. ID NO. 11:     Pfreudenreichii_5S (332)   AE PVR AAG   PLVTP SQ VG Q V NV M ----  YR  G FA
SEQ. ID NO. 71:     Dpropionicus_5S_1.3S (349)  Y E PVR  L  QI PLVTP SQ VG IQ V NV F TPDER Y  AQV
SEQ. ID NO. 41:     Cbescii_5S         (323)    E PVR  FG  PLVTP SQ VG Q V NV T       YK   T A
SEQ. ID NO. 33:     Tsaccharolyticum_5S (323)    E PVR  LG  PLVTP SQ VG Q V NV T       YK   I
                    Consensus          (351)   LKEVPRVRKD GYPPLVTPTSQIVGTQAVLNVL GER YKMVTKE KD
                                                  401                                               450
SEQ. ID NO. 25:     Cthermocellum_5S   (371)     GY       D  KA  G---      T  VRPA  
SEQ. ID NO. 49:     Ccellulolyticum_5S (371)    GEY       D  KA   G----    T  VRPA  
SEQ. ID NO. 63:     Gbemidjiensis_5S   (370)   HLGY GL  GER  VEQAPHHA-- NK  E RPA    WG  AA
SEQ. ID NO. 55:     Ckroppenstedtii_5S (382)    LGY  GA  ERK   IRQAK QT--   V  RPA    W N VEE
SEQ. ID NO. 11:     Pfreudenreichii_5S (378)    LGY   A  DRE   V LAERQS--  GK   RPA    W EQSKE
SEQ. ID NO. 71:     Dpropionicus_5S_1.3S (399)   CY GL  AV    Q   GYPR      E  RPA    I  --
SEQ. ID NO. 41:     Cbescii_5S         (370)   Y   GEY G  E     G  ---    E  RPA     P  NA --
SEQ. ID NO. 33:     Tsaccharolyticum_5S (370)   Y  LYG M  A SDS RK  G----   V  RPA     E  NA --
                    Consensus          (401)   LMKG YGKTPAPINPEV KKILK DBEPITCRPADLLEPELEKIK
```

FIG. 31 (cont.)

```
                                                          451                                              500
SEQ. ID NO. 25:        Cthermocellum_5S   (415) -NEIKEYIEQDEDVLTYALFPQVAEKFFQYRK----------------AQ
SEQ. ID NO. 49:       Ccellulolyticum_5S  (415) -EAVNDYIKQDEDVLSYAMLPQVAEKFFKQRI----------------ED
SEQ. ID NO. 63:        Gbemidjiensis_5S   (418) ALPLEGCDGSEEDVLTYALFPQVAPKFFATRS----------------EG
SEQ. ID NO. 55:      Ckroppenstedtii_5S   (430) ADKLDGTDGSDEDVLINALFPQVAPGEFKTRP----------------DG
SEQ. ID NO. 11:       Pfreudenreichii_5S  (426) AAALKSGNGTDEDVLTYALFPQVAPVFFEHRA----------------EG
SEQ. ID NO. 71:    Dpropionicus_5S_1.3S   (447) -KEIGPLAKQIEDVLKYALFPVTKKKFFEWKYGITPAPPEVKPLTLEDVK
SEQ. ID NO. 41:              Cbescii_5S   (414) -EKIKEYIEKQTDVVTYCLFPQLAENFFKLRF----------------AK
SEQ. ID NO. 33:     Tsaccharolyticum_5S   (414) -NEIKEYIEQDEDVLTYALFPQVARKFFEYRQ----------------AK
                              Consensus   (451)   EIKEYIEQDEDVLTYALFPQVA KFF  R                 E
                                                          501                                              550
SEQ. ID NO. 25:        Cthermocellum_5S   (448) KYKVEPDMVQYEKRVHPV--------------------------------
SEQ. ID NO. 49:       Ccellulolyticum_5S  (448) RNKATAPASDEIKFEVVAAISAVVNEMGERDGTQYRIGNISKLNQNQNRW
SEQ. ID NO. 63:        Gbemidjiensis_5S   (452) PRKVGRDPVTGASETSIPEGHPGKITGPVTYTVTLSGQPHKVTVAPYGQE
SEQ. ID NO. 55:      Ckroppenstedtii_5S   (464) PKNVGKTKEQLEKEEAKASGDATAIREPIMYKVTTGGRSHTVSVEPA---
SEQ. ID NO. 11:       Pfreudenreichii_5S  (460) PKSVALTDAQLK-AEAEGDEKSLAVAGPVTYNVNVGGTVREVTVQQA---
SEQ. ID NO. 71:    Dpropionicus_5S_1.3S   (496) KRDELVAKAKAGKLIEPKPAAPEKTANVRTYNVFVDGEYFNVEVDPTGDF
SEQ. ID NO. 41:              Cbescii_5S   (447) KYKVDADLVQGNKVYPV---------------------------------
SEQ. ID NO. 33:     Tsaccharolyticum_5S   (447) KYKVDSTLVQIEERVHPI--------------------------------
                              Consensus   (501) KYKV    VQ  K                 Y V   G    V V
                                                          551                                              600
SEQ. ID NO. 25:        Cthermocellum_5S   (466) --------------------------------------------------
SEQ. ID NO. 49:       Ccellulolyticum_5S  (498) SLYGMLDRFRTKI-------------------------------------
SEQ. ID NO. 63:        Gbemidjiensis_5S   (502) --------------------------------------------------
SEQ. ID NO. 55:      Ckroppenstedtii_5S   (511) --------------------------------------------------
SEQ. ID NO. 11:       Pfreudenreichii_5S  (506) --------------------------------------------------
SEQ. ID NO. 71:    Dpropionicus_5S_1.3S   (546) QPMVAAAPRPAAPAAAPKAAAPAAAAPAAAPKAAAPAAAAPAPAAVEGGT
SEQ. ID NO. 41:              Cbescii_5S   (464) --------------------------------------------------
SEQ. ID NO. 33:     Tsaccharolyticum_5S   (465) --------------------------------------------------
                              Consensus   (551)
                                                          601                                              650
SEQ. ID NO. 25:        Cthermocellum_5S   (466) --------------------------------------------------
SEQ. ID NO. 49:       Ccellulolyticum_5S  (511) --------------------------------------------------
SEQ. ID NO. 63:        Gbemidjiensis_5S   (502) --------------------------------------------------
SEQ. ID NO. 55:      Ckroppenstedtii_5S   (511) --------------------------------------------------
SEQ. ID NO. 11:       Pfreudenreichii_5S  (506) --------------------------------------------------
SEQ. ID NO. 71:    Dpropionicus_5S_1.3S   (596) PLLAPMPGMIVKNLVNVGDAVKAGDPILVLEAMKMENNLGSPCDGTVKAL
SEQ. ID NO. 41:              Cbescii_5S   (464) --------------------------------------------------
SEQ. ID NO. 33:     Tsaccharolyticum_5S   (465) --------------------------------------------------
                              Consensus   (601)
                                                          651             668
SEQ. ID NO. 25:        Cthermocellum_5S   (466) ------------------
SEQ. ID NO. 49:       Ccellulolyticum_5S  (511) ------------------
SEQ. ID NO. 63:        Gbemidjiensis_5S   (502) ------------------
SEQ. ID NO. 55:      Ckroppenstedtii_5S   (511) ------------------
SEQ. ID NO. 11:       Pfreudenreichii_5S  (506) ------------------
SEQ. ID NO. 71:    Dpropionicus_5S_1.3S   (646) NFGSGDSVAKDTVLAIIG
SEQ. ID NO. 41:              Cbescii_5S   (464) ------------------
SEQ. ID NO. 33:     Tsaccharolyticum_5S   (465) ------------------
                              Consensus   (651)
```

FIG. 31 (cont.)

1.3S subunits

```
                                                1                                                50
SEQ. ID NO. 31:      Tsaccharolyticum_1.3S   (1) MKKFIVTVNGKKYDVEVEEIKVEVASEKKAKEDTAAKNASDASVKSK---
SEQ. ID NO.  8:       Pfreudenreichii_1.3S   (1) -MKLKVTVNGTAYDVDVEVDKSEENPMGTILFGGATGGAPAPRAAGGAG-
SEQ. ID NO. 53:      Ckroppenstedtii_1.3S   (1) -MKLTVTVNGVPYSVDVEVEHEERPTLGTIITGGNSN-APTPTAPTTTS-
SEQ. ID NO. 61:        Gbemidjiensis_1.3S   (1) -VQLTVTIDGKKYRVDVEVEEGEEVRTEGAFPPTATMQAYPVYSAHPTAT
SEQ. ID NO. 39:              Cbescii_1.3S   (1) MRKFKVKINSQEYVVEVEVEEIGVENATSVVPRPKIGHFEPKQEKHEDKTK-
SEQ. ID NO. 47:       Ccellulolyticum_1.3S   (1) MSKFIIKVNGTPYDVEVEVEVGGCRPISAAPKLRATKPGHTSAAKAAQP--
SEQ. ID NO. 23:        Cthermocellum_1.3S   (1) MKKFLIKVNGNQYDVEVEVEEIRDGASAPQVTLSTPSAAPAPSPAPAQETKT
                               Consensus   (1) M KF VTVNG  YDVEVEEI  E                 A   A     A T
                                                51                                              100
SEQ. ID NO. 31:      Tsaccharolyticum_1.3S  (48) --QVEVKNEVKDAFSINAPMPGTILDVKISQGDTVKRGDVLLILEAMKME
SEQ. ID NO.  8:       Pfreudenreichii_1.3S  (49) -------AGKAGEGEIPAPLAGTVSKILVKEGDTVKAGQTVLVLEAMKME
SEQ. ID NO. 53:      Ckroppenstedtii_1.3S  (48) -------VQGVSANAVTAPLAGTVSKVLVEEGQAVTAGDVLVVLEAMKME
SEQ. ID NO. 61:        Gbemidjiensis_1.3S  (50) PPLAAPTPASASEKICRAPLAGVVPKIVAQVGDHVEMNDVLVVLEAMKME
SEQ. ID NO. 39:              Cbescii_1.3S  (50) ----QSPVLSADKNSAVAQLPGTIVKILKSEGDVVEANKPVLILEAMKME
SEQ. ID NO. 47:       Ccellulolyticum_1.3S  (49) --------QAGKAGDVAAPMPGTVLKVKVAIGDEVKKGQVLLILEAMKME
SEQ. ID NO. 23:        Cthermocellum_1.3S  (51) AAPKKDSTVPAGATVIKAPMPGTILDIRVNQGDTVKKGDVLLILEAMKME
                               Consensus  (51)             A A SI APLPGTVLKILV  GD VK GDVLLILEAMKME
                                                101                            133
SEQ. ID NO. 31:      Tsaccharolyticum_1.3S  (96) NEITAPYDGKIISINVSKGASVNTGDVLLYIK-
SEQ. ID NO.  8:       Pfreudenreichii_1.3S  (92) TEINAATDGKVEKVLVKERDAVQGGQGLIKIA-
SEQ. ID NO. 53:      Ckroppenstedtii_1.3S  (91) TEITAPNDGKVTKLHVQPGDAVQGGQSLIEIAD
SEQ. ID NO. 61:        Gbemidjiensis_1.3S (100) TNITAHMSGKVEKILVSVGEAVQPGDALAEFA-
SEQ. ID NO. 39:              Cbescii_1.3S  (96) NEITAPVKGKIKRIHVKEGQKVAKGDLLFEIE-
SEQ. ID NO. 47:       Ccellulolyticum_1.3S  (91) NEIVAPAAGKVTRINVEAGKSVTAGDTMVSIA-
SEQ. ID NO. 23:        Cthermocellum_1.3S (101) NEIVAPNDGKVASINVSKGASVNVGEVLVSIK-
                               Consensus (101) NEITAP DGKV AI V  G AVQ GDLLL IA
```

12S C-term subunit

```
                                                    1                                                50
SEQ. ID NO. 57:    Ckroppenstedtii_12Scterm   (1) MNTDNASSAELSQLLARLSNQVEKLSRNVTKLENEVAALKQRSDEEIPEE
SEQ. ID NO. 16:    Pfreudenreichii_12Scterm   (1) -----------MADEEEKDLMIATLNKRVASLESELGSLQS-DTQGITEE
SEQ. ID NO. 27:      Cthermocellum_12Scterm   (1) ------------------------------------------MKEQINEE
SEQ. ID NO. 35:   Tsaccharolyticum_12Scterm   (1) -------------------------------------------MEEINEE
SEQ. ID NO. 43:            Cbescii_12Scterm   (1) ------------------------------------MYAQVSTISTITKE
SEQ. ID NO. 69:      Dpropionicus_12Scterm   (1) -----------------------------------MAKLNKKMAAAIAAV
SEQ. ID NO. 65:      Gbemidjiensis_12Scterm   (1) ---------------------------------VDEELEQEHDPEITPE
                                   Consensus   (1)                                      L        I EE
                                                    51                                              100
SEQ. ID NO. 57:    Ckroppenstedtii_12Scterm  (51) ILIAISAAIAAYLGNRGTVKAVHFLK-----HRSWSQQGRQALQHKSKWQ
SEQ. ID NO. 16:    Pfreudenreichii_12Scterm  (39) ILTAISAAIAAYLGNDGSAEVKHFAP-----SPNWVREGRRALQNHSIR-
SEQ. ID NO. 27:      Cthermocellum_12Scterm   (9) IILAISAAIAALETRPGYKLVKRSFKRIPQTSPVWSATGKIERLRRSM--
SEQ. ID NO. 35:   Tsaccharolyticum_12Scterm   (8) ILAVISAAIYAAFGGYEKNFRIKVIKRVDSNMPEWRKAGLYNQSR-----
SEQ. ID NO. 43:            Cbescii_12Scterm  (15) ELACICACLHIVLGK-GQYKIIENITKQ----QNKWVKGGREMLMNQSQMF
SEQ. ID NO. 69:      Dpropionicus_12Scterm  (16) NAYLLQEEEAAYQAGLLAAKSKAPAG-----PSLWAIAGRQDLMNFRRLI
SEQ. ID NO. 65:      Gbemidjiensis_12Scterm  (17) ILMVISAAIAAYLGKTVRIKRARFVDPN--LINAWGQSGRVVSQASHNLR
                                   Consensus  (51) IL  ISAAIAAYLGN G  K V   K        W    GR  LM  S
                                                    101
SEQ. ID NO. 57:    Ckroppenstedtii_12Scterm  (96) -----
SEQ. ID NO. 16:    Pfreudenreichii_12Scterm  (83) -----
SEQ. ID NO. 27:      Cthermocellum_12Scterm  (57) -----
SEQ. ID NO. 35:   Tsaccharolyticum_12Scterm  (53) -----
SEQ. ID NO. 43:            Cbescii_12Scterm  (60) YRWR-
SEQ. ID NO. 69:      Dpropionicus_12Scterm  (61) QMKAF
SEQ. ID NO. 65:      Gbemidjiensis_12Scterm  (65) R----
                                   Consensus (101)
```

fdh1::Badoles ADH PFL rc flanks
25779 bp

FDH2:: Badoles ADH PFL
25358 bp gpd2:adoles ADH-fba term pfk-adh pMU2770 - pMU2606-AA46
25247 bp GPD1:adoles-ADH-YCL183-pMU2606 with primers
24329 bp PDC5 knt in frame
28254 bp

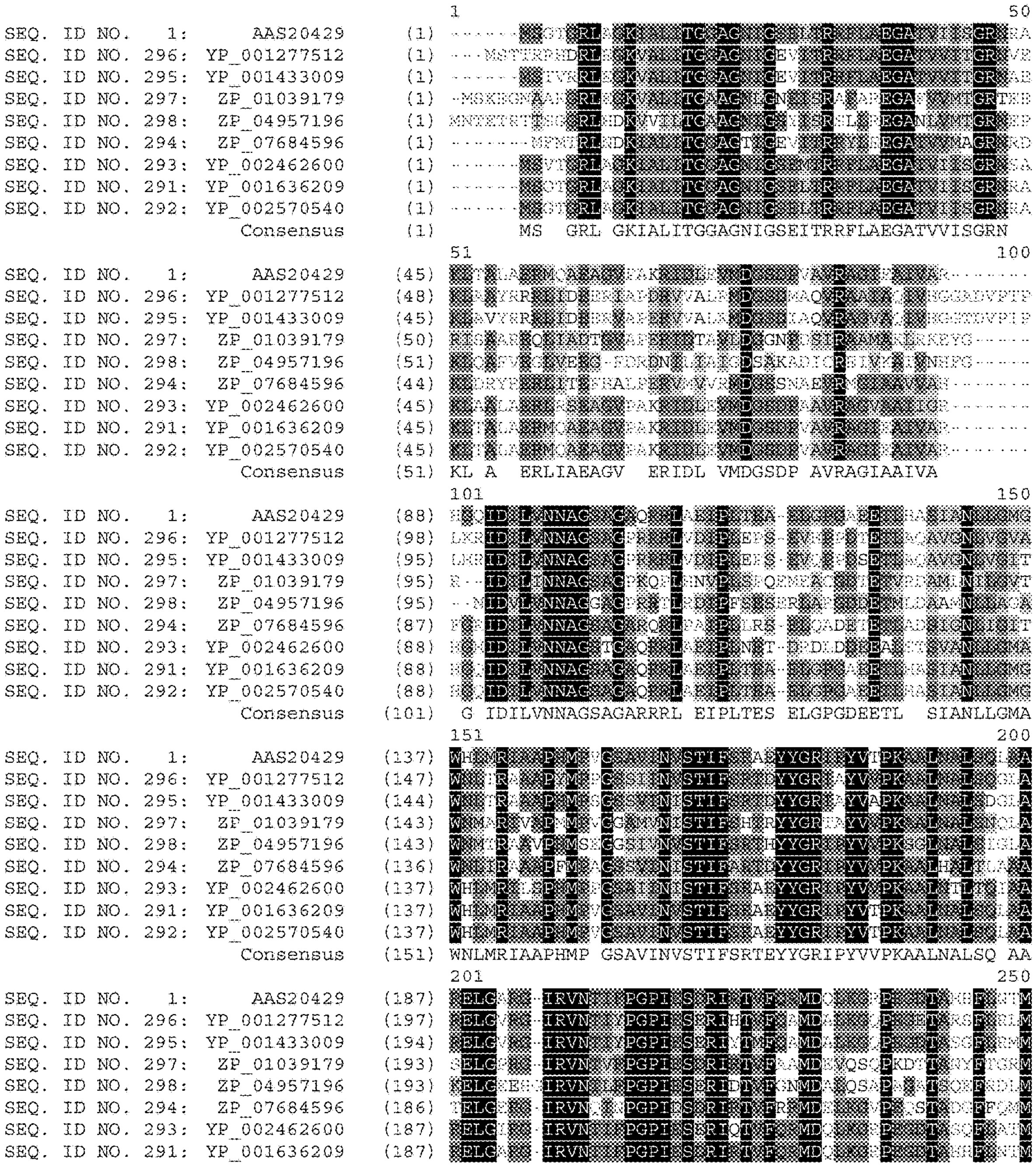

FIG. 46

```
                                          1                                                  50
SEQ. ID NO.   1: AAS20429       (1)  ----- GRL GKI TG AG G R EGA GR A
SEQ. ID NO. 296: YP_001277512   (1)  --MSTERPRDRL V TG AG GV R EGA GR VE
SEQ. ID NO. 295: YP_001433009   (1)  -----VRL VL TG AG GEV R EGA GR AE
SEQ. ID NO. 297: ZP_01039179    (1)  -MSKRGNA RL GKI TG AG GN RA EGA GR T
SEQ. ID NO. 298: ZP_04957196    (1)  MNTETSRL DVVL TG AG GV RL EGAN GR EP
SEQ. ID NO. 294: ZP_07684596    (1)  --------MFRI DK TG AGT GE RY EGA AGR KD
SEQ. ID NO. 293: YP_002462600   (1)  -------VT RLK TG AG GE R EGA GR A
SEQ. ID NO. 291: YP_001636209   (1)  -----RL GK TG AG G R EGA GR RA
SEQ. ID NO. 292: YP_002570540   (1)  -----GRL GK TG AG G R EGA GR RA
                     Consensus  (1)       MS  GRL GKIALITGGAGNIGSEITRRFLAEGATVVISGRN
                                          51                                                 100
SEQ. ID NO.   1: AAS20429      (45)  LAAEAPAKDVARAR
SEQ. ID NO. 296: YP_001277512  (48)  AYRPIDRAPDVALADAQRARGADVPTP
SEQ. ID NO. 295: YP_001433009  (45)  AVYRPIDRAPVVALADAQPAKGTDVPIP
SEQ. ID NO. 297: ZP_01039179   (50)  RIARRQRIADTLETALDGNSIRAMKLRKEYG----
SEQ. ID NO. 298: ZP_04957196   (51)  QFVAVEG-FDKDNLAIDSAKADCRIVMINPG----
SEQ. ID NO. 294: ZP_07684596   (44)  DRYEITFRALPEVVRDSNAERAVA-----
SEQ. ID NO. 293: YP_002462600  (45)  ALAAEAPAKARVIGR-------
SEQ. ID NO. 291: YP_001636209  (45)  ALAAEAPAKARAA-------
SEQ. ID NO. 292: YP_002570540  (45)  ALAAEAPAKARAA-------
                     Consensus (51)       KL A  ERLIAEAGV  ERIDL VMDGSDP  AVRAGIAAIVA
                                          101                                                150
SEQ. ID NO.   1: AAS20429      (88)  IDL NNACGQLAEAAEANMG
SEQ. ID NO. 296: YP_001277512  (98)  LKRIDL NNACGEVDETSVDEAVNVSVA
SEQ. ID NO. 295: YP_001433009  (95)  LKRIDL NNACGRVDEESVSEAVNVIT
SEQ. ID NO. 297: ZP_01039179   (95)  R--IDL NNACGPKQNVPSQEMRIEVAMNIIVT
SEQ. ID NO. 298: ZP_04957196   (95)  --M IDL NNACGRTRDFSSERADEWLAANQ
SEQ. ID NO. 294: ZP_07684596   (87)  PIDL NNACCRQLPAPLRSADEIEASIGNET
SEQ. ID NO. 293: YP_002462600  (88)  HIDL NNACTGQOLAENT-DPDLDEAVANMA
SEQ. ID NO. 291: YP_001636209  (88)  HIDL NNACAGOLELGAEARIANMG
SEQ. ID NO. 292: YP_002570540  (88)  HIDL NNACGLELGRAAMG
                     Consensus (101)     G IDILVNNAGSAGARRRL EIPLTES ELGPGDEETL  SIANLLGMA
                                          151                                                200
SEQ. ID NO.   1: AAS20429      (137) WRDMGAV NSTIFAAYYGRYVTPKLA
SEQ. ID NO. 296: YP_001277512  (147) WRAVDMGSSI NSTIFYYGRYVPKLA
SEQ. ID NO. 295: YP_001433009  (144) WRDMGSS NSTIFYYGRYVAPKLDGA
SEQ. ID NO. 297: ZP_01039179   (143) WMARVDMRSX NSTIFHRYYGRDYPKLA
SEQ. ID NO. 298: ZP_04957196   (143) WMTRAVES GGSI NSTIFYYGRYVPKGLA
SEQ. ID NO. 294: ZP_07684596   (136) WRAPMAGSA NSTIFYYGRYVPKLHTLAA
SEQ. ID NO. 293: YP_002462600  (137) WHRDMCAIT NSTIFAAYYGRYVPKLITIA
SEQ. ID NO. 291: YP_001636209  (137) WHRDMMCAV NSTIFAAYYGRYVTPKLA
SEQ. ID NO. 292: YP_002570540  (137) WHRDMMCAV NSTIFAAYYGRYVTPKLA
                     Consensus (151)     WNLMRIAAPHMP GSAVINVSTIFSRTEYYGRIPYVVPKAALNALSQ AA
                                          201                                                250
SEQ. ID NO.   1: AAS20429      (187) ELGIRVNPGPISRITFMDYM
SEQ. ID NO. 296: YP_001277512  (197) ELGVIRVNPGPISRITFMDKFRM
SEQ. ID NO. 295: YP_001433009  (194) ELGIRVNPGPISRITFMDFRM
SEQ. ID NO. 297: ZP_01039179   (193) ELGEIRVNLPGPISRIDDTAMDVQSQPKDTRYETSRM
SEQ. ID NO. 298: ZP_04957196   (193) ELGESIRVNLPGPISRIDTNMDAQSAPATQFDM
SEQ. ID NO. 294: ZP_07684596   (186) TELGIRVNTPGPISRITFRMLVPSTDFFAM
SEQ. ID NO. 293: YP_002462600  (187) ELGIRVNPGPISRIQTTFMDVESTRIM
SEQ. ID NO. 291: YP_001636209  (187) ELGIRVNPGPISRITFMDERNM
```

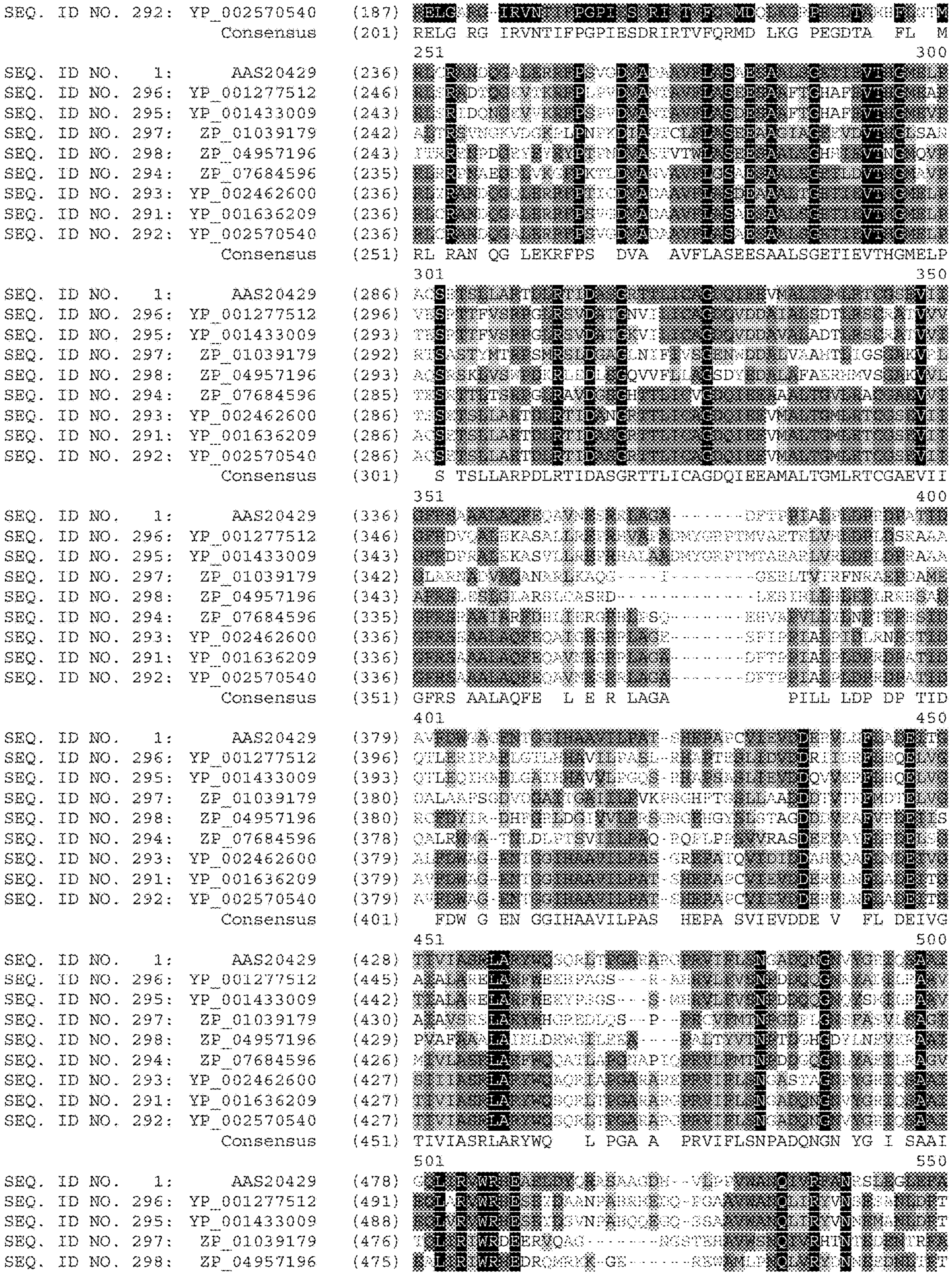

FIG. 46 (cont.)

```
SEQ. ID NO. 292:  YP_002570540  (187) ELG   IRVN  PGPI S RI T F MD    P  D   F  M
                  Consensus     (201) RELG RG IRVNTIFPGPIESDRIRTVFQRMD LKG PEGDTA   FL    M
                                      251                                              300
SEQ. ID NO.   1:  AAS20429      (236)  R          PSVGDA     LS EA  G   VT C
SEQ. ID NO. 296:  YP_001277512  (246)  RDT  V  P  S DAN    LG  A PTGHAF VT C A
SEQ. ID NO. 295:  YP_001433009  (243)  RDQ  V  L  S VDAN    LS EA PTGHAF VT C V
SEQ. ID NO. 297:  ZP_01039179   (242) A  RV GK VD  LPNFK DIA  CL  SEAA AG  V VT C SA
SEQ. ID NO. 298:  ZP_04957196   (243)  RR  PD   Y  T  DVASEVTD LSE A G   V VT C Q
SEQ. ID NO. 294:  ZP_07684596   (235)  R  AE  VK   KTLDAN    SE A  G     VT C A
SEQ. ID NO. 293:  YP_002462600  (236)  R    V  P  DDADA   LS EA  G   VT C
SEQ. ID NO. 291:  YP_001636209  (236)  RAN     RS  DADA   LS EA  G   VT C
SEQ. ID NO. 292:  YP_002570540  (236)  R        PSVGDAD    LS EA  G   VT C
                  Consensus     (251) RL RAN QG LEKRFPS  DVA  AVFLASEESAALSGETIEVTHGMELP
                                      301                                              350
SEQ. ID NO.   1:  AAS20429      (286) A S  LA T  RT D  G          C      VM        V
SEQ. ID NO. 296:  YP_001277512  (296) V S  TFVS  C RS D TGNV        VDDA    SDT  S   VW
SEQ. ID NO. 295:  YP_001433009  (293) T S  TFVS  C RS D TGKV        VDDA    ADT  S   VW
SEQ. ID NO. 297:  ZP_01039179   (292) R A TYNT  S R SID G LNI   V E N DD  VAAHT GS   V
SEQ. ID NO. 298:  ZP_04957196   (293) A SK VS    R LED  GQVVFL  GSD   L  FAER MVS   KV
SEQ. ID NO. 294:  ZP_07684596   (285) T S  T   C RAVD GH      VG     A A   VA  S    KV
SEQ. ID NO. 293:  YP_002462600  (286) T S  LA T  RT D  G          C      VM   T     V
SEQ. ID NO. 291:  YP_001636209  (286) A S  LA T  RT D  G          C      VM   T     V
SEQ. ID NO. 292:  YP_002570540  (286) A S  LA T  RT D  G          C      VM   T     V
                  Consensus     (301)   S TSLLARPDLRTIDASGRTTLICAGDQIEEAMALTGMLRTCGAEVII
                                      351                                              400
SEQ. ID NO.   1:  AAS20429      (336) A     A   R           -----DFT  IA
SEQ. ID NO. 296:  YP_001277512  (346)  DV   EKASALLR    DMYGP TMVAETR V     SRAA
SEQ. ID NO. 295:  YP_001433009  (343)  DP   EKASVLLR   RALA DMYGP TMTARA LV     RAAA
SEQ. ID NO. 297:  ZP_01039179   (342)  LAR   V  ANAR KAQS---- I----  GERLTV RFNRA   AME
SEQ. ID NO. 298:  ZP_04957196   (343) A   E G LARSL ASRD----------- LES EL    RRESA
SEQ. ID NO. 294:  ZP_07684596   (335)  A    RP  I ERG   SQ---- EHVA VL VN     S
SEQ. ID NO. 293:  YP_002462600  (336) T     BQA    GE---- SF P IAP L RN   T
SEQ. ID NO. 291:  YP_001636209  (336) A     QA   GG----- DFT P IA     T
SEQ. ID NO. 292:  YP_002570540  (336) A     QA N    GG----- DFT P IA     T
                  Consensus     (351) GFRS AALAQFE  L E R LAGA        PILL LDP DP TID
                                      401                                              450
SEQ. ID NO.   1:  AAS20429      (379) AV   A   S      APC   DE  L   T
SEQ. ID NO. 296:  YP_001277512  (396) QTL R PA LGTL  VILPASL-R  T L  DR   PQ V
SEQ. ID NO. 295:  YP_001433009  (393) QTLEQ   LG T  VI PGS R  L    DQV E  HQ V
SEQ. ID NO. 297:  ZP_01039179   (380) DALAAPSG V  A G I  VK SCHPT  LLAA DIV  MD  V
SEQ. ID NO. 298:  ZP_04957196   (380) R    YR -DH   LDG IV RS NC HGY ISTAG DDL EA V D S
SEQ. ID NO. 294:  ZP_07684596   (378) QALR MA -T DLF SV  G Q PQ LP  VVRAS DE  A   H
SEQ. ID NO. 293:  YP_002462600  (379) A    G         -GR ATQ  DI A  G E V
SEQ. ID NO. 291:  YP_001636209  (379) A    G         -       DE  L  A   T
SEQ. ID NO. 292:  YP_002570540  (379) A    G         -  PA C   DE  L  A   T
                  Consensus     (401)  FDW G EN GGIHAAVILPAS  HEPA SVIEVDDE V   FL DEIVG
                                      451                                              500
SEQ. ID NO.   1:  AAS20429      (428) TIVI    LA    SR T     AP     A        GN    A
SEQ. ID NO. 296:  YP_001277512  (445) A AL RELA  EERPAGS---  R  A    VN DQ GA   LA V
SEQ. ID NO. 295:  YP_001433009  (442) T ALARELA  EEYP GS--- S  M  VL VN DQ GYS  LA V
SEQ. ID NO. 297:  ZP_01039179   (430) A AV S LA    HQPEDLQS-P     V  MN GL  PA V A
SEQ. ID NO. 298:  ZP_04957196   (429) PVAF  A LA  YLDRWG L S----- A TY TN T HGDYLNE  A
SEQ. ID NO. 294:  ZP_07684596   (426) M VL  A   QA LA  RAP     M T ND GG    LA A
SEQ. ID NO. 293:  YP_002462600  (427)      LA    QR A  R     L N AS AG    A  A
SEQ. ID NO. 291:  YP_001636209  (427) TIVI    LA    SR T     AP     A    NG VG  A
SEQ. ID NO. 292:  YP_002570540  (427) TIVI    LA    SR T     AP     A        GN    A
                  Consensus     (451) TIVIASRLARYWQ   L PGA A  PRVIFLSNPADQNGN YG I SAAI
                                      501                                              550
SEQ. ID NO.   1:  AAS20429      (478) G   WR          AAGD - VP      Q  AN SI G
SEQ. ID NO. 296:  YP_001277512  (491)  L RWR   AMNPAB KEDQ -PGA     QLI YVN    T
SEQ. ID NO. 295:  YP_001433009  (488)  L RWR   S VNPABQQ -BSA     QLI YVN    T
SEQ. ID NO. 297:  ZP_01039179   (476) TL RWRDEEFYQAG-------BGSTER    QL HIN    TR
SEQ. ID NO. 298:  ZP_04957196   (475)  L RWR EDRQMYK-GE-----REV  LP QLR N    T
```

FIG. 46 (cont.)

```
SEQ. ID NO. 294:  ZP_07684596  (476)
SEQ. ID NO. 293:  YP_002462600 (477)
SEQ. ID NO. 291:  YP_001636209 (477)
SEQ. ID NO. 292:  YP_002570540 (477)
                     Consensus (501) EQLIRVWRHEAELDY R A   D    L AVWANQIVRFAN ELENLEFA
                                     551                                           600
SEQ. ID NO.   1:      AAS20429 (526)
SEQ. ID NO. 296:  YP_001277512 (540)
SEQ. ID NO. 295:  YP_001433009 (537)
SEQ. ID NO. 297:   ZP_01039179 (519)
SEQ. ID NO. 298:   ZP_04957196 (518)
SEQ. ID NO. 294:   ZP_07684596 (526)
SEQ. ID NO. 293:  YP_002462600 (525)
SEQ. ID NO. 291:  YP_001636209 (525)
SEQ. ID NO. 292:  YP_002570540 (525)
                     Consensus (551) CAW A LL S R I EI L IPANISATTGAR ASVGWAESLIGLHLGKV
                                     601                                           650
SEQ. ID NO.   1:      AAS20429 (576)
SEQ. ID NO. 296:  YP_001277512 (590)
SEQ. ID NO. 295:  YP_001433009 (587)
SEQ. ID NO. 297:   ZP_01039179 (569)
SEQ. ID NO. 298:   ZP_04957196 (568)
SEQ. ID NO. 294:   ZP_07684596 (576)
SEQ. ID NO. 293:  YP_002462600 (575)
SEQ. ID NO. 291:  YP_001636209 (575)
SEQ. ID NO. 292:  YP_002570540 (575)
                     Consensus (601) ALITGGSAGIGGQIGRLLALSGARVMLAARD  KLEQMRAMIVSEL EVG
                                     651                                           700
SEQ. ID NO.   1:      AAS20429 (626)
SEQ. ID NO. 296:  YP_001277512 (640)
SEQ. ID NO. 295:  YP_001433009 (637)
SEQ. ID NO. 297:   ZP_01039179 (619)
SEQ. ID NO. 298:   ZP_04957196 (618)
SEQ. ID NO. 294:   ZP_07684596 (626)
SEQ. ID NO. 293:  YP_002462600 (625)
SEQ. ID NO. 291:  YP_001636209 (625)
SEQ. ID NO. 292:  YP_002570540 (625)
                     Consensus (651) Y DVE RV I PGCDVSDEEQLE LVERTL  FG VDYLINNAGIAGAEE
                                     701                                           750
SEQ. ID NO.   1:      AAS20429 (676)
SEQ. ID NO. 296:  YP_001277512 (690)
SEQ. ID NO. 295:  YP_001433009 (687)
SEQ. ID NO. 297:   ZP_01039179 (669)
SEQ. ID NO. 298:   ZP_04957196 (668)
SEQ. ID NO. 294:   ZP_07684596 (676)
SEQ. ID NO. 293:  YP_002462600 (675)
SEQ. ID NO. 291:  YP_001636209 (675)
SEQ. ID NO. 292:  YP_002570540 (675)
                     Consensus (701) MVIDMPVEAWRHTLFANLISNYSLMRKLAPLMK QGSGYVLNVSSYFGGE
                                     751                                           800
SEQ. ID NO.   1:      AAS20429 (726)
SEQ. ID NO. 296:  YP_001277512 (740)
SEQ. ID NO. 295:  YP_001433009 (737)
SEQ. ID NO. 297:   ZP_01039179 (719)
SEQ. ID NO. 298:   ZP_04957196 (718)
SEQ. ID NO. 294:   ZP_07684596 (726)
SEQ. ID NO. 293:  YP_002462600 (725)
SEQ. ID NO. 291:  YP_001636209 (725)
SEQ. ID NO. 292:  YP_002570540 (725)
                     Consensus (751) KYAAIPYPNRADYAVSKAGQRAMAEVFARFLGPEIQINAIAPGPVEGDRL
                                     801                                           850
SEQ. ID NO.   1:      AAS20429 (776)
SEQ. ID NO. 296:  YP_001277512 (790)
```

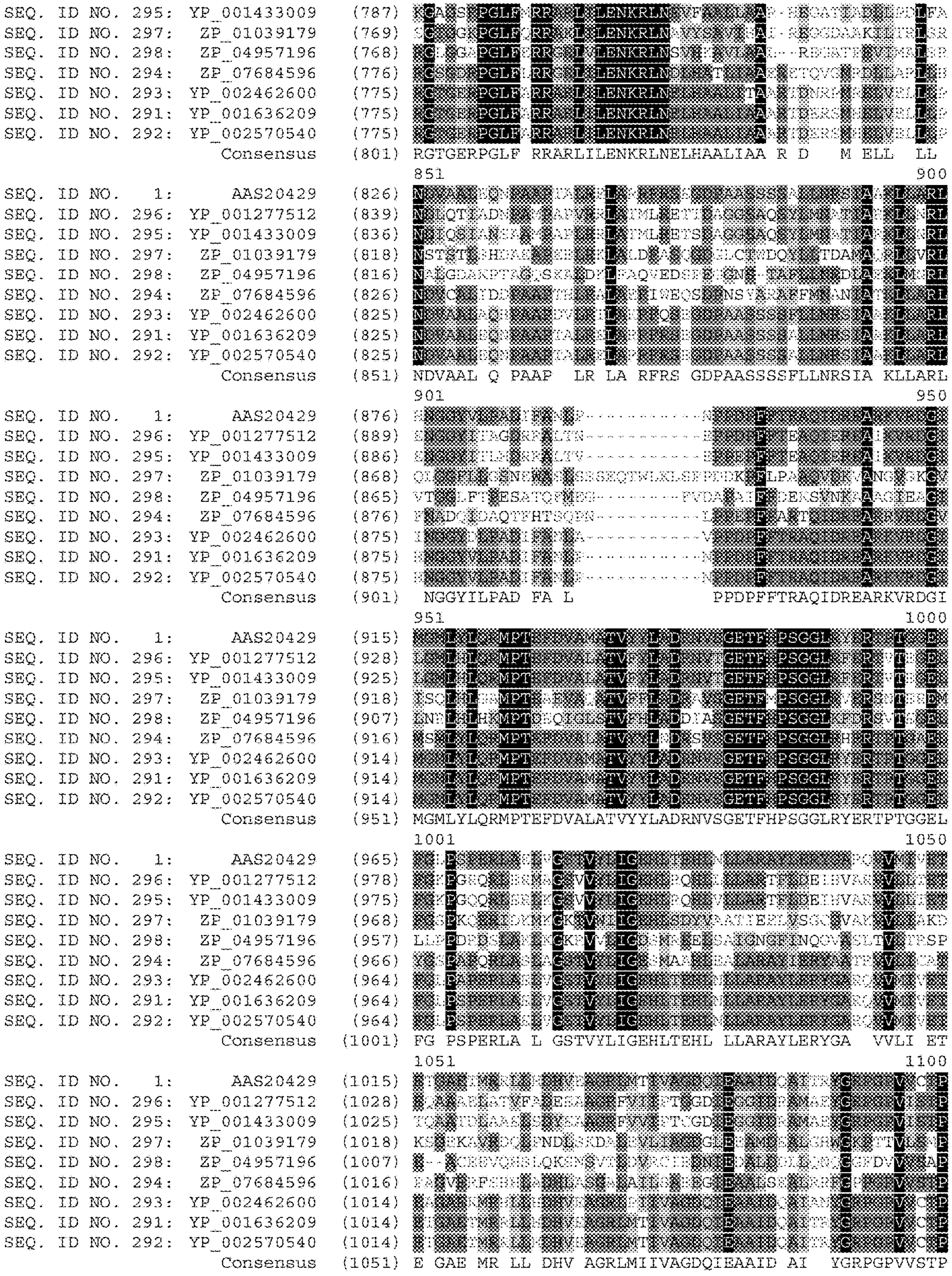

FIG. 46 (cont.)

```
SEQ. ID NO. 295:  YP_001433009   (787)  KGAAS PGLF RR L LENKRLN VF  L A  -  B ATIAD   PLFA
SEQ. ID NO. 297:  ZP_01039179    (769)  S  G PGLF RR L LENKRLN VYS VI AL -  GDAAKIL TR SR
SEQ. ID NO. 298:  ZP_04957196    (768)  S  GA PGLF RR L LENKRLN SVI  VL AL - - R  T V M  P
SEQ. ID NO. 294:  ZP_07684596    (776)  KG   PGLF RR L LENKRLN    T   A  ETQV   DLAP L
SEQ. ID NO. 293:  YP_002462600   (775)  G    PGLF RR L LENKRLN     TA  IDNR    V L P
SEQ. ID NO. 291:  YP_001636209   (775)  G    PGLF RR L LENKRLN     A   IDERS   V IL P
SEQ. ID NO. 292:  YP_002570540   (775)  G    PGLF RR L LENKRLN     A   IDERS   V IL P
                       Consensus  (801)  RGTGERPGLF RRARLILENKRLNELHAALIAA  R D    M ELL    LL
                                  851                                                        900
SEQ. ID NO.   1:  AAS20429       (826)  N      Q        L           AASSS    A      RL
SEQ. ID NO. 296:  YP_001277512   (839)  N LQTIAD   AP  RL ML ETI AGG AQS IM  T A  L  RL
SEQ. ID NO. 295:  YP_001433009   (836)  N IQS A     AP  RL ML ETS AGG AQS IM  T A  L  RL
SEQ. ID NO. 297:  ZP_01039179    (818)  NSTS T  HD           LD       CTEDQV  TDAMA  L VRL
SEQ. ID NO. 298:  ZP_04957196    (816)  NA GDAKPTAG  SKA  DP  AQVEDS   GN -  TAP   DI V  M RL
SEQ. ID NO. 294:  ZP_07684596    (826)  N   C  TD      T   A   R  IWEQS  NS VARAFFM AN T  L  RL
SEQ. ID NO. 293:  YP_002462600   (825)  N AA   Q     A   V   L   IQS   GBAASSS FLL NSIA  L  RL
SEQ. ID NO. 291:  YP_001636209   (825)  N AA   Q     A   L      A      AAASSS  LLN SIA  L  RL
SEQ. ID NO. 292:  YP_002570540   (825)  N AA   Q     A   L      A      AAASSS  LLN SIA  L  RL
                       Consensus  (851)  NDVAAL Q PAAP   LR LA RFRS  GDPAASSSSFLLNRSIA KLLARL
                                  901                                                        950
SEQ. ID NO.   1:  AAS20429       (876)  E     G  T  N P - - - - - - - - - N      E       A       C
SEQ. ID NO. 296:  YP_001277512   (889)  E    T  AG  F A TN - - - - - - - -      E A QE A     I   C
SEQ. ID NO. 295:  YP_001433009   (886)  E    T    REA T V - - - - - - - -      E E QE A     I   C
SEQ. ID NO. 297:  ZP_01039179    (868)  QI   PL  NEW  S SEQTWLKLSFPDDK  LPA  V KN  K  C V
SEQ. ID NO. 298:  ZP_04957196    (865)  VT   LFT  ESATQ MKG - - - - - - - PVDA  A   EKSVNKA A G EA  C
SEQ. ID NO. 294:  ZP_07684596    (876)  F  AD  DAQTFHTSQ N - - - - - - - -    L   E   AS T    A  C V
SEQ. ID NO. 293:  YP_002462600   (875)  I      A   P A - - - - - - - - - V      E       A       C
SEQ. ID NO. 291:  YP_001636209   (875)  N  VAA   P   - - - - - - - - - N       E       A       C
SEQ. ID NO. 292:  YP_002570540   (875)  N  VAA   P   - - - - - - - - - N       E       A       C
                       Consensus  (901)  NGGYILPAD FA L                PPDPFFTRAQIDREARKVRDGI
                                  951                                                        1000
SEQ. ID NO.   1:  AAS20429       (915)   L  L MPT    VAM TV  LD   GETF PSGGL YR   T   E
SEQ. ID NO. 296:  YP_001277512   (928)   L IL MPT    V   TV  LD N  GETF PSGGL  R   T   E
SEQ. ID NO. 295:  YP_001433009   (925)   L IL MPT    V   TV  LD N  GETF PSGGL  R   T   E
SEQ. ID NO. 297:  ZP_01039179    (918)  IS Q L MPT   E     TV D A  GETF PSGGL   R  T  EP
SEQ. ID NO. 298:  ZP_04957196    (907)  LN      MPT  EQIGLSTVF LDD IA  GETF PSGGL KF R  T  SE
SEQ. ID NO. 294:  ZP_07684596    (916)   S  KI L    A  TV  LD S    GETF PSGGL  R   T   E
SEQ. ID NO. 293:  YP_002462600   (914)    I L MPT    A TV  LD      GETF PSGGL  R   T   E
SEQ. ID NO. 291:  YP_001636209   (914)    I L MPT    A TV  LD      GETF PSGGL  R   T   E
SEQ. ID NO. 292:  YP_002570540   (914)    I L MPT    A TV  LD      GETF PSGGL YR   T   E
                       Consensus  (951)  MGMLYLQRMPTEFDVALATVYYLADRNVSGETFHPSGGLRYERTPTGGEL
                                  1001                                                       1050
SEQ. ID NO.   1:  AAS20429       (965)    E       G V  IG            L           PG   V
SEQ. ID NO. 296:  YP_001277512   (978)   PGEQ    R   G VV  IG    PQ         TE DE   VA   VV
SEQ. ID NO. 295:  YP_001433009   (975)   PGQQ    R   G VV  IG    P          TE DE   VA   VV  KD
SEQ. ID NO. 297:  ZP_01039179    (968)  R PK   D E  GK VV  IG    SDYV AA EELVSGC  VA V      D
SEQ. ID NO. 298:  ZP_04957196    (957)  LL  DP E    D     IG      E GA TQNGF INQV  SLT V   PSP
SEQ. ID NO. 294:  ZP_07684596    (966)  Y    A Q    E     IG        A    M A    E         V A
SEQ. ID NO. 293:  YP_002462600   (964)    PA     E  G V   IG              A     E         V
SEQ. ID NO. 291:  YP_001636209   (964)    PS     E  G V   IG             LA     E         VI
SEQ. ID NO. 292:  YP_002570540   (964)    PS     E  G V   IG             LA     E         VI
                       Consensus (1001)  FG PSPERLA L GSTVYLIGEHLTEHL LLARAYLERYGA  VVLI  ET
                                  1051                                                       1100
SEQ. ID NO.   1:  AAS20429       (1015)           MR  LL    MT V GD  E    A      G   V  D
SEQ. ID NO. 296:  YP_001277512   (1028)   A   LA  YP ESA   FV  T GD  E  I   MA E   G   VI  D
SEQ. ID NO. 295:  YP_001433009   (1025)  TQ  T  AA  YE     FV  T GD  E  I   MA E   G   VI  D
SEQ. ID NO. 297:  ZP_01039179    (1018)  KS  PKA  D   PND  KDA  V L   GL     M       C  TTV  E
SEQ. ID NO. 298:  ZP_04957196    (1007)  - -  KR V QH  QKEN S T D V C    N      MA      C FDV  A E
SEQ. ID NO. 294:  ZP_07684596    (1016)  FA V F    A LAS  AAIL  EG A SL  RF G   V  D
SEQ. ID NO. 293:  YP_002462600   (1014)  K   MR  LL    V      T VAG   D  E C    A AN  C   V  D
SEQ. ID NO. 291:  YP_001636209   (1014)      MR  LL    V      T VAG   D  I  C    A AN  C   V  D
SEQ. ID NO. 292:  YP_002570540   (1014)      MR  LL    V      T VAG   D  I  C    A AN  C   V  D
                       Consensus (1051)  E GAE MR LL  DHV  AGRLMIIVAGDQIEAAID AI  YGRPGPVVSTP
```

PRODUCTION OF MALONYL-COA DERIVED PRODUCTS VIA ANAEROBIC PATHWAYS

CROSS-REFERENCE TO RELATED APPLICATIONS

The present application is a continuation of U.S. application Ser. No. 16/166,274 filed Oct. 22, 2018 (now U.S. Pat. No. 11,162,125), which is a continuation of U.S. application Ser. No. 13/814,616 filed Aug. 23, 2013 (now U.S. Pat. No. 10,138,504), which is a '371 U.S. national phase application of PCT/US2011/046869, filed Aug. 5, 2011, entitled "Production of Malonyl-COA Derived Products Via Anaerobic Pathways," which claims priority to U.S. Provisional Application No. 61/371,582 filed Aug. 6, 2010, each application of which is hereby incorporated by reference in its entirety.

REFERENCE TO SEQUENCE LISTING SUBMITTED ELECTRONICALLY VIA EFS-WEB

This application contains a Sequence Listing which has been submitted electronically in ASCII format and is hereby incorporated by reference in its entirety. Said ASCII copy, created on Sep. 30, 2021, is named 115235-280_sequence_ST25.txt and is 448.753 bytes in size.

BACKGROUND OF THE INVENTION

Depleting petroleum reserves, recurrent energy crises, increasing demand, and climate change have provided significant impetus in the search for sustainable technologies to replace petroleum as a source of fuels and chemical feedstocks. Long chain fatty acids and other derivatives are commercially attractive as fuel and chemical feedstocks because they can directly replace crude petroleum (as "biocrude"), which is composed primarily of alkanes, alkenes, and aromatic hydrocarbons. In particular, cellulosic biomass is a preferred source of generating long chain fatty acids and other derivatives for use as fuel and chemical feedstocks, which are compatible with existing petroleum refining and distribution and can substitute for diesel, gasoline, jet fuel, and other derivatives of crude oil.

Currently, commercial and academic efforts are focused on bio-based petroleum replacement fuels made from microorganisms such as microalgae and that require aerobic microbial production. Algae bio-petroleum can appear as a very attractive option because fuel production occurs directly from sunlight and CO2. However, algal volumetric productivities are 100-fold lower than fermentative processes, requiring significantly higher biorefinery capital expenditures. See Liliana et al., Biotechnology and Bioengineering 102:100-12 (2009). In addition, lower capital algal options, such as open pond culturing, have many technical hurdles to clear before commercial deployment despite decades of research into the issue.

Other efforts are underway to produce fatty acid compounds from sugars and plant biomass, but all current methods require oxygen to be supplied during fermentation, and are not full consolidated bioprocessing (CBP) processes. Unlike traditional ethanol fermentations, aerobic biofuel synthesis routes feature product formation which is uncoupled from ATP generation and cell growth. Uncoupling of product formation from cell growth simplifies metabolic engineering and has allowed for rapid development of first generation biocatalysts. However, there is a price to be paid for aerobic production when the technology is scaled up to meet industrial needs. First, there are significant costs associated with scaling-up aerobic fermentations, such as, those due to the need for aeration and heat removal. In practice, these constraints limit the size of aerobic fermentors, with those used in anaerobic fuel ethanol production being an order of magnitude larger. Second, although maximum theoretical product yields from an aerobic process are only slightly lower than an anaerobic process, in practice it is extraordinarily difficult to approach this maximum since there is no biological incentive for microbes to reach high product yields.

To reach the best aerobic process hydrocarbon yields to date, researchers have resorted to high cell density fermentation, which resulted in product yields between 30-40% of the theoretical maximum. See Tsuruta et al., *PLoS ONE* 4:e4489 (2009); Whited et al., *Industrial Biotechnology* 6:152-163 (2010). While these yields may be quite acceptable for pharmaceutical or specialty chemical production, fuel biorefinery process models have shown that fermentation yields lower than 85% of theoretical result in unattractive process economics. However, an anaerobic, oxygen-free fermentation not only creates higher product yields, but also removes many significant scale-up problems associated with aerobic fermentation. Hydrocarbon fuel production also has process benefits compared to ethanol fuel production, such as a lower product recovery cost and a lower product toxicity to fermenting organisms. The latter could result in smaller fermentation volumes needed to reach equivalent productivities.

An anaerobic biocatalyst requires a higher degree of metabolic pathway integration to couple product formation with ATP generation, NAD(P)H regeneration, and cell growth. However, once these requirements are met, natural evolutionary forces can be harnessed to increase product yields and productivities, driving them towards theoretical maxima. See Burgard et al., *Biotechnology and Bioengineering* 84:647-57 (2003); Sauer, *Advances in Biochemical Engineering/Biotechnology* 73:129-69 (2001). Higher yields, combined with a lower-cost path for scale-up, make an anaerobic process a preferred option for developing microbes to produce fungible biofuels. The invention describes a method to produce long chain fatty acids and their derivatives in an organism or consortia of organisms in a CBP process that is anaerobic.

Integral to the process of producing any end product, including those that can be produced using the methods of the invention, is an adequate supply of metabolic substrates. Malonyl-CoA is such a key metabolic precursor for the biological synthesis of various bioproducts, including, but not limited to, fatty acid derived long chain hydrocarbon compounds such as fatty alcohols, fatty aldehydes, fatty acids, wax esters, and alkanes. However, the biosynthesis of malonyl-CoA is known to occur through only a few mechanisms in vivo—namely from acetyl-CoA, carbon dioxide, and ATP by acetyl-CoA carboxylase (acc, EC 6.4.1.2) or from malonate, CoA, and ATP by malonyl-CoA synthetase (matB) (An and Kim, *Eur. J Biochem.* 257:395-402 (1998)). Yet, both of these mechanisms require the consumption of ATP to drive the reaction towards malonyl-CoA. In contrast, to produce fatty acid derived hydrocarbons, or any other bioproducts that use malonyl-CoA as a precursor, anaerobically at high yield, the route to malonyl-CoA should result in a net production of ATP. The invention describes recombinant microorganisms, pathways, and methods for producing desired end-products from malonyl-CoA precursors with a net production of ATP.

BRIEF SUMMARY OF THE INVENTION

The recombinant microorganisms and methods of the invention use metabolic pathways that allow for the production of malonyl-CoA derived products, such as hydrocarbons and hydrocarbon derivatives and other bioproducts, under anaerobic conditions. The metabolic pathways allow for the production of long chain compounds, including, e.g., chain lengths from four carbon atoms up to 40 or more carbon atoms per molecule, and cellular growth in the absence of oxygen or other mechanisms to generate cellular energy (ATP) besides fermentative metabolism.

An aspect of the invention is the ability to produce long chain compounds at high yield with an anaerobic process rather than with an aerobic process. Anaerobic production results in a higher product yield, easier scalability, and better process thermodynamics. For lignocellulosic biomass conversion, an anaerobic process is even more desirable, as the requirement for oxygen transfer in a medium with suspended solids is highly unattractive from an engineering perspective. Additional advantages include, but are not limited to:

1) Production of a direct (fungible) replacement for petroleum;
2) Lower separation costs from a dilute aqueous fermentation as a result of the immiscible nature of long chain hydrocarbons compared to fully miscible shorter chain compounds;
3) Greater downstream product diversity and flexibility; and
4) Potentially lower product toxicity for fermenting organism which will allow for reduced fermentor volume and lower capital costs in a cellulosic biomass process.

One aspect of the invention relates to a recombinant microorganism comprising one or more native and/or heterologous enzymes that function in one or more engineered metabolic pathways to convert a carbohydrate source to a hydrocarbon, wherein the one or more native and/or heterologous enzymes is activated, upregulated, downregulated, or deleted. In certain embodiments, the conversion of a carbohydrate source to a hydrocarbon is under anaerobic conditions. In certain embodiments, the conversion of a carbohydrate source to a hydrocarbon is under microaerophilic conditions.

In certain embodiments, the one or more engineered metabolic pathways produce net ATP. In some embodiments, the one or more engineered metabolic pathway produces at least about 0.5 net ATP; at least about 1.0 net ATP; at least about 1.5 net ATP; or at least about 2.0 net ATP. In other embodiments the net ATP production is at least about at least about 0.1 net ATP; at least about 0.2 net ATP; at least about 0.3 net ATP; at least about 0.4 net ATP; at least about 0.5 net ATP; at least about 0.6 net ATP; at least about 0.7 net ATP; at least about 0.8 net ATP; at least about 0.9 net ATP; at least about 1.0 net ATP; 1.1 net ATP; at least about 1.2 net ATP; at least about 1.3 net ATP; at least about 1.4 net ATP; at least about 1.5 net ATP; at least about 1.6 net ATP; at least about 1.7 net ATP; at least about 1.8 net ATP; at least about 1.9 net ATP; or at least about 2.0 net ATP.

In particular aspects of the invention, the hydrocarbon produced by the recombinant microorganism is an alkane, an alkene, a hydrocarbon derivative, or a combination of any of these hydrocarbons. In some embodiments, the hydrocarbon produced is selected from the group consisting of an alkane; an alkene; an alkyne; a hydrocarbon derivative; and combinations of these hydrocarbons. In certain aspects, the hydrocarbon derivative is an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; or a dicarboxylic acid. In some embodiments, the hydrocarbon derivative is selected from the group consisting of an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; a dicarboxylic acid; and combinations of these hydrocarbon derivatives.

In certain aspects of the invention, the hydrocarbon or hydrocarbon derivative produced by the recombinant microorganism comprises a carbon backbone of $C_4$-$C_{40}$. In some embodiments, the hydrocarbon or hydrocarbon derivative comprises a carbon backbone selected from the group consisting of $C_6$-$C_{36}$; $C_8$-$C_{32}$; $C_{10}$-$C_{28}$; $C_{12}$-$C_{24}$; $C_{14}$-$C_{22}$; $C_{16}$-$C_{20}$; and combinations thereof. In other embodiments, the hydrocarbon or hydrocarbon derivative comprises a carbon backbone selected from the group consisting of $C_{12}$; $C_{14}$; $C_{16}$; Cig; $C_{20}$; $C_{22}$; $C_{24}$; and combinations of thereof. In one embodiment, the hydrocarbon or hydrocarbon derivative comprises a carbon backbone of $C_{16}$.

In some aspects of the invention, the carbohydrate source converted to a hydrocarbon is from biomass or from carbohydrates, such as a sugar or a sugar alcohol. In one embodiment, the carbohydrate source converted to a hydrocarbon is a lignocellulosic material. In some embodiments, the carbohydrate is a monosaccharides (e.g., glucose, fructose, galactose, xylose, arabinose, rhamnose, galacturonic acid, xylitol, sorbitol, or ribose), a disaccharide (e.g., sucrose, cellobiose, maltose, or lactose), an oligosaccharide (e.g., xylooligomers, cellodextrins, or maltodextrins), or a polysaccharide (e.g., xylan, cellulose, starch, mannan, or pectin).

In a particular aspect of the invention, one of the engineered metabolic pathways in the recombinant microorganism comprises the conversion of oxaloacetate and acetyl-CoA to malonyl-CoA and pyruvate. In one embodiment, the oxaloacetate and acetyl-CoA is converted to malonyl-CoA and pyruvate by a transcarboxylase. In some embodiments, the transcarboxylase is encoded by a heterologous transcarboxylase polynucleotide. In certain embodiments, the transcarboxylase is encoded by a polynucleotide from a *Thermoanaerobacter* species, *P. freudenreichii, P. acnes*, or *C. thermocellum*. In one embodiment, the transcarboxylase is genetically modified In another aspect of the invention, one of the engineered metabolic pathways comprises the conversion of phosphoenolpyruvate to oxaloacetate. In one embodiment, the phosphoenolpyruvate is converted to oxaloacetate by a phosphoenolpyruvate carboxykinase. In some embodiments, the phosphoenolpyruvate carboxykinase is encoded by a heterologous phosphoenolpyruvate carboxykinase polynucleotide. In certain embodiments, the phosphoenolpyruvate carboxykinase is encoded by a polynucleotide from a *Thermoanaerobacter* species, *E. coli, S. cerevisiae*, or *C. thermocellum.*

In other aspects of the invention, one of the engineered metabolic pathways further comprises at least one of the following steps: conversion of malonyl-CoA to malonyl-ACP; conversion of malonyl-ACP to an acyl$_n$-ACP; conversion of an acyl$_n$-ACP to a β-keto ester$_{n+2}$-ACP; conversion of a β-keto ester$_{n+2}$-ACP to a β-D-hydroxyacyl$_{n+2}$-ACP; conversion of a β-D-hydroxyacyl$_{n+2}$-ACP to a trans-2-unsaturated acyl$_{n+2}$-ACP; or conversion of a trans-2-unsaturated acyl$_{n+2}$-ACP to an acyl$_{n+2}$-ACP.

In some aspects of the invention, one of the engineered metabolic pathways further comprises the conversion of pyruvate and CoA-SH into acetyl-CoA and $CO_2$ and NAD(P)H.

In some aspects of the invention, one or more of the native enzymes in the engineered metabolic pathways are downregulated or deleted. In certain embodiments, the downregulated or deleted native enzyme is an enzyme involved in central metabolism. In some embodiments, the downregulated or deleted native enzyme is selected from the group consisting of a pyruvate kinase; a hydrogenase; a lactate dehydrogenase; a phosphotransacetylase; an acetate kinase; an acetaldehyde dehydrogenase; an alcohol dehydrogenase; a pyruvate formate lyase; a pyruvate decarboxylase; an enzyme involved in degradation of fatty acids and their derivatives; and combinations of thereof.

In some aspects of the invention, the microorganism is a thermophilic or a mesophilic bacterium. In certain embodiments, the thermophilic or mesophilic bacterium is a species of the genera *Escherichia, Propionibacterium, Thermoanaerobacterium, Thermoanaerobacter, Clostridium, Geobacillus, Saccharococcus, Paenibacillus, Bacillus, Caldicellulosiruptor, Anaerocellum, Anoxybacillus, Klebsiella, Lactobacillus, Lactococcus*, or *Corynebacterium*. In other embodiments, the microorganism is a bacterium selected from the group consisting of: *E. coli* strain B, strain C, strain K, strain W, *Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium clariflavum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Lactobacillus thermophilus, Lactobacillus bulgaricus, Lactococcus lactis*, and *Anaerocellum thermophilum*. In one embodiment, recombinant microorganism is selected from the group consisting of *Clostridium thermocellum*, and *Thermoanaerobacterium saccharolyticum.*

Another aspect of the invention relates to a process for converting a carbohydrate source to a hydrocarbon comprising contacting the carbohydrate source with a recombinant microorganism of the invention. In some embodiments, the carbohydrate source comprises lignocellulosic biomass. In certain embodiments, the lignocellulosic biomass is selected from the group consisting of grass, switch grass, cord grass, rye grass, reed canary grass, mixed prairie grass, *miscanthus*, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In other embodiments, the carbohydrate source comprises a carbohydrate. In certain embodiments, the carbohydrate is a sugar, a sugar alcohol, or a mixture thereof.

In some aspects of the invention, the hydrocarbon produced by the recombinant microorganism is secreted.

Another aspect of the invention relates to an engineered metabolic pathway for producing a hydrocarbon from consolidated bioprocessing media.

One aspect of the invention relates to a recombinant microorganism comprising a native and/or heterologous enzyme that converts oxaloacetate and acetyl-CoA to malonyl-CoA and pyruvate, wherein said one or more native and/or heterologous enzymes is activated, upregulated, downregulated, or deleted. In some embodiments, the microorganism produces a hydrocarbon. In some embodiments, the enzyme is a transcarboxylase. In one embodiment, the transcarboxylase is encoded by a polynucleotide from a *Thermoanaerobacter* species, *P. freudenreichii P. acnes*, or *C. thermocellum*. In another embodiment, the transcarboxylase is genetically modified.

In some embodiments, the genetic modification produces an altered catalytic activity and/or an altered substrate specificity to improve the conversion of a substrate to a product as compared to the native enzyme. In some embodiments, the genetic modification alters catalytic activity and/or substrate specificity to provide a genetically modified polypeptide that converts a substrate to a product that is not catalyzed by the native enzyme in vivo, or is catalyzed at only minimal turnover.

BRIEF DESCRIPTION OF THE DRAWINGS/FIGURES

FIG. 3A depicts the net reaction and a native pathway for the conversion of glucose to butyryl-ACP.

FIG. 3B depicts the net reaction and a Clostridial pathway for the conversion of glucose to butyryl-ACP.

FIG. 3C depicts the net reaction and a pathway for the conversion of glucose to butyryl-ACP using a transcarboxylase catalyst.

FIG. 7A is an alignment of the transcarboxylase 5S subunits from *P. freudenreichii, P. acnes, C. thermocellum*, and *T. saccharolyticum.*

FIG. 7B is an alignment of the transcarboxylase 1.3S subunits from *P. freudenreichii, P. acnes, C. thermocellum*, and *T. saccharolyticum.*

FIG. 7C is an alignment of the transcarboxylase 12S subunit (N-terminus) from *P. freudenreichii, P. acnes, C. thermocellum*, and *T. saccharolyticum*.

FIG. 13 depicts the final step of the anaerobic fatty acid pathway.

Figures 20A, 20B:
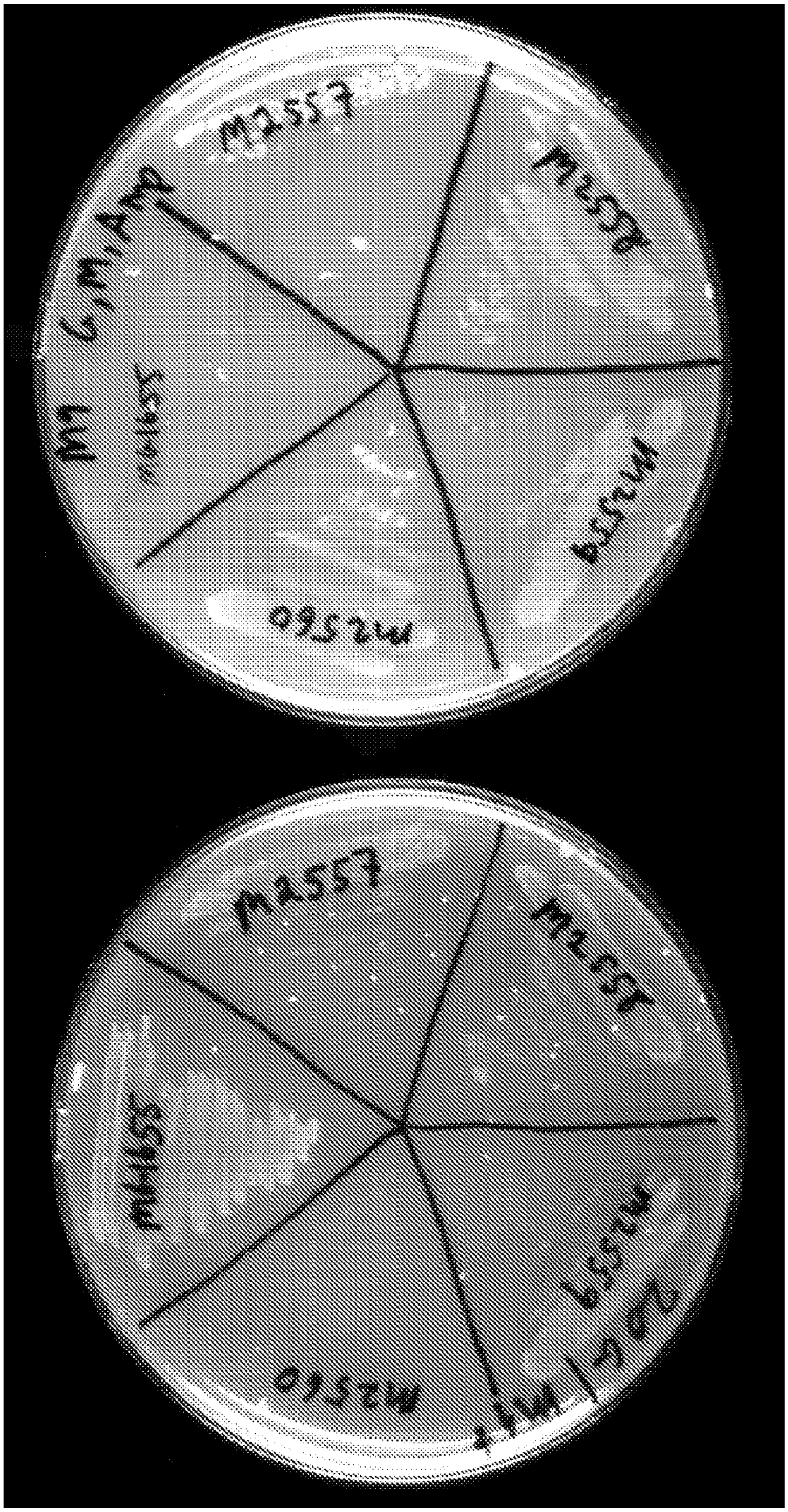

FIG. 20A and FIG. 20B demonstrate growth of transformants containing putative transcarboxylases on selective media.

Figure 21A:
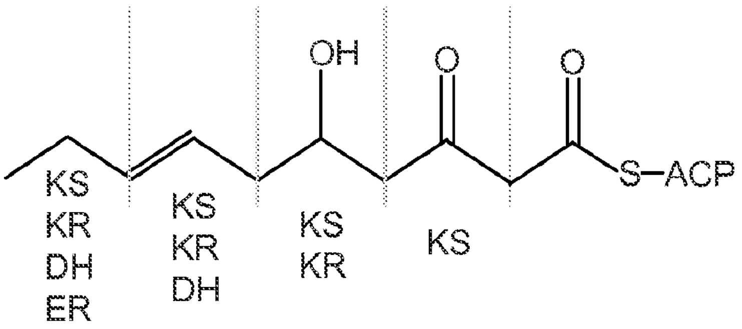

FIG. 21A depicts polyketide chain synthesis, which proceeds by the addition or condensation of different functional groups to an acyl-ACP chain using a combination of enzymatic activities per two-carbon chain extension.

Figure 21B:
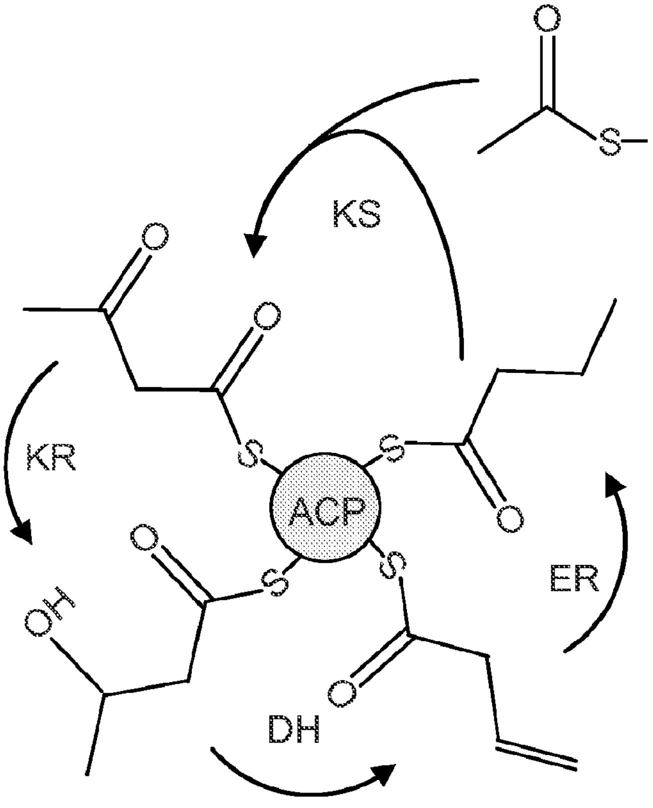

FIG. 21B depicts fatty acid chain synthesis, which proceeds by four enzymatic steps per two-carbon chain extension.

FIG. 22A depicts the total fatty acid content (shown in µg/mL) for *E. coli* strain M2933 carrying different acyl-ACP chain termination enzymes.

Figure 22B:
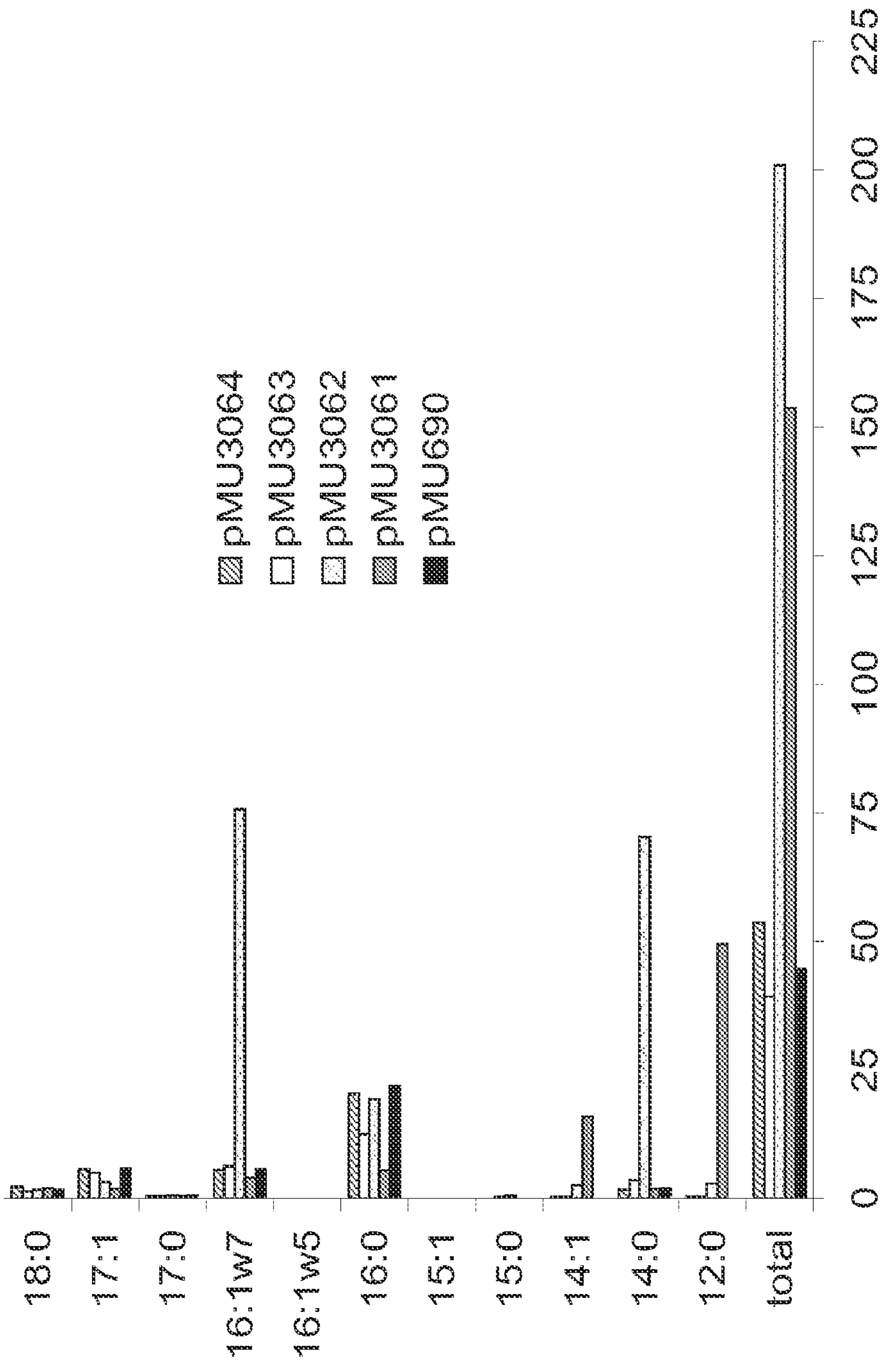

FIG. 22B is a graphical representation of the data from FIG. 22A.

Figure 23:
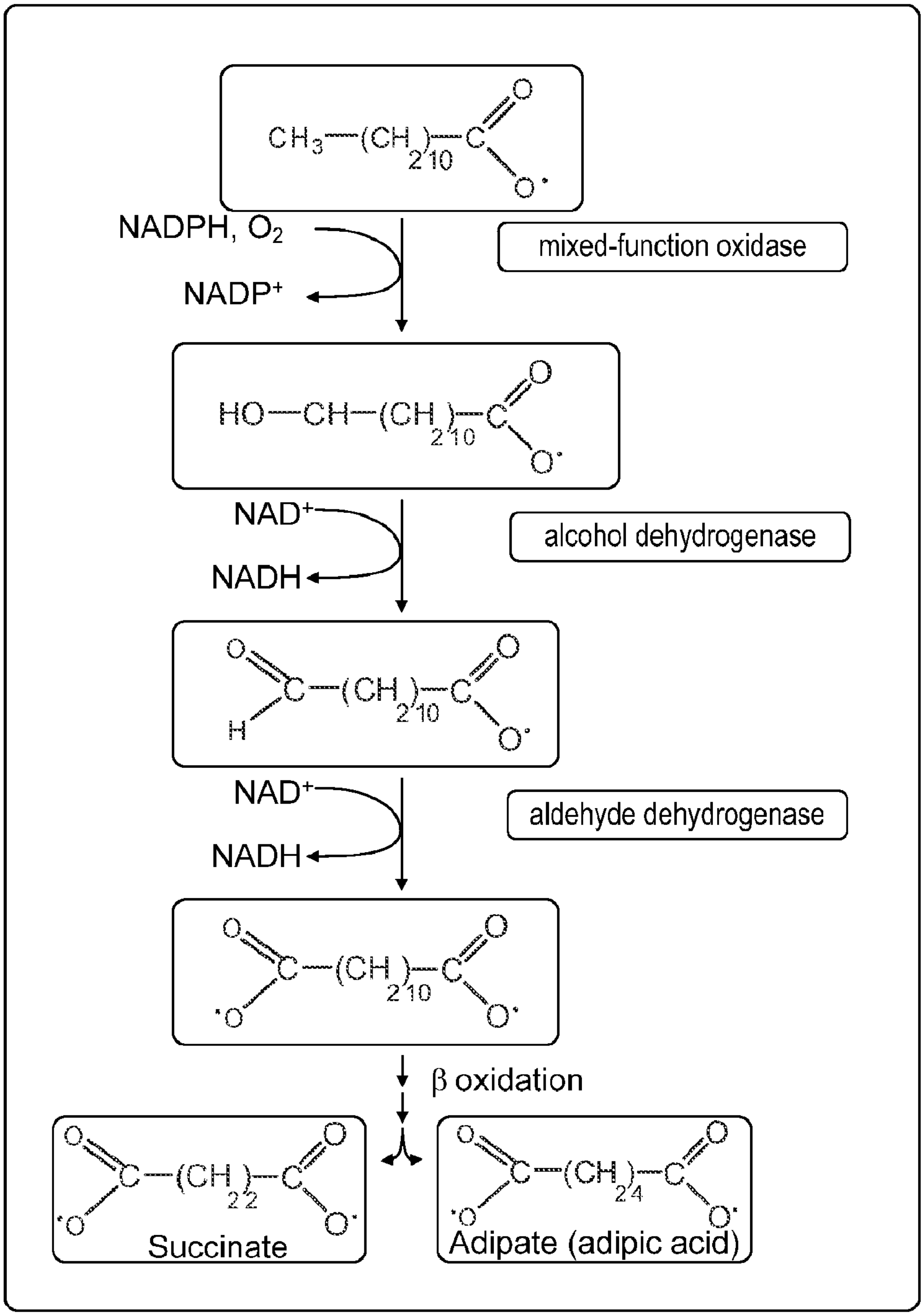

FIG. 23 depicts the synthesis of succinate and adipate using omega oxidation.

Figure 24:
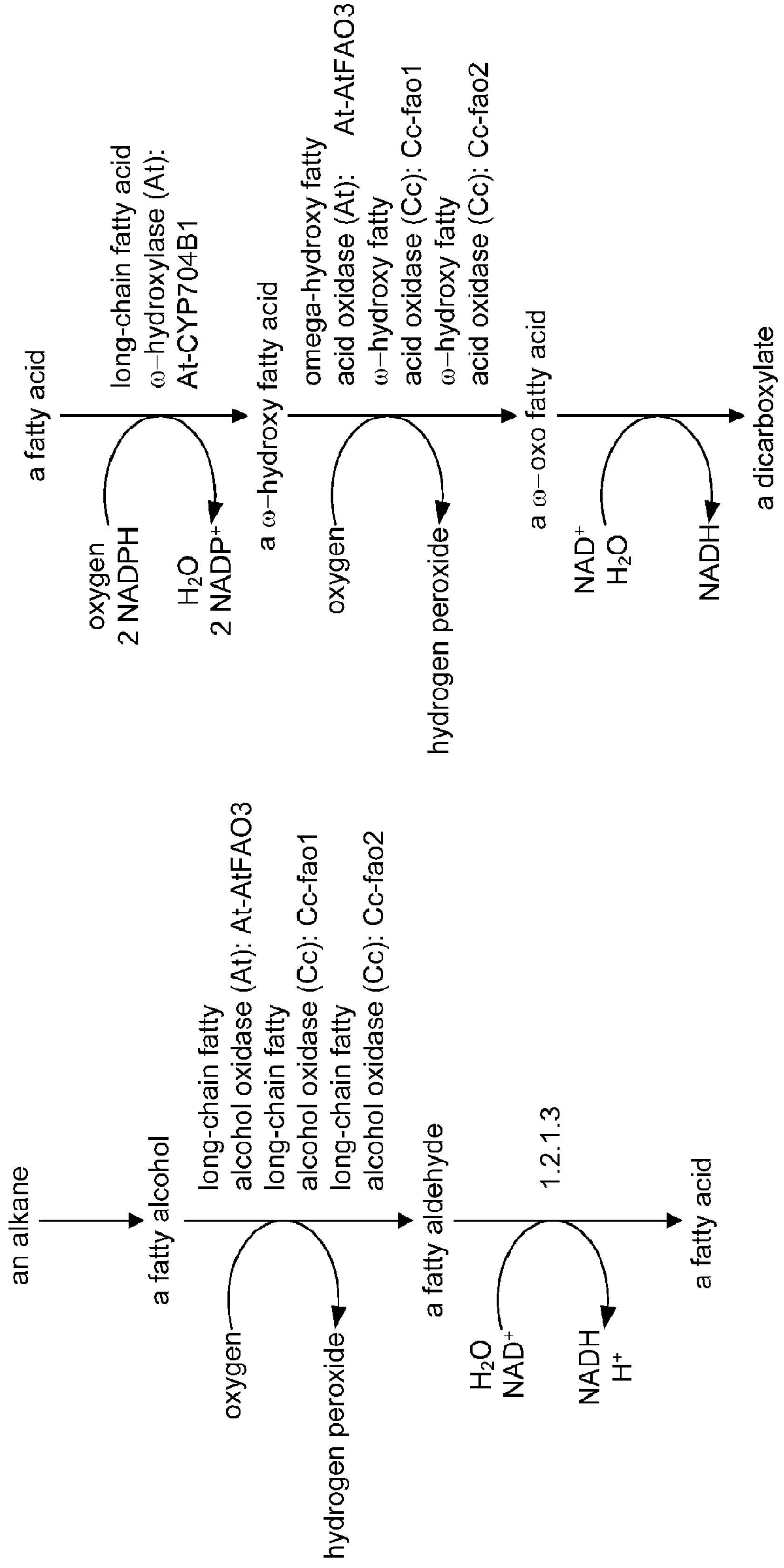

FIG. 24 depicts the synthesis of a dicarboxylate using omega oxidation.

Figure 25:
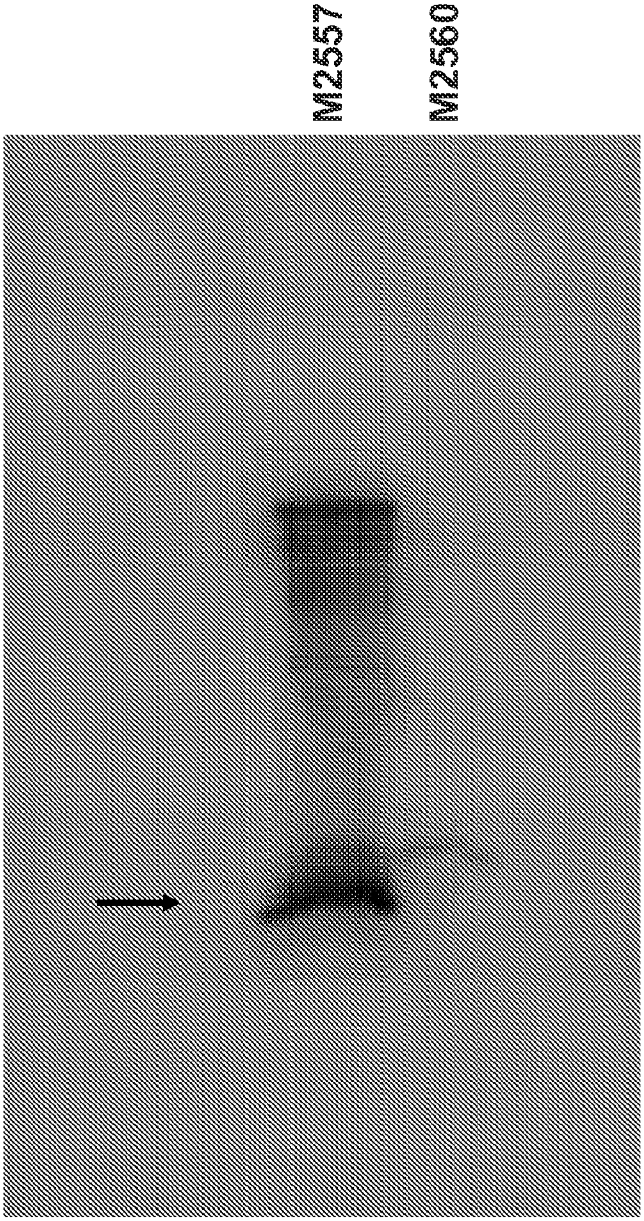

FIG. 25 is a western blot demonstrating the presence of biotinylated enzyme in construct M2557 but not in M2560.

Figure 26A:
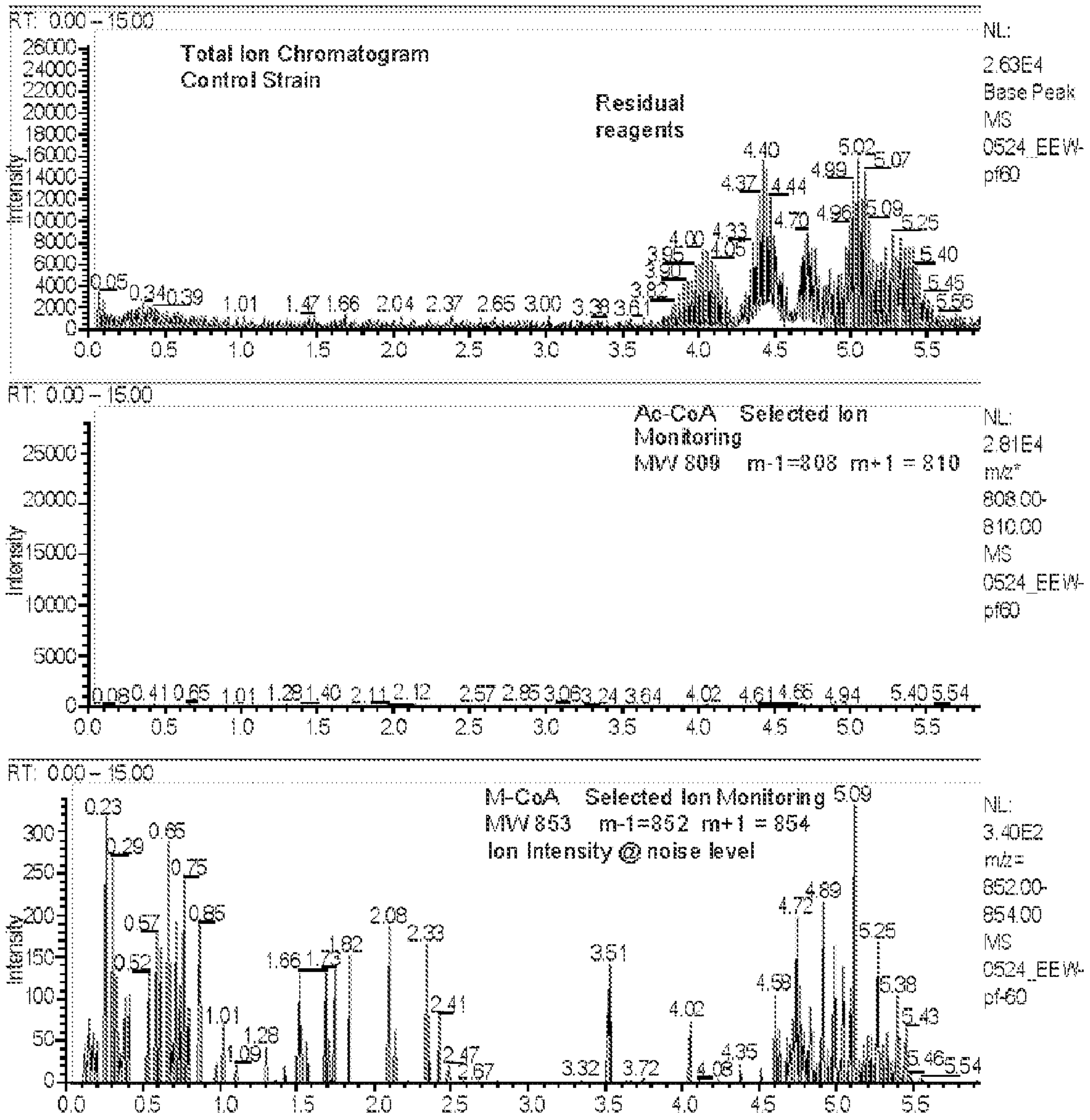
Figure 26A:
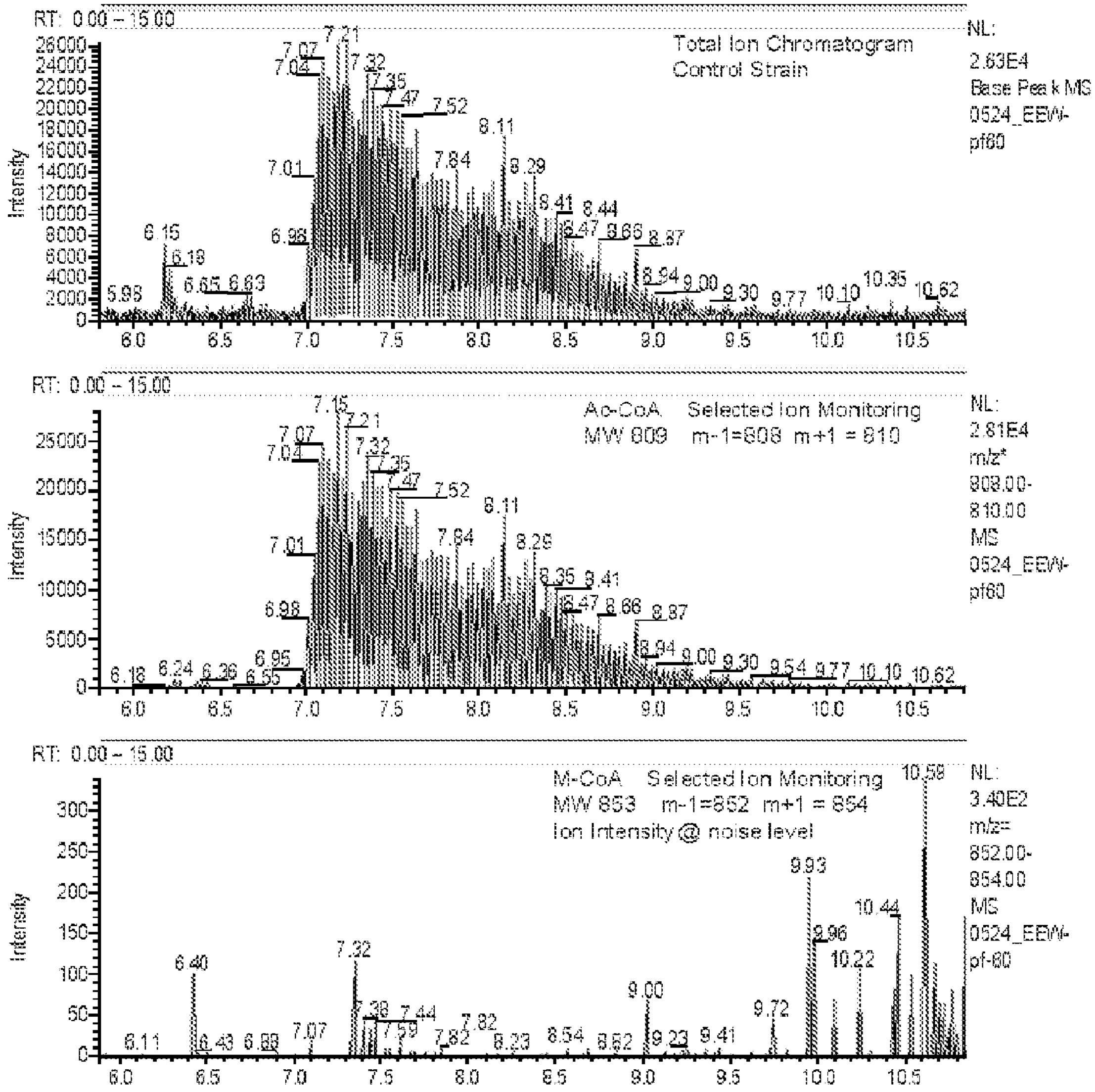
Figure 26A:
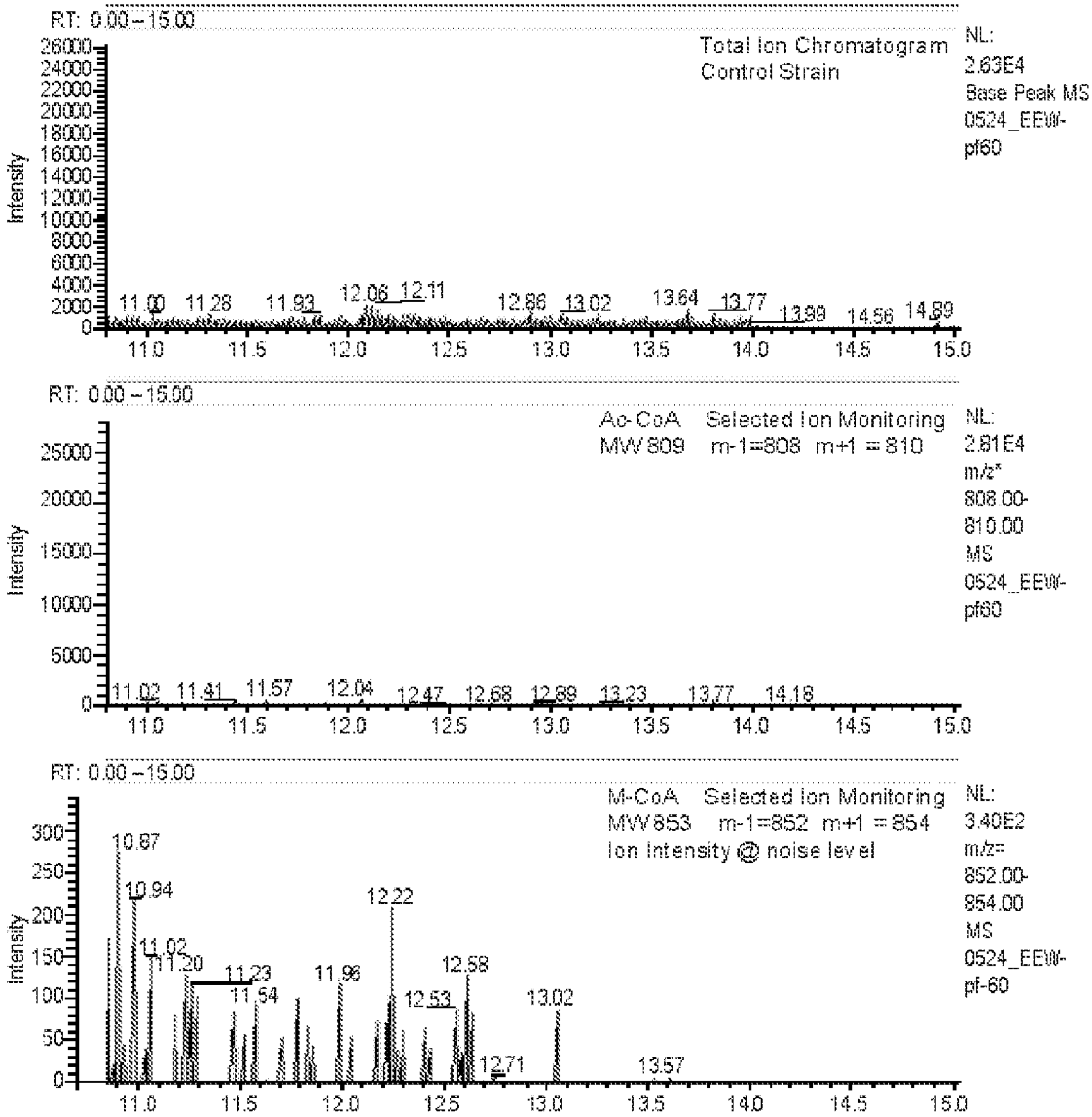

FIG. 26A depicts a mass spectrum of the transcarboxylase assay products for the negative control sample.

Figure 26B:
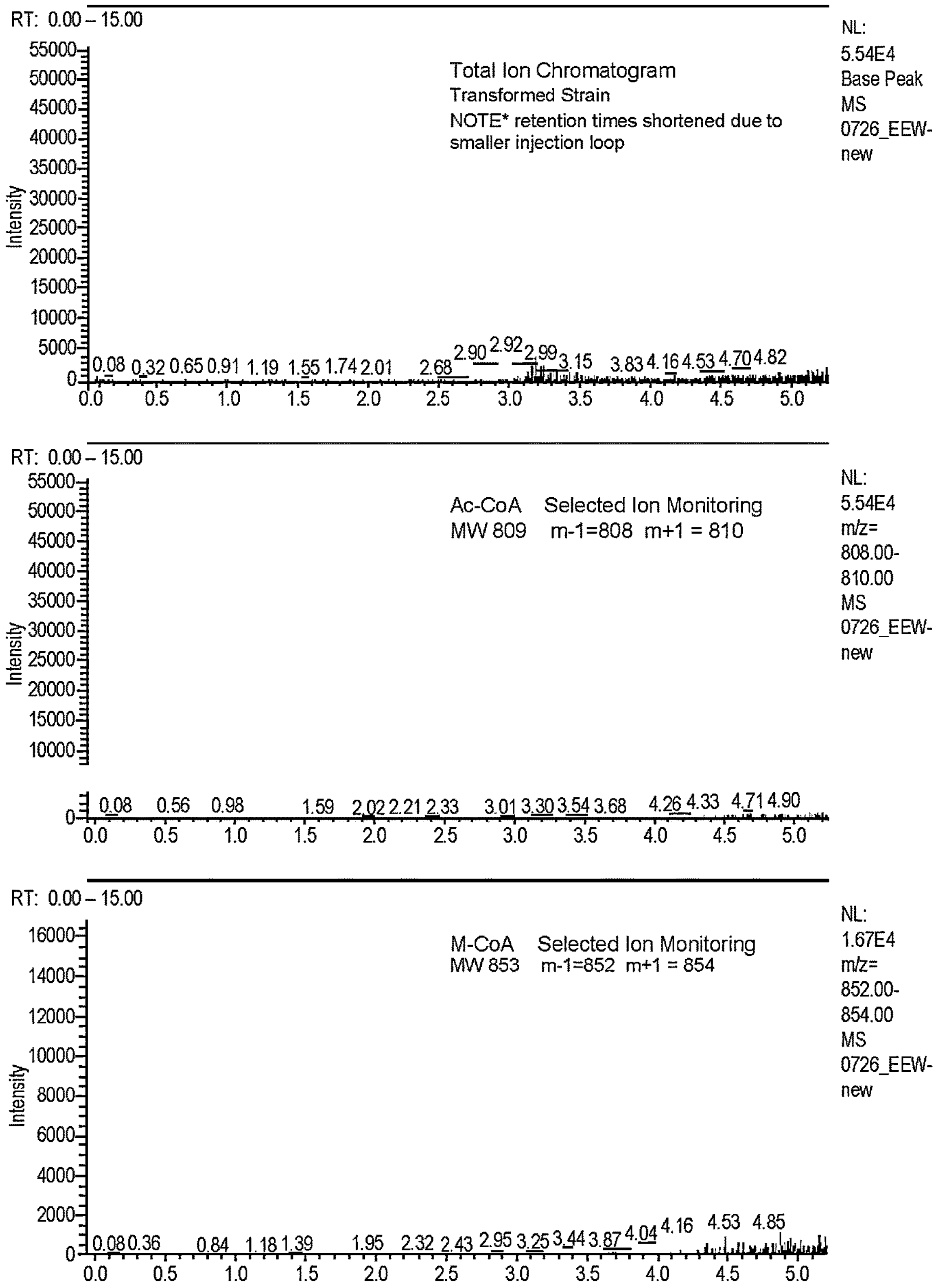
Figure 26B:
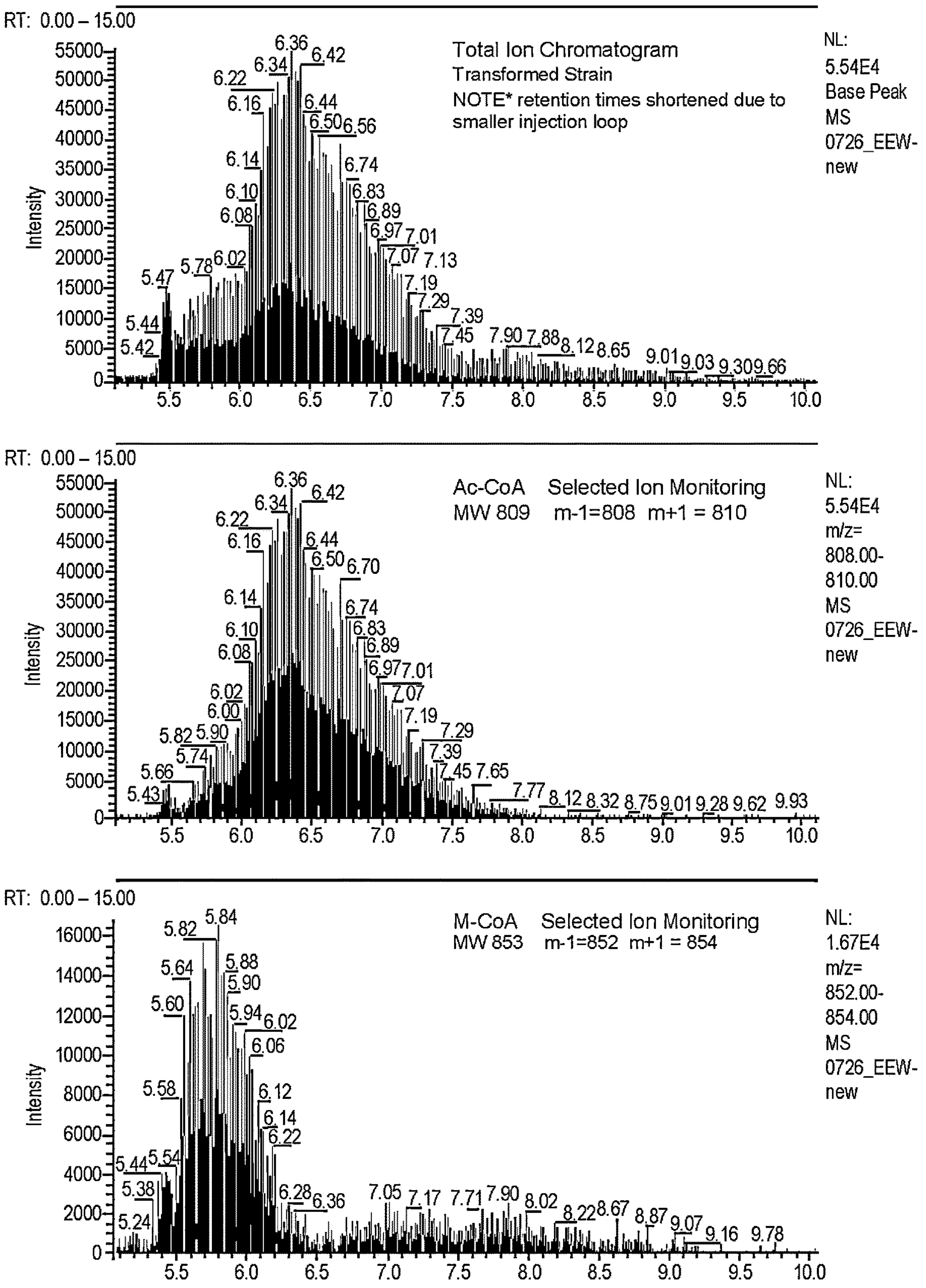

FIG. 26B depicts a mass spectrum of the transcarboxylase assay products for the transcarboxylase sample.

Figure 27A:
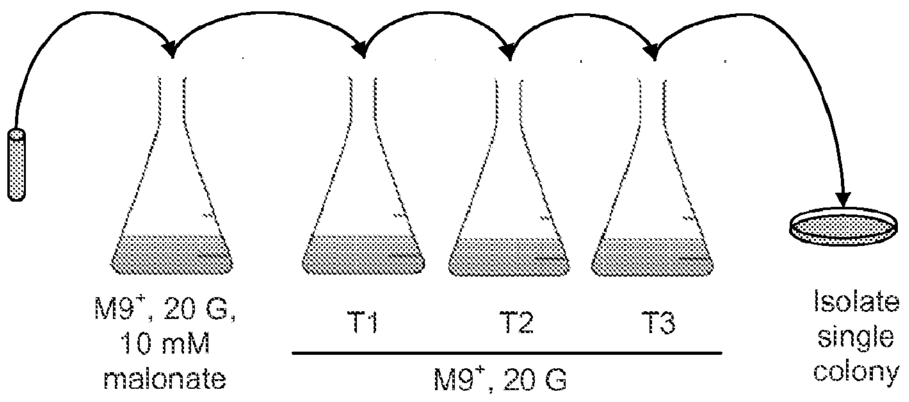

FIG. 27A depicts a schematic for the use of the accC::matBC *E. coli* strain M2470 to select for more efficient malonyl-CoA production by transcarboxylases.

Figure 27B:
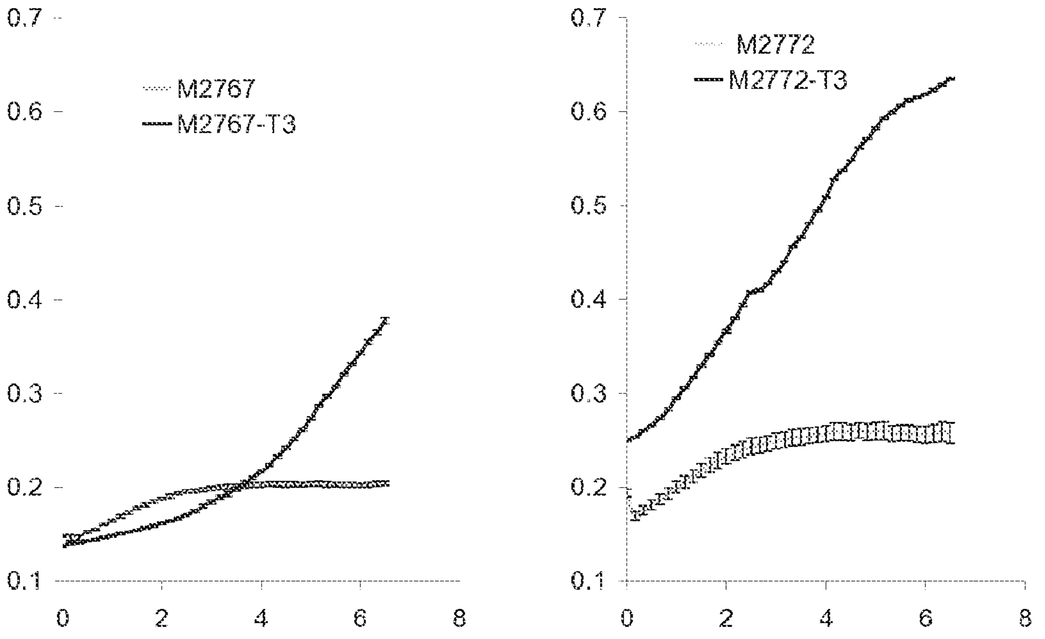

FIG. 27B shows the growth rates for the original strain and T3 strain.

Figure 28:
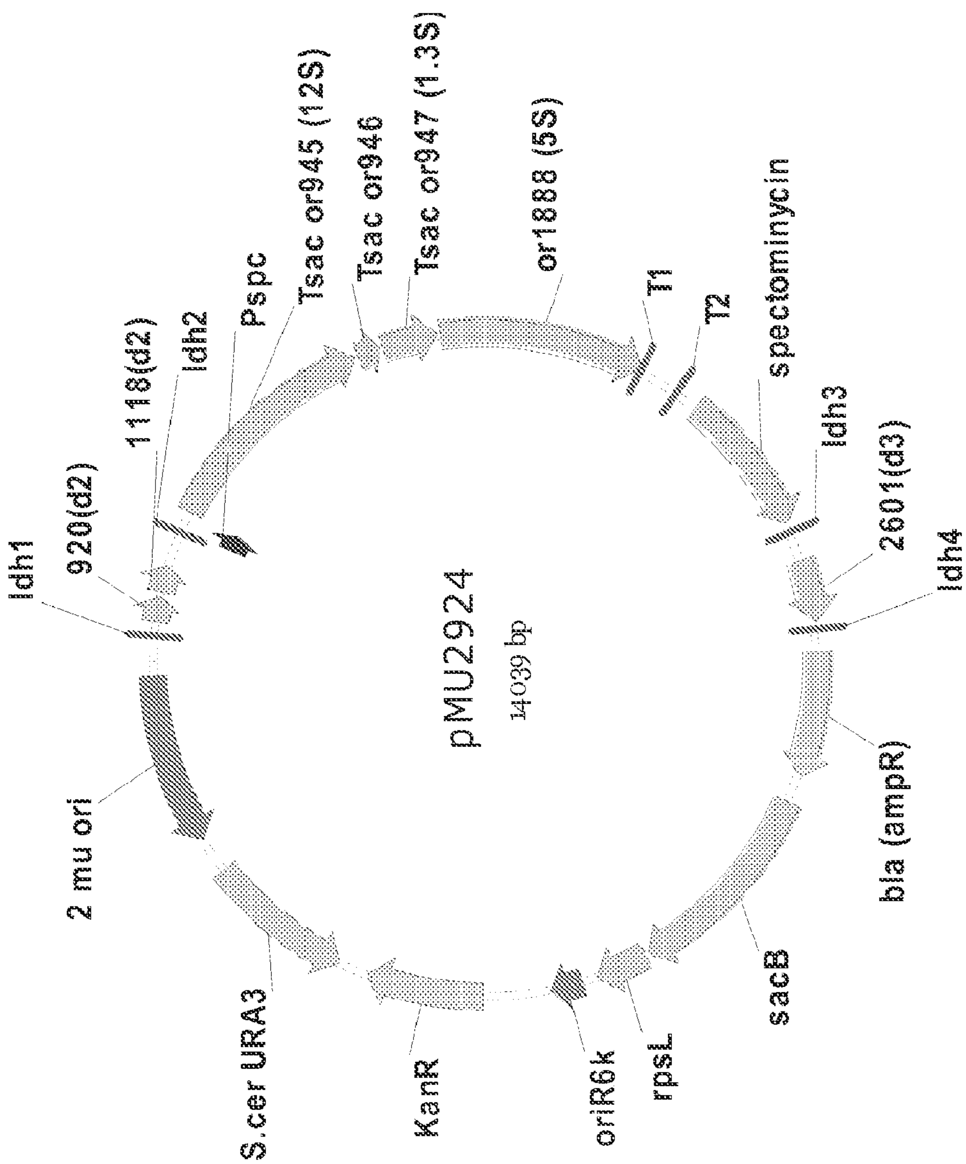

FIG. 28 depicts the vector pMU2924.

Figure 29:
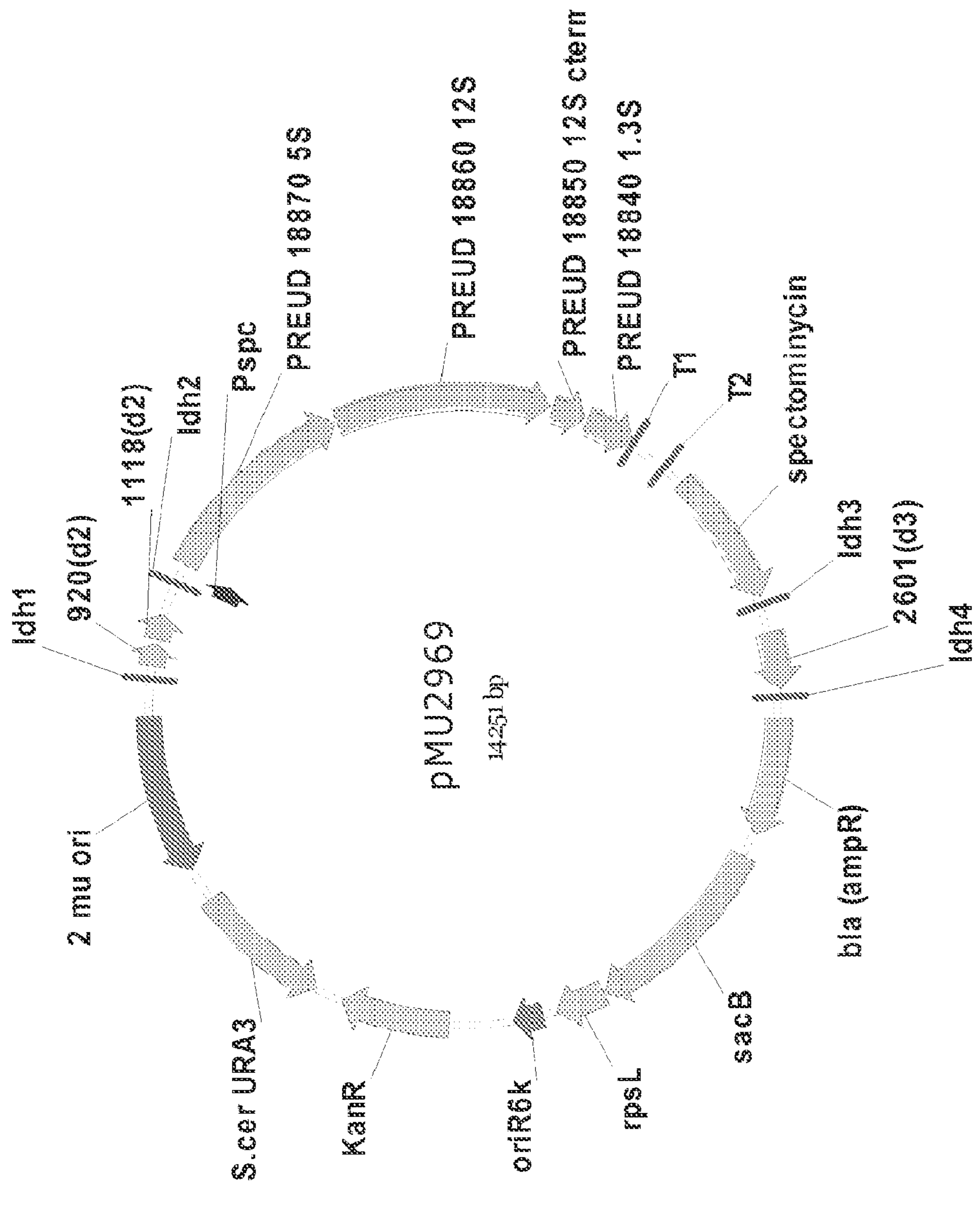

FIG. 29 depicts the vector pMU2969.

Figure 30:
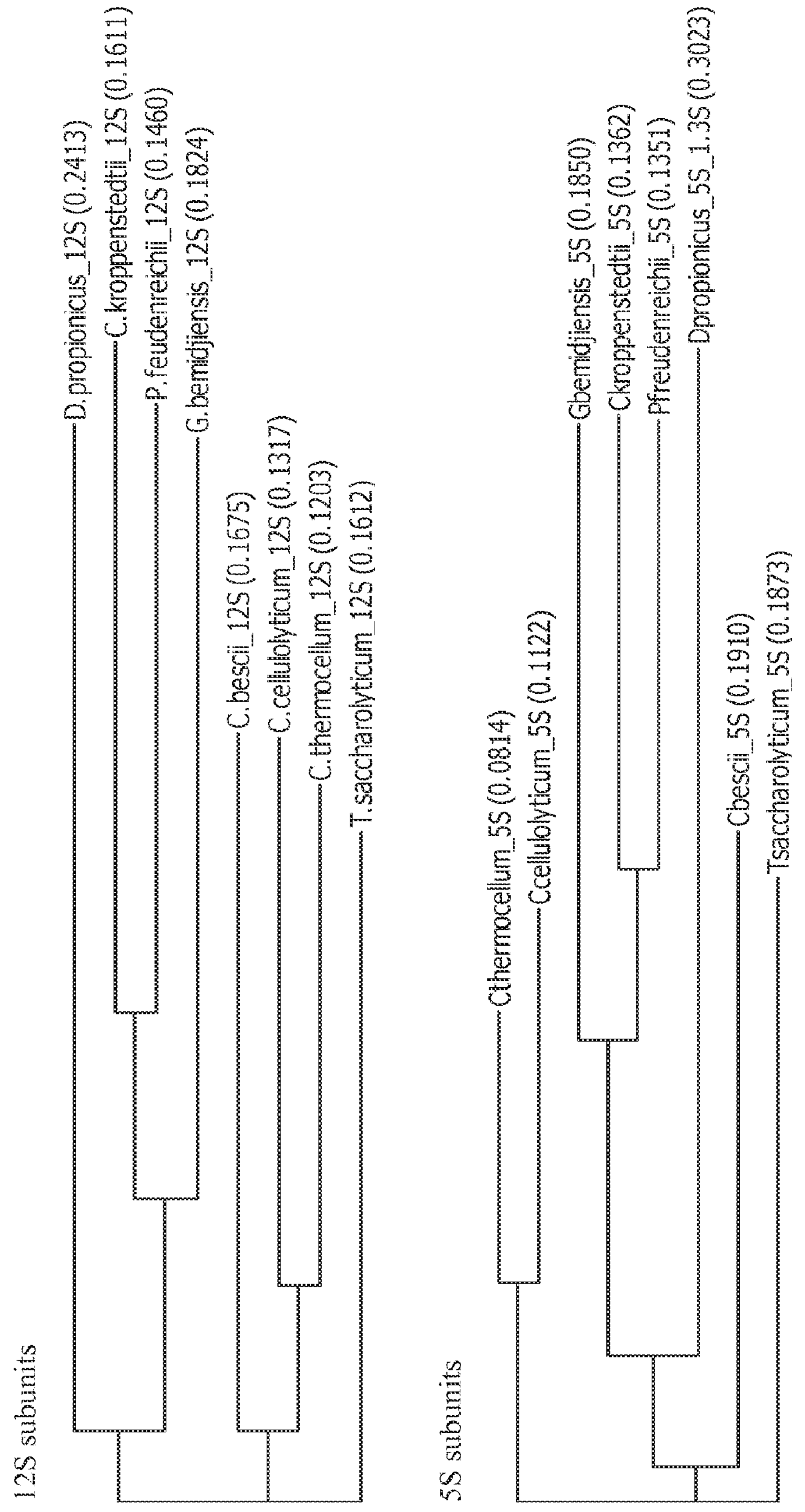
Figure 30:
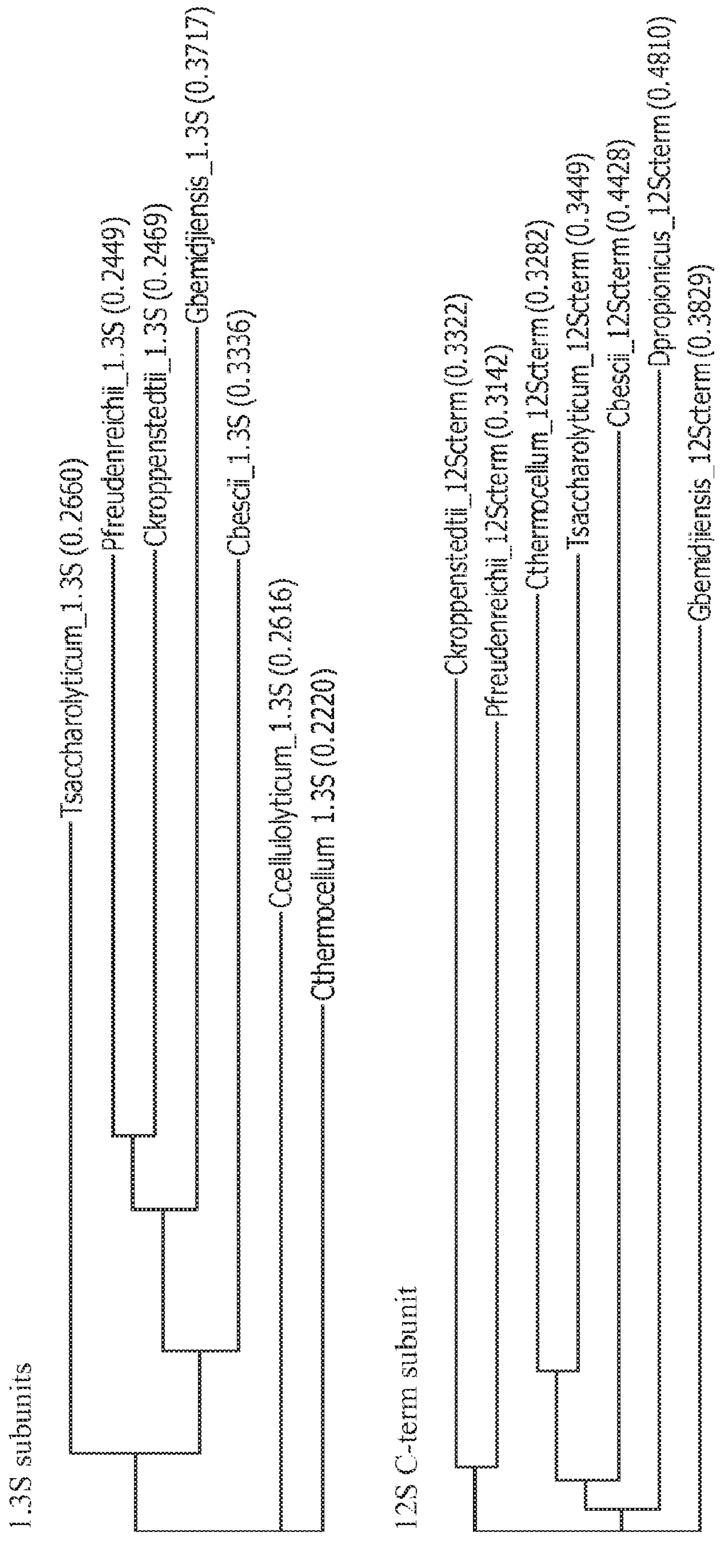
Figure 32B:
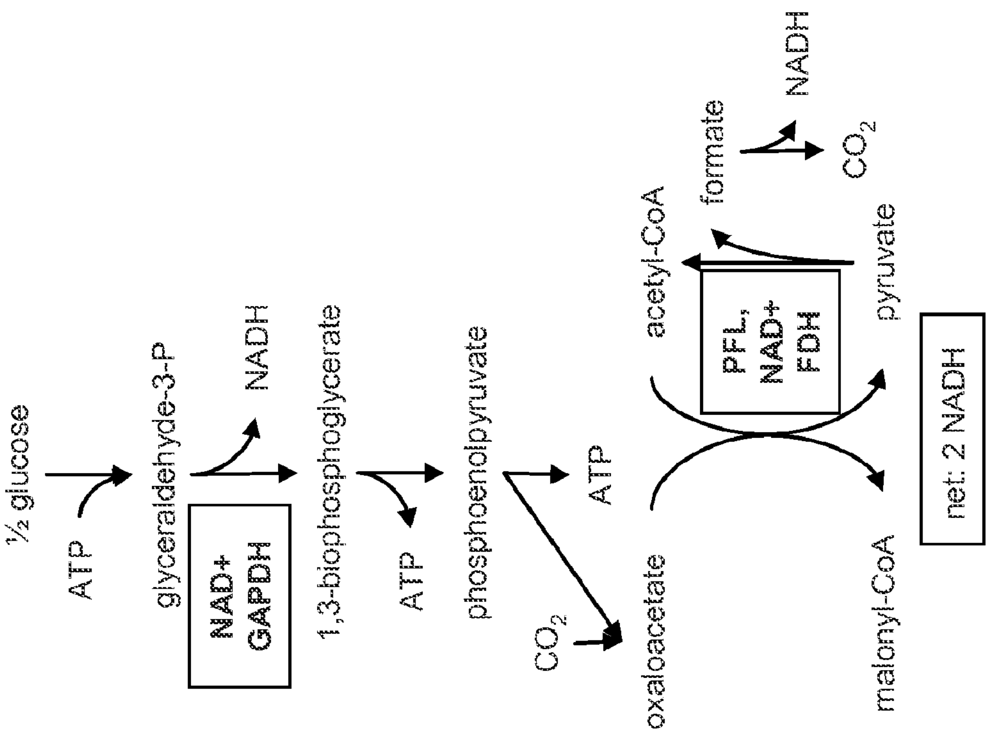
Figure 32A:
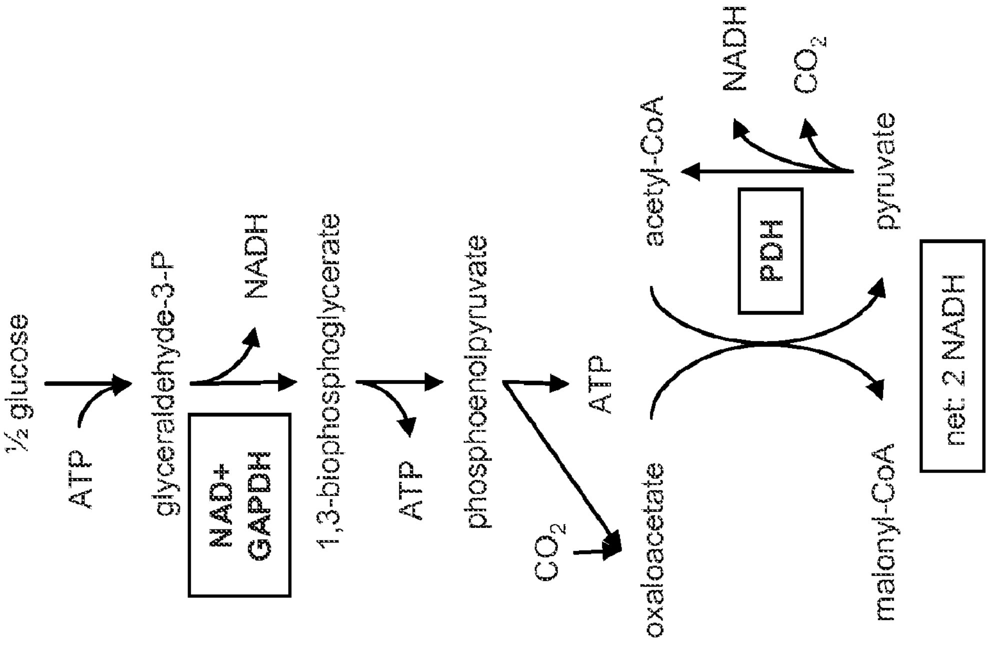
Figure 32C:
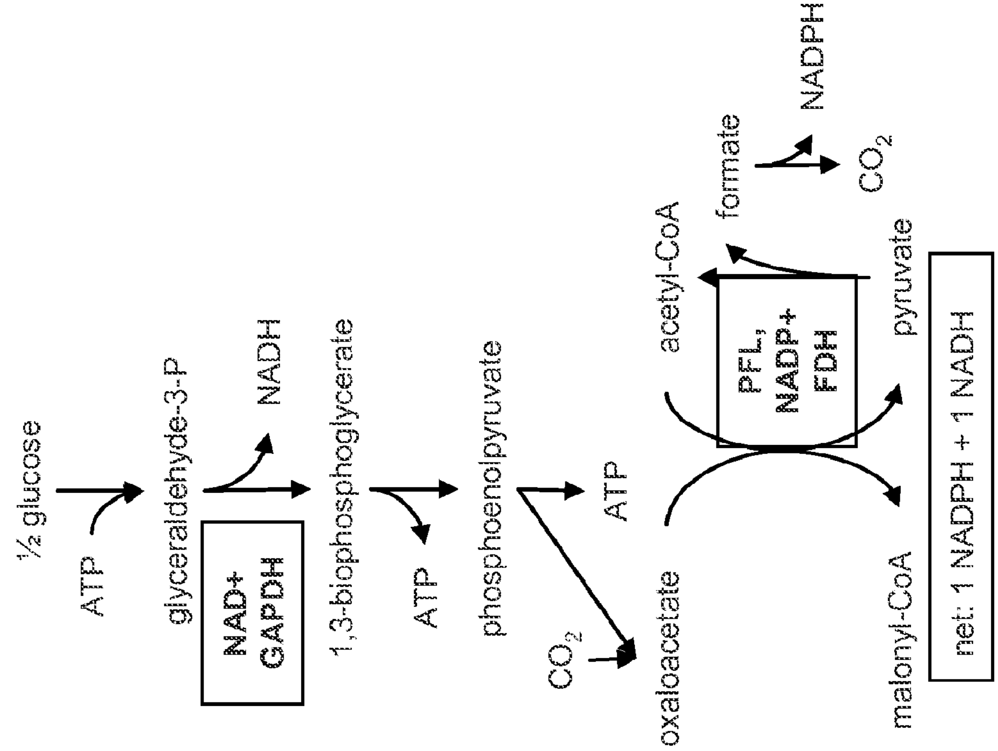
Figure 32D:
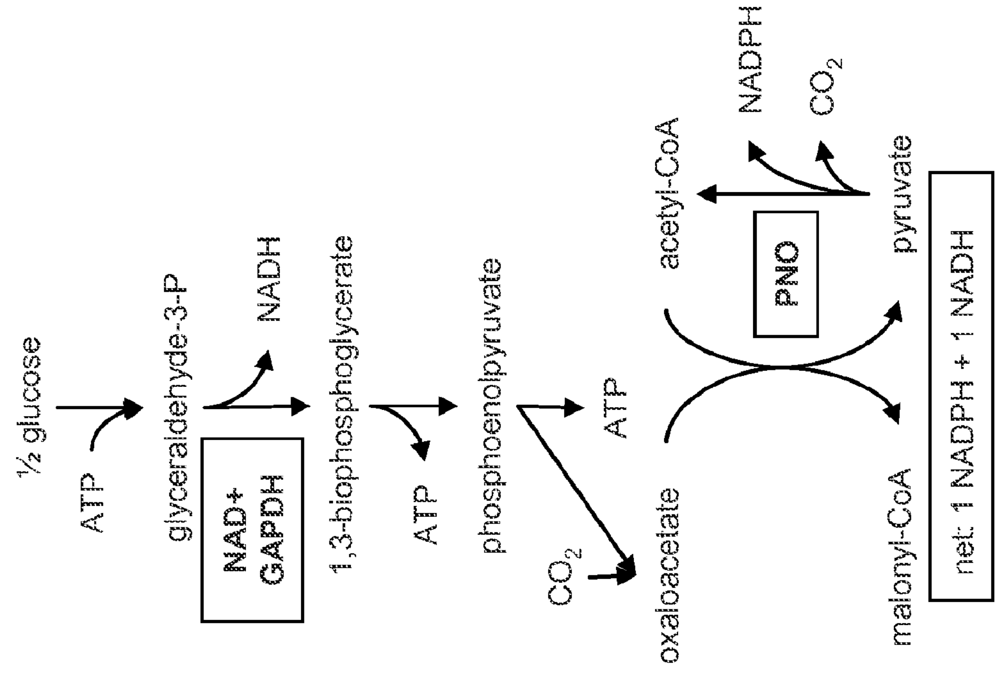
Figure 32F:
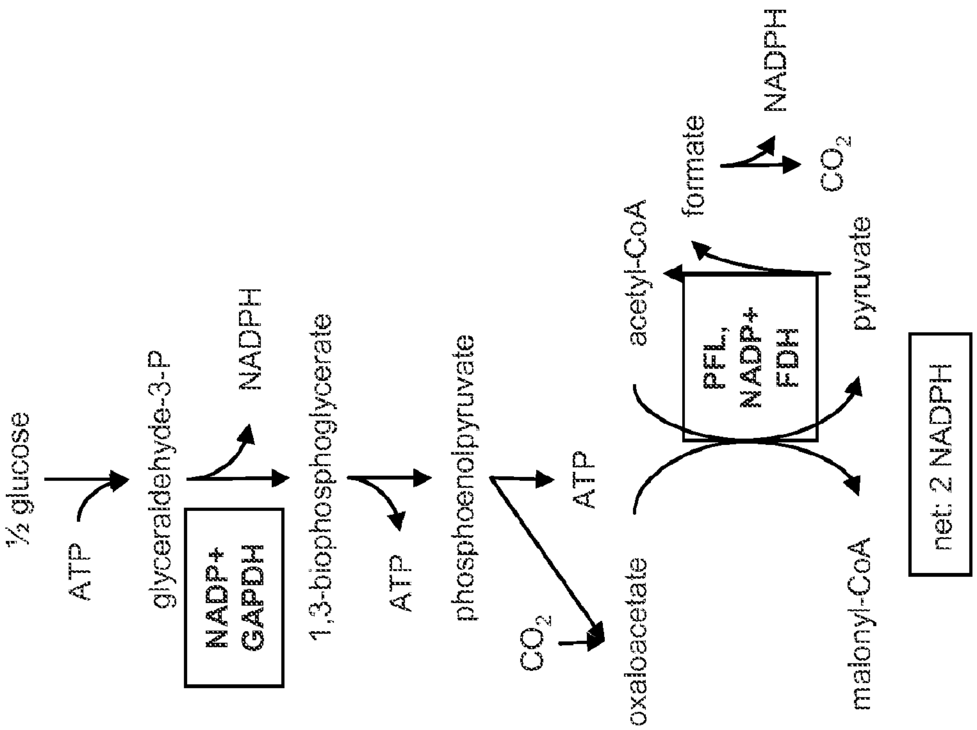
Figure 32E:
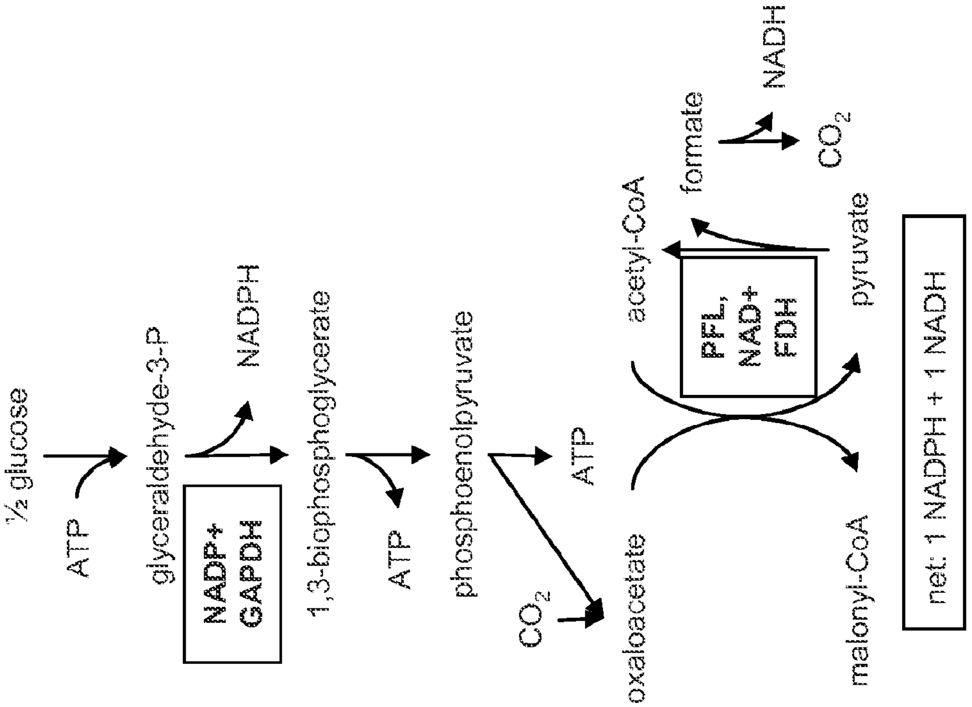
Figure 32G:
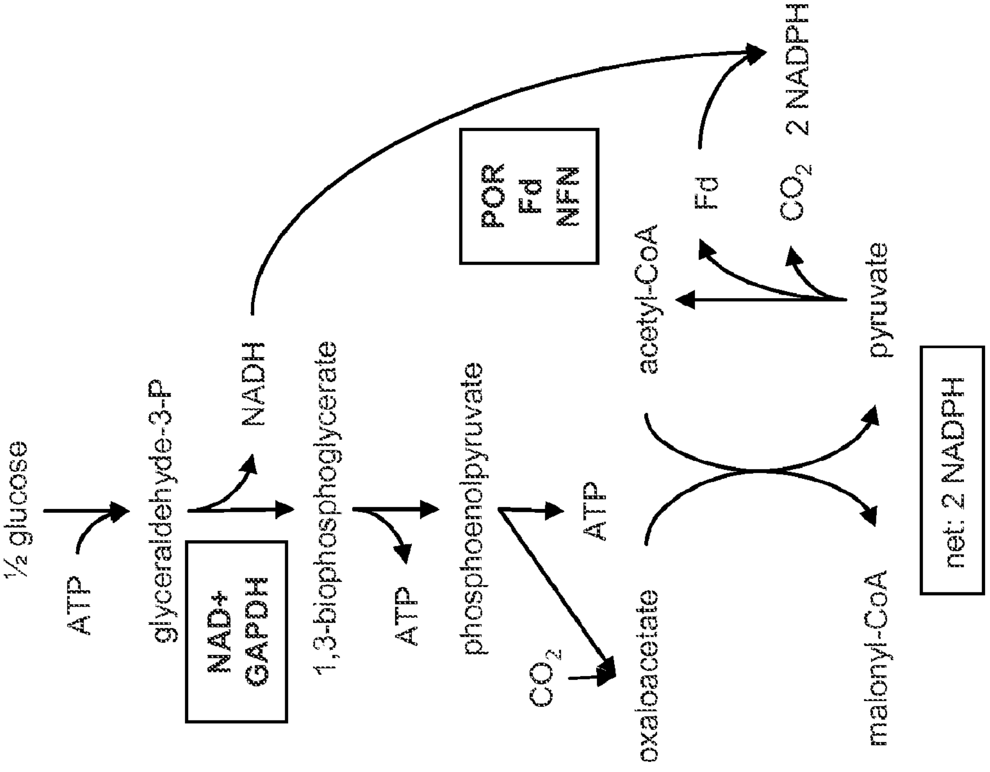
Figure 32H:
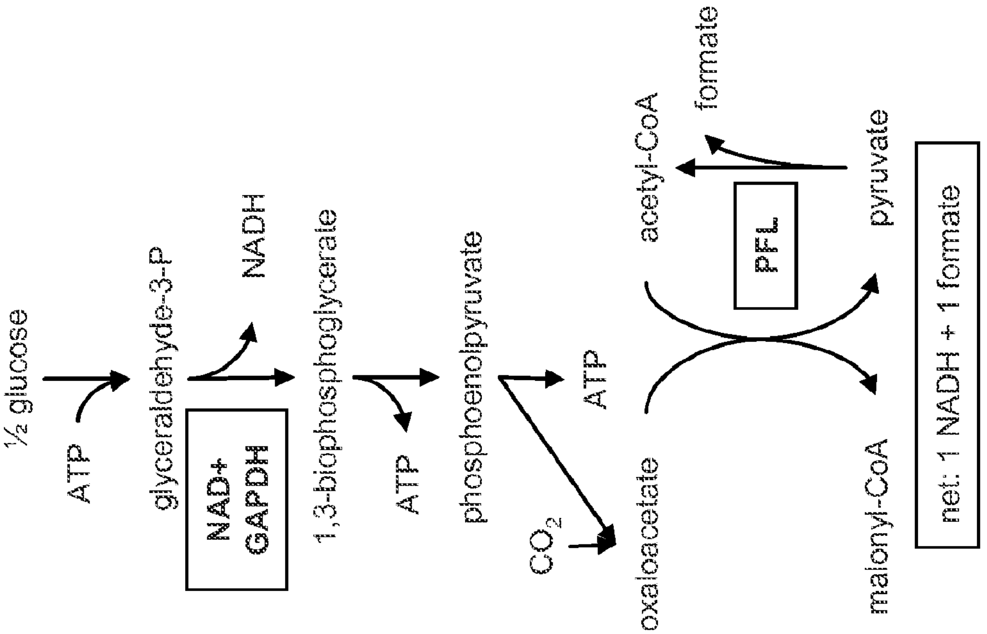
Figure 32I:
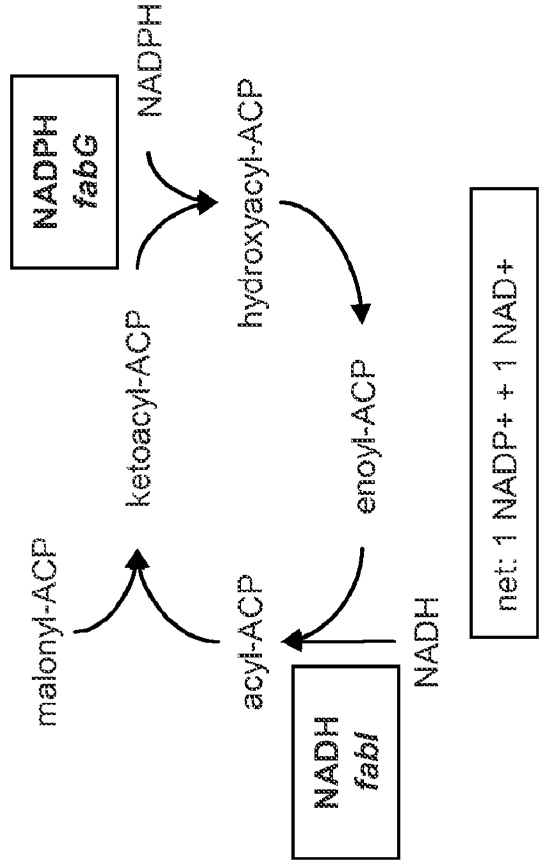
Figure 32J:
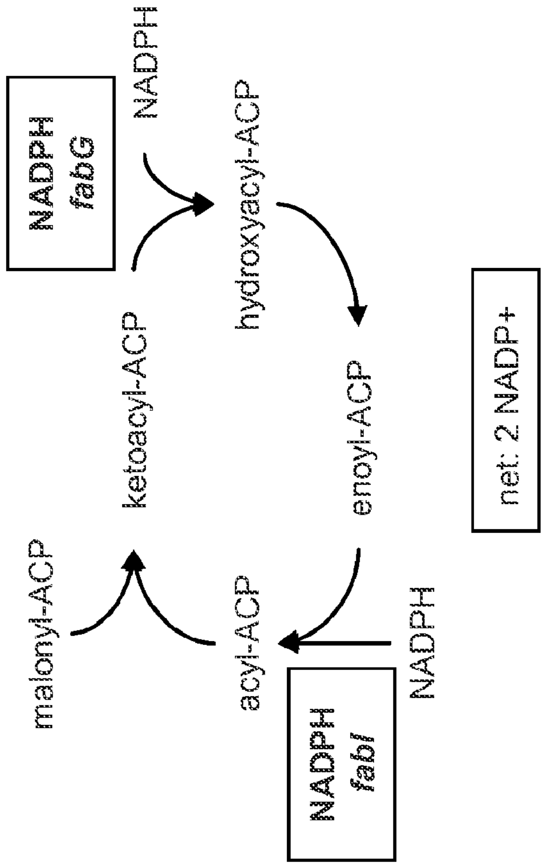
Figure 32K:
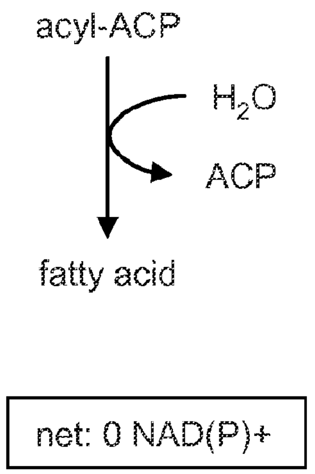
Figure 32L:
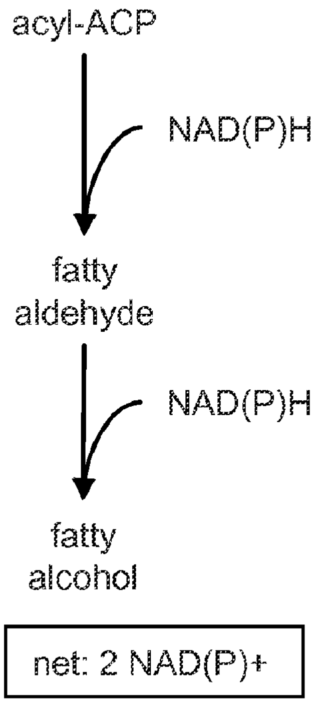

FIG. 30 is a phylogenetic tree depicting relatedness between 12S, 5S, 1.3S, and 12S C-term subunits of transcarboxylases from *D. propionicus, C. kroppenstedtii, P. fuedenreichii, G. bemidjiensis, C. bescii, C. Cellulolyticum, C. thermocellum*, and *T. saccharolyticum*.

FIG. 31 is an alignment of the transcarboxylase subunits from *D. propionicus, C. kroppenstedtii, P. fuedenreichii, G. bemidjiensis, C. bescii, C. Cellulolyticum, C. thermocellum*, and *T. saccharolyticum*.

FIG. 32A to FIG. 32L depict different schematic routes that correspond to co-factor pathway selection presented in Table 10.

Figure 33:
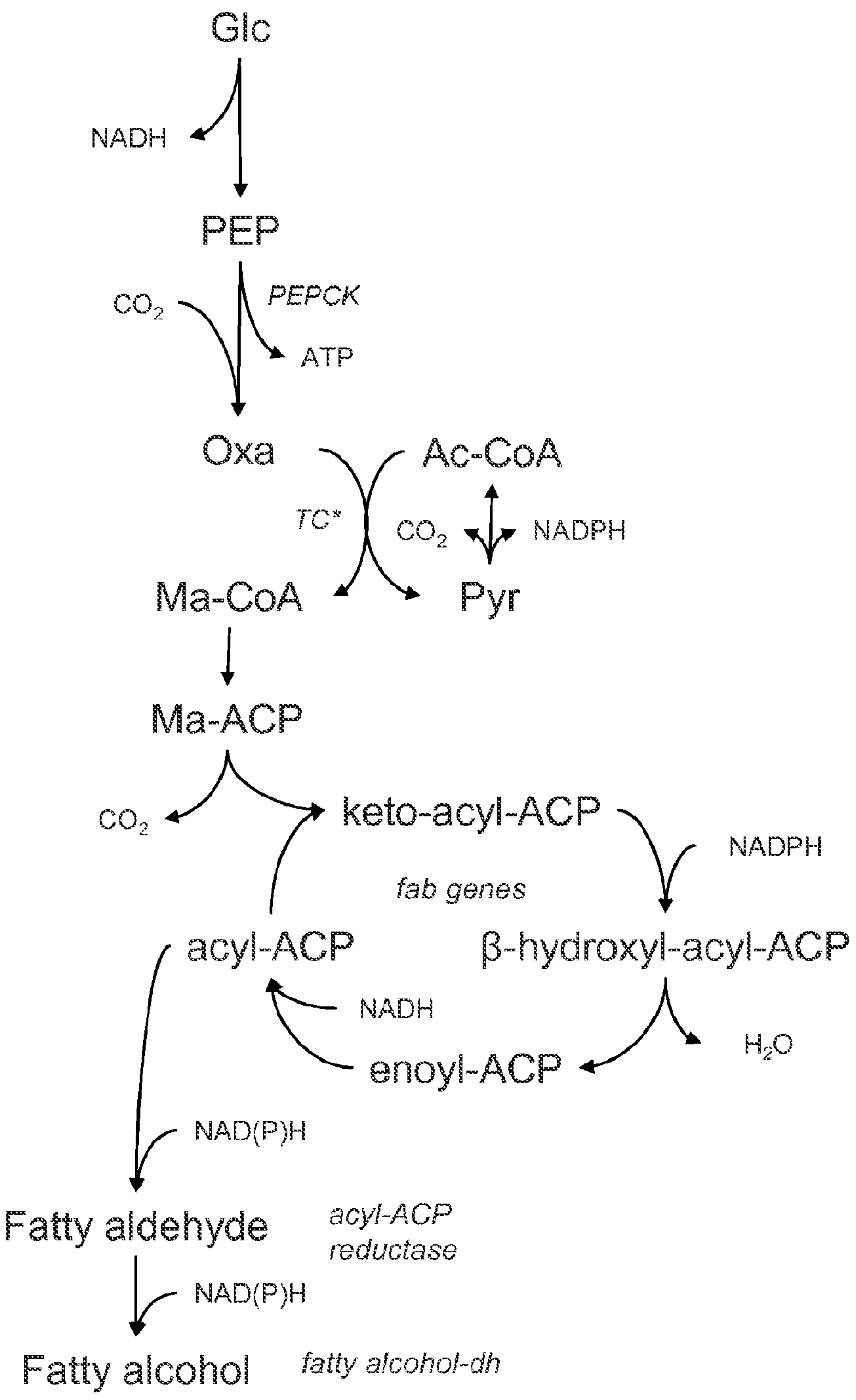

FIG. 33 depicts a pathway for the conversion of glucose to fatty aldehyde or fatty alcohol.

Figure 34A:
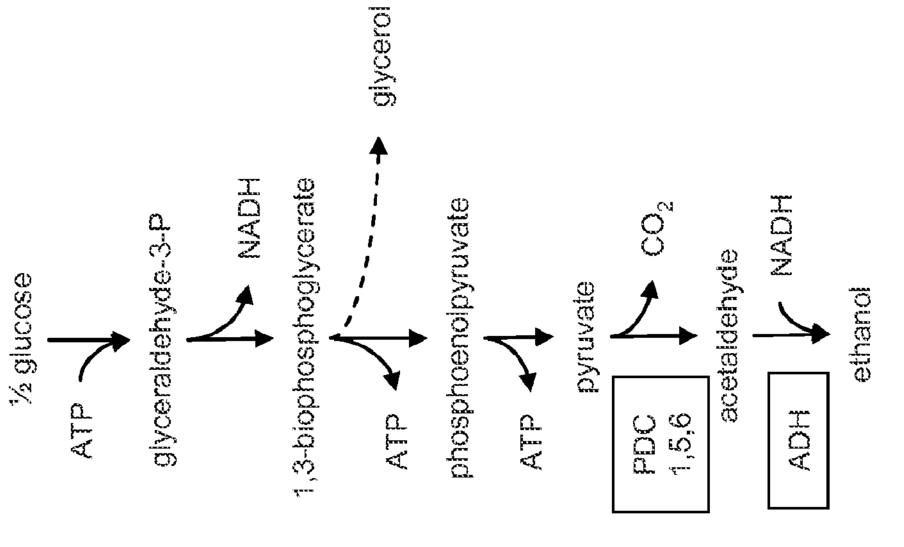

FIG. 34A depicts the pathways of the fermentative metabolism of *S. cerevisiae* involving the native pyruvate decarboxylase (pdc) based ethanol pathway.

Figure 34B:
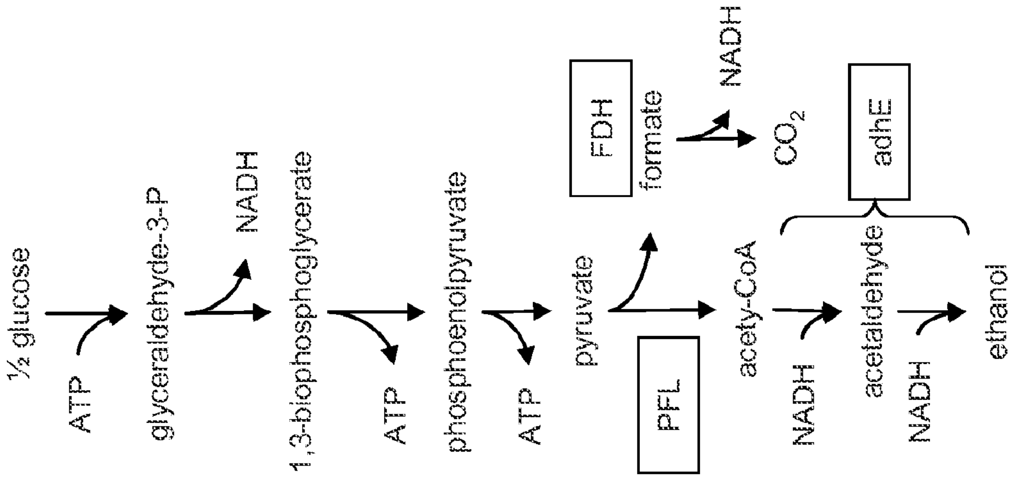

FIG. 34B depicts the pathways for the conversion of the fermentative metabolism of *S. cerevisiae*, as shown in FIG. 34A, into the one involving an intermediary pyruvate formate lyase and alcohol/aldehyde dehydrogenase (pfl adhE) based ethanol pathway.

Figure 34C:
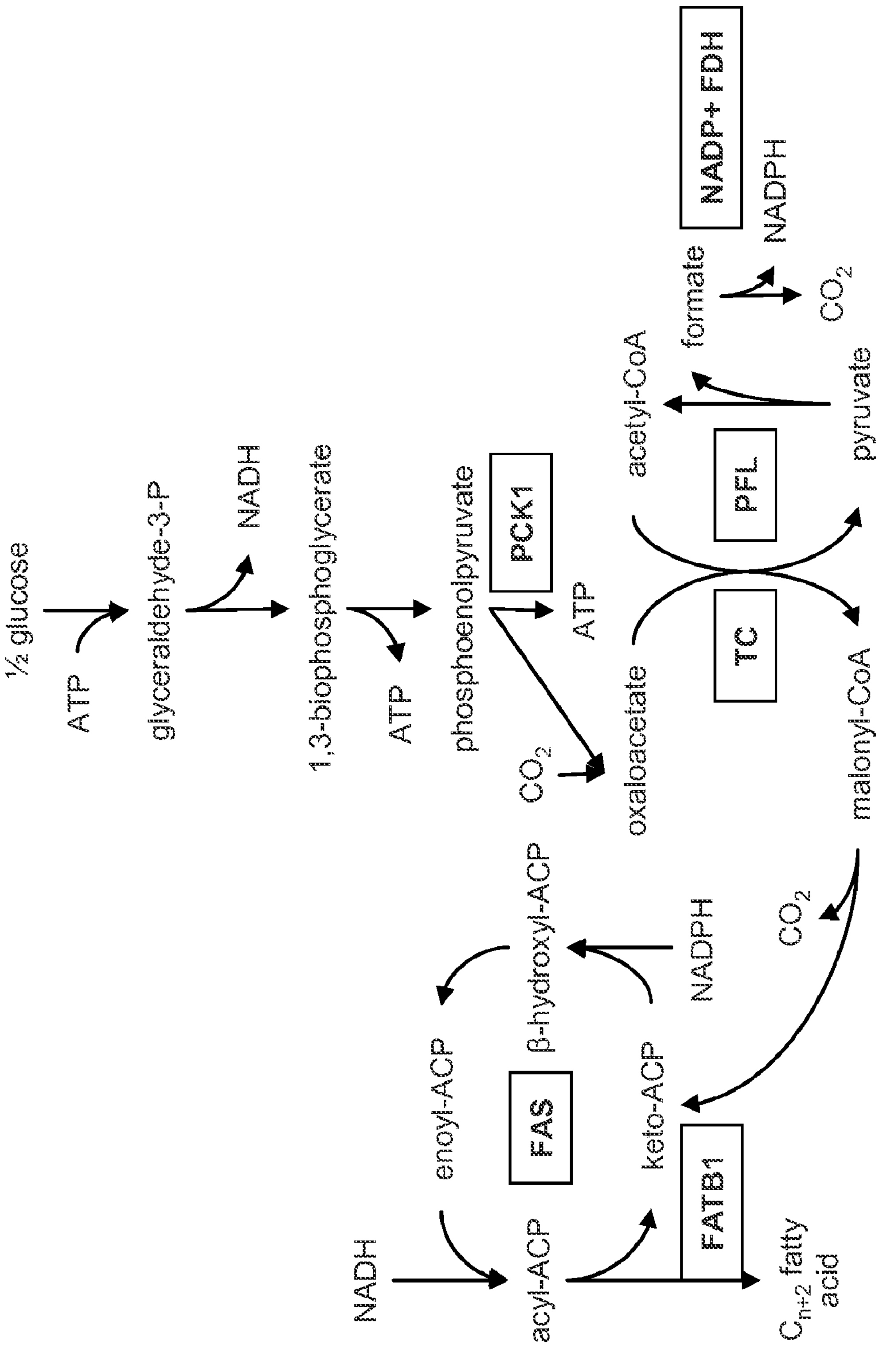

FIG. 34C depicts the pathways for the conversion of the fermentative metabolism of *S. cerevisiae*, as in shown in FIG. 34B, into the one involving an the transcarboxylase based palmitic acid pathway.

Figure 35:
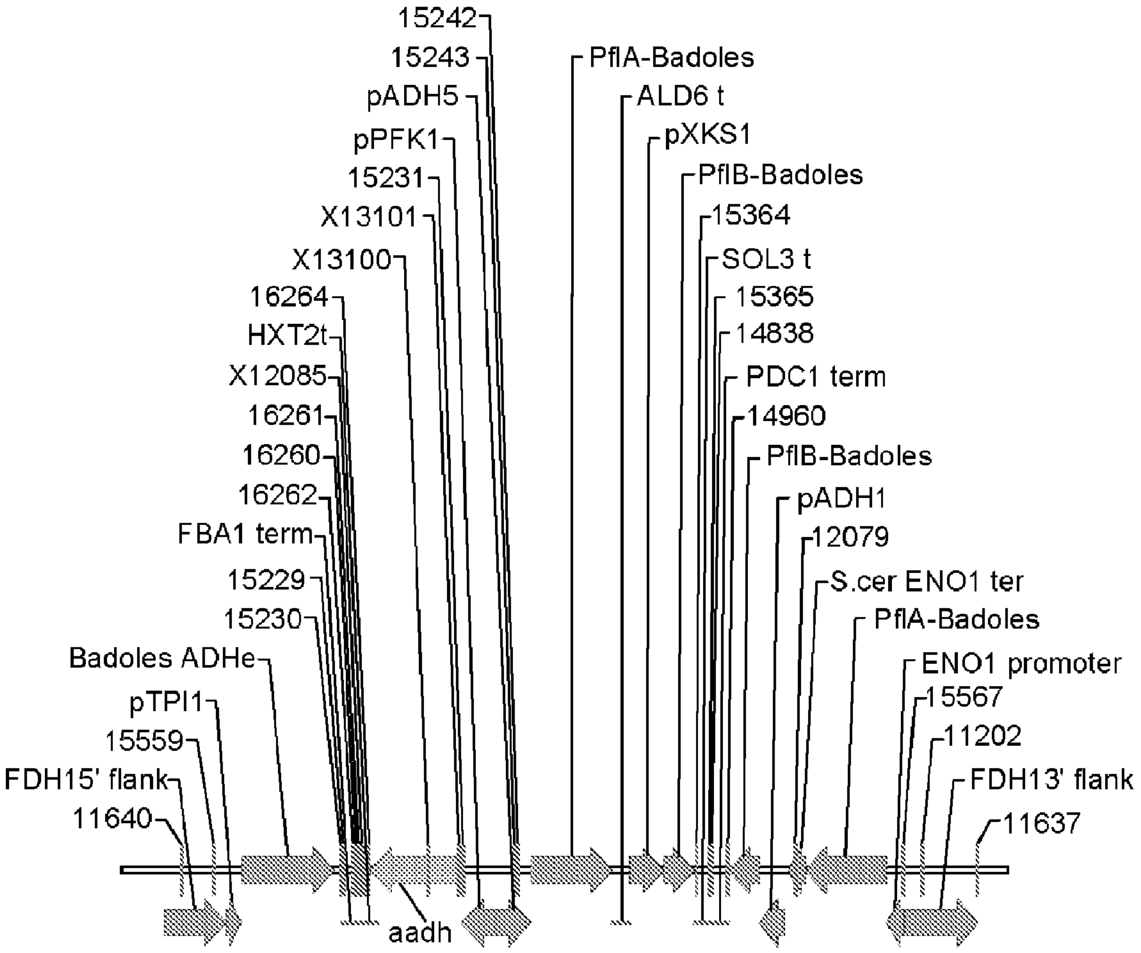

FIG. 35 depicts an integration design which deletes FDH1 and replaces the gene with two copies of ADH and two copies of PFL.

Figure 36:
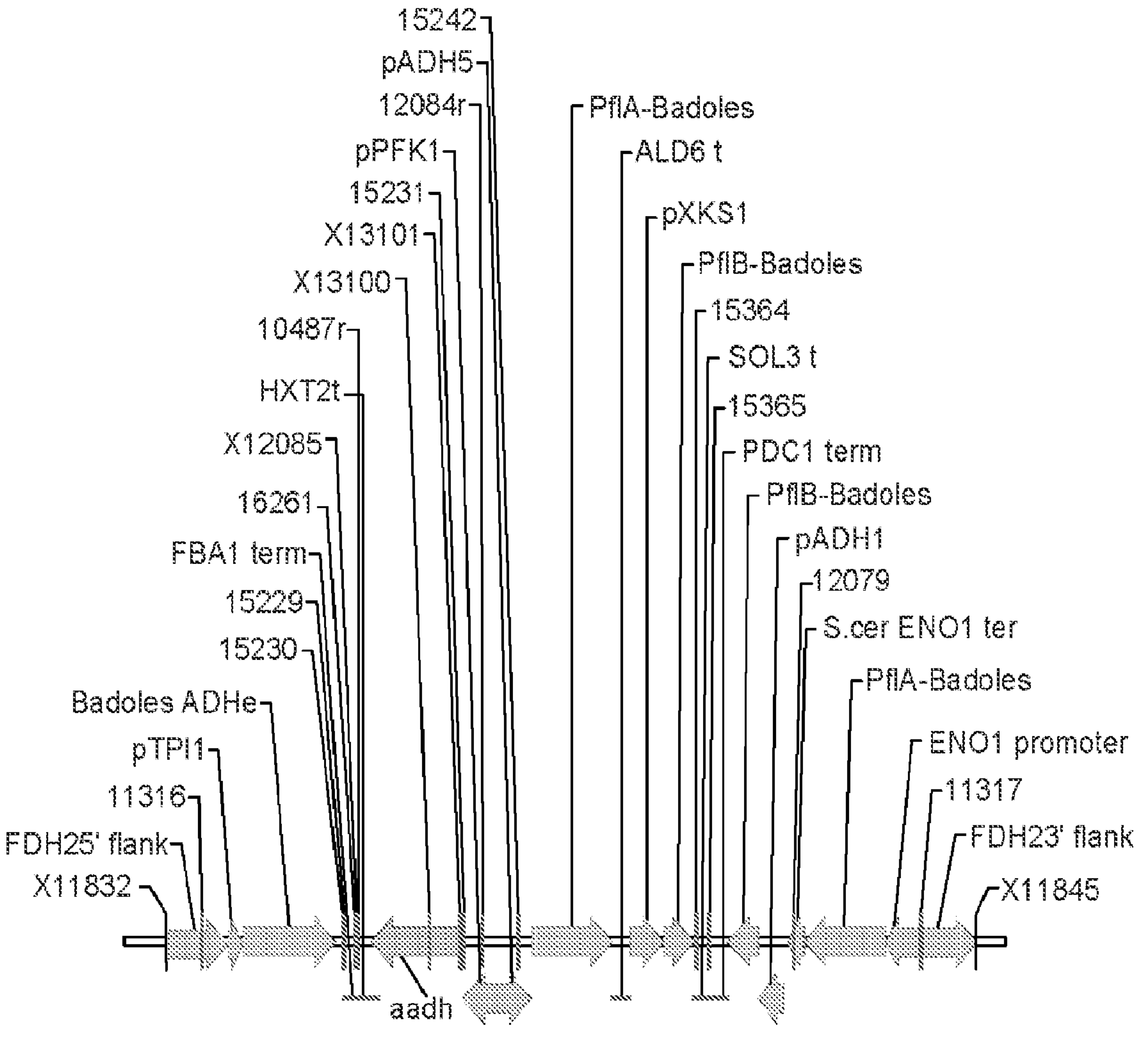

FIG. 36 depicts an integration design which deletes FDH2 and replaces the gene with two copies of ADH and two copies of PFL.

Figure 37:
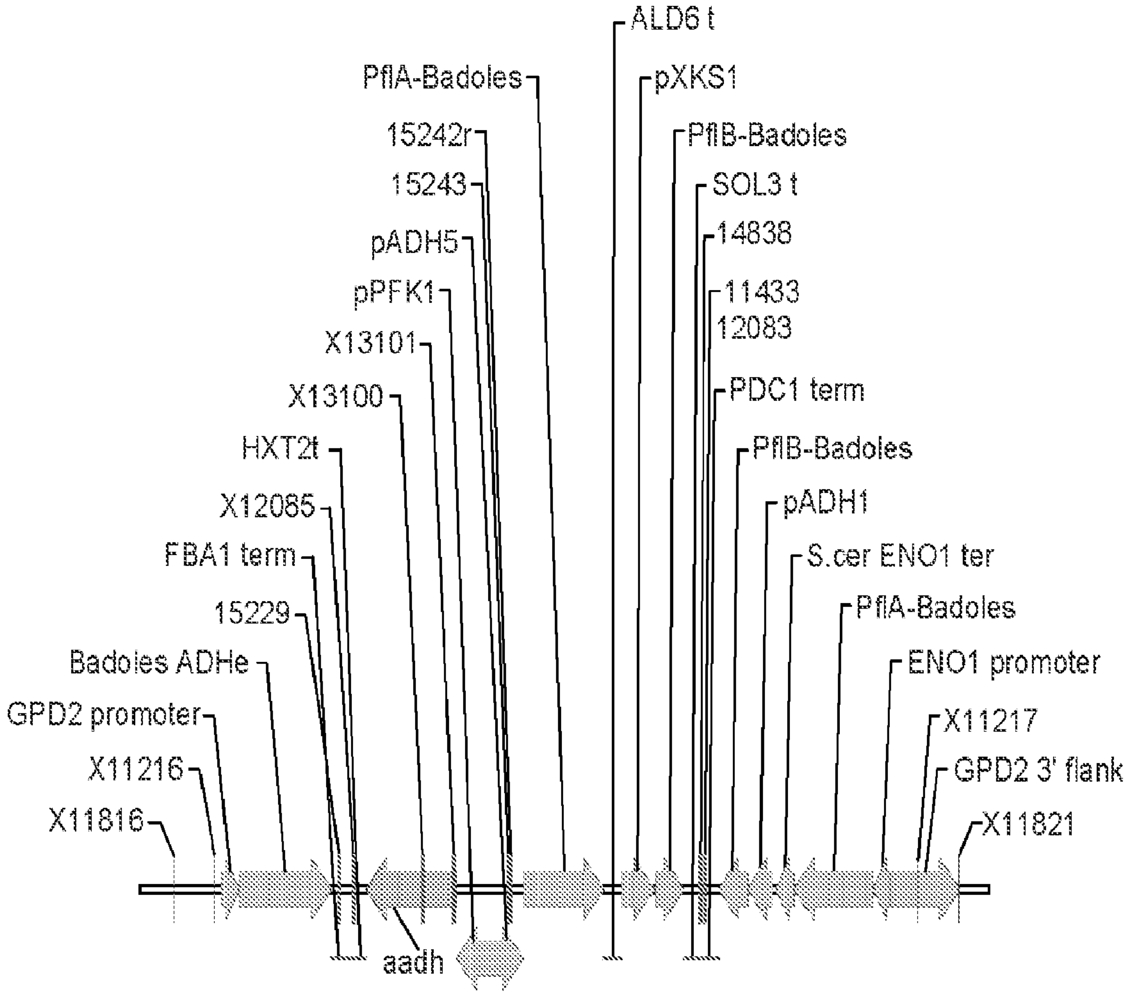

FIG. 37 depicts an integration design which deletes GPD2 and replaces the gene with two copies of ADH and two copies of PFL.

Figure 38:
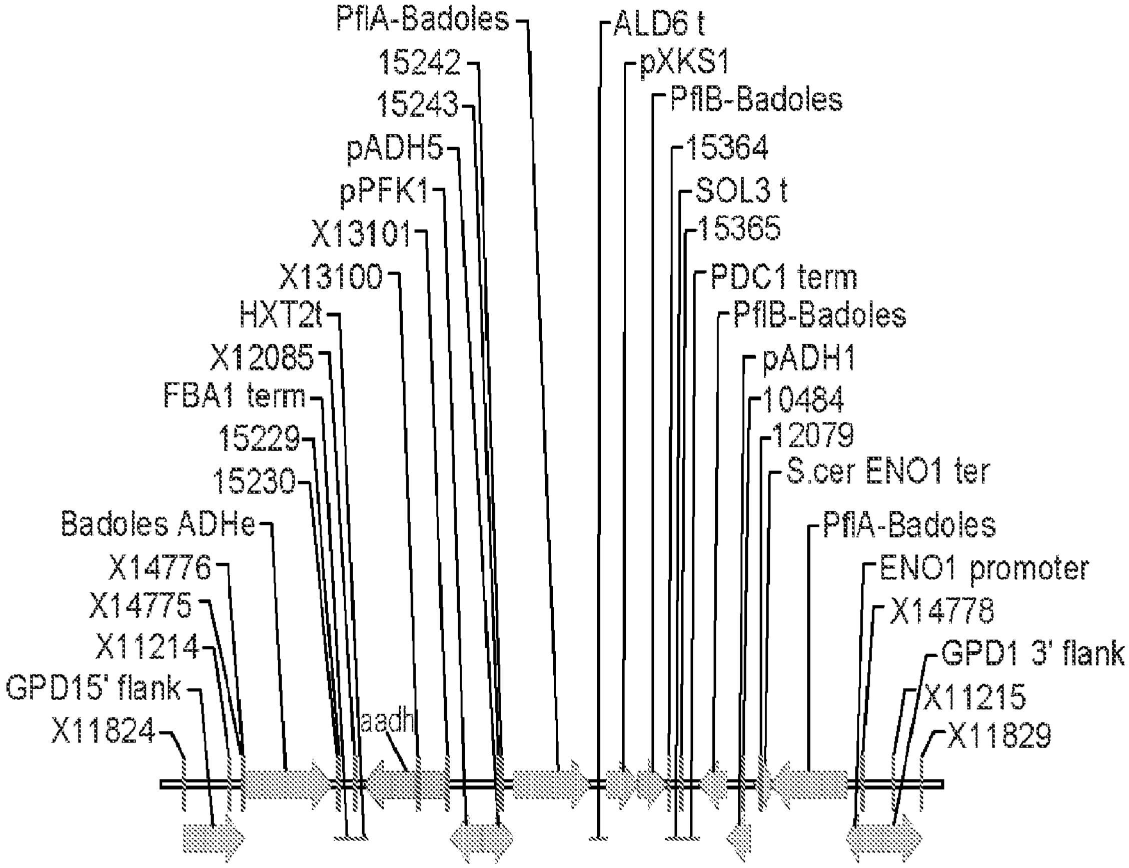

FIG. 38 depicts an integration design which deletes GPD1 and replaces the gene with two copies of ADH and two copies of PFL.

Figure 39:
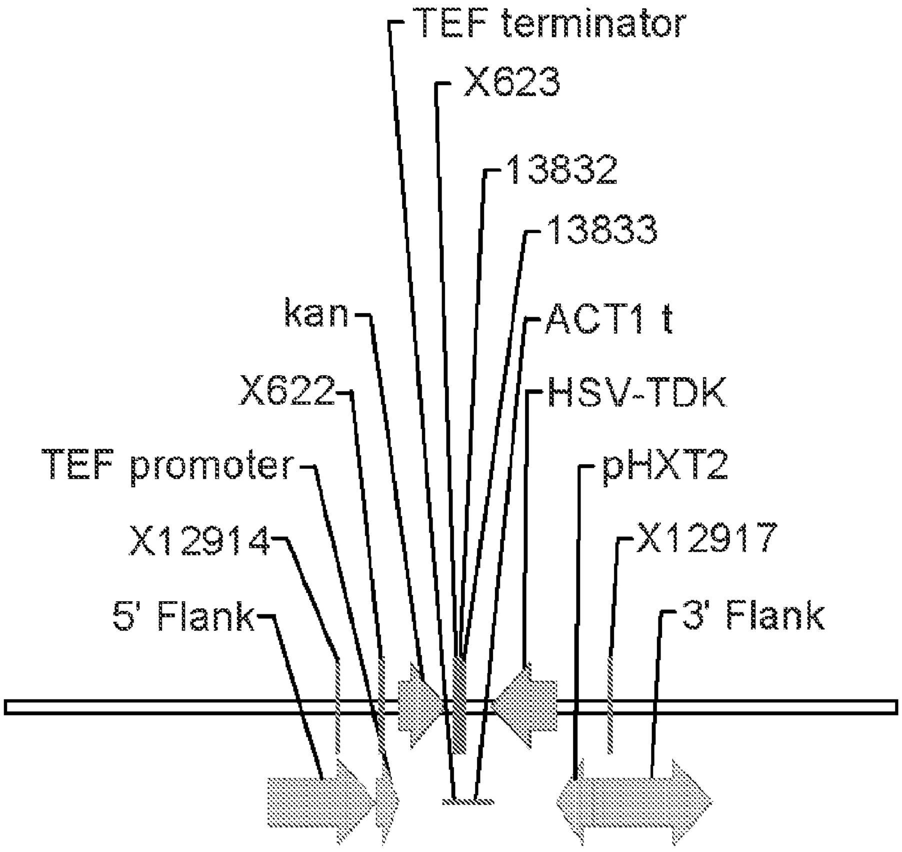

FIG. 39 depicts an integration design which deletes PDC5 and replaces a counter selective gene HSV-TDK and an antibiotic marker (Kan).

Figure 40:
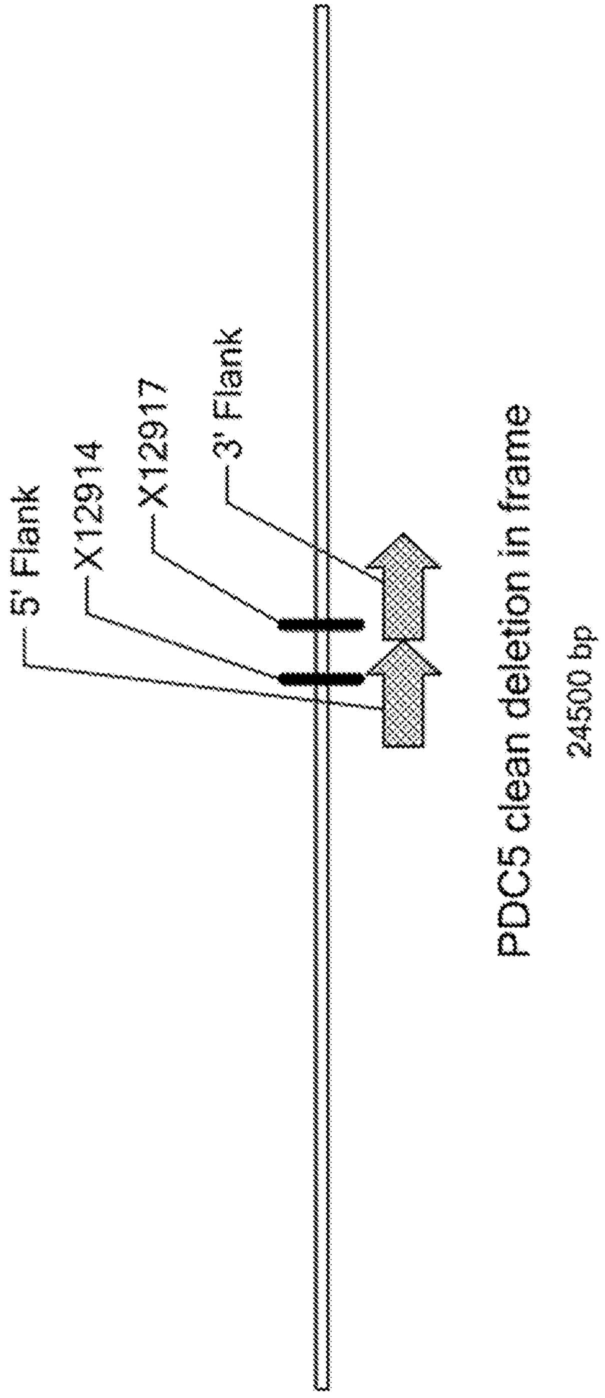

FIG. 40 depicts an integration design which removes the marker shown in FIG. 39 resulting in a clean deletion of PDC5.

Figure 41:
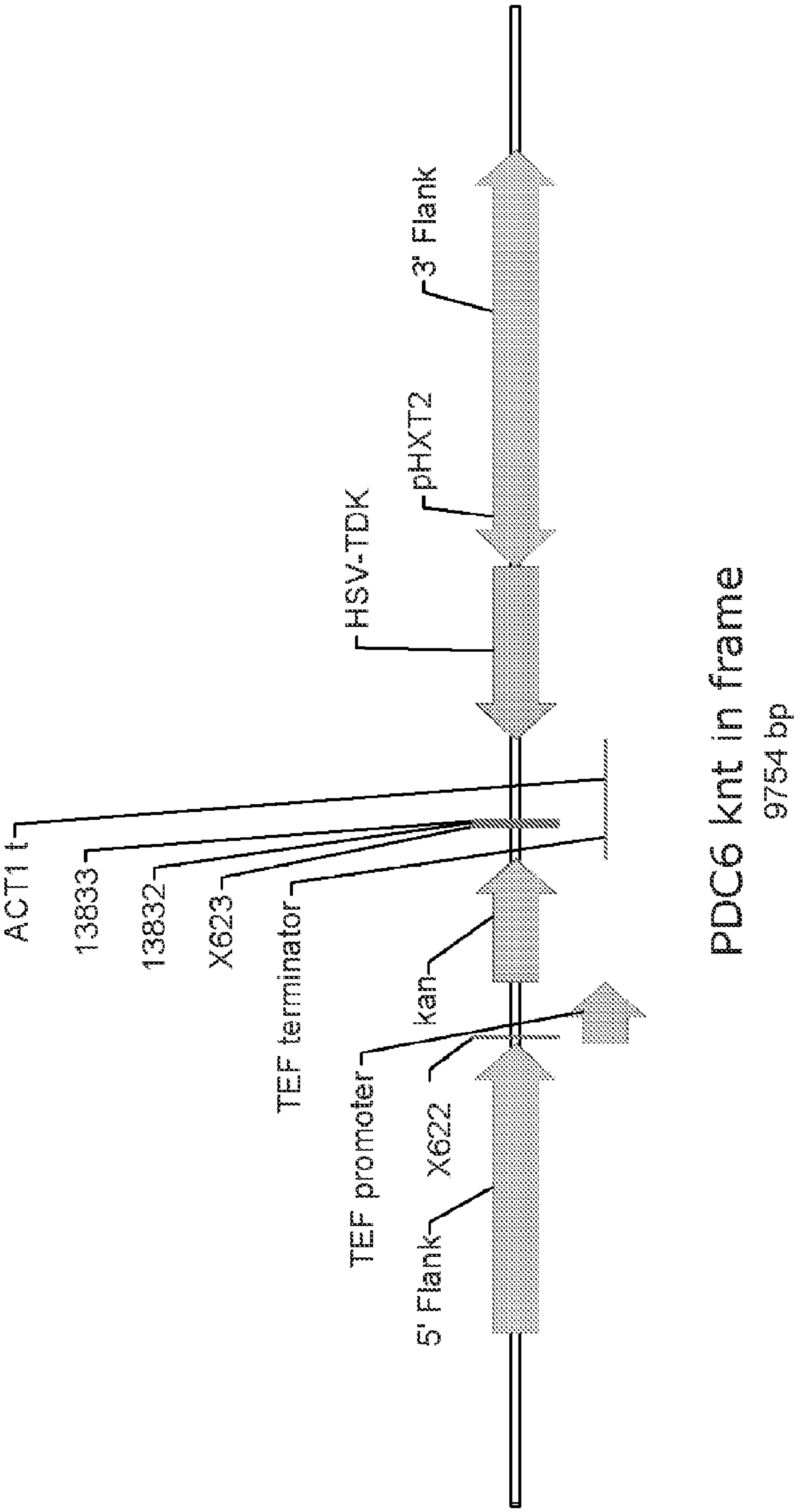

FIG. 41 depicts an integration design which deletes PDC6 and replaces a counter selective gene HSV-TDK and an antibiotic marker (Kan).

Figure 42:
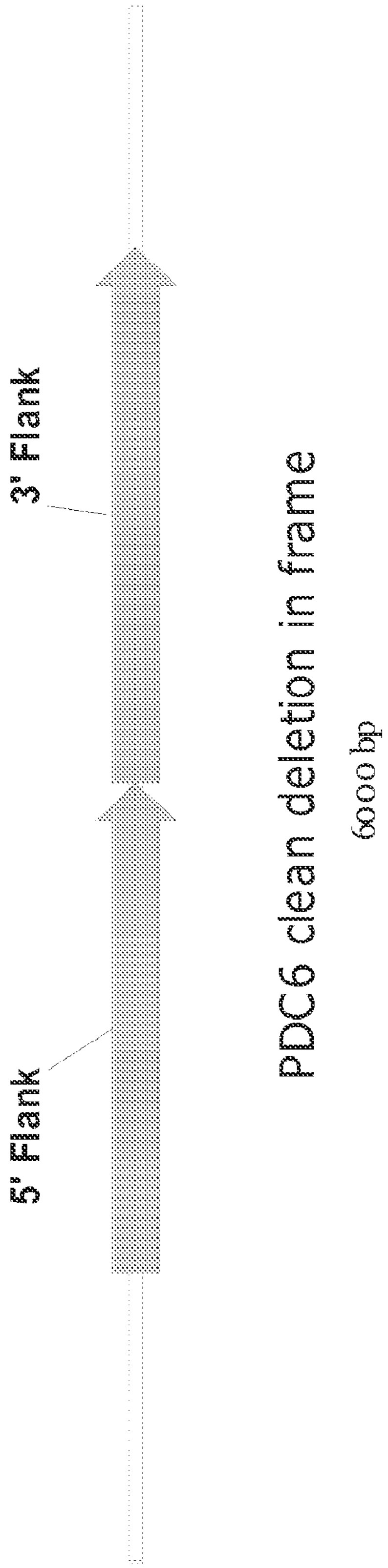

FIG. 42 depicts an integration design which removes the marker shown in FIG. 41 resulting in a clean deletion of PDC6.

Figure 43:
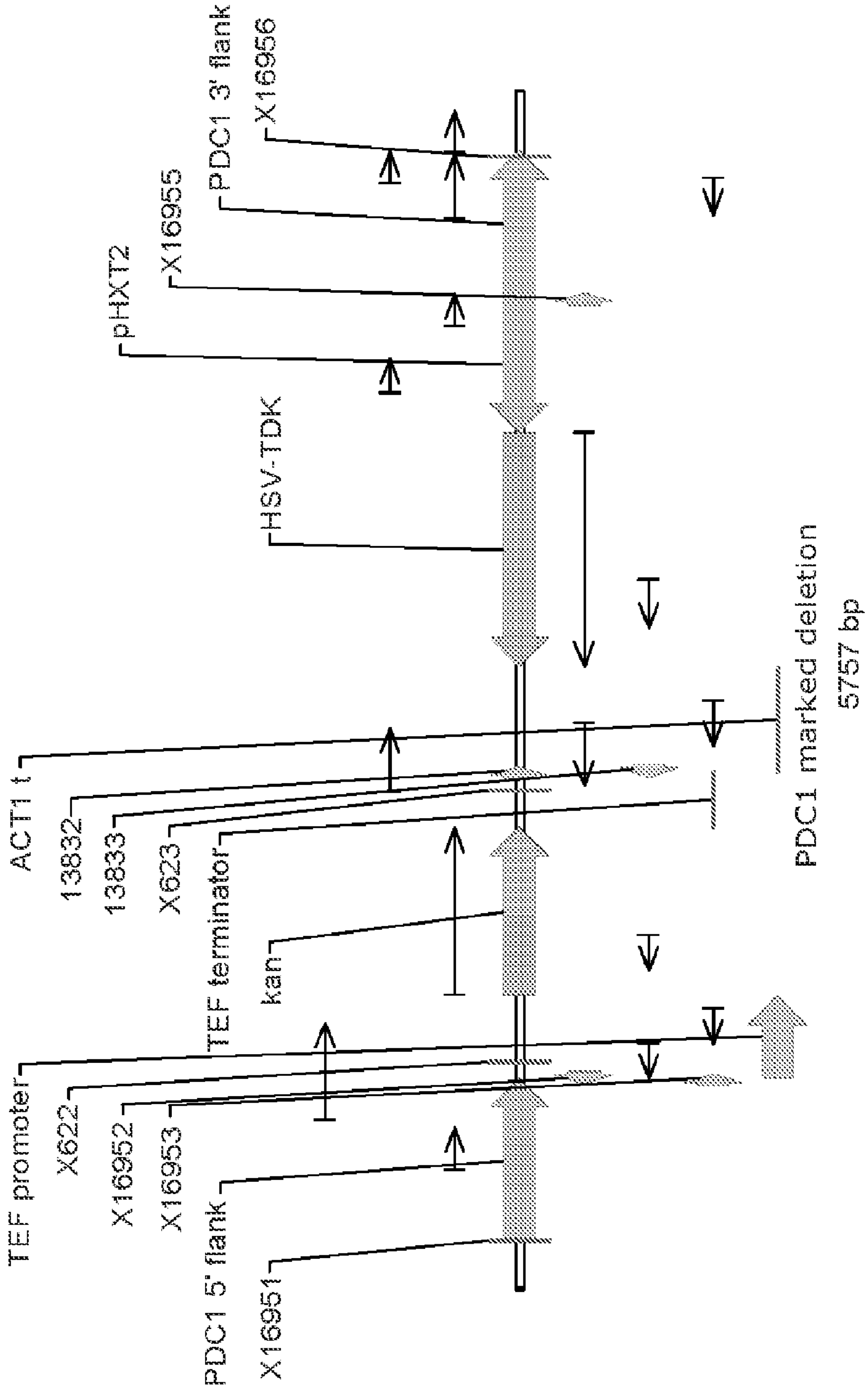

FIG. 43 depicts an integration design which deletes PDC1 and replaces it with a counter selective gene HSV-TDK and an antibiotic marker (Kan).

Figure 44:
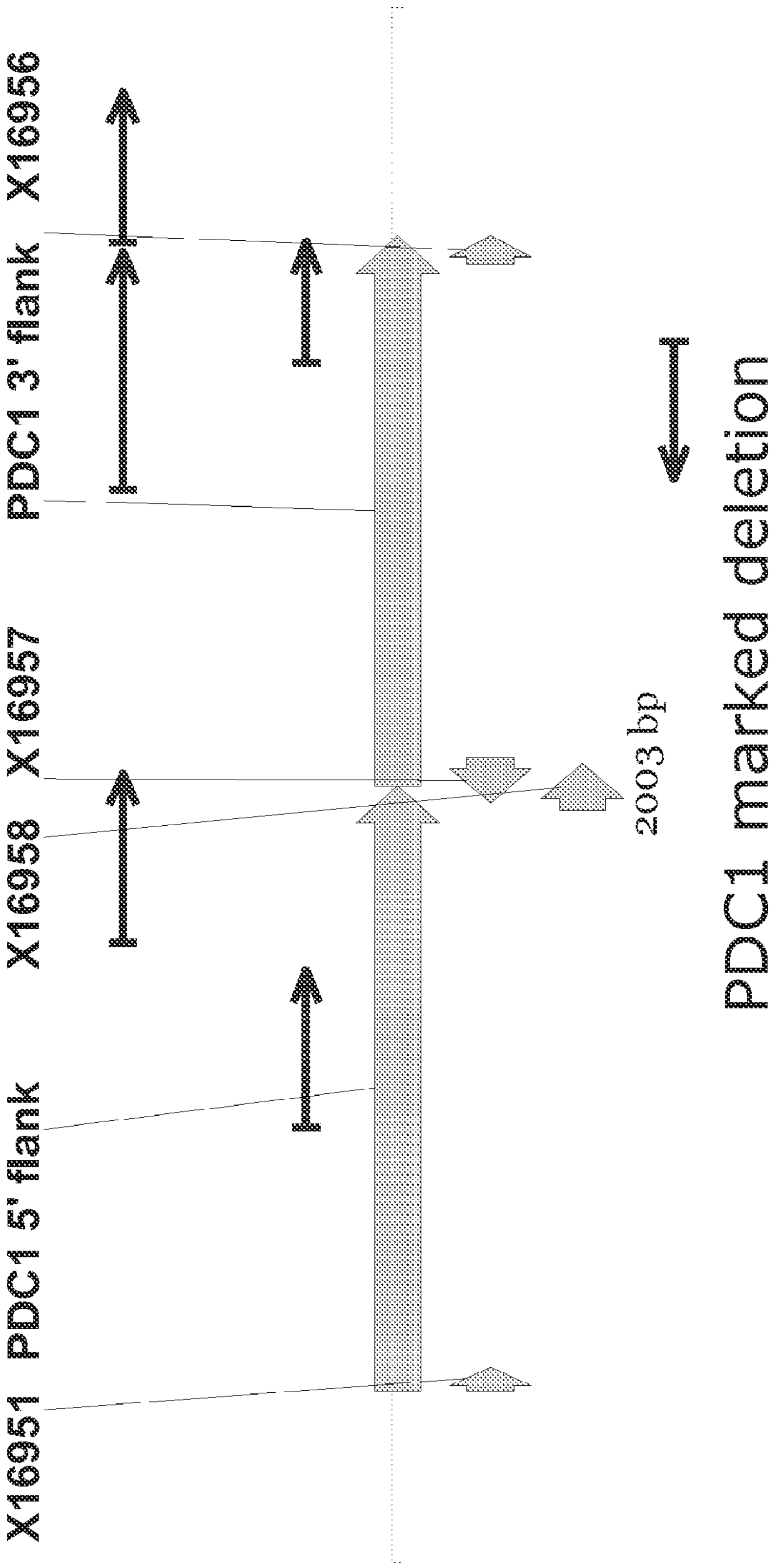

FIG. 44 depicts an integration design which removes the marker shown in FIG. 41 resulting in a clean deletion of PDC1.

Figure 45:
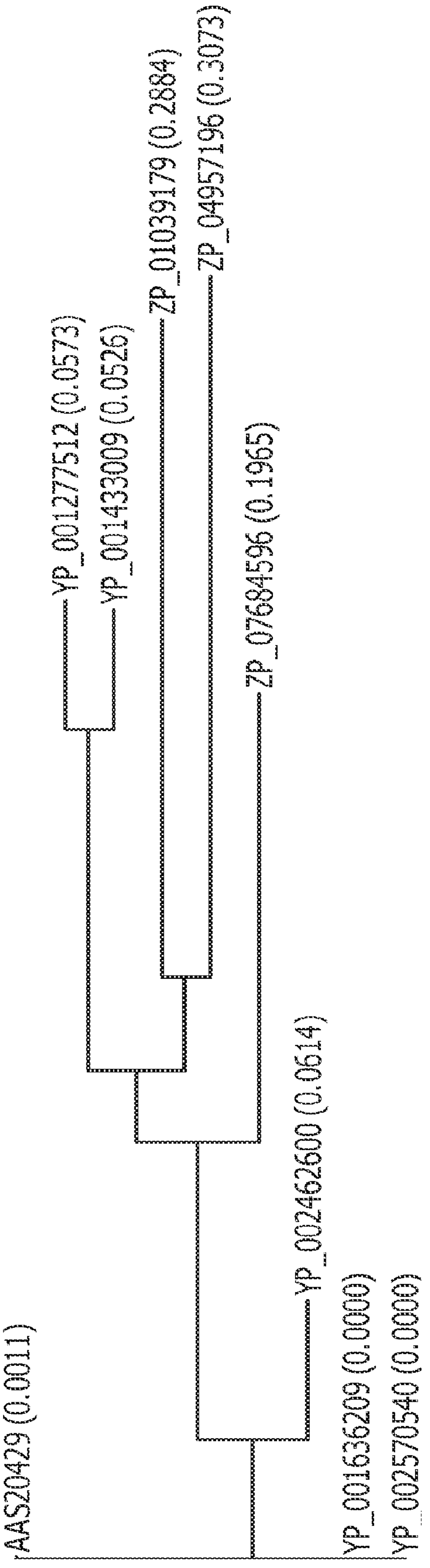

FIG. 45 is a phylogenetic tree depicting relatedness between bifunctional malonyl-CoA reductases from *C. aurantiacus, C. aurantiacus* J-10-fl, *Chloroflexus* sp. Y-400-fl, *C. aggregans* DSM 9485, *O. trichoides* DG6, *R. castenholzii* DSM 13941, *R. oseiflexus* sp. RS-1, *Erythrobacter* sp. NAP1, and *gamma proteobacterium* NOR51-B.

Figure 46:
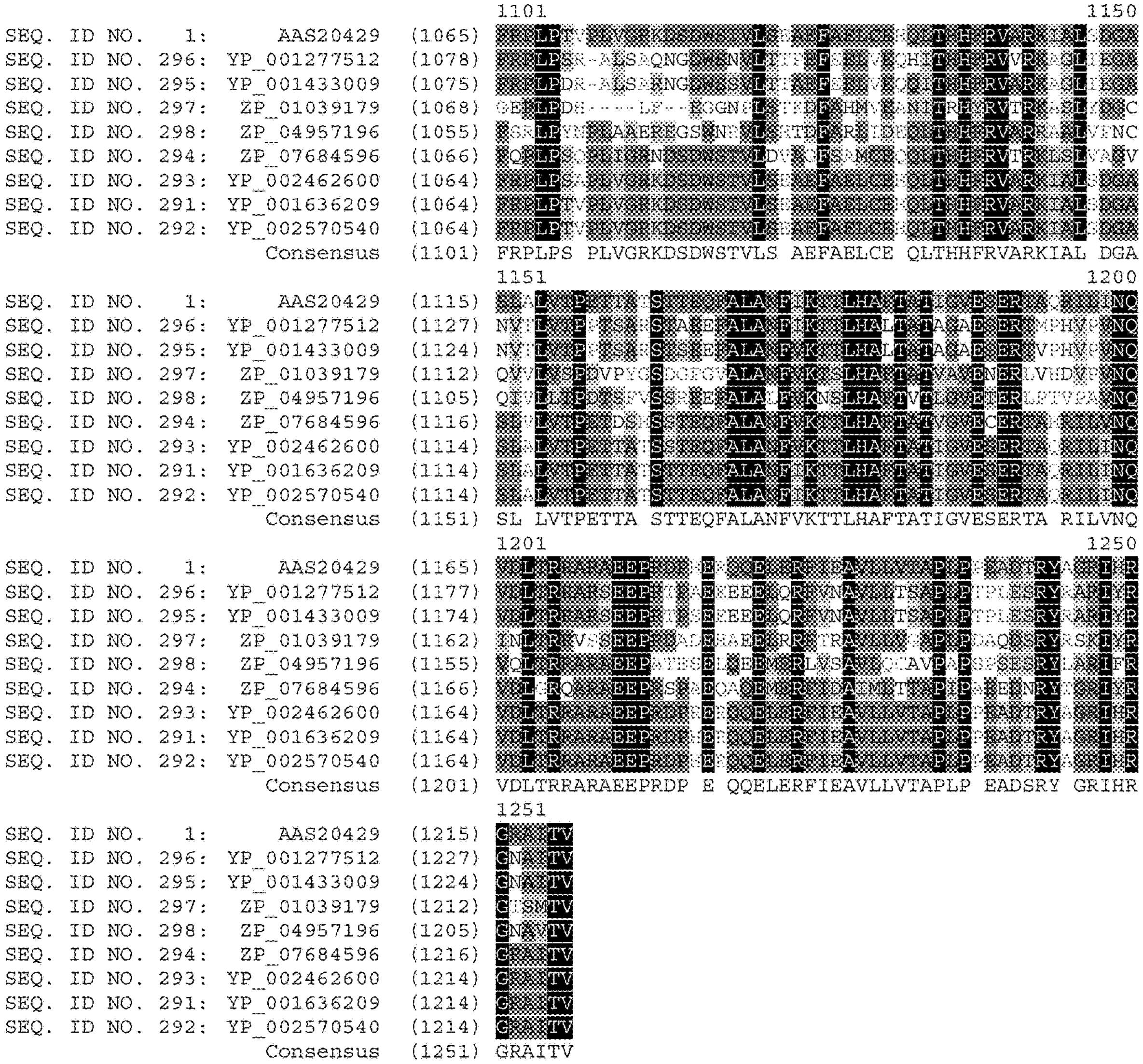

FIG. 46 is an alignment of bifunctional malonyl-CoA reductases from *C. aurantiacus, C. aurantiacus* J-10-fl, *Chloroflexus* sp. Y-400-fl, *C. aggregans* DSM 9485, *O. trichoides DG6, R. castenholzii* DSM 13941, *R. oseiflexus* sp. RS-1, *Erythrobacter* sp. NAP1, and *gamma proteobacterium* NOR51-B.

DETAILED DESCRIPTION OF THE INVENTION

Definitions

The indefinite articles "a" and "an" preceding an element or component of the invention are intended to include plurals of the element or component, e.g., one or at least one of the element or component, unless the context is such that only the singular form is intended.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "polypeptide" is intended to encompass a singular "polypeptide," as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the amino acids. Thus, peptides, dipeptides, tripeptides, oligopeptides, "protein," "amino acid chain," "enzyme," or any other term used to refer to a chain or chains of two or more amino acids, are included within the definition of "polypeptide," and the term "polypeptide" may be used instead of, or interchangeably with, any of these terms. A polypeptide may be derived from a natural biological source or produced by recombinant technology. It may be generated in any manner, including by chemical synthesis.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity of, the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type II secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

By "thermophilic" is meant an organism that thrives at a temperature of about 45° C. or higher.

By "mesophilic" is meant an organism that thrives at a temperature of about 20-45° C.

Certain embodiments of the present invention provide for the "insertion," (e.g., the addition, integration, incorporation, or introduction) of certain genes or particular polynucleotide sequences within the thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

In certain embodiments, the polynucleotide sequences of the invention are genetically modified such that the encoded enzyme is engineered to alter catalytic activity and/or alter substrate specificity to improve the conversion of a substrate to a product as compared to the native enzyme. In certain aspects, the genetic modification alters catalytic activity and/or substrate specificity to provide an encoded enzyme that converts a substrate to a product that is not catalyzed by the native enzyme in vivo, or is catalyzed at only minimal turnover. Techniques to genetically modify polynucleotides are known in the art and include, but are not limited to, alteration, insertion, and/or deletion of one or more nucleic acids in the polynucleotide. Such techniques to alter, insert, and/or delete nucleic acids include, but are not limited to, random, site-directed, or saturating mutagenesis.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "consolidated bioprocessing" or "CBP" is intended to include a processing strategy for cellulosic biomass that involves consolidating into a single process step, four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of fatty acids may be added to a mesophilic or a thermophilic organism.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

As used herein, the term "hydrocarbon" is intended to include compounds containing only carbon and hydrogen, such as aliphatic hydrocarbons and aromatic hydrocarbons. Examples of hydrocarbons include, but are not limited to, alkanes, alkenes, or alkynes.

As used herein, the term "hydrocarbon derivative" is intended to include compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

The term “carbohydrate source” is intended to include any source of carbohydrate including, but not limited to, biomass or carbohydrates, such as a sugar or a sugar alcohol. “Carbohydrates” include, but are not limited to, monosaccharides (e.g., glucose, fructose, galactose, xylose, arabinose, or ribose), sugar derivatives (e.g., sorbitol, glycerol, galacturonic acid, rhamnose, xylitol), disaccharides (e.g., sucrose, cellobiose, maltose, or lactose), oligosaccharides (e.g., xylooligomers, cellodextrins, or maltodextrins), and polysaccharides (e.g., xylan, cellulose, starch, mannan, alginate, or pectin).

As used herein, the term “microaerophilic” is intended to include conditions in which oxygen is present at lower concentrations than atmospheric oxygen content. A microaerophilic organism is one that requires a lower concentration of oxygen for growth than is present in the atmosphere. Microaerophilic conditions include those in which oxygen is present at less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, or less than about 99% of atmospheric oxygen concentration.

As used herein, the term “malonyl-CoA derived product” or “malonyl-CoA derived bioproduct” is intended to include those products that are synthesized from, derived from, or are used as an intermediate in their synthesis from, malonyl-CoA. The term includes products such as hydrocarbons, hydrocarbon derivatives, polyketides, organic acids, including but not limited to adipic acid and 3-hydroxyproprionate, and any other products from which malonyl-CoA can serve as a precursor.

Metabolic Pathway Engineering

7J Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl CoA), which then enters the tricarboxylic acid cycle (TCA), which in turn generates synthetic precursors, $CO_2$ and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Biomass

Biomass can include any type of biomass known in the art or described herein. The terms “lignocellulosic material,” “lignocellulosic substrate,” and “cellulosic biomass” mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms “hemicellulosics,” “hemicellulosic portions,” and “hemicellulosic fractions” mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, *miscanthus*, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and *miscanthus*; or combinations thereof.

Paper sludge is also a viable feedstock for lactate or acetate production. Paper sludge is solid residue arising from pulping and paper-making, and is typically removed from process wastewater in a primary clarifier. At a disposal cost of \$30/wet ton, the cost of sludge disposal equates to \$5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the “Xylose Reductase-Xylitol Dehydrogenase” or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor NAD+. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene. See Jeppsson et al., *Appl. Environ. Microbiol.* 68:1604-09 (2002). Since the pentose phosphate pathway produces additional NADPH during metabolism, limiting this step will help to correct the already evident imbalance between NAD(P)H and NAD+ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production. See Karhumaa et al., *Microb Cell Fact.* 6:5 (Feb. 5, 2007); see also International Publication No. WO2006/009434, incorporated herein by reference in its entirety.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; B.C. 5.1.3.4) to sequentially convert L-arabinose to D-xylulose-5-phosphate through L-ribulose and L-ribulose 5-phosphate. See, e.g., Sa-Nogueira I., et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S., et al., *J Biol. Chem.* 281:2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD(P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at the website of National Microbial Pathogen Data Resource (NMPDR) nmpdr.org/FIG/wiki/rest.cgi/NmpdrPlugin/SeedViewer?page=Subsystems;subsystem=L-Arabinose_utilization, visited Jul. 29, 2011, which is incorporated by reference herein in its entirety.

AraC protein regulates expression of its own synthesis and the other genes of the Ara system. See Schleif, R., *Trends Genet.* 16(12):559-65 (2000). In *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J. Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, or a proton symporter. Additional arabinose transporters include those identified from *K marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Vectors and Host Cells

The present invention also relates to vectors which include genes encoding for enzymes of the present invention, as described above, as well as host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The DNA sequence in the expression vector is operatively associated with an appropriate expression control sequence(s) (promoter) to direct mRNA synthesis. Any suitable promoter to drive gene expression in the host cells of the invention can be used. Additionally, promoters known to control expression of genes in prokaryotic or lower eukaryotic cells can be used. The expression vector also contains a ribosome binding site for translation initiation and a transcription terminator. The vector can also include appropriate sequences for amplifying expression, or can include additional regulatory regions.

The vector containing the appropriate selectable marker sequence as used herein, as well as an appropriate promoter or control sequence, can be employed to transform an appropriate thermophilic host to permit the host to express the protein.

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Aspergillus, Bacillus, Escherichia, Kluyveromyces, Pichia, Rhodococcus, Saccharomyces* and *Streptomyces.*

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, Issatchenkia *orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K marxianus, K. blattae, K. phaffii, K. yarrowii, K. aestuarii, K. dobzhanskii, K. wickerhamii K. thermotolerans*, or *K. waltii* host cell. In one embodiment, the host cell is a *K. lactis*, or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M., et al., *FEMS Yeast Res.* 4: 655-64 (2004); Kuyper M., et al., *FEMS Yeast Res.* 5:399-409 (2005); and Kuyper M., et al., *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g., from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimize xylitol production.

The host cells can contain antibiotic markers or can contain no antibiotic markers.

Aspects of the present invention relate to the use of thermophilic and thermotolerant microorganisms as hosts. Their potential in process applications in biotechnology stems from their ability to grow at relatively high temperatures with attendant high metabolic rates, production of physically and chemically stable enzymes, elevated yields of end products, and lower susceptibility to microbial contamination. Major groups of thermophilic bacteria include eubacteria and archaebacteria. Thermophilic eubacteria include: phototropic bacteria, such as cyanobacteria, purple bacteria and green bacteria; Gram-positive bacteria, such as *Bacillus, Clostridium*, Lactic acid bacteria, and *Actinomyces*; and other eubacteria, such as *Thiobacillus*, Spirochete, *Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Saphylothermus, Desulfurococcus, Archaeoglobus*, and *Methanopyrus*.

Some examples of thermophilic or mesophilic (including bacteria, procaryotic microorganism, and fungi), which may be suitable for the present invention include, but are not limited to: *Clostridium thermosulfurogenes, Clostridium cellulolyticum, Clostridium thermocellum, Clostridium thermohydrosulfuricum, Clostridium thermoaceticum, Clostridium thermosaccharolyticum, Clostridium tartarivorum, Clostridium thermocellulaseum, Clostridium phytofermentans, Clostridium straminosolvens, Thermoanaerobacterium thermosaccarolyticum, Thermoanaerobacterium saccharolyticum, Thermobacteroides acetoethylicus, Thermoanaerobium brockii, Methanobacterium thermoautotrophicum, Anaerocellum thermophilium, Pyrodictium occultum, Thermoproteus neutrophilus, Thermofilum librum, Thermothrix thioparus, Desulfovibrio thermophilus, Thermoplasma acidophilum, Hydrogenomonas thermophilus, Thermomicrobium roseum, Thermus flavas, Thermus ruber, Pyrococcus furiosus, Thermus aquaticus, Thermus thermophilus, Chloroflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium bijahensi, Oscillatoria filformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus lichenformis, Bacillus pamilas, Bacillus macerans, Bacillus circulans, Bacillus laterosporus, Bacillus brevis, Bacillus subtilis, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogena, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Clostridium clariflavum, E. coli* strain B, strain C, strain K, strain W, *Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Lactobacillus thermophilus, Lactobacillus bulgaricus, Lactococcus lactis*, variants thereof, and/or progeny thereof.

In particular embodiments, the present invention relates to thermophilic bacteria selected from the group consisting of *Clostridium cellulolyticum, Clostridium thermocellum*, and *Thermoanaerobacterium saccharolyticum.*

In certain embodiments, the present invention relates to thermophilic bacteria selected from the group consisting of *Fervidobacterium gondwanense, Clostridium thermolacticum, Moorella* sp., and *Rhodothermus marinus.*

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii*, variants thereof, and progeny thereof.

In certain embodiments, the present invention relates to microorganisms of the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis*, variants thereof, and progeny thereof.

In certain embodiments, the present invention relates to mesophilic bacteria selected from the group consisting of *Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens; Alkalibacter saccharofomentans*, variants thereof, and progeny thereof. In certain embodiments, the present invention relates to mesophilic bacteria selected from the group consisting of *Escherichia coli, E. coli* strain B, strain C, strain K, strain W, *Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii*, variants thereof, and progeny thereof.

Codon-Optimized Polynucleotides

The polynucleotides encoding heterologous polypeptides can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CCT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | AAT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the website of Codon Usage Database kazusa.or.jp/codon/ (visited Jul. 30, 2010), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | GAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |

TABLE 2-continued

Codon Usage Table for *Saccharomyces cerevisiae* Genes

| Amino Acid | Codon | Number | Frequency per hundred |
|---|---|---|---|
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, WI, the backtranslation function in the VectorNTI Suite, available from InforMax, Inc., Bethesda, MD, and the "backtranslate" function in the GCG-Wisconsin Package, available from Accelrys, Inc., San Diego, CA In addition, various resources are publicly available to codon-optimize coding region sequences, e.g., the "backtranslation" function at the website of Eurofins Genomics entelechon.com/bioinformatics/backtranslation.php?lang=eng (visited Jul. 30, 2010) and the "backtranseq" function available at the website of EMBOSS explorer emboss.bioinformatics.nl/cgi-bin/emboss/backtranseq (visited Jul. 30, 2010). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they are ligated together and cloned into a standard bacterial cloning vector, for example, a TOPO® vector available from Invitrogen Corporation, Carlsbad, CA The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The disadvantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Hydrocarbon Synthesis

Hydrocarbons consist of carbon and hydrogen and include aliphatic hydrocarbons and aromatic hydrocarbons. Non-limiting examples of hydrocarbons include, alkanes, alkenes, alkynes, and hydrocarbon derivatives. The latter of which includes those compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

Hydrocarbons produced by the recombinant microorganisms and methods of the invention include carbon backbones of at least 4 carbons and up to 40 or more carbons. Such chain lengths are referred to as long-chain hydrocarbons. In certain aspects, the chain lengths include $C_6$-$C_{36}$; $C_8$-$C_{32}$; $C_{10}$-$C_{28}$; $C_{12}$-$C_{24}$; $C_{14}$-$C_{22}$; or $C_{16}$-$C_{20}$. In some embodiments, the chain length comprises a carbon backbone of $C_{12}$, $C_{14}$, $C_{16}$, $C_{18}$, $C_{20}$, and/or $C_{22}$. In further embodiments, the chain length comprises a carbon backbone of $C_{16}$.

To produce hydrocarbons and hydrocarbon derivatives according to the invention, the following stoichiometric equations provide examples of an electron-balanced process.

Fatty Acid: $2C_6H_{12}O_6 \rightarrow C_8H_{16}O_2+4CO_2+2H_2O+2H_2$

Fatty Alcohol: $2C_6H_{12}O_6 \rightarrow C_8H_{18}O \rightarrow 4CO_2+3H_2O$

N-alkane: $2C_6H_{12}O_6+O_2 \rightarrow C_7H_{16}+5CO_2+4H_2O$

Wax ester: $4C_6H_{12}O_6 \rightarrow C_{16}H_{32}O_2+8CO_2+6H_2O+2H_2$

Figure 6:
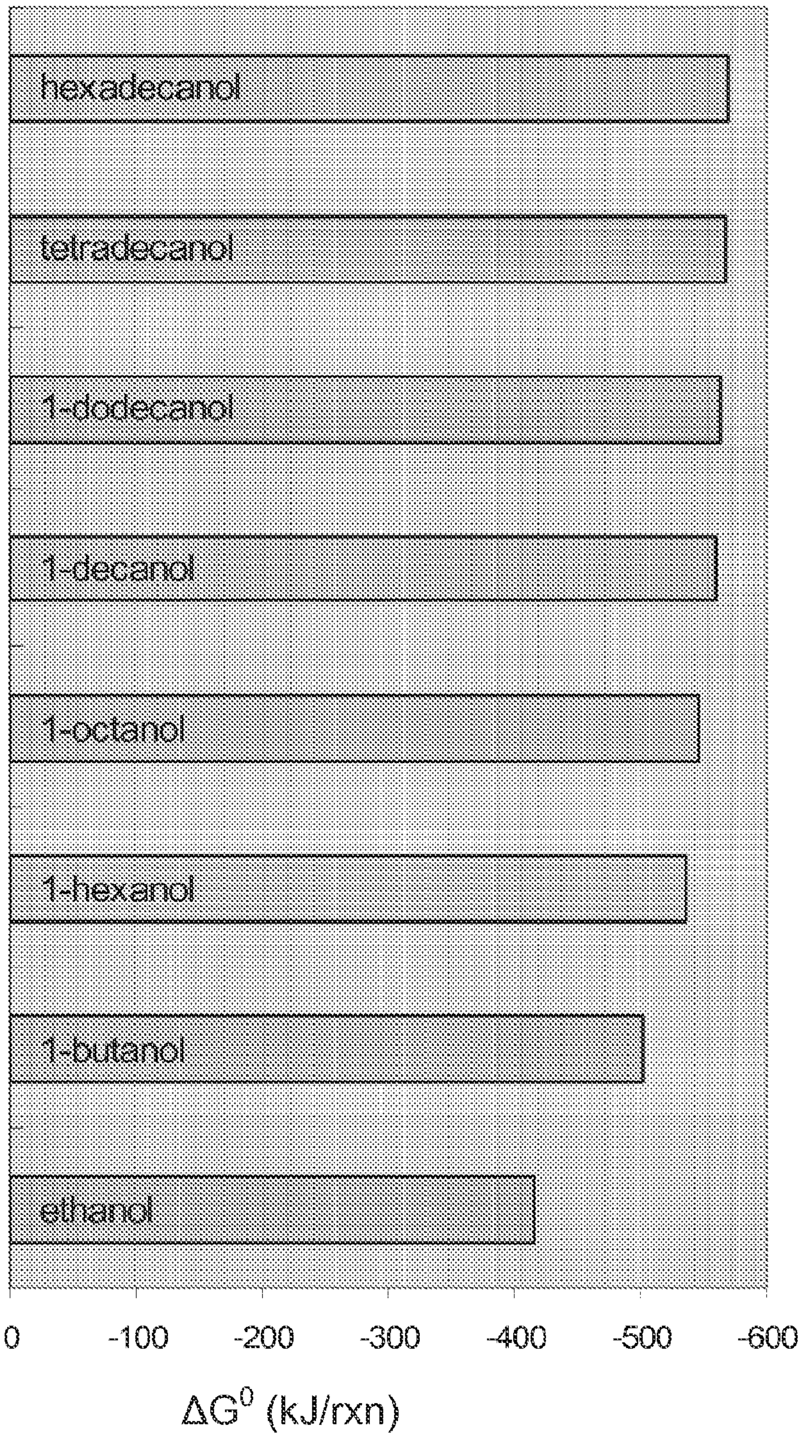
FIG. 6 depicts the Gibbs free energy change for the conversion of glucose into the specified alcohols.

The synthesis of hydrocarbons becomes more thermodynamically favorable as the chain length increases (see FIG. 6 (values derived from Stull et al., The Chemical Thermodynamics of Organic Compounds, Wiley, New York, NY (1969))). For example, the stoichiometry for the production of a fatty alcohol proceeds according to the following equation, where n is the number of glucose molecules and x is the number of carbon atoms in the saturated fatty alcohol.

$$n\ \text{Glucose} \rightarrow (4n/x)C_x\text{alcohol}+2nCO_2+n[2-(4/x)]H_2O$$

As can be seen, the number of $H_2O$ molecules generated increases as chain length increases. This helps contribute to a more overall thermodynamically favorable reaction. Gibbs free energy changes per 2 glucose molecules (n=2) for specific alcohols are shown in FIG. 6.

The Gibbs free energy change for the production of heptane, accounting for the requirement of elemental oxygen for the conversion of a fatty aldehyde to alkane by aldehyde decarbonylase (Li et al., *JACS,* 133:6158-6161 (2011) is:

$$2\ \text{Glucose}+O_2 \rightarrow 1\ \text{heptane}+5CO_2+4H_2O$$

$$\Delta G^o=-1044.0\ \text{kJ/reaction}$$

The Gibbs free energy change for the production of octanal is:

$$2\ \text{Glucose} \rightarrow 1\ \text{octanal}+4CO_2+3H_2O+H_2$$

$$\Delta G^o=-512.2\ \text{kJ/reaction}$$

Other sugars, including, but not limited to, xylose or arabinose, have a similar Gibbs free energy change as glucose. While some steps in the production of hydrocarbons or hydrocarbon derivatives can be slightly unfavorable, e.g., aldolase or triosephosphate isomerase in glycolysis, the overall reaction will be thermodynamically favorable when the final steps include chain termination steps, e.g., acid, aldehyde, alcohol, and/or ester formation. The very low aqueous concentrations of the final hydrocarbons or hydrocarbon derivatives will further drive the thermodynamic equilibrium towards product formation.

Polyketide Synthesis

Polyketides are a structurally and functionally diverse family of natural products that possess a wide range of biological and pharmacological properties. Such properties include, but are not limited to, antibiotic, antitumor, antifungal, and immunosuppressive activities. Jenke-Kodama, H., et al., *Mol. Biol. Evol.* 22(10):2027-39 (2005). Polyketides are synthesized as secondary metabolites in bacteria, fungi, plants, and animals by different classes of polyketide synthases (PKS), which resemble the classes of fatty acid synthases. Id Polyketide synthesis proceeds by the addition or condensation of different functional groups to an acyl-ACP chain. See FIG. 21. And while fatty acid elongation includes four enzymatic steps per two carbon chain extension (KS (ketosynthase), KR (ketoreductase), DH (dehydratase), ER (enoyl reductase)) (FIG. 21B), PKS elongation can include a combination of enzymatic activities, e.g., (KS), (KS, KR), (KS, KR, DH), or (KS, KR, DH, ER), at each step (FIG. 21A). Malonyl-CoA produced by the recombinant microorganisms and pathways of the invention can be used as a metabolic precursor for polyketides.

Organic Acid Synthesis

Malonyl-CoA produced by the recombinant microorganisms and pathways of the invention can be used as a metabolic precursor for number of bioproducts. For example, the organic acid 3-hydroxypropionic acid ("3-HP"), also known as 3-hydroxypropanoate, is used in the production of various industrial chemicals such as renewable polyesters, acrylic acid, malonic acid, and co-polymers with lactic acid. Although 3-HP can be produced by organic chemical synthesis, it is desireable to use bio-alternative methods that allow for more cost effective, efficient, and renewable production. While some microorganisms are known to produce 3-HP (see, e.g., WO 01/16346; WO 02/42418; US 2011/0144377; US 2011/0125118, each of which is incorporated by reference herein), few biological systems have been developed that would result in its efficient production. Production of malonyl-CoA at high yield via transcarboxylase in an anaerobic process would allow for efficient high yield 3-hydroxypropionic acid production using a suitable enzymatic pathway from malonyl-CoA to 3-hydroxypropionic acid and a suitable redox system to generate NADPH during carbohydrate deconstruction. See, e.g., redox systems are "F" and "G" in Table 10.

Enzymes employed for the production of 3-HP by the recombinant microorganisms and methods of the invention include 1) malonyl-CoA reductase (EC 1.2.7.5), 2) 3-hydroxypropionate dehydrogenase (EC 1.1.1.59 and EC 1.1.1.298), and 3) a bifunctional enzyme which harbors aldehyde dehydrogenase and alcohol dehydrogenase domains (Hugler et al., *J. Bacteriol.* 184:2402-2410 (2002)).

The following example pathways demonstrate the production of 3-HP from a malonyl-CoA metabolic precursor using the above-referenced enzymes:

1) Malonyl CoA Reductase (EC 1.2.1.75)

Malonate semialdehyde+coenzyme A+NADP(+) <=>malonyl-CoA+NADPH 2a) 3-Hydroxypropionate Dehydrogenase (EC 1.1.1.59

3-hydroxypropanoate+NAD(+)<=>Malonate semialdehyde+NADH 2b) 3-Hydroxypropionate Dehydrogenase (EC 1.1.1.298)

3-hydroxypropanoate+NADP(+)<=>Malonate semialdehyde+NADPH 3) bifunctional dehydrogenase (aldehyde-alcohol) malonyl-CoA+NADPH+$H^+$→malonate semialdehyde+$NADP^+$+CoA malonate semialdehyde (3-oxopropanoate)+NADPH+$H^+$ →3-hydroxypropionate+$NADP^+$ The sequence of a malonyl-CoA reductase from *Chloroflexus aurantiacus* is provided below:

*C. aurantiacus* Malonyl-CoA Reductase (amino acid sequence; >gi|42561982|gb|AAS20429.1)
(SEQ ID NO: 1)

```
MSGTGRLAGKIALITGGAGNIGSELTRRFLAEGATVIISGRNRAKLTALA
ERMQAEAGVPAKRIDLEVMDGSDPVAVRAGIEAIVARHGQIDILVNNAGS
AGAQRRLAEIPLTEAELGPGAEETLHASIANLLGMGWHLMRIAAPHMPVG
SAVINVSTIFSRAEYYGRIPYVTPKAALNALSQLAARELGARGIRVNTIF
PGPIESDRIRTVEQRMDQLKGRPEGDTAHHFLNTMRLCRANDQGALERRE
PSVGDVADAAVFLASAESAALSGETIEVTHGMELPACSETSLLARTDLRT
IDASGRTTLICAGDQIEEVMALTGMLRTCGSEVIIGERSAAALAQFEQAV
NESRRLAGADFTPPIALPLDPRDPATIDAVFDWGAGENTGGIHAAVILPA
TSHEPAPCVIEVDDERVLNFLADEITGTIVIASRLARYWQSQRLTPGARA
RGPRVIFLSNGADQNGNVYGRIQSAAIGQLIRVWRHEAELDYQRASAAGD
HVLPPVWANQIVRFANRSLEGLEFACAWTAQLLHSQRHINEITLNIPANI
SATTGARSASVGWAESLIGLHLGKVALITGGSAGIGGQIGRLLALSGARV
MLAARDRHKLEQMQAMIQSELAEVGYTDVEDRVHIAPGCDVSSEAQLADL
VELTLSAFGTVDYLINNAGIAGVEEMVIDMPVEGWRHTLFANLISNYSLM
RKLAPLMKKQGSGYILNVSSYFGGEKDAAIPYPNRADYAVSKAGQRAMAE
VFARFLGPEIQINAIAPGPVEGDRLRGTGERPGLFARRARLILENKRLNE
LHAALIAAARTDERSMHELVELLLPNDVAALEQNPAAPTALRELARRFRS
EGDPAASSSSALLNRSIAAKLLARLHNGGYVLPADIFANLPNPPDPFFTR
AQIDREARKVRDGIMGMLYLQRMPTEFDVAMATVYYLADRNVSGETFHPS
GGLRYERTPTGGELFGLPSPERLAELVGSTVYLIGEHLTEHLNLLARAYL
ERYGARQVVMIVETETGAETMRRLLHDHVEAGRLMTIVAGDQIEAAIDQA
ITRYGRPGPVVCTPFRPLPTVPLVGRKDSDWSTVLSEAEFAELCEHQLTH
HFRVARKIALSDGASLALVTPETTATSTTEQFALANFIKTTLHAFTATIG
VESERTAQRILINQVDLTRRARAEEPRDPHERQQELERFIEAVLLVTAPL
PPEADTRYAGRIHRGRAITV
```

Additional malonyl-CoA reductase enzyme examples include, but are not limited to, those from *Chloroflexus* sp., *Oscillochloris* sp., *Roseiflexus* sp., and marine *gamma proteobacterium*. See, e.g., Hügler et al., *J. Bacteriol.* 184: 2402-2410 (2002); Rathnasingh, C., et al., *Biotech. Bioeng.* 104(4) (2009); Rathnasingh, C., et al., "Production of 3-hydroxypropionic acid via malonyl-CoA pathway using recombinant *Escherichia coli* strains," *J Biotech.* (Epub Jun. 23, 2011). A phylogenctic tree and an alignment of several malonyl-CoA reductase enzymes is shown in FIGS. 45 and 46. These alignments were made using malonyl-CoA reductase enzymes from *Chloroflexus aurantiacus* (GenBank Accession No. AAS20429; SEQ ID NO:1); *Chloroflexus aurantiacus* J-10-fl (GenBank Accession No. YP_001636209; SEQ ID NO:291); *Chloroflexus* sp. Y-400-fl (GenBank Accession No. YP_002570540; SEQ ID NO:292); *Chloroflexus aggregans* DSM 9485 (GenBank Accession No. YP_002462600; SEQ ID NO:293); *Oscillochloris trichoides* DG6 (GenBank Accession No. ZP_07684596; SEQ ID NO:294); *Roseiflexus castenholzii*

DSM 13941 (GenBank Accession No. YP_001433009; SEQ ID NO:295); *Roseiflexus* sp. RS-1 (GenBank Accession No. YP_001277512; SEQ ID NO:296); *Erythrobacter* sp. NAP1 (GenBank Accession No. ZP_01039179; SEQ ID NO:297); *gamma proteobacterium* NOR51-B (GenBank Accession No. ZP_04957196 SEQ ID NO:298).

Another product that can be produced from a malonyl-CoA metabolic precursor, and/or as an end-product of the fatty acid syntheses described herein, is adipic acid. Adipic acid is a six-carbon dicarboxylic acid, which is used as a chemical intermediate in the synthesis of polymers, such as polyamides (nylons), polyurethanes, and plasticizers, as well as a food acidulant. Chemical synthesis of adipic acid uses various noxious chemicals for oxidation and/or hydration of ketoalcohols or cyclohexanes, which present environmental safety and energy input concerns. Engineering a biological system to produce adipic acid from a carbohydrate source can avoid these concerns and provide a renewable means for producing adipic acid-derived products.

Attempts at the bioproduction of adipic acid have used alternative synthetic pathways, catalysts, substrates, intermediates, and/or recombinant microorganisms. See, e.g., WO2011/003034, WO1995/007996, WO2009/151728, and WO2010/144862, each of which is incorporated by reference herein. In particular, WO2011/003034 discloses the synthesis of adipic acid from, inter alia, fatty acids, fatty alcohols, alkanes, and oils, but does not, however, disclose the synthesis of adipic acid from a malonyl-CoA metabolic precursor. The pathways of the invention for producing malonyl-CoA can be used to produce a $C_{12}$ fatty acid or fatty alcohol, which can be further engineered to produce adipic acid via omega oxidation using. See, e.g., FIGS. 23 and 24 ("At" is *Arabidopsis thaliana*; "Ce" is *Candida cloacae*); WO2011/003034; Vanhanen S., et al., *J. Biol. Chem.* 275 (6):4445-52 (2000); Picataggio, S., et al., *Bio/Technology* 10(8):894-98 (1992). To accommodate the oxidation of the fatty acid or fatty alcohol, either a facultative anaerobe (e.g., *E. coli* or *S. cerevisiae*) can be engineered to include an adipic acid pathway that can be switched to aerobic conditions after a pool of malonyl-CoA or fatty acids/alcohols is synthesized, or a facultative anaerobe or aerobe comprising an adipic acid pathway can be engineered to use in tandem or in series with a recombinant microorganism of the invention that produces fatty acids or fatty alcohols.

To generate adipic acid from a fatty acid or fatty alcohol using omega oxidation pathway, enzymes such as, e.g., a mixed function oxidase to hydroxylate the omega carbon and alcohol and aldehyde dehydrogenases to oxidate the introduced hydroxyl group, can be used.

Phosphoenolpyruvate Carboxykinase

Figure 1A:
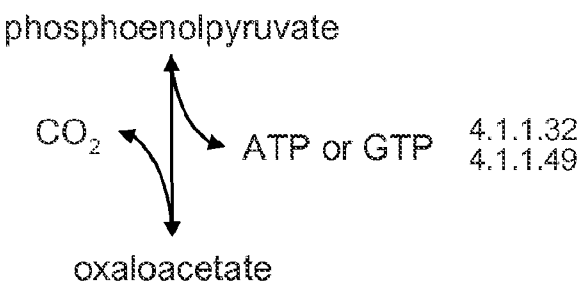
FIG. 1A depicts the conversion of phosphoenolpyruvate to oxaloacetate catalyzed by an enzyme from EC 4.1.1.32 or 4.1.1.49.

Phosphoenolpyruvate carboxykinase (PEPCK) includes those enzymes that catalyze the conversion of phosphoenolpyruvate (PEP) to oxaloacetate (see FIG. 1A) and that correspond to Enzyme Commission Number 4.1.1.49 or 4.1.1.32. See, e.g., Matte, A., et al., *J. Biol. Chem.* 272: 8105-08 (1997). The reaction is reversible and is used in succinic acid producing bacteria to convert PEP to oxaloacetate. *E. coli* can mutate to use PEPCK when flux is directed primarily to succinic acid. PEPCK requires $Mg^{2+}$ as a co-factor. A number of ATP and GTP using enzymes have been described, including, e.g., a GTP-utilizing PEPCK in *C. thermocellum* and ATP-utilizing PEPCK in *T. saccharolyticum, T tengcongensis, E. coli* and *S. cerevisiae.*

PEPCKs have been classified according to nucleotide specificity, i.e., those that are ATP-dependent and those that are GTP- or ITP-dependent. Within each group, the species show significant amino acid sequence identity, in the range of 40-80%, and share similar nucleotide and oxaloacetate binding "consensus motifs" between the groups, including key conserved residues at or near the active sites. See Matte, A., et al., *J. Biol. Chem.* 272:8105-08 (1997). Additional structural characterizations have been described in, e.g., Matte, A., et al., *J. Biol. Chem.* 272:8105-08 (1997). Examples of PEPCK sequences include:

*C. thermocellum* PEPCK (GTP)
>Cthe_2874

(SEQ ID NO: 2)

atgacatcaacaaacatgacaaaaaacaaaaaactgctggattgggttaaggaaatggctgaaatgtgtcagCctgatgaaattt attggtgcgatggttcggaggaagaaaatgagcgcttgataaagttgatggtggattcaggtttggctacgcctttgaatcctgaa aagcgacctggatgttatctcttccgcagcgatccgtccgacgttgcccgtgttgaggacagaacttttattgcatccaaaaccaa agaagatgcaggacctacaaacaactggatagatccggttgagctcaaggcaactatgaaagagttgtacaagggttgtatgaa gggaagaacaatgtatgttattcctttctccatgggacctatcggttcacccatttcaaaaatcggcgttgaattgaccgacagccct tatgttgttgttaacatgcgcattatgactcgcataggcaaggctgtgttggatcagctcggagaagacggagattttgtaccttgtc tccactcagtcggtgctccgctcaaagagggagaaaaggataaaggttggccatgcgcaccaatcgaaaagaaatacataagc cacttcccggaagaaaggactatatggtcatatggttccggatacggtggaaatgcgcttttaggaaagaaatgctttgcacttcgt attgcatctgttatggcacgtgacgaaggttggcttgctgaacacatgcttatccttcgcataacagaccctgaaggaaacaagac atatgttacaggtgctttcccaagcgcatgcggaaagacgaacctggctatgcttattcctacaattcccggatggaaagttgaaa caatcggtgacgatattgcatggatgagatttggaaaagacggccgtttgtatgctatcaaccctgaagcaggattctttggtgttg ctccgggtacatccatggattcaaatccgaacgcaatgcatacaattaagaaaaatactatatttacaaacgttgcattgactgatg acggcgatgtttggtgggaaggcatcggaactgaaccgccggctcatctcatagactggcagggtaaagactggactcctgatt ccggaactttggcagcacatcccaacggacgttttacagcacctgcaagtcagtgccctgtaattgctcctgaatgggaggatcc ggaaggtgtgccgatttcagcaatccttatcggtggacgccgtccgaacaccattccgcttgttcatgaaagctttgactggaacc atggtgtattcatgggttcaatcatgggttctgaaattacggctgccgcaatttcaaacaaaatcggacaggtacgccgtgacccg -continued tttgctatgctgcctttcataggctacaacgtaaatgactatttgcagcactggttgaacatgggtaccaagactgacccaagcaag cttcccaagatattctatgtaaactggttccgcaaggacagcaacggtaaatggttgtggcctggatacggtgaaaacagccgtgt gacacaaccggccttgatgtaagcaaagaggatatggaagaactcttgagcgttaacaaagaacagtggctccaggaagttga gtcaataaaagaacattataagtcatacggagaaaaactgccgaaagaattgtgggcacaattggaggctcttgaacaacgttg aaagagtataacggttaa

*T. saccharolyticum* PEPCK
>or2173

(SEQ ID NO: 3)

ATGATTATGAAAAAATCAAAGAAATGTTTCAATCTGAATATTGACGACAAAG

AAACCTTGAATACTTTTGGAAGTTCGAGAGGAGAATTGTTTATGATAGATTTA

GATGATGTATTTAAAAATTCTGGCAGTATTCTTTACAATTTACCTGTTTCAGA

TTTGATAGAGGAAGCCATAAGAAATAATGAAGGGAAATTGTTAGAAAATGGT

GCATTAGATGTTTTTACAGGTAAATATACGGGAAGAATACCAAAAGATAAAT

ACATTGTAAATGAAGAATCTATTCATAATGATATTTGGTGGGAAAATAATAA

TTCAATGGAAAAAGAAAATTTTATTAGAGTTTTAAACAGAGTAATTGATTATT

TAAAAAAGAGCAGAAAATTGTATGTTTTAAAGGTTTTGTTGGCGCAGACCC

GCGATATAGATATCAAGTAACCGTTATTAATGAATATGCCTATCAAAACGCTT

TTGTACATCAATTATTTATTAATCCTAAAAATGAAGAAGAACTTAAAAAGGA

ATCCGATTTTACAGTTATTTGTGTGCCGAATTTTTTAGCTGATCCAATTTATGA

TGGAACTAATTCTGAGGCATTTATTATTATAAGTTTTGAAGAAAAATTTAATTT

TAATTGGTGGAACAAGATATTCAGGAGAAATAAAAAAATCTGTCTTCACAAT

GATGAATTATTTGATGTTAAAAAGGAATGTACTGCCTATGCATTGTGCAGCTA

ATATAGGTTCCAATAATGATACAGCGCTTTTTTTTGGGTTGTCGGGAACCGGC

AAGACAACTTTATCAACGGATCCAGAAAGATTTTTAATTGGCGACGATGAAC

ATGGATGGTCTTCACATGGAATTTTTAATTTTGAGGGTGGATGCTATGCAAAG

TGTATAAATTTATCCCCATATAATGAACCTGAAATATGGAATGCAATTAGATT

TGGAACAATTTTAGAAAATGTTATTTATGATGTAAATAATATGCCAGTCTATA

CAAGTAGTAAAATAACTGAAAATACAAGAGCTTCATATCCACTTGAGTACAT

CCCTAGGAAAGCGTCAAATGGCATTGGCGGTAATCCTAAAATTATATTTTTCT

TGGCAGCCGATGCTTTTGGAGTATTGCCTCCAATTTCTAAGCTGACAAATGAA

CAGGCTGTTGACTATTTCTTATTAGGATATACGAGCAAAATACCAGGAACAG

AAAAGGGAATTTGCGAACCACAAGCAACGTTTTCATCATGTTTTGGAGCACC

ATTTTTGCCATCATATCCAATGAGGTATGCTGAATTGTTAAAGAAAAAAATCG

CAGAAAATGATTCAGTTGTTTATTTAATAAATACTGGATGGATAGGTGGACA

TTATGGAATTGGCAAAAGGATAGATTTAAAATACACAAGAGAAATCATAAAA

AATGTTTTAAATGGTGAATTGGAAAAAGCAAAATTTAAAAAAGATACAGTAT

TTGATTTGATGATACCAGAAAAGTGCAATAACATTCCAGATGAATTATTAGA

TCCTATAAAAACATGGGAAGACAAAAATGATTACTTCCAAACTGCTAATAAT

TTATTATCTGCATTTAAAGCGAGATTAGATTATATAAAAAATGGGATTCATCA

ATAA

-continued

*E. coli* K12 PEPCK (ATP)

(SEQ ID NO: 4)

ATGCGCGTTAACAATGGTTTGACCCCGCAAGAACTCGAGGCTTATGGTATCA
GTGACGTACATGATATCGTTTACAACCCAAGCTACGACCTGCTGTATCAGGA
AGAGCTCGATCCGAGCCTGACAGGTTATGAGCGCGGGGTGTTAACTAATCTG
GGTGCCGTTGCCGTCGATACCGGGATCTTCACCGGTCGTTCACCAAAAGATA
AGTATATCGTCCGTGACGATACCACTCGCGATACTTTCTGGTGGGCAGACAA
AGGCAAAGGTAAGAACGACAACAAACCTCTCTCTCCGGAAACCTGGCAGCAT
CTGAAAGGCCTGGTGACCAGGCAGCTTTCCGGCAAACGTCTGTTCGTTGTCG
ACGCTTTCTGTGGTGCGAACCCGGATACTCGTCTTTCCGTCCGTTTCATCACC
GAAGTGGCCTGGCAGGCGCATTTTGTCAAAAACATGTTTATTCGCCCGAGCG
ATGAAGAACTGGCAGGTTTCAAACCAGACTTTATCGTTATGAACGGCGCGAA
GTGCACTAACCCGCAGTGGAAAGAACAGGGTCTCAACTCCGAAAACTTCGTG
GCGTTTAACCTGACCGAGCGCATGCAGCTGATTGGCGGCACCTGGTACGGCG
GCGAAATGAAGAAAGGGATGTTCTCGATGATGAACTACCTGCTGCCGCTGAA
AGGTATCGCTTCTATGCACTGCTCCGCCAACGTTGGTGAGAAAGGCGATGTT
GCGGTGTTCTTCGGCCTTTCCGGCACCGGTAAAACCACCCTTTCCACCGACCC
GAAACGTCGCCTGATTGGCGATGACGAACACGGCTGGGACGATGACGGCGTG
TTTAACTTCGAAGGCGGCTGCTACGCAAAAACTATCAAGCTGTCGAAAGAAG
CGGAACCTGAAATCTACAACGCTATCCGTCGTGATGCGTTGCTGGAAAACGT
CACCGTGCGTGAAGATGGCACTATCGACTTTGATGATGGTTCAAAAACCGAG
AACACCCGCGTTTCTTATCCGATCTATCACATCGATAACATTGTTAAGCCGGT
TTCCAAAGCGGGCCACGCGACTAAGGTTATCTTCCTGACTGCTGATGCTTTCG
GCGTGTTGCCGCCGGTTTCTCGCCTGACTGCCGATCAAACCCAGTATCACTTC
CTCTCTGGCTTCACCGCCAAACTGGCCGGTACTGAGCGTGGCATCACCGAAC
CGACGCCAACCTTCTCCGCTTGCTTCGGCGCGGCATTCCTGTCGCTGCACCCG
ACTCAGTACGCAGAAGTGCTGGTGAAACGTATGCAGGCGGCGGGCGCGCAG
GCTTATCTGGTTAACACTGGCTGGAACGGCACTGGCAAACGTATCTCGATTA
AAGATACCCGCGCCATTATCGACGCCATCCTCAACGGTTCGCTGGATAATGC
AGAAACCTTCACTCTGCCGATGTTTAACCTGGCGATCCCAACCGAACTGCCG
GGCGTAGACACGAAGATTCTCGATCCGCGTAACACCTACGCTTCTCCGGAAC
AGTGGCAGGAAAAAGCCGAAACCCTGGCGAAACTGTTTATCGACAACTTCGA
TAAATACACCGACACCCCTGCGGGTGCCGCGCTGGTAGCGGCTGGTCCGAAA
CTGTAA

*S. cerevisiae* PEPCK (ATP)

(SEQ ID NO: 5)

ATGTCCCCTTCTAAAATGAATGCTACAGTAGGATCTACTTCCGAAGTTGAACA
AAAAATCAGACAAGAATTGGCTCTTAGTGACGAAGTCACCACCATCAGACGC
AATGCTCCAGCTGCCGTTTTGTATGAAGATGGTCTAAAAGAAAATAAAACTG
TCATTTCATCAAGCGGTGCATTGATCGCTTATTCCGGTGTTAAAACCGGAAGA
TCTCCAAAGGACAAACGTATTGTTGAAGAACCTACCTCGAAAGACGAAATTT
GGTGGGGTCCGGTCAATAAACCATGTTCTGAAAGAACATGGTCTATCAACCG

-continued

```
TGAAAGAGCTGCAGATTACTTGAGAACAAGAGACCACATTTATATTGTCGAT

GCATTTGCAGGATGGGATCCAAAATACAGAATCAAAGTCCGCGTTGTTTGTG

CCAGGGCTTACCACGCTTTATTCATGACAAATATGCTTATTAGACCTACAGAA

GAAGAATTAGCCCATTTTGGAGAACCTGATTTTACTGTCTGGAACGCTGGTCA

GTTCCCAGCCAATTTACACACCCAGGATATGTCTTCAAAGAGTACTATAGAA

ATTAACTTCAAAGCAATGGAAATGATCATTTTAGGTACCGAATACGCCGGTG

AAATGAAAAAAGGTATTTTCACAGTTATGTTTTACTTGATGCCTGTGCACCAT

AACGTTTTAACTTTGCACTCTTCCGCCAACCAGGGTATTCAAAACGGTGACGT

TACTTTATTCTTTGGCCTAAGTGGTACCGGGAAAACCACTTTATCCGCAGACC

CACATAGATTGTTGATCGGCGATGATGAACATTGTTGGTCCGACCATGGTGTC

TTCAATATCGAAGGTGGTTGTTACGCCAAGTGTATTAATTTATCTGCCGAAAA

GGAGCCTGAAATTTTCGACGCTATCAAGTTTGGTTCTGTATTAGAAAACGTTA

TCTATGACGAGAAGTCGCATGTAGTCGACTATGACGACTCTTCTATTACTGAA

AATACTAGATGTGCCTACCCAATTGACTACATTCCAAGTGCCAAGATTCCATG

TTTGGCGGACTCTCATCCAAAGAACATTATCCTGCTAACTTGTGATGCTTCGG

GTGTTTTACCACCAGTATCTAAATTGACTCCTGAACAAGTCATGTACCATTTC

ATCTCTGGTACACTTCTAAAATGGCTGGTACTGAGCAAGGTGTCACTGAACC

TGAACCAACATTTTCATCTTGTTTCGGACAACCCTTCCTAGCCTTGCACCCTAT

TAGATACGCAACCATGTTAGCTACAAAGATGTCTCAACATAAAGCTAATGCG

TACTTAATCAACACCGGCTGGACTGGTTCTTCCTACGTATCTGGTGGTAAACG

TTGCCCATTGAAGTACACAAGGGCCATTCTGGATTCTATTCATGATGGTTCGT

TAGCCAATGAAACGTACGAAACTTTACCGATTTTCAATCTTCAAGTACCTACC

AAGGTTAACGGTGTTCCAGCTGAGCTTTTGAATCCTGCTAAAAACTGGTCTCA

AGGTGAATCCAAATACAGAGGTGCAGTTACCAACTTGGCCAACTTGTTTGTTC

AAAATTTCAAGATTTATCAAGACAGAGCCACACCAGATGTATTAGCCGCTGG

TCCTCAATTCGAGTAA
```

Transcarboxylase

The conversion of oxaloacetate and acetyl-CoA to pyruvate and malonyl-CoA allows for the anaerobic high yield production of fatty acid derived hydrocarbons. This reaction has not been reported to occur in vivo. However, an in vitro substrate specificity study for fraction-purified (S)-methylmalonyl-CoA:pyruvate carboxytransferase (a transcarboxylase, "Me-TC," E.C. 2.1.3.1) showed the ability of this enzyme to utilize oxaloacetate and acetyl-CoA as substrates. See Wood and Stjernholm, *PNAS* 47:289-303 (1961). The in vitro reaction occurred at one half the velocity of the enzyme's natural substrates, oxaloacetate and propionyl-CoA, however, and the ability of the enzyme to produce malonyl-CoA in its native organism (*Propionibacterium shermanii*) was not determined. Me-TC enzymes are known to be present in other Propionibacteria (e.g., *Propionibacterium freudenreichii* and *Propionibacterium acnes*), which ferment carbohydrates and lactate to propionate and acetate, and in obligately syntrophic bacteria such as *Pelotomaculum thermopropionicum, Candidatus Cloacamonas acidaminovorans*, and *Geobacter bemidjiensis*, which convert propionate and other medium chain organic acids and alcohols to acetate and hydrogen or reduced metals. Falentin et al., *PLOS one* 5(7): e11748 (2010); Kosaka et al., *Genome Res.* 18:442-448 (2008); Pelletier et al., *J. Bact.* 190:2572-2579 (2008); Aklujkar et al., *BMC Genomics* 11:490 (2010).

Figure 1B:
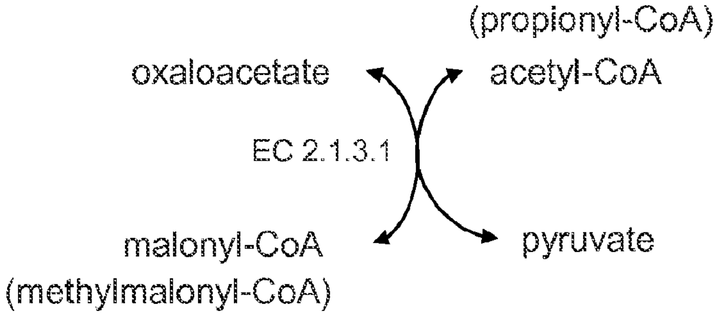
FIG. 1B depicts the conversion of oxaloacetate and acetyl-CoA to malonyl-CoA and pyruvate catalyzed by an enzyme from EC 2.1.3.1.

As used herein, transcarboxylase (TC) includes enzymes that catalyze the conversion of oxaloacetate and acetyl-CoA to malonyl-CoA and pyruvate (see FIG. 1B) and that correspond to Enzyme Commission Number 2.1.3.1 (methylmalonyl-CoA carboxyltransferase). In vivo, TC also catalyzes the conversion of methylmalonyl-CoA and pyruvate to oxaloacetate and propionyl-CoA. The reaction is reversible and requires co-factors such as Biotin, Co, or $Zn^{2+}$, TC consists of 3-4 subunits encoding domains for: a 5S subunit, a 12S subunit, and a 1.3S subunit; a 12S C-terminal subunit may also be present. See Carey et al., *IUBMB Life* 56:575-83 (2004). TC enzymatic activity has been observed in *Propionibacterium* species such as *Propionibacterium freudenreichii* and *Propionibacterium acnes, Bacteroides fragilis, Veillonella parvula, Veillonella gazogenes, Pelotomaculum thermopropionicum, Candidatus Cloacamonas acidaminovorans*, and *Geobacter bemidjiensis*. See Falentin et al., *PLoS One* 5:e11748 (2010); Kosaka et al., *Genome Res.* 18:442-448 2008 (2008); Pelletier et al., *J. Bact.* 190:2572-2579 (2008); and Aklujkar et al., *BMC Genomics* 11:490 (2010). Based on similarity to TC enzymes, high similarity TC genes have been identified in *Thermoanaerobacter* strains (*T. saccharolyticum* or0945, or0947, and or1888), *C. thermocellum* (Cthe_0699, Cthe_0700, and Cthe_0701), *Caldicellulosiruptor bescii, Clostridium cellulolyticum*, and

*Corynebacterium kroppenstedtii*. Protein engineering, either across all subunits or on a specific subunit, using techniques known to those in the art, can be employed to increase enzymatic activity towards malonyl-CoA generation.

An alignment of *C. thermocellum* and *T. saccharolyticum* homologs of TC from *Propionibacterium freudenreichii* CIRM-BIA1 and *Propionibacterium acnes* is shown in FIGS. 7A-7C. Additional sequences of TC include:

*Propionibacterium freudenreichii* subsp. *shermanii* CIRM-BIA1
Transcarboxylase
>PFREUD_18840 (1.3S subunit nucleotide sequence)
Antisense strand:

(SEQ ID NO: 6)

```
tcagccgatc ttgatgagac cctgaccgcc ctgcacggcg tcacgctcct tgacaaggac cttctcgacc ttgccgtcgg

tgggagcgtt gatctcggtc tccatatca tggcctcgag aacgagcacg gtctgaccag ccttgaccgt gtcaccacc

ttcacgagga tcttggagac ggtgccggcc agcggagcgg gaatctcgcc ctctccggcc ttaccggcgc

ctgcgccacc tgctgcgcgc ggtgccggcg cgccgccggt gccgccgccg aacaggatgg tgcccatcgg

gttttcgtgt gacttgtcga cgtcaacgtc aacgtcatac gcagtgccgt tgactgttac cttcagtttc at
```

Sense strand:

(SEQ ID NO: 7)

```
atgaaactgaaggtaacagtcaacggcactgcgtatgacgttgacgttgacgtcgacaagtcacacgaaaacccgatgggcac

catcctgttcggcggcggcaccggcggcgcgccggcaccgcgcgcagcaggtggcgcaggcgccggtaaggccggaga

gggcgagattcccgctccgctggccggcaccgtctccaagatcctcgtgaaggagggtgacacggtcaaggctggtcagacc

gtgctcgttctcgaggccatgaagatggagaccgagatcaacgctcccaccgacggcaaggtcgagaaggtccttgtcaagga

gcgtgacgccgtgcagggcggtcagggtctcatcaagatcggc
```

>PFREUD_18840 (1.3S subunit amino acid sequence)

(SEQ ID NO: 8)

```
MKLKVTVNGTAYDVDVDVDKSHENPMGTILFGGGTGGAPAPRAAGGAGAGKA

GEGEIPAPLAGTVSKILVKEGDTVKAGQTVLVLEAMKMETEINAPTDGKVEKVL

VKERDAVQGGQGLIKIG
```

>PFREUD_18870 (5S subunit nucletotide sequence)
Antisense strand:

(SEQ ID NO: 9)

```
tcacgcctgc tgaacggtga cttcgcggac ggttccgccc acgttcacgt tgtaggtgac gggaccggcc

acggcgagcg acttctcgtc gccctcggcc tcggccttca gctgggcatc ggtgagagcc acgctgtgcg

ggccctcggc gcgatgctcg aagaagaccg gagcgacctg cgggaacagt gcataggtga gcacgtcctc

gtcggtgccg ttgaagccct tgagggccgc ggcctccttg gactgctcct cccactcggg gggcagcaga

tcggccgggc gctgggtgat cggcttcttg ccggactgct cctcggccaa cttgaccacc ttcggatcgc gatcggccgg

gctggcgccg tagtagccga gcatgatgtc ggcgaactcg ccggtcatcc tcttgtactc gcccatcatc acgttgaaca

cggcctgcgt gccgacgatc tggctggacg gggtgaccag gggcgggaag ccggcggcct tgcggacgcg

cggcacctct gccatgacct cgtccatctt gtcctcggcg ccctgggcgc gcagctgcga ctccatgttg gagagcatgc

cgccggggat ctgcgacttg aagatcgagg tgtcgacaag cgtcttcgac tcgaacttct tgtacttcgg gcggatggcc

ttgaagtgat cgcggatctt gtgcaggcga tcgtagtcaa ggttggtggt gtacccggtg ccctcgagca tctcggcaac

cgactcggtg gggttgtggc ccgggccgag cgacatggac gagatggcgg tgtcgacgac gtcgacgccg

gcctcgatgg ccttcatgag ggagacctcg gtgacacccg tggtggagtg gcagtgcagg ttgatctgcg tcttctggcc

gtaggtgtcc ttgatggcct tgatgatgtc gtaggccggc tgcggcttga gcagggcggc catgtccttc agggcgatgg

aatcagcacc catgtcgagc agctgaccag caagcttgac atagccctca acggtgtgga ccgggctgat

cgtgtagcaa atggtgccct gcgcgtgctt gccggccttc ttgacggcag ccatggcgtg cgccatgttg cggggatcat

tcatggcgtc gaagacacgg aacacgtcca tgccgttctc agcggacttg tcgacgaagc gatcgacgac ctcgtcgttg

tagtggcggt aacccagcag gttctggcca cgcagcagca tctggagacg gctgttgggc atcagcttgc

ggaacgtgcg cagacgctcc caaggatcct cgttgaggaa gcggatacac gagtcatacg tggcaccacc

ccaacactcc actgaccagt acccggcagc atcaatgtct gcacaggcgc cgaccatgtc ttccattgcc attcgtgtgg
```

-continued ccatcaggct ctgatgggca tcgcgcagca cgagctcggt gataccaacc tcgcgcggct cggaaacctc aatttctcgc ggactcat Sense strand:

(SEQ ID NO: 10)

atgagtccgcgagaaattgaggtttccgagccgcgcgaggttggtatcaccgagctcgtgctgcgcgatgcccatcagagcct gatggccacacgaatggcaatggaagacatggtcggcgcctgtgcagacattgatgctgccgggtactggtcagtggagtgtt ggggtggtgccacgtatgactcgtgtatccgcttcctcaacgaggatccttgggagcgtctgcgcacgttccgcaagctgatgcc caacagccgtctccagatgctgctgcgtggccagaacctgctgggttaccgccactacaacgacgaggtcgtcgatcgatcgt cgacaagtccgctgagaacggcatggacgtgttccgtgtcttcgacgccatgaatgatccccgcaacatggcgcacgccatgg ctgccgtcaagaaggccggcaagcacgcgcagggcaccatttgctacacgatcagcccggtccacaccgttgagggctatgt caagcttgctggtcagctgctcgacatgggtgctgattccatcgccctgaaggacatggccgccctgctcaagccgcagccgg cctacgacatcatcaaggccatcaaggacacctacggccagaagacgcagatcaacctgcactgccactccaccacgggtgtc accgaggtctccctcatgaaggccatcgaggccggcgtcgacgtcgtcgacaccgccatctcgtccatgtcgctcggcccggg ccacaaccccaccgagtcggttgccgagatgctcgagggcaccgggtacaccaccaaccttgactacgatcgcctgcacaag atccgcgatcacttcaaggccatccgcccgaagtacaagaagttcgagtcgaagacgcttgtcgacacctcgatcttcaagtcgc agatccccggcggcatgctctccaacatggagtcgcagctgcgcgcccagggcgccgaggacaagatggacgaggtcatgg cagaggtgccgcgcgtccgcaaggccgccggcttcccgcccctggtcaccccgtccagccagatcgtcggcacgcaggccg tgttcaacgtgatgatgggcgagtacaagaggatgaccggcgagttcgccgacatcatgctcggctactacggcgccagcccg gccgatcgcgatccgaaggtggtcaagttggccgaggagcagtccggcaagaagccgatcacccagcgcccggccgatctg ctgcccccccgagtgggaggagcagtccaaggaggccgcggccctcaagggcttcaacggcaccgacgaggacgtgctcac ctatgcactgttcccgcaggtcgctccggtcttcttcgagcatcgcgccgagggcccgcacagcgtggctctcaccgatgccca gctgaaggccgaggccgagggcgacgagaagtcgctcgccgtggccggtcccgtcacctacaacgtgaacgtgggcggaa ccgtccgcgaagtcaccgttcagcaggcgtga >PFREUD_18870 (5S subunit amino acid sequence)

(SEQ ID NO: 11)

MSPREIEVSEPREVGITELVLRDAHQSLMATRMAMEDMVGACADIDAAGYWSV

ECWGGATYDSCIRFLNEDPWERLRTFRKLMPNSRLQMLLRGQNLLGYRHYNDE

VVDRFVDKSAENGMDVFRVFDAMNDPRNMAHAMAAVKKAGKHAQGTICYTIS

PVHTVEGYVKLAGQLLDMGADSIALKDMAALLKPQPAYDIIKAIKDTYGQKTQI

NLHCHSTTGVTEVSLMKAIEAGVDVVDTAISSMSLGPGHNPTESVAEMLEGTGY

TTNLDYDRLHKIRDHFKAIRPKYKKFESKTLVDTSIFKSQIPGGMLSNMESQLRA

QGAEDKMDEVMAEVPRVRKAAGFPPLVTPSSQIVGTQAVFNVMMGEYKRMTG

EFADIMLGYYGASPADRDPKVVKLAEEQSGKKPITQRPADLLPPEWELQSKEAA

ALKGFNGTDEDVLTYALFPQVAPVFFEHRAEGPHSVALTDAQLKAEAEGDEKSL

AVAGPVTYNVNVGGTVREVTVQQA

>PFREUD_18860 (12S subunit nucleotide sequence)
Antisense strand:

(SEQ ID NO: 12)

tcagcagggg aagtttccat gcttcttcgc cgggcgggtc tgacgcttgg tggcgtacat ctccagggcg gaagcaatct ttcgacgggt atcagccggg tcaatcacgt cgtcgacctg accgcgggcg gcggccacgt acggcgtgtt gaacgcgttc tggtactcct cgatcttctc ggcgcgcatg gcgtcgggat cgtcggcagc cttgatctcc ttgcggaaga tcacatttgc cgcaccctcg gcgcccatca ccgcaatctc ggcgctgggc caggcgtaca cggcgtcggc accaaggtca cggttgcaca tggccaggta ggagccgccg taggccttgc ggagcaccac ggtgatcttc ggcacggtgg cctcggagta ggcgtacagc atcttcgcgc catggcgaat gatgccgccg tactcctgct -continued gcacgccggg caggaagccc ggcacgtcga ccagctgcac cagcgggatg ttgaacgaat cgcagaaatt cacgaattcg gcggccttgt cagaggcgtt gatgtcgagg caacccgaca tcaccgacgg ctgattggcc acgatgccca ccgaacgacc attgacccgg gcgaaggcgg tcacgaggtt ggtggcatag ccggccttga cctcgaggta gtcaccccag tcgacgatct tggcaatgac atcgcgcacg tcatagccct tcttgccgtc aatcggaacg atgtcgcgca gctcggtatt ggggctgacg tcattgttcg ggttgacgaa ggatgcttcc tcagtgttgt tctgcggaag gaagctcagc agcttcttgg caatgagctc cgcggcgtcg tcgtcctcgg ccacgaagtg gatattgccc gagatggcca tatgggcctc agcgccaccg agttcgtcag cggtgacatc ctcgccggtg accgacttga tgacctgggg gcccgtgatg aacatatggg ccttcttggt catgatgatg aagtcagtca gtgccggcga atacgaggcg ccaccggcac aggggccggc aatgatggcg atctgcggca cgacgcccga cagcttcacg ttggcgaaga acatcttgcc gtaaccgctc agcgagtcga tgccctcctg gatccgggcg ccgcccgaat cgtagaagaa caggaagggc gtgccggtga gcagcgcctg ttccatcgtc tcgacgacct tcgtggactg cgtctcgcca gccgaaccac ccatgaccgt gaagtcctgg gacgcggcgt gcacgggacg accaaggatg gtgccacggc cggtgaccac gccatctgcc gggacgacgg ccttgtccat gccgaacaac gtggtgcggt gcttgcggaa agcgccgacc tcgtcgaacg aatggggatc gagcaggttg ttcaggcgct cacgagcggt ctgcttaccc tgggaatgtt gcttctcgac gcgacgttcg ccgccaccgg cttcgatcac ctggcgctgc tctgcgagct gctccacgcg accttccatg gtgctggcga gcttcaaatt gttgttttca gccat Sense Strand:

(SEQ ID NO: 13)

atggctgaaaacaacaatttgaagctcgccagcaccatggaaggtcgcgtggagcagctcgcagagcagcgccaggtgatcg aagccggtggcggcgaacgtcgcgtcgagaagcaacattcccagggtaagcagaccgctcgtgagcgcctgaacaacctgc tcgatccccattcgttcgacgaggtcggcgattccgcaagcaccgcaccacgttgttcggcatggacaaggccgtcgtcccgg cagatggcgtggtcaccggccgtggcaccatccttggtcgtcccgtgcacgccgcgtcccaggacttcacggtcatgggtggtt cggctggcgagacgcagtccacgaaggtcgtcgagacgatggaacaggcgctgctcaccggcacgcccttcctgttatctac gattcgggcggcgcccggatccaggagggcatcgactcgctgagcggttacggcaagatgttcttcgccaacgtgaagctgtc gggcgtcgtgccgcagatcgccatcattgccggcccctgtgccggtggcgcctcgtattcgccggcactgactgacttcatcatc atgaccaagaaggcccatatgttcatcacgggcccccaggtcatcaagtcggtcaccggcgaggatgtcaccgctgacgaact cggtggcgctgaggcccatatggccatctcgggcaatatccacttcgtggccgaggacgacgacgccgcggagctcattgcc aagaagctgctgagcttccttccgcagaacaacactgaggaagcatccttcgtcaacccgaacaatgacgtcagccccaatacc gagctgcgcgacatcgttccgattgacggcaagaagggctatgacgtgcgcgatgtcattgccaagatcgtcgactggggtga ctacctcgaggtcaaggccggctatgccaccaacctcgtgaccgccttcgcccgggtcaatggtcgttcggtgggcatcgtggc caatcagccgtcggtgatgtcgggttgcctcgacatcaacgcctctgacaaggccgccgaattcgtgaatttctgcgattcgttca acatcccgctggtgcagctggtcgacgtgccgggcttcctgcccggcgtgcagcaggagtacggcggcatcattcgccatggc gcgaagatgctgtacgcctactccgaggccaccgtgccgaagatcaccgtggtgctccgcaaggcctacggcggctcctacct ggccatgtgcaaccgtgaccttggtgccgacgccgtgtacgcctggcccagcgccgagattgcggtgatgggcgccgagggt gcggcaaatgtgatcttccgcaaggagatcaaggctgccgacgatcccgacgccatgcgcgccgagaagatcgaggagtac cagaacgcgttcaacacgccgtacgtggccgccgcccgcggtcaggtcgacgacgtgattgacccggctgatacccgtcgaa agattgatccgccctggagatgtacgccaccaagcgtcagacccgcccggcgaagaagcatggaaacttcccctgc >PFREUD_18860 (12S subunit amino acid sequence)

(SEQ ID NO: 14)

MAENNNLKLASTMEGRVEQLAEQRQVIEAGGGERRVEKQHSQGKQTARERLNN

LLDPHSFDEVGAFRKHRTTLFGMDKAVVPADGVVTGRGTILGRPVHAASQDFTV

MGGSAGETQSTKVVETMEQALLTGTPFLFFYDSGGARIQEGIDSLSGYGKMFFA

-continued

NVKLSGVVPQIAIIAGPCAGGASYSPALTDFIIMTKKAHMFITGPQVIKSVTGEDV

TADELGGAEAHMAISGNIHFVAEDDDAAELIAKKLLSFLPQNNTEEASFVNPNND

VSPNTELRDIVPIDGKKGYDVRDVIAKIVDWGDYLEVKAGYATNLVTAFARVNG

RSVGIVANQPSVMSGCLDINASDKAAEFVNFCDSFNIPLVQLVDVPGFLPGVQQE

YGGIIRHGAKMLYAYSEATVPKITVVLRKAYGGSYLAMCNRDLGADAVYAWPS

AEIAVMGAEGAANVIFRKEIKAADDPDAMRAEKIEEYQNAFNTPYVAAARGQV

DDVIDPADTRRKIASALEMYATKRQTRPAKKHGNFPC

>*P. freudenreichii*_(12S_C-term nucleotide sequence)

(SEQ ID NO: 15)

atggctgatgaggaagagaaggacctgatgatcgccacgctcaacaagcgcgtcgcgtcattggagtct gagttgggttcactccagagcgatacccagggtgtcaccgaggacgtactgacggccatttcggccgcc gttgcggcctatctcggcaacgatggatcggctgaggtcgtccatttcgccccgagcccgaactgggtcc gcgagggtcgtcgggctctgcagaaccattccattcgt >*P. freudenreichii*_(12S_C-term amino acid sequence)

(SEQ ID NO: 16)

MADEEEKDLMIATLNKRVASLESELGSLQSDTQGVTEDVLTAISAAVAAYLGND

GSAEVVHFAPSPNWVREGRRALQNHSIR

*Propionibacterium acnes* SK137 Transcarboxylase
*P. acnes* (12S subunit)

(SEQ ID NO: 17)

atggctgagaagaaaccaatcaagaggccgataccatggccggccggatcgagcagctcgccgacgagcgccacgctgtg gagcttggcgggggcgaggatcgcctgcaaaagcagcgtgacaggggcaagcagacagcccgtgaacggatcgacaacct cgttgatgcttattccttcgatgaggtgggtgcgttccgtaagcaccgcaccacccttttcggcatggacaaggccgaagttcccg ccgacggcgtagtcaccggtcgtgcgaccatccatggtcgcccggtccacatcgcgtctcaggacttcaccgtcatgggtgggt cggctggcgagacccagtcgacgaaggtcgtcgagacgatggaacagtccctgctgaccggcactccgtttctgttatctatga ctcgggcggcgcccgaattcaagaaggcatcgactcgctgtccgggtacggcaagatgttctacgcgaacgtcaagctgtcgg gcgtcgtgccgcagatcgccatcattgctggcccctgcgccggcggcgcctcctattccccggccagaccgacttcatcatcat gacgaagaaggcccacatgttcattacgggccccggagtcatcaagtcggttaccggtgaggaggtgactgctgacgacctgg gtggtgcggatgcgcacatgtccacctcgggcaatatccacttcgtggccgaagatgacgacgccgcagtgctcatcgcgcag aagttgctgagcttcctgccgcaaaacaacactgaggacgcccagatctccaaccccaatgacgatgtctccccgcagcctgag ctgcgcgacatcgttccgctggatggtaagaagggctacgacgtccgcgacgtcatctccaagatcgtcgactggggcgacta cctagaggtcaaggccggttgggcgaccaacatcgtcaccgcctttgcccgggtcaatggtcgtaccgtcggcatcgtggcca accagccgaaggtgatgtcgggttgccttgacatcaatgcttcggacaaggctgccgagttcattaccttctgcgactcgttcaat attccgttggtgcagttggttgacgttcctggcttcctgcctggtgtccagcaggagtacggcggcatcatccgccacggcgcga agatgctgtatgcctactccgaggccaccgtcccgaagatcaccgtggtgctgcgtaaggcttacggcggctcctaccttgccat gtgcaaccgtgacctgggtgctgacgccgtctatgcctggccgagcgcggagattgcggtgatgggtgccgatggcgctgcc aacgtcattttccgtcgccagatcaaggactctgaggatcccgcagccacccgtgccgcgaagatcgaggagtaccgcaacgc cttcaacacgccttacgtggctgccgcccgtggacaggttgacgacgtgatcgatcccgcggacacccgtcgcaagatcaccg ccgctctggagacctacgccactaagcgtcagtcccgtccggccaagaagcacggcgtcatgccttgctga

*P. acnes* (5S subunit)

(SEQ ID NO: 18)

atgagtccacgaaagattggcgttaccgagacgtgctccgcgacgcgcatcagagcctgcttgccactcgcatggccatgga ggacatggttgatgcctgtgccgacattgatgcggcaggcttctggtccgttgaatgctggggcggagctaccttcgattcttgca tccgattcctcaacgaagacccatgggagcgtctgcgtactttccgcaagctgctgccgaactcccggttgcagatgctgctgcg tggccaaaaccttctgggctaccgccactacaacgacgaggtcgtcgacaagtttgtcgagaagtcggccgagaacggcatgg -continued acgtgttccgggtgttcgacgctctgaacgatcctcgcaaccttgagcacgcgatggcagccgtcaagaagaccggcaagcac gcccagggcaccatctgctacaccacttccccgattcacaccccagagagcttcgtcaagcaggccgatcgtctcatcgacatg ggtgccgactcgatcgccttcaaggacatggctgctttgctcaagccgcagcctgcctacgacatcatcaagggcattaaggag aaccatccggacgtgcagatcaacctgcactgccactccaccacgggcgtcaccctggtcaccctgcagaaggccatcgagg ctggtgtcgacgtcgtcgacaccgctatctcgtcgatgtcgctcggcccggggcacaacccaaccgagtctttggtcgagatgct cgagggcaccgagtacaccaccggcctcgacatggatcgcctgctcaagatccgcgaccacttcaagaaggtgcgtccgaag tacaagaagttcgagtcgaagacgctggtcaacaccaacatcttccagtcccagatcccgggcggaatgactccaacatggag tcccagctcgaggcccagggtgctggagaccgcatggatgaggtcatgaaggaggtgccgcgcgttcgtaaggatgccggct acccgccgctggtcaccccgtcctcccagatcgtgggaacccaggcggtgttcaacgtcctgatgggcaatggttcgtacaaga acctcactgccgagtttgccgacctcatgcttggctactacggcaagcccattggcgagctcaatcccgagatcgttgagatggc caagaagcagaccggcaaggagccgatcgactgccgtcccgccgacctgctcgagcctgagtgggaccagaggtcgagca ggccaagagtcttgagggcttcgacggctccgacgaggacgttcttaccaacgccctgttcccgggagttgccccgaagttcct caaggaacgcgcacagggcccgaagagcgtcgcgatgaccgaggcacagagaaggccgagaaggaaggcaccggcgc tgccggcatcgccggaccggtcaactacaacgtgacggtcggtggcaacagccaccaggtgaccgtcgagcctgcgtga

*P. acnes* (1.3S subunit)

(SEQ ID NO: 19)

atgaagctcaaggtgaccgtcaatgacgtcgcatacgacgttgacgttgacgttgataagaccgccaatgcgccgatggcgcc gatcctctttggtggcggcgccggcggcccgatgaaggcatccggtggcggcgccggtaaggccggtgagggcgaggttcc cgcaccgctagagggactgttgccaagatcctggtggccgaaggagatgccgtcaaggccggtcaggtgctcctgaccctcg aggccatgaagatggagaccgagatcaatgccccggcggacggaaccgtcaaggggatcctggtggagtcggtgacgccg tccagggtggtcagggcctggtggctctgggctga

*C. thermocellum* Transcarboxylase
>Cthe_0699 (12S subunit nucleotide sequence)

(SEQ ID NO: 20)

atggacaaagtagacaagatcggccttctccgtgaaaaactggcccaggttgaacagggcggaggagctgaaaaaatcgcaa aacagcatgatgccggaaaaatgacagcaagagaaagaatccaggctttatttgatgaaaacagctttgttgagatcgacacattt gttgagacaagaagcattgacttcgatatgcaaaaaaagaaagtcccgggagacggtgttgtaacagggtatggttccatagac ggacgtctggtctttgttgcggcgcaggactttactgtaatcggtgggtctttgggtgaaatgcatgccgcaaaaatcaccaaagt aatggacatggcaatgaaaatgggcgcaccgtttataagcattaatgattccggcggtgcaagaattgaagaaggaattgacgc actcaagggatttggagatatcttctacagaaatactttggcttcaggtgtaattccccagatttcagttatcatgggaccatgcgca ggcggagcggtatattctcctgcaataaccgactttatatttatggttgacaaaaccagtcagatgtttataacgggaccccaggta attaagtccgtaaccggagaagacgtgacttttgaaaaacttggcggtgcggaaacccacaactccataagcggtgttgctcact tcagaagttcaagtgaaaaagaatgtatagagcaaatcaaaaagcttattagttatcttcctgataacaatctttccgatgttccgatt gttccaactcaggatgacataaacagaattactgacaacctggtcgatatcattccgcaggactccaacaagccttatgacatgat ggaaataatcacttccgtagttgacaacggtgactttttttgaaattcaaaaagactttgcaaaaaacattataataggtttcggcaga atgaacggcggaaccgtcggtatagtggcaaatcagccaaaagttgccgcaggggttttggatgtgaactcactgacaaagcc gcaaggtttgttcgtttctgtgatgcgttcaacattccaattataacctttaccgatgtaccggggtatctgcccggagtaggccagg agcacagcggagtaataagacacggtgcaaagcttctttatgctttctctgaagccaccgttccaaaaatcaatgttattgtcagaa aagcttacggcggtgcatatattgccatgaacagcaagcaccttggagcggacatggtatttgcgtggccttcggcggaaattgc agttatgggaccggaaggtgcggcaaacatcattttcaagaaagatatagctgctgccgatgacccaatggaaacaagaaaga ggctcattgaagaatatcgtgaaaaattctccaatccgtatgttgcagcttcaaggggttatgttgatgatgtaattgatccggcaac aacaaggataagactgattagtgcccttgaaatgcttgcaagtaagagagaaaacagacctgccaaaaagcatggaaatattcc attataa -continued >*C. thermocellum*_(12S subunit amino acid sequence)

(SEQ ID NO: 21)

MDKVDKIGLLREKLAQVEQGGGAEKIAKQHDAGKMTARERIQALFDENSFVEID

TFVETRSIDFDMQKKKVPGDGVVTGYGSIDGRLVFVAAQDFTVIGGSLGEMHAA

KITKVMDMAMKMGAPFISINDSGGARIEEGIDALKGFGDIFYRNTLASGVIPQISV

IMGPCAGGAVYSPAITDFIFMVDKTSQMFITGPQVIKSVTGEDVTFEKLGGAETH

NSISGVAHFRSSSEKECIEQIKKLISYLPDNNLSDVPIVPTQDDINRITDNLVDIIPQD

SNKPYDMMEIITSVVDNGDFFEIQKDFAKNIIIGFGRMNGGTVGIVANQPKVAAG

VLDVNSSDKAARFVRFCDAFNIPIITFTDVPGYLPGVGQEHSGVIRHGAKLLYAFS

EATVPKINVIVRKAYGGAYIAMNSKHLGADMVFAWPSAEIAVMGPEGAANIIFK

KDIAAADDPMETRKRLIEEYREKFSNPYVAASRGYVDDVIDPATTRIRLISALEM

LASKRENRPAKKHGNIPL

>Cthe_0700 (1.3S subunit nucleotide sequence)

(SEQ ID NO: 22)

atgaaaaagtttttgataaaggtaaacggaaatcaatatgaggttgaagttgaagaaatcagagacggtgcttcagcaccacagg ttactctcagcacaccttcggctgcacctgcgccttcaccggcaccggctcaggaaacgaaaacagctgcaccaaagaaagac agcacagtaccggcaggtgctacggcaattaaagctccgatgccggtaccatactcgacattcgtgtaaatcaaggggatacg gtaaagaaaggccaagttcttttaattcttgaagcaatgaagatggaaaatgaaatagttgctccaaatgacggtacagttgcatca attaatgtttcaaagggtgcatctgtaaacgtcggagaggttcttgtctcattaaaatag >*C. thermocellum*_1.3S subunit amino acid sequence)

(SEQ ID NO: 23)

MKKFLIKVNGNQYEVEVEEIRDGASAPQVTLSTPSAAPAPSPAPAQETKTAAPKK

DSTVPAGATAIKAPMPGTILDIRVNQGDTVKKGQVLLILEAMKMENEIVAPNDG

TVASINVSKGASVNVGEVLVSLK

>Cthe_0701 (5S subunit nucleotide sequence)

(SEQ ID NO: 24)

atggctaaggtaaaaattaccgaaacggcgctgagggatgcccatcaatctctcattgcaacaagaatgagaatagaagagatg cttcctatcatagataaactggacgagatcggttatcattctaggaggtatggggcggtgcaacctttgatgcctgcctgagatttt gaatgaagacccgtgggaaaggcttagaattataaaaagccactgcaagaaaactccccttcaaatgcttttaagaggccagaat cttttgggttacaagcattatgccgatgacgttgtggagtactttgtacaaaagagcgttgcaaacggtataaacataataagaatttt cgacgccttgaatgacaccagaaatatagaaactgcaatcaaagcctgcaaaaaagaaggcggtcatgctcagggaacggtat gttatacaataagtcccgttcacaatcttgaactttttgtcaaagatgcaaagactcttgtggaaatgggagagactccatatgcgt aaaggatatggcaggacttctgcttccatatgttgcatatgaccttatcaaagcattaaaagaaaacgtaaaagtgccgattcaactt catacccactatacgagcggtgttgcttcaatgacatatctgaaggcaattgaggcagggtgcgatgttgtggactgcgctatctc accaatgtcaatgggaacatcccagcctccgacagaacctcttgtggcaacctttaaaaggcacgccgtacgataccggacttga cctggataaattaagtgaaatcgcagactacttcagacctctcaaagaaaagtatatttcagaaggacttcttgatgtaaaggttatg ggagttgacgtaaacactctcaaataccaggtacccggtggaatgctttcaaacctggtgtctcagttaaagcagtccaatgcggt tgataaattcgaagaggttctgaaagaagtgccaagagtaagagaagacttcggatatcctccgttggttacacctacaagccag attgtaggtactcaggcagttttaaatgtggtaacgggtgaaagatacaaaatggttccaaaagaatccaaggcactgatcaagg gtgaatacggcagaacaccggctccggtcaaccctgaagttcagaagaagattttaaaagatgaagagccgattacagttagac ctgctgatttgatagagcccgagcttgacaagatcagaaatgaaatgaaagaatacctggaacaagacgaggacgttttgtccta tgcactgttcccgcaggtggcagagaagttcttccaatacaggaaagctcaaaaatataagatagaaccggacatggtcgattac gaaaacagggttcatccggtttaa -continued >*C. thermocellum*_(5S subunit amino acid sequence)

(SEQ ID NO: 25)

MAKVKITETALRDAHQSLIATRMRIEEMLPIIDKLDEIGYHSLEVWGGATFDACL

RFLNEDPWERLRIIKSHCKKTPLQMLLRGQNLLGYKHYADDVVEYFVQKSVAN

GINIIRIFDALNDTRNIETAIKACKKEGGHAQGTVCYTISPVHNLELFVKDAKTLV

EMGADSICVKDMAGLLLPYVAYDLIKALKENVKVPIQLHTHYTSGVASMTYLK

AIEAGCDVVDCAISPMSMGTSQPPTEPLVATLKGTPYDTGLDLDKLSEIADYFRP

LKEKYISEGLLDVKVMGVDVNTLKYQVPGGMLSNLVSQLKQSNAVDKFEEVLK

EVPRVREDFGYPPLVTPTSQIVGTQAVLNVVTGERYKMVPKESKALIKGEYGRTP

APVNPEVQKKILKDEEPITVRPADLIEPELDKIRNEMKEYLEQDEDVLSYALFPQV

AEKFFQYRKAQKYKIEPDMVDYENRVHPV

>*C. thermocellum*_(12S_C-term nucleotide sequence)

(SEQ ID NO: 26)

atgaaagagcaaataaatgaagaaattattctggcaatatcagcggccattgctgctttggaaacaagacccggatacaagcttgt agtaagatcatttaaaagaatacccaaaacttctcctgtatggtccgctacaggaaaaatcgagagaatcagaagaagtatg >*C. thermocellum*_12S_C-term amino acid sequence (SEQ ID NO: 27)

MKEQINEEIILAISAAIAALETRPGYKLVVRSFKRIPQTSPVWSATGKIERIRRSM

*T. saccharolyticum* Transcarboxylase
>or0945 (12S subunit nucleotide sequence)

(SEQ ID NO: 28)

atgtcaatagatgataggattgaagaccttcttagaagaagagagatggttttagaaggcggtggtttagataaagtagagaaaca acaccaaaagggaaagcttaccgcaagagagaggatatacaagcttttagatgaagatagctttgtggaaatagatgcgtatgtt gagcacaggtgtattgactttggcatggaaaagcaaaggatacctggcgaaggcgtagtgacagggtatgggacgatagatgg aaggcttgtctacgtttatgcacaggattttacggttttaggaggatcattaggcgagtatcatgcaaagaaaatcacaaaaatcat ggatatggattaaagatgggagcaccgctcattggattaaatgattccggaggtgccagaatacaggaaggcgtcgatgcttat cgggatatggcaacatatttttcagaaacacgctggcatcaggcgtaataccgcaaatatcggtgataatggggcccagcgctg gaggtgcagtttattcgcctgctcttactgactttatattcatggtagacaagacaagtcagatgtttataactggaccgcaggtcata aaagccgtcacaggtgaagatgtttcggcagaggagcttggtggatcgattactcacagcacgaaaagcggtgtggcgcatttt agggctgaaaacgacgaagagtgtttgaagatggtgaggaagctattaagttaccttccatcaaacaatttggaagatccgccac agttggcgacagatgacgacataaacagattttccgataggcttattgagataatcccagatagtcctaataagccatacgatatga aagaagtaatttcggaaatagtggatgaaggcgtgtattttgaatcacaggcaatgtatgcgcaaaacataataacggcatttgca aggcttaatggaaggacggtagggataatagcaaatcagcctaaagttttggctggatgtctcgacatcaatgcgtctgataagg catcgaggtttataaggttttgcgatgcatttaacatcccgcttacaatatagtagatgttccaggatttttgcctggaacgaatcaa gagtacggtggaataatacgccatggggcaaagatgttgtacgcttactctgaggctacagtgccaaaagtgactctcattgtga ggaaagcttatggcggtgcttaccttgccatgtgcagcaaagacttaggagctgattttgttttggcatggcctactgctgaaatag cggtcatgggacctgatggggcagcaaacatcgtgtttaaaaatgaaataaaatcgtagatgatcagtggctgcaagaaatga aaagataaatgagtacagggagaatttcgcaaatccatacagggcagcagcgagaggatatgtagatgatgtagttctgccgca agagacgagacctcgcctcatctcggcgttcgatatgcttatgagcaaaagggagtcaaggcccagcaaaaagcatggcaattt tcctgtttaa >*T. saccharolyticum*_(12S subunit amino acid sequence)

(SEQ ID NO: 29)

MSIDDRIEDLLRRREMVLEGGGLDKVEKQHQKGKLTARERIYKLLDEDSFVEIDA

YVEHRCIDFGMEKQRIPGEGVVTGYGTIDGRLVYVYAQDFTVLGGSLGEYHAKK

ITKIMDMALKMGAPLIGLNDSGGARIQEGVDALSGYGNIFFRNTLASGVIPQISVI

MGPSAGGAVYSPALTDFIFMVDKTSQMFITGPQVIKAVTGEDVSAEELGGSITHS

-continued

TKSGVAHFRAENDEECLKMVRKLLSYLPSNNLEDPPQLATDDDINRFSDRLIEIIP

DSPNKPYDMKEVISEIVDEGVYFESQAMYAQNIITAFARLNGRTVGIIANQPKVL

AGCLDINASDKASRFIRFCDAFNIPLLNIVDVPGFLPGTNQEYGGIIRHGAKMLYA

YSEATVPKVTLIVRKAYGGAYLAMCSKDLGADFVLAWPTAEIAVMGPDGAANI

VFKNEIKSSDDPVAARNEKINEYRENFANPYRAAARGYVDDVVLPQETRPRLISA

FDMLMSKRESRPSKKHGNFPV

>or0947 (1.3S subunit nucleotide sequence)

(SEQ ID NO: 30)

atgaaaaaatttatagtaactgtcaatggaaaaaaatacgatgtggaagtagaagaagtaaaagtcgacgtggcaagtgagaaa aaagcaaaagaagatactgctgctaaaaatgcgtcagatgcaagtgtaaaaagcaaacaggttgaagtaaaaaacgaagtcaa agacggtttctcaatcaatgcaccgatgccgggaactatattggatgtcaaaataagccaaggccagactgtcagacgaggcga tgtgcttttaatactggaagccatgaagatggaaaatgaaatcacgtcaccttacgatggcacaataatatccataaatgtttcaaaa ggtgcctctgtaaatacaggcgatgtgcttttgtacttaaaatga >*T. saccharolyticum*_(1.3S subunit amino acid sequence)

(SEQ ID NO: 31)

MKKFIVTVNGKKYDVEVEEVKVDVASEKKAKEDTAAKNASDASVKSKQVEVK

NEVKDGFSINAPMPGTILDVKISQGQTVRRGDVLLILEAMKMENEITSPYDGTIISI

NVSKGASVNTGDVLLYLK

>or1888 (5S subunit nucleotide sequence)

(SEQ ID NO: 32)

atgtctaagataaaaataacggagactgttttaagagatgcacatcaatcgttgctggcaaccagaatgacaaccgatgaaatgct tcctatagcagaaaaattagatgaagttggtttttctcgctggaagcatggggcggtgctacatttgatgcatgtatgagatttttga atgaagacccatgggaaagattaagacttttaaagaaggcgattaagaagacacctcttcaaatgcttttaagaggtcaaaatttac tcggatataaacactatcccgatgatgtcgtaaatgaatttataataaaatctgttgaaaatggtatagatataataagaatttttgatg cgttaaatgatgtgagaaatttagaagtgccaataaaatctgcaaaaagtgcaggtgctcatgtacaggcagctattgtatatacag ttagtcctgtacataatacagatcattatttgaaagtggcaaagtctcttcaagatatgggtgcggattccatatgcattaaggatatg tctggaatattatcaccctatgttgcatacgatttgattaaatctctgaaaagagcactttacacgccaattcaactgcatagccattat acagcaggactggcttcaatgacttatttaaaagccatagaagctggtgtagacggggttgatacagctatttcttcgcttgccttag gaacatcacaaccagctacagaatcaatcgtggctgcattgaaagatacagaatatgatacagggctagatttaaaattgcttgct gagatagctcagcattttaatgtagtcaaacagaatcacaaaaatgacagcgatatgtctttgcttatgtctgttgatgttaaagcatt agaaagtcaaataccaggggggaatgttatcaaatttggtttcacagctaaagcagcagaatgcattaaacaaatatcaagacgtct tgaaagaagttccaagggtacgcgaagatttgggatatcctcctcttgttactccaatgagccagatggttggaacccaggctgttt taaatgttattacaggggagagatataaaatcgttcctaaagaaattaaagattatgtcaaaggtttatatgggatgccaccagctcc aatttcagattctatacgaaagaaaataatcggcgatgaagaagtaatttcaaagaggccagcagatttactaagtcctcaattgga tgaatttaaaaatgagataaaggaatttatagagcaagatgaagatgttttatcatatgcattatttcctcaagtagcaagaagattttt cgagtataggcaagccaaaaaatacagaattgattcaacattattaaatatcgaagaaagggttcatccgatataa >*T. saccharolyticum*_(5S subunit amino acid sequence)

(SEQ ID NO: 33)

MSKIKITETVLRDAHQSLLATRMTTDEMLPIAEKLDEVGFFSLEAWGGATFDAC

MRFLNEDPWERLRLLKKAIKKTPLQMLLRGQNLLGYKHYPDDVVNEFIIKSVEN

GIDIIRIFDALNDVRNLEVPIKSAKSAGAHVQAAIVYTVSPVHNTDHYLKVAKSL

QDMGADSICIKDMSGILSPYVAYDLIKSLKR.ALYTPIQLHSHYTAGLASMTYLKA

IEAGVDGVDTAISSLALGTSQPATESIVAALKDTEYDTGLDLKLLAEIAQHFNVV

KQNHKNDSDMSLLMSVDVKALESQIPGGMLSNLVSQLKQQNALNKYQDVLKE

-continued

VPRVREDLGYPPLVTPMSQMVGTQAVLNVITGERYKIVPKEIKDYVKGLYGMPP

APISDSIRKKIIGDEEVISKRPADLLSPQLDEFKNEIKEFIEQDEDVLSYALFPQVAR

RFFEYRQAKKYRIDSTLLNIEERVHPI

>*T. saccharolyticum*_(12S_C-term nucleotide sequence)

(SEQ ID NO: 34)

atggaagagataaatgaagaaatagttgagtcattgaagagcgatttacgcggcatttggtcagtacgaaaagaatttccgcat caaggtaataaagagagtggactcaaatatgccggaatggagaaaagctggcctttacaatcagatgagatag >*T. saccharolyticum*_(12S_C-term amino acid sequence)

(SEQ ID NO: 35)

MEEINEEIVAVIEAAIYAAFGQYEKNFRIKVIKRVDSNMPEWRKAGLYNQMR

*Caldicellulosiruptor bescii* DSM 6725 Transcarboxylase
>*C. bescii*_(12S subunit nucleotide sequence)

(SEQ ID NO: 36)

atgacaaacaagctcagagagctcaagcaaaagagagaaagaatactaaagcttggtggagaagataaaataaaaaaacagc atgatagcaaaaaacttacttgtagagagagaatagaatatttacttgaccctggaagcttcaatgaaatagatatgtttgttgaaca cagatgtcaagaatttgatatgaaagatacatttgtcccctgtgatggtgttgtaacgggttatggaacaatcaatggcagaaaagtt tttgtttatgctcaagattttacttcgataggcggttctcttggcgagatgcatgcaaaaaagatttgtaaagttttggacttagcattaa aatatggttgtccagtgataggtataaatgattctggtggtgcaagaattcaagaaggtgttgatgcattagcaggatatggtgaaa tcttctatagaaataccatggcatcaggtgtaattccacaaattgcagctataatgggaccttgtgcaggtggagctgtatactctcc tgctattatggattttattttatggtggacaaaaccagccaaatgtttgttacaggacctcaggttataaaagctgtgactggagagg agatatcctttgaagagcttggtggcgcttacactcacagctcaaagagtggagttgacattttattgcagaggatgagtatcacct acttgatatgataaagtatttattgtcgtttataccttcaaataacatggaagacccaccttttataatgtcatctgattcagaaaaaaga tttgttcccgagctcgaaaatataattccgcaagagccaaacaaagcttatgatgtaaaagaaataatttataaagtagtagacaac caagaatttttagaagtacaaccttattttgctcaaaatgctgttgtaggatttggtagaatagggggctttagcgtaggaattgtagc aaatcagcccaaagtgaacgctggagtgcttgattatgattcgtctgacaagatagcacgatttgtaagattttgtgatgcttttaata ttcccataataacatttacagacgtgcctggatttttgccaggtgttaaccaagagcacaatggaataattcgtcatggggctaagg ttttgtatgcatactcagaggcaacagttccaaagataaatgtaattttgagaaaagcatatggtggggcttacattgcaatgagca gcaaacacattggtgcagactttgtgtttgcatggccaactgccgagatagctgttatgggaccagatggcgcagcaaatattata tttagaaaagagatacaaagcgctcaaaatcccgaagaggaaagaaaaagaaggatagaagagtatactcaaaagtttgcaaat ccatacattgcagctgcccgtgggtatgttgacgatgtgattgagccacagcttacccgtaacaaaatcattgaggcgctcaaaat ttccattacaaaaagagagcaaaggcccccaaaaaagcatggcaatattccatta >*C. bescii*_(12S subunit amino acid sequence)

(SEQ ID NO: 37)

MTNKLRELKQKRERILKLGGEDKIKKQHDSKKLTCRERIEYLLDPGSFNEIDMFV

EHRCQEFDMKDTFVPCDGVVTGYGTINGRKVFVYAQDFTSIGGSLGEMHAKKIC

KVLDLALKYGCPVIGINDSGGARIQEGVDALAGYGEIFYRNTMASGVIPQIAAIM

GPCAGGAVYSPAIMDFIFMVDKTSQMFVTGPQVIKAVTGEEISFEELGGAYTHSS

KSGVAHFIAEDEYHLLDMIKYLLSFIPSNNMEDPPFIMSSDSEKRFVPELENIIPQE

PNKAYDVKEIIYKVVDNQEFLEVQPYFAQNAVVGFGRIGGFSVGIVANQPKVNA

GVLDYDSSDKIARFVRFCDAFNIPIITFTDVPGFLPGVNQEHNGIIRHGAKVLYAY

SEATVPKINVILRKAYGGAYIAMSSKHIGADFVFAWPTAEIAVMGPDGAANIIFR

KEIQSAQNPEEERKRRIEEYTQKFANPYIAAARGYVDDVIEPQLTRNKIIEALKISI

TKREQRPPKKHGNIPL

-continued

>*C. bescii*_(1.3S subunit nucleotide sequence)

(SEQ ID NO: 38)

atgagaaagttcaaggtgaagatcaatagccaagaatttgttgtagaagtggaagaaataggagttgaaaatgctacttctgtcgt gccaaggcctaagattggccattttgagccaaaacaggaaaaacatgaggataaaacaaaacaaagccctgtactttatctgat aaaaattcggttgttgcccagcttccgggtactattgtaaggctgctaaaaagtgaaggtgatgttgttgatgcaaatgaacctgtttt aattcttgaagccatgaaaatggaaaatgaaataactgcacctgtcaaaggaaaaattaaaagaatacatgtaaaggaagggca gaaggtagcaaaaggagatttgctatttgaaatagag >*C. bescii*_(1.3S subunit amino acid sequence)

(SEQ ID NO: 39)

MRKFKVKINSQEFVVEVEEIGVENATSVVPRPKIGHFEPKQEKHEDKTKQSPVLS

SDKNSVVAQLPGTIVRLLKSEGDVVDANEPVLILEAMKMENEITAPVKGKIKRIH

VKEGQKVAKGDLLFEIE

>*C. bescii*_(5S subunit nucleotide sequence)

(SEQ ID NO: 40)

atgggggtaaaaataacagaaacaatactcagagatgctcatcagtcactcattgcaacccgcatgacaactgaacagatgatg agattgctcctgtgcttgaccaagttggttattattcggttgagtgctggggcggtgctacatttgatgcgtgtctgaggtttttcaatg aagacccatgggaaagattaaaaagactgagaactgcttttaaaaagacaaagctccagatgcttcttcgaggacaaaatcttgtt gggtatagacattattctgatgatgttgttgaagagtttgtaaaaaggccatatactatggcattgatattataagaatatttgatgca cttaatgacatccggaatattgaaatggctctaaaaataacaaaaaaagaaaaaggacatgcccaggttgccatatcatacactgt ctcaccttatcatactattgaaaactatgtaaatttggcaaaacaaatagaagaacttggggcagactcaatttgtataaaagacatg gctgggcttctctctccatttgatgcttataaacttgtaaaagcgttaaaagagcaggtaaaacttcctattcatcttcatacacactac accacaggatttggatcaatgacatatttgaaagctgtcgaagcaggtgtggatggtattgacacggctttatctccgcttgcactg ggcacatcccagcctccaaccgaaacaattgtatatgcacttgaaaatacagaatatgaccaaaacttgatttagaaaagatcaa cgaggcaagcgaatattttaaagtactcagagaagaatatataagaaaagggcttatgacccgaaagtattaagtgttgatataa acgctcttcattatcaaatacctggtggaatgctatcaaatcttatttctcagctaaaagaacaagggcaggaagacaagttagatg aggttttaaaagaggtacctgaggttcgaaaagattttggatatccgccacttgtaactcctacgagtcaaattgtgggaacacaag ctgttttgaatgttatagcaggtgagagatacaaacttgtcacaaaagaaacaaaagcatattttaaaggtgagtatgggaaacctc cagctcctgtgaatgaagaggtaaaaagaaaaatcttgaaagacgaaaaagagataacctgcagacctgcagatttgattttgcc agagcttgaaaatgcaaaagaaaagattaaggagtatattgaaaatgatactgatgtggtaacttactgtttattccacaacttgca gaaaatttttcaaattaaggttcgcaaaaaaatacaaggttgacgctgatcttgttcagggtaacaaagtgtatcctgtg >*C. bescii*_(5S subunit amino acid sequence)

(SEQ ID NO: 41)

MGVKITETILRDAHQSLIATRMTTEQMLEIAPVLDQVGYYSVECWGGATFDACL

RFFNEDPWERLKRLRTAFKKTKLQMLLRGQNLVGYRHYSDDVVEEFVKKAIYY

GIDIIRIFDALNDIRNIEMALKITKKEKGHAQVAISYTVSPYHTIENYVNLAKQIEE

LGADSICIKDMAGLLSPFDAYKLVKALKEQVKLPIHLHTHYTTGFGSMTYLKAV

EAGVDGIDTALSPLALGTSQPPTETIVYALENTEYAPKLDLEKINEASEYFKVLRE

EYIRKGLLDPKVLSVDINALHYQIPGGMLSNLISQLKEQGQEDKLDEVLKEVPEV

RKDFGYPPLVTPTSQIVGTQAVLNVIAGERYKLVTKETKAYFKGEYGKPPAPVN

EEVKRKILKDEKEITCRPADLILPELENAKEKIKEYIENDTDVVTYCLFPQLAENFF

KLRFAKKYKVDADLVQGNKVYPV

-continued

>*C. bescii*_(12S_C-term nucleotide sequence)

(SEQ ID NO: 42)

atgtatgctcaggtcagtactatttcaaccattacaaaagaagaacttgcttgtatttgtgcatgtctgcacattgtgatgggtgaagg tcaatataaaattaccaacataactaaacagcaaaacaagtgggtcaaaggtgcaagagaaatgatgctcaatcagtcacagatg ttttatagatggagg >*C. bescii*_(12S_C-term amino acid sequence)

(SEQ ID NO: 43)

MYAQVSTISTITKEELACICACLHIVMGEGQYKITNITKQQNKWVKGAREMMLN

QSQMFYRWR

*Clostridium cellulolyticum* H10 ATCC 35319 Transcarboxylase
>*C. cellulolyticum*_(12S subunit nucleotide sequence)

(SEQ ID NO: 44)

atgtcacaaattgaaaagatacaaaatttaaaaaacatgaaaaaaactatagctaaaggcggcggagaagagaaaatagcaaaa agacacgcagatggaaagctttctgccagagaaagaatccatttgttgtttgatgaaaacagttttgttgaggtagatgcattcatag aatccagatgctttgactttggtatgcagaagaagaaacttccaggtgacggggttgttaccggttacggaacagttaatggcaga aaggtctttgtttcatcacaggactttactgttataggcggttcattgggagagatgcacgcaaagaaaattacaaaggttatggata tggctctgaaaatgggagcaccgttcatagccattaatgattccggcggagctcgtattgaggaaggtctggatgctctttcaggtt acggagatatttttacaggaatactcttgcatcaggcgttattccgcagatatcagtaataatggggccatgtgcaggtggtgcgg tatattccccggccataactgattttatattcatggtggaaaaaacaagtcagatgtttattacaggcccacaggtaataaagtctgtt acgggtgaagatgtatcagttgaaaatctgggaggtgcagatgttcatactgctacaagcggtgtagcacatttcaaatcttcaag cgaagaagagtgtatagaagatataaagaggcttttaagttttattcccgataataatgtatcagatactatgtactacggagtgtctg atgctgccgacagattagccgaaagcctcaacagcattattccagaagagtcaaacaagccatatgacatgtttgacgtaatagc agaagtagtagatgatggagatttctttgaagttcagagttatttctctcagaatataataatcggatttgcaagaatgaatggcaga agtgttggtattgttgcaaaccagcctaagataatggcagggtcactagatatgaacgcggctgataaggcggcacgtttcgttcg tttctgtgatgcatttaatattcctgtcgtttcattaaccgatgtacctgcattcctgcccggggtagcccaggagcataacggcataa tacgtcacggtgcaaaactcctatatgctttctctgaagcaacagtaccaaagataaatgttattcttagaaaggcatatggaggag catatattgctatgaacagtaaaacaataggtgccgatatggttttggcatggccatcagagaaattgcagttatgggacctgacg gagcagcaaatattatatttaaaaaggatattgctgcgtcggaagatccagcagaaaccagaaaggaaaagattgcggaatata gagataaattctcaaatccttatgtagcagcatcaagagggtatattgatgatgttatcgagccttctgaaaccagagtaaaaattat aactgactggaaatgctggatacaaagagggaaaacaggccttcaaaaaaacatggaaacattccgcta >*C. cellulolyticum*_(12S subunit amino acid sequence)

(SEQ ID NO: 45)

MSQIEKTQNLKNMKKTIAKGGGEEKIAKRHADGKLSARERIHLLFDENSFVEVDA

FIESRCFDFGMQKKKLPGDGVVTGYGTVNGRKVFVSSQDFTVIGGSLGEMHAKK

ITKVMDMALKMGAPFIAINDSGGARIEEGLDALSGYGDIFYRNTLASGVIPQISVI

MGPCAGGAVYSPAITDFIFMVEKTSQMFITGPQVIKSVTGEDVSVENLGGADVHT

ATSGVAHFKSSSEEECIEDIKRLLSFIPDNNVSDTMYYGVSDAADRLAESLNSIIPE

ESNKPYDMFDVIAEVVDDGDFFEVQSYFSQNIIIGFARMNGRSVGIVANQPKIMA

GSLDMNAADKAARFVRFCDAFNIPVVSLTDVPAFLPGVAQEHNGIIRHGAKLLY

AFSEATVPKINVILRKAYGGAYIAMNSKTIGADMVLAWPSAEIAVMGPDGAANII

FKKDIAASEDPAETRKEKIAEYRDKFSNPYVAASRGYIDDVIEPSETRVKIITALE

MLDTKRENRPSKKHGNIPL

>*C. cellulolyticum*_(1.3S subunit nucleotide sequence)

(SEQ ID NO: 46)

atgagtaaatatataataaaggtaaacggaactccttatgaagtagaggttgaagaagtgggcgggggaaggcccatttcagct gctccaaagctaagagctaccaagccgggacatacctctgctgcaaaagcagcacagccgcaggcaggtaaagcaggtgat -continued gttgctgctccaatgccgggaactgttttaaaggtaaaggttgctatcggtgatgaagtaaagaaggggcaggractntaatactt gaagctatgaaaatggagaatgaaatagttgctccggctgacggtaaagttacggcgttaaacgtcgaggccggaaagtctgtt actgctggagaactaatggtgtctatagcc >*C. cellulolyticum*_(1.3S subunit amino acid sequence)

(SEQ ID NO: 47)

MSKYIIKVNGTPYEVEVEEVGGGRPISAAPKLRATKPGHTSAAKAAQPQAGKAG

DVAAPMPGTVLKVKVAIGDEVKKGQVLLILEAMKMENEIVAPADGKVTALNVE

AGKSVTAGELMVSIA

>*C. cellulolyticum*_(5S subunit nucleotide sequence)

(SEQ ID NO: 48)

atgccaggcgtaagaattacggaaacagttttaagagatgctcaccagtcccttatagcaaccagaatgaagaccgaagaaatg cttccaattgttgagaagcttgacaatattggttaccattcactggaagcttggggcggagctacttttgactcatgtatgagatttttg aatgaagatccatggatgagacttagaaaaataaaagatgttgcaaagaaaacacctctgcaaatgcttcttaggggccagaacc ttttaggatacaaacactatgccgatgatatagttgagtactttgttcagaaggctgttgcaaacggcatggacattatgagaatattc gatgcactaaatgatgccaggaatatcgagacggcaattaaggcatgtaaaaaggaaggcggccatgctcagggctgtatttgc tatactataagtcctgttcacaatcttgagctttttgtaaaagatgcaaagcagttggagagcatgggagcagattctatctgtataaa agacatggccggacttctggtgccgtatcaggcttatgaactggtaaaggattgaaagaaagtgtaaagataccgatacaattgc acactcactatactagcggtgtagcatctatgacgtatttgaaggctatagaagcaggtatagatattgttgactgtgcaatttcacct atgtcaatgggaacgtcacagccgcctacagagcctttggtggcaactttaaagggaactgatttcgatactggactggatttgga aaaactcagtgaaattgcagactatttcagaccccttaaagaaaaatatattgagagcggactattagacgttaaggtaatgggtgt tgacgttaacactcttatttatcaggtacctggtggaatgctttcaaatcttgtttcacaattgaagcagtcaaatgctttggataaatat gaagaggttctcaaggaagttcccagagtaagagccgatttcggctatcctccgcttgtaacaccatcaagtcagatagttggtac ccaagcggtacttaatgtattgactggtgagagatacaagatggtaccaaaggaatcaaaaggcgttgtaaaggggggaatacgg taaaacccctgcacctattagtgatgaaataaaagctaagattctgggcgatgaaaagcctataacatgcagacctgctgacctta ttgaacctgagcttgaaaagattagagaagctgttaaggattatatagagcaggatgaagatgtactttcatacgcaatgcttcctc aggttgccgagaagttattaaacagcgtattgaggatagaaataaggctactgcacccgcatcagacgaaataaaacccgaag ttgtagcggcaatatcagccgtagtaaacgaaatgggcgaaagagacggcacacagtacagaatcggaaatatctctaagttga accagaatcagaacagatggagtctgtatggtatgcttgatagattcagaacaaaaatt >*C. cellulolyticum*_(5S subunit amino acid sequence)

(SEQ ID NO: 49)

MPGVRITETVLRDAHQSLIATRMKTEEMLPIVEKLDNIGYHSLEAWGGATFDSC

MRFLNEDPWMRLRKIKDVAKKTPLQMLLRGQNLLGYKHYADDIVEYFVQKAV

ANGMDIMRIFDALNDARNIETAIKACKKEGGHAQGCICYTISPVHNLELFVKDAK

QLESMGADSICIKDMAGLLVPYQAYELVKALKESVKIPIQLHTHYTSGVASMTYL

KAIEAGIDIVDCAISPMSMGTSQPPTEPLVATLKGTDFDTGLDLEKLSEIADYFRPL

KEKYIESGLLDVKVMGVDVNTLIYQVPGGMLSNLVSQLKQSNALDKYEEVLKE

VPRVRADFGYPPLVTPSSQIVGTQAVLNVLTGERYKMVPKESKGVVKGEYGKTP

APISDEIKAKILGDEKPITCRPADLIEPELEKIREAVKDYIEQDEDVLSYAMLPQVA

EKFFKQRIEDRNKATAPASDEIKPEVVAAISAVVNEMGERDGTQYRIGNISKLNQ

NQNRWSLYGMLDRFRTKI

*Corynebacterium kroppenstedtii* DSM 44385Transcarboxylase

>*C. kroppenstedtii*_(12S subunit nucleotide sequence)

(SEQ ID NO: 50)

atgagtgagcaacctcacgatcccagcatgcctgagcgcctcggacagctggaagaagaaagaaaccgcatccgactcggc ggcgggcaggcacgcctggacaagcagcacgaccgcggcaagatgaccgcccgcgagcgcatcaccaagcttgtcgacg -continued aagacacgttccaggaaaccggaatgttcgccaagcaccggacaacgcacttcggcatggacaaggccgacgcccccgccg
acggcgtcgtcaccggatccggcgcggtctacggacggccagtgcacatcgcgtcccaggacttcagcgtcatgggcggatc
tgctggcgaaatgcagtccaacaaagtggtcgccatgatgaaggcgtccgcgaccaccggcacccccttcgtctttatcaacga
ctccggcggagctcgtgtccaagagggcatcgactccactccggatacggccgcgtgttctacaacaacgtgctgctaccgg
actcgtaccgcaggtaccatcatcgccggcccgtgcgctggtggtgcggcctactcgccggcactgacggacttcatcatcca
gacccgcaaggccaacatgttcatcaccggccccaaggtcatccagtccgtgaccggcgaaaaagtcacggccgacgaactc
ggtggtgccgatgcccacatgagcacagctggcaacattcacttcgtcgccgacgatgacgagcaagccatcctgatcgcgca
gaagctcctgagcttcctgccgcaaaacaacaccgaagagccgcccatcgtcgatccggacgaggttgtcgagcccgacgatt
ccctccgcgacatcgtccccgtcgatggccgcaagggctacgacgtccgcgatatcatccgcaagatcgtcgactacggcgac
ttcctcgaggtccaggccggatacgcccaaaacctcgtggtcggatttgcccgcgtcgttggccggacagtcggtatcgtcgct
aaccagtcgcaagtgatgtccggcgttctggacatcaactcgtcggacaaaggcgcaagcttcgttcgcttctgcgactccttca
atattccgctcctcaccctcgtcgacgtccccggcttcatgccaggtgtcgcacaagagcatggcggaatcattcgccacggcg
cgaagatgctgttcgcctactcggcggccaccgtgccgaagctgaccgtggtcctccgcaaatcctatggcggatcgtacctgg
ccatgtgctccaaggaccttggcgcggaccgcgtctgggcgtggcccaccgctgaaattgcggtcatgggtgccgacggagc
cgtgaacgtcgtcttccgtaaggaaatcaagaaagcccaggaagagggtggcgacgaagccgctgcagcaaagaagagcga
actcgtccagctctacaaagacaccttctcgacgccatacatggcggcgtcccgaggcctcgtcgatgacatcatcgaccccgc
ggacacacgtcgcgaaattgctctggccctggagttgctgaccaacaagcgtgagaaccggccgtccaagaagcacggcctg
gcacccaac >*C. kroppenstedtii*_(12S subunit amino acid sequence)

(SEQ ID NO: 51)

MSEQPHDPSMPERLGQLEEERNRIRLGGGQARLDKQHDRGKMTARERITKLVDE
DTFQETGMFAKHRTTHFGMDKADAPADGVVTGSGAVYGRPVHIASQDFSVMG
GSAGEMQSNKVVAMMKASATTGTPFVFINDSGGARVQEGIDSLSGYGRVFYNN
VLLSGLVPQVSIIAGPCAGGAAYSPALTDFIIQTRKANMFITGPKVIESVTGEKVT
ADELGGADAHMSTAGNIHFVADDDEQAILIAQKLLSFLPQNNTEEPPIVDPDEVV
EPDDSLRDIVPVDGRKGYDVRDIIRKIVDYGDFLEVQAGYAQNLVVGFARVVGR
TVGIVANQSQVMSGVLDINSSDKGASFVRFCDSFNIPLLTLVDVPGFMPGVAQEH
GGIIRHGAKMLFAYSAATVPKLTVVLRKSYGGSYLAMCSKDLGADRVWAWPT
AEIAVMGADGAVNVVFRKEIKKAQEEGGDEAAAAKKSELVQLYKDTFSTPYMA
ASRGLVDDIIDPADTRREIALALELLTNKRENRPSKKHGLAPN

>*C. kroppenstedtii*_(1.3S subunit nucleotide sequence)

(SEQ ID NO: 52)

atgaaactgacagttaccgtcaacggcgtcccctattccgtggacgtagaagttgaacacgaagaacgccccacactcggcac
catcatcactggtggcaacagcaacgggccaacacccaccgcgccgaccacctcatctgtccagggtgtcagcgccaattcgg
tcacggcacccctggctggttccgtcagcaaggtgcttgtggaggaaggccaagccatcacggccggcgaagtgatcgttgtc
cttgaagccatgaagatggaaaccgaaattacggcccccaacgacggcaccgtcaccgcgcttcacgtgcaacccggcgacg
ccgttcagggtggacagtctctgctggagatcggggac >*C. kroppenstedtii*_(1.3S subunit amino acid sequence)

(SEQ ID NO: 53)

MKLTVTVNGVPYSVDVEVEHEERPTLGTIITGGNSNGPTPTAPTTSSVQGVSANS
VTAPLAGSVSKVLVEEGQAITAGEVIVVLEAMKMETEITAPNDGTVTALHVQPG
DAVQGGQSLLEIGD

-continued

>*C. kroppenstedtii*_(5S subunit nucleotide sequence)

(SEQ ID NO: 54)

atgaccacgcgaaaaattggagtgaccgaactggctctgcgtgatgctcaccagagcctcatggcaacacgcatggccctcga agacatggtcgatgcctgtgaggatatagacaaagccgggtactggagcgtggaatgctggggcggggcaaccttcgacgcc tgcattcgcttcctgaacgaagacccgtgggagagactgcgcacattccgcaagctcatgcccaactcacgccttcagatgctg cttcgtggccagaatcttctgggataccgtcactacgaggacggcgtcgtcgataagtttgttgaaaaatccgctgaaaacggcat ggacgtcttcagggttttcgacgcgctcaacgacccccgcaacctcgagcacgccatgcaagctgtgaaaaaagtgggcaagc acgcgcagggcaccatctgctacaccgtgtccccgctacacgacgtgcagggctacattgatctagcagggcgtttgctggaca tgggcgcggattcgatcgcgctcaaagacatggcagcgctgctcaaaccacagcccgcctacgacattatccgtggcattaag gacacctacggcgaggatacgcagatcaacgtccactgccactccaccaccggcgtcacgatggtcaccctcatgaaggccat tgaagccggtgcggatgtcgtcgacaccgccatttcctccatgtccctcggcccagggcataaccccaccgagtctacgtcga aatgctcgaaggaaccgactacgagaccgggcttgacatggatcggctcattaacatccgcgaccacttcaagacagtgcgcc cgaagtacgcggagtttgagtcgaaaacactggtcaacaccaatattttccaatcgcagattccgggcggaatgctctccaacat ggaatcgcagctcaaagcccagggcgcgggcgaccgtatcgacgaggtcatgaaagaagtccccgtcgttcggaaagagc cggatacccgccgttggtgacgccatcgtcccagatcgtcggcacccaggccgtgttcaacgtgctgatgggccgctacaaag tactcacggctgaattcgccgacctcctcacgggtactacggcgaagcaccaggtgagagggataaagacctcatcgagcaa gccaagaagcagaccggcaaagagcccatcaccgagcgtcctgctgacctccttgagcccgaatgggacaacctggttgagg aagagacgaactcgacggcaccgacgggtccgacgaagacgtcctcacaaacgccagttcccgcaggtcgcgccgggatt cttcaagactcgccccgacggcccgaagaacgtcggcaagactaaggaacagacgagcgcgaagaggcgaaggcctccg gcgacgccactgccatccgcgaaccgattatgtacaaagtcaccacaggcggccgcagccacactgtctccgtggaacccgc a >*C. kroppenstedtii*_(5S subunit amino acid sequence)

(SEQ ID NO: 55)

MTTRKIGVTELALRDAHQSLMATRMALEDMVDACEDIDKAGYWSVECWGGAT

FDACIRFLNEDPWERLRTFRKLMPNSRLQMLLRGQNLLGYRHYEDGVVDKFVE

KSAENGMDVFRVEDALNDPRNLEHAMQAVKKVGKHAQGTICYTVSPLHDVQG

YIDLAGRLLDMGADSIALKDMAALLKPQPAYDIIRGIKDTYGEDTQINVHCHSTT

GVTMVTLMKAIEAGADVVDTAISSMSLGPGHNPTESLVEMLEGTDYETGLDMD

RLINIRDHFKTVRPKYAEFESKTLVNTNIFQSQIPGGMLSNMESQLKAQGAGDRI

DEVMKEVPVVRKAAGYPPLVTPSSQIVGTQAVFNVLMGRYKVLTAEFADLLLG

YYGEAPGERDKDLIEQAKKQTGKEPITERPADLLEPEWDNLVEEADELDGTDGS

DEDVLTNALFPQVAPGFEKTRPDGPKNVGKTKEQLEREEAKASGDATAIREPIM

YKVTTGGRSHTVSVEPA

>*C. kroppenstedtii*_(12S_C-term subunit nucleotide sequence)

(SEQ ID NO: 56)

atgaatacagacaatgcatcctctgctgaactcagtcagttgttggcccgcctgtccaaccaggtagaaaagctctcccgcaacg tcaccaagctcgaaaatgaagttgcggcactgaagcagcgctctgacgaggaaattcctgaagatgtatgattgcgatcagtgc ggccgtatccgcctacatgggtaaccgcggaaccgtgcgcgcagttcacttcttgcgccatcgcagaggtcacagcaaggtc ggcaggcagttcagcacaaggcgaaatggcaa >*C. kroppenstedtii*_(12S C-term subunit amino acid sequence)

(SEQ ID NO: 57)

MNTDNASSAELSQLLARLSNQVEKLSRNVTKLENEVAALKQRSDEEIPEDVLIA1

SAAVSAYMGNRGTVRAVHFLRHRSWSQQGRQAVQHKAKWQ

-continued

*Geobacter bemidjiensis* BEM($^{T}$) Transcarboxylase

>*G. bemidjiensis*_(12S subunit nucleotide sequence)

(SEQ ID NO: 58)

atgtccatagaagagaagataaaagcgctgaacgacaagaagagcaagctgaagctgggcggcgggcgctcgaagatcgac cagcagcacgcccagggaagcctgaccgcccgggagcggatagaggcgctggtggacaaggacagcttccaggaaatcg gcatcttcgccaggcaccgctgcaccaatttcggcatggccgggaaggaactgccggccgaaggggtggtcaccggcgcag ggagcgtgggcgggaggatggtgcacctggcgagccaggatttcaccgtcgccgggggatcggcgggcgaggtgcacagc gacaagatcgtgcaggcgatgctggggtcgctgaagaccggaaccccccttcgtcttcatgaacgattccggcggcgccaggat ccaggaagggatcgactcgttagccggctacggcaaggtcttctaccacaacgtgatgctcagcggggtggtgccgcagatct cgctcatctgcggcccctgtgccgggggcgcggcctacagcccggcgctcaccgatttcatcatccagaccgccaaggcgcg catgttcatcaccggcccttccgtgatcaaggaggcgaccggcgaagagatcagcgccgaggagctgggagggccactgtc gcagatgaaccatagcggcgtagcccatttcgtggcggagaacgacctggtggcgcttcgcatctgcaagaagacctttccta cctcccctccaacaacatcgaggacccgccgcagttggaaagcgacgacgtcatcgtcccggacaagacgttgaacagcatc gtgccgtcggagcagaagaaggcctacgacgtgaggaacgtgatcacgcgcctgatcgacggcggcgacttcctggaggtg cagcctctgttcgctgccaacatcgtggtcgggttcggcaggatactcgggcggagcgtcggcatcgtcgccaatcagccgtc ggtcttggcgggggcgctggacatcaacgcttcggacaagggagccaggttcgtccggttctgcaacgccttcaacatcccgct ggtgaccctggtggacgttccgggttttctccccggggtacagcaggagaagggggggatcatccgccacggcgccaagatg ctcttcgcctacgccgcggccaccgtcccgaagataaccgtcatcatgcgcaaggcgtacggcggcgccttcctcgccatgtg cggcaaggagttggagaccgatcgggttttcgcctggcccagcgccgagatcgcggtcatgggaccgcagggagcggtcaa cgtcatcttccggaacgagatcgcccaggcggaagatcccaagaaaaagcgcgacgagctgatcgcttcttaccagggaacct tcgccactccctatgcggccgcggcacgccgcgatgtggacgacatcatcgagcccgccgatacgaggcgccacctcgccat gacgctggacatcctgagcaccaagcgcgaattcaggcccatgaagaagcatggcctcattccgctg >*G. bemidjiensis* (12S subunit amino acid sequence)

(SEQ ID NO: 59)

MSIEEKIKALNDKKSKLKLGGGRSKIDQQHAQGSLTARERIEALVDKDSFQEIGIF

ARHRCTNFGMAGKELPAEGVVTGAGSVGGRMVHLASQDFTVAGGSAGEVHSD

KIVQAMLGSLKTGTPFVFMNDSGGARIQEGIDSLAGYGKVFYHNVMLSGVVPQI

SLICGPCAGGAAYSPALTDFIIQTAKARMFITGPSVIKEATGEEISAELLGGPLSQM

NHSGVAHFVAENDLVALRICKKLLSYLPSNNIEDPPQLESDDVIVPDKTLNSIVPS

EQKKAYDVRNVITRLIDGGDFLEVQPLFAANIVVGFGRILGRSVGIVANQPSVLA

GALDINASDKGARFVRFCNAFNIPLVTLVDVPGFLPGVQQEKGGIIRHGAKMLFA

YAAATVPKITVIMRKAYGGAFLAMCGKELETDRVFAWPSAEIAVMGPQGAVNV

IFRNEIAQAEDPKKKRDELIASYQGTFATPYAAAARRDVDDIIEPADTRRHLAMT

LDILSTKREFRPMKKHGLIPL

>*G. bemidjiensis*_(1.3S subunit nucleotide sequence)

(SEQ ID NO: 60)

gtgcaactgaccatgaccattgacggaaagaaataccgggtggacgtagaagtcgaggaaggggaagaggtgcgtacggaa ggggccttccctcccaccgcgactatgcaggcgtacccggtgtattcggcgcatccaaccgcgaccccgccgctggccgcgc cgaccccggcctccagttcggaaaagatctgccgcagtcccatcgcgggggtggttttcaagatcgtggcgcaggtgggtcaa cacctggagatgaacgacctgctggtcgtcctcgaggcgatgaagatggagaccaacatcaccgcgcacatgtccgggaagg tggaaaagattctggtttccgtgggcgaagcggtgcagcctggacaggcaattgccgaatttgcc -continued >*G. bemidjiensis*_(1.3S subunit amin acid sequence)

(SEQ ID NO: 61)

VQLTMTIDGKKYRVDVEVEEGEEVRTEGAFPPTATMQAYPVYSAHPTATPPLAA

PTPASSSEKICRSPIAGVVFKIVAQVGQHLEMNDLLVVLEAMKMETNITAHMSG

KVEKILVSVGEAVQPGQAIAEFA

>*G. bemidjiensis*_(5S subunit nucleotide sequence)

(SEQ ID NO: 62)

atggaccgcattatcgacataaccgaactggctctgcgcgacgcgcaccagagccttatcgctacgaggctcgggatagacga catggttccggtgtgcgaggacctggaccaggcgggctactggtccatcgagtgctggggcggggccacctatgacgcctgc atccgctttctcaacgaagatccgtgggtgaggcttaggaccttcaaggagctgagccgaaaaccccgctgcagatgcttttgc gggggcagaaccttttgggataccggcattaccaggacgaggtggtggaccggttcgtccagaagagcgccgagaacggcat cgacgtgttccggatcttcgatgcgctgaacgatctgaggaacctggagcggtcggtccaggcggtgaagcagtgcggaaag cacgcgcaggtcgccatctcctataccatcagccccattcacaccacggcgaaattcgtggagcaggcgaagcgcctggtcga catggggtgcgactccatctgcatcaaggacatggcggcgctgatcaagccgcacgcgacatacgacctggtgagagggatc aaagaggcctgcggcgaccggatccggatacagagcatgcgcacgccaccagcggcgtgaccatggtgagttacatgaag gcggtggaggcgggcgtggacggcgtggacacggcggtgagttccatgagcctcgggcccggacacaacccgacggaga gctttgcggagatgctggaaaatacgggctacaccacgcgcatcgacctcggccgggtgaacaaggtgaaggagcatttcgc caaggtgctccccaggtactcagaattcctctccaccatcaccggcgcggagacggagatcttcaggagccagattccaggcg ggatgctttccaacatggagagccagttgaagcagcagggggctggggaccggatgcgcgacgtgctggaagagataccgc tggtgagaaaggacacgggatacgtcccgaggtaaccccgaccagccagatcgtcgggacccaggcggtgctgaacgtatt gatggggcgctacaaggtgctgaccggcgagttcgccgacctgatgctcggctactacggcctcacgccgggagaacggaa cccggaggtggtggagcaggcgcgccgccacgcgaataaggagccgatagagtgccgccccgcagatctattggagccgg aatggggcaagctgcgggcggcggcgctccccttggagggttgcgacggcagcgacgaggacgtgctcacctacgccctctt tccgcaggtggcgccgaagttcttcgccacgaggagtgaaggaccccgaaacctggggcgcgatcccgtcaccggagcttcg gaaaccagcattcccgaagggcaccccgggaagatcaccggccccgtcacctacacggtcaccttgagcgggcagccgcac aaggtgacggttgcaccctacggccaggaat >*G. bemidjiensis*_(5S subunit amino acid sequence)

(SEQ ID NO: 63)

MDRIIDITELALRDAHQSLIATRLGIDDMVPVCEDLDQAGYWSIECWGGATYDA

CIRFLNEDPWVRLRTFKELMPKTPLQMLLRGQNLLGYRHYQDEVVDRFVQKSA

ENGIDVFRIFDALNDLRNLERSVQAVKQCGKHAQVAISYTISPIHTTAKFVEQAK

RLVDMGCDSICIKDMAALIKPHATYDLVRGIKEACGDRIRIQLHAHATSGVTMVS

YMKAVEAGVDGVDTAVSSMSLGPGHNPTESFAEMLENTGYTTRIDLGRVNKVK

EHFAKVLPRYSEFLSTITGAETEIFRSQIPGGMLSNMESQLKQQGAGDRMRDVLE

EIPLVRKDTGYVPLVTPTSQIVGTQAVLNVLMGRYKVLTGEFADLMLGYYGLTP

GERNPEVVEQARRHANKEPIECRPADLLEPEWGKLRAAALPLEGCDGSDEDVLT

YALFPQVAPKFFATRSEGPRNLGRDPVTGASETSIPEGHPGKITGPVTYTVTLSGQ

PHKVTVAPYGQE

>*G. bemidjiensis*_(12S_C-term subunit nucleotide sequence)

(SEQ ID NO: 64)

gtggacgaagagatggagcaggaacacgatccggaaatcacgcccgaactgctgatggtgatgtccgccgcgatagccgcgt atctgggcaagaccgtgaggataaggcgggccaggttcgtcgacccgaatctgatcaacgcctggggacagtcgagccgcgt ggtgctgcaggcgtcgcacaacttgaggaga -continued >*G. bemidjiensis*_(12S_C-term subunit amino acid sequence)

(SEQ ID NO: 65)

VDEEMEQEHDPEITPELLMVMSAAIAAYLGKTVRIRRARFVDPNLINAWGQSSR

VVLQASHNLRR

*Desulfobulbus propionicus* DSM 2032 Transcarboxylase

>*D. propionieus* DSM 2032_(12S subunit nucleotide sequence)

(SEQ ID NO: 66)

atgagcacaaaggaaaaattagagcagctaaagcaaaaaagggccaaagccttgctgggcggcggtcaggataaaatcgac aagatccactcccagggcaaatataccgcccgtgagcgtattcaactcctcctcgacccaggcaccttcgaggaatacgatgctt tcaagctccatcgctgctacaacttcggcatggaaaaaatcaagtttttcggcgacggtatcgtcaccggatatggcaagctggc cggccggccggtttatatttacgcgcaggacttttcggtcctcgccggttctctttccggaaccttggctgaaaaaatatgcaaaat catggatctgggcatgaaaaacggcattccggtcatcggattgaacgactccggtggcgcccgtatccaggaaggtatcgagg ccctggcaggatataccgaaatcttcacccgtaatgttacgcttcgggtgttgttccccagatttccggtgttttcggaccctgcgc cggtggcgccgtttactacctgccctgaccgacttcatcatccaggtcaagatccagtcctacatgttcctgacaggtcccaagg tcgttaagactgtgttaaacgaggacgtcaccaccgagcagttgggtggtgcggccatgcataccaccaagtccggcgtcacc gactatgctgccgagaacgaggacgacgccattcagtacatcaaggatctgatgagctatttgccgcagaacaatctggagaat cctccggatgccccctgcgacgatccgatcacccgccgctccgaactgctcaacgacatcattccggacaacccgaatgccgc ctacgacatgaaaaaggtcatcaccgagacggcagacaacggtatcttctttgaaatcaagaagaatttcgctccgaacatcgtc atcggttttgcccgttatggtggcaaggctattggcatcgttgccaaccagccgtcctactacgccggtgttctcgacatcgattcct cgatcaaaggtgcccgcttcatccgcttctgcgactgcttcaacattccgatccttaccttcgtcgacgtccctggcttcctgcccg gcactgcacaggaattcggcggcgttatccgcaacggcgccaagatgctgtatgcctacgccgaatcgacagtgccaaaggta acgattattacccgtaaatcctatggcggcgcctactgcgctatgtcgtccaagcacctgcgaaccgatatcaactactcctggcc gaccggtgaaatcgccgttatgggctccaaaggcgcggtcgaagtcctgcacgccaagggcgctaaagcagcagaagatcc cagagcgttcctggccgaaaaagaaaacgagtacaacgagcagttctccaatccatattgtgcggccgagcgtggctatatcga cgatgtcattgaaccggccgaaaccaggtaccgtatcatcaacgcgtttgagtcgatctctggaaagcgtgacacgatcccgatg aagaaacacggcaatatcccgctg >*D. propionicus* DSM 2032_(12S subunit amino acid sequence)

(SEQ ID NO: 67)

MSTKEKLEQLKQKRAKALLGGGQDKIDKIHSQGKYTARERIQLLLDPGTFEEYD

AFKLHRCYNFGMEKIKFFGDGIVTGYGKLAGRPVYIYAQDFSVLAGSLSGTLAE

KICKIMDLGMKNGIPVIGLNDSGGARIQEGIEALAGYTEIFTRNVLASGVVPQISG

VFGPCAGGAVYSPALTDFIIQVKIQSYMFLTGPKVVKTVLNEDVTTEQLGGAAM

HTTKSGVTDYAAENEDDAIQYIKDLMSYLPQNNLENPPDAPCDDPITRRSELLND

IIPDNPNAAYDMKKVITETADNGIFFEIKKNFAPNIVIGFARYGGKAIGIVANQPSY

YAGVLDIDSSIKGARFIRFCDCFNIPILTFVDVPGFLPGTAQEFGGVIRNGAKMLY

AYAESTVPKVTIITRKSYGGAYCAMSSKHLRTDINYSWPTGEIAVMGSKGAVEV

LHAKGAKAAEDPRAFLAEKENEYNEQFSNPYCAAERGYIDDVIEPAETRYRIINA

FESISGKRDTIPMKKHGNIPL

>*D. propionicus* DSM 2032_(12S_c-terminal nucleotide sequence)

(SEQ ID NO: 68)

atggcaaaaatgaacaaaaaaaatggctgcggcccttgcagccgttaatgcctacctgatgcaggaagaggaggcggcatacca ggcccagttgctggctgccaaatctgttgcaccagccgggccaagcttatgggcaattgccggccgtcaggatatcatgaatttc cgcaggctgattcaaatgaaagccttc -continued >*D. propionicus* DSM 2032_(12S_c-terminal amino acid sequence)

(SEQ ID NO: 69)

MAKMNKKMAAALAAVNAYLMQEEEAAYQAQLLAAKSVAPAGPSLWAIAGRQ

DIMNFRRLIQMKAF

>*D. propionicus* DSM 2032_(5S_1.3S_fusion nucleotide sequence)

(SEQ ID NO: 70)

atgagcgaccaagtgaaaatgaccgccatgaattatgcaactgaccggcctgctgcagaaaatccggtcaaagttatggacttg agccttcgtgacggccaccagtctctgttcgccacccgcgggcgcaccgaggacatgattccgatcgcggaaatgatggacga gatcggcttctgggcagttgagacctggggtggcgccacctttgacaccatgcaccgcttcctcaacgaggacccgtgggagc gtctccgcaccctgaaacgttacatcaagaagacccccttctccatgttgctgcgcgcgcagaacctggttggataccgtaactat gccgatgacttggccaccgcctttgttgagcgcgctgccgagaacggtatggatatcttccggacctttgacgccacaacgatta ccgtaacttcgagaccgttgttaaacagatcaagaagagcggcaagcacttccagggttgtatttgctattcgctgaccgaaccg cgtctgggcggggatgtttatgacctgaagtactatgtcgaccgcgccaaagcgcttgacgacatgggcgctgactccatctgc atcaaggacatggccggtctgatcgccccatacgacgcctacgccatcgtcaaggctatcaaggaagtcaccaagaccccgat ccacctgcacagccacttcacctctggtatggcgtccatgagtcatctgaaggccattgaggctggcgtagatatcgttgacacct gcatgaccccgtacgctttccgtaccgcccatccggccatcgagccgttggtcatggccctgctcggcaccaaccgcgacacc ggtttcgacatcaagaaactggccgccatcaacgaggtgctagagaaagaggttatgccgaaatacaagcacctcatggatga ctccaaggctcaatcatcgatatcaacgttcttctccatcagaccccgggcggcatgctaccaacctggtcaaccagttgcgtg agatggatgctctggacaagatcgatcaggtctacaaagagctgccgaaagttcggaaagacctcggccagattccgctggtta ccccgaccagccagatcgttggcatccagaccgtgaacaacgtgctgtttgacactcctgatgagcgctacaagatgatcaccg cccaggtcaaagacctgtgctacggtactatggtaaaaccgctgtgccgatcaaccagaactgcagaagaaggctctgaaag gctatccgcgcggtgaagagccgatcacctgccgtccggcagaggtgcttgagcccgagttggaaaaggccaagaaagagat tggcgatctcgccaaggatatcgatgacttggtactctacgccatctacccggtcaccgggaagaagttccttgagtggaagtat ggcattaccccggcaccgcccgaagtcaagccgctcacccttgaggatgtcaagaagcgtgatgaactggtggccaaggcca aggctggcaagctcatcgagcccaagcccgctgctccggagaagaccgctaacgttcggaccttcaacgtcttcgtcgacggt gagtatttcaacgttgaggtcgacccgaccggtgacttccagccgatggtcgccgctgctccgcggcctgccgcacctgccgct gcaccgaaagctgctgcacctgccgctgctgcacctgctgccgcgccgaaggctgctgcacctgccgccgccgaccggctc cagccgctgttgagggaggaaccccgctgttggccccccatgcccggcatgatcgtcaagaatctggtcaatgttggtgatgcgg tcaaagaggcgaccccatcctcgttcttgaggccatgaagatggagaacaatctcggttctccgtgcgatggtactgtgaaggc gcttaattttggcagcggtgactcggttgccaaggataccgtcctggcaatcatcgga >*D. propionicus* DSM 2032_(5S_1.3S_fusion amino acid sequence)

(SEQ ID NO: 71)

MSDQVKMTAMNYATDRPAAENPVKVMDLSLRDGHQSLFATRGRTEDMIPIAE

MMDEIGFWAVETWGGATFDTMHRFLNEDPWERLRTLKRYIKKTPFSMLLRAQN

LVGYRNYADDLATAFVERAAENGMDIFRTFDALNDYRNFETVVKQIKKSGKHF

QGCICYSLTEPRLGGDVYDLKYYVDRAKALDDMGADSICIKDMAGLIAPYDAY

AIVKAIKEVTKTPIHLHSHFTSGMASMSHLKAIEAGVDIVDTCMTPYAFRTAHPAI

EPLVMALLGTNRDTGFDIKKLAAINEVLEKEVMPKYKHLMDDSKCSIIDINVLLH

QTPGGMLSNLVNQLREMDALDKIDQVYKELPKVRKDLGQIPLVTPTSQIVGIQTV

NNVLFDTPDERYKMITAQVKDLCYGLYGKTAVPINPELQKKALKGYPRGEEPIT

CRPAEVLEPELEKAKKEIGDLAKDIDDLVLYAIYPVTGKKFLEWKYGITPAPPEV

KPLTLEDVKKRDELVAKAKAGKLIEPKPAAPEKTANVRTENVFVDGEYFNVEVD

-continued

```
PTGDFQPMVAAAPRPAAPAAAPKAAAPAAAAPAAAPKAAAPAAAAPAPAAVE

GGTPLLAPMPGMIVKNLVNVGDAVKAGDPILVLEAMKMENNLGSPCDGTVKAL

NFGSGDSVAKDTVLAIIG
```

Engineered Pathways to Produce Hydrocarbons and Other Malonyl-CoA Derived Products Production of a bio-product at high yield requires a balanced chemical equation describing the conversion of substrate to product and a thermodynamically feasible reaction with a negative change in Gibbs free energy. Long chain hydrocarbons, e.g., those that have carbon backbones of at least four carbons and up, derived from fatty acids satisfy both of these requirements. For example, production of a $C_{16}$ fatty alcohol can be described by the following equation:

$$4C_6H_{12}O_6 \rightarrow C_{16}H_{34}O+8CO_2+7H_2O$$

Production of a $C_{16}$ fatty alcohol results in a Gibbs free energy change of −285 kJ/mol glucose. For comparison, production of ethanol results in a Gibbs free energy change of −208 kJ/mol glucose.

The present invention describes the engineering of a recombinant microorganism to convert a native fatty acid biosynthetic pathway into a fermentative pathway, i.e., one that generates net positive ATP and is redox neutral. As shown below, a native fatty acid pathway generates zero net ATP, which stems from the mechanism of producing malonyl-CoA, the acyl-ACP chain precursor used to increase chain length. Malonyl-CoA is formed from the conversion of one glucose into two acetyl-CoA, which produces two ATP and four NAD(P)H. However, ATP is required to produce malonyl-CoA from acetyl-CoA, which results in a net zero ATP balance. In the synthetic route shown below, malonyl-CoA formation is accomplished without the concomitant use of ATP.

Native Pathway: Glucose+CoA→2Malonyl-CoA+2NADH+2NAD(P)H

Synthetic Pathway: Glucose+CoA→2Malonyl-CoA+2ATP+2NADH+2NAD(P)H

In either case, the NAD(P)H produced during malonyl-CoA synthesis is balanced via reduction of the growing acyl-ACP chain.

Figure 2:
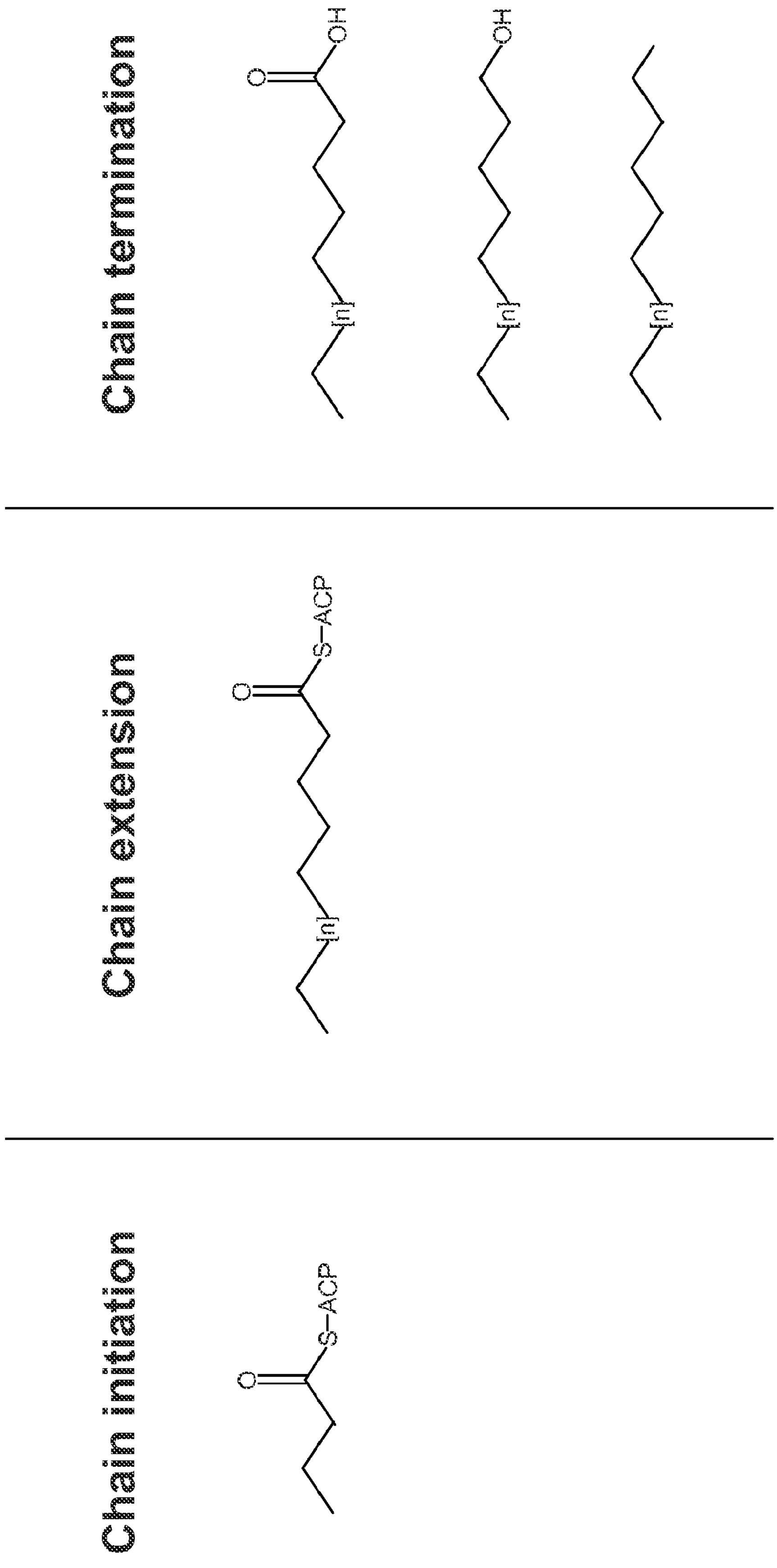
FIG. 2 depicts three steps in the synthesis of hydrocarbons and hydrocarbon derivatives.

The synthetic pathways described herein proceed according to three steps: chain initiation, chain extension, and chain termination (see FIG. 2) and can be carried out in aerobic or anaerobic conditions. In some embodiments, the synthetic pathways produce a hydrocarbon and/or a hydrocarbon derivative under anaerobic conditions. In some embodiments, the synthetic pathways produce a polyketide or an organic acid under aerobic or anaerobic conditions. Chain initiation can proceed by one of several options that are ATP positive and in which NAD(P)H is balanced by chain termination and $H_2$ generation (see FIG. 3A-3C).

Figure 4:
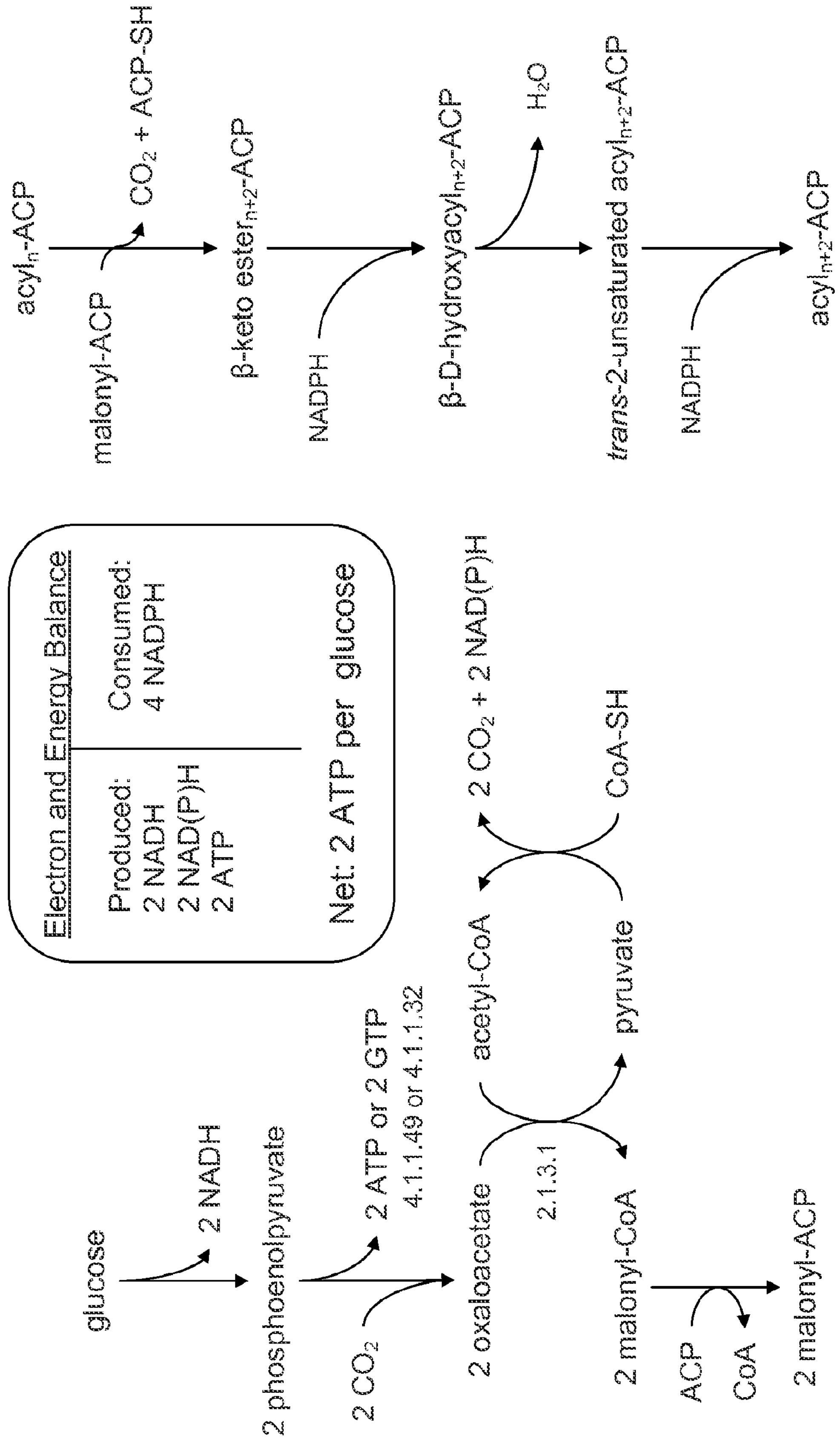
FIG. 4 depicts a pathway for the conversion of glucose to acyl$_{n+2}$-ACP.

5J In native cells, e.g., *E. coli*, chain extension proceeds from pyruvate to acetyl-CoA to malonyl-CoA. See Steen et al., *Nature* 463:559-562 (2010). To conserve ATP during the generation of malonyl-CoA, two enzymes are introduced into the central metabolic network for chain extension: a phosphoenolpyruvate carboxykinase (PEPCK) to convert phosphoenolpyruvate to oxaloacetate and a transcarboxylase (TC) to convert oxaloacetate and acetyl-CoA to malonyl-CoA and pyruvate (see FIG. 4 or FIG. 33). The introduction of these enzymes results in the production of 2 NADH, 2 NAD(P)H, and 2 ATP, resulting in a net production of ATP per carbohydrate, such as but not limited to, glucose. For example, for glucose, the net production of ATP per 6 carbons is about 2. For xylose, the net production of ATP per 5 carbons is about 1.67 ATP. When considering the net production of ATP per hydrocarbon produced rather than sugar consumed, for every 4 carbons of hydrocarbon, the net is about 2 ATP. Thus, for a $C_{16}$ fatty acid, the net ATP is about 8. The conversion of phosphoenolpyruvate to oxaloacetate using PEPCK results in the net production of ATP. See FIG. 4. For example, the net production of ATP in the recombinant microorganisms of the invention includes at least about 0.5 net ATP; at least about 1.0 net ATP; at least about 1.5 net ATP; or at least about 2.0 net ATP during anaerobic growth. The conversion of oxaloacetate and acetyl-CoA to malonyl-CoA and pyruvate by TC then requires the regeneration of acetyl-CoA from the TC-generated pyruvate. The recycling of pyruvate by conversion of pyruvate and CoA-SH into acetyl-CoA and $CO_2$ and NAD(P)H not only facilitates flux in the direction of producing malonyl-CoA, but also generates the reduced NAD(P)H needed to balance redox. Enzymes that can be used to catalyze this pyruvate recycling pathway include, but are not limited to, a pyruvate dehydrogenase, a pyruvate:ferredoxin oxidoreductase and ferredoxin:NAD(P)H oxidoreductase, or a pyruvate formate lyase and formate dehydrogenase.

In addition, competing metabolic pathways can be removed or attenuated. These include, but are not limited to, pyruvate kinase, hydrogenase, lactate dehydrogenase, phosphotransacetylase, acetate kinase, acetaldehyde dehydrogenase, alcohol (ethanol) dehydrogenase, pyruvate formate lyase, pyruvate decarboxylase, and native enzymes involved in the degradation of fatty acids and their derivatives.

PEPCK and TC can be derived from *C. thermocellum* and *T. saccharolyticum* or other organisms. Engineering of these enzymes into the recombinant microorganism of the invention may require alteration of substrate specificity to minimize undesirable side reactions. In addition, cofactor specificity in the overall metabolic pathway can be modified, which has been done with other, similar proteins. To increase flux to malonyl-CoA production, native pathways for organic acid and ethanol production can be modified. Each of these engineering steps is within the abilities of those skilled in the art.

The acyl-ACP chain can be extended though the fatty acid biosynthesis (Fab) enzymes present in all organisms that produce fatty acids. These include FabB, FabF, FabG, FabZ, and FabI. Overexpression of these enzymes can benefit hydrocarbon formation; however, the native biosynthetic pathway is largely regulated by the availability of the malonyl-CoA precursor and the accumulation of long-chain fatty acyl-ACP compounds. See Li et al., *Journal of Bacteriology* 175:332-340 (1993); Davis et al., *Journal of Biological Chemistry* 275:28593-28598 (2000); Davis and Cronan, *Journal of Bacteriology* 183; Heath and Rock, *Journal of Biological Chemistry* 271:1833-1836 (1996)). Supply of sufficient precursor and removal of fatty acyl-ACP via chain termination steps allows for sufficient flux through this chain extension pathway.

Figure 5A:
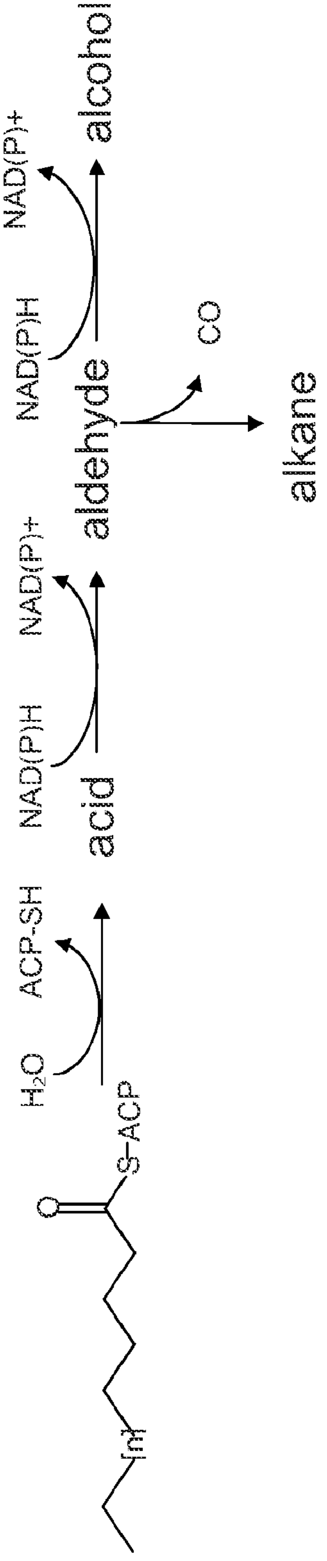
FIG. 5A depicts a pathway for the conversion of a fatty acyl-ACP to a fatty alcohol.
Figure 5B:
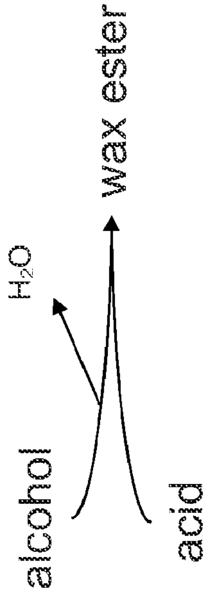
FIG. 5B depicts a pathway for the conversion of an alcohol and an acid to a wax ester.

Once an acyl-ACP chain has reached its desired length, the reaction is terminated and the hydrocarbon product is excreted from the cell. Many chain termination options are available in the art to produce hydrocarbon products or hydrocarbon derivative products, including, but not limited to, fatty acids, alcohols, aldehydes, wax esters, or alkanes (see FIGS. 5A and 5B). See Steen et al., *Nature* 463:559-562 (2010); Sukovich, et al., *Applied and Environmental Microbiology* 76:3850-62 (2010); Kalschener and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010). The termination steps, in concert with chain extension, impart properties on the final compound to mimic petroleum based diesel, gasoline, or jet fuel. For example, production of $C_{14-18}$ fatty alcohols and esters as first generation products can be directly blended to create cellulosic diesel, or serve as a bio-crude that could be converted into other fuels with conventional catalysis technology. Production of fatty alcohols requires expression of a fatty acyl reductase and a fatty aldehyde reductase. See Reiser and Somerville, *Journal of Bacteriology* 179:2969-75 (1997); Steen et al., *Nature* 463:559-562 (2010). Some organisms, such as *E. coli*, have native fatty aldehyde reductase activity, while enzymes such as the jojoba acyl reductase is a bifunctional acyl-ACP/aldehyde reductase. See Reiser and Somerville, *Journal of Bacteriology* 179: 2969-75 (1997). Wax esters can be produced via an acyltransferase in the presence of ethanol or a long-chain alcohol. See Kalscheuer and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006).

The chain length of the hydrocarbon product or hydrocarbon derivative product is controlled based on, e.g., the specificity of the native organism. See Wang et al., *Extremophiles* 10:347-56 (2006); van Beilen et al., *Microbiology* 147:1621-30 (2001). Based on techniques known in the art, termination enzymes can be screened and engineered to develop hydrocarbon products or hydrocarbon derivative products with the desired chain length. See Steen et al., *Nature* 463:559-562 (2010); Sukovich, et al., *Applied and Environmental Microbiology* 76:3850-62 (2010); Kalscheuer and Steinbüchel, *Journal Biological Chemistry* 278: 8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010).

Hydrocarbon products or hydrocarbon derivative products can exit the cell through a membrane "flip" mechanism. In such a mechanism, the polar hydrophilic-hydrophobic compound enters the lipid bi-layer on the intracellular side with the hydrophilic head pointing towards the inside of the cell, flips over so that the hydrophilic head points outside of the cell, and then exits the bi-layer into the extracellular environment. See Black and DiRusso, *Microbiology and Molecular Biology Reviews* 67:454-472 (2003). Alternatively, to ensure efflux from the recombinant microorganism, high efficiency hydrophobic compound efflux transporters can be engineered, although at a cost of one ATP per molecule extruded. See Kieboom et al., *Journal of Biological Chemistry* 273:85-91 (1998). Such mechanisms allow for collection of the hydrocarbon products or hydrocarbon derivative products in the fermentation medium, in addition to other products naturally secreted or expelled by the host cell.

As hydrocarbon products or hydrocarbon derivative products accumulate in the fermentation media, the products can form a 2-phase organic layer after saturating the aqueous fermentation volume. See Neumann et al., *Applied and Environmental Microbiology* 71:6606-612 (2005). At saturating concentrations, toxicity correlates to the "minimum membrane concentration" of a compound, which is a function of the octanol/water partition coefficient and the aqueous solubility. Generally, as chain length increases, compounds become less toxic.

Product recovery and product toxicity are independent of substrate concentration. This provides the advantages that either a minimal pretreatment can be run at low fermentor solids or, when using refined material, the refined material can be run at very high solids without product toxicity to the fermenting organisms. In addition, because the hydrocarbon products are insoluble, product recovery can be at low cost. This means that the hydrocarbon products can be readily purified for use in fuels and chemical feedstocks.

EXEMPLIFICATION

The invention now being generally described, it will be more readily understood by reference to the following examples, which are included merely for purposes of illustration of certain aspects and embodiments of the present invention, and are not intended to limit the invention.

Example 1

The present prophetic example describes the engineering of a recombinant microorganism to convert a native fatty acid biosynthetic pathway into a fermentative pathway, i.e., one that generates net positive ATP and is redox neutral during anaerobic growth.

1.1 Production of Hexadecanol in *T. saccharolyticum*

Gene overexpression and gene deletion followed by evolutionary engineering will be performed to create a strain producing 1-hexadecanol.

The strain *T. saccharolyticum* JW/SL-YS485 has an established transformation system based on a natural competence protocol. See Shaw et al., *Applied and Environmental Microbiology* 76:4713-4719 (2010). Recombinant DNA, either linear or plasmid based, can be introduced with the following protocol.

1.1.1 *T. saccharolyticum* Transformation Protocol

Prior to use, petri dishes, 50 mL and 15 mL conical falcon tubes, and pipet tips are all placed in the anaerobic chamber at least overnight. Transformations are performed in an anaerobic chamber by inoculation of 10 mL liquid medium M 122 (pH 6.1 or 6.7—there is less precipitation at pH 6.1 and it facilitates OD measurement, but kanamycin selection is better at pH 6.7) with 1-3 μL of a frozen working stock culture of *T. saccharolyticum*, which has been frozen-down when in exponential growth. After mixing, 1 mL aliquots of the 10 mL medium are transferred to tubes containing between 0.25 μg-1 μg DNA. The tubes are then incubated at 55° C. for 16-18 hours (overnight) to an OD of 0.6-1. Maintaining cells past 18 hours in stationary phase can dramatically reduce transformation efficiencies.

Next, 100 μL and 500 μL aliquots of the transformant culture are mixed with 25 mL liquid medium M122 pH 6.7 at 55° C. containing 1.2% agar and kanamycin at 200 μg/mL. The mixture is poured into petri dishes and allowed to solidify at room temperature for 30 minutes, or until completely solid, and the petri dishes are incubated at 55° C. in a moisture retaining container until colony formation (24-48 hours).

1.1.2 Gene Deletion

Figure 8:
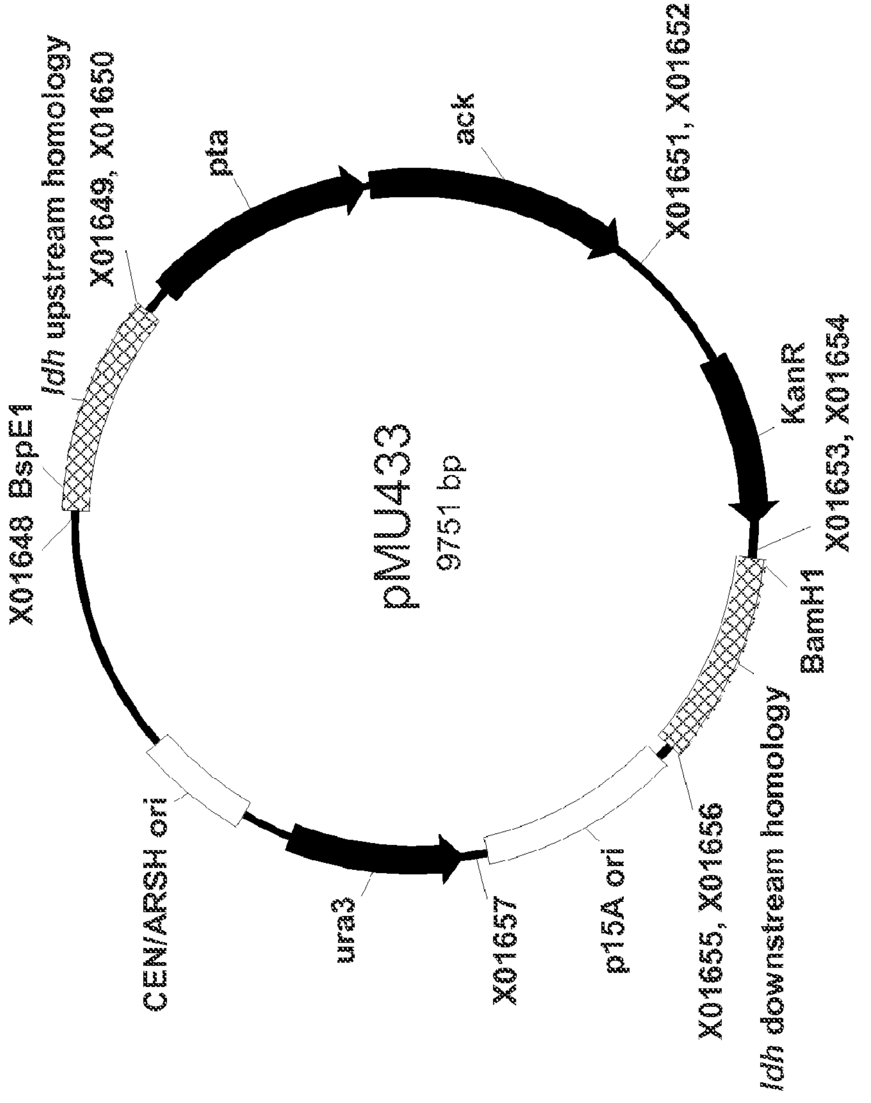
FIG. 8 depicts the vector pMU433.

Gene deletions will be performed with a marker removal system, which allows for clean genomic deletions and marker recycling. The plasmid pMU433 (see FIG. 8) contains the marker removal cassette, namely the pta and ack genes linked to a kanamycin resistance gene. Genes targeted for deletion include L-lactate dehydrogenase, bifunctional alcohol dehydrogenase adhE, pyruvate kinase, pyruvate formate lyase, and phosphotransacetylase and acetate kinase. To construct deletion vectors, homology regions are generated from the target gene sequences from *T. saccharolyticum* and cloned into pMU433.

L-lactate dehydrogenase (SEQ ID NO: 72)

```
atgagcaaggtagcaataataggatctggttttgtaggtgcaacatcggcatttacgctggcattaagtgggactgtgacagatat
cgtgctggtggatttaaacaaggacaaggctataggcgatgcactggacataagccatggcataccgctaatacagcctgtaaat
gtgtatgcaggtgactacaaagatgtgaaaggcgcagatgtaatagttgtgacagcaggtgctgctcaaaagccgggagagac
acggcttgaccttgtaaagaaaaatacagccatatttaagtccatgatacctgagcttttaaagtacaatgacaaggccatatatttg
attgtgacaaatcccgtagatatactgacgtacgttacatacaagatttctggacttccatggggcagagtttttggttctggcaccg
ttcttgacagctcaaggtttagatacctttttaagcaagcactgcaatatagatccgagaaatgtccacggaaggataatcggcgag
catggtgacacagagtttgcagcatggagcataacaaacatatcgggtatatcatttaatgagtactgcagcatatgcggacgcgt
ctgcaacacaaatttcagaaaggaagtagaagaagaagtcgtaaatgctgcttacaagataatagacaaaaaaggtgctacata
ctatgctgtggcagttgcagtaagaaggattgtggagtgcatcttaagagatgaaaattccatcctcacagtatcatctccattaaat
ggacagtacggcgtgaaagatgtttcattaagcttgccatctatcgtaggcaggaatggcgttgccaggattttggacttgcctttat
ctgacgaagaagtggagaagtttaggcattcagcaagtgtcatggcagatgtcataaaacaattagatata
```

Bifunctional alcohol dehydrogenase adhE (SEQ ID NO: 73)

```
atggcaacgacaaaaacggaattagacgttcagaagcagatagatctacttgtgtcaagagcacaagaggctcagaaaaaattc
atgtcttacacgcaagagcaaatcgacgcaatagttaaggcaatggctttagcaggcgttgacaaacacgtagagctggcaaag
atggcgtacgaagagacaaaaatgggtgtatacgaagataagataacaaaaaatctcttcgcaacagagtacgtgtaccacgac
ataaaaaatgaaaagactgtaggaatcataaacgagaacatagaagaaaactacatggaagtggcagaaccgataggcgtaat
tgccggtgtcacacctgtcacaaacccaacatctaccacgatgtttaaatgcttaatatccataaagacgcgaaatcctataatattc
agcttccatccaaaggcaataaagtgcagcatcgcagcagccaaagtgatgtatgaagctgcactaaaggcaggcgcacctga
aggatgcataggatggatagaaacgccatcaattgaggccacacagcttctcatgacacatccaggcgtatcgctgatccttgca
acgggcggtgcaggaatggtaaaagcggcatacagctcaggaaaaccggcattaggcgtaggtcctggcaatgtgccatgct
acatcgaaaaatcagcaaacataaagagggctgtatcggatacatactaagcaagacatttgacaatggagtaatatgcgcatc
agagcaggccgtaataatagacgaggaaatagcagatgaagtcaaaaagcttatgaaagaatacggctgctacttcttaaacaa
agatgaaataaagaagcttgagaaatttgcaattgatgagcaaagctgcgccatgagccctgcagtggtaggtcagccagcgg
cgaagattgctgaaatggcaggcttcaaagtccccgaaggcacaaagatattagtggcagagtacgaaggagtaggtccaaaa
tatcctctatcaagggagaaactaagcccgattcttgcttgctacaccgtcaaagactacaatgaaggaatcaaaaagtgcgagg
aaatgactgaattcggaggtttaggccactctgctgtaatacactctgaaaatcaaaacgtcataaatgaatttgcaaggcgagtcc
gcacaggaagacttatcgtaaattcaccatcatcacagggagcaataggagatatatacaatacaaacacgccatcacttacatta
ggctgtggttctatgggaagaaactcaacgacagacaatgtaagcgtcaagaaccttttgaatattaagcgtgtcgtgataaggaa
tgatagaatgaaatggttcaagattccaccgaagatttactttgaaagcgggtcactccagtacctgtgcaaagtcaaaagaaaaa
aagcgtttatcgtcacagatccattcatggttaagcttggcttcgtagacaaagtgacatatcaattagacaaagcaaacatcgaat
acgaaatattctcagaagtagagccagatccatctgttgacacagtcatgaacggcgtaaaaataatgaattcgtacaatcctgac
ttaataatcgctgtaggcggtggctctgcaatagacgcagcaaagggaatgtggcttttctacgaatatcctgatacagagtttgaa
acattgaggcttaaatttgcagacatcagaaaaagggcatttaagttcccagaacttggcaaaaaagcgctattcatcgcaatacc
gacaacaagcggcacaggctcagaagtgacagcatttgccgtaataaccgacaaaaagagaaacatcaagtatccactggca
```

-continued gactacgaacttacacctgacatagccataatagatcctgaccttacaaagactgtaccgccatctgtaacagcagacacaggca tggatgtgctgacacacgccatagaagcatacgtatcagtaatggcatcagactacacagatgcactggcggaaaaggctataa agatcgtatttgaatacctgccaagggcttataaaaacggcaatgatgaagaagcccgcgaaaagatgcacaatgcttcctgcat ggctggtatggcattcacaaatgcattcttaggaataaaccacagcatggcacacatactgggcggaaagttccacataccacac ggaagagcaaatgcaatacttctgccgtatgtaataaggtacaatgcagaaaaacctacaaagtttgtggcattcccacaatacga atatccaaaagcagcagaaagatatgcggaaatcgccaaattcttaggactgcctgcttcaactgttgaagaaggcgtagaaag cttaatagaagctataaagaacctcatgaaagagcttaacattccgcttacacttaaagacgccggcatcaacaaagaacagtttg aaaaagaaatagaggaaatgtcagacatcgccttcaacgatcagtgcacagggacaaacccgagaatgcctctcacaaaagaa attgcagagatctacagaaaagcatacggtgca Pyruvate kinase (SEQ ID NO: 74)

atgcgtagaactaagataatatgcacgattggtcctgccagtgaaaaatatgagatattgaaagagcttatagaaagcggtcttaat atttgcaggttgaattttcacatggggatcatgaagagcatggaagcagaatagacaatattataaagattagagaagaacttaag ctgcctattgcaattatgcttgatacaaaagggcctgaaataaggactggcagatttaaaggcggtgttgcagagcttaaagaag gccagacatttacgataacatcaagggaaattgaaggagataacactatttgttctgtttcatacaaggggcttcctcaagatgtgg agagaggttctcgcatattgattgatgacggattagtatcattgaaagtcaatgacgtaaaaggtgaagatatagtatgcactgtgg agaattctggtacaataggtgatcacaaaggtgtaaatgtacctggtacaaagcttaatttgcctgccataacgcaaaaagacgtg gatgatatagagtttggaataaaaaaaggaatcgacatgattgcagcgtcttttgtcagaaaagcagcagatgtaattgccataag gagattgttagaagacaatgacgctggccatatacttatcatatcaaaaattgaaaatcgcgaaggcgtagaaaatattgacgaaa taatcaaagtctctgatggcataatggtagcccgcggcgatttgggtgtcgaaattcctatagaggaaatacctatcgttcagaaaa ggataattgaaaaatgcaacaaagcaggtaaaccagtagttactgctacacagatgcttgactctatgataagaaatccaaggcc aacaagggcagaagtaacagatgtagccaatgctatattggatggcactgatgcgataatgttgtctggtgaaacagcgcaagg caaatatcctgtagaggcttttaagacgatgtcaaagatagctgaaaagattgagacgtatataaattacaaagaaaatttagataa aaatgtggattacaatatttctatgacaaatgccataagccatgctacgtgcactaccgcgagagatataggcgcaactgccattat tacatctacaatatcaggttatactgcgagaatggtgtctaagtatagaccgtcagcacctataatagcagtgacgccaaacaaag atgttgcaagaaggcttagcatcgtgtggggtgtacatccattgatatcacaggaagtcaattctacagatgaaatgatagaagtat cagtaaatacggctttaaatgaaggattaattcgaaatggcgatattgtagtaatatcggcaggaatacctgtcgcgactacaggc acaacaaatatgttgaaggttcatattgtgggagatgtaatagtaaaaggcacaggcataggcactaaatccataagtggtgttgtt tccatcataagagatccatacaaggacaaagataagttcagagaaggagatatcatcgttgctcaaaaaactgaaagggattatat gcctataattgagaaggcttcagctatcataacagaagaaggtggactaacgtcccatgctgcaatagttggattgaactatggatt acctgtcattgtaggctgtgaaggagtaacttcaaagcttaaagatggaatgacggtaactctcgatactgccagaggattggtct acaaaggtatagtgaatataaaatag Pyruvate formate lyase (SEQ ID NO: 75)

atgatcaatgaatggcgcgggtttcaggagggcaaatggcaaaagactattgacgttcaagattttatccagaaaaattacacatt atacgaaggcgatgatagtttttttagaagggcctacagaaaagactattaagctttggaacaaagttcttgagctaatgaaggaag aactgaaaaaaggtgtgttagatattgatacaaaaaagtatcgtctataacatcccatgatgcggggtatatagacaaagatcttg aggaaatagttggattgcagacagacaaacctcttaaaagagctataatgccttacggtggcataagaatggtcaaqaaagcttg cgaagcttatggatataaagtggacccaaaagtagaagagatatttacgaagtacagaaagacccacaatgatggtgtatttgat gcatatactccagaaataagagcagcaagacatgccggcataataacaggtcttccagatgcatatggcagaggaagaatcata ggtgattacagaagagttgctctttatggaattgatagactcatcgaagaaaaggaaaaagaaaaacttgagcttgattacgatga atttgatgaagcaactattcgcttgagagaagaattgacagaacagataaaagcattaaacgaaatgaaagagatggctttaaagt acggttatgacatatcaaagcctgcaaaaaatgcaaaagaagctgtgcagtggacttactttgccttccttgctgctataaaggaac -continued aaaatggtgccgctatgtcgctgggcagagtatctactttttttagatatatacattgaaagagatcttaaagaaggaacattgacag
agaaacaagcacaagagttaatggatcactttgtcatgaagcttagaatggtgaggttcttaaggactcctgattacaatgaactatt
tagtggcgatcctgtttgggtgactgaatcaattggcggtgtaggcgtagacggaagacctcttgtcactaaaaattcattcaggat
attaaatactttatataacttaggtcctgcacctgagccaaacttgacggttttatggtccaaaaaccttcctgaaaactttaaaagatt
ctgtgccaaggtatcaatagatacaagttctattcaatatgaaaatgacgacttaatgaggccaatatacaatgacgactatagcat
cgcctgctgtgtgtcagctatgaagacgggagaacagatgcaatttttttggagcaagggcaaatctcgcgaaggcgctactgtat
gctataaacggcggtatcgatgaaaggtataaaacgcaagtggcaccaaaatttaatcctataacgtctgagtatttagactacgat
gaggtaatggcagcatatgacaatatgttagagtggcttgcaaaagtgtatgttaaagctatgaatataatacactacatgcacgat
aaatacgcttatgaaagatcccttatggctttgcatgatagagacatcgtaaggacgatggcttttggaatcgcaggtctttctgttg
cggcagattcgttaagcgccataaagtatgctaaagtaaaagccataagagatgaaaatggcatagcaatagattatgaagtgga
aggagatttccctaagtttggcaatgatgatgacagggttgactcaatagcagttgacattgtagaaagattcatgaataagcttaa
aaagcacaagacttacagaaactctataccaacactgtctgttttgacaataacgtcaaatgtggtgtacggcaaaaagacgggt
gctacacctgacggaagaaaagcgggagaaccttttgcgccaggcgcaaatccgatgcacggcagagatacaaaaggtgcc
atagcatcaatgaattcagtatcaaaaataccttatgacagttcattggatggtatatcatacacatttacgattgtaccaaatgcgctt
ggcaaggatgacgaagataaaattaataatcttgtaggactattagatggatatgcatttaatgcggggcaccacataaacatcaa
tgttttaaacagagatatgttgcttgatgctatggagcatcctgaaaaatatccgcagcttactataagggtttcagggtatgctgtca
atttcaataaattaacgagagagcaacagttggaggttatatcccgcacttttcacgaatctatg Phosphotransacetylase and acetate kinase (SEQ ID NO: 76)

gtgtatacaatatatttcttcttagtaagaggaatgtataaaaataaatattttaaaggaagggacgatcttatgagcattattcaaaac
atcattgaaaaagctaaaagcgataaaaagaaaattgttctgccagaaggtgcagaacccaggacattaaaagctgctgaaata
gttttaaaagaagggattgcagatttagtgcttcttggaaatgaagatgagataagaaatgctgcaaaagacttggacatatccaaa
gctgaaatcattgaccctgtaaagtctgaaatgtttgataggtatgctaatgatttctatgagttaaggaagaacaaaggaatcacgt
tggaaaaagccagagaaacaatcaaggataatatctattttggatgtatgatggttaaagaaggttatgctgatggattggtatctg
gcgctattcatgctactgcagatttattaagacctgcatttcagataattaaaacggctccaggagcaaagatagtatcaagcttttt
ataatggaagtgcctaattgtgaatatggtgaaaatggtgtattatgtttgctgattgtgcggtcaacccatcgcctaatgcagaag
aacttgcttctattgccgtacaatctgctaatactgcaaagaatttgttgggctttgaaccaaaagttgccatgctatcattttctacaa
aaggtagtgcatcacatgaattagtagataaagtaagaaaagcgacagagatagcaaaagaattgatgccagatgttgctatcga
cggtgaattgcaattggatgctgctcttgttaaagaagttgcagagctaaaagcgccgggaagcaaagttgcgggatgtgcaaat
gtgcttatattccctgatttacaagctggtaatataggatataagcttgtacagaggttagctaaggcaaatgcaattggacctataa
cacaaggaatgggtgcaccggttaatgatttatcaagaggatgcagctatagagatattgttgacgtaatagcaacaacagctgtg
caggctcaataaaatgtaaagtatggaggatgaaaattatgaaaatactggttattaattgcggaagttcttcgctaaaatatcaact
gattgaatcaactgatggaaatgtgttggcaaaaggccttgctgaaagaatcggcataaatgattccatgttgacacataatgctaa
cggagaaaaaatcaagataaaaaaagacatgaaagatcacaaagacgcaataaaattggttttagatgctttggtaaacagtgac
tacggcgttataaaagatatgtctgagatagatgctgtaggacatagagttgttcacggaggagaatcttttacatcatcagttctca
taaatgatgaagtgttaaaagcgataacagattgcatagaattagctccactgcacaatcctgctaatatagaaggaattaaagctt
gccagcaaatcatgccaaacgttccaatggtggcggtatttgatacagcctttcatcagacaatgcctgattatgcatatctttatcc
aataccttatgaatactacacaaagtacaggattagaagatatggatttcatggcacatcgcataaatatgtttcaaatagggctgca
gagattttgaataaacctattgaagatttgaaaatcataacttgtcatcttggaaatggaccagcattgctgctgtcaaatatggtaa
atcaattgacacaagcatgggatttacaccattagaaggtttggctatgggtacacgatctggaagcatagacccatccatcatttc
gtatcttatggaaaaagaaaatataagcgctgaagaagtagtaaatatattaaataaaaaatctggtgtttacggtatttcaggaata

```
agcagcgattttagagacttagaagatgccgcctttaaaaatggagatgaaagagctcagttggctttaaatgtgtttgcatatcga

gtaaagaagacgattggcgcttatgcagcagctatgggaggcgtcgatgtcattgtatttacagcaggtgttggtgaaaatggtcc

tgagatacgagaatttatacttgatggattagagttttagggttcagcttggataaagaaaaaaataaagtcagaggaaaagaaac

tattatatctacgccgaattcaaaagttagcgtgatggttgtgcctactaatgaagaatacatgattgctaaagatactgaaaagatt

gtaaagagtataaaa
```

For knockout vector construction, the 0.8-1.2 kb flanking regions (with primers) on both sides of target are first identified. Once identified, the new flanking regions are used to replace the L-ldh flanking regions in pMU433 using in silico analysis. Yeast-mediated ligation primers (4 total) for the two new flanking regions are made by adding to the targeting primers 5' regions homologous to DNA segments labeled "X01648,", "X01649," "X01654," and "X01655" on pMU433 shown in Table 3. Total primer length should be about 55-65 bp.

Next, the flanking regions from *T. saccharolyticum* YS485 genomic DNA are PCR amplified. PCR cleanup is not necessary if correct product was highly amplified.

TABLE 3

Primers for Knockout Vector Construction

| | | | |
|---|---|---|---|
| X01648 | (SEQ ID NO: 77) | GTCTTTCGACTGAGCCTTTCGTTTTATTTG ATGCCTGG | pMU433 construction |
| X01649 | (SEQ ID NO: 78) | AATTGTAGAATACAATCCACTTCACAATG GGCACG | pMU433 construction |
| X01654 | (SEQ ID NO: 79) | AGGGGTCCCGAGCGCCTACGAGGAATTT GTATCG | pMU433 construction |
| X01655 | (SEQ ID NO: 80) | CCGTCAGTAGCTGAACAGGAGGGACAGC TGATAGA | pMU433 construction |

About 100-200 ng pMU433 per yeast transformation is then digested with BamH1/BspE1. Allowing digestion to proceed to completion helps reduce background during yeast transformation.

The digested DNA is transformed into ura3-*S. cerevisiae* (Invitrogen INVSc1 cat #C81000 or equivalent) following the "Lazy bones" yeast transformation protocol. See Shanks et al., *Applied and Environmental Microbiology* 72:5027-5036 (2006). Briefly, about 100 ng digested plasmid and 10-50 μL of each PCR amplified flanking region are mixed. Prior purification is not necessary for either plasmid or PCR unless there are BamH1/BspE1 sites in the flanking regions. Other yeast transformation protocols can suitably be used. To control for background, a plasmid only control can be used.

The transformed yeast are plated on SD-URA plates (SD Medium-URA MP Biomedicals #4812-075 or equivalent) and incubated at 30° C. The plates are incubated for 3-5 days and then yeast total DNA is harvested from plates containing colonies. If cell mass is low, the colonies can be streaked on a new plate to increase the number of colonies. Yeast DNA is isolated using the "Smash and Grab" protocol (see Shanks et al., *Applied and Environmental Microbiology* 72:5027-5036 (2006)), or an equivalent protocol.

Next, competent *E. coli* are transformed with 1-5 μL of yeast total DNA and selected on 50 or 100 Kan LB plates. Colonies are screened to verify the constructs. 2-5 μg total plasmid DNA is then used for *T. saccharolyticum* transformations.

A second vector for gene deletion/marker removal is constructed using in silico analysis to place the two flanking regions adjacent to each other. Overlapping regions are added to the two adjacent primers on the flanking regions to obtain about 40 kb of homology between the regions when amplified.

Using two rounds of PCR amplification, the flanking regions can be connected. The first PCR amplification is a traditional amplification, and the second amplification is a dilution of the first round products to approximately 1 ng/μL. This dilution is used as a template; and the upstream flanking region 5' primer and downstream flanking region 3' primer are used for amplification. If necessary, optimization of annealing temperature or MgCl$_2$ can be performed. Alternatively, TOPO cloning (Invitrogen) or other known techniques can be used to make the second construct.

Following a PCR clean-up, 2-3 μg of the vector product is then used to transform *T. saccharolyticum*.

1.1.3 Gene Insertion

To create a metabolic route to 1-hexadecanol, native and/or recombinant genes are overexpressed. The native PEPCK and TC genes are overexpressed via insertion of high level promoters in front of the coding sequence for these genes. This is accomplished through the pMU433-based marker cycling system, except that the recombinant promoter region will remain behind after the marker is removed. High expression level promoter regions can be chosen, without limitation, from any of the following promoters:

adhE promoter (SEQ ID NO: 81)

tcatataagtgtaaggtgattgttaaatgaataacaaaaattatttacatcacacagtcc aaaattcaattcattcaagcgaatttcctgttgaaatgcttgaaaaactgatacaatcac ctgaaatgtagagatttattgttaataaattaacacggaggtgtttatt cbp promoter (SEQ ID NO: 82)

gagtcgtgactaagaacgtcaaagtaattaacaatacagctatttttctcatgcttttac ccctttcataaaatttaattttatcgttatcataaaaaattatagacgttatattgcttg ccgggatatagtgctgggcattcgttggtgcaaaatgttcggagtaaggtggatattgat ttgcatgttgatctattgcattgaaatgattagttatccgtaaatattaattaatcatat cataaattaattatatcataattgttttgacgaatgaaggtttttggataaattatcaag taaaggaacgctaaaaattttggcgtaaaatatcaaaatgaccacttgaattaatatggt aaagtagatataatattttggtaaacatgccttcagcaaggttagattagctgtttccgt ataaattaaccgtatggtaaaacggcagtcagaaaaataagtcataagattccgttatga aaatatacttcggtagttaataataagagatatgaggtaagagatacaagataagagata taaggtacgaatgtataagatggtgcttttaggcacactaaataaaaaacaaataaacga aaattttaaggaggacgaaag pta promoter (SEQ ID NO: 83)

gtattctacaattaaacctaatacgctcataatatgcgcctttctaaaaaattattaatt gtacttattattttataaaaaatatgttaaaatgtaaaatgtgtatacaatatatttctt cttagtaagaggaatgtataaaaataaatattttaaaggaagggacgatctt hyd promoter (SEQ ID NO: 84)

ataagcgaaagggtaaattgctttgatttagatgatttgaatatggtagtcgactggatg tgcaagtaaagaaaacatatcaaattagtcgggattatcagaaaataaaaaaatttttat ttttaactgttaaaaaaataattaacatatggtataataattatgtcctattttgcaatt ttaaagattaattttttttaaaaggagggtattag hfs promoter (SEQ ID NO: 85)

gctgtaattgtccttgatgacgataggaagataaacattccaacaaaatatcttcccagc aatattgctgaagaagatgccatagatatttcattggatgtcaatgaaagaggacgaaaa ttaaaaaagttgattgaagaatcaagggaggaagactaatttttttaattttttttaacgtt aattgttaataaattaactattgtttacacactttcttttatgtaataaaataattgtat acagtatacgg ech promoter (SEQ ID NO: 86)

tactgaatggagaaactgcacaaaaagcttgttgacggcagcagaggagattattcctct gctatttttgtgggaaaaactgcaaaattcattgaaatattgttaaataataaacaaaat taattaatattaaatacaattgacttatcatttaattagatttataatcaaaatgggtat ttaaaaatgtatacaatatataatattcattaaatgaaataaagaaggagtgaaaaa Next, recombinant genes encoding a fatty acyl-ACP reductase and hexadecanal dehydrogenase from organisms such as *Acinetobacter calcoaceticus* and *Geobacillus thermodenitrificans* (see Reiser and Somerville, *Journal of Bacteriology* 179:2969-2975 (1997); Liu et al., *Microbiology* 155:2078-2085 (2009)) are identified (see below). These recombinant genes can be integrated into the genome, driven by a high level expression promoter, or expressed via a replicating plasmid such as pMU131 (see WO 2009/035595).

Nucleotide sequence of Acinetobacter acr1 fatty acyl-ACP (-CoA) reductase
(GenBank# U77680)

(SEQ ID NO: 87)

```
cagaagatat ggttcggtta tcggttggga ttgaacatat tgatgatttg attgcagatctggaacaagc attggccaca

gtttgagcgt aaattttata aaaaacctct gcaatttcag aggttttttt atatttgctt tattatcgta tgatgttcat

aattgatcta

gcaaataata aaaattagag caattactct aaaaacattt gtaatttcag atacttaaca ctagattttt taaccaaatc

actttagatt aactttagtt ctggaaattt tatttccctt taaccgtctt caatccaaat acaataatga cagcctttac

agtttgatat caatcaggga aaaacgcgtg aacaaaaaac ttgaagctet cttccgagag aatgtaaaag gtaaagtggc

tttgatcact ggtgcatcta gtggaatcgg tttgacgatt gcaaaaagaa ttgctgcggc aggtgctcat gtattattgg

ttgcccgaac ccaagaaaca ctggaagaag tgaaagctgc aattgaacag caagggggac aggcctctat ttttccttgt

gacctgactg acatgaatgc gattgaccag ttatcacaac aaattatggc cagtgtcgat catgtcgatt tcctgatcaa

taatgcaggg cgttcgattc gccgtgccgt acacgagtcg tttgatcgct tccatgattt tgaacgcacc atgcagctga

attactttgg tgcggtacgt ttagtgttaa atttactgcc acatatgattaagcgtaaaa atggccagat catcaatatc

agctctattg gtgtattggc caatgcgacccgtttttctg cttatgtcgc gtctaaagct gcgctggatg ccttcagtcg

ctgtctttca gccgaggtac tcaagcataa aatctcaatt acctcgattt atatgccatt ggtgcgtacc ccaatgatcg

cacccaccaa aatttataaa tacgtgccca cgctttcccc agaagaagcc gcagatctca ttgtctacgc cattgtgaaa

cgtccaacac gtattgcgac gcacttgggt cgtctggcgt caattaccta tgccatcgca ccagacatca ataatattct

gatgtcgatt ggatttaacc tattcccaag ctcaacggct gcactgggtg aacaggaaaa attgaatctg ctacaacgtg

cctatgceeg cttgttccea ggcgaacact ggtaaaattt ataaaagaag cctctcatac cgagaggctt ttttatggtt

acgaccatca gccagattta gaggaaattg acttttcctg tttttacatc ataaatcgca ccaacaatat caatttcttt

gcgatccagc atatctttaa gtacagaact atgctgaata atgtattgaa tattatagtg aacattcata gcagtcacct

gatcaataaa tgctttgctt aattcacgcg gttgcataat atcaaataea ctgccaaccg aatgcatgag tggcccaagc

acgtattgga tgtgtggcat ttcctgaata tcggaaatct gcttatgttg caatcttaac tggcatgcgc tggtgaccgc

accacagtcg gtatgtccca aaaccagaat cactttggaa cctttggctt gacaggcaaa
```

Nucleotide sequence of Geobacillus thermodenitrificans NG80-2 adh1
(Genbank Nucleotide CP000557, Protein ABO67118)

(SEQ ID NO: 88)

```
ttacgccttg tgcggctcta cgatcgtccc ggcaaacgcg gcttcgtaaa tcgcacggat gtcggcttcc aacagcggca

acggactgcg ggcaagcaaa cgtttetgtt ggacagcatc tttcgtcaag ctttctagcg cgctttcggg gatgccaaat

ccccccaatg ttttcggaat gccgacatcg gcgacgaacc gttctagttc ctcgacgcac cgataagacg cttccacttc

ggacaaaaaa cttgagttgc cgccaagcgc gttgaaaata tcggccattc tcttcgtaca gctttgacgg atgtagccca

tcacatacgg caacagcaca gcaticgatt caccatgagc gatatgaaac tgaccaccga gcggataagc

gagcgcatgc acaccggcta ccccggcgtt gaaaaatgcc aagccggcca aataactgcc gttcgccata

tcaatgcgcg cctgtttgtc cgaaccgttg gccaccgctt tgcgcagtga gcgtgaaatc agccgaatag cggcaacggc

caatccatcc gatgttgggc tcgcattgac cgacacatac gcctcaactg catgggtgag tgcatcaatt cccgttgcgg

ccgttacccg cggtggaacg gaaacggtca gctgcggatc aacgatcgcg acgtcggcca ataagtaatc

gtgcgtcacg acatctttcg tcgtttccaa agacaagaca gagatgtttg tcacttccga cccggtgccc gatgtcgtgg

gaatcaaaat tttcggcaac ccttttttct caagtgttcg cgttcctgtc aaatttaaat agtcagcgac cgagccatca

tgcaccgcca aaacagccgc cagtttcgcc aaatccagcg cgctgccacc accaacaccg atgacaaggt
```

-continued

```
caaactttcc gtcgcgggca aacgccactg ccttttcccc tgtctcaagc ggcggctctg gcacaacatc cgtatacaca

tgcacgctat acccttcttg acggagcggg gacgtcactt gatcgactag gccgatcttc acaagcatcg ggtcggtaat

caccaaaata tgttttgctc ccaaccgctt cacttcagga actaactggt caagcgctcc ccagccgaca tggctgagcg

gcggaaagac aatgcgggct acactcat
```

Nucleotide sequence of Geobacillus thermodenitrificans NG80-2 adh1 (Genbank Nucleotide CP000557, Protein ABO68223)

(SEQ ID NO: 89)

```
ttataaagac gcacgcaaaa tggcgagcac atcatcacga tttaacgttt tgaaacggcc aaactcacca aacgccatcg

ctttatccgc catcagctcg agattttcct cgccgatgcc ataatcagcc aatcgagacg gcgccccgag gctcgaccaa

aacgcgcgca accgctcgat gccctcaagc gccacgtcgc gctccgtttt gcccgtcgga tcgacgtcaa

agacgcgcac cgccagttgg gcgaaacggc tgacattttc atcaagcaca tgtttcatcc aattcgggaa caaaatggcc

aatcccccgg cgtgcgggat atcgtataca gcagagaccg catgctcgat atcatgcgtc gcccaatcac

cgcgcacgcc catttgcaaa aagccgttta aggcgatcgt gcccgagtac atgatcgtct cgcgcagctc gtagttctct

aagtcgtcaa ccaatttggg cgccgcctca atgaccgttt ttaacactgc ctcgcacatc cggtcttgca gcggcgtgtt

cggcgtatga tggaaatatt gctcaaacac atgggacatc atatcgacga tgccgtaaac ggtatggtct ttcggcaccg

tcatcgtgta cgtcggatcc aaaatcgaaa attgcgggaa tgtcaccggg ctgccccagc cgtatttttc tttcgtctcc

caattggtga tcaccgatcc ggcgttcatt tccgagccgg tcgctgccag cgtcaggacc gtcccaaacg gcaacgcctc

agtgacagtc gctttttttcg taatgaactc ccacggatcg ccatcaaact tcgcgccggc tgcaatcgct ttcgtacagt

cgatcacact gccgccgcca acggcaagca aaaattcaat tccttcccgt ctgcaaatgt ctacccctttt tttgacggtc

gaaaggcgcg ggttcggttc gacgcctggc agttcaacga cttcggcgcc aatgtccgtc aataggctca tgacttcatc

atatagtccg tttcgtttaa tgctgccgcc cccatagaca agcagcactt ttttgccata tttcggcact tcttctttga

gctgctcaat ttgtcctctc ccaaaaatga gtttggtcgg attgcgaaac gtaaaatttt gcat
```

1.1.4 Selection and Optimization of Engineered Strains

The engineered strain is cultured continuously via any of several methods, including chemostat, pH-auxostat, or serial batch transfer, to select for naturally occurring mutations that impart a benefit upon cellular growth and 1-hexadecanol formation. Because ATP generation and NAD(P)H regeneration are both coupled to 1-hexadecanol formation in the engineered strain, evolutionary forces will select for cells that are better able to carry out this conversion.

1.1.5 Detection of 1-Hexadecanol 1-hexadecanol formation in cultured engineered strains is detected via gas chromatography-mass spectrometry (GC/MS) with or without an extraction step prior to analysis. See Steen et al., *Nature* 463:559-562 (2010); Aldai et al., *Journal of Chromotography* 1110:133-139 (2006).

Example 2

2.1 Diverting Central Metabolic Flux Through Oxaloacetate in *E. coli*

Figure 9:
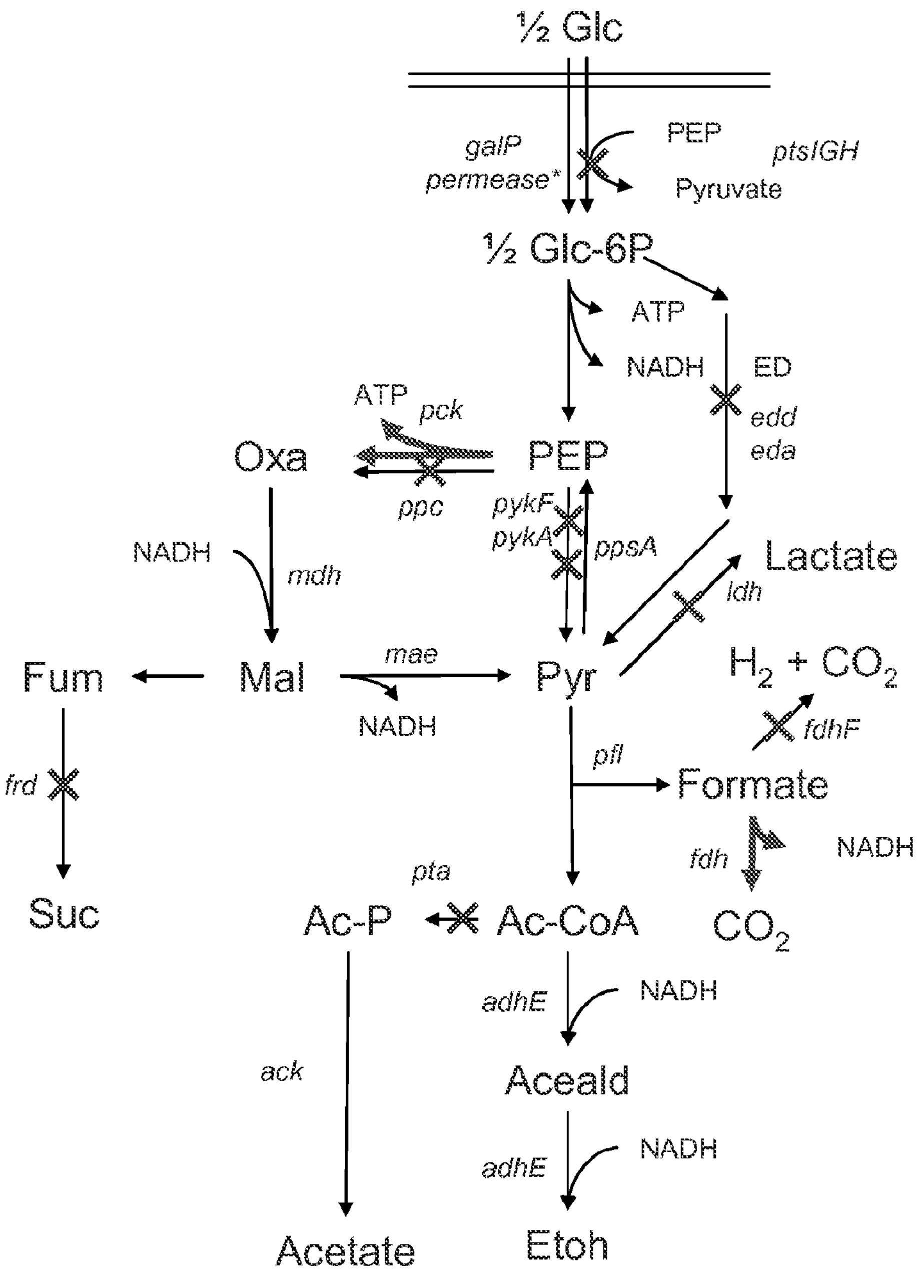
FIG. 9 depicts gene knockout and overexpression strategy to route anaerobic central metabolic flux through oxaloacetate as a key intermediate. Abbreviations: Glc—glucose, Glc-6P—glucose-6-phosphate, PEP—phosphoenolpyruvate, Oxa—oxaloacetate, Fum—fumarate, Mal—malate, Pyr—pyruvate, Ac-CoA—acetyl-CoA, Ac—P—acetylphosphate, Aceald—acetaldehyde, Etoh—ethanol.

This example describes engineering the central metabolic flux in *Escherichia coli* so that the majority of glycolytic flux passes from phosphoenolpyruvate to oxaloacetate rather than from phosphoenolpyruvate to pyruvate. See FIG. 9. This is accomplished via a series of gene deletions that inactivate competing pathways and gene overexpressions that activate desired pathways. Target genes are shown in Table 4. A set of minimal target gene deletions is shown in Table 5.

TABLE 4

Targets for Gene Inactivation

| *E. coli* gene name | description | locus tag [a] |
|---|---|---|
| edd | 6-phosphogluconate dehydratase | b1851 |
| ldhA | lactate dehydrogenase | b1380 |
| pta | phosphate acetyltransferase | b2297 |
| adhE | acetaldehyde dehydrogenase/alcohol dehydrogenase | b1241 |
| frdABCD | fumarate reductase (anaerobic) | b4151-b4154 |
| fdhF | formate dehydrogenase-H | b4079 |
| ppc | phosphoenolpyruvate carboxylase | b3956 |
| pykA | pyruvate kinase | b1854 |
| pykF | pyruvate kinase | b1676 |
| mdh | malate dehydrogenase | b3236 |
| maeA | malic enzyme NADH | b1479 |
| maeB | malic enzyme NADPH | b2463 |
| fadE | acyl coenzyme A dehydrogenase | b0221 |
| ptsI | PEP-protein phosphotransferase of PTS system | b2416 |
| PflB | pyruvate formate lyase | b0903 |
| aceEF | pyruvate dehydrogenase | b0114 |
| poxB | pyruvate oxidase | b0871 |
| mgsA | methylglyoxal synthase | b0963 |
| ppsA | phosphoenolpyruvate synthase | b1702 |

[a] locus tag numbers are given for the genome sequence of *E. coli* MG1655, which can be accessed via Genbank (Accession No. U00096) or the Kyoto Encyclopedia of Genes and Genomes (KEGG).

TABLE 5

| Minimal Targets for Gene Inactivation | | |
|---|---|---|
| gene name | description | locus tag |
| ldhA | lactate dehydrogenase | b1380 |
| pta | phosphate acetyltransferase | b2297 |
| adhE | acetaldehyde dehydrogenase/alcohol dehydrogenase | b1241 |
| pykA | pyruvate kinase | b1854 |
| pykF | pyruvate kinase | b1676 |
| mdh | malate dehydrogenase | b3236 |
| ptsI | PEP-protein phosphotransferase of PTS system | b2416 |

2.1.1 Deletion and Overexpression of Target Genes

Figure 11:
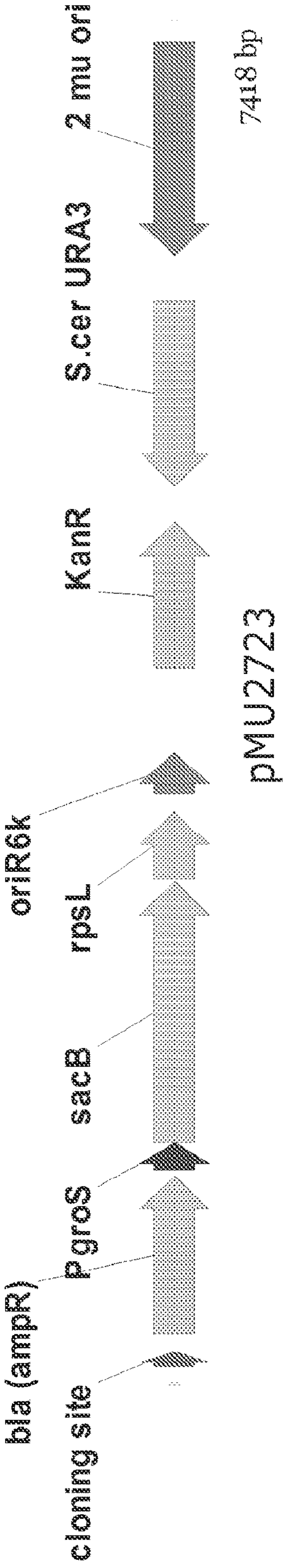
FIG. 11 depicts the vector pMU2723 used to construct gene knockouts and chromosomal integrations in *E. coli*.

In order to perform gene modifications (either deletion or overexpression) in *E. coli* to redirect metabolic flux through oxaloacetate, 500 bp to 2000 bp flanking regions upstream and downstream of a target gene were amplified via PCR using primers (Table 6) and ligated into pMU2723 (FIG. 11) using standard molecular biology methods. See Shanks et al., *AEM* 72: 5027-5036 (2006). The pta::fdh and Pspc pckA promoter exchange modifications were performed by placement of the heterologous DNA (fdh or Pspc) between the two homologous flanking regions of the target gene, with appropriate design to allow either expression of fdh from the native pta promoter, or heterologous expression of the native pckA gene. The protocol used is described briefly below.

The starting strain, M2162 or subsequent progeny, was grown overnight in 8 mL of LB medium at 37° C. Two 500 mL baffled flasks, each containing 150 mL of LB, were pre-incubated at 37° C. and then inoculated with 2 mL of the overnight culture. These cultures were incubated at 37° C. with shaking until the OD reached 0.5 to 0.8 (checked OD every 20 min. after 2 hrs). The flasks were then placed in an ice bath for about 15 minutes after which the cultures were transferred to six 50 mL conical tubes. The tubes were spun at 4000 rpm for 8 minutes in a clinical swinging bucket centrifuge at 4° C. Following centrifugation, the supernatant was removed, about 10 mL of ice cold water was added to each tube, and the pellets were resuspended and transferred to two 50 mL tubes which were balanced to 50 mL with ice cold water. The tubes were centrifuged for 8 minutes in the conditions described above. The supernatants were removed and the pellets were resuspended with about 200 μL of cold water, after which 80 μL of the resuspended cells were transferred to a cold 1 mm gap cuvette which contained 2-4 μL of pre-added plasmid DNA targeting the gene of interest. The cuvette was electropulsed using an exponential decay pulse, 1.8 kV voltage, 25 ρF capatance, 200Ω resistance, and a 1 mm gap cuvette method. 1 mL of SOC medium was added to the cuvette and the entire volume was then transferred to a 14 mL falcon tube and incubated at 37° C. for 1 hour. 250 μL of cells were removed, plated on LB plates containing 50 μg/mL kanamycin, and incubated at 37° C. for 24-48 hours. Colony PCR was performed on kanamycin resistant colonies using one internal and one external primer to the site of integration with primers listed in Table 8. Two positive colonies we re-streaked on 50 μg/mL kanamycin plates and incubated overnight at 37° C. Two colonies were selected and grown in 5 mL of LB medium, either for 8 hours or overnight at 37° C. Serial dilutions of 1:10, 1:100, and 1:1000 of each LB culture were prepared, and 20 μL of each dilution was plated on 10% w/v sucrose+500 μg/mL streptomycin plates. The plates were incubated overnight at either 37° C. or 42° C. Colony PCR was performed on 7 colonies from each initial LB culture with two primers, as listed in Table 8, external to the site of integration. Two positive colonies were re-streaked on 500 μg/mL streptomycin plates and incubated at 37° C. overnight. One colony from each plate was selected and re-patched on a kanamycin 50 μg/mLplate and a streptomycin 500 μg/mL plate. The patches that grew on the streptomycin but not the kanamycin plates were then used to make culture collection stocks.

TABLE 6

| Primers Used to Create Gene Deletion and Gene Overexpression Plasmids for Routing Metabolic Flux Through Oxaleacetate | | | |
|---|---|---|---|
| Primer # | SEQ ID NO: | Primer sequence | Description |
| X12312 | 90 | TTTTGTCTGTCTTAATTTTTGGTATCATTATAGGATCTATGTAACCCAGGAAGCGG CAA | pta 1 |
| X12313 | 91 | ACGAGATTACTGCTGCTGTGCAGACTTTGCGTTCCATTGCACGGATCA | pta 2 |
| X12314 | 92 | TGATCCGTGCAATGGAACGCAAAGTCTGCACAGCAGCAGTAATCTCGT | pta 3 |
| X12315 | 93 | GATAACAATTTCACACAGGAAACAGCTATGACCATACGGCCTCTTCTCCCATACC AAAT | pta 4 |
| X12316 | 94 | TTTTGTCTGTCTTAATTTTTGGTATCATTATAGGAACGCAGTTGCTGGATATCAGA GGT | ldh 1 |
| X12317 | 95 | TACTGGTCAGAGCTTCTGCTGTCAACTCGTTCACCTGTTGCAGGTACT | ldh 2 |
| X12318 | 96 | AGTACCTGCAACAGGTGAACGAGTTGACAGCAGAAGCTCTGACCAGTA | ldh 3 |
| X12319 | 97 | GATAACAATTTCACACAGGAAACAGCTATGACCATTTGGGATGTGTGCATTACCC AACG | ldh 4 |
| X12320 | 98 | TTTTGTCTGTCTTAATTTTTGGTATCATTATAGGATACTGGTAAACGTCTGCCGACC AA | edd 1 |
| X12321 | 99 | ACAGCTTAGCGCCTTCTACAGCTTCGCGCGAACGTTCAATGATTCGAT | edd 2 |
| X12322 | 100 | ATCGAATCATTGAACGTTCGCGCGAAGCTGTAGAAGGCGCTAAGCTGT | edd 3 |

TABLE 6-continued

Primers Used to Create Gene Deletion and Gene Overexpression Plasmids for Routing Metabolic Flux Through Oxaleacetate

| Primer # | SEQ ID NO: | Primer sequence | Description |
|---|---|---|---|
| X12323 | 101 | GATAACAATTTCACACAGGAAACAGCTATGACCATGCTGACATTGGCTATCCCTGCATT | edd 4 |
| X12324 | 102 | TTTTGTCTGTCTTAATTTTTGGTATCATTATAGGAGCGGGTCAATTTCCAGATAACGCA | frd 1 |
| X12325 | 103 | TCAGGAACAGGAATACGCGACCAAGATCGGCTTGAAAGGTTTGCACGA | frd 2 |
| X12326 | 104 | TCGTGCAAACCTTTCAAGCCGATCTTGGTCGCGTATTCCTGTTCCTGA | frd 3 |
| X12327 | 105 | GATAACAATTTCACACAGGAAACAGCTATGACCATGCGAAACATGCACTGCCTTACCTT | frd 4 |
| X12328 | 106 | TTTTGTCTGTCTTAATTTTTGGTATCATTATAGGATGGACCGAATGGACGATGGAGTTT | pfl 1 |
| X12329 | 107 | AGAATGCCTTTCACGCGTTCCATGTCGTTGCTTTATAGACACCCGCCT | pfl 2 |
| X12330 | 108 | AGGCGGGTGTCTATAAAGCAACGACATGGAACGCGTGAAAGGCATTCT | pfl 3 |
| X12331 | 109 | GATAACAATTTCACACAGGAAACAGCTATGACCATTTCCGTTAACGATACGCTTCGGGT | pfl 4 |
| X12332 | 110 | TTTTGTCTGTCTTAATTTTTGGTATCATTATAGGAATTCAAACGTTATGCCCGACGCTG | ppc 1 |
| X12333 | 111 | AGCGGGTCGGTGTAAATATTCCGTTCCTTGATGGTTTCTCCCAGCACT | ppc 2 |
| X12334 | 112 | AGTGCTGGGAGAAACCATCAAGGAACGGAATATTTACACCGACCCGCT | ppc 3 |
| X12335 | 113 | GATAACAATTTCACACAGGAAACAGCTATGACCATTTGAAATTAGCCAGTGGCGGCAAG | ppc 4 |
| X12336 | 114 | TTTTGTCTGTCTTAATTTTTGGTATCATTATAGGACAGCCGCTACATTAAAGGCACCAA | ptsI 1 |
| X12337 | 115 | CCAGCAGCGGCAGATCAAA1TCAATGGCGGTTCGACTTTAGCCTGTAT | ptsI 2 |
| X12338 | 116 | ATACAGGCTAAAGTCGAACCGCCATTGAATTTGATCTGCCGCTGCTGG | ptsI 3 |
| X12339 | 117 | GATAACAATTTCACACAGGAAACAGCTATGACCATATGGTTTAGCGGCTATTTGCGTGC | ptsI 4 |
| X12340 | 118 | TTTTGTCTGTCTTAATTTTTGGTATCATTATAGGATGGCGAATGGCACTCCCTATGTTA | pykA 1 |
| X12341 | 119 | TGACAATCACCAGGTCACCAGACATCCGAATGAAATAACGCCGCGATG | pykA 2 |
| X12342 | 120 | CATCGCGGCGTTATTTCATTCGGATGTCTGGTGACCTGGTGATTGTCA | pykA 3 |
| X12343 | 121 | GATAACAATTTCACACAGGAAACAGCTATGACCATTGTTGATGAGATGTTTGCCACCGC | pykA 4 |
| X12344 | 122 | TTTTGTCTGTCTTAATTTTTGGTATCATTATAGGAATGCTGTACGTAATACGCCTGCGA | pykF 1 |
| X12345 | 123 | TCTTTAACAAGCTGCGGCACAACGATGGGAGAAACTTGCTTTCTGGGC | pykF 2 |
| X12346 | 124 | GCCCAGAAAGCAAGTTTCTCCCATCGTTGTGCCGCAGCTTGTTAAAGA | pykF 3 |
| X12347 | 125 | GATAACAATTTCACACAGGAAACAGCTATGACCATATCTTTAGCAGCCTGAACGTCGGA | pykF 4 |
| X13802 | 126 | TTATAGGTTAATGTCATGATAATAATGGTTTCTTCCGTCAAAGGGCAAATCACCGAAA | fdhF 1 |
| X13803 | 127 | GGGTTCCGCGCACATTTCCCCGAAAAGTGCCACCACTCGGAATAACCGGTTCGGGAAA | fdhF 2 |
| X13804 | 128 | CGCCTTCTATCGCCTTCTTGACGAGTTCTTCTGATACGACAAAGCGTTCGTCGCTTCA | fdhF 3 |
| X13805 | 129 | ACTGTTGGGAAGGGCGATCGGTGCGGGCCTCTTCGAATGAAGCCCAGTTCGCCCATTT | fdhF 4 |

TABLE 6-continued

Primers Used to Create Gene Deletion and Gene Overexpression Plasmids for Routing Metabolic Flux Through Oxaleacetate

| Primer # | SEQ ID NO: | Primer sequence | Description |
|---|---|---|---|
| X14576 | 130 | TTATAGGTTAATGTCATGATAATAATGGTTTCTTGCGGATGCGAAGGCTTTGTTGTAT | Pspc pckA 1 |
| X14577 | 131 | TGGGTAGAAAAAATAAACGGCTCAGATTCCTGTCACGAAACGGTTGCT | Pspc pckA 2 |
| X14578 | 132 | AGCAACCGTTTCGTGACAGGAATCTGAGCCGTTTATTTTTTCTACCCA | Pspc pckA 3 |
| X14579 | 133 | GGTCAAACCATTGTTAACGCGCATTTTAGTGCTCCGCTAATGTCAACT | Pspc pckA 4 |
| X14580 | 134 | AGTTGACATTAGCGGAGCACTAAAATGCGCGTTAACAATGGTTTGACC | Pspc pckA 5 |
| X14581 | 135 | GGGTTCCGCGCACATTTCCCCGAAAAGTGCCACCTAGAAGCGATACCTTTCAGCGGCA | Pspc pckA 6 |
| X14588 | 136 | TTATAGGTTAATGTCATGATAATAATGGTTTCTTTCTATGTAACCCAGGAAGCGGCAA | pta::fdh3 1 |
| X14589 | 137 | TGGGTAGAAAAAATAAACGGCTCACTTTGCGTTCCATTGCACGGATCA | pta::fdh3 2 |
| X14590 | 138 | TGATCCGTGCAATGGAACGCAAAGTGAGCCGTTTATTTTTTCTACCCA | pta::fdh3 3 |
| X14591 | 139 | ATAAAGAACTAAGACAATCTTCATTTTAGTGCTCCGCTAATGTCAACT | pta::fdh3 4 |
| X14592 | 140 | AGTTGACATTAGCGGAGCACTAAAATGAAGATTGTCTTAGTTCTTTAT | pta::fdh3 5 |
| X14593 | 141 | ACGAGATTACTGCTGCTGTGCAGACTATTTCTTATCGTGTTTACCGTA | pta::fdh3 6 |
| X14594 | 142 | TACGGTAAACACGATAAGAAATAGTCTGCACAGCAGCAGTAATCTCGT | pta::fdh3 7 |
| X14595 | 143 | GGGTTCCGCGCACATTTCCCCGAAAAGTGCCACCACGGCCTCTTCTCCCATACCAAAT | pta::fdh3 8 |
| X15570 | 144 | TTATAGGTTAATGTCATGATAATAATGGTTTCTTTGCGATCCGTAGCAGACACCATAA | maeA 1 |
| X15571 | 145 | GAATACTGCGCCAGCGTTTCACTTCGTTCCGCTTGTTCTTCGATGGTT | maeA 2 |
| X15572 | 146 | AACCATCGAAGAACAAGCGGAACGAAGTGAAACGCTGGCGCAGTATTC | maeA 3 |
| X15573 | 147 | GGGTTCCGCGCACATTTCCCCGAAAAGTGCCACCCATCAATGGCGATCACTTTGGCGT | maeA 4 |
| X15574 | 148 | TTATAGGTTAATGTCATGATAATAATGGTTTCTTAATTGACCGCCAGTTTGTCACACG | maeB 1 |
| X15575 | 149 | TCGCCGTGCATTTCACCATCAATCGAGCGCGGCGACAACTTCAATAAA | maeB 2 |
| X15576 | 150 | TTTATTGAAGTTGTCGCCGCGCTCGATTGATGGTGAAATGCACGGCGA | maeB 3 |
| X15577 | 151 | GGGTTCCGCGCACATTTCCCCGAAAAGTGCCACCGCCATAAATCACCAATGCACCGCT | maeB 4 |
| X15578 | 152 | TTATAGGTTAATGTCATGATAATAATGGTTTCTTCAGCTGGCAGGCAGTAAACCATTT | mdh 1 |
| X15579 | 153 | TCAAATGCGCTCAGGGTACCGATATTCTGAACCTGAAGGCAGTTGGGT | mdh 2 |
| X15580 | 154 | ACCCAACTGCCTTCAGGTTCAGAATATCGGTACCCTGAGCGCATTTGA | mdh 3 |
| X15581 | 155 | GGGTTCCGCGCACATTTCCCCGAAAAGTGCCACCACTGGCGGTTTACCTACCATTCCA | mdh 4 |
| X15586 | 156 | TTATAGGTTAATGTCATGATAATAATGGTTTCTTTCGACATCGCTATTGTCACCACCA | adhE 1 |
| X15587 | 157 | TTTCGGAAGTTTGTGCCACAACATAATGCTCTCCTGATAATGTTAAAC | adhE 2 |
| X15588 | 158 | GTTTAACATTATCAGGAGAGCATTATGTTGTGGCACAAACTTCCGAAA | adhE 3 |
| X15589 | 159 | GGGTTCCGCGCACATTTCCCCGAAAAGTGCCACCCCAAGTGGTCGGCAATTTCAGCAT | adhE 4 |

Figure 10:
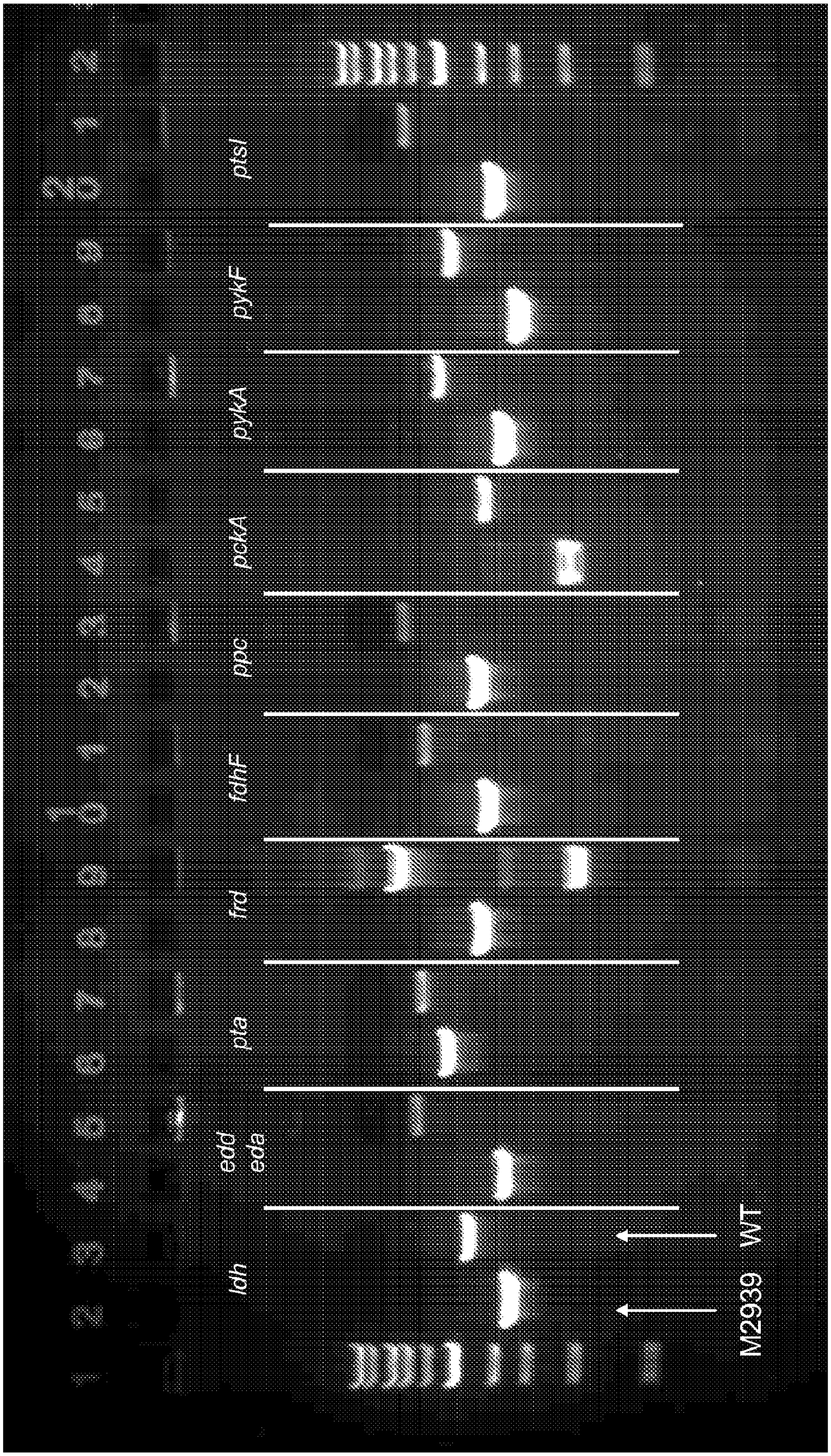
FIG. 10 is an agarose gel image showing deletions and overexpressions of target genes in the *E. coli* chromosome to redirect metabolic flux through oxaloacetate.

Gene modifications were confirmed on an agarose gel. See FIG. 10 and Table 7. Primers external to each region of interest were used to amplify DNA (Table 8), which was subsequently run on an agarose gel and stained with ethidium bromide to visualize DNA length. The ladder shown in lanes 1 and 22 of FIG. 10 is New England Biolabs 1 kb. DNA was amplified from strains M2939 (deletion and overexpression strain) and M2162 (wildtype). See Table 9 for a description of the bacterial strains.

TABLE 7

Predicted Size of Wildtype and Modified Target Genes

| Target | WT length (bp) | KO length (bp) |
|---|---|---|
| ldhA | 2686 | 1855 |
| edd | 4343 | 1931 |
| pta::fdh | 3992 | 3186 |
| frd | 5358 | 2241 |
| fdhF | 3927 | 2141 |
| ppc | 4739 | 2321 |
| pckA (promoter exchange) | 2003 | 1053/958 * |
| pykA | 3204 | 1803 |
| pykF | 2863 | 1594 |
| ptsI | 4418 | 1938 |

* after psiI restriction digest of PCR product to distinguish the wildtype (2003 bp) and promoter exchange (2011 bp) alleles.

TABLE 8

Primers Used to Verify Genome Alterations

| Primer # | SEQ ID NO: | Primer sequence | Description |
|---|---|---|---|
| X12354 | 160 | TTGCTGTATTTGACACCGCGTTCC | pta ext 1 |
| X12355 | 161 | TTTCACGAAAGAAGCGGTCGGACT | pta ext 2 |
| X12356 | 162 | GGCAAGTTTAACGTCGCAGTAGCA | ldh ext 1 |
| X12357 | 163 | TTTATGGCGGTGTCGTTTGGCTTG | ldh ext 2 |
| X12358 | 164 | ATATCTGGAAGAAGAGGGCGCGAA | edd ext 1 |
| X12359 | 165 | GATGCATTACGCCGTGTGGTTGAA | edd ext 2 |
| X12360 | 166 | AACAGCAATTGTAGCAGCGTGTCG | frd ext 1 |
| X12361 | 167 | TTGTTTGCCAGCATCACGATACCC | frd ext 2 |
| X12362 | 168 | CTGGGCGTTTATGCTTGCCGTATT | pfl ext 1 |
| X12363 | 169 | AGTCGTCAGTTGTGAGCTCGACTT | pfl ext 2 |
| X12364 | 170 | TATTCACGGTGGCGACGCTTCTAA | ppc ext 1 |
| X12365 | 171 | CGCCTGTTGCAGGATTTCAATGGT | ppc ext 2 |
| X12366 | 172 | AAAGCGTTAGGTGCAAACCTGGTG | pts ext 1 |
| X12367 | 173 | ATTGCCGTGCCTGCTATCAAACAG | pts ext 2 |
| X12368 | 174 | GCTATGGCACTGGAAGCCAATGTT | pykA ext 1 |
| X12369 | 175 | AGAACGTAGTGAAGCTGAACGCGA | pykA ext 2 |
| X12370 | 176 | TGAAGCTTACCGCCTCATCCTGAA | pykF ext 1 |
| X12371 | 177 | AGAATGGTGAACCAGAGCAAGGGA | pykF ext 2 |
| X12801 | 178 | GATTGATTACGCGGTGAAAGCGCA | fdh ext 1 |
| X12802 | 179 | ACACCCGGTATCAAACCCTTCCAT | fdh ext 2 |
| X14574 | 180 | CCGTGGCGATTAACGTGAACAACT | pckA ext 1 |

TABLE 8-continued

Primers Used to Verify Genome Alterations

| Primer # | SEQ ID NO: | Primer sequence | Description |
|---|---|---|---|
| X14575 | 181 | AGTCGATAGTGCCATCTTCACGCA | pckA ext 2 |
| X15500 | 182 | ACTGTTCCCTTCCCGCGTTTGATA | maeA ext 1 |
| X15591 | 183 | GCATCAACTGCCGAGTTAAACGCA | maeA ext 2 |
| X15592 | 184 | AGGTCGAAGCCAGCTTGATCAGAA | maeB ext 1 |
| X15593 | 185 | CGCTGACGGTTTGTGATAACGCTT | maeB ext 2 |
| X15594 | 186 | TACCTTCTGCTTTGCCCAGTGAGT | mdh ext 1 |
| X15595 | 187 | TGAAGCATTGCTGGTGGGATCTGA | mdh ext 2 |
| X15596 | 188 | AGTGGCACCACACCAATGCTTTCA | adhE ext 1 |
| X15597 | 189 | TGAACGCCAGCTTCACGGATAGAT | adhE ext 2 |
| X13673 | 300 | ATACGGGATAATACCGCGCCACAT | internal 1 |
| X13674 | 301 | CCATTCGACCACCAAGCGAAACAT | internal 2 |

TABLE 9

Lineage of Strains From M2162 to M2939

| M number | Genotype | Parent |
|---|---|---|
| M2162 | strepR | MG1655 |
| M2264 | strepR, Δedd Δeda | M2162 |
| M2273 | strepR, Δedd Δeda Δldh | M2264 |
| M2348 | strepR, Δedd Δeda Δldh Δppc | M2273 |
| M2371 | strepR, Δedd Δeda Δldh Δppc ΔfdhF | M2348 |
| M2379 | strepR, Δedd Δeda Δldh Δppc ΔfdhF Δfrd | M2371 |
| M2492 | strepR, Δedd Δeda Δldh Δppc ΔfdhF Δfrd ΔPpckA::Pspc pckA | M2379 |
| M2590 | strepR, Δedd Δeda Δldh Δppc ΔfdhF Δfrd ΔPpckA::Pspc pckA Δpta::fdh3 | M2492 |
| M2645 | strepR, Δedd Δeda Δldh Δppc ΔfdhF Δfrd ΔPpckA::Pspc pckA Δpta::fdh3 ΔpykF | M2590 |
| M2698 | strepR, Δedd Δeda Δldh Δppc ΔfdhF Δfrd ΔPpckA::Pspc pckA Δpta::fdh3 ΔpykF ΔpykA | M2645 |
| M2939 | strepR, Δedd Δeda Δldh Δppc ΔfdhF Δfrd ΔPpckA::Pspc pckA Δpta::fdh3 ΔpykF ΔpykA ΔptsI | M2909 |

2.2 Creating a Balanced Reduction/Oxidation Pathway During Anaerobic Fatty Acid Production Reduction and oxidation (redox) reactions play a key role in catabolic metabolism, allowing the transfer of electrons from one compound to another, and in the process, creating free energy for use elsewhere in cellular metabolism. To facilitate transfer of electrons from one compound to another, cells use redox co-factors to shuttle electrons. Several compounds and proteins can function as redox co-factors—the most relevant for anaerobic growth on carbohydrates are the nicotinamide adenine dinucleotides NADH and NADPH, and the iron-sulfur protein Ferredoxin (Fd).

Since NADH, NADPH, and Fd function as electron shuttles, they must discharge as many electrons as they accept, i.e., their net electron accumulation is zero. Catabolic metabolism can be thought of in two parts: carbohydrate deconstruction, where electrons are placed onto redox co-factors, and end-product construction, where electrons are removed from redox co-factors. In order for a metabolic pathway to function efficiently and at high yield, the type of co-factors used in carbohydrate deconstruction must balance those used in end product construction.

During carbohydrate deconstruction, which in the anaerobic fatty acid pathway ultimately results in acetyl-CoA, electrons are removed at two steps: the conversion of glyceraldehyde-3-phosphate to 1,3-biphosphoglycerate+$2e^-$ and the conversion of pyruvate to acetyl-CoA+$CO_2$+$2e^-$. In *E. coli*, NAD+ is used as electron acceptor for the first conversion. For the second conversion, *E. coli* employs a NAD+ linked pyruvate dehydrogenase during aerobic growth, and pyruvate formate lyase (pfl) and a formate dehydrogenase directly linked to hydrogen production (fdhF) to produce formate or $H_2$ from the $2e^-$ removed from pyruvate.

*E. coli* strains have been engineered to produce ethanol from acetyl-CoA at high yield via anaerobic expression of pyruvate dehydrogenase (PDH) (Kim et al., *AEM* 73: 1766-1771 (2007)) or via heterologous expression of NAD+ formate dehydrogenase (Berríos-Rivera et al., *Met Eng* 4:217-229 (2002)). In both wildtype and these engineered *E. coli* strains, NADH is the primary redox co-factor.

In contrast, the electron accepting reactions of fatty acid elongation require either exclusively NADPH or 1:1 stoichiometric levels of NADPH and NADH, depending on the co-factor specificity (NADPH or NADH) of enoyl-ACP reductase.

In order to balance the NADPH necessary for fatty acid elongation, the redox enzymes involved in carbohydrate deconstruction should be engineered to produce NADPH. In Table 10 below, different redox enzyme systems are described that can produce, per ½ glucose molecule, 2 NADH, 1 NADH and 1 NADPH, or 2 NADPH. Use of one of these systems in a host microorganism, or a combination thereof, will allow for an overall balanced co-factor pathway for anaerobic fatty acid production. In addition to, or instead of, using these systems, the enzymes can be modified to have different cofactor specificities.

TABLE 10

Enzymes for an overall balanced co-factor pathway for anaerobic fatty acid production

| FIG. 32 | Carbohydrate deconstruction reactions | Redox enzymes | NADH | NADPH |
|---|---|---|---|---|
| A | ½ glucose -> acetyl-CoA + $CO_2$ + $4e^-$ | NAD+ GAPDH, PDH | 2 | 0 |
| B | ½ glucose -> acetyl-CoA + $CO_2$ + $4e^-$ | NAD+ GAPDH, PFL, NAD+ FDH | 2 | 0 |
| C | ½ glucose -> acetyl-CoA + $CO_2$ + $4e^-$ | NAD+ GAPDH, PFL, NADP+ FDH | 1 | 1 |
| D | ½ glucose -> acetyl-CoA + $CO_2$ + $4e^-$ | NAD+ GAPDH, PNO | 1 | 1 |
| E | ½ glucose -> acetyl-CoA + $CO_2$ + $4e^-$ | NADP+ GAPDH, PFL, NAD+ FDH | 1 | 1 |
| F | ½ glucose -> acetyl-CoA + $CO_2$ + $4e^-$ | NADP+ GAPDH, PFL, NADP+ FDH | 0 | 2 |
| G | ½ glucose -> acetyl-CoA + $CO_2$ + $4e^-$ | NAD+ GAPDH, POR, Fd, NFN | 0 | 2 |
| H | ½ glucose -> acetyl-CoA + $CH_2O_2$ + $2e^-$ | NAD+ GAPDH, PFL | 1 | 0 |
| | End product construction reactions | Redox enzymes | NAD+ | NADP+ |
| I | acetyl-CoA + 4e− + $acyl_{(n)}$-ACP -> $acyl_{(n+2)}$-ACP | FabG (NADPH), FabI (NADH) | 1 | 1 |
| J | acetyl-CoA + 4e− + $acyl_{(n)}$-ACP -> $acyl_{(n+2)}$-ACP | FabG (NADPH), FabI (NADPH) | 0 | 2 |
| K | $acyl_{(n+2)}$-ACP + 4e− -> acyl alcohol (fatty alcohol) | AcDH, ADH | 0-2 | 0-2 |
| L | $acyl_{(n+2)}$-ACP + $H_2O$ -> acyl acid (fatty acid) + 2 $CH_2O_2$ | BTE | 0 | 0 |

Abbreviations: GAPDH—glycerol-3-phosphosate dehydrogenase, PFL—pyruvate formate lyase, PDH—pyruvate dehydrogenase, PNO—pyruvate:NADP+ oxidoreductase, POR—pyruvate:ferredoxin oxidoreductase, Fd—ferredoxin, NFN—NADH ferredoxin:NADP+ oxidoreductase, FabG—β-ketoacyl-ACP reductase, FabI enoylacyl-ACP reductase, AAR—acyl-ACP reductase, ADH—alcohol dehydrogenase, BTE—acyl-ACP thioesterase, AdhE—bifunctional acetaldehyde/alcohol dehydrogenase.

Figure 12:
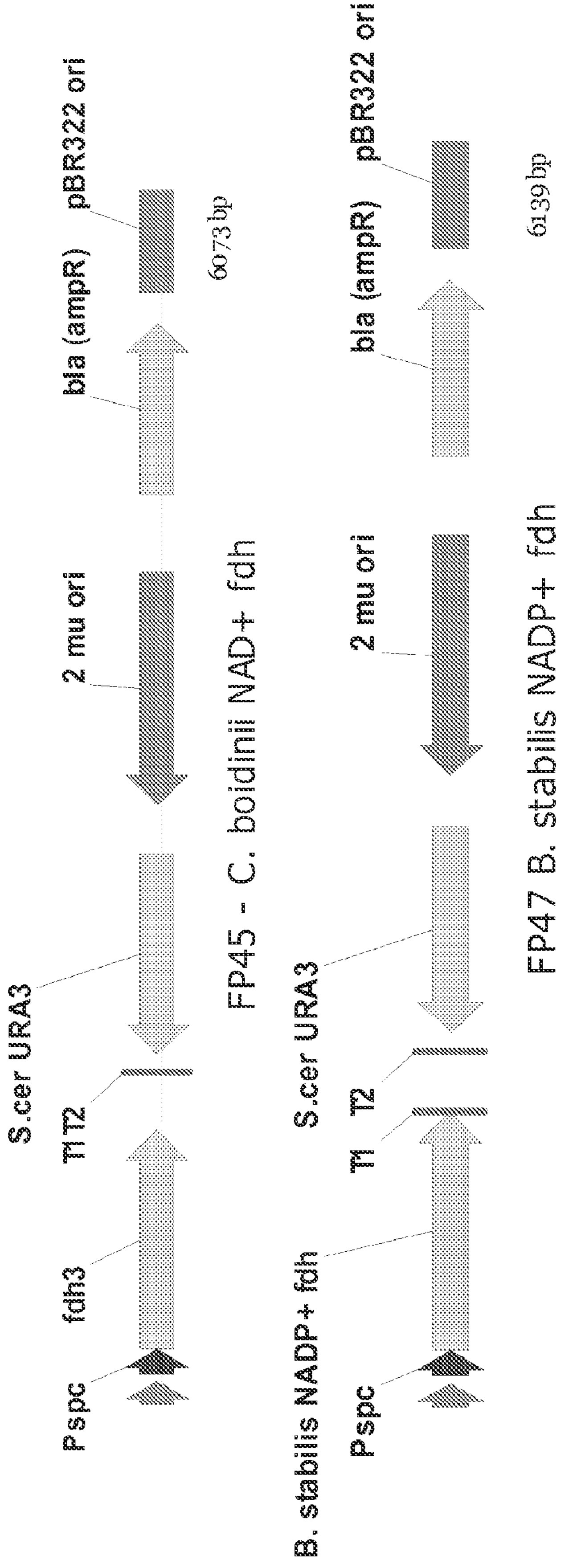
FIG. 12 depicts vectors FP45, FP47, FP66, FP67, FP68, and FP75, which are examples of heterologous redox enzymes designed for expression in *E. coli* to modify the native carbohydrate deconstruction pathway.
Figure 12:
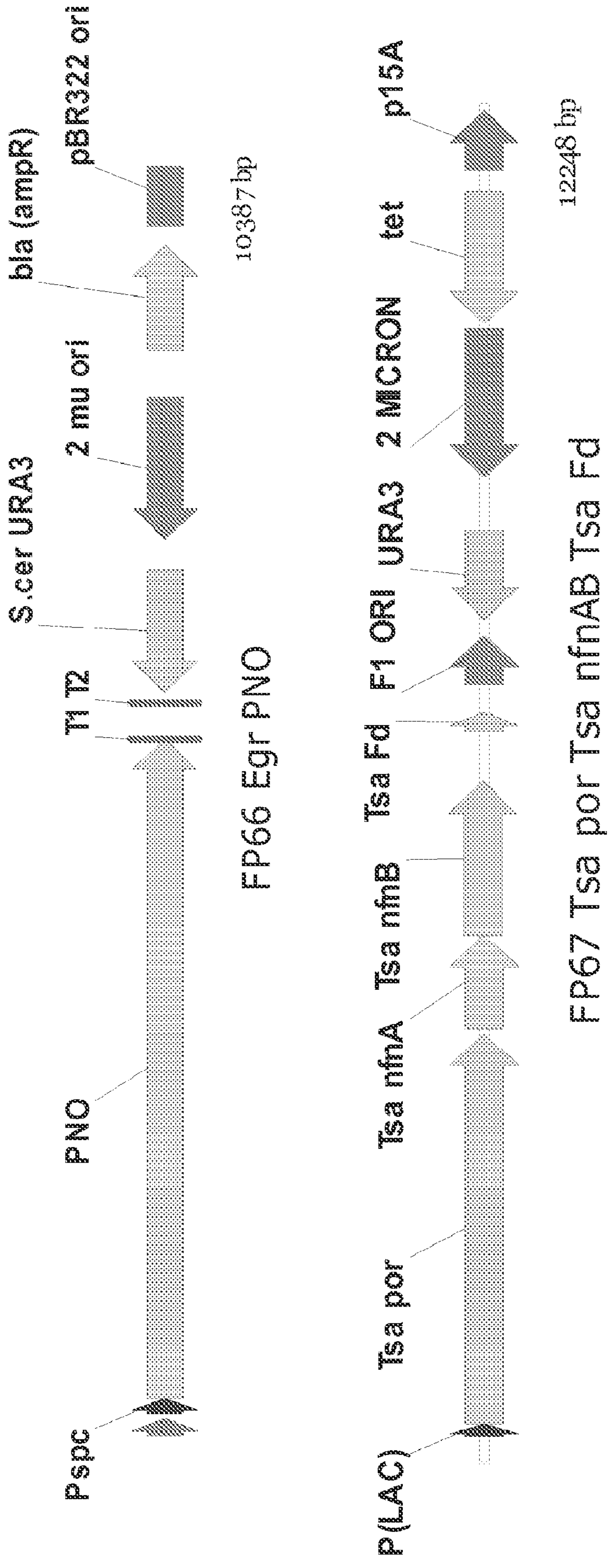
Figure 12:
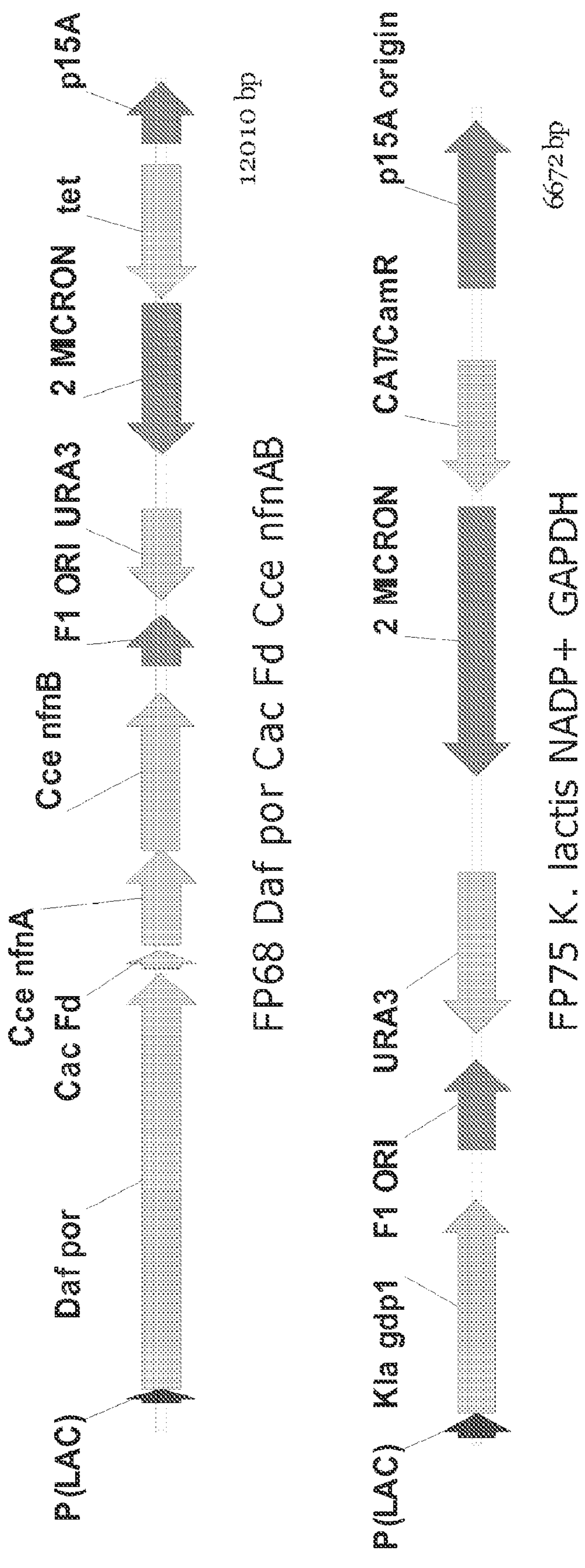

Enzymes used in the carbohydrate deconstruction reactions can be cloned into plasmids for expression in a host strain. For example, plasmids FP45, FP47, FP66, FP67, FP68, and FP75 are examples of heterologous redox enzymes designed for expression in *E. coli* to modify the native carbohydrate deconstruction pathway. See FIG. 12. Genes or gene operons are cloned under expression of either the constitutively active Pspc ribosomal promoter or the inducible Plac promoter. Cloning was performed via PCR amplification, using the primers listed in Table 11, or direct DNA synthesis of the desired gene products, followed by yeast gap-repair cloning with 30-60 bp homologous flanking regions. See Shanks et al., *AEM* 72:5027-5036 (2006). Transformed yeasts were selected via growth on SD-ura minimal medium for the presence of the ura3 gene. Plasmids were recovered from ura3+ yeast strains by standard mini-prep (Qiagen) or phenol extract and ethanol precipitation. Crude yeast plasmid preps were then used to transform *E. coli* TOP10 cells (Invitrogen) using selection with the plasmid appropriate antibiotic, either carbenicillin (100 μg/mL), tetracycline (15 μg/mL), or chloroamphenicol (25 μg/mL). *E. coli* mini-prepped plasmids were confirmed by restriction digest and agarose gel analysis.

TABLE 11

Primers for the Construction of Redox Balancing Plasmids FP45, FP47, FP67, FP68, and FP75 (FP66 was created from direct DNA synthesis (SEQ ID NO:206), so no primers were used during its construction)

| Primer # | SEQ ID NO: | Primer sequence | Description |
|---|---|---|---|
| X16072 | 190 | TCTCAGTAGTAGTTGACATTAGCGGAGCACTAAAATGAAGATTGTCTTAGTTCTTTAT | FP45 1 |
| X16073 | 191 | CAGTCTTTCGACTGAGCCTTTCGTTTTACGGCCGCTATTTCTTATCGTGTTTACCGTA | FP45 2 |
| X16082 | 192 | TCTCAGTAGTAGTTGACATTAGCGGAGCACTAAAATGGCAACCGTTCTGTGTGTTCTG | FP47 1 |
| X16083 | 193 | CAGTCTTTCGACTGAGCCTTTCGTTTTACGGCCGTTAGGTCAGACGATAGCTCTGTGC | FP47 2 |
| X16829 | 194 | TGTGAGCGGATAACAATTTCACACAGGAAACAGCTATGTCGAAGGTTATGAAAACCATG | FP67 1 |
| X16064 | 195 | GCTTTCACACCTCCAAGATTTCGTCTAATTTTGTTCAGCAAGCTTCTT | FP67 2 |
| X16065 | 196 | AAGAAGCTTGCTGAACAAAATTAGACGAAATCTTGGAGGTGTGAAAGC | FP67 3 |
| X16830 | 197 | CCTCGAGGTCGACGGTATCGATAAGCTTGATATCTTATTCAGCCTTAATAGCTCCTGTT | FP67 4 |
| X16831 | 198 | TGTGAGCGGATAACAATTTCACACAGGAAACAGCTATGGGAAAGAAAATGATGACGACT | FP68 1 |
| X16075 | 199 | TACACCTCCTTATCTTAATAGGCGTTCTACTTCTTCGTCCGCTTGCTGAG | FP68 2 |
| X16076 | 200 | CTCAGCAAGCGGACGAAGAAGTAGAACGCCTATTAAGATAAGGAGGTGTA | FP68 3 |
| X16077 | 201 | CCCGTCTGATATTTATGGTTCTACGACTTACTCTTGAACTGGAGCTCCTAC | FP68 4 |
| X16078 | 202 | GTAGGAGCTCCAGTTCAAGAGTAAGTCGTAGAACCATAAATATCAGACGGG | FP68 5 |
| X16832 | 203 | CCCTCGAGGTCGACGGTATCGATAAGCTTGATATCCTATTGGTTCTGCCGGATATATAT | FP68 6 |
| X16981 | 204 | TGTGAGCGGATAACAATTTCACACAGGAAACAGCTATGCCCGATATGACAAACGAATCT | FP75 1 |
| X16982 | 205 | CCCTCGAGGTCGACGGTATCGATAAGCTTGATATCTTAAACACCAGCTTCGAAGTCCTT | FP75 2 |

Sequence of the PNO gene and flanking regions used to create FP66 (SEQ ID NO: 206):
tgagccgtttatttttctacccatatccttgaagcggtgttataatgccgcgccctcgatatggggattttaacgacctgattttcggg tctcagtagtagttgacattagcggagcactaaaatgaaacagagcgttcgtccgattattagcaatgttctgcgtaaagaagttgc cctgtatagcaccattattggtcaggataaaggtaaagaaccgacaggtcgtacctataccagcggtccgaaaccggcaagcca tattgaagttccgcaccatgttaccgttccggcaaccgatcgtaccccgaatccggatgcacagtttttcagagcgttgatggtagc caggcaaccagccatgttgcatatgccctgagcgataccgcatttatctatccgattaccccgagcagcgttatgggtgaactggc agatgtttggatggcacagggtcgtaaaaatgcctttggtcaggttgttgatgttcgtgaaatgcagagcgaagccggtgcagcg ggtgcactgcatggtgcactggcagccggtgcgattgcaaccacctttaccgcaagccagggtctgctgctgatgattccgaata tgtataaaatcgcaggcgaactgatgccgagcgttattcatgttgcagcacgtgagctggcaggtcatgcactgagcatttttggtg -continued gtcatgcagatgttatggcagttcgtcagaccggttgggcaatgctgtgtagccataccgttcagcagagccatgatatggcactg attagccatgtggcaaccctgaaaagcagcattccgtttgttcatttttttgatggttttcgcaccagccacgaagtgaacaaaatca aaatgctgccgtatgccgaactgaaaaaactggttccgcctggcaccatggaacagcattgggcacgtagcctgaatccgatgc atccgaccattcgtggcaccaatcagagcgcagatatctattttcagaatatggaaagcgccaaccagtattataccgatctggca gttagttgttcaagaaaccatggatgaagttgcaccgtatattggtcgtcattacaaaatctttgagtatgttggtgcaccggatgcag aagaggtgaccgttctgatgggtagcggtgccaccaccgttaatgaagcagttgatctgctggttaaacgcggtaaaaaagttgg tgcagttctggttcatctgtatcgtccgtggtcaaccaaagcatttgaaaaagttctgccgaaaaccgtgaaacgtattgcagcact ggatcgttgcaaagaagttaccgcactgggcgaaccgctgtatctggatgttagcgccaccctgaacctgtttccggaacgtcag aatgttaaagttauggtggtcgttatggtctgggtagcaaagatttcattccggaacatgcactggccatttatgcaaatctggcaa gcgaaaatccgattcagcgttttaccgttggtattaccgatgatgttaccggcaccagcgtgccgtttgttaatgaacgtgttgatac cctgccggaaggcacccgtcagtgtgtttttggggtattggtagtgatggcaccgttggtgcaaatcgtagcgcagttcgtattatt ggtgataatagcgatctgatggtgcaggcgtattttcagtttgatgcatttaaaagcggtggtgttaccagcagccatctgcgttttg gtcctaaaccgattaccgcacagtatctggttaccaatgcagattatattgcctgccactttcaagagtatgtgaaacgttttgatatg ctggatgcaattcgtgaaggtggcacctttgttagaatagccgttggaccaccgaagatatggaaaaagaaattccggcagatttt cgtcgtaatgtggcacagaaaaaagtgcgcttttataacgttgatgcccgtaaaatttgcgatagctttggtctgggcaaacgcatt aacatgctgatgcaggcatgtttttcaaactgagcggtgttctgccgctggccgaagcacagcgtctgctgaatgttaagcattgtt catgagtatggcaaaaaaggtggtaaagtggtggaaatgaatcaggcagttgttaatgcagtgtttgccggtgatctgcctcaaga agttcaggttccggcagcatgggcaaatgcagttgataccagcacccgcaccccgaccggtattgaatttgttgataaaatcatgc gtccgctgatggatttcaaaggtgatcagctgccggttagcgttatgacaccgggtggtacatttccggttggcaccacccagtat gcaaaacgtgcaattgcggcatttattccgcagtggattccggcaaattgtacccagtgtaattattgcagctatgtttgtccgcatg caaccattcgtccgtttgtgctgaccgatcaagaagtgcagctggcaccggaaagctttgttacccgtaaagcaaaaggtgattat cagggtatgaactttcgtattcaggttgcaccggaagattgtaccggttgtcaggtttgtgttgaaacctgtccggatgatgcactgg aaatgaccgatgcgtttaccgccacaccggttcagcgtaccaattgggaatttgcaattaaagttccgaatcgtggtacgatgacc gatcgctatagcctgaaaggtagccagtttcagcaaccgctgctggaatttagcggtgcatgtgaaggttgtggtgaaaccccgt atgttaaactgctgacccagctgtttggtgaacgtaccgttattgcaaatgccaccggttgtagcagcatttggggtggtacggcag gtctggctccgtataccaccaatgcaaaaggtcagggtccggcatggggtaatagcctgtttgaagataatgccgaatttggttttg gtattgcagttgccaatgcacagaaacgtagccgtgttcgtgattgtattctgcaggccgttgaaaaaaaagtggccgatgaaggt ctgaccaccctgctggcacagtggctgcaggattggaataccggtgataaaacactgaaatatcaggaccagattattgccggtc tggcacagcagcgtagtaaagatcctctgctggaacaaatttatggcatgaaagatatgctgccgaatatcagccagtggattatt ggcggtgatggttgggccaatgatattggctttggtggcctggatcatgttctggcgagcggtcagaatctgaatgttctggtgctg gataccgaaatgtatagcaatacaggtggtcaggcaagcaaaagcacccatatggcaagcgttgcaaaatttgccctgggtggt aaacgtaccaacaaaaaaaacctgaccgaaatggccatgagctatggtaatgtttatgttgcaaccgttagccatggtaatatggc ccagtgtgttaaagcctttgttgaagcagaaagctatgatggtccgagcctgattgttggttatgcaccgtgcattgaacatggtctg cgtgcaggtatggcacgtatggttcaagaatcagaagcagcaattgcaaccggttattggccactgtatcgttttgatccgcgtctg gcaaccgaaggtaaaaacccgtttcagctggatagcaaacgtattaaaggtaacctgcaagaatatctggatcgccagaatcgtt atgtgaacctgaaaaaaaacaatccgaaaggtgccgatctgctgaaaagccagatggcagataacattacagcacgctttaatcg ttatcgtcgtatgctggaaggtccgaataccaaagcagcagcaccgagcggtaatcatgtgaccattctgtatggtagtgaaacc ggtaatagcgaaggtctggcaaaagaactggccaccgattttgaacgtcgtgaatatagcgttgcagttcaggccctggatgatat tgatgttgcggatctggaaaatatgggctttgttgttattgccgtttcaacctgtggtcagggccagtttccgcgtaatagtcagctgtt ttggcgtgaactgcagcgtgataaaccggaaggttggctgaaaaatctgaaatacaccgtttttggcctgggtgatagcacctatt acttttattgtcataccgccaaacaaatcgatgcacgtctggcagcgctgggtgcacagcgtgttgttccgattggtttcggtgatga -continued

```
tggtgatgaagatatgtttcataccggcttcaataattggattccgagcgtttggaatgagctgaaaaccaaaactccggaagaag

cactgtttaccccgtcaattgccgttcagctgaccccgaatgcaacaccgcaggattttcattttgccaaaagcacaccggtgctga

gcattaccggtgcagaacgtattacaccggcagatcatacccgcaattttgttaccattcgttggaaaaccgatctgagctatcagg

ttggtgatagcctgggtgtttttccagaaaatacccgtagcgttgttgaagaattcctgcagtattatggcctgaacccgaaagatgt

tattaccattgaaaataaaggctcacgcgaactgccgcattgtatggccgttggtgacctgtttaccaaagttctggatattctgggt

aaaccgaataaccgcttctataaaaccctgagctatttcgccgttgataaagcagaaaaagaacgcctgctgaaaattgcagaaat

gggtccggaatatagcaacattctgtcagagatgtatcattatgccgacatctttcatatgtttccgagcgcacgtccgacactgca

gtatctgattgaaatgatcccgaacattaaaccgcgttattatagcattagtagcgcaccgattcatactccgggtgaagtgcatag

cctggttctgattgatacctggattaccctgagcggtaaacatcgtacgggtctgacctgtaccatgctggaacatctgcaggcag

gtcaggtggtggatggttgtattcatccgaccgcaatggaatttccggatcatgaaaaaccggttgttatgtgtgcaatgggttcag

gtctggcaccttttgttgcatttctgcgtgaacgtagcaccctgcgtaaacagggtaaaaaaacgggcaatatggcgctgtattttg

gcaatcgttacgaaaaaaccgaatttctgatgaaagaggaactgaaaggccatatcaatgatggtctgctgacactgcgttgtgca

tttagccgtgatgatccgaaaaaaaaagtctatgtgcaggatctgatcaaaatggatgaaaaaatgatgtatgattacctggtggttc

agaaaggcagcatgtattgttgtggtagccgtagttttatcaaaccggtgcaagaaagcctgaaacattgttttatgaaagcgggtg

gtctgaccgcagaacaggcagaaaatgaagttattgatatgtttaccacgggtcgctataacattgaagcgtggcggccgtaaaa

cgaaaggctcagtcgaaagactg
```

NAD+ linked fdh from *Candida boidinii* and NADP+ linked fdh from *Burkholderia stabilis* were expressed in *E. coli* TOP10. Biochemical activity measurements were made on cell free extracts, which resulted in the data presented in Table 12 below. The assay was conducted with 50 mM sodium formate and 1.1 mM NAD+ or NADP+ at pH 7.0 in sodium phosphate buffer, as adapted from Hopner, T. and Knappe, J., *Methods of Enzymatic Analysis,* 3:1551-1555 (1974). In a final volume of 1 mL, 0.55 mL of water, 0.375 mL of 200 mM sodium phosphate, pH 7.0, 0.375 mL of 200 mM sodium formate, 0.15 mL of 10.5 mM β-NAD+ or 10.5 mM β-NADP+, and 0.05 mL of crude enzyme prep were added to a 1.5 mL plastic cuvette in the order indicated. Absorbance at 340 nm was recorded for 1 minute with a Shimadzu spectrophotometer, and the rate was used to determine specific activity. Protein concentrations were determined by the Bradford method with BSA as the standard. As expected, fdh from *C. boidinii* preferred NAD+ as a co-factor, while fdh from *B. stabilis* preferred NADP+.

TABLE 12

Biochemical activity of Cell-free Extracts

| plasmid | description | μmol $min^{-1}$ $mg^{-1}$ NAD+ | NADP± |
|---|---|---|---|
| pMU2726 | empty vector | 0.00 ± 0.00 | 0.00 ± 0.01 |
| FP45 | *C. boidinii* fdh | 0.39 ± 0.04 | 0.01 ± 0.01 |
| FP47 | *B. stabilis* fdh | 0.06 ± 0.00 | 0.31 ± 0.02 |

2.3 Acyl-ACP Chain Termination Enzymes

The final step of the anaerobic fatty acid pathway involves cleavage of the acyl carrier protein (ACP) from the acyl chain, and addition of a functional group to the final carbon of the growing chain (FIG. 13). The chain termination enzyme(s) determine both the terminal functional group and the overall acyl chain length.

Figure 14:
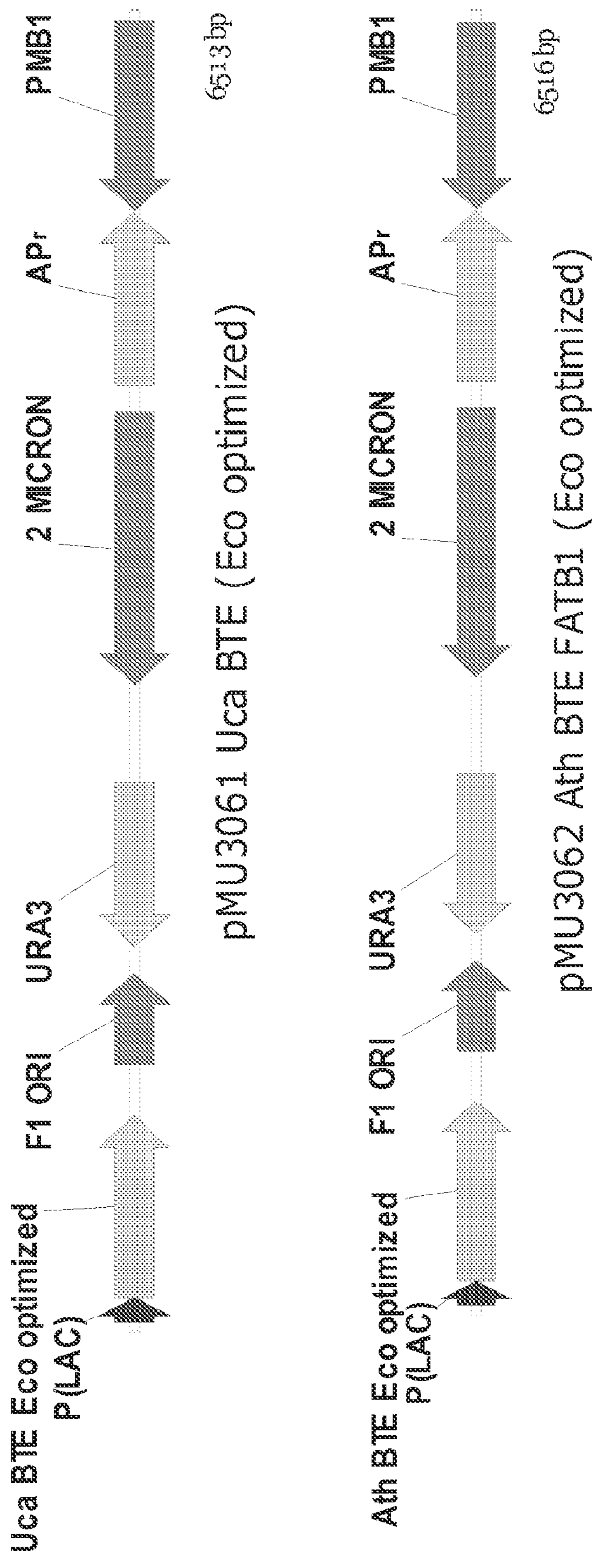
FIG. 14 depicts vectors pMU3061, pMU3062, pMU3063, and pMU3064.
Figure 14:
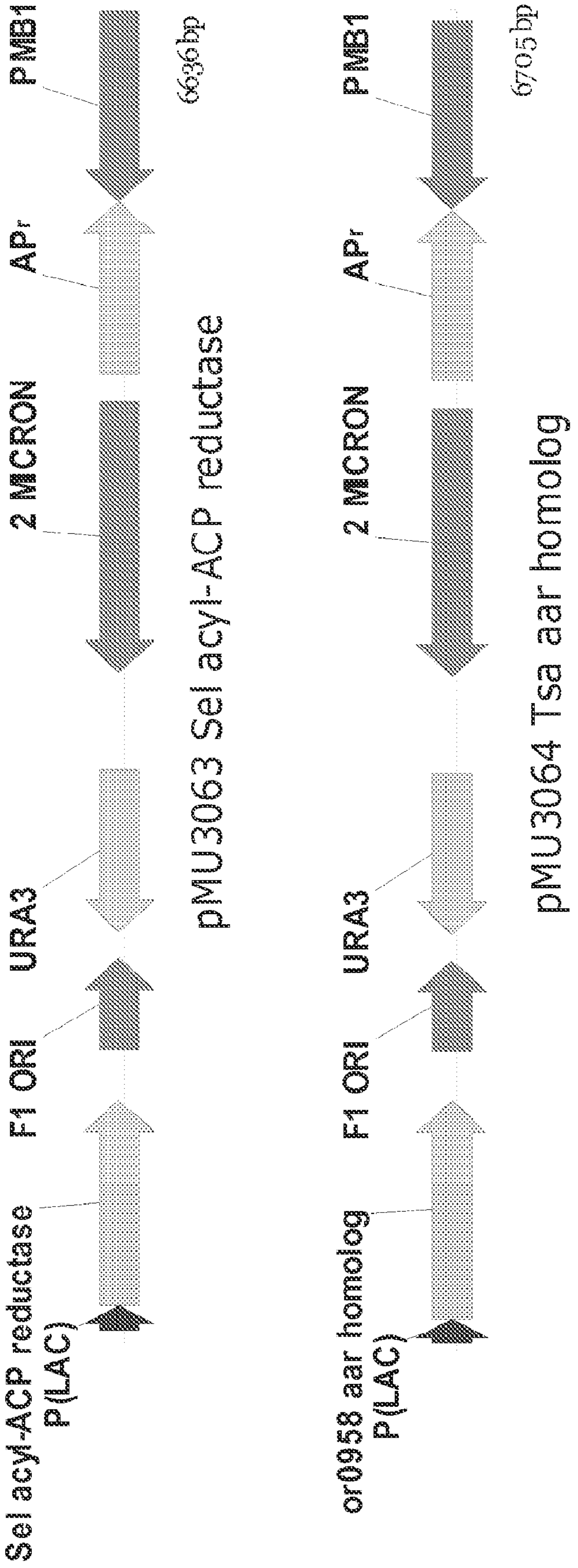

Plasmids encoding an *E. coli* codon optimized C12 acyl-ACP thioesterase (pMU3061), an *E. coli* codon optimized C16 acyl-ACP thioesterase (pMU3062), an acyl-ACP reductase (pMU3063), and an acyl-ACP reductase homolog (pMU3064) have been expressed in *E. coli* strain M2933 harboring a deletion in the acyl-CoA dehydrogenase fadE, an enzyme involved in fatty acid degradation. The expression plasmids used for these enzymes are shown in FIG. 14.

*E. coli* strains were grown to saturation over 48 hours in 5 mL LB medium at 30° C. in aerobic culture tubes containing 100 μg/mL Carbenicillin and 1 mM IPTG. Total fatty acid quantification was performed by lipid extraction followed by methyl ester derivatization and analysis by gas chromatograph with flame ionization detection. Extraction and derivatization was performed by adding 0.5 mL sample to a 13×100 mm glass tube with Teflon coated cap, addition of 4 mL 4% sulfuric acid in methanol followed by vortexing. The samples were then incubated at 70° C. in a water bath for 30 minutes, cooled to room temperature, followed by addition of 2 mL water and 2 mL hexane with vortexing at each step. The hexane layer was transferred to a new tube and dried under nitrogen. 50 μL hexane was then used to re-constiture the fatty acids for gas chromotograph analysis. Total fatty acids for M2933 strains carrying either plasmid pMU960 (empty vector), pMU3061, pMU3062, pMU3063, or pMU3064 are shown in FIGS. 22A and 22B. Individual fatty acids are also shown using a standard naming convention of X:Y, where X is the carbon number and Y is the number of unsaturated bonds.

Example 3

3.1 Methodology to Screen for Transcarboxylase Activity

To confirm that putative transcarboxylase genes have in vivo oxaloacetate:acetyl-CoA carboxytransferase activity, an *E. coli* strain was constructed that requires recombinant production of malonyl-CoA for growth. Wildtype *E. coli* produces malonyl-CoA, a metabolite essential for growth, exclusively via the enzyme acetyl-CoA carboxylase (ACC). ACC is composed of the four subunit genes accA, accB, accC, and accD, which are located at three different loci on the *E. coli* genome.

Because malonyl-CoA is essential, ACC cannot be disrupted directly in wildtype *E. coli* without resulting in a lethal phenotype. To overcome this, a conditional pathway for malonyl-CoA biosynthesis was first introduced into wildtype *E. coli*. This pathway, encoded by matBC from *Rhizobacterium trifolii*, transports exogenous malonate across the cell membrane, and then uses malonate, ATP, and CoA to produce malonyl-CoA, AMP, and $PP_i$. See An and Kim, *Eur. J. Biochem.*, 257:395-402 (1998).

3.1.1 Construction of Strain M2470

Figure 15:
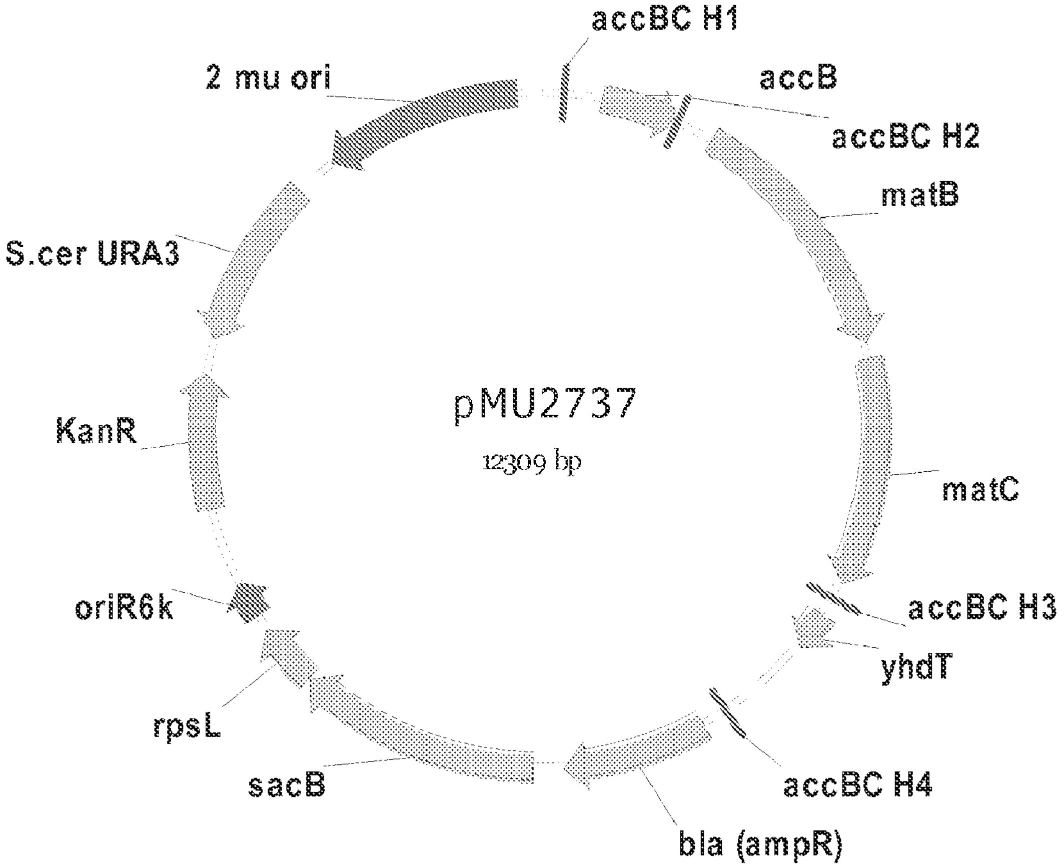
FIG. 15 depicts the vector pMU2737.
Figure 16:
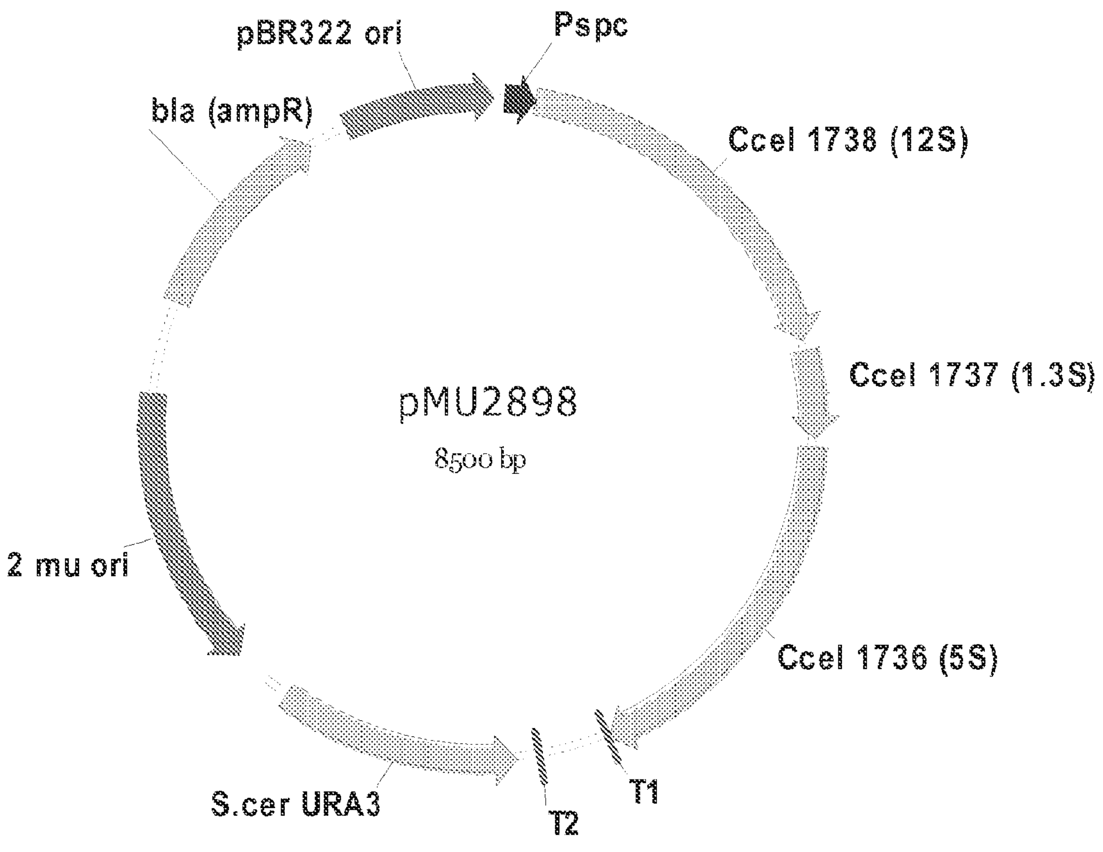
FIG. 16 depicts the vector pMU2898.
Figure 17:
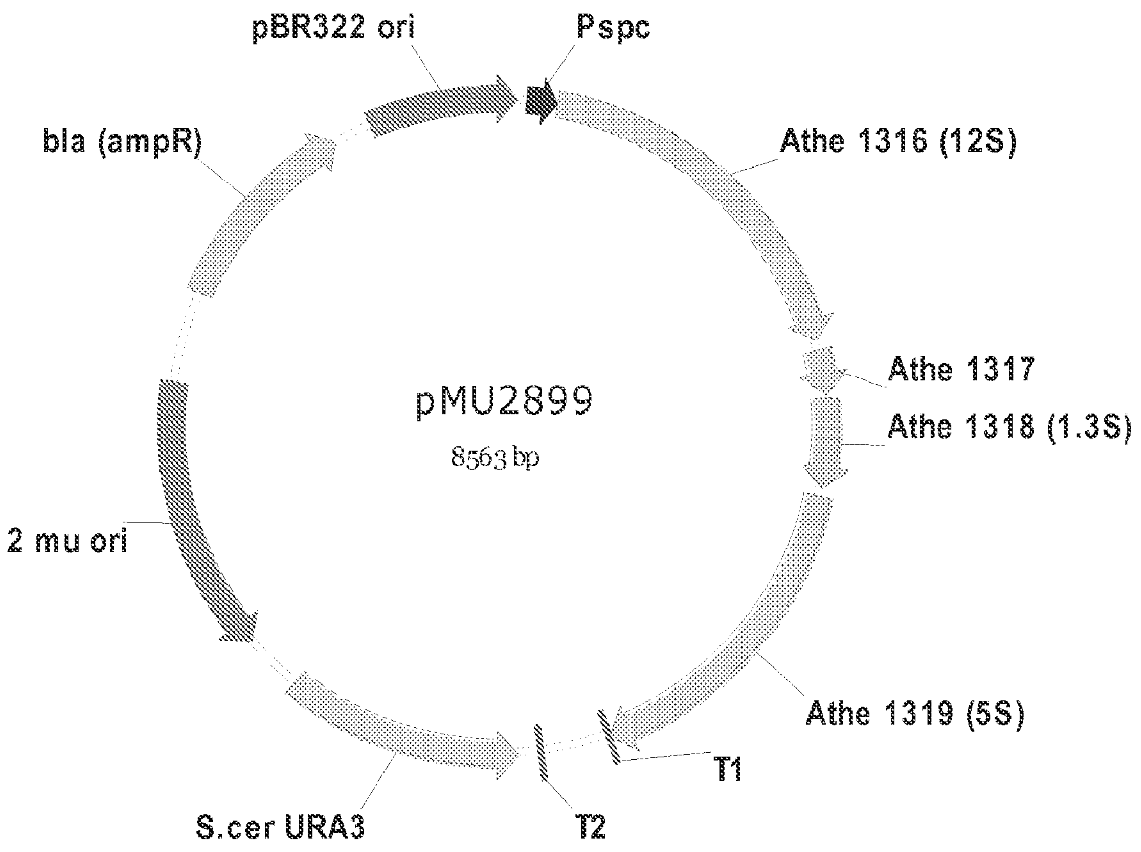
FIG. 17 depicts the vector pMU2899.
Figure 18:
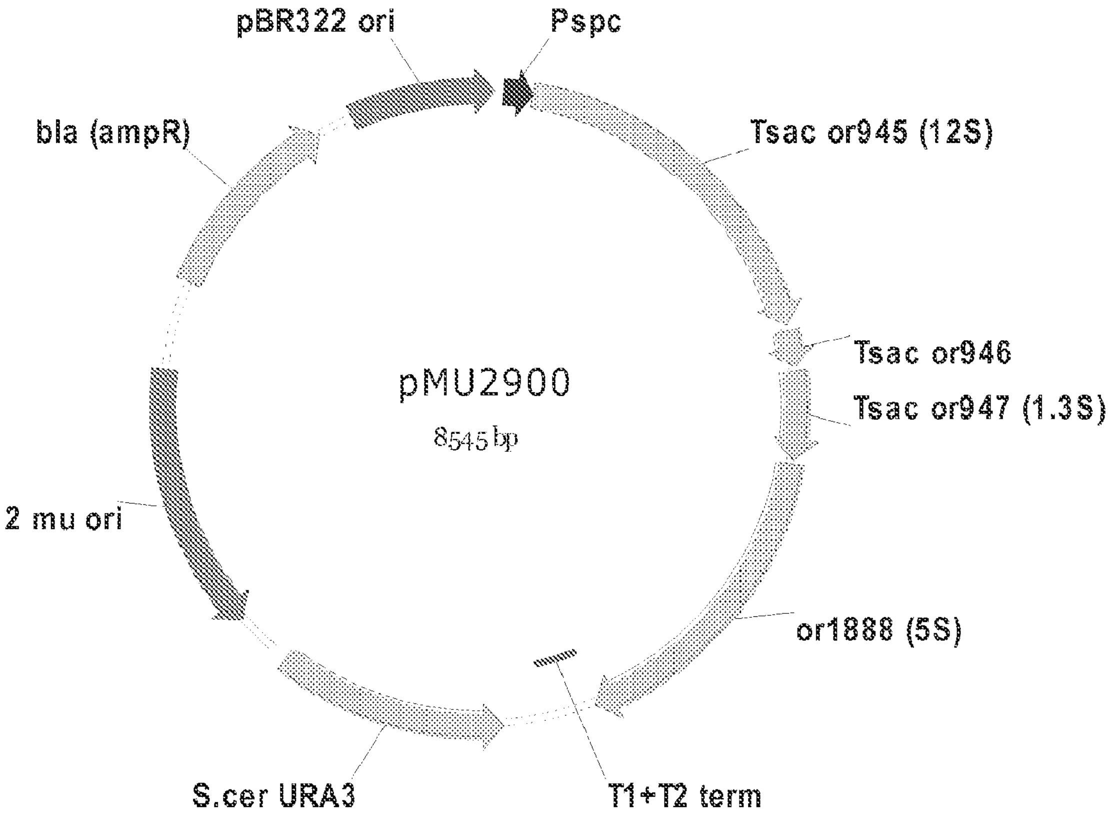
FIG. 18 depicts the vector pMU2900.
Figure 19:
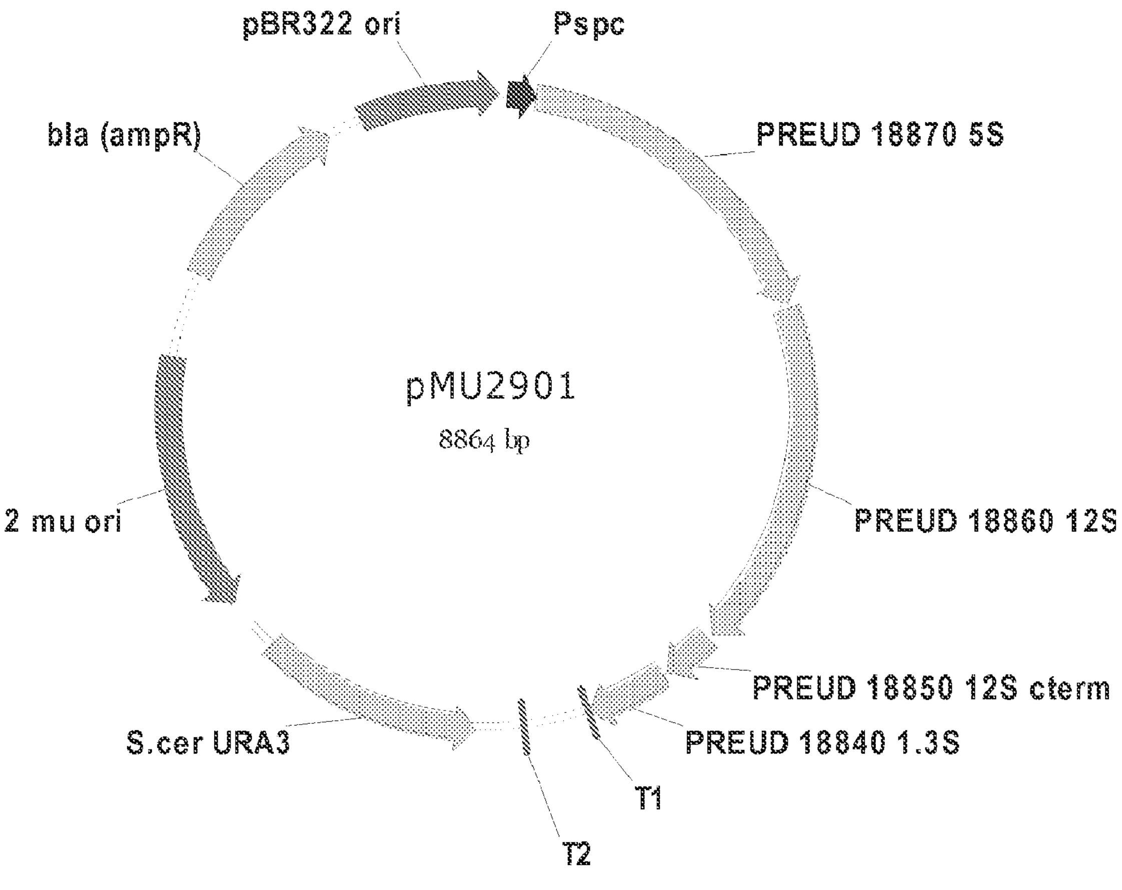
FIG. 19 depicts the vector pMU2901.

Strain M2470 is a ΔaccC::matBC strain built from *E. coli* K12 strain MG1655 (ATCC Accession No. 700926). To construct M2470, plasmid pMU2737 (FIG. 15; SEQ ID NO: 285) was transformed into strain MG1655 with selection on 100 μg/mL ampicillin and 50 μg/mL kanamycin. pMU2737 is a non-replicating plasmid, and confirmation of a single cross over integration was detected via colony PCR. The single cross-over meridiploid contains both a functional and a non-functional copy of accC, as well as the matBC genes, and positive ($amp^R$, $kan^R$) and negative selective (sacB, rpsL) markers. Upon plating on the negative selective condition, 10% w/v sucrose supplemented with 10 mM sodium malonate, the meridiploid resolved exclusively to the wild-type, functional accC gene copy. This suggested that matBC was not able to catalyze the conversion of exogenous malonate to malonyl-CoA at a rate sufficient to allow for observable colony formation. To overcome this, the meridiploid strain was grown aerobically in M9 minimal medium supplemented with 1.4 mM glucose and 10 mM malonate. After two transfers, each lasting ~48 hours in 50 mL of this medium, the culture was re-plated on 10% w/v sucrose supplemented with 10 mM sodium malonate. Upon screening, most (>90%) of the colony isolates now had the non-functional accC copy and matBC genes. An isolate was further purified and designated M2470. It is able to grow only when exogenous malonate is present in the medium.

3.1.2 Construction and Screening of Putative Transcarboxylase Genes

Plasmids pMU2898 (SEQ ID NO:286), pMU2899 (SEQ ID NO:287), pMU2900 (SEQ ID NO:288), and pMU2901 (SEQ ID NO:289) (FIGS. 16-19) were constructed via yeast homologous cloning to express putative transcarboxylases from *Clostridium cellulolyticum* H10 ATCC 35319*, Caldicellulosiruptor bescii* DSM 6725, *Thermoanaerobacterium saccharolyticum* JW/SL-YS485, and *Propionibacterium freudenreichii* CIRM-BIA1$^T$, respectively. Percent consensus and identity positions across the four subunits of these putative transcarboxylases, as well as from *Corynebacterium kroppenstedtii* DSM 44385*, Geobacter bemidjiensis* Bemi($^T$), and *Clostridium thermocellum* ATCC 27405, is depicted in Table 13. A phylogenetic tree and alignment of these transcarboxylases, including from *D. propionincus* DSM 2032, is shown in FIGS. 30-31.

TABLE 13

Percent Consensus and Identity Positions Across Putative Transcarboxylases

| | Consensus positions | Identity positions |
|---|---|---|
| 5S subunit | 75.5% | 29.8% |
| 1.3S subunit | 58.6% | 12.0% |
| 12S subunit | 85.0% | 35.0% |
| 12S C-terminal subunit* | 36.5% | 1.9% |

**C. cellulolyticum* does not have a 12S C-terminal subunit

The four putative transcarboxylases were cloned into pMU2727, a replicating vector with the pBR322 origin, $amp^R$, Pspc promoter, and T1T2 terminator. Pspc is a moderately high level constitutive ribosomal promoter. See Liang et al., *J. Mol Bio* 292:19-37 (1999).

These plasmids were then transformed into M2470 and transformants were selected on medium containing, per liter, 10 g glucose, 1.48 g disodium malonate, 100 mg ampicillin, 15 g agar, and the modified M9 base medium: 12.8 g $Na_2HPO_4.7H_2O$, 3 g $KH_2PO_4$, 0.5 g NaCl, 1 g $NH_4Cl$, 0.5 g $MgSO_4$, 0.015 g $CaCl_2$, 0.02 g thiamine, 0.02 g $CoSO_4$, 0.02 g $ZnSO_4$, 0.02 g $MnSO_4$, 0.015 g biotin. Transformants were confirmed by plasmid mini-prep, and re-patched onto modified M9 medium plates containing 20 g glucose and 15 g agar per liter ("M9+20 glucose"). If growth was observed on M9+20 glucose plates, colonies were re-grown in either liquid or solid medium of the same composition, and scored for growth and growth rate (Table 14 and FIG. 20A). As a control, transformants were also plated on solid medium comprising M9 base medium, 10 g/L glucose, 10 mM malonate, and 100 μg/mL ampicillin (Table 14 and FIG. 20B). The following transformants were isolated and tested for growth: MG1655—wildtype, M2560—ΔaccC::matBC+pMU2727 empty vector ($amp^R$), and M2557, M2558, M2559—ΔaccC::matBC+pMU2900 *T. saccharolyticum* TC ($amp^R$).

TABLE 14

Growth of Transformants Containing Putative Transcarboxylases

| Strain | M9 + 20 glu | M9 + malonate + amp |
|---|---|---|
| MG1655 WT | ++++ | − |
| M2470 | − | +++ |
| M2560 (aka. M2470 + pMU2727) | − | +++ |
| M2557 (aka. M2470 + pMU2900) #1 | +++ | +++ |
| M2558 (aka. M2470 + pMU2900) #2 | +++ | +++ |
| M2559 (aka. M2470 + pMU2900) #3 | +++ | +++ |
| M2470 + pMU2898 | + | +++ |
| M2470 + pMU2899 | ++ | +++ |
| M2470 + pMU2901 | + | +++ |

++++ = visible growth within 24 hours
+++ = visible growth within 48 hours
++ = visible growth within 96 hours
+ = visible growth within 168 hours
− = no visible growth after 200+ hours 3.2 Assays for Recombinant Transcarboxylase and In Vitro Transcarboxylase Activity To determine the presence and activity of the *T. saccharolyticum* transcarboxylase enzyme that was engineered into the *E. coli* ΔaccC::matBC strain and screened using the assay above, several biochemical assays were conducted. Initial evaluation of activity in cell lysate was inconclusive. The *T. saccharolyticum* transcarboxylase enzyme was then purified using the biotin binding domain located in the 1.3S protein. Without wishing to be bound by theory, Streptavidin binding of the 1.3S subunit could co-purify both the 5S and 12S proteins which associate with the 1.3S subunit in the native host. *E. coli* ΔaccC::matBC cells were grown in M9+ medium at 37° C. in aerobic shake flasks to an OD of 6 in 1.8 L total volume and lysed with Y-PER® (Pierce) according to product instructions, in the presence of 100 mM potassium phosphate, pH 6.8, 1 mg/mL reduced glutathione, 1:10,000 dilution of Sigma bacterial protease inhibitors, and 0.5 U/mL DNase I. After 2-3 freeze/thaw cycles, the cells were lysed as determined by microscopic evaluation. The lysate was centrifuged to remove debris and the supernatant was retained for further evaluation of activity. Two constructs were evaluated using this affinity assay, M2557 and M2560, which were either the strain engineered to produce the 12S, 5S, 1.3S, and 12S C-terminal components of the *T. saccharolyticum* transcarboxylase system or the empty vector control strain, respectively (see above).

To determine the presence of the biotin-containing enzyme, the lysates were then purified using monomeric avidin resin with a batch binding protocol (Pierce) according to product instructions. After the sample was incubated with the resin, the protein was eluted from the column with 4 mM biotin. The eluted fractions were analyzed on via Western blot with avidin-HRP as the detection. Samples were run on a 4-20% tris glycine gel then transferred to a PVDF membrane. After overnight blocking in TBS/1% BSA, streptavidin HRP was added. The HRP was detected with ECL chemilunescent and imaged on a chemiluminescent gel doc system. FIG. 25 depicts the results of this affinity assay comparing M2557 and M2560.

The monomeric avidin-purified lysate was purified again with Streptavidin Dynabeads with a batch binding system carried out with 1 mL of lysate mixed with 100 L of washed streptavidin Dynabeads. After incubation at room temperature for 30 min, the sample was washed with 100 mM potassium phosphate, 1 mg/mL reduced glutathione, pH 6.8 and eluted from the beads by boiling in SDS-PAGE sample buffer. The re-purified lysate was then analyzed via Western Blot as above. The band on the Western Blot that ran at the same location as the one indicated with an arrow in FIG. 25 was sequenced on a Procise N-terminal sequencer. The sequencing data indicated that the N-terminus of the protein was MKKFIVTVNG (SEQ ID NO:299), consistent with the N-terminus of the 1.3S protein.

The enzymatic activity of the monomeric avidin-purified transcarboxylase complex was then assessed using an LC/MS detection assay. The monomeric avidin purified lysate was mixed with oxaloacetate, acetyl CoA and reduced glutathione and incubated at 40° C. for 1.5 hours. The sample was then analyzed by LC/MS using a BioRad 87H column and a Thermo LCQ (HPLC $C_{18}$ column-formate/methanol eluent) ion trap mass spectrometer. The results are shown in FIGS. 26A and 26B. In FIG. 26A, the negative control sample was analyzed. Using selected ion monitoring, acetyl CoA was detected but no malonyl CoA was detected (FIG. 26A, lower two panels). When the transcarboxylase sample was analyzed with selected ion monitoring both acetyl and malonyl CoA (FIG. 26B, lower two panels) were detected thereby indicating that the transcarboxylase enzyme complex was functional.

3.3 Use of *E. coli* ΔaccC::matBC Strain to Select for Faster-Growing Transcarboxylase-Expressing Strains The *E. coli* accC::matBC strain M2470 can also be used to select for more efficient malonyl-CoA production by transcarboxylases. This selection is based on the principle that malonyl-CoA generation is the rate-limiting factor for growth of this strain. Thus, more efficient generation of malonyl-CoA will result in a faster growing strain which is able to out-compete the remaining culture and dominate the cell population during serial transfer or other continuous or semi-continuous selection systems. See, e.g., FIG. 27A.

First, strain M2470 was transformed with an integrating plasmid (e.g., pMU2924, pMU2969) carrying a transcarboxylase and spectinomycin antibiotic resistance marker flanked by DNA regions homologous to the ldh gene (lactate dehydrogenase). Using kanR, ampR, sacB, and rpsL based selections, the transcarboxylase and specR marker were securely integrated into the genome via two homologous recombination events. During this period, the strain was grown on M9+ base medium with the addition of 2-20 g/L glucose and 1.48 g/L disodium malonate. The medium was prepared at room temperature, adjusted to pH 7.5 with 10 M NaOH or 10 M HCl, and filter sterilized into a pre-sterilized bottle with a 0.22 μm filter. Subsequently, the strain was grown aerobically at 37° C. in 350 mL of M9+ medium with only glucose in a 1 L shake flask. If substantial growth (OD>1) occurred, a 0.1 mL transfer was made to a fresh 350 mL flask, which is repeated 3 times, at which point a small culture volume is plated to isolate a single colony on solid M9+ glucose medium (prepared via addition of 15 g/L melted agar as a 2× stock to 2× liquid media, pre-incubated at 50° C.). See FIG. 27A. This strain is referred to as the $3^{rd}$ transfer (T3) isolate. Growth rates for the original strain and T3 isolate were then compared in M9+ medium with 20 g/L glucose as the sole carbon and energy source. An increased growth rate indicates an improved ability to generate malonyl-CoA. Plasmids used for this example were pMU2924 (*T. saccharolyticum* TC; FIG. 28; SEQ ID NO:207) and pMU2969 (*P. freudenreichii* TC; FIG. 29; SEQ ID NO:208), which generated strains M2767 and M2772, respectively. Growth rates for the original strain and T3 strain of each are shown in FIG. 27B.

Example 4

4.1 High Yield Palmitic Acid Production in *S. cerevisiae*

The present prophetic example describes the engineering of a recombinant yeast microorganism to convert a native pyruvate decarboxylase (pdc) based ethanol pathway (FIG. 34A) to an intermediary pyruvate formate lyase and alcohol/aldehyde dehydrogenase (pfl adhE) based ethanol pathway (FIG. 34B), and finally to a transcarboxylase based palmitic acid pathway (FIG. 34C).

The genetic modifications described below are used to create a strain capable of anaerobic growth in the absence of functional pyruvate decarboxylase and glycerol-3-phosphate dehydrogenase. To accomplish this, constructs were designed to replace GPD1, GPD2, FDH1, and FDH2 with two copies of a bifunctional alcohol/aldehyde dehydrogenase and two copies of a pyruvate formate lyase, both of which were cloned from *B. adolescentis* (Table 15). See, e.g., PCT/US2011/035416, which is incorporated by reference herein in its entirety, for additional details on the construction of such strain. Additionally, constructs were designed to make deletions of PDC5, PDC6, and PDC1. Either a NAD+ or NADP+ linked formate dehydrogenase is then re-introduced into the strain to create the metabolic pathway shown in (FIG. 34B).

TABLE 15

Coding sequences of pfl and adhE

| GenBank Accession # | Host strain | Gene donor | gene | protein |
|---|---|---|---|---|
| YP_909854 | *S. cerevisiae* | *Bifidobacterioum adolescentis* | pflA | pyruvate formate lyase activating enzyme |
| YP_909855 | *S. cerevisiae* | *Bifidobacterioum adolescentis* | pflB | pyruvate formate lyase |
| YP_909182 | *S. cerevisiae* | *Bifidobacterioum adolescentis* | adhE | alcohol/aldehyde dehydrogenase |

*B. adolescentis* adhE (amino acid sequence)

(SEQ ID NO: 209)

MADAKKKEEPTKPTPEEKLAAAEAEVDALVKKGLKALDEFEKLDQKQVDHI

VAKASVAALNKHLVLAKMAVEETHRGLVEDKATKNIFACEHVTNYLAGQKT

VGIIREDDVLGIDEIAEPVGVVAGVTPVTNPTSTAIFKSLIALKTRCPIIF

GFHPGAQNCSVAAAKIVRDAAIAAGAPENCIQWIEHPSIEATGALMKHDGV

ATILATGGPGMVKAAYSSGKPALGVGAGNAPAYYDKNVDVVRAANDLILSK

HFDYGMICATEQAIIADKDIYAPLVKELKRRKAYFVNADEKAKLEQYMFGC

TAYSGQTPKLNSVVPGKSPQYIAKAAGFEIPEDATILAAECKEVGENEPLT

MEKLAPVQAVLKSDNKEQAFEMCEAMLKHGAGHTAAIHTNDRDLVREYGQR

MHACRIIWNSPSSLGGVGDIYNAIAPSLTLGCGSYGGNSVSGNVQAVNLIN

IKRIARRNNNMQWFKIPAKTYFEPNAIKYLRDMYGIEKAVIVCDKVMEQLG

IVDKIIDQLRARSNRVTFRIIDYVEPEPSVETVERGAAMMREEFEPDTIIA

VGGGSPMDASKIMWLLYEHPEISFSDVREKFFDIRKRAFKIPPLGKKAKLV

CIPTSSGTGSEVTPFAVITDHKTGYKYPITDYALTPSVAIVDPVLARTQPR

KLASDAGFDALTHAFEAYVSVYANDFTDGMALHAAKLVWDNLAESVNGEPG

EEKTRAQEKMHNAATMAGMAFGSAFLGMCHGMAHTIGALCHVAHGRTNSIL

LPYVIRYNGSVPEEPTSWPKYNKYIAPERYQEIAKNLGVNPGKTPEEGVEN

LAKAVEDYRDNKLGMNKSFQECGVDEDYYWSIIDQIGMRAYEDQCAPANPR

IPQIEDMKDIAIAAYYGVSQAEGHKLRVQRQGEAATEEASERA

*B. adolescentis* pflA (amino acid sequence)

(SEQ ID NO: 210)

MSEHIFRSTTRHMLRDSKDYVNQTLMGGLSGFESPIGLDRLDRIKALKSGD

IGFVHSWDINTSVDGPGTRMTVFMSGCPLRCQYCQNPDTWKMRDGKPVYYE

AMVKKIERYADLFKATGGGITFSGGESMMQPAFVSRVEHAAKQMGVHTCLD

TSGELGASYTDDMVDDIDLCLLDVKSGDEETYHKVTGGILQPTIDEGQRLA

-continued

KAGKKIWVRFVLVPGLTSSEENVENVAKICETEGDALEHIDVLPFHQLGRP

KWHMLNIPYPLEDQKGPSAAMKQRVVEQFQSHGFTVY

*B. adolescentis* pflB (amino acid sequence)

(SEQ ID NO: 211)

MAAVDATAVSQEELEAKAWEGFTEGNWQKDIDVRDFIQKNYTPYEGDESFL

ADATDKTKHLWKYLDDNYLSVERKQRVYDVDTHTPAGIDAFPAGYIDSPEV

DNVIVGLQTDVPCKRAMMPNGGWRMVEQAIKEAGKEPDPEIKKIFTKYRKT

HNDGVFGVYTKQIKVARHNKILTGLPDAYGRGRIIGDYRRVALYGVNALIK

FKQRDKDSIPYRNDFTEPEIEHWIRFREEHDEQIKALKQLINLGNEYGLDL

SRPAQTAQEAVQWTYMGYLASVKSQDGAAMSFGRVSTFFDVYFERDLKAGK

ITETDAQEIIDNLVMKLRIVRFLRTKDYDAIFSGDPYWATWSDAGFGDDGR

TMVTKTSFRLLNTLTLEHLGPGPEPNITIFWDPKLPEAYKRFCARISIDTS

AIQYESDKEIRSHWGDDAAIACCVSPMRVGKQMQFFAARVNSAKALLYAIN

GGRDEMTGMQVIDKGVIDPIKPEADGTLDYEKVKANYEKALEWLSETYVMA

LNIIHYMHDKYAYESIEMALHDKEVYRTLGCGMSGLSIAADSLSACKYAKV

YPIYNKDAKTTPGHENEYVEGADDDLIVGYRTEGDFPLYGNDDDRADDIAK

WVVSTVMGQVKRLPVYRDAVPTQSILTITSNVEYGKATGAFPSGHKKGTPY

APGANPENGMDSHGMLPSMFSVGKIDYNDALDGISLTNTITPDGLGRDEEE

RIGNLVGILDAGNGHGLYHANINVLRKEQLEDAVEHPEKYPHLTVRVSGYA

VNFVKLTKEQQLDVISRTFHQGAVVD

To generate a recombinant yeast microorganism as described in this example, individual molecular components are integratively assembled.

1) The deletion of the FDH1 gene and replacement with two copies of ADH and two copies of PFL is illustrated in FIG. 35. The primers used to generate the molecular components of this integrative assembly are shown in FIG. 35, Table 16, and Table 26 (below).

TABLE 16

Primers used to generate the integrative assembly of FIG. 35. Each column indicates a PCR fragment that needs to be generated.

| Name | FDH15' Flank rc | pTPI-ADH-FBAt | ADHpPFKrc | PFL-pADH5 | PFL -pENORC | FDH13' Flank rc |
|---|---|---|---|---|---|---|
| Primers | X15559/X15565 | X15564/X14843 | X14844/X14835 | X14836/X14837 | X14838/X15567 | X15566/X15553 |
| Template | *S. ce* gDNA | pMU2746 | pMU2745 | pMU2770 | PMU2606 | *S. ce* gDNA |

2) The deletion of the FDH2 gene and replacement with two copies of ADH and two copies of PFL is illustrated in FIG. 36. The primers used to generate the molecular components of this integrative assembly are shown in FIG. 36, Table 17, and Table 26 (below).

TABLE 17

Primers used to generate the integrative assembly of FIG. 36. Each column indicates a PCR fragment that needs to be generated.

| Name | FDH2 5' Flank | FBA(t)-ADH1 | PFK-ADH2 | PFL-F | PFL-R | FDH2 3' Flank |
|---|---|---|---|---|---|---|
| Primers | X16096/X16097 | X16098/X14843 | X14844/X14835 | X14836/X14837 | X14838/X16099 | X16100/X11845 |
| Template | *S. ce* gDNA | pMU2746 | pMU2745 | pMU2770 | pMU2606 | *S. ce* gDNA |

3) The deletion of the GPD2 gene and replacement with two copies of ADH and two copies of PFL is illustrated in FIG. 37. The primers used to generate the molecular components of this integrative assembly are shown in FIG. 37, Table 18, and Table 26 (below).

TABLE 18

Primers used to generate the integrative assembly of FIG. 37. Each column indicates a PCR fragment that needs to be generated.

| Name | GPD2 5' flank | FBA(t)-ADH1 | PFK-ADH2 | PFL-F | PFL-R | GPD2 3' flank |
|---|---|---|---|---|---|---|
| Primers | X11816/X14847 | X14845/X14843 | X14844/X14835 | X14836/X14837 | X14838/X14849 | X14850/X11821 |
| Template | *S. ce* gDNA | YCL150 | YCL149 | pMU2770 | pMU2760 | *S. ce* gDNA |

4) The deletion of the GPD1 gene and replacement with two copies of ADH and two copies of PFL is illustrated in FIG. 38. The primers used to generate the molecular components of this integrative assembly are shown in FIG. 38, Table 19, and Table 26 (below).

TABLE 19

Primers used to generate the integrative assembly of FIG. 38. Each column indicates a PCR fragment that needs to be generated.

| Name | GPD1 5' flank | FBA(t)-ADH1 | PFK-ADH2 | PFL-F | PFL-R | GPD1 3' flank |
|---|---|---|---|---|---|---|
| Primers | X11824/X14776 | X14775/X14843 | X14844/X14835 | X14836/X14837 | X14838/X14829 | X14778/X11829 |
| Template | *S. ce* gDNA | pMU2746 | pMU2745 | pMU2770 | pMU2606 | *S. ce* gDNA |

5) The deletion of the PDC5 gene and replacement with a counter selective gene HSV-TDK and an antibiotic marker (Kan) is illustrated in FIG. 39. The primers used to generate the molecular components of this integrative assembly are shown in FIG. 39, Table 20, and Table 26 (below).

TABLE 20

Primers used to generate the integrative assembly of FIG. 39. Each column indicates a PCR fragment that needs to be generated.

| Name | PDC5 5' Flank | KNT | PDC5 3' Flank |
|---|---|---|---|
| Primers | X16463/X16464 | X16467/X16468 | X16465/X16466 |
| Template | *S. ce* gDNA | M2543/TB396 | *S. ce* gDNA |

6) The removal of the marker shown in FIG. 39 resulting in a clean deletion of the PDC5 gene is illustrated in FIG. 40. The primers used to generate the molecular components of this integrative assembly are shown in FIG. 40, Table 21, and Table 26 (below).

TABLE 21

Primers used to generate the integrative assembly of FIG. 40. Each column indicates a PCR fragment that needs to be generated.

| Name | PDC5 5' Flank | PDC5 3' Flank |
|---|---|---|
| Primers | X16463/X16495 | X16494/X16466 |
| Template | *S. ce* gDNA | *S. ce* gDNA |

7) The deletion of the PDC6 gene and replacement with a counter selective gene HSV-TDK and an antibiotic marker (Kan) is illustrated in FIG. 41. The primers used to generate the molecular components of this integrative assembly are shown in FIG. 41, Table 22, and Table 26 (below).

TABLE 22

Primers used to generate the integrative assembly of FIG. 41. Each column indicates a PCR fragment that needs to be generated.

| Name | PDC6 5' Flank | KNT | PDC6 3' Flank |
|---|---|---|---|
| Primers | X16471/X16472 | X16475/X16476 | X16473/X16474 |
| Template | *S. ce* gDNA | M2543/TB396 | *S. ce* gDNA |

8) The removal of the marker shown in FIG. 41 resulting in a clean deletion of the PDC6 gene is illustrated in FIG. 42. The primers used to generate the molecular components of this integrative assembly are shown in FIG. 42, Table 23, and Table 26 (below).

TABLE 23

Primers used to generate the integrative assembly of FIG. 42. Each column indicates a PCR fragment that needs to be generated.

| Name | PDC6 5' Flank | PDC6 3' Flank |
|---|---|---|
| Primers | X16471/X16497 | X16496/X16474 |
| Template | *S. ce* gDNA | *S. ce* gDNA |

9) The deletion of the PDC1 gene and replacement with a counter selective gene HSV-TDK and an antibiotic marker (Kan) is illustrated in FIG. 43. The primers used to generate the molecular components of this integrative assembly are shown in FIG. 43, Table 24, and Table 26 (below).

TABLE 24

Primers used to generate the integrative assembly of FIG. 43. Each column indicates a PCR fragment that needs to be generated.

| Name | PDC1 5' Flank | KNT | PDC1 3' Flank |
|---|---|---|---|
| Primers | X16951/X16952 | X16953/X16954 | X16955/X16956 |
| Template | *S. ce* gDNA | M2543/TB396 | *S. ce* gDNA |

10) The removal of the marker shown in FIG. 43 resulting in a clean deletion of the PDC1 gene is illustrated in FIG. 44.

The primers used to generate the molecular components of this integrative assembly are shown in FIG. 44, Table 25, and Table 26 (below).

TABLE 25

Primers used to generate the integrative assembly of FIG. 44. Each column indicates a PCR fragment that needs to be generated.

| Name | PDC1 5' Flank | PDC1 3' Flank |
|---|---|---|
| Primers | X16952/X16953 | X16954/X16955 |
| Template | *S. ce* gDNA | *S. ce* gDNA |

TABLE 26

Primer sequences used to create the integrative assemblies illustrated in FIG. 35-44.

| Primer # | SEQ ID NO. | Primer sequence |
|---|---|---|
| X11316 | 212 | GTAATACATCACCTCGATGAAAGAGA |
| X11816 | 213 | GCAGTCATCAGGATCGTAGGAGATAAGCA |
| X11821 | 214 | TCACAAGAGTGTGCAGAAATAGGAGGTGGA |
| X11822 | 215 | GTTGGGGGAAAAAGAGGCAACAGGAAAGATCAGAGACAGCAA GCATTGATAAGGAAGGG |
| X11823 | 216 | CCCTTCCTTATCAATGCTTGCTGTCTCTGATCTTTCCTGTTGCCTC TTTTTCCCCCAAC |
| X11824 | 217 | AAGCCTACAGGCGCAAGATAACACATCAC |
| X11829 | 218 | CTCAGCATTGATCTTAGCAGATTCAGGATCTAGGT |
| X11830 | 219 | TATGTTATCTTTCTCCAATAAATCTAATCTTCATGTAGACTATCA GCAGCAGCAGACAT |
| X11831 | 220 | GATAATATAAAGATGTCTGCTGCTGCTGATAGTCTACATGAAGA TTAGATTTATTGGAG |
| X11845 | 221 | TTACTTGTGAAACTGTCTCCGCTATGTCAG |
| X14775 | 222 | CCCCCTCCACAAACACAAATATTGATAATATAAAGATGGCAGAC GCAAAGAAGAAGGAA |
| X14778 | 223 | ATTTATTGGAGAAAGATAACATATCATACTTTCC |
| X14829 | 224 | GAAAGTATGATATGTTATCTTTCTCCAATAAATCTAGTCTTCTAG GCGGGTTATCTACT |
| X14835 | 225 | CAAATTCTAACCAACTTCAAAATGACATAGTACCTCATCTATAA TTTTTACCCTGATCT |
| X14836 | 226 | AGTTAGATCAGGGTAAAAATTATAGATGAGGTACTATGTCATTT TGAAGTTGGTTAGAA |
| X14837 | 227 | GGTCCATGTAAAATGATTGCTCCAATGATTGAAATTGATTCAGG TCAAAATGGATTCAG |
| X14838 | 228 | ACGTCCCTGAATCCATTTTGACCTGAATCAATTTCAATCATTGGA GCAATCATTTTACA |
| X14843 | 229 | GGTGGAACCATTTACTGTATTTTCAATGTAACGCTAGAGAATAA ATTCAAGTTAAAAGA |
| X14844 | 230 | CATCATCTTTTAACTTGAATTTATTCTCTAGCGTTACATTGAAAA TACAGTAAATGGTT |
| X15380 | 231 | TAGGTCTAGAGATCTGTTTAGCTTGC |
| X15382 | 232 | GAGACTACATGATAGTCCAAAGA |
| X15546 | 233 | GGACGAGGCAAGCTAAACAGATCTCTAGACCTACTTTATATTAT CAATATTTGTGTTTG |

TABLE 26-continued

Primer sequences used to create the integrative assemblies illustrated in FIG. 35-44.

| Primer # | SEQ ID NO. | Primer sequence |
|---|---|---|
| X15547 | 234 | CCGTTTCTTTTCTTTGGACTATCATGTAGTCTCATTTATTGGAGA AAGATAACATATCA |
| X15548 | 235 | GGACGAGGCAAGCTAAACAGATCTCTAGACCTATGATAAGGAA GGGGAGCGAAGGAAAA |
| X15549 | 236 | CCGTTTCTTTTCTTTGGACTATCATGTAGTCTCCTCTGATCTTTCC TGTTGCCTCTTTT |
| X15552 | 237 | CCGTTTCTTTTCTTTGGACTATCATGTAGTCTCGAGTGATTATGA GTATTTGTGAGCAG |
| X15553 | 238 | ACCAGCGTCTGGTGGACAAACGGCCTTCAAC |
| X15554 | 239 | GGACGAGGCAAGCTAAACAGATCTCTAGACCTAATTAATTTTCA GCTGTTATTTCGATT |
| X15555 | 240 | CCGTTTCTTTTCTTTGGACTATCATGTAGTCTCGAGTGATTATGA GTATTTGTGAGCAG |
| X15559 | 241 | GGAAGGCACCGATACTAGAACTCCG |
| X15564 | 242 | CTAATCAAATCAAAATAACAGCTGAAAATTAATCTACTTATTCC CTTCGAGATTATATC |
| X15565 | 243 | GTTCCTAGATATAATCTCGAAGGGAATAAGTAGATTAATTTTCA GCTGTTATTTTGATT |
| X15566 | 244 | TCGGATCAGTAGATAACCCGCCTAGAAGACTAGGAGTGATTATG AGTATTTGTGAGCAG |
| X15567 | 245 | AAAACTTCTGCTCACAAATACTCATAATCACTCCTAGTCTTCTAG GCGGGTTATCTACT |
| X15870 | 246 | CTAATCAAATCAAAATAACAGCTGAAAATTAATGAGTGATTATG AGTATTTGTGAGCAG |
| X15871 | 247 | AAAACTTCTGCTCACAAATACTCATAATCACTCATTAATTTTCAG CTGTTATTTGATT |
| X16096 | 248 | CATGGTGCTTAGCAGCAGATGAAAGTGTCA |
| X16097 | 249 | GTTCCTAGATATAATCTCGAAGGGAATAAGTAGATTAATTTTCA GCTGTTATTTCGATT |
| X16098 | 250 | CTAATCAAATCGAAATAACAGCTGAAAATTAATCTACTTATTCC CTTCGAGATTATATC |
| X16099 | 251 | AAAACTTCTGCTCACAAATACTCATAATCACTCCTAGTCTTCTAG GCGGGTTATCTACT |
| X16100 | 252 | TCGGATCAGTAGATAACCCGCCTAGAAGACTAGGAGTGATTATG AGTATTTGTGAGCAG |
| X16463 | 253 | CAGAGTTTGAAGATATCCAAATGGT |
| X16464 | 254 | TTTGTTCTTCTTGTTATTGTATTGTGTTG |
| X16465 | 255 | GCTAATTAACATAAAACTCATGATTCAACG |
| X16466 | 256 | ACATAGGTTTGCAAGCTTTATAATCTG |
| X16467 | 257 | AGAACAACACAATACAATAACAAGAAGAACAAATAGGTCTAGA GATCTGTTTAGCTTGC |
| X16468 | 258 | AAACGTTGAATCATGAGTTTTATGTTAATTAGCGAGACTACATG ATAGTCCAAAGAAAA |
| X16469 | 259 | AGAACAACACAATACAATAACAAGAAGAACAAACTACTTATTC CCTTCGAGATTATATC |
| X16470 | 260 | AAACGTTGAATCATGAGTTTTATGTTAATTAGCCTAGTCTTCTAG GCGGGTTATCTACT |

TABLE 26-continued

Primer sequences used to create the integrative assemblies illustrated in FIG. 35-44.

| Primer # | SEQ ID NO. | Primer sequence |
|---|---|---|
| X16471 | 261 | AAGAATCTGTTAGTTCGAACTCCAG |
| X16472 | 262 | TTTGTTGGCAATATGTTTTTGCTATATTAC |
| X16473 | 263 | GCCATTAGTAGTGTACTCAAACGAA |
| X16474 | 264 | ACGACTCAACATATGTATGTTGCT |
| X16475 | 265 | CACGTAATATAGCAAAAACATATTGCCAACAAATAGGTCTAGA GATCTGTTTAGCTTGC |
| X16476 | 266 | AACAATAATTCGTTTGAGTACACTACTAATGGCGAGACTACATG ATAGTCCAAAGAAAA |
| X16477 | 267 | CACGTAATATAGCAAAAACATATTGCCAACAAACTACTTATTCC CTTCGAGATTATATC |
| X16478 | 268 | AACAATAATTCGTTTGAGTACACTACTAATGGCCTAGTCTTCTA GGCGGGTTATCTACT |
| X16951 | 269 | ATGTTCCGCTGATGTGATGTGCAAGATAAAC |
| X16952 | 270 | GAGGCAAGCTAAACAGATCTCTAGACCTATTTGATTGATTTGAC TGTGTTATTTTGCGT |
| X16953 | 271 | ATAACCTCACGCAAAATAACACAGTCAAATCAATCAAATAGGT CTAGAGATCTGTTTAG |
| X16954 | 272 | AAAACTTTAACTAATAATTAGAGATTAAATCGCTTAGAGACTAC ATGATAGTCCAAAGA |
| X16955 | 273 | GTCCCCCCGTTTCTTTTCTTTGGACTATCATGTAGTCTCTAAGCG ATTTAATCTCTAAT |
| X16956 | 274 | TCGGTCATTGGGTGAGTTTAAGCATTAGCAGCAATG |
| X16957 | 275 | TAAAACTTTAACTAATAATTAGAGATTAAATCGCTTATTTGATT GATTTGACTGTGTTA |
| X16958 | 276 | CACGCAAAATAACACAGTCAAATCAATCAAATAAGCGATTTAA TCTCTAATTATTAGTT |

Heterologous genes for the production of a transcarboxylase based palmitic acid pathway (FIG. 34C) can then be introduced in a yeast microorganism engineered using the above integrative assemblies to replace GPD1, GPD2, FDH1, and FDH2 with two copies of a bifunctional alcohol/aldehyde dehydrogenase and two copies of a pyruvate formate lyase and to delete PDC5, PDC6, and PDC1. Such heterologous genes include, but are not limited to, *S. cerevisiae* NAD+ FDH1 to create the metabolic pathway in (FIG. 34B) and *B. stabilis* NADP+ FDH, *S. cerevisiae* PCK1, *P. freudenreichii* Transcarboxylase (see SEQ ID NOs:6-16), *A. thaliana* FATB1 to create the metabolic pathway in (FIG. 34C). Additional enzymes are identified in PCT/US2011/035416, which is incorporated by reference herein in its entirety. The pathways described herein can be engineered for production of a malonyl-CoA derived product in the yeast cytosol.

>SceNAD+_FDH1

(SEQ ID NO: 277)

atgtcgaagggaaaggttttgctggttctttacgaaggtggtaagcatgctgaagagcagg aaaagttattggggtgtattgaaaatgaacttggtatcagaaatttcattgaagaacaggg atacgagttggttactaccattgacaaggaccctgagccaacctcaacggtagacaggga g ttgaaagacgctgaaattgtcattactacgcccttttttccccgcctacatctcgagaaaca ggattgcagaagctcctaacctgaagctctgtgtaaccgctggcgtcggttcagaccatgt cgatttagaagctgcaaatgaacggaaaatcacggtcaccgaagttactggttctaacgtc gtttctgtcgcagagcacgttatggccacaattttggttttgataagaaactataatggtg gtcatcaacaagcaattaatggtgagtgggatattgccggcgtggctaaaaatgagtatga -continued tctggaagacaaaataatttcaacggtaggtgccggtagaattggatatagggttctggaa agattggtcgcatttaatccgaagaagttactgtactacgactaccaggaactacctgcgg aagcaatcaatagattgaacgaggccagcaagcttttcaatggcagaggtgatattgttca gagagtagagaaattggaggatatggttgctcagtcagatgttgttaccatcaactgtcca ttgcacaaggactcaaggggtttattcaataaaaagcttatttcccacatgaaagatggtg catacttggtgaataccgctagaggtgctatttgtgtcgcagaagatgttgccgaggcagt caagtctggtaaattggctggctatggtggtgatgtctgggataagcaaccagcaccaaaa gaccatccctggaggactatggacaataaggaccacgtgggaaacgcaatgactgttcata tcagtggcacatctctggatgctcaaaagaggtacgctcagggagtaaagaacatcctaaa tagttacttttccaaaaagtttgattaccgtccacaggatattattgtgcagaatggttct tatgccaccagagcttatggacagaagaaa >SceNAD+_FDH1

(SEQ ID NO: 278)

MSKGKVLLVLYEGGKHAEEQEKLLGCIENELGIRNFIEEQGYELVTTIDKDPEPTSTVDRE

LKDAEIVITTPFFPAYISRNRIAEAPNLKLCVTAGVGSDHVDLEAANERKITVTEVTGSNV

VSVAEHVMATILVLIRNYNGGHQQAINGEWDIAGVAKNEYDLEDKIISTVGAGRIGYRVLE

RLVAFNPKKLLYYDYQELPAEAINRLNEASKLFNGRGDIVQRVEKLEDMVAQSDVVTINCP

LHKDSRGLFNKKLISHMKDGAYLVNTARGAICVAEDVAEAVKSGKLAGYGGDVWDKQPAPK

DHPWRTMDNKDHVGNAMTVHISGTSLDAQKRYAQGVKNILNSYFSKKFDYRPQDIIVQNGS

YATRAYGQKK

>BstabilisNADP+_FDH (SEQ ID NO: 279)

atggctaccgttttgtgtgtcttgtatccagatccagttgatggttatccaccacattatg ttagagataccattccagttattaccagatacgctgatggtcaaactgctccaactccagc tggtccaccaggttttagaccaggtgaattggttggttctgtttctggtgctttgggtttg agaggttatttggaagctcatggtcatactttgatcgttacctctgataaggatggtccag attctgaattcgaaagaagattgccagacgccgatgttgttatttctcaaccattttggcc agcttacttgaccgctgaaagaattgctagagcaccaaaattgagattggctttgactgct ggtattggttctgatcatgttgatttggatgctgctgctagagcccatattactgttgctg aagttactggttccaactctatttcagttgccgaacacgttgttatgactactttggcttt ggtcagaaactacttgccatctcatgctattgctcaacaaggtggttggaatattgctgat tgtgtctctagatcctacgatgttgaaggtatgcattttggtactgttggtgctggtagaa ttggtttggctgttttgagaagattgaagccatttggtttacacttgcactacacccaaag acatagattggatgcagctatcgaacaagaattgggtttaacttatcatgctgatccagct tcattggctgctgctgttgatatagttaacttgcaaatcccattatacccatccaccgaac atttgtttgatgctgctatgattgctagaatgaagagaggtgcatacttgattaacaccgc tagagctaaattggttgatagagatgctgttgttagagctgttacttctggtcatttggct ggttatggtggtgatgtttggtttccacaaccagctccagctgatcatccttggagagcta tgccttttaatggtatgactccacatatctccggtacatctttgtctgctcaagctagata tgctgctggtactttggaaatattgcaatgttggtttgacggtagaccaatcagaaacgaa tatttgattgtcgacggtggtactttagctggtactggtgctcaatcttacagattaact -continued >BstabilisNADP+_FDH (SEQ ID NO: 280)

MATVLCVLYPDPVDGYPPHYVRDTIPVITRYADGQTAPTPAGPPGFRPGELVGSVSGALGL

RGYLEAHGHTLIVTSDKDGPDSEFERRLPDADVVISQPFWPAYLTAERIARAPKLRLALTA

GIGSDHVDLDAAARAHITVAEVTGSNSISVAEHVVMTTLALVRNYLPSHAIAQQGGWNIAD

CVSRSYDVEGMHFGTVGAGRIGLAVLRRLKPFGLHLHYTQRHRLDAAIEQELGLTYHADPA

SLAAAVDIVNLQIPLYPSTEHLFDAAMIARMKRGAYLINTARAKLVDRDAVVRAVTSGHLA

GYGGDVWFPQPAPADHPWRAMPFNGMTPHISGTSLSAQARYAAGTLEILQCWFDGRPIRNE

YLIVDGGTLAGTGAQSYRLT

>ScePCK1

(SEQ ID NO: 281)

atgtccccttctaaaatgaatgctacagtaggatctacttccgaagttgaacaaaaaatca gacaagaattggctcttagtgacgaagtcaccaccatcagacgcaatgctccagctgccgt tttgtatgaagatggtctaaaagaaaataaaactgtcatttcatcaagcggtgcattgatc gcttattccggtgrtaaaaccggaagatctccaaaggacaaacgtattgttgaagaaccta cctcgaaagacgaaatttggtggggtccggtcaataaaccatgttctgaaagaacatggtc tatcaaccgtgaaagagctgcagattacttgagaacaagagaccacatttatattgtcgat gcatttgcaggatgggatccaaaatacagaatcaaagtccgcgttgtttgtgccagggctt accacgctttattcatgacaaatatgcttattagacctacagaagaagaattagcccattt tggagaacctgattttactgtctggaacgctggtcagttcccagccaatttacacacccag gatatgtcttcaaagagtactatagaaattaacttcaaagcaatggaaatgatcattttag gtaccgaatacgccggtgaaatgaaaaaaggtattttcacagttatgttttacttgatgcc tgtgcaccataacgttttaactttgcactcttccgccaaccagggtattcaaaacggtgac gttactttattctttggcctaagtggtaccgggaaaaccactttatccgcagacccacata gattgttgatcggcgatgatgaacattgttggtccgaccatggtgtcttcaatatcgaagg tggttgttacgccaagtgtattaatttatctgccgaaaaggagcctgaaattttcgacgct atcaagtttggttctgtattagaaaacgttatctatgacgagaagtcgcatgtagtcgact atgacgactcttctattactgaaaatactagatgtgcctacccaattgactacattccaag tgccaagattccatgtttggcggactctcatccaaagaacattatcctgctaacttgtgat gcttcgggtgttttaccaccagtatctaaattgactcctgaacaagtcatgtaccatttca tctctggttacacttctaaaatggctggtactgagcaaggtgtcactgaacctgaaccaac attttcatcttgtttcggacaacccttcctagccttgcaccctattagatacgcaaccatg ttagctacaaagatgtctcaacataaagctaatgcgtacttaatcaacaccggctggactg gttcttcctacgtatctggtggtaaacgttgcccattgaagtacacaagggccattctgga ttctattcatgatggttcgttagccaatgaaacgtacgaaactttaccgattttcaatctt caagtacctaccaaggttaacggtgttccagctgagcttttgaatcctgctaaaaactggt ctcaaggtgaatccaaatacagaggtgcagttaccaacttggccaacttgtttgttcaaaa tttcaagatttatcaagacagagccacaccagatgtattagccgctggtcctcaattcgag >ScePCK1

(SEQ ID NO: 282)

MSPSKMNATVGSTSEVEQKIRQELALSDEVTTIRRNAPAAVLYEDGLKENKTVISSSGALI

AYSGVKTGRSPKDKRIVEEPTSKDEIWWGPVNKPCSERTWSINRERAADYLRTRDHIYIVD

AFAGWDPKYRIKVRVVCARAYHALFMTNMLIRPTEEELAHFGEPDFTVWNAGQFPANLHTQ

-continued

DMSSKSTIEINFKAMEMIILGTEYAGEMKKGIFTVMFYLMPVHHNVLTLHSSANQGIQNGD

VTLFFGLSGTGKTTLSADPHRLLIGDDEHCWSDHGVFNIEGGCYAKCINLSAEKEPEIFDA

IKFGSVLENVIYDEKSHVVDYDDSSITENTRCAYPIDYIPSAKIPCLADSHPKNIILLTCD

ASGVLPPVSKLTPEQVMYHFISGYTSKMAGTEQGVTEPEPTFSSCFGQPFLALHPIRYATM

LATKMSQHKANAYLINTGWTGSSYVSGGKRCPLKYTRAILDSIHDGSLANETYETLPIFNL

QVPTKVNGVPAELLNPAKNWSQGESKYRGAVTNLANLFVQNFKIYQDRATPDVLAAGPQFE

>Ath_FATB1_mature_peptide (SEQ ID NO: 283)

atgcttgattggaaacctaggcgttctgacatgctggtggatccttttggtatagggagaa ttgttcaggatggccttgtgttccgtcagaatttttctattaggtcatatgaaataggtgc tgatcgctctgcatctatagaaaccgtcatgaatcatctgcaggaaacggcgcttaatcat gttaagactgctggattgcttggagatgggtttggctctacacctgagatgtttaagaaga acttgatatgggttgtcactcgtatgcaggttgtggttgataaatatcctacttggggaga tgttgttgaagtagacacctgggtcagtcaatctggaaagaatggtatgcgtcgtgattgg ctagttcgggattgtaatactggagaaaccttaacacgagcatcaagtgtgtgggtgatga tgaataaactgacaaggagattgtcaaagattcctgttagaggttcgaggggaaatagagc cttattttgtgaattctgatcctgtccttgccgaggacagcagaaagttaacaaaaattga tgacaagactgctgactatgttcgatctggtctcactcctcgatggagtgacctagatgtt aaccagcatgtgaataatgtaaagtacattgggtggatcctggagagtgctccagtgggaa taatggagaggcagaagctgaaaagcatgactctggagtatcggagggaatgcgggagaga cagtgtgcttcagtccctcactgcagttacgggttgcgatatcggtaacctggcaacagcg ggggatgtggaatgtcagcatttgctccgactccaggatggagcggaagtggtgagaggaa gaacagagtggagtagtaaaacaccaacaacaacttggggaactgcaccg >Ath_FATB1_mature_peptide (SEQ ID NO: 284)

MLDWKPRRSDMLVDPFGIGRIVQDGLVFRQNFSIRSYEIGADRSASIETVMNHLQETALNH

VKTAGLLGDGFGSTPEMFKKNLIWVVTRMQVVVDKYPTWGDVVEVDTWVSQSGKNGMRRDW

LVRDCNTGETLTRASSVWVMMNKLTRRLSKIPEEVRGEIEPYFVNSDPVLAEDSRKLTKID

DKTADYVRSGLTPRWSDLDYNQHVNNVKYIGWILESAPVGIMERQKLKSMTLEYRRECGRD

SVLQSLTAVTGCDIGNLATAGDVECQHLLRLQDGAEVVRGRTEWSSKTPTTTWGTAP

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant yeast microorganism comprising one or more engineered metabolic pathways to convert a carbohydrate source to ethanol and a malonyl-CoA derived product, wherein the one or more engineered metabolic pathways comprises (a) the conversion of phosphoenolpyruvate to oxaloacetate by a phosphoenolpyruvate carboxykinase and (b) the conversion of oxaloacetate and acetyl-CoA to malonyl-CoA and pyruvate by a heterologous transcarboxylase Enzyme Commission Number 2.1.3.1; wherein the one or more engineered metabolic pathways further comprises heterologous pyruvate formate lyase.

2. The recombinant yeast microorganism of claim 1, wherein the conversion of a carbohydrate source to a malonyl-CoA derived product is under anaerobic or microaerophilic conditions.

3. The recombinant yeast microorganism of claim 1, wherein at least one of said engineered metabolic pathways produces net ATP.

4. The recombinant yeast microorganism of claim 1, wherein said product is a polyketide or an organic acid.

5. The recombinant yeast microorganism of claim 4, wherein said polyketide is an antibiotic, antitumor, antifungal, or immunosuppressive.

6. The recombinant yeast microorganism of claim 4, wherein said organic acid is 3-hydroxypropionic acid.

7. The recombinant yeast microorganism of claim 6, wherein one of said engineered metabolic pathways comprises the following steps: (a) conversion of malonyl-CoA to malonate semialdehyde and coA; and (b) conversion of malonate semialdehyde to 3-hydroxypropanoate.

8. The recombinant yeast microorganism of claim 7, wherein said malonyl-CoA is converted to malonate semialdehyde and coA by a malonyl-CoA reductase.

9. The recombinant yeast microorganism of claim 8, wherein said malonyl-CoA reductase is encoded by a polynucleotide from a *C. aurantiacus*.

10. The recombinant yeast microorganism of claim 7, wherein said malonate semialdehyde is converted to 3-hydroxypropanoate by a 3-hydroxypropionate dehydrogenase.

11. The recombinant yeast microorganism of claim 7, wherein said malonyl-CoA is converted to 3-hydroxypropanoate by a bifunctional dehydrogenase.

12. The recombinant yeast microorganism of claim 4, wherein said organic acid is adipic acid.

13. The recombinant yeast microorganism of claim 1, wherein said carbohydrate source is a lignocellulosic material.

14. The recombinant yeast microorganism of claim 1, wherein one of said engineered metabolic pathways further comprises the conversion of pyruvate and CoA-SH into acetyl-CoA and $CO_2$ and NAD(P)H.

15. The recombinant yeast microorganism of claim 1, wherein said phosphoenolpyruvate carboxykinase is encoded by a polynucleotide from a *Thermoanaerobacter* species, *E. coli, S. cerevisiae*, or *C. thermocellum.*

16. The recombinant yeast microorganism of claim 1, wherein the one or more engineered metabolic pathways further comprises downregulation or deletion of native enzymes selected from the group consisting of: (a) a pyruvate carboxykinase; (b) a hydrogenase; (c) a lactate dehydrogenase; (d) a phosphotransacetylase; (e) an acetate kinase; (f) an acetaldehyde dehydrogenase; (g) an alcohol dehydrogenase; (h) an enzyme involved in degradation of fatty acids and their derivatives; and (i) combinations of (a)-(h).

17. The recombinant yeast microorganism of claim 1, wherein the one or more engineered metabolic pathways further comprises downregulation or deletion of native enzymes selected from the group consisting of: (a) a lactate dehydrogenase; (b) a phosphate acetyltransferase; (c) an acetaldehyde dehydrogenase/alcohol dehydrogenase; (d) a pyruvate carboxykinase; (e) a malate dehydrogenase; (f) a PEP-protein phosphotransferase of PTS system; and (g) combinations of (a)-(f).

18. An engineered metabolic pathway for producing a malonyl-CoA derived product in a consolidated bioprocessing (CBP) organism according to claim 1.

19. The recombinant yeast microorganism of claim 1, wherein the conversion of a carbohydrate source to a malonyl-CoA derived product is redox neutral.

20. The recombinant yeast microorganism of claim 1, wherein one of said engineered metabolic pathways further comprises one or more formate dehydrogenases capable of converting formate to $CO_2$ and NAD(P)H.

21. The recombinant yeast microorganism of claim 20, wherein said formate dehydrogenase is encoded by an *S. cerevisiae* NAD+FDH1, a *B. stabilis* NADP+FDH, or both.

22. The recombinant yeast microorganism of claim 1, wherein one of said engineered metabolic pathways further comprises an enzyme encoding a palmitoyl-acyl carrier protein thioesterase (FatB1).

23. The recombinant yeast microorganism of claim 22, wherein said palmitoyl-acyl carrier protein thioesterase (FatB1) is from *A. thaliana.*

24. The recombinant yeast microorganism of claim 1, wherein the one or more engineered metabolic pathways further comprises downregulation or deletion of native enzymes selected from a glycerol-3-phosphate dehydrogenase 1 (GPD1), a glycerol-3-phosphate dehydrogenase 2 (GPD2), a formate dehydrogenase 1 (FDH1), a formate dehydrogenase 2 (FDH2), or a combination thereof.

25. The recombinant yeast microorganism of claim 24, wherein said native enzyme is downregulated or deleted by insertion of a heterologous enzyme at the locus of the native enzyme.

26. The recombinant yeast microorganism of claim 1, wherein said heterologous pyruvate formate lyase enzyme is a pyruvate formate lyase A (PFLA), a pyruvate formate lyase B (PFLB), or a combination thereof.

27. The recombinant yeast microorganism of claim 1, wherein said yeast microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida* utliis, *Arxula adeninivorans, Pichia stipitis, Debaryomyces* hansenit, *Debaryomyces polymorphus, Schizosaccharomyces pombe, Candida albicans*, and *Schwanniomyces occidentalis.*

* * * * *

SEQUENCE LISTING

<160> NUMBER OF SEQ ID NOS: 301

<210> SEQ ID NO 1
<211> LENGTH: 1220
<212> TYPE: PRT

<213> ORGANISM: C. aurantiacus

<400> SEQUENCE: 1

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Gly
    370                 375                 380

Ala Gly Glu Asn Thr Gly Gly Ile His Ala Ala Val Ile Leu Pro Ala
385                 390                 395                 400
```

-continued

```
Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
        435                 440                 445

Arg Ala Arg Gly Pro Arg Val Ile Phe Leu Ser Asn Gly Ala Asp Gln
    450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
        675                 680                 685

Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
    770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Ala Arg Thr Asp Glu Arg Ser Met
                805                 810                 815

His Glu Leu Val Glu Leu Leu Leu Pro Asn Asp Val Ala Ala Leu Glu
```

-continued

```
            820                 825                 830

Gln Asn Pro Ala Ala Pro Thr Ala Leu Arg Glu Leu Ala Arg Arg Phe
        835                 840                 845

Arg Ser Glu Gly Asp Pro Ala Ala Ser Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
        915                 920                 925

Val Ala Met Ala Thr Val Tyr Tyr Leu Ala Asp Arg Asn Val Ser Gly
    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu  Glu Arg Tyr Gly Ala  Arg Gln Val
        995                 1000                1005

Val Met  Ile Val Glu Thr Glu  Thr Gly Ala Glu Thr  Met Arg Arg
    1010                1015                1020

Leu Leu  His Asp His Val Glu  Ala Gly Arg Leu Met  Thr Ile Val
    1025                1030                1035

Ala Gly  Asp Gln Ile Glu Ala  Ala Ile Asp Gln Ala  Ile Thr Arg
    1040                1045                1050

Tyr Gly  Arg Pro Gly Pro Val  Val Cys Thr Pro Phe  Arg Pro Leu
    1055                1060                1065

Pro Thr  Val Pro Leu Val Gly  Arg Lys Asp Ser Asp  Trp Ser Thr
    1070                1075                1080

Val Leu  Ser Glu Ala Glu Phe  Ala Glu Leu Cys Glu  His Gln Leu
    1085                1090                1095

Thr His  His Phe Arg Val Ala  Arg Lys Ile Ala Leu  Ser Asp Gly
    1100                1105                1110

Ala Ser  Leu Ala Leu Val Thr  Pro Glu Thr Thr Ala  Thr Ser Thr
    1115                1120                1125

Thr Glu  Gln Phe Ala Leu Ala  Asn Phe Ile Lys Thr  Thr Leu His
    1130                1135                1140

Ala Phe  Thr Ala Thr Ile Gly  Val Glu Ser Glu Arg  Thr Ala Gln
    1145                1150                1155

Arg Ile  Leu Ile Asn Gln Val  Asp Leu Thr Arg Arg  Ala Arg Ala
    1160                1165                1170

Glu Glu  Pro Arg Asp Pro His  Glu Arg Gln Gln Glu  Leu Glu Arg
    1175                1180                1185

Phe Ile  Glu Ala Val Leu Leu  Val Thr Ala Pro Leu  Pro Pro Glu
    1190                1195                1200

Ala Asp  Thr Arg Tyr Ala Gly  Arg Ile His Arg Gly  Arg Ala Ile
    1205                1210                1215

Thr Val
    1220
```

<210> SEQ ID NO 2
<211> LENGTH: 1818
<212> TYPE: DNA
<213> ORGANISM: C. thermocellum

<400> SEQUENCE: 2
atgacatcaa caaacatgac aaaaaacaaa aaactgctgg attgggttaa ggaaatggct 60
gaaatgtgtc agcctgatga aatttattgg tgcgatggtt cggaggaaga aaatgagcgc 120
ttgataaagt tgatggtgga ttcaggtttg gctacgcctt tgaatcctga aaagcgacct 180
ggatgttatc tcttccgcag cgatccgtcc gacgttgccc gtgttgagga cagaactttt 240
attgcatcca aaaccaaaga agatgcagga cctacaaaca actggataga tccggttgag 300
ctcaaggcaa ctatgaaaga gttgtacaag ggttgtatga agggaagaac aatgtatgtt 360
attcctttct ccatgggacc tatcggttca cccatttcaa aaatcggcgt tgaattgacc 420
gacagccctt atgttgttgt taacatgcgc attatgactc gcataggcaa ggctgtgttg 480
gatcagctcg gagaagacgg agattttgta ccttgtctcc actcagtcgg tgctccgctc 540
aaagagggag aaaaggataa aggttggcca tgcgcaccaa tcgaaaagaa atacataagc 600
cacttcccgg aagaaaggac tatatggtca tatggttccg gatacggtgg aaatgcgctt 660
ttaggaaaga aatgctttgc acttcgtatt gcatctgtta tggcacgtga cgaaggttgg 720
cttgctgaac acatgcttat ccttcgcata acagaccctg aaggaaacaa gacatatgtt 780
acaggtgctt tcccaagcgc atgcggaaag acgaacctgg ctatgcttat tcctacaatt 840
cccggatgga aagttgaaac aatcggtgac gatattgcat ggatgagatt tggaaaagac 900
ggccgtttgt atgctatcaa ccctgaagca ggattctttg gtgttgctcc gggtacatcc 960
atggattcaa atccgaacgc aatgcataca attaagaaaa atactatatt tacaaacgtt 1020
gcattgactg atgacggcga tgtttggtgg gaaggcatcg gaactgaacc gccggctcat 1080
ctcatagact ggcagggtaa agactggact cctgattccg gaactttggc agcacatccc 1140
aacggacgtt ttacagcacc tgcaagtcag tgccctgtaa ttgctcctga atgggaggat 1200
ccggaaggtg tgccgatttc agcaatcctt atcggtggac gccgtccgaa caccattccg 1260
cttgttcatg aaagctttga ctggaaccat ggtgtattca tgggttcaat catgggttct 1320
gaaattacgg ctgccgcaat ttcaaacaaa atcggacagg tacgccgtga cccgtttgct 1380
atgctgcctt tcataggcta caacgtaaat gactatttgc agcactggtt gaacatgggt 1440
accaagactg acccaagcaa gcttcccaag atattctatg taaactggtt ccgcaaggac 1500
agcaacggta aatggttgtg gcctggatac ggtgaaaaca gccgtgttct caagtggatt 1560
gttgaaagag tcaacggaaa aggtaaagca gtaaagacac ctataggata tatgcctaca 1620
gttgacgcta tcgacacaac cggccttgat gtaagcaaag aggatatgga agaactcttg 1680
agcgttaaca aagaacagtg gctccaggaa gttgagtcaa taaaagaaca ttataagtca 1740
tacggagaaa aactgccgaa agaattgtgg gcacaattgg aggctcttga acaacgtttg 1800
aaagagtata acggttaa 1818

<210> SEQ ID NO 3
<211> LENGTH: 1632
<212> TYPE: DNA
<213> ORGANISM: T. saccharolyticum

<400> SEQUENCE: 3

-continued

```
atgattatga aaaaatcaaa gaaatgtttc aatctgaata ttgacgacaa agaaaccttg      60
aatacttttg gaagttcgag aggagaattg tttatgatag atttagatga tgtatttaaa     120
aattctggca gtattcttta caatttacct gtttcagatt tgatagagga agccataaga     180
aataatgaag ggaaattgtt agaaaatggt gcattagatg tttttacagg taaatatacg     240
ggaagaatac caaaagataa atacattgta aatgaagaat ctattcataa tgatatttgg     300
tgggaaaata ataattcaat ggaaaaagaa aattttatta gagttttaaa cagagtaatt     360
gattatttaa aaaagagcag aaaattgtat gtttttaaag gttttgttgg cgcagacccg     420
cgatatagat atcaagtaac cgttattaat gaatatgcct atcaaaacgc ttttgtacat     480
caattattta ttaatcctaa aaatgaagaa gaacttaaaa aggaatccga ttttacagtt     540
atttgtgtgc cgaatttttt agctgatcca atttatgatg gaactaattc tgaggcattt     600
attattataa gttttgaaga aaaattaatt ttaattggtg gaacaagata ttcaggagaa     660
ataaaaaaat ctgtcttcac aatgatgaat tatttgatgt taaaaaggaa tgtactgcct     720
atgcattgtg cagctaatat aggttccaat aatgatacag cgcttttttt tgggttgtcg     780
ggaaccggca agacaacttt atcaacggat ccagaaagat tttaattgg cgacgatgaa      840
catggatggt cttcacatgg aatttttaat tttgagggtg gatgctatgc aaagtgtata     900
aatttatccc catataatga acctgaaata tggaatgcaa ttagatttgg aacaatttta     960
gaaaatgtta tttatgatgt aaataatatg ccagtctata caagtagtaa aataactgaa    1020
aatacaagag cttcatatcc acttgagtac atccctagga aagcgtcaaa tggcattggc    1080
ggtaatccta aaattatatt tttcttggca gccgatgctt ttggagtatt gcctccaatt    1140
tctaagctga caaatgaaca ggctgttgac tatttcttat taggatatac gagcaaaata    1200
ccaggaacag aaaagggaat ttgcgaacca caagcaacgt tttcatcatg ttttggagca    1260
ccatttttgc catcatatcc aatgaggtat gctgaattgt taaagaaaaa aatcgcagaa    1320
aatgattcag ttgtttattt aataaatact ggatggatag gtggacatta tggaattggc    1380
aaaaggatag atttaaaata cacaagagaa atcataaaaa atgttttaaa tggtgaattg    1440
gaaaaagcaa aatttaaaaa agatacagta tttgatttga tgataccaga aaagtgcaat    1500
aacattccag atgaattatt agatcctata aaaacatggg aagacaaaaa tgattacttc    1560
caaactgcta ataatttatt atctgcattt aaagcgagat tagattatat aaaaaatggg    1620
attcatcaat aa                                                        1632
```

<210> SEQ ID NO 4
<211> LENGTH: 1623
<212> TYPE: DNA
<213> ORGANISM: E. coli

<400> SEQUENCE: 4

```
atgcgcgtta acaatggttt gaccccgcaa gaactcgagg cttatggtat cagtgacgta      60
catgatatcg tttacaaccc aagctacgac ctgctgtatc aggaagagct cgatccgagc     120
ctgacaggtt atgagcgcgg ggtgttaact aatctgggtg ccgttgccgt cgataccggg     180
atcttcaccg gtcgttcacc aaaagataag tatatcgtcc gtgacgatac cactcgcgat     240
actttctggt gggcagacaa aggcaaaggt aagaacgaca acaaacctct ctctccggaa     300
acctggcagc atctgaaagg cctggtgacc aggcagcttt ccggcaaacg tctgttcgtt     360
gtcgacgctt tctgtggtgc gaacccggat actcgtcttt ccgtccgttt catcaccgaa     420
gtggcctggc aggcgcattt tgtcaaaaac atgtttattc gcccgagcga tgaagaactg     480
```

```
gcaggtttca aaccagactt tatcgttatg aacggcgcga agtgcactaa cccgcagtgg    540

aaagaacagg gtctcaactc cgaaaacttc gtggcgttta acctgaccga gcgcatgcag    600

ctgattggcg gcacctggta cggcggcgaa atgaagaaag ggatgttctc gatgatgaac    660

tacctgctgc cgctgaaagg tatcgcttct atgcactgct ccgccaacgt tggtgagaaa    720

ggcgatgttg cggtgttctt cggcctttcc ggcaccggta aaaccaccct ttccaccgac    780

ccgaaacgtc gcctgattgg cgatgacgaa cacggctggg acgatgacgg cgtgtttaac    840

ttcgaaggcg gctgctacgc aaaaactatc aagctgtcga aagaagcgga acctgaaatc    900

tacaacgcta tccgtcgtga tgcgttgctg gaaaacgtca ccgtgcgtga agatggcact    960

atcgactttg atgatggttc aaaaaccgag aacacccgcg tttcttatcc gatctatcac   1020

atcgataaca ttgttaagcc ggtttccaaa gcgggccacg cgactaaggt tatcttcctg   1080

actgctgatg ctttcggcgt gttgccgccg gtttctcgcc tgactgccga tcaaacccag   1140

tatcacttcc tctctggctt caccgccaaa ctggccggta ctgagcgtgg catcaccgaa   1200

ccgacgccaa ccttctccgc ttgcttcggc gcggcattcc tgtcgctgca cccgactcag   1260

tacgcagaag tgctggtgaa acgtatgcag gcggcgggcg cgcaggctta tctggttaac   1320

actggctgga acggcactgg caaacgtatc tcgattaaag atacccgcgc cattatcgac   1380

gccatcctca acggttcgct ggataatgca gaaaccttca ctctgccgat gtttaacctg   1440

gcgatcccaa ccgaactgcc gggcgtagac acgaagattc tcgatccgcg taacacctac   1500

gcttctccgg aacagtggca ggaaaaagcc gaaaccctgg cgaaactgtt tatcgacaac   1560

ttcgataaat acaccgacac ccctgcgggt gccgcgctgg tagcggctgg tccgaaactg   1620

taa                                                                 1623
```

<210> SEQ ID NO 5
<211> LENGTH: 1650
<212> TYPE: DNA
<213> ORGANISM: S. cerevisiae

<400> SEQUENCE: 5

```
atgtcccctt ctaaaatgaa tgctacagta ggatctactt ccgaagttga acaaaaaatc     60

agacaagaat tggctcttag tgacgaagtc accaccatca gacgcaatgc tccagctgcc    120

gttttgtatg aagatggtct aaaagaaaat aaaactgtca tttcatcaag cggtgcattg    180

atcgcttatt ccggtgttaa aaccggaaga tctccaaagg acaaacgtat tgttgaagaa    240

cctacctcga aagacgaaat ttggtggggt ccggtcaata aaccatgttc tgaaagaaca    300

tggtctatca accgtgaaag agctgcagat tacttgagaa caagagacca catttatatt    360

gtcgatgcat ttgcaggatg ggatccaaaa tacagaatca aagtccgcgt tgtttgtgcc    420

agggcttacc acgctttatt catgacaaat atgcttatta gacctacaga agaagaatta    480

gcccattttg gagaacctga ttttactgtc tggaacgctg gtcagttccc agccaattta    540

cacacccagg atatgtcttc aaagagtact atagaaatta acttcaaagc aatggaaatg    600

atcattttag gtaccgaata cgccggtgaa atgaaaaaag gtattttcac agttatgttt    660

tacttgatgc ctgtgcacca taacgtttta actttgcact cttccgccaa ccagggtatt    720

caaaacggtg acgttacttt attctttggc ctaagtggta ccgggaaaac cactttatcc    780

gcagacccac atagattgtt gatcggcgat gatgaacatt gttggtccga ccatggtgtc    840

ttcaatatcg aaggtggttg ttacgccaag tgtattaatt tatctgccga aaaggagcct    900
```

-continued

```
gaaattttcg acgctatcaa gtttggttct gtattagaaa acgttatcta tgacgagaag    960

tcgcatgtag tcgactatga cgactcttct attactgaaa atactagatg tgcctaccca   1020

attgactaca ttccaagtgc caagattcca tgtttggcgg actctcatcc aaagaacatt   1080

atcctgctaa cttgtgatgc ttcgggtgtt ttaccaccag tatctaaatt gactcctgaa   1140

caagtcatgt accatttcat ctctggttac acttctaaaa tggctggtac tgagcaaggt   1200

gtcactgaac ctgaaccaac attttcatct tgtttcggac aacccttcct agccttgcac   1260

cctattagat acgcaaccat gttagctaca aagatgtctc aacataaagc taatgcgtac   1320

ttaatcaaca ccggctggac tggttcttcc tacgtatctg gtggtaaacg ttgcccattg   1380

aagtacacaa gggccattct ggattctatt catgatggtt cgttagccaa tgaaacgtac   1440

gaaactttac cgattttcaa tcttcaagta cctaccaagg ttaacggtgt tccagctgag   1500

cttttgaatc ctgctaaaaa ctggtctcaa ggtgaatcca aatacagagg tgcagttacc   1560

aacttggcca acttgtttgt tcaaaatttc aagatttatc aagacagagc cacaccagat   1620

gtattagccg ctggtcctca attcgagtaa                                    1650
```

<210> SEQ ID NO 6
<211> LENGTH: 372
<212> TYPE: DNA
<213> ORGANISM: Propionibacterium freudenreichii

<400> SEQUENCE: 6

```
tcagccgatc ttgatgagac cctgaccgcc ctgcacggcg tcacgctcct tgacaaggac     60

cttctcgacc ttgccgtcgg tgggagcgtt gatctcggtc tccatcttca tggcctcgag    120

aacgagcacg gtctgaccag ccttgaccgt gtcaccctcc ttcacgagga tcttggagac    180

ggtgccggcc agcggagcgg gaatctcgcc ctctccggcc ttaccggcgc ctgcgccacc    240

tgctgcgcgc ggtgccggcg cgccgccggt gccgccgccg aacaggatgg tgcccatcgg    300

gttttcgtgt gacttgtcga cgtcaacgtc aacgtcatac gcagtgccgt tgactgttac    360

cttcagtttc at                                                        372
```

<210> SEQ ID NO 7
<211> LENGTH: 369
<212> TYPE: DNA
<213> ORGANISM: Propionibacterium freudenreichii

<400> SEQUENCE: 7

```
atgaaactga aggtaacagt caacggcact gcgtatgacg ttgacgttga cgtcgacaag     60

tcacacgaaa acccgatggg caccatcctg ttcggcggcg gcaccggcgg cgcgccggca    120

ccgcgcgcag caggtggcgc aggcgccggt aaggccggag agggcgagat tcccgctccg    180

ctggccggca ccgtctccaa gatcctcgtg aaggagggtg acacggtcaa ggctggtcag    240

accgtgctcg ttctcgaggc catgaagatg gagaccgaga tcaacgctcc caccgacggc    300

aaggtcgaga aggtccttgt caaggagcgt gacgccgtgc agggcggtca gggtctcatc    360

aagatcggc                                                            369
```

<210> SEQ ID NO 8
<211> LENGTH: 123
<212> TYPE: PRT
<213> ORGANISM: Propionibacterium freudenreichii

<400> SEQUENCE: 8

Met Lys Leu Lys Val Thr Val Asn Gly Thr Ala Tyr Asp Val Asp Val

-continued

```
1               5                   10                  15

Asp Val Asp Lys Ser His Glu Asn Pro Met Gly Thr Ile Leu Phe Gly
            20                  25                  30

Gly Gly Thr Gly Gly Ala Pro Ala Pro Arg Ala Ala Gly Gly Ala Gly
        35                  40                  45

Ala Gly Lys Ala Gly Glu Gly Glu Ile Pro Ala Pro Leu Ala Gly Thr
    50                  55                  60

Val Ser Lys Ile Leu Val Lys Glu Gly Asp Thr Val Lys Ala Gly Gln
65                  70                  75                  80

Thr Val Leu Val Leu Glu Ala Met Lys Met Glu Thr Glu Ile Asn Ala
                85                  90                  95

Pro Thr Asp Gly Lys Val Glu Lys Val Leu Val Lys Glu Arg Asp Ala
            100                 105                 110

Val Gln Gly Gly Gln Gly Leu Ile Lys Ile Gly
        115                 120


<210> SEQ ID NO 9
<211> LENGTH: 1518
<212> TYPE: DNA
<213> ORGANISM: Propionibacterium freudenreichii

<400> SEQUENCE: 9

tcacgcctgc tgaacggtga cttcgcggac ggttccgccc acgttcacgt tgtaggtgac     60

gggaccggcc acggcgagcg acttctcgtc gccctcggcc tcggccttca gctgggcatc    120

ggtgagagcc acgctgtgcg ggccctcggc gcgatgctcg aagaagaccg gagcgacctg    180

cgggaacagt gcataggtga gcacgtcctc gtcggtgccg ttgaagccct tgagggccgc    240

ggcctccttg gactgctcct cccactcggg gggcagcaga tcggccgggc gctgggtgat    300

cggcttcttg ccggactgct cctcggccaa cttgaccacc ttcggatcgc gatcggccgg    360

gctggcgccg tagtagccga gcatgatgtc ggcgaactcg ccggtcatcc tcttgtactc    420

gcccatcatc acgttgaaca cggcctgcgt gccgacgatc tggctggacg gggtgaccag    480

gggcgggaag ccggcggcct tgcggacgcg cggcacctct gccatgacct cgtccatctt    540

gtcctcggcg ccctgggcgc gcagctgcga ctccatgttg gagagcatgc cgccggggat    600

ctgcgacttg aagatcgagg tgtcgacaag cgtcttcgac tcgaacttct tgtacttcgg    660

gcggatggcc ttgaagtgat cgcggatctt gtgcaggcga tcgtagtcaa ggttggtggt    720

gtacccggtg ccctcgagca tctcggcaac cgactcggtg gggttgtggc ccgggccgag    780

cgacatggac gagatggcgg tgtcgacgac gtcgacgccg gcctcgatgg ccttcatgag    840

ggagacctcg gtgacacccg tggtggagtg gcagtgcagg ttgatctgcg tcttctggcc    900

gtaggtgtcc ttgatggcct tgatgatgtc gtaggccggc tgcggcttga gcagggcggc    960

catgtccttc agggcgatgg aatcagcacc catgtcgagc agctgaccag caagcttgac   1020

atagccctca acggtgtgga ccgggctgat cgtgtagcaa atggtgccct gcgcgtgctt   1080

gccggccttc ttgacggcag ccatggcgtg cgccatgttg cggggatcat tcatggcgtc   1140

gaagacacgg aacacgtcca tgccgttctc agcggacttg tcgacgaagc gatcgacgac   1200

ctcgtcgttg tagtggcggt aacccagcag gttctggcca cgcagcagca tctggagacg   1260

gctgttgggc atcagcttgc ggaacgtgcg cagacgctcc caaggatcct cgttgaggaa   1320

gcggatacac gagtcatacg tggcaccacc ccaacactcc actgaccagt acccggcagc   1380

atcaatgtct gcacaggcgc cgaccatgtc ttccattgcc attcgtgtgg ccatcaggct   1440
```

ctgatgggca tcgcgcagca cgagctcggt gataccaacc tcgcgcggct cggaaacctc 1500
aatttctcgc ggactcat 1518

<210> SEQ ID NO 10
<211> LENGTH: 1518
<212> TYPE: DNA
<213> ORGANISM: Propionibacterium freudenreichii

<400> SEQUENCE: 10
atgagtccgc gagaaattga ggtttccgag ccgcgcgagg ttggtatcac cgagctcgtg 60
ctgcgcgatg cccatcagag cctgatggcc acacgaatgg caatggaaga catggtcggc 120
gcctgtgcag acattgatgc tgccgggtac tggtcagtgg agtgttgggg tggtgccacg 180
tatgactcgt gtatccgctt cctcaacgag gatccttggg agcgtctgcg cacgttccgc 240
aagctgatgc ccaacagccg tctccagatg ctgctgcgtg gccagaacct gctgggttac 300
cgccactaca acgacgaggt cgtcgatcgc ttcgtcgaca agtccgctga gaacggcatg 360
gacgtgttcc gtgtcttcga cgccatgaat gatccccgca acatggcgca cgccatggct 420
gccgtcaaga aggccggcaa gcacgcgcag ggcaccattt gctacacgat cagcccggtc 480
cacaccgttg agggctatgt caagcttgct ggtcagctgc tcgacatggg tgctgattcc 540
atcgccctga aggacatggc cgccctgctc aagccgcagc cggcctacga catcatcaag 600
gccatcaagg acacctacgg ccagaagacg cagatcaacc tgcactgcca ctccaccacg 660
ggtgtcaccg aggtctccct catgaaggcc atcgaggccg gcgtcgacgt cgtcgacacc 720
gccatctcgt ccatgtcgct cggcccgggc cacaacccca ccgagtcggt tgccgagatg 780
ctcgagggca ccgggtacac caccaacctt gactacgatc gcctgcacaa gatccgcgat 840
cacttcaagg ccatccgccc gaagtacaag aagttcgagt cgaagacgct tgtcgacacc 900
tcgatcttca agtcgcagat ccccggcggc atgctctcca acatggagtc gcagctgcgc 960
gcccagggcg ccgaggacaa gatggacgag gtcatggcag aggtgccgcg cgtccgcaag 1020
gccgccggct tcccgcccct ggtcaccccg tccagccaga tcgtcggcac gcaggccgtg 1080
ttcaacgtga tgatgggcga gtacaagagg atgaccggcg agttcgccga catcatgctc 1140
ggctactacg gcgccagccc ggccgatcgc gatccgaagg tggtcaagtt ggccgaggag 1200
cagtccggca agaagccgat cacccagcgc ccggccgatc tgctgccccc cgagtgggag 1260
gagcagtcca aggaggccgc ggccctcaag ggcttcaacg gcaccgacga ggacgtgctc 1320
acctatgcac tgttcccgca ggtcgctccg gtcttcttcg agcatcgcgc cgagggcccg 1380
cacagcgtgg ctctcaccga tgcccagctg aaggccgagg ccgagggcga cgagaagtcg 1440
ctcgccgtgg ccggtcccgt cacctacaac gtgaacgtgg gcggaaccgt ccgcgaagtc 1500
accgttcagc aggcgtga 1518

<210> SEQ ID NO 11
<211> LENGTH: 505
<212> TYPE: PRT
<213> ORGANISM: Propionibacterium freudenreichii

<400> SEQUENCE: 11

Met Ser Pro Arg Glu Ile Glu Val Ser Glu Pro Arg Glu Val Gly Ile
1 5 10 15

Thr Glu Leu Val Leu Arg Asp Ala His Gln Ser Leu Met Ala Thr Arg
20 25 30

Met Ala Met Glu Asp Met Val Gly Ala Cys Ala Asp Ile Asp Ala Ala

-continued

```
        35                  40                  45

Gly Tyr Trp Ser Val Glu Cys Trp Gly Gly Ala Thr Tyr Asp Ser Cys
    50                  55                  60

Ile Arg Phe Leu Asn Glu Asp Pro Trp Glu Arg Leu Arg Thr Phe Arg
65                  70                  75                  80

Lys Leu Met Pro Asn Ser Arg Leu Gln Met Leu Leu Arg Gly Gln Asn
                85                  90                  95

Leu Leu Gly Tyr Arg His Tyr Asn Asp Glu Val Val Asp Arg Phe Val
            100                 105                 110

Asp Lys Ser Ala Glu Asn Gly Met Asp Val Phe Arg Val Phe Asp Ala
        115                 120                 125

Met Asn Asp Pro Arg Asn Met Ala His Ala Met Ala Ala Val Lys Lys
    130                 135                 140

Ala Gly Lys His Ala Gln Gly Thr Ile Cys Tyr Thr Ile Ser Pro Val
145                 150                 155                 160

His Thr Val Glu Gly Tyr Val Lys Leu Ala Gly Gln Leu Leu Asp Met
                165                 170                 175

Gly Ala Asp Ser Ile Ala Leu Lys Asp Met Ala Ala Leu Leu Lys Pro
            180                 185                 190

Gln Pro Ala Tyr Asp Ile Ile Lys Ala Ile Lys Asp Thr Tyr Gly Gln
        195                 200                 205

Lys Thr Gln Ile Asn Leu His Cys His Ser Thr Thr Gly Val Thr Glu
    210                 215                 220

Val Ser Leu Met Lys Ala Ile Glu Ala Gly Val Asp Val Val Asp Thr
225                 230                 235                 240

Ala Ile Ser Ser Met Ser Leu Gly Pro Gly His Asn Pro Thr Glu Ser
                245                 250                 255

Val Ala Glu Met Leu Glu Gly Thr Gly Tyr Thr Thr Asn Leu Asp Tyr
            260                 265                 270

Asp Arg Leu His Lys Ile Arg Asp His Phe Lys Ala Ile Arg Pro Lys
        275                 280                 285

Tyr Lys Lys Phe Glu Ser Lys Thr Leu Val Asp Thr Ser Ile Phe Lys
    290                 295                 300

Ser Gln Ile Pro Gly Gly Met Leu Ser Asn Met Glu Ser Gln Leu Arg
305                 310                 315                 320

Ala Gln Gly Ala Glu Asp Lys Met Asp Glu Val Met Ala Glu Val Pro
                325                 330                 335

Arg Val Arg Lys Ala Ala Gly Phe Pro Pro Leu Val Thr Pro Ser Ser
            340                 345                 350

Gln Ile Val Gly Thr Gln Ala Val Phe Asn Val Met Met Gly Glu Tyr
        355                 360                 365

Lys Arg Met Thr Gly Glu Phe Ala Asp Ile Met Leu Gly Tyr Tyr Gly
    370                 375                 380

Ala Ser Pro Ala Asp Arg Asp Pro Lys Val Val Lys Leu Ala Glu Glu
385                 390                 395                 400

Gln Ser Gly Lys Lys Pro Ile Thr Gln Arg Pro Ala Asp Leu Leu Pro
                405                 410                 415

Pro Glu Trp Glu Glu Gln Ser Lys Glu Ala Ala Ala Leu Lys Gly Phe
            420                 425                 430

Asn Gly Thr Asp Glu Asp Val Leu Thr Tyr Ala Leu Phe Pro Gln Val
        435                 440                 445

Ala Pro Val Phe Phe Glu His Arg Ala Glu Gly Pro His Ser Val Ala
    450                 455                 460
```

-continued

```
Leu Thr Asp Ala Gln Leu Lys Ala Glu Ala Glu Gly Asp Glu Lys Ser
465                 470                 475                 480

Leu Ala Val Ala Gly Pro Val Thr Tyr Asn Val Asn Val Gly Gly Thr
                485                 490                 495

Val Arg Glu Val Thr Val Gln Gln Ala
            500                 505
```

<210> SEQ ID NO 12
<211> LENGTH: 1575
<212> TYPE: DNA
<213> ORGANISM: Propionibacterium freudenreichii

<400> SEQUENCE: 12

```
tcagcagggg aagtttccat gcttcttcgc cgggcgggtc tgacgcttgg tggcgtacat      60

ctccagggcg gaagcaatct ttcgacgggt atcagccggg tcaatcacgt cgtcgacctg     120

accgcgggcg gcggccacgt acggcgtgtt gaacgcgttc tggtactcct cgatcttctc     180

ggcgcgcatg gcgtcgggat cgtcggcagc cttgatctcc ttgcggaaga tcacatttgc     240

cgcaccctcg gcgcccatca ccgcaatctc ggcgctgggc caggcgtaca cggcgtcggc     300

accaaggtca cggttgcaca tggccaggta ggagccgccg taggccttgc ggagcaccac     360

ggtgatcttc ggcacggtgg cctcggagta ggcgtacagc atcttcgcgc catggcgaat     420

gatgccgccg tactcctgct gcacgccggg caggaagccc ggcacgtcga ccagctgcac     480

cagcgggatg ttgaacgaat cgcagaaatt cacgaattcg gcggccttgt cagaggcgtt     540

gatgtcgagg caacccgaca tcaccgacgg ctgattggcc acgatgccca ccgaacgacc     600

attgacccgg gcgaaggcgg tcacgaggtt ggtggcatag ccggccttga cctcgaggta     660

gtcaccccag tcgacgatct tggcaatgac atcgcgcacg tcatagccct tcttgccgtc     720

aatcggaacg atgtcgcgca gctcggtatt ggggctgacg tcattgttcg ggttgacgaa     780

ggatgcttcc tcagtgttgt tctgcggaag gaagctcagc agcttcttgg caatgagctc     840

cgcggcgtcg tcgtcctcgg ccacgaagtg gatattgccc gagatggcca tatgggcctc     900

agcgccaccg agttcgtcag cggtgacatc ctcgccggtg accgacttga tgacctgggg     960

gcccgtgatg aacatatggg ccttcttggt catgatgatg aagtcagtca gtgccggcga    1020

atacgaggcg ccaccggcac aggggccggc aatgatggcg atctgcggca cgacgcccga    1080

cagcttcacg ttggcgaaga acatcttgcc gtaaccgctc agcgagtcga tgccctcctg    1140

gatccgggcg ccgcccgaat cgtagaagaa caggaagggc gtgccggtga gcagcgcctg    1200

ttccatcgtc tcgacgacct tcgtggactg cgtctcgcca gccgaaccac ccatgaccgt    1260

gaagtcctgg gacgcggcgt gcacgggacg accaaggatg gtgccacggc cggtgaccac    1320

gccatctgcc gggacgacgg ccttgtccat gccgaacaac gtggtgcggt gcttgcggaa    1380

agcgccgacc tcgtcgaacg aatggggatc gagcaggttg ttcaggcgct cacgagcggt    1440

ctgcttaccc tgggaatgtt gcttctcgac gcgacgttcg ccgccaccgg cttcgatcac    1500

ctggcgctgc tctgcgagct gctccacgcg accttccatg gtgctggcga gcttcaaatt    1560

gttgttttca gccat                                                     1575
```

<210> SEQ ID NO 13
<211> LENGTH: 1572
<212> TYPE: DNA
<213> ORGANISM: Propionibacterium freudenreichii

<400> SEQUENCE: 13

-continued

```
atggctgaaa acaacaattt gaagctcgcc agcaccatgg aaggtcgcgt ggagcagctc     60
gcagagcagc gccaggtgat cgaagccggt ggcggcgaac gtcgcgtcga gaagcaacat    120
tcccagggta agcagaccgc tcgtgagcgc ctgaacaacc tgctcgatcc ccattcgttc    180
gacgaggtcg gcgctttccg caagcaccgc accacgttgt tcggcatgga caaggccgtc    240
gtcccggcag atggcgtggt caccggccgt ggcaccatcc ttggtcgtcc cgtgcacgcc    300
gcgtcccagg acttcacggt catgggtggt tcggctggcg agacgcagtc cacgaaggtc    360
gtcgagacga tggaacaggc gctgctcacc ggcacgccct tcctgttctt ctacgattcg    420
ggcggcgccc ggatccagga gggcatcgac tcgctgagcg gttacggcaa gatgttcttc    480
gccaacgtga agctgtcggg cgtcgtgccg cagatcgcca tcattgccgg cccctgtgcc    540
ggtggcgcct cgtattcgcc ggcactgact gacttcatca tcatgaccaa gaaggcccat    600
atgttcatca cgggccccca ggtcatcaag tcggtcaccg gcgaggatgt caccgctgac    660
gaactcggtg gcgctgaggc ccatatggcc atctcgggca atatccactt cgtggccgag    720
gacgacgacg ccgcggagct cattgccaag aagctgctga gcttccttcc gcagaacaac    780
actgaggaag catccttcgt caacccgaac aatgacgtca gccccaatac cgagctgcgc    840
gacatcgttc cgattgacgg caagaagggc tatgacgtgc gcgatgtcat tgccaagatc    900
gtcgactggg gtgactacct cgaggtcaag gccggctatg ccaccaacct cgtgaccgcc    960
ttcgcccggg tcaatggtcg ttcggtgggc atcgtggcca atcagccgtc ggtgatgtcg   1020
ggttgcctcg acatcaacgc ctctgacaag gccgccgaat tcgtgaattt ctgcgattcg   1080
ttcaacatcc cgctggtgca gctggtcgac gtgccgggct tcctgcccgg cgtgcagcag   1140
gagtacggcg gcatcattcg ccatggcgcg aagatgctgt acgcctactc cgaggccacc   1200
gtgccgaaga tcaccgtggt gctccgcaag gcctacggcg gctcctacct ggccatgtgc   1260
aaccgtgacc ttggtgccga cgccgtgtac gcctggccca gcgccgagat tgcggtgatg   1320
ggcgccgagg gtgcggcaaa tgtgatcttc cgcaaggaga tcaaggctgc cgacgatccc   1380
gacgccatgc gcgccgagaa gatcgaggag taccagaacg cgttcaacac gccgtacgtg   1440
gccgccgccc gcggtcaggt cgacgacgtg attgacccgg ctgatacccg tcgaaagatt   1500
gcttccgccc tggagatgta cgccaccaag cgtcagaccc gcccggcgaa gaagcatgga   1560
aacttcccct gc                                                        1572
```

<210> SEQ ID NO 14
<211> LENGTH: 524
<212> TYPE: PRT
<213> ORGANISM: Propionibacterium freudenreichii

<400> SEQUENCE: 14

```
Met Ala Glu Asn Asn Asn Leu Lys Leu Ala Ser Thr Met Glu Gly Arg
1               5                   10                  15

Val Glu Gln Leu Ala Glu Gln Arg Gln Val Ile Glu Ala Gly Gly Gly
            20                  25                  30

Glu Arg Arg Val Glu Lys Gln His Ser Gln Gly Lys Gln Thr Ala Arg
        35                  40                  45

Glu Arg Leu Asn Asn Leu Leu Asp Pro His Ser Phe Asp Glu Val Gly
    50                  55                  60

Ala Phe Arg Lys His Arg Thr Thr Leu Phe Gly Met Asp Lys Ala Val
65                  70                  75                  80

Val Pro Ala Asp Gly Val Val Thr Gly Arg Gly Thr Ile Leu Gly Arg
```

```
                85                  90                  95

Pro Val His Ala Ala Ser Gln Asp Phe Thr Val Met Gly Gly Ser Ala
            100                 105                 110

Gly Glu Thr Gln Ser Thr Lys Val Val Glu Thr Met Glu Gln Ala Leu
        115                 120                 125

Leu Thr Gly Thr Pro Phe Leu Phe Phe Tyr Asp Ser Gly Gly Ala Arg
    130                 135                 140

Ile Gln Glu Gly Ile Asp Ser Leu Ser Gly Tyr Gly Lys Met Phe Phe
145                 150                 155                 160

Ala Asn Val Lys Leu Ser Gly Val Val Pro Gln Ile Ala Ile Ile Ala
                165                 170                 175

Gly Pro Cys Ala Gly Gly Ala Ser Tyr Ser Pro Ala Leu Thr Asp Phe
            180                 185                 190

Ile Ile Met Thr Lys Lys Ala His Met Phe Ile Thr Gly Pro Gln Val
        195                 200                 205

Ile Lys Ser Val Thr Gly Glu Asp Val Thr Ala Asp Glu Leu Gly Gly
    210                 215                 220

Ala Glu Ala His Met Ala Ile Ser Gly Asn Ile His Phe Val Ala Glu
225                 230                 235                 240

Asp Asp Asp Ala Ala Glu Leu Ile Ala Lys Lys Leu Leu Ser Phe Leu
                245                 250                 255

Pro Gln Asn Asn Thr Glu Glu Ala Ser Phe Val Asn Pro Asn Asn Asp
            260                 265                 270

Val Ser Pro Asn Thr Glu Leu Arg Asp Ile Val Pro Ile Asp Gly Lys
        275                 280                 285

Lys Gly Tyr Asp Val Arg Asp Val Ile Ala Lys Ile Val Asp Trp Gly
    290                 295                 300

Asp Tyr Leu Glu Val Lys Ala Gly Tyr Ala Thr Asn Leu Val Thr Ala
305                 310                 315                 320

Phe Ala Arg Val Asn Gly Arg Ser Val Gly Ile Val Ala Asn Gln Pro
                325                 330                 335

Ser Val Met Ser Gly Cys Leu Asp Ile Asn Ala Ser Asp Lys Ala Ala
            340                 345                 350

Glu Phe Val Asn Phe Cys Asp Ser Phe Asn Ile Pro Leu Val Gln Leu
        355                 360                 365

Val Asp Val Pro Gly Phe Leu Pro Gly Val Gln Gln Glu Tyr Gly Gly
    370                 375                 380

Ile Ile Arg His Gly Ala Lys Met Leu Tyr Ala Tyr Ser Glu Ala Thr
385                 390                 395                 400

Val Pro Lys Ile Thr Val Val Leu Arg Lys Ala Tyr Gly Gly Ser Tyr
                405                 410                 415

Leu Ala Met Cys Asn Arg Asp Leu Gly Ala Asp Ala Val Tyr Ala Trp
            420                 425                 430

Pro Ser Ala Glu Ile Ala Val Met Gly Ala Glu Gly Ala Ala Asn Val
        435                 440                 445

Ile Phe Arg Lys Glu Ile Lys Ala Ala Asp Asp Pro Asp Ala Met Arg
    450                 455                 460

Ala Glu Lys Ile Glu Glu Tyr Gln Asn Ala Phe Asn Thr Pro Tyr Val
465                 470                 475                 480

Ala Ala Ala Arg Gly Gln Val Asp Asp Val Ile Asp Pro Ala Asp Thr
                485                 490                 495

Arg Arg Lys Ile Ala Ser Ala Leu Glu Met Tyr Ala Thr Lys Arg Gln
            500                 505                 510
```

```
Thr Arg Pro Ala Lys Lys His Gly Asn Phe Pro Cys
        515                 520


<210> SEQ ID NO 15
<211> LENGTH: 246
<212> TYPE: DNA
<213> ORGANISM: P.freudenreichii

<400> SEQUENCE: 15

atggctgatg aggaagagaa ggacctgatg atcgccacgc tcaacaagcg cgtcgcgtca      60

ttggagtctg agttgggttc actccagagc gatacccagg gtgtcaccga ggacgtactg     120

acggccattt cggccgccgt tgcggcctat ctcggcaacg atggatcggc tgaggtcgtc     180

catttcgccc cgagcccgaa ctgggtccgc gagggtcgtc gggctctgca gaaccattcc     240

attcgt                                                                246


<210> SEQ ID NO 16
<211> LENGTH: 82
<212> TYPE: PRT
<213> ORGANISM: P.freudenreichii

<400> SEQUENCE: 16

Met Ala Asp Glu Glu Glu Lys Asp Leu Met Ile Ala Thr Leu Asn Lys
1               5                   10                  15

Arg Val Ala Ser Leu Glu Ser Glu Leu Gly Ser Leu Gln Ser Asp Thr
            20                  25                  30

Gln Gly Val Thr Glu Asp Val Leu Thr Ala Ile Ser Ala Ala Val Ala
        35                  40                  45

Ala Tyr Leu Gly Asn Asp Gly Ser Ala Glu Val Val His Phe Ala Pro
    50                  55                  60

Ser Pro Asn Trp Val Arg Glu Gly Arg Arg Ala Leu Gln Asn His Ser
65                  70                  75                  80

Ile Arg


<210> SEQ ID NO 17
<211> LENGTH: 1575
<212> TYPE: DNA
<213> ORGANISM: P. acnes

<400> SEQUENCE: 17

atggctgaga agaaaccaat caagctggcc gataccatgg ccggccggat cgagcagctc      60

gccgacgagc gccacgctgt ggagcttggc gggggcgagg atcgcctgca aaagcagcgt     120

gacaggggca agcagacagc ccgtgaacgg atcgacaacc tcgttgatgc ttattccttc     180

gatgaggtgg gtgcgttccg taagcaccgc accacccttt tcggcatgga caaggccgaa     240

gttcccgccg acggcgtagt caccggtcgt gcgaccatcc atggtcgccc ggtccacatc     300

gcgtctcagg acttcaccgt catgggtggg tcggctggcg agacccagtc gacgaaggtc     360

gtcgagacga tggaacagtc cctgctgacc ggcactccgt ttctgttctt ctatgactcg     420

ggcggcgccc gaattcaaga aggcatcgac tcgctgtccg ggtacggcaa gatgttctac     480

gcgaacgtca agctgtcggg cgtcgtgccg cagatcgcca tcattgctgg cccctgcgcc     540

ggcggcgcct cctattcccc ggccctgacc gacttcatca tcatgacgaa gaaggcccac     600

atgttcatta cgggccccgg agtcatcaag tcggttaccg gtgaggaggt gactgctgac     660

gacctgggtg gtgcggatgc gcacatgtcc acctcgggca atatccactt cgtggccgaa     720
```

gatgacgacg ccgcagtgct catcgcgcag aagttgctga gcttcctgcc gcaaaacaac 780
actgaggacg cccagatctc caaccccaat gacgatgtct ccccgcagcc tgagctgcgc 840
gacatcgttc cgctggatgg taagaagggc tacgacgtcc gcgacgtcat ctccaagatc 900
gtcgactggg gcgactacct agaggtcaag gccggttggg cgaccaacat cgtcaccgcc 960
tttgcccggg tcaatggtcg taccgtcggc atcgtggcca accagccgaa ggtgatgtcg 1020
ggttgccttg acatcaatgc ttcggacaag gctgccgagt tcattacctt ctgcgactcg 1080
ttcaatattc cgttggtgca gttggttgac gttcctggct tcctgcctgg tgtccagcag 1140
gagtacggcg gcatcatccg ccacggcgcg aagatgctgt atgcctactc cgaggccacc 1200
gtcccgaaga tcaccgtggt gctgcgtaag gcttacggcg gctcctacct tgccatgtgc 1260
aaccgtgacc tgggtgctga cgccgtctat gcctggccga gcgcggagat tgcggtgatg 1320
ggtgccgatg gcgctgccaa cgtcattttc cgtcgccaga tcaaggactc tgaggatccc 1380
gcagccaccc gtgccgcgaa gatcgaggag taccgcaacg ccttcaacac gccttacgtg 1440
gctgccgccc gtggacaggt tgacgacgtg atcgatcccg cggacacccg tcgcaagatc 1500
accgccgctc tggagaccta cgccactaag cgtcagtccc gtccggccaa gaagcacggc 1560
gtcatgcctt gctga 1575

<210> SEQ ID NO 18
<211> LENGTH: 1494
<212> TYPE: DNA
<213> ORGANISM: P. acnes

<400> SEQUENCE: 18
atgagtccac gaaagattgg cgttaccgag ctcgtgctcc gcgacgcgca tcagagcctg 60
cttgccactc gcatggccat ggaggacatg gttgatgcct gtgccgacat tgatgcggca 120
ggcttctggt ccgttgaatg ctggggcgga gctaccttcg attcttgcat ccgattcctc 180
aacgaagacc catgggagcg tctgcgtact ttccgcaagc tgctgccgaa ctcccggttg 240
cagatgctgc tgcgtggcca aaaccttctg ggctaccgcc actacaacga cgaggtcgtc 300
gacaagtttg tcgagaagtc ggccgagaac ggcatggacg tgttccgggt gttcgacgct 360
ctgaacgatc ctcgcaacct tgagcacgcg atggcagccg tcaagaagac cggcaagcac 420
gcccagggca ccatctgcta caccacttcc ccgattcaca ccccagagag cttcgtcaag 480
caggccgatc gtctcatcga catgggtgcc gactcgatcg ccttcaagga catggctgct 540
ttgctcaagc cgcagcctgc ctacgacatc atcaagggca ttaaggagaa ccatccggac 600
gtgcagatca acctgcactg ccactccacc acgggcgtca ccctggtcac cctgcagaag 660
gccatcgagg ctggtgtcga cgtcgtcgac accgctatct cgtcgatgtc gctcggcccg 720
gggcacaacc caaccgagtc tttggtcgag atgctcgagg gcaccgagta caccaccggc 780
ctcgacatgg atcgcctgct caagatccgc gaccacttca agaaggtgcg tccgaagtac 840
aagaagttcg agtcgaagac gctggtcaac accaacatct tccagtccca gatcccgggc 900
ggaatgctct ccaacatgga gtcccagctc gaggcccagg gtgctggaga ccgcatggat 960
gaggtcatga aggaggtgcc gcgcgttcgt aaggatgccg gctacccgcc gctggtcacc 1020
ccgtcctccc agatcgtggg aacccaggcg gtgttcaacg tcctgatggg caatggttcg 1080
tacaagaacc tcactgccga gtttgccgac ctcatgcttg gctactacgg caagcccatt 1140
ggcgagctca atcccgagat cgttgagatg gccaagaagc agaccggcaa ggagccgatc 1200
gactgccgtc ccgccgacct gctcgagcct gagtgggacc agctggtcga gcaggccaag 1260
agtcttgagg gcttcgacgg ctccgacgag gacgttctta ccaacgccct gttcccggga 1320
gttgccccga agttcctcaa ggaacgcgca cagggcccga agagcgtcgc gatgaccgag 1380
gcacagctga aggccgagaa ggaaggcacc ggcgctgccg gcatcgccgg accggtcaac 1440
tacaacgtga cggtcggtgg caacagccac caggtgaccg tcgagcctgc gtga 1494

<210> SEQ ID NO 19
<211> LENGTH: 363
<212> TYPE: DNA
<213> ORGANISM: P. acnes

<400> SEQUENCE: 19
atgaagctca aggtgaccgt caatgacgtc gcatacgacg ttgacgttga cgttgataag 60
accgccaatg cgccgatggc gccgatcctc tttggtggcg gcgccggcgg cccgatgaag 120
gcatccggtg gcggcgccgg taaggccggt gagggcgagg ttcccgcacc gctagctggg 180
actgttgcca agatcctggt ggccgaagga gatgccgtca aggccggtca ggtgctcctg 240
accctcgagg ccatgaagat ggagaccgag atcaatgccc cggcggacgg aaccgtcaag 300
gggatcctgg tggctgtcgg tgacgccgtc cagggtggtc agggcctggt ggctctgggc 360
tga 363

<210> SEQ ID NO 20
<211> LENGTH: 1551
<212> TYPE: DNA
<213> ORGANISM: C. thermocellum

<400> SEQUENCE: 20
atggacaaag tagacaagat cggccttctc cgtgaaaaac tggcccaggt tgaacagggc 60
ggaggagctg aaaaaatcgc aaaacagcat gatgccggaa aaatgacagc aagagaaaga 120
atccaggctt tatttgatga aaacagcttt gttgagatcg acacatttgt tgagacaaga 180
agcattgact tcgatatgca aaaaaagaaa gtcccgggag acggtgttgt aacagggtat 240
ggttccatag acggacgtct ggtctttgtt gcggcgcagg actttactgt aatcggtggg 300
tctttgggtg aaatgcatgc cgcaaaaatc accaaagtaa tggacatggc aatgaaaatg 360
ggcgcaccgt ttataagcat taatgattcc ggcggtgcaa gaattgaaga aggaattgac 420
gcactcaagg gatttggaga tatcttctac agaaatactt tggcttcagg tgtaattccc 480
cagatttcag ttatcatggg accatgcgca ggcggagcgg tatattctcc tgcaataacc 540
gactttatat ttatggttga caaaaccagt cagatgttta taacgggacc ccaggtaatt 600
aagtccgtaa ccggagaaga cgtgactttt gaaaaacttg gcggtgcgga aacccacaac 660
tccataagcg gtgttgctca cttcagaagt tcaagtgaaa aagaatgtat agagcaaatc 720
aaaaagctta ttagttatct tcctgataac aatctttccg atgttccgat tgttccaact 780
caggatgaca taaacagaat tactgacaac ctggtcgata tcattccgca ggactccaac 840
aagccttatg acatgatgga aataatcact tccgtagttg acaacggtga ctttttttgaa 900 attcaaaaag actttgcaaa aaacattata ataggtttcg gcagaatgaa cggcggaacc 960
gtcggtatag tggcaaatca gccaaaagtt gccgcagggg ttttggatgt gaactcctct 1020
gacaaagccg caaggtttgt tcgtttctgt gatgcgttca acattccaat tataaccttt 1080
accgatgtac cggggtatct gcccggagta ggccaggagc acagcggagt aataagacac 1140
ggtgcaaagc ttctttatgc tttctctgaa gccaccgttc caaaaatcaa tgttattgtc 1200

-continued

```
agaaaagctt acggcggtgc atatattgcc atgaacagca agcaccttgg agcggacatg   1260

gtatttgcgt ggccttcggc ggaaattgca gttatgggac cggaaggtgc ggcaaacatc   1320

attttcaaga aagatatagc tgctgccgat gacccaatgg aaacaagaaa gaggctcatt   1380

gaagaatatc gtgaaaaatt ctccaatccg tatgttgcag cttcaagggg ttatgttgat   1440

gatgtaattg atccggcaac aacaaggata agactgatta gtgcccttga aatgcttgca   1500

agtaagagag aaaacagacc tgccaaaaag catggaaata ttccattata a            1551


<210> SEQ ID NO 21
<211> LENGTH: 516
<212> TYPE: PRT
<213> ORGANISM: C. thermocellum

<400> SEQUENCE: 21

Met Asp Lys Val Asp Lys Ile Gly Leu Leu Arg Glu Lys Leu Ala Gln
1               5                   10                  15

Val Glu Gln Gly Gly Gly Ala Glu Lys Ile Ala Lys Gln His Asp Ala
            20                  25                  30

Gly Lys Met Thr Ala Arg Glu Arg Ile Gln Ala Leu Phe Asp Glu Asn
        35                  40                  45

Ser Phe Val Glu Ile Asp Thr Phe Val Glu Thr Arg Ser Ile Asp Phe
    50                  55                  60

Asp Met Gln Lys Lys Lys Val Pro Gly Asp Gly Val Val Thr Gly Tyr
65                  70                  75                  80

Gly Ser Ile Asp Gly Arg Leu Val Phe Val Ala Ala Gln Asp Phe Thr
                85                  90                  95

Val Ile Gly Gly Ser Leu Gly Glu Met His Ala Ala Lys Ile Thr Lys
            100                 105                 110

Val Met Asp Met Ala Met Lys Met Gly Ala Pro Phe Ile Ser Ile Asn
        115                 120                 125

Asp Ser Gly Gly Ala Arg Ile Glu Glu Gly Ile Asp Ala Leu Lys Gly
    130                 135                 140

Phe Gly Asp Ile Phe Tyr Arg Asn Thr Leu Ala Ser Gly Val Ile Pro
145                 150                 155                 160

Gln Ile Ser Val Ile Met Gly Pro Cys Ala Gly Gly Ala Val Tyr Ser
                165                 170                 175

Pro Ala Ile Thr Asp Phe Ile Phe Met Val Asp Lys Thr Ser Gln Met
            180                 185                 190

Phe Ile Thr Gly Pro Gln Val Ile Lys Ser Val Thr Gly Glu Asp Val
        195                 200                 205

Thr Phe Glu Lys Leu Gly Gly Ala Glu Thr His Asn Ser Ile Ser Gly
    210                 215                 220

Val Ala His Phe Arg Ser Ser Ser Glu Lys Glu Cys Ile Glu Gln Ile
225                 230                 235                 240

Lys Lys Leu Ile Ser Tyr Leu Pro Asp Asn Asn Leu Ser Asp Val Pro
                245                 250                 255

Ile Val Pro Thr Gln Asp Asp Ile Asn Arg Ile Thr Asp Asn Leu Val
            260                 265                 270

Asp Ile Ile Pro Gln Asp Ser Asn Lys Pro Tyr Asp Met Met Glu Ile
        275                 280                 285

Ile Thr Ser Val Val Asp Asn Gly Asp Phe Phe Glu Ile Gln Lys Asp
    290                 295                 300

Phe Ala Lys Asn Ile Ile Ile Gly Phe Gly Arg Met Asn Gly Gly Thr
305                 310                 315                 320
```

-continued

Val Gly Ile Val Ala Asn Gln Pro Lys Val Ala Ala Gly Val Leu Asp
325 330 335

Val Asn Ser Ser Asp Lys Ala Ala Arg Phe Val Arg Phe Cys Asp Ala
340 345 350

Phe Asn Ile Pro Ile Ile Thr Phe Thr Asp Val Pro Gly Tyr Leu Pro
355 360 365

Gly Val Gly Gln Glu His Ser Gly Val Ile Arg His Gly Ala Lys Leu
370 375 380

Leu Tyr Ala Phe Ser Glu Ala Thr Val Pro Lys Ile Asn Val Ile Val
385 390 395 400

Arg Lys Ala Tyr Gly Gly Ala Tyr Ile Ala Met Asn Ser Lys His Leu
405 410 415

Gly Ala Asp Met Val Phe Ala Trp Pro Ser Ala Glu Ile Ala Val Met
420 425 430

Gly Pro Glu Gly Ala Ala Asn Ile Ile Phe Lys Lys Asp Ile Ala Ala
435 440 445

Ala Asp Asp Pro Met Glu Thr Arg Lys Arg Leu Ile Glu Glu Tyr Arg
450 455 460

Glu Lys Phe Ser Asn Pro Tyr Val Ala Ala Ser Arg Gly Tyr Val Asp
465 470 475 480

Asp Val Ile Asp Pro Ala Thr Thr Arg Ile Arg Leu Ile Ser Ala Leu
485 490 495

Glu Met Leu Ala Ser Lys Arg Glu Asn Arg Pro Ala Lys Lys His Gly
500 505 510

Asn Ile Pro Leu
515

<210> SEQ ID NO 22
<211> LENGTH: 399
<212> TYPE: DNA
<213> ORGANISM: C. thermocellum

<400> SEQUENCE: 22
atgaaaaagt ttttgataaa ggtaaacgga aatcaatatg aggttgaagt tgaagaaatc 60
agagacggtg cttcagcacc acaggttact ctcagcacac cttcggctgc acctgcgcct 120
tcaccggcac cggctcagga aacgaaaaca gctgcaccaa agaaagacag cacagtaccg 180
gcaggtgcta cggcaattaa agctccgatg ccgggtacca tactcgacat tcgtgtaaat 240
caaggggata cggtaaagaa aggccaagtt cttttaattc ttgaagcaat gaagatggaa 300
aatgaaatag ttgctccaaa tgacggtaca gttgcatcaa ttaatgtttc aaagggtgca 360
tctgtaaacg tcggagaggt tcttgtctca ttaaaatag 399

<210> SEQ ID NO 23
<211> LENGTH: 132
<212> TYPE: PRT
<213> ORGANISM: C. thermocellum

<400> SEQUENCE: 23

Met Lys Lys Phe Leu Ile Lys Val Asn Gly Asn Gln Tyr Glu Val Glu
1 5 10 15

Val Glu Glu Ile Arg Asp Gly Ala Ser Ala Pro Gln Val Thr Leu Ser
20 25 30

Thr Pro Ser Ala Ala Pro Ala Pro Ser Pro Ala Pro Ala Gln Glu Thr
35 40 45

```
Lys Thr Ala Ala Pro Lys Lys Asp Ser Thr Val Pro Ala Gly Ala Thr
    50                  55                  60

Ala Ile Lys Ala Pro Met Pro Gly Thr Ile Leu Asp Ile Arg Val Asn
65                  70                  75                  80

Gln Gly Asp Thr Val Lys Lys Gly Gln Val Leu Leu Ile Leu Glu Ala
                85                  90                  95

Met Lys Met Glu Asn Glu Ile Val Ala Pro Asn Asp Gly Thr Val Ala
            100                 105                 110

Ser Ile Asn Val Ser Lys Gly Ala Ser Val Asn Val Gly Glu Val Leu
        115                 120                 125

Val Ser Leu Lys
    130
```

<210> SEQ ID NO 24
<211> LENGTH: 1398
<212> TYPE: DNA
<213> ORGANISM: C. thermocellum

<400> SEQUENCE: 24

```
atggctaagg taaaaattac cgaaacggcg ctgagggatg cccatcaatc tctcattgca     60

acaagaatga gaatagaaga gatgcttcct atcatagata aactggacga gatcggttat    120

cattctttgg aggtatgggg cggtgcaacc tttgatgcct gcctgagatt tttgaatgaa    180

gacccgtggg aaaggcttag aattataaaa agccactgca agaaaactcc ccttcaaatg    240

cttttaagag gccagaatct tttgggttac aagcattatg ccgatgacgt tgtggagtac    300

tttgtacaaa agagcgttgc aaacggtata aacataataa gaattttcga cgccttgaat    360

gacaccagaa atatagaaac tgcaatcaaa gcctgcaaaa aagaaggcgg tcatgctcag    420

ggaacggtat gttatacaat aagtcccgtt cacaatcttg aactttttgt caaagatgca    480

aagactcttg tggaaatggg agctgactcc atatgcgtaa aggatatggc aggacttctg    540

cttccatatg ttgcatatga ccttatcaaa gcattaaaag aaaacgtaaa agtgccgatt    600

caacttcata cccactatac gagcggtgtt gcttcaatga catatctgaa ggcaattgag    660

gcagggtgcg atgttgtgga ctgcgctatc tcaccaatgt caatgggaac atcccagcct    720

ccgacagaac ctcttgtggc aaccttaaaa ggcacgccgt acgataccgg acttgacctg    780

gataaattaa gtgaaatcgc agactacttc agacctctca aagaaaagta tatttcagaa    840

ggacttcttg atgtaaaggt tatgggagtt gacgtaaaca ctctcaaata ccaggtaccc    900

ggtggaatgc tttcaaacct ggtgtctcag ttaaagcagt ccaatgcggt tgataaattc    960

gaagaggttc tgaaagaagt gccaagagta agagaagact tcggatatcc tccgttggtt   1020

acacctacaa gccagattgt aggtactcag gcagttttaa atgtggtaac gggtgaaaga   1080

tacaaaatgg ttccaaaaga atccaaggca ctgatcaagg gtgaatacgg cagaacaccg   1140

gctccggtca accctgaagt tcagaagaag attttaaaag atgaagagcc gattacagtt   1200

agacctgctg atttgataga gcccgagctt gacaagatca gaaatgaaat gaaagaatac   1260

ctggaacaag acgaggacgt tttgtcctat gcactgttcc cgcaggtggc agagaagttc   1320

ttccaataca ggaaagctca aaaatataag atagaaccgg acatggtcga ttacgaaaac   1380

agggttcatc cggtttaa                                                 1398
```

<210> SEQ ID NO 25
<211> LENGTH: 465
<212> TYPE: PRT
<213> ORGANISM: C.thermocellum

<400> SEQUENCE: 25

```
Met Ala Lys Val Lys Ile Thr Glu Thr Ala Leu Arg Asp Ala His Gln
1               5                   10                  15

Ser Leu Ile Ala Thr Arg Met Arg Ile Glu Glu Met Leu Pro Ile Ile
            20                  25                  30

Asp Lys Leu Asp Glu Ile Gly Tyr His Ser Leu Glu Val Trp Gly Gly
        35                  40                  45

Ala Thr Phe Asp Ala Cys Leu Arg Phe Leu Asn Glu Asp Pro Trp Glu
    50                  55                  60

Arg Leu Arg Ile Ile Lys Ser His Cys Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Val Val Glu Tyr Phe Val Gln Lys Ser Val Ala Asn Gly Ile Asn Ile
            100                 105                 110

Ile Arg Ile Phe Asp Ala Leu Asn Asp Thr Arg Asn Ile Glu Thr Ala
        115                 120                 125

Ile Lys Ala Cys Lys Lys Glu Gly Gly His Ala Gln Gly Thr Val Cys
    130                 135                 140

Tyr Thr Ile Ser Pro Val His Asn Leu Glu Leu Phe Val Lys Asp Ala
145                 150                 155                 160

Lys Thr Leu Val Glu Met Gly Ala Asp Ser Ile Cys Val Lys Asp Met
                165                 170                 175

Ala Gly Leu Leu Leu Pro Tyr Val Ala Tyr Asp Leu Ile Lys Ala Leu
            180                 185                 190

Lys Glu Asn Val Lys Val Pro Ile Gln Leu His Thr His Tyr Thr Ser
        195                 200                 205

Gly Val Ala Ser Met Thr Tyr Leu Lys Ala Ile Glu Ala Gly Cys Asp
    210                 215                 220

Val Val Asp Cys Ala Ile Ser Pro Met Ser Met Gly Thr Ser Gln Pro
225                 230                 235                 240

Pro Thr Glu Pro Leu Val Ala Thr Leu Lys Gly Thr Pro Tyr Asp Thr
                245                 250                 255

Gly Leu Asp Leu Asp Lys Leu Ser Glu Ile Ala Asp Tyr Phe Arg Pro
            260                 265                 270

Leu Lys Glu Lys Tyr Ile Ser Glu Gly Leu Leu Asp Val Lys Val Met
        275                 280                 285

Gly Val Asp Val Asn Thr Leu Lys Tyr Gln Val Pro Gly Gly Met Leu
    290                 295                 300

Ser Asn Leu Val Ser Gln Leu Lys Gln Ser Asn Ala Val Asp Lys Phe
305                 310                 315                 320

Glu Glu Val Leu Lys Glu Val Pro Arg Val Arg Glu Asp Phe Gly Tyr
                325                 330                 335

Pro Pro Leu Val Thr Pro Thr Ser Gln Ile Val Gly Thr Gln Ala Val
            340                 345                 350

Leu Asn Val Val Thr Gly Glu Arg Tyr Lys Met Val Pro Lys Glu Ser
        355                 360                 365

Lys Ala Leu Ile Lys Gly Glu Tyr Gly Arg Thr Pro Ala Pro Val Asn
    370                 375                 380

Pro Glu Val Gln Lys Lys Ile Leu Lys Asp Glu Glu Pro Ile Thr Val
385                 390                 395                 400

Arg Pro Ala Asp Leu Ile Glu Pro Glu Leu Asp Lys Ile Arg Asn Glu
```

405 410 415

Met Lys Glu Tyr Leu Glu Gln Asp Glu Asp Val Leu Ser Tyr Ala Leu
420 425 430

Phe Pro Gln Val Ala Glu Lys Phe Phe Gln Tyr Arg Lys Ala Gln Lys
435 440 445

Tyr Lys Ile Glu Pro Asp Met Val Asp Tyr Glu Asn Arg Val His Pro
450 455 460

Val
465

<210> SEQ ID NO 26
<211> LENGTH: 168
<212> TYPE: DNA
<213> ORGANISM: C.thermocellum

<400> SEQUENCE: 26
atgaaagagc aaataaatga agaaattatt ctggcaatat cagcggccat tgctgctttg 60
gaaacaagac ccggatacaa gcttgtagta agatcattta aaagaatacc ccaaacttct 120
cctgtatggt ccgctacagg aaaaatcgag agaatcagaa gaagtatg 168

<210> SEQ ID NO 27
<211> LENGTH: 56
<212> TYPE: PRT
<213> ORGANISM: C.thermocellum

<400> SEQUENCE: 27

Met Lys Glu Gln Ile Asn Glu Glu Ile Ile Leu Ala Ile Ser Ala Ala
1 5 10 15

Ile Ala Ala Leu Glu Thr Arg Pro Gly Tyr Lys Leu Val Val Arg Ser
20 25 30

Phe Lys Arg Ile Pro Gln Thr Ser Pro Val Trp Ser Ala Thr Gly Lys
35 40 45

Ile Glu Arg Ile Arg Arg Ser Met
50 55

<210> SEQ ID NO 28
<211> LENGTH: 1551
<212> TYPE: DNA
<213> ORGANISM: T. saccharolyticum

<400> SEQUENCE: 28
atgtcaatag atgataggat tgaagacctt cttagaagaa gagagatggt tttagaaggc 60
ggtggtttag ataaagtaga gaaacaacac caaaagggaa agcttaccgc aagagagagg 120
atatacaagc ttttagatga agatagcttt gtggaaatag atgcgtatgt tgagcacagg 180
tgtattgact ttggcatgga aaagcaaagg atacctggcg aaggcgtagt gacagggtat 240
gggacgatag atggaaggct tgtctacgtt tatgcacagg attttacggt tttaggagga 300
tcattaggcg agtatcatgc aaagaaaatc acaaaaatca tggatatggc tttaaagatg 360
ggagcaccgc tcattggatt aaatgattcc ggaggtgcca gaatacagga aggcgtcgat 420
gctttatcgg gatatggcaa catatttttc agaaacacgc tggcatcagg cgtaataccg 480
caaatatcgg tgataatggg gcccagcgct ggaggtgcag tttattcgcc tgctcttact 540
gactttatat tcatggtaga caagacaagt cagatgttta taactggacc gcaggtcata 600
aaagccgtca caggtgaaga tgtttcggca gaggagcttg gtggatcgat tactcacagc 660
acgaaaagcg gtgtggcgca ttttagggct gaaaacgacg aagagtgttt gaagatggtg 720

```
aggaagctat taagttacct tccatcaaac aatttggaag atccgccaca gttggcgaca    780

gatgacgaca taaacagatt ttccgatagg cttattgaga taatcccaga tagtcctaat    840

aagccatacg atatgaaaga agtaatttcg gaaatagtgg atgaaggcgt gtattttgaa    900

tcacaggcaa tgtatgcgca aaacataata acggcatttg caaggcttaa tggaaggacg    960

gtagggataa tagcaaatca gcctaaagtt ttggctggat gtctcgacat caatgcgtct   1020

gataaggcat cgaggtttat aaggttttgc gatgcattta acatcccgct tctcaatata   1080

gtagatgttc caggattttt gcctggaacg aatcaagagt acggtggaat aatacgccat   1140

ggggcaaaga tgttgtacgc ttactctgag gctacagtgc caaaagtgac tctcattgtg   1200

aggaaagctt atggcggtgc ttaccttgcc atgtgcagca aagacttagg agctgatttt   1260

gttttggcat ggcctactgc tgaaatagcg gtcatgggac ctgatggggc agcaaacatc   1320

gtgtttaaaa atgaaataaa atcgtctgat gatcctgtgg ctgcaagaaa tgaaaagata   1380

aatgagtaca gggagaattt cgcaaatcca tacagggcag cagcgagagg atatgtagat   1440

gatgtagttc tgccgcaaga gacgagacct cgcctcatct cggcgttcga tatgcttatg   1500

agcaaaaggg agtcaaggcc cagcaaaaag catggcaatt ttcctgttta a            1551
```

<210> SEQ ID NO 29
<211> LENGTH: 516
<212> TYPE: PRT
<213> ORGANISM: T. saccharolyticum

<400> SEQUENCE: 29

```
Met Ser Ile Asp Asp Arg Ile Glu Asp Leu Leu Arg Arg Arg Glu Met
1               5                   10                  15

Val Leu Glu Gly Gly Gly Leu Asp Lys Val Glu Lys Gln His Gln Lys
            20                  25                  30

Gly Lys Leu Thr Ala Arg Glu Arg Ile Tyr Lys Leu Leu Asp Glu Asp
        35                  40                  45

Ser Phe Val Glu Ile Asp Ala Tyr Val Glu His Arg Cys Ile Asp Phe
    50                  55                  60

Gly Met Glu Lys Gln Arg Ile Pro Gly Glu Gly Val Val Thr Gly Tyr
65                  70                  75                  80

Gly Thr Ile Asp Gly Arg Leu Val Tyr Val Tyr Ala Gln Asp Phe Thr
                85                  90                  95

Val Leu Gly Gly Ser Leu Gly Glu Tyr His Ala Lys Lys Ile Thr Lys
            100                 105                 110

Ile Met Asp Met Ala Leu Lys Met Gly Ala Pro Leu Ile Gly Leu Asn
        115                 120                 125

Asp Ser Gly Gly Ala Arg Ile Gln Glu Gly Val Asp Ala Leu Ser Gly
    130                 135                 140

Tyr Gly Asn Ile Phe Phe Arg Asn Thr Leu Ala Ser Gly Val Ile Pro
145                 150                 155                 160

Gln Ile Ser Val Ile Met Gly Pro Ser Ala Gly Gly Ala Val Tyr Ser
                165                 170                 175

Pro Ala Leu Thr Asp Phe Ile Phe Met Val Asp Lys Thr Ser Gln Met
            180                 185                 190

Phe Ile Thr Gly Pro Gln Val Ile Lys Ala Val Thr Gly Glu Asp Val
        195                 200                 205

Ser Ala Glu Glu Leu Gly Gly Ser Ile Thr His Ser Thr Lys Ser Gly
    210                 215                 220
```

-continued

```
Val Ala His Phe Arg Ala Glu Asn Asp Glu Glu Cys Leu Lys Met Val
225                 230                 235                 240

Arg Lys Leu Leu Ser Tyr Leu Pro Ser Asn Asn Leu Glu Asp Pro Pro
                245                 250                 255

Gln Leu Ala Thr Asp Asp Asp Ile Asn Arg Phe Ser Asp Arg Leu Ile
            260                 265                 270

Glu Ile Ile Pro Asp Ser Pro Asn Lys Pro Tyr Asp Met Lys Glu Val
        275                 280                 285

Ile Ser Glu Ile Val Asp Glu Gly Val Tyr Phe Glu Ser Gln Ala Met
    290                 295                 300

Tyr Ala Gln Asn Ile Ile Thr Ala Phe Ala Arg Leu Asn Gly Arg Thr
305                 310                 315                 320

Val Gly Ile Ile Ala Asn Gln Pro Lys Val Leu Ala Gly Cys Leu Asp
                325                 330                 335

Ile Asn Ala Ser Asp Lys Ala Ser Arg Phe Ile Arg Phe Cys Asp Ala
            340                 345                 350

Phe Asn Ile Pro Leu Leu Asn Ile Val Asp Val Pro Gly Phe Leu Pro
        355                 360                 365

Gly Thr Asn Gln Glu Tyr Gly Gly Ile Ile Arg His Gly Ala Lys Met
    370                 375                 380

Leu Tyr Ala Tyr Ser Glu Ala Thr Val Pro Lys Val Thr Leu Ile Val
385                 390                 395                 400

Arg Lys Ala Tyr Gly Gly Ala Tyr Leu Ala Met Cys Ser Lys Asp Leu
                405                 410                 415

Gly Ala Asp Phe Val Leu Ala Trp Pro Thr Ala Glu Ile Ala Val Met
            420                 425                 430

Gly Pro Asp Gly Ala Ala Asn Ile Val Phe Lys Asn Glu Ile Lys Ser
        435                 440                 445

Ser Asp Asp Pro Val Ala Ala Arg Asn Glu Lys Ile Asn Glu Tyr Arg
    450                 455                 460

Glu Asn Phe Ala Asn Pro Tyr Arg Ala Ala Ala Arg Gly Tyr Val Asp
465                 470                 475                 480

Asp Val Val Leu Pro Gln Glu Thr Arg Pro Arg Leu Ile Ser Ala Phe
                485                 490                 495

Asp Met Leu Met Ser Lys Arg Glu Ser Arg Pro Ser Lys Lys His Gly
            500                 505                 510

Asn Phe Pro Val
        515


<210> SEQ ID NO 30
<211> LENGTH: 384
<212> TYPE: DNA
<213> ORGANISM: T. saccharolyticum

<400> SEQUENCE: 30

atgaaaaaat ttatagtaac tgtcaatgga aaaaaatacg atgtggaagt agaagaagta      60

aaagtcgacg tggcaagtga gaaaaaagca aaagaagata ctgctgctaa aaatgcgtca     120

gatgcaagtg taaaaagcaa acaggttgaa gtaaaaaacg aagtcaaaga cggtttctca     180

atcaatgcac cgatgccggg aactatattg gatgtcaaaa taagccaagg ccagactgtc     240

agacgaggcg atgtgctttt aatactggaa gccatgaaga tggaaaatga aatcacgtca     300

ccttacgatg gcacaataat atccataaat gtttcaaaag gtgcctctgt aaatacaggc     360

gatgtgcttt tgtacttaaa atga                                            384
```

<210> SEQ ID NO 31
<211> LENGTH: 127
<212> TYPE: PRT
<213> ORGANISM: T. saccharolyticum

<400> SEQUENCE: 31

```
Met Lys Lys Phe Ile Val Thr Val Asn Gly Lys Lys Tyr Asp Val Glu
1               5                   10                  15

Val Glu Glu Val Lys Val Asp Val Ala Ser Glu Lys Lys Ala Lys Glu
            20                  25                  30

Asp Thr Ala Ala Lys Asn Ala Ser Asp Ala Ser Val Lys Ser Lys Gln
        35                  40                  45

Val Glu Val Lys Asn Glu Val Lys Asp Gly Phe Ser Ile Asn Ala Pro
    50                  55                  60

Met Pro Gly Thr Ile Leu Asp Val Lys Ile Ser Gln Gly Gln Thr Val
65                  70                  75                  80

Arg Arg Gly Asp Val Leu Leu Ile Leu Glu Ala Met Lys Met Glu Asn
                85                  90                  95

Glu Ile Thr Ser Pro Tyr Asp Gly Thr Ile Ile Ser Ile Asn Val Ser
            100                 105                 110

Lys Gly Ala Ser Val Asn Thr Gly Asp Val Leu Leu Tyr Leu Lys
        115                 120                 125
```

<210> SEQ ID NO 32
<211> LENGTH: 1395
<212> TYPE: DNA
<213> ORGANISM: T. saccharolyticum

<400> SEQUENCE: 32

```
atgtctaaga taaaaataac ggagactgtt ttaagagatg cacatcaatc gttgctggca     60

accagaatga caaccgatga aatgcttcct atagcagaaa aattagatga agttggtttt    120

ttctcgctgg aagcatgggg cggtgctaca tttgatgcat gtatgagatt tttgaatgaa    180

gacccatggg aaagattaag acttttaaag aaggcgatta agaagacacc tcttcaaatg    240

cttttaagag gtcaaaattt actcggatat aaacactatc ccgatgatgt cgtaaatgaa    300

tttataataa aatctgttga aaatggtata gatataataa gaatttttga tgcgttaaat    360

gatgtgagaa atttagaagt gccaataaaa tctgcaaaaa gtgcaggtgc tcatgtacag    420

gcagctattg tatatacagt tagtcctgta cataatacag atcattattt gaaagtggca    480

aagtctcttc aagatatggg tgcggattcc atatgcatta aggatatgtc tggaatatta    540

tcaccctatg ttgcatacga tttgattaaa tctctgaaaa gagcacttta cacgccaatt    600

caactgcata gccattatac agcaggactg gcttcaatga cttatttaaa agccatagaa    660

gctggtgtag acggggttga tacagctatt tcttcgcttg ccttaggaac atcacaacca    720

gctacagaat caatcgtggc tgcattgaaa gatacagaat atgatacagg gctagattta    780

aaattgcttg ctgagatagc tcagcatttt aatgtagtca aacagaatca caaaaatgac    840

agcgatatgt ctttgcttat gtctgttgat gttaaagcat tagaaagtca aataccaggg    900

ggaatgttat caaatttggt ttcacagcta aagcagcaga atgcattaaa caaatatcaa    960

gacgtcttga aagaagttcc aagggtacgc gaagatttgg gatatcctcc tcttgttact   1020

ccaatgagcc agatggttgg aacccaggct gttttaaatg ttattacagg ggagagatat   1080

aaaatcgttc ctaaagaaat taaagattat gtcaaaggtt tatatgggat gccaccagct   1140

ccaatttcag attctatacg aaagaaaata atcggcgatg aagaagtaat ttcaaagagg   1200
```

```
ccagcagatt tactaagtcc tcaattggat gaatttaaaa atgagataaa ggaatttata   1260

gagcaagatg aagatgtttt atcatatgca ttatttcctc aagtagcaag aagatttttc   1320

gagtataggc aagccaaaaa atacagaatt gattcaacat tattaaatat cgaagaaagg   1380

gttcatccga tataa                                                    1395


<210> SEQ ID NO 33
<211> LENGTH: 464
<212> TYPE: PRT
<213> ORGANISM: T. saccharolyticum

<400> SEQUENCE: 33

Met Ser Lys Ile Lys Ile Thr Glu Thr Val Leu Arg Asp Ala His Gln
1               5                   10                  15

Ser Leu Leu Ala Thr Arg Met Thr Thr Asp Glu Met Leu Pro Ile Ala
            20                  25                  30

Glu Lys Leu Asp Glu Val Gly Phe Phe Ser Leu Glu Ala Trp Gly Gly
        35                  40                  45

Ala Thr Phe Asp Ala Cys Met Arg Phe Leu Asn Glu Asp Pro Trp Glu
    50                  55                  60

Arg Leu Arg Leu Leu Lys Lys Ala Ile Lys Lys Thr Pro Leu Gln Met
65                  70                  75                  80

Leu Leu Arg Gly Gln Asn Leu Leu Gly Tyr Lys His Tyr Pro Asp Asp
                85                  90                  95

Val Val Asn Glu Phe Ile Ile Lys Ser Val Glu Asn Gly Ile Asp Ile
            100                 105                 110

Ile Arg Ile Phe Asp Ala Leu Asn Asp Val Arg Asn Leu Glu Val Pro
        115                 120                 125

Ile Lys Ser Ala Lys Ser Ala Gly Ala His Val Gln Ala Ala Ile Val
    130                 135                 140

Tyr Thr Val Ser Pro Val His Asn Thr Asp His Tyr Leu Lys Val Ala
145                 150                 155                 160

Lys Ser Leu Gln Asp Met Gly Ala Asp Ser Ile Cys Ile Lys Asp Met
                165                 170                 175

Ser Gly Ile Leu Ser Pro Tyr Val Ala Tyr Asp Leu Ile Lys Ser Leu
            180                 185                 190

Lys Arg Ala Leu Tyr Thr Pro Ile Gln Leu His Ser His Tyr Thr Ala
        195                 200                 205

Gly Leu Ala Ser Met Thr Tyr Leu Lys Ala Ile Glu Ala Gly Val Asp
    210                 215                 220

Gly Val Asp Thr Ala Ile Ser Ser Leu Ala Leu Gly Thr Ser Gln Pro
225                 230                 235                 240

Ala Thr Glu Ser Ile Val Ala Ala Leu Lys Asp Thr Glu Tyr Asp Thr
                245                 250                 255

Gly Leu Asp Leu Lys Leu Leu Ala Glu Ile Ala Gln His Phe Asn Val
            260                 265                 270

Val Lys Gln Asn His Lys Asn Asp Ser Asp Met Ser Leu Leu Met Ser
        275                 280                 285

Val Asp Val Lys Ala Leu Glu Ser Gln Ile Pro Gly Gly Met Leu Ser
    290                 295                 300

Asn Leu Val Ser Gln Leu Lys Gln Gln Asn Ala Leu Asn Lys Tyr Gln
305                 310                 315                 320

Asp Val Leu Lys Glu Val Pro Arg Val Arg Glu Asp Leu Gly Tyr Pro
                325                 330                 335
```

```
Pro Leu Val Thr Pro Met Ser Gln Met Val Gly Thr Gln Ala Val Leu
            340                 345                 350

Asn Val Ile Thr Gly Glu Arg Tyr Lys Ile Val Pro Lys Glu Ile Lys
        355                 360                 365

Asp Tyr Val Lys Gly Leu Tyr Gly Met Pro Pro Ala Pro Ile Ser Asp
    370                 375                 380

Ser Ile Arg Lys Lys Ile Ile Gly Asp Glu Glu Val Ile Ser Lys Arg
385                 390                 395                 400

Pro Ala Asp Leu Leu Ser Pro Gln Leu Asp Glu Phe Lys Asn Glu Ile
                405                 410                 415

Lys Glu Phe Ile Glu Gln Asp Glu Asp Val Leu Ser Tyr Ala Leu Phe
            420                 425                 430

Pro Gln Val Ala Arg Arg Phe Phe Glu Tyr Arg Gln Ala Lys Lys Tyr
        435                 440                 445

Arg Ile Asp Ser Thr Leu Leu Asn Ile Glu Glu Arg Val His Pro Ile
    450                 455                 460
```

<210> SEQ ID NO 34
<211> LENGTH: 159
<212> TYPE: DNA
<213> ORGANISM: T. saccharolyticum

<400> SEQUENCE: 34

```
atggaagaga taaatgaaga aatagttgct gtcattgaag ctgcgattta cgcggcattt     60

ggtcagtacg aaaagaattt ccgcatcaag gtaataaaga gagtggactc aaatatgccg    120

gaatggagaa aagctggcct ttacaatcag atgagatag                           159
```

<210> SEQ ID NO 35
<211> LENGTH: 52
<212> TYPE: PRT
<213> ORGANISM: T. saccharolyticum

<400> SEQUENCE: 35

```
Met Glu Glu Ile Asn Glu Glu Ile Val Ala Val Ile Glu Ala Ala Ile
1               5                   10                  15

Tyr Ala Ala Phe Gly Gln Tyr Glu Lys Asn Phe Arg Ile Lys Val Ile
            20                  25                  30

Lys Arg Val Asp Ser Asn Met Pro Glu Trp Arg Lys Ala Gly Leu Tyr
        35                  40                  45

Asn Gln Met Arg
    50
```

<210> SEQ ID NO 36
<211> LENGTH: 1542
<212> TYPE: DNA
<213> ORGANISM: C. bescii

<400> SEQUENCE: 36

```
atgacaaaca agctcagaga gctcaagcaa aagagagaaa gaatactaaa gcttggtgga     60

gaagataaaa taaaaaaaca gcatgatagc aaaaaactta cttgtagaga gagaatagaa    120

tatttacttg accctggaag cttcaatgaa atagatatgt ttgttgaaca cagatgtcaa    180

gaatttgata tgaaagatac atttgtcccc tgtgatggtg ttgtaacggg ttatggaaca    240

atcaatggca gaaaagtttt tgtttatgct caagatttta cttcgatagg cggttctctt    300

ggcgagatgc atgcaaaaaa gatttgtaaa gttttggact tagcattaaa atatggttgt    360
```

-continued

```
ccagtgatag gtataaatga ttctggtggt gcaagaattc aagaaggtgt tgatgcatta    420

gcaggatatg gtgaaatctt ctatagaaat accatggcat caggtgtaat tccacaaatt    480

gcagctataa tgggaccttg tgcaggtgga gctgtatact ctcctgctat tatggatttt    540

atttttatgg tggacaaaac cagccaaatg tttgttacag gacctcaggt tataaaagct    600

gtgactggag aggagatatc ctttgaagag cttggtggcg cttacactca cagctcaaag    660

agtggagttg ctcattttat tgcagaggat gagtatcacc tacttgatat gataaagtat    720

ttattgtcgt ttataccttc aaataacatg gaagacccac cttttataat gtcatctgat    780

tcagaaaaaa gatttgttcc cgagctcgaa aatataattc cgcaagagcc aaacaaagct    840

tatgatgtaa aagaaataat ttataaagta gtagacaacc aagaattttt agaagtacaa    900

ccttattttg ctcaaaatgc tgttgtagga tttggtagaa tagggggctt tagcgtagga    960

attgtagcaa atcagcccaa agtgaacgct ggagtgcttg attatgattc gtctgacaag   1020

atagcacgat ttgtaagatt ttgtgatgct tttaatattc ccataataac atttacagac   1080

gtgcctggat tttgccagg tgttaaccaa gagcacaatg gaataattcg tcatggggct   1140

aaggttttgt atgcatactc agaggcaaca gttccaaaga taaatgtaat tttgagaaaa   1200

gcatatggtg gggcttacat tgcaatgagc agcaaacaca ttggtgcaga ctttgtgttt   1260

gcatggccaa ctgccgagat agctgttatg ggaccagatg gcgcagcaaa tattatattt   1320

agaaaagaga tacaaagcgc tcaaaatccc gaagaggaaa gaaaaagaag gatagaagag   1380

tatactcaaa agtttgcaaa tccatacatt gcagctgccc gtgggtatgt tgacgatgtg   1440

attgagccac agcttacccg taacaaaatc attgaggcgc tcaaaatttc cattacaaaa   1500

agagagcaaa ggcccccaaa aaagcatggc aatattccat ta                      1542
```

<210> SEQ ID NO 37
<211> LENGTH: 514
<212> TYPE: PRT
<213> ORGANISM: C. bescii

<400> SEQUENCE: 37

```
Met Thr Asn Lys Leu Arg Glu Leu Lys Gln Lys Arg Glu Arg Ile Leu
1               5                   10                  15

Lys Leu Gly Gly Glu Asp Lys Ile Lys Lys Gln His Asp Ser Lys Lys
            20                  25                  30

Leu Thr Cys Arg Glu Arg Ile Glu Tyr Leu Leu Asp Pro Gly Ser Phe
        35                  40                  45

Asn Glu Ile Asp Met Phe Val Glu His Arg Cys Gln Glu Phe Asp Met
    50                  55                  60

Lys Asp Thr Phe Val Pro Cys Asp Gly Val Val Thr Gly Tyr Gly Thr
65                  70                  75                  80

Ile Asn Gly Arg Lys Val Phe Val Tyr Ala Gln Asp Phe Thr Ser Ile
                85                  90                  95

Gly Gly Ser Leu Gly Glu Met His Ala Lys Lys Ile Cys Lys Val Leu
            100                 105                 110

Asp Leu Ala Leu Lys Tyr Gly Cys Pro Val Ile Gly Ile Asn Asp Ser
        115                 120                 125

Gly Gly Ala Arg Ile Gln Glu Gly Val Asp Ala Leu Ala Gly Tyr Gly
    130                 135                 140

Glu Ile Phe Tyr Arg Asn Thr Met Ala Ser Gly Val Ile Pro Gln Ile
145                 150                 155                 160

Ala Ala Ile Met Gly Pro Cys Ala Gly Gly Ala Val Tyr Ser Pro Ala
```

```
                165                 170                 175

Ile Met Asp Phe Ile Phe Met Val Asp Lys Thr Ser Gln Met Phe Val
            180                 185                 190

Thr Gly Pro Gln Val Ile Lys Ala Val Thr Gly Glu Glu Ile Ser Phe
        195                 200                 205

Glu Glu Leu Gly Gly Ala Tyr Thr His Ser Ser Lys Ser Gly Val Ala
    210                 215                 220

His Phe Ile Ala Glu Asp Glu Tyr His Leu Leu Asp Met Ile Lys Tyr
225                 230                 235                 240

Leu Leu Ser Phe Ile Pro Ser Asn Asn Met Glu Asp Pro Pro Phe Ile
                245                 250                 255

Met Ser Ser Asp Ser Glu Lys Arg Phe Val Pro Glu Leu Glu Asn Ile
            260                 265                 270

Ile Pro Gln Glu Pro Asn Lys Ala Tyr Asp Val Lys Glu Ile Ile Tyr
        275                 280                 285

Lys Val Val Asp Asn Gln Glu Phe Leu Glu Val Gln Pro Tyr Phe Ala
    290                 295                 300

Gln Asn Ala Val Val Gly Phe Gly Arg Ile Gly Gly Phe Ser Val Gly
305                 310                 315                 320

Ile Val Ala Asn Gln Pro Lys Val Asn Ala Gly Val Leu Asp Tyr Asp
                325                 330                 335

Ser Ser Asp Lys Ile Ala Arg Phe Val Arg Phe Cys Asp Ala Phe Asn
            340                 345                 350

Ile Pro Ile Ile Thr Phe Thr Asp Val Pro Gly Phe Leu Pro Gly Val
        355                 360                 365

Asn Gln Glu His Asn Gly Ile Ile Arg His Gly Ala Lys Val Leu Tyr
    370                 375                 380

Ala Tyr Ser Glu Ala Thr Val Pro Lys Ile Asn Val Ile Leu Arg Lys
385                 390                 395                 400

Ala Tyr Gly Gly Ala Tyr Ile Ala Met Ser Ser Lys His Ile Gly Ala
                405                 410                 415

Asp Phe Val Phe Ala Trp Pro Thr Ala Glu Ile Ala Val Met Gly Pro
            420                 425                 430

Asp Gly Ala Ala Asn Ile Ile Phe Arg Lys Glu Ile Gln Ser Ala Gln
        435                 440                 445

Asn Pro Glu Glu Glu Arg Lys Arg Arg Ile Glu Glu Tyr Thr Gln Lys
    450                 455                 460

Phe Ala Asn Pro Tyr Ile Ala Ala Ala Arg Gly Tyr Val Asp Asp Val
465                 470                 475                 480

Ile Glu Pro Gln Leu Thr Arg Asn Lys Ile Ile Glu Ala Leu Lys Ile
                485                 490                 495

Ser Ile Thr Lys Arg Glu Gln Arg Pro Pro Lys Lys His Gly Asn Ile
            500                 505                 510

Pro Leu


<210> SEQ ID NO 38
<211> LENGTH: 381
<212> TYPE: DNA
<213> ORGANISM: C. bescii

<400> SEQUENCE: 38

atgagaaagt tcaaggtgaa gatcaatagc caagaatttg ttgtagaagt ggaagaaata      60

ggagttgaaa atgctacttc tgtcgtgcca aggcctaaga ttggccattt tgagccaaaa     120
```

caggaaaaac atgaggataa aacaaaacaa agccctgtac tttcttctga taaaaattcg 180
gttgttgccc agcttccggg tactattgta aggctgctaa aaagtgaagg tgatgttgtt 240
gatgcaaatg aacctgtttt aattcttgaa gccatgaaaa tggaaaatga aataactgca 300
cctgtcaaag gaaaaattaa aagaatacat gtaaaggaag ggcagaaggt agcaaaagga 360
gatttgctat ttgaaataga g 381

<210> SEQ ID NO 39
<211> LENGTH: 127
<212> TYPE: PRT
<213> ORGANISM: C. bescii

<400> SEQUENCE: 39

Met Arg Lys Phe Lys Val Lys Ile Asn Ser Gln Glu Phe Val Val Glu
1 5 10 15

Val Glu Glu Ile Gly Val Glu Asn Ala Thr Ser Val Val Pro Arg Pro
20 25 30

Lys Ile Gly His Phe Glu Pro Lys Gln Glu Lys His Glu Asp Lys Thr
35 40 45

Lys Gln Ser Pro Val Leu Ser Ser Asp Lys Asn Ser Val Val Ala Gln
50 55 60

Leu Pro Gly Thr Ile Val Arg Leu Leu Lys Ser Glu Gly Asp Val Val
65 70 75 80

Asp Ala Asn Glu Pro Val Leu Ile Leu Glu Ala Met Lys Met Glu Asn
85 90 95

Glu Ile Thr Ala Pro Val Lys Gly Lys Ile Lys Arg Ile His Val Lys
100 105 110

Glu Gly Gln Lys Val Ala Lys Gly Asp Leu Leu Phe Glu Ile Glu
115 120 125

<210> SEQ ID NO 40
<211> LENGTH: 1389
<212> TYPE: DNA
<213> ORGANISM: C. bescii

<400> SEQUENCE: 40
atgggggtaa aaataacaga aacaatactc agagatgctc atcagtcact cattgcaacc 60
cgcatgacaa ctgaacagat gcttgagatt gctcctgtgc ttgaccaagt tggttattat 120
tcggttgagt gctggggcgg tgctacattt gatgcgtgtc tgaggttttt caatgaagac 180
ccatgggaaa gattaaaaag actgagaact gcttttaaaa agacaaagct ccagatgctt 240
cttcgaggac aaaatcttgt tgggtataga cattattctg atgatgttgt tgaagagttt 300
gtaaaaaagg ccatatacta tggcattgat attataagaa tatttgatgc acttaatgac 360
atccggaata ttgaaatggc tctaaaaata acaaaaaaag aaaaaggaca tgcccaggtt 420
gccatatcat acactgtctc accttatcat actattgaaa actatgtaaa tttggcaaaa 480
caaatagaag aacttggggc agactcaatt tgtataaaag acatggctgg gcttctctct 540
ccatttgatg cttataaact tgtaaaagcg ttaaaagagc aggtaaaact tcctattcat 600
cttcatacac actacaccac aggatttgga tcaatgacat atttgaaagc tgtcgaagca 660
ggtgtggatg gtattgacac ggctttatct ccgcttgcac tgggcacatc ccagcctcca 720
accgaaacaa ttgtatatgc acttgaaaat acagaatatg ctccaaaact tgatttagaa 780
aagatcaacg aggcaagcga atattttaaa gtactcagag aagaatatat aagaaaaggg 840
cttcttgacc cgaaagtatt aagtgttgat ataaacgctc ttcattatca aatacctggt 900

```
ggaatgctat caaatcttat ttctcagcta aaagaacaag ggcaggaaga caagttagat    960

gaggttttaa aagaggtacc tgaggttcga aaagattttg gatatccgcc acttgtaact   1020

cctacgagtc aaattgtggg aacacaagct gttttgaatg ttatagcagg tgagagatac   1080

aaacttgtca caaaagaaac aaaagcatat tttaaaggtg agtatgggaa acctccagct   1140

cctgtgaatg aagaggtaaa aagaaaaatc ttgaaagacg aaaaagagat aacctgcaga   1200

cctgcagatt tgattttgcc agagcttgaa aatgcaaaag aaaagattaa ggagtatatt   1260

gaaaatgata ctgatgtggt aacttactgt ttattccctc aacttgcaga aaatttttc   1320

aaattaaggt tcgcaaaaaa atacaaggtt gacgctgatc ttgttcaggg taacaaagtg   1380

tatcctgtg                                                          1389
```

<210> SEQ ID NO 41
<211> LENGTH: 463
<212> TYPE: PRT
<213> ORGANISM: C. bescii

<400> SEQUENCE: 41

```
Met Gly Val Lys Ile Thr Glu Thr Ile Leu Arg Asp Ala His Gln Ser
1               5                   10                  15

Leu Ile Ala Thr Arg Met Thr Thr Glu Gln Met Leu Glu Ile Ala Pro
            20                  25                  30

Val Leu Asp Gln Val Gly Tyr Tyr Ser Val Glu Cys Trp Gly Gly Ala
        35                  40                  45

Thr Phe Asp Ala Cys Leu Arg Phe Phe Asn Glu Asp Pro Trp Glu Arg
    50                  55                  60

Leu Lys Arg Leu Arg Thr Ala Phe Lys Lys Thr Lys Leu Gln Met Leu
65                  70                  75                  80

Leu Arg Gly Gln Asn Leu Val Gly Tyr Arg His Tyr Ser Asp Asp Val
                85                  90                  95

Val Glu Glu Phe Val Lys Lys Ala Ile Tyr Tyr Gly Ile Asp Ile Ile
            100                 105                 110

Arg Ile Phe Asp Ala Leu Asn Asp Ile Arg Asn Ile Glu Met Ala Leu
        115                 120                 125

Lys Ile Thr Lys Lys Glu Lys Gly His Ala Gln Val Ala Ile Ser Tyr
    130                 135                 140

Thr Val Ser Pro Tyr His Thr Ile Glu Asn Tyr Val Asn Leu Ala Lys
145                 150                 155                 160

Gln Ile Glu Glu Leu Gly Ala Asp Ser Ile Cys Ile Lys Asp Met Ala
                165                 170                 175

Gly Leu Leu Ser Pro Phe Asp Ala Tyr Lys Leu Val Lys Ala Leu Lys
            180                 185                 190

Glu Gln Val Lys Leu Pro Ile His Leu His Thr His Tyr Thr Thr Gly
        195                 200                 205

Phe Gly Ser Met Thr Tyr Leu Lys Ala Val Glu Ala Gly Val Asp Gly
    210                 215                 220

Ile Asp Thr Ala Leu Ser Pro Leu Ala Leu Gly Thr Ser Gln Pro Pro
225                 230                 235                 240

Thr Glu Thr Ile Val Tyr Ala Leu Glu Asn Thr Glu Tyr Ala Pro Lys
                245                 250                 255

Leu Asp Leu Glu Lys Ile Asn Glu Ala Ser Glu Tyr Phe Lys Val Leu
            260                 265                 270

Arg Glu Glu Tyr Ile Arg Lys Gly Leu Leu Asp Pro Lys Val Leu Ser
```

```
        275                 280                 285

Val Asp Ile Asn Ala Leu His Tyr Gln Ile Pro Gly Gly Met Leu Ser
    290                 295                 300

Asn Leu Ile Ser Gln Leu Lys Glu Gln Gly Gln Glu Asp Lys Leu Asp
305                 310                 315                 320

Glu Val Leu Lys Glu Val Pro Glu Val Arg Lys Asp Phe Gly Tyr Pro
                325                 330                 335

Pro Leu Val Thr Pro Thr Ser Gln Ile Val Gly Thr Gln Ala Val Leu
            340                 345                 350

Asn Val Ile Ala Gly Glu Arg Tyr Lys Leu Val Thr Lys Glu Thr Lys
        355                 360                 365

Ala Tyr Phe Lys Gly Glu Tyr Gly Lys Pro Pro Ala Pro Val Asn Glu
    370                 375                 380

Glu Val Lys Arg Lys Ile Leu Lys Asp Glu Lys Glu Ile Thr Cys Arg
385                 390                 395                 400

Pro Ala Asp Leu Ile Leu Pro Glu Leu Glu Asn Ala Lys Glu Lys Ile
                405                 410                 415

Lys Glu Tyr Ile Glu Asn Asp Thr Asp Val Val Thr Tyr Cys Leu Phe
            420                 425                 430

Pro Gln Leu Ala Glu Asn Phe Phe Lys Leu Arg Phe Ala Lys Lys Tyr
        435                 440                 445

Lys Val Asp Ala Asp Leu Val Gln Gly Asn Lys Val Tyr Pro Val
    450                 455                 460


<210> SEQ ID NO 42
<211> LENGTH: 189
<212> TYPE: DNA
<213> ORGANISM: C. bescii

<400> SEQUENCE: 42

atgtatgctc aggtcagtac tatttcaacc attacaaaag aagaacttgc ttgtatttgt     60

gcatgtctgc acattgtgat gggtgaaggt caatataaaa ttaccaacat aactaaacag    120

caaaacaagt gggtcaaagg tgcaagagaa atgatgctca atcagtcaca gatgttttat    180

agatggagg                                                            189


<210> SEQ ID NO 43
<211> LENGTH: 63
<212> TYPE: PRT
<213> ORGANISM: C. bescii

<400> SEQUENCE: 43

Met Tyr Ala Gln Val Ser Thr Ile Ser Thr Ile Thr Lys Glu Glu Leu
1               5                   10                  15

Ala Cys Ile Cys Ala Cys Leu His Ile Val Met Gly Glu Gly Gln Tyr
            20                  25                  30

Lys Ile Thr Asn Ile Thr Lys Gln Gln Asn Lys Trp Val Lys Gly Ala
        35                  40                  45

Arg Glu Met Met Leu Asn Gln Ser Gln Met Phe Tyr Arg Trp Arg
    50                  55                  60


<210> SEQ ID NO 44
<211> LENGTH: 1548
<212> TYPE: DNA
<213> ORGANISM: C. cellulolyticum

<400> SEQUENCE: 44
```

atgtcacaaa ttgaaaagat acaaaattta aaaaacatga aaaaaactat agctaaaggc 60
ggcggagaag agaaaatagc aaaaagacac gcagatggaa agctttctgc cagagaaaga 120
atccatttgt tgtttgatga aacagtttt gttgaggtag atgcattcat agaatccaga 180
tgctttgact ttggtatgca gaagaagaaa cttccaggtg acggggttgt taccggttac 240
ggaacagtta atggcagaaa ggtctttgtt tcatcacagg actttactgt tataggcggt 300
tcattgggag agatgcacgc aaagaaaatt acaaaggtta tggatatggc tctgaaaatg 360
ggagcaccgt tcatagccat taatgattcc ggcggagctc gtattgagga aggtctggat 420
gctctttcag gttacggaga tattttttac aggaatactc ttgcatcagg cgttattccg 480
cagatatcag taataatggg gccatgtgca ggtggtgcgg tatattcccc ggccataact 540
gattttatat tcatggtgga aaaaacaagt cagatgttta ttacaggccc acaggtaata 600
aagtctgtta cgggtgaaga tgtatcagtt gaaaatctgg gaggtgcaga tgttcatact 660
gctacaagcg gtgtagcaca tttcaaatct tcaagcgaag aagagtgtat agaagatata 720
aagaggcttt taagttttat tcccgataat aatgtatcag atactatgta ctacggagtg 780
tctgatgctg ccgacagatt agccgaaagc ctcaacagca ttattccaga agagtcaaac 840
aagccatatg acatgtttga cgtaatagca gaagtagtag atgatggaga tttctttgaa 900
gttcagagtt atttctctca gaatataata atcggatttg caagaatgaa tggcagaagt 960
gttggtattg ttgcaaacca gcctaagata atggcagggt cactagatat gaacgcggct 1020
gataaggcgg cacgtttcgt tcgtttctgt gatgcattta atattcctgt cgtttcatta 1080
accgatgtac ctgcattcct gcccggggta gcccaggagc ataacggcat aatacgtcac 1140
ggtgcaaaac tcctatatgc tttctctgaa gcaacagtac caaagataaa tgttattctt 1200
agaaaggcat atggaggagc atatattgct atgaacagta aaacaatagg tgccgatatg 1260
gttttggcat ggccatcagc tgaaattgca gttatgggac ctgacggagc agcaaatatt 1320
atatttaaaa aggatattgc tgcgtcggaa gatccagcag aaaccagaaa ggaaaagatt 1380
gcggaatata gagataaatt ctcaaatcct tatgtagcag catcaagagg gtatattgat 1440
gatgttatcg agccttctga aaccagagta aaaattataa ctgctctgga aatgctggat 1500
acaaagaggg aaaacaggcc ttcaaaaaaa catggaaaca ttccgcta 1548

<210> SEQ ID NO 45
<211> LENGTH: 516
<212> TYPE: PRT
<213> ORGANISM: C. cellulolyticum

<400> SEQUENCE: 45

Met Ser Gln Ile Glu Lys Ile Gln Asn Leu Lys Asn Met Lys Lys Thr
1 5 10 15

Ile Ala Lys Gly Gly Gly Glu Glu Lys Ile Ala Lys Arg His Ala Asp
20 25 30

Gly Lys Leu Ser Ala Arg Glu Arg Ile His Leu Leu Phe Asp Glu Asn
35 40 45

Ser Phe Val Glu Val Asp Ala Phe Ile Glu Ser Arg Cys Phe Asp Phe
50 55 60

Gly Met Gln Lys Lys Lys Leu Pro Gly Asp Gly Val Val Thr Gly Tyr
65 70 75 80

Gly Thr Val Asn Gly Arg Lys Val Phe Val Ser Ser Gln Asp Phe Thr
85 90 95

Val Ile Gly Gly Ser Leu Gly Glu Met His Ala Lys Lys Ile Thr Lys

```
            100                 105                 110

Val Met Asp Met Ala Leu Lys Met Gly Ala Pro Phe Ile Ala Ile Asn
        115                 120                 125

Asp Ser Gly Gly Ala Arg Ile Glu Glu Gly Leu Asp Ala Leu Ser Gly
    130                 135                 140

Tyr Gly Asp Ile Phe Tyr Arg Asn Thr Leu Ala Ser Gly Val Ile Pro
145                 150                 155                 160

Gln Ile Ser Val Ile Met Gly Pro Cys Ala Gly Gly Ala Val Tyr Ser
                165                 170                 175

Pro Ala Ile Thr Asp Phe Ile Phe Met Val Glu Lys Thr Ser Gln Met
            180                 185                 190

Phe Ile Thr Gly Pro Gln Val Ile Lys Ser Val Thr Gly Glu Asp Val
        195                 200                 205

Ser Val Glu Asn Leu Gly Gly Ala Asp Val His Thr Ala Thr Ser Gly
    210                 215                 220

Val Ala His Phe Lys Ser Ser Ser Glu Glu Glu Cys Ile Glu Asp Ile
225                 230                 235                 240

Lys Arg Leu Leu Ser Phe Ile Pro Asp Asn Asn Val Ser Asp Thr Met
                245                 250                 255

Tyr Tyr Gly Val Ser Asp Ala Ala Asp Arg Leu Ala Glu Ser Leu Asn
            260                 265                 270

Ser Ile Ile Pro Glu Glu Ser Asn Lys Pro Tyr Asp Met Phe Asp Val
        275                 280                 285

Ile Ala Glu Val Val Asp Asp Gly Asp Phe Phe Glu Val Gln Ser Tyr
    290                 295                 300

Phe Ser Gln Asn Ile Ile Ile Gly Phe Ala Arg Met Asn Gly Arg Ser
305                 310                 315                 320

Val Gly Ile Val Ala Asn Gln Pro Lys Ile Met Ala Gly Ser Leu Asp
                325                 330                 335

Met Asn Ala Ala Asp Lys Ala Ala Arg Phe Val Arg Phe Cys Asp Ala
            340                 345                 350

Phe Asn Ile Pro Val Val Ser Leu Thr Asp Val Pro Ala Phe Leu Pro
        355                 360                 365

Gly Val Ala Gln Glu His Asn Gly Ile Ile Arg His Gly Ala Lys Leu
    370                 375                 380

Leu Tyr Ala Phe Ser Glu Ala Thr Val Pro Lys Ile Asn Val Ile Leu
385                 390                 395                 400

Arg Lys Ala Tyr Gly Gly Ala Tyr Ile Ala Met Asn Ser Lys Thr Ile
                405                 410                 415

Gly Ala Asp Met Val Leu Ala Trp Pro Ser Ala Glu Ile Ala Val Met
            420                 425                 430

Gly Pro Asp Gly Ala Ala Asn Ile Ile Phe Lys Lys Asp Ile Ala Ala
        435                 440                 445

Ser Glu Asp Pro Ala Glu Thr Arg Lys Glu Lys Ile Ala Glu Tyr Arg
    450                 455                 460

Asp Lys Phe Ser Asn Pro Tyr Val Ala Ala Ser Arg Gly Tyr Ile Asp
465                 470                 475                 480

Asp Val Ile Glu Pro Ser Glu Thr Arg Val Lys Ile Ile Thr Ala Leu
                485                 490                 495

Glu Met Leu Asp Thr Lys Arg Glu Asn Arg Pro Ser Lys Lys His Gly
            500                 505                 510

Asn Ile Pro Leu
        515
```

<210> SEQ ID NO 46
<211> LENGTH: 366
<212> TYPE: DNA
<213> ORGANISM: C. cellulolyticum

<400> SEQUENCE: 46
atgagtaaat atataataaa ggtaaacgga actccttatg aagtagaggt tgaagaagtg 60
ggcgggggaa ggcccatttc agctgctcca aagctaagag ctaccaagcc gggacatacc 120
tctgctgcaa aagcagcaca gccgcaggca ggtaaagcag gtgatgttgc tgctccaatg 180
ccgggaactg ttttaaaggt aaaggttgct atcggtgatg aagtaaagaa ggggcaggta 240
cttttaatac ttgaagctat gaaaatggag aatgaaatag ttgctccggc tgacggtaaa 300
gttacggcgt taaacgtcga ggccggaaag tctgttactg ctggagaact aatggtgtct 360
atagcc 366

<210> SEQ ID NO 47
<211> LENGTH: 122
<212> TYPE: PRT
<213> ORGANISM: C. cellulolyticum

<400> SEQUENCE: 47

Met Ser Lys Tyr Ile Ile Lys Val Asn Gly Thr Pro Tyr Glu Val Glu
1 5 10 15

Val Glu Glu Val Gly Gly Gly Arg Pro Ile Ser Ala Ala Pro Lys Leu
20 25 30

Arg Ala Thr Lys Pro Gly His Thr Ser Ala Ala Lys Ala Ala Gln Pro
35 40 45

Gln Ala Gly Lys Ala Gly Asp Val Ala Ala Pro Met Pro Gly Thr Val
50 55 60

Leu Lys Val Lys Val Ala Ile Gly Asp Glu Val Lys Lys Gly Gln Val
65 70 75 80

Leu Leu Ile Leu Glu Ala Met Lys Met Glu Asn Glu Ile Val Ala Pro
85 90 95

Ala Asp Gly Lys Val Thr Ala Leu Asn Val Glu Ala Gly Lys Ser Val
100 105 110

Thr Ala Gly Glu Leu Met Val Ser Ile Ala
115 120

<210> SEQ ID NO 48
<211> LENGTH: 1530
<212> TYPE: DNA
<213> ORGANISM: C. cellulolyticum

<400> SEQUENCE: 48
atgccaggcg taagaattac ggaaacagtt ttaagagatg ctcaccagtc ccttatagca 60
accagaatga agaccgaaga aatgcttcca attgttgaga agcttgacaa tattggttac 120
cattcactgg aagcttgggg cggagctact tttgactcat gtatgagatt tttgaatgaa 180
gatccatgga tgagacttag aaaaataaaa gatgttgcaa agaaaacacc tctgcaaatg 240
cttcttaggg gccagaacct tttaggatac aaacactatg ccgatgatat agttgagtac 300
tttgttcaga aggctgttgc aaacggcatg gacattatga gaatattcga tgcactaaat 360
gatgccagga atatcgagac ggcaattaag gcatgtaaaa aggaaggcgg ccatgctcag 420
ggctgtattt gctatactat aagtcctgtt cacaatcttg agctttttgt aaaagatgca 480

```
aagcagttgg agagcatggg agcagattct atctgtataa aagacatggc cggacttctg    540

gtgccgtatc aggcttatga actggtaaag gctttgaaag aaagtgtaaa gataccgata    600

caattgcaca ctcactatac tagcggtgta gcatctatga cgtatttgaa ggctatagaa    660

gcaggtatag atattgttga ctgtgcaatt tcacctatgt caatgggaac gtcacagccg    720

cctacagagc ctttggtggc aactttaaag ggaactgatt tcgatactgg actggatttg    780

gaaaaactca gtgaaattgc agactatttc agacccctta aagaaaaata tattgagagc    840

ggactattag acgttaaggt aatgggtgtt gacgttaaca ctcttattta tcaggtacct    900

ggtggaatgc tttcaaatct tgtttcacaa ttgaagcagt caaatgcttt ggataaatat    960

gaagaggttc tcaaggaagt tcccagagta agagccgatt tcggctatcc tccgcttgta   1020

acaccatcaa gtcagatagt tggtacccaa gcggtactta atgtattgac tggtgagaga   1080

tacaagatgg taccaaagga atcaaaaggc gttgtaaagg gggaatacgg taaaacccct   1140

gcacctatta gtgatgaaat aaaagctaag attctgggcg atgaaaagcc tataacatgc   1200

agacctgctg accttattga acctgagctt gaaaagatta gagaagctgt taaggattat   1260

atagagcagg atgaagatgt actttcatac gcaatgcttc ctcaggttgc cgagaagttc   1320

tttaaacagc gtattgagga tagaaataag gctactgcac ccgcatcaga cgaaataaaa   1380

cccgaagttg tagcggcaat atcagccgta gtaaacgaaa tgggcgaaag agacggcaca   1440

cagtacagaa tcggaaatat ctctaagttg aaccagaatc agaacagatg gagtctgtat   1500

ggtatgcttg atagattcag aacaaaaatt                                    1530


<210> SEQ ID NO 49
<211> LENGTH: 510
<212> TYPE: PRT
<213> ORGANISM: C. cellulolyticum

<400> SEQUENCE: 49

Met Pro Gly Val Arg Ile Thr Glu Thr Val Leu Arg Asp Ala His Gln
1               5                   10                  15

Ser Leu Ile Ala Thr Arg Met Lys Thr Glu Glu Met Leu Pro Ile Val
            20                  25                  30

Glu Lys Leu Asp Asn Ile Gly Tyr His Ser Leu Glu Ala Trp Gly Gly
        35                  40                  45

Ala Thr Phe Asp Ser Cys Met Arg Phe Leu Asn Glu Asp Pro Trp Met
    50                  55                  60

Arg Leu Arg Lys Ile Lys Asp Val Ala Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Ile Val Glu Tyr Phe Val Gln Lys Ala Val Ala Asn Gly Met Asp Ile
            100                 105                 110

Met Arg Ile Phe Asp Ala Leu Asn Asp Ala Arg Asn Ile Glu Thr Ala
        115                 120                 125

Ile Lys Ala Cys Lys Lys Glu Gly Gly His Ala Gln Gly Cys Ile Cys
    130                 135                 140

Tyr Thr Ile Ser Pro Val His Asn Leu Glu Leu Phe Val Lys Asp Ala
145                 150                 155                 160

Lys Gln Leu Glu Ser Met Gly Ala Asp Ser Ile Cys Ile Lys Asp Met
                165                 170                 175

Ala Gly Leu Leu Val Pro Tyr Gln Ala Tyr Glu Leu Val Lys Ala Leu
            180                 185                 190
```

-continued

```
Lys Glu Ser Val Lys Ile Pro Ile Gln Leu His Thr His Tyr Thr Ser
        195                 200                 205

Gly Val Ala Ser Met Thr Tyr Leu Lys Ala Ile Glu Ala Gly Ile Asp
    210                 215                 220

Ile Val Asp Cys Ala Ile Ser Pro Met Ser Met Gly Thr Ser Gln Pro
225                 230                 235                 240

Pro Thr Glu Pro Leu Val Ala Thr Leu Lys Gly Thr Asp Phe Asp Thr
                245                 250                 255

Gly Leu Asp Leu Glu Lys Leu Ser Glu Ile Ala Asp Tyr Phe Arg Pro
            260                 265                 270

Leu Lys Glu Lys Tyr Ile Glu Ser Gly Leu Leu Asp Val Lys Val Met
        275                 280                 285

Gly Val Asp Val Asn Thr Leu Ile Tyr Gln Val Pro Gly Gly Met Leu
    290                 295                 300

Ser Asn Leu Val Ser Gln Leu Lys Gln Ser Asn Ala Leu Asp Lys Tyr
305                 310                 315                 320

Glu Glu Val Leu Lys Glu Val Pro Arg Val Arg Ala Asp Phe Gly Tyr
                325                 330                 335

Pro Pro Leu Val Thr Pro Ser Ser Gln Ile Val Gly Thr Gln Ala Val
            340                 345                 350

Leu Asn Val Leu Thr Gly Glu Arg Tyr Lys Met Val Pro Lys Glu Ser
        355                 360                 365

Lys Gly Val Val Lys Gly Glu Tyr Gly Lys Thr Pro Ala Pro Ile Ser
    370                 375                 380

Asp Glu Ile Lys Ala Lys Ile Leu Gly Asp Glu Lys Pro Ile Thr Cys
385                 390                 395                 400

Arg Pro Ala Asp Leu Ile Glu Pro Glu Leu Glu Lys Ile Arg Glu Ala
                405                 410                 415

Val Lys Asp Tyr Ile Glu Gln Asp Glu Asp Val Leu Ser Tyr Ala Met
            420                 425                 430

Leu Pro Gln Val Ala Glu Lys Phe Phe Lys Gln Arg Ile Glu Asp Arg
        435                 440                 445

Asn Lys Ala Thr Ala Pro Ala Ser Asp Glu Ile Lys Pro Glu Val Val
    450                 455                 460

Ala Ala Ile Ser Ala Val Val Asn Glu Met Gly Glu Arg Asp Gly Thr
465                 470                 475                 480

Gln Tyr Arg Ile Gly Asn Ile Ser Lys Leu Asn Gln Asn Gln Asn Arg
                485                 490                 495

Trp Ser Leu Tyr Gly Met Leu Asp Arg Phe Arg Thr Lys Ile
            500                 505                 510
```

<210> SEQ ID NO 50
<211> LENGTH: 1581
<212> TYPE: DNA
<213> ORGANISM: C. kroppenstedtii

<400> SEQUENCE: 50

```
atgagtgagc aacctcacga tcccagcatg cctgagcgcc tcggacagct ggaagaagaa      60

agaaaccgca tccgactcgg cggcgggcag gcacgcctgg acaagcagca cgaccgcggc     120

aagatgaccg cccgcgagcg catcaccaag cttgtcgacg aagacacgtt ccaggaaacc     180

ggaatgttcg ccaagcaccg gacaacgcac ttcggcatgg acaaggccga cgcccccgcc     240

gacggcgtcg tcaccggatc cggcgcggtc tacggacggc cagtgcacat cgcgtcccag     300
```

```
gacttcagcg tcatgggcgg atctgctggc gaaatgcagt ccaacaaagt ggtcgccatg    360

atgaaggcgt ccgcgaccac cggcaccccc ttcgtcttta tcaacgactc cggcggagct    420

cgtgtccaag agggcatcga ctccctctcc ggatacggcc gcgtgttcta caacaacgtg    480

ctgctctccg gactcgtacc gcaggtctcc atcatcgccg gcccgtgcgc tggtggtgcg    540

gcctactcgc cggcactgac ggacttcatc atccagaccc gcaaggccaa catgttcatc    600

accggcccca aggtcatcga gtccgtgacc ggcgaaaaag tcacggccga cgaactcggt    660

ggtgccgatg cccacatgag cacagctggc aacattcact tcgtcgccga cgatgacgag    720

caagccatcc tgatcgcgca gaagctcctg agcttcctgc cgcaaaacaa caccgaagag    780

ccgcccatcg tcgatccgga cgaggttgtc gagcccgacg attccctccg cgacatcgtc    840

cccgtcgatg gccgcaaggg ctacgacgtc cgcgatatca tccgcaagat cgtcgactac    900

ggcgacttcc tcgaggtcca ggccggatac gcccaaaacc tcgtggtcgg atttgcccgc    960

gtcgttggcc ggacagtcgg tatcgtcgct aaccagtcgc aagtgatgtc cggcgttctg   1020

gacatcaact cgtcggacaa aggcgcaagc ttcgttcgct tctgcgactc cttcaatatt   1080

ccgctcctca ccctcgtcga cgtccccggc ttcatgccag gtgtcgcaca agagcatggc   1140

ggaatcattc gccacggcgc gaagatgctg ttcgcctact cggcggccac cgtgccgaag   1200

ctgaccgtgg tcctccgcaa atcctatggc ggatcgtacc tggccatgtg ctccaaggac   1260

cttggcgcgg accgcgtctg ggcgtggccc accgctgaaa ttgcggtcat gggtgccgac   1320

ggagccgtga acgtcgtctt ccgtaaggaa atcaagaaag cccaggaaga gggtggcgac   1380

gaagccgctg cagcaaagaa gagcgaactc gtccagctct acaaagacac cttctcgacg   1440

ccatacatgg cggcgtcccg aggcctcgtc gatgacatca tcgaccccgc ggacacacgt   1500

cgcgaaattg ctctggccct ggagttgctg accaacaagc gtgagaaccg gccgtccaag   1560

aagcacggcc tggcacccaa c                                              1581
```

```
<210> SEQ ID NO 51
<211> LENGTH: 527
<212> TYPE: PRT
<213> ORGANISM: C. kroppenstedtii

<400> SEQUENCE: 51

Met Ser Glu Gln Pro His Asp Pro Ser Met Pro Glu Arg Leu Gly Gln
1               5                   10                  15

Leu Glu Glu Glu Arg Asn Arg Ile Arg Leu Gly Gly Gly Gln Ala Arg
            20                  25                  30

Leu Asp Lys Gln His Asp Arg Gly Lys Met Thr Ala Arg Glu Arg Ile
        35                  40                  45

Thr Lys Leu Val Asp Glu Asp Thr Phe Gln Glu Thr Gly Met Phe Ala
    50                  55                  60

Lys His Arg Thr Thr His Phe Gly Met Asp Lys Ala Asp Ala Pro Ala
65                  70                  75                  80

Asp Gly Val Val Thr Gly Ser Gly Ala Val Tyr Gly Arg Pro Val His
                85                  90                  95

Ile Ala Ser Gln Asp Phe Ser Val Met Gly Gly Ser Ala Gly Glu Met
            100                 105                 110

Gln Ser Asn Lys Val Val Ala Met Met Lys Ala Ser Ala Thr Thr Gly
        115                 120                 125

Thr Pro Phe Val Phe Ile Asn Asp Ser Gly Gly Ala Arg Val Gln Glu
    130                 135                 140
```

Gly Ile Asp Ser Leu Ser Gly Tyr Gly Arg Val Phe Tyr Asn Asn Val
145 150 155 160

Leu Leu Ser Gly Leu Val Pro Gln Val Ser Ile Ile Ala Gly Pro Cys
165 170 175

Ala Gly Gly Ala Ala Tyr Ser Pro Ala Leu Thr Asp Phe Ile Ile Gln
180 185 190

Thr Arg Lys Ala Asn Met Phe Ile Thr Gly Pro Lys Val Ile Glu Ser
195 200 205

Val Thr Gly Glu Lys Val Thr Ala Asp Glu Leu Gly Gly Ala Asp Ala
210 215 220

His Met Ser Thr Ala Gly Asn Ile His Phe Val Ala Asp Asp Asp Glu
225 230 235 240

Gln Ala Ile Leu Ile Ala Gln Lys Leu Leu Ser Phe Leu Pro Gln Asn
245 250 255

Asn Thr Glu Glu Pro Pro Ile Val Asp Pro Asp Glu Val Val Glu Pro
260 265 270

Asp Asp Ser Leu Arg Asp Ile Val Pro Val Asp Gly Arg Lys Gly Tyr
275 280 285

Asp Val Arg Asp Ile Ile Arg Lys Ile Val Asp Tyr Gly Asp Phe Leu
290 295 300

Glu Val Gln Ala Gly Tyr Ala Gln Asn Leu Val Val Gly Phe Ala Arg
305 310 315 320

Val Val Gly Arg Thr Val Gly Ile Val Ala Asn Gln Ser Gln Val Met
325 330 335

Ser Gly Val Leu Asp Ile Asn Ser Ser Asp Lys Gly Ala Ser Phe Val
340 345 350

Arg Phe Cys Asp Ser Phe Asn Ile Pro Leu Leu Thr Leu Val Asp Val
355 360 365

Pro Gly Phe Met Pro Gly Val Ala Gln Glu His Gly Gly Ile Ile Arg
370 375 380

His Gly Ala Lys Met Leu Phe Ala Tyr Ser Ala Ala Thr Val Pro Lys
385 390 395 400

Leu Thr Val Val Leu Arg Lys Ser Tyr Gly Gly Ser Tyr Leu Ala Met
405 410 415

Cys Ser Lys Asp Leu Gly Ala Asp Arg Val Trp Ala Trp Pro Thr Ala
420 425 430

Glu Ile Ala Val Met Gly Ala Asp Gly Ala Val Asn Val Val Phe Arg
435 440 445

Lys Glu Ile Lys Lys Ala Gln Glu Glu Gly Gly Asp Glu Ala Ala Ala
450 455 460

Ala Lys Lys Ser Glu Leu Val Gln Leu Tyr Lys Asp Thr Phe Ser Thr
465 470 475 480

Pro Tyr Met Ala Ala Ser Arg Gly Leu Val Asp Asp Ile Ile Asp Pro
485 490 495

Ala Asp Thr Arg Arg Glu Ile Ala Leu Ala Leu Glu Leu Leu Thr Asn
500 505 510

Lys Arg Glu Asn Arg Pro Ser Lys Lys His Gly Leu Ala Pro Asn
515 520 525

<210> SEQ ID NO 52
<211> LENGTH: 369
<212> TYPE: DNA
<213> ORGANISM: C. kroppenstedtii

<400> SEQUENCE: 52

-continued

```
atgaaactga cagttaccgt caacggcgtc ccctattccg tggacgtaga agttgaacac     60

gaagaacgcc ccacactcgg caccatcatc actggtggca acagcaacgg gccaacaccc    120

accgcgccga ccacctcatc tgtccagggt gtcagcgcca attcggtcac ggcacccctg    180

gctggttccg tcagcaaggt gcttgtggag gaaggccaag ccatcacggc cggcgaagtg    240

atcgttgtcc ttgaagccat gaagatggaa accgaaatta cggcccccaa cgacggcacc    300

gtcaccgcgc ttcacgtgca acccggcgac gccgttcagg gtggacagtc tctgctggag    360

atcggggac                                                            369
```

<210> SEQ ID NO 53
<211> LENGTH: 123
<212> TYPE: PRT
<213> ORGANISM: C. kroppenstedtii

<400> SEQUENCE: 53

```
Met Lys Leu Thr Val Thr Val Asn Gly Val Pro Tyr Ser Val Asp Val
1               5                   10                  15

Glu Val Glu His Glu Glu Arg Pro Thr Leu Gly Thr Ile Ile Thr Gly
            20                  25                  30

Gly Asn Ser Asn Gly Pro Thr Pro Thr Ala Pro Thr Thr Ser Ser Val
        35                  40                  45

Gln Gly Val Ser Ala Asn Ser Val Thr Ala Pro Leu Ala Gly Ser Val
    50                  55                  60

Ser Lys Val Leu Val Glu Glu Gly Gln Ala Ile Thr Ala Gly Glu Val
65                  70                  75                  80

Ile Val Val Leu Glu Ala Met Lys Met Glu Thr Glu Ile Thr Ala Pro
                85                  90                  95

Asn Asp Gly Thr Val Thr Ala Leu His Val Gln Pro Gly Asp Ala Val
            100                 105                 110

Gln Gly Gly Gln Ser Leu Leu Glu Ile Gly Asp
        115                 120
```

<210> SEQ ID NO 54
<211> LENGTH: 1494
<212> TYPE: DNA
<213> ORGANISM: C. kroppenstedtii

<400> SEQUENCE: 54

```
atgaccacgc gaaaaattgg agtgaccgaa ctggctctgc gtgatgctca ccagagcctc     60

atggcaacac gcatggccct cgaagacatg gtcgatgcct gtgaggatat agacaaagcc    120

gggtactgga gcgtggaatg ctggggcggg gcaaccttcg acgcctgcat tcgcttcctg    180

aacgaagacc cgtgggagag actgcgcaca ttccgcaagc tcatgcccaa ctcacgcctt    240

cagatgctgc ttcgtggcca gaatcttctg ggataccgtc actacgagga cggcgtcgtc    300

gataagtttg ttgaaaaatc cgctgaaaac ggcatggacg tcttcagggt tttcgacgcg    360

ctcaacgacc cccgcaacct cgagcacgcc atgcaagctg tgaaaaaagt gggcaagcac    420

gcgcagggca ccatctgcta caccgtgtcc ccgctacacg acgtgcaggg ctacattgat    480

ctagcagggc gtttgctgga catgggcgcg gattcgatcg cgctcaaaga catggcagcg    540

ctgctcaaac cacagcccgc ctacgacatt atccgtggca ttaaggacac ctacggcgag    600

gatacgcaga tcaacgtcca ctgccactcc accaccggcg tcacgatggt caccctcatg    660

aaggccattg aagccggtgc ggatgtcgtc gacaccgcca tttcctccat gtccctcggc    720
```

-continued

```
ccagggcata accccaccga gtctctcgtc gaaatgctcg aaggaaccga ctacgagacc    780

gggcttgaca tggatcggct cattaacatc cgcgaccact tcaagacagt gcgcccgaag    840

tacgcggagt ttgagtcgaa aacactggtc aacaccaata ttttccaatc gcagattccg    900

ggcggaatgc tctccaacat ggaatcgcag ctcaaagccc agggcgcggg cgaccgtatc    960

gacgaggtca tgaaagaagt ccccgtcgtt cggaaagctg ccggataccc gccgttggtg   1020

acgccatcgt cccagatcgt cggcacccag gccgtgttca acgtgctgat gggccgctac   1080

aaagtactca cggctgaatt cgccgacctc ctcctcgggt actacggcga agcaccaggt   1140

gagagggata aagacctcat cgagcaagcc aagaagcaga ccggcaaaga gcccatcacc   1200

gagcgtcctg ctgacctcct tgagcccgaa tgggacaacc tggttgagga agctgacgaa   1260

ctcgacggca ccgacgggtc cgacgaagac gtcctcacaa acgccctgtt cccgcaggtc   1320

gcgccgggat tcttcaagac tcgccccgac ggcccgaaga acgtcggcaa gactaaggaa   1380

cagctcgagc gcgaagaggc gaaggcctcc ggcgacgcca ctgccatccg cgaaccgatt   1440

atgtacaaag tcaccacagg cggccgcagc cacactgtct ccgtggaacc cgca         1494


<210> SEQ ID NO 55
<211> LENGTH: 498
<212> TYPE: PRT
<213> ORGANISM: C. kroppenstedtii

<400> SEQUENCE: 55

Met Thr Thr Arg Lys Ile Gly Val Thr Glu Leu Ala Leu Arg Asp Ala
1               5                   10                  15

His Gln Ser Leu Met Ala Thr Arg Met Ala Leu Glu Asp Met Val Asp
            20                  25                  30

Ala Cys Glu Asp Ile Asp Lys Ala Gly Tyr Trp Ser Val Glu Cys Trp
        35                  40                  45

Gly Gly Ala Thr Phe Asp Ala Cys Ile Arg Phe Leu Asn Glu Asp Pro
    50                  55                  60

Trp Glu Arg Leu Arg Thr Phe Arg Lys Leu Met Pro Asn Ser Arg Leu
65                  70                  75                  80

Gln Met Leu Leu Arg Gly Gln Asn Leu Leu Gly Tyr Arg His Tyr Glu
                85                  90                  95

Asp Gly Val Val Asp Lys Phe Val Glu Lys Ser Ala Glu Asn Gly Met
            100                 105                 110

Asp Val Phe Arg Val Phe Asp Ala Leu Asn Asp Pro Arg Asn Leu Glu
        115                 120                 125

His Ala Met Gln Ala Val Lys Lys Val Gly Lys His Ala Gln Gly Thr
    130                 135                 140

Ile Cys Tyr Thr Val Ser Pro Leu His Asp Val Gln Gly Tyr Ile Asp
145                 150                 155                 160

Leu Ala Gly Arg Leu Leu Asp Met Gly Ala Asp Ser Ile Ala Leu Lys
                165                 170                 175

Asp Met Ala Ala Leu Leu Lys Pro Gln Pro Ala Tyr Asp Ile Ile Arg
            180                 185                 190

Gly Ile Lys Asp Thr Tyr Gly Glu Asp Thr Gln Ile Asn Val His Cys
        195                 200                 205

His Ser Thr Thr Gly Val Thr Met Val Thr Leu Met Lys Ala Ile Glu
    210                 215                 220

Ala Gly Ala Asp Val Val Asp Thr Ala Ile Ser Ser Met Ser Leu Gly
225                 230                 235                 240
```

-continued

```
Pro Gly His Asn Pro Thr Glu Ser Leu Val Glu Met Leu Glu Gly Thr
                245                 250                 255

Asp Tyr Glu Thr Gly Leu Asp Met Asp Arg Leu Ile Asn Ile Arg Asp
            260                 265                 270

His Phe Lys Thr Val Arg Pro Lys Tyr Ala Glu Phe Glu Ser Lys Thr
        275                 280                 285

Leu Val Asn Thr Asn Ile Phe Gln Ser Gln Ile Pro Gly Gly Met Leu
    290                 295                 300

Ser Asn Met Glu Ser Gln Leu Lys Ala Gln Gly Ala Gly Asp Arg Ile
305                 310                 315                 320

Asp Glu Val Met Lys Glu Val Pro Val Val Arg Lys Ala Ala Gly Tyr
                325                 330                 335

Pro Pro Leu Val Thr Pro Ser Ser Gln Ile Val Gly Thr Gln Ala Val
            340                 345                 350

Phe Asn Val Leu Met Gly Arg Tyr Lys Val Leu Thr Ala Glu Phe Ala
        355                 360                 365

Asp Leu Leu Leu Gly Tyr Tyr Gly Glu Ala Pro Gly Glu Arg Asp Lys
    370                 375                 380

Asp Leu Ile Glu Gln Ala Lys Lys Gln Thr Gly Lys Glu Pro Ile Thr
385                 390                 395                 400

Glu Arg Pro Ala Asp Leu Leu Glu Pro Glu Trp Asp Asn Leu Val Glu
                405                 410                 415

Glu Ala Asp Glu Leu Asp Gly Thr Asp Gly Ser Asp Glu Asp Val Leu
            420                 425                 430

Thr Asn Ala Leu Phe Pro Gln Val Ala Pro Gly Phe Phe Lys Thr Arg
        435                 440                 445

Pro Asp Gly Pro Lys Asn Val Gly Lys Thr Lys Glu Gln Leu Glu Arg
    450                 455                 460

Glu Glu Ala Lys Ala Ser Gly Asp Ala Thr Ala Ile Arg Glu Pro Ile
465                 470                 475                 480

Met Tyr Lys Val Thr Thr Gly Gly Arg Ser His Thr Val Ser Val Glu
                485                 490                 495

Pro Ala


<210> SEQ ID NO 56
<211> LENGTH: 285
<212> TYPE: DNA
<213> ORGANISM: C. kroppenstedtii

<400> SEQUENCE: 56

atgaatacag acaatgcatc ctctgctgaa ctcagtcagt tgttggcccg cctgtccaac      60

caggtagaaa agctctcccg caacgtcacc aagctcgaaa atgaagttgc ggcactgaag     120

cagcgctctg acgaggaaat tcctgaagat gtcttgattg cgatcagtgc ggccgtatcc     180

gcctacatgg gtaaccgcgg aaccgtgcgc gcagttcact tcttgcgcca tcgcagctgg     240

tcacagcaag gtcggcaggc agttcagcac aaggcgaaat ggcaa                     285


<210> SEQ ID NO 57
<211> LENGTH: 95
<212> TYPE: PRT
<213> ORGANISM: C. kroppenstedtii

<400> SEQUENCE: 57

Met Asn Thr Asp Asn Ala Ser Ser Ala Glu Leu Ser Gln Leu Leu Ala
1               5                   10                  15
```

```
Arg Leu Ser Asn Gln Val Glu Lys Leu Ser Arg Asn Val Thr Lys Leu
            20                  25                  30

Glu Asn Glu Val Ala Ala Leu Lys Gln Arg Ser Asp Glu Glu Ile Pro
        35                  40                  45

Glu Asp Val Leu Ile Ala Ile Ser Ala Ala Val Ser Ala Tyr Met Gly
    50                  55                  60

Asn Arg Gly Thr Val Arg Ala Val His Phe Leu Arg His Arg Ser Trp
65                  70                  75                  80

Ser Gln Gln Gly Arg Gln Ala Val Gln His Lys Ala Lys Trp Gln
                85                  90                  95
```

<210> SEQ ID NO 58
<211> LENGTH: 1542
<212> TYPE: DNA
<213> ORGANISM: G. bemidjiensis

<400> SEQUENCE: 58

```
atgtccatag aagagaagat aaaagcgctg aacgacaaga agagcaagct gaagctgggc     60

ggcgggcgct cgaagatcga ccagcagcac gcccagggaa gcctgaccgc ccgggagcgg    120

atagaggcgc tggtggacaa ggacagcttc caggaaatcg gcatcttcgc caggcaccgc    180

tgcaccaatt tcggcatggc cgggaaggaa ctgccggccg aaggggtggt caccggcgca    240

gggagcgtgg gcgggaggat ggtgcacctg gcgagccagg atttcaccgt cgccggggga    300

tcggcgggcg aggtgcacag cgacaagatc gtgcaggcga tgctggggtc gctgaagacc    360

ggaacccccct tcgtcttcat gaacgattcc ggcggcgcca ggatccagga agggatcgac    420

tcgttagccg gctacggcaa ggtcttctac cacaacgtga tgctcagcgg ggtggtgccg    480

cagatctcgc tcatctgcgg cccctgtgcc gggggcgcgg cctacagccc ggcgctcacc    540

gatttcatca tccagaccgc caaggcgcgc atgttcatca ccggcccttc cgtgatcaag    600

gaggcgaccg gcgaagagat cagcgccgag gagctgggag ggccactgtc gcagatgaac    660

catagcggcg tagcccattt cgtggcggag aacgacctgg tggcgcttcg catctgcaag    720

aagctccttt cctacctccc ctccaacaac atcgaggacc cgccgcagtt ggaaagcgac    780

gacgtcatcg tcccggacaa gacgttgaac agcatcgtgc cgtcggagca gaagaaggcc    840

tacgacgtga ggaacgtgat cacgcgcctg atcgacggcg gcgacttcct ggaggtgcag    900

cctctgttcg ctgccaacat cgtggtcggg ttcggcagga tactcgggcg gagcgtcggc    960

atcgtcgcca atcagccgtc ggtcttggcg ggggcgctgg acatcaacgc ttcggacaag   1020

ggagccaggt tcgtccggtt ctgcaacgcc ttcaacatcc cgctggtgac cctggtggac   1080

gttccgggtt ttctccccgg ggtacagcag gagaaggggg ggatcatccg ccacggcgcc   1140

aagatgctct tcgcctacgc cgcggccacc gtcccgaaga taaccgtcat catgcgcaag   1200

gcgtacggcg gcgccttcct cgccatgtgc ggcaaggagt tggagaccga tcgggttttc   1260

gcctggccca gcgccgagat cgcggtcatg ggaccgcagg gagcggtcaa cgtcatcttc   1320

cggaacgaga tcgcccaggc ggaagatccc aagaaaaagc gcgacgagct gatcgcttct   1380

taccagggaa ccttcgccac tccctatgcg gccgcggcac gccgcgatgt ggacgacatc   1440

atcgagcccg ccgatacgag gcgccacctc gccatgacgc tggacatcct gagcaccaag   1500

cgcgaattca ggcccatgaa gaagcatggc ctcattccgc tg                      1542
```

<210> SEQ ID NO 59
<211> LENGTH: 514
<212> TYPE: PRT

<213> ORGANISM: G. bemidjiensis

<400> SEQUENCE: 59

```
Met Ser Ile Glu Glu Lys Ile Lys Ala Leu Asn Asp Lys Lys Ser Lys
1               5                   10                  15

Leu Lys Leu Gly Gly Gly Arg Ser Lys Ile Asp Gln Gln His Ala Gln
            20                  25                  30

Gly Ser Leu Thr Ala Arg Glu Arg Ile Glu Ala Leu Val Asp Lys Asp
        35                  40                  45

Ser Phe Gln Glu Ile Gly Ile Phe Ala Arg His Arg Cys Thr Asn Phe
    50                  55                  60

Gly Met Ala Gly Lys Glu Leu Pro Ala Glu Gly Val Val Thr Gly Ala
65                  70                  75                  80

Gly Ser Val Gly Gly Arg Met Val His Leu Ala Ser Gln Asp Phe Thr
                85                  90                  95

Val Ala Gly Gly Ser Ala Gly Glu Val His Ser Asp Lys Ile Val Gln
            100                 105                 110

Ala Met Leu Gly Ser Leu Lys Thr Gly Thr Pro Phe Val Phe Met Asn
        115                 120                 125

Asp Ser Gly Gly Ala Arg Ile Gln Glu Gly Ile Asp Ser Leu Ala Gly
    130                 135                 140

Tyr Gly Lys Val Phe Tyr His Asn Val Met Leu Ser Gly Val Val Pro
145                 150                 155                 160

Gln Ile Ser Leu Ile Cys Gly Pro Cys Ala Gly Gly Ala Ala Tyr Ser
                165                 170                 175

Pro Ala Leu Thr Asp Phe Ile Ile Gln Thr Ala Lys Ala Arg Met Phe
            180                 185                 190

Ile Thr Gly Pro Ser Val Ile Lys Glu Ala Thr Gly Glu Glu Ile Ser
        195                 200                 205

Ala Glu Glu Leu Gly Gly Pro Leu Ser Gln Met Asn His Ser Gly Val
    210                 215                 220

Ala His Phe Val Ala Glu Asn Asp Leu Val Ala Leu Arg Ile Cys Lys
225                 230                 235                 240

Lys Leu Leu Ser Tyr Leu Pro Ser Asn Asn Ile Glu Asp Pro Pro Gln
                245                 250                 255

Leu Glu Ser Asp Asp Val Ile Val Pro Asp Lys Thr Leu Asn Ser Ile
            260                 265                 270

Val Pro Ser Glu Gln Lys Lys Ala Tyr Asp Val Arg Asn Val Ile Thr
        275                 280                 285

Arg Leu Ile Asp Gly Gly Asp Phe Leu Glu Val Gln Pro Leu Phe Ala
    290                 295                 300

Ala Asn Ile Val Val Gly Phe Gly Arg Ile Leu Gly Arg Ser Val Gly
305                 310                 315                 320

Ile Val Ala Asn Gln Pro Ser Val Leu Ala Gly Ala Leu Asp Ile Asn
                325                 330                 335

Ala Ser Asp Lys Gly Ala Arg Phe Val Arg Phe Cys Asn Ala Phe Asn
            340                 345                 350

Ile Pro Leu Val Thr Leu Val Asp Val Pro Gly Phe Leu Pro Gly Val
        355                 360                 365

Gln Gln Glu Lys Gly Gly Ile Ile Arg His Gly Ala Lys Met Leu Phe
    370                 375                 380

Ala Tyr Ala Ala Ala Thr Val Pro Lys Ile Thr Val Ile Met Arg Lys
385                 390                 395                 400
```

-continued

```
Ala Tyr Gly Gly Ala Phe Leu Ala Met Cys Gly Lys Glu Leu Glu Thr
                405                 410                 415

Asp Arg Val Phe Ala Trp Pro Ser Ala Glu Ile Ala Val Met Gly Pro
            420                 425                 430

Gln Gly Ala Val Asn Val Ile Phe Arg Asn Glu Ile Ala Gln Ala Glu
        435                 440                 445

Asp Pro Lys Lys Lys Arg Asp Glu Leu Ile Ala Ser Tyr Gln Gly Thr
    450                 455                 460

Phe Ala Thr Pro Tyr Ala Ala Ala Ala Arg Arg Asp Val Asp Asp Ile
465                 470                 475                 480

Ile Glu Pro Ala Asp Thr Arg Arg His Leu Ala Met Thr Leu Asp Ile
                485                 490                 495

Leu Ser Thr Lys Arg Glu Phe Arg Pro Met Lys Lys His Gly Leu Ile
            500                 505                 510

Pro Leu


<210> SEQ ID NO 60
<211> LENGTH: 393
<212> TYPE: DNA
<213> ORGANISM: G. bemidjiensis

<400> SEQUENCE: 60

gtgcaactga ccatgaccat tgacggaaag aaataccggg tggacgtaga agtcgaggaa      60

ggggaagagg tgcgtacgga aggggccttc cctcccaccg cgactatgca ggcgtacccg     120

gtgtattcgg cgcatccaac cgcgaccccg ccgctggccg cgccgacccc ggcctccagt     180

tcggaaaaga tctgccgcag tcccatcgcg gggtggtttt tcaagatcgt ggcgcaggtg     240

ggtcaacacc tggagatgaa cgacctgctg gtcgtcctcg aggcgatgaa gatggagacc     300

aacatcaccg cgcacatgtc cgggaaggtg gaaaagattc tggtttccgt gggcgaagcg     360

gtgcagcctg gacaggcaat tgccgaattt gcc                                  393


<210> SEQ ID NO 61
<211> LENGTH: 131
<212> TYPE: PRT
<213> ORGANISM: G. bemidjiensis

<400> SEQUENCE: 61

Val Gln Leu Thr Met Thr Ile Asp Gly Lys Lys Tyr Arg Val Asp Val
1               5                   10                  15

Glu Val Glu Glu Gly Glu Glu Val Arg Thr Glu Gly Ala Phe Pro Pro
            20                  25                  30

Thr Ala Thr Met Gln Ala Tyr Pro Val Tyr Ser Ala His Pro Thr Ala
        35                  40                  45

Thr Pro Pro Leu Ala Ala Pro Thr Pro Ala Ser Ser Ser Glu Lys Ile
    50                  55                  60

Cys Arg Ser Pro Ile Ala Gly Val Val Phe Lys Ile Val Ala Gln Val
65                  70                  75                  80

Gly Gln His Leu Glu Met Asn Asp Leu Leu Val Val Leu Glu Ala Met
                85                  90                  95

Lys Met Glu Thr Asn Ile Thr Ala His Met Ser Gly Lys Val Glu Lys
            100                 105                 110

Ile Leu Val Ser Val Gly Glu Ala Val Gln Pro Gly Gln Ala Ile Ala
        115                 120                 125

Glu Phe Ala
    130
```

<210> SEQ ID NO 62
<211> LENGTH: 1504
<212> TYPE: DNA
<213> ORGANISM: G. bemidjiensis

<400> SEQUENCE: 62
atggaccgca ttatcgacat aaccgaactg gctctgcgcg acgcgcacca gagccttatc 60
gctacgaggc tcgggataga cgacatggtt ccggtgtgcg aggacctgga ccaggcgggc 120
tactggtcca tcgagtgctg ggcggggcc acctatgacg cctgcatccg ctttctcaac 180
gaagatccgt gggtgaggct taggaccttc aaggagctga tgccgaaaac cccgctgcag 240
atgcttttgc gggggcagaa ccttttggga taccggcatt accaggacga ggtggtggac 300
cggttcgtcc agaagagcgc cgagaacggc atcgacgtgt tccggatctt cgatgcgctg 360
aacgatctga ggaacctgga gcggtcggtc caggcggtga agcagtgcgg aaagcacgcg 420
caggtcgcca tctcctatac catcagcccc attcacacca cggcgaaatt cgtggagcag 480
gcgaagcgcc tggtcgacat ggggtgcgac tccatctgca tcaaggacat ggcggcgctg 540
atcaagccgc acgcgacata cgacctggtg agagggatca aagaggcctg cggcgaccgg 600
atccggatac agctgcatgc gcacgccacc agcggcgtga ccatggtgag ttacatgaag 660
gcggtggagg cgggcgtgga cggcgtggac acggcggtga gttccatgag cctcgggccc 720
ggacacaacc cgacggagag ctttgcggag atgctggaaa atacgggcta caccacgcgc 780
atcgacctcg gccgggtgaa caaggtgaag gagcatttcg ccaaggtgct ccccaggtac 840
tcagaattcc tctccaccat caccggcgcg gagacggaga tcttcaggag ccagattcca 900
ggcgggatgc tttccaacat ggagagccag ttgaagcagc agggggctgg ggaccggatg 960
cgcgacgtgc tggaagagat accgctggtg agaaaggaca cgggatacgt cccgctggta 1020
accccgacca gccagatcgt cgggacccag gcggtgctga acgtattgat ggggcgctac 1080
aaggtgctga ccggcgagtt cgccgacctg atgctcggct actacggcct cacgccggga 1140
gaacggaacc cggaggtggt ggagcaggcg cgccgccacg cgaataagga gccgatagag 1200
tgccgccccg cagatctatt ggagccggaa tggggcaagc tgcgggcggc ggcgctcccc 1260
ttggagggtt gcgacggcag cgacgaggac gtgctcacct acgccctctt tccgcaggtg 1320
gcgccgaagt tcttcgccac gaggagtgaa ggaccccgaa acctggggcg cgatcccgtc 1380
accggagctt cggaaaccag cattcccgaa gggcaccccg ggaagatcac cggccccgtc 1440
acctacacgg tcaccttgag cgggcagccg cacaaggtga cggttgcacc ctacggccag 1500
gaat 1504

<210> SEQ ID NO 63
<211> LENGTH: 501
<212> TYPE: PRT
<213> ORGANISM: G. bemidjiensis

<400> SEQUENCE: 63

Met Asp Arg Ile Ile Asp Ile Thr Glu Leu Ala Leu Arg Asp Ala His
1 5 10 15

Gln Ser Leu Ile Ala Thr Arg Leu Gly Ile Asp Asp Met Val Pro Val
20 25 30

Cys Glu Asp Leu Asp Gln Ala Gly Tyr Trp Ser Ile Glu Cys Trp Gly
35 40 45

Gly Ala Thr Tyr Asp Ala Cys Ile Arg Phe Leu Asn Glu Asp Pro Trp

-continued

```
    50                  55                  60

Val Arg Leu Arg Thr Phe Lys Glu Leu Met Pro Lys Thr Pro Leu Gln
65                  70                  75                  80

Met Leu Leu Arg Gly Gln Asn Leu Leu Gly Tyr Arg His Tyr Gln Asp
                85                  90                  95

Glu Val Val Asp Arg Phe Val Gln Lys Ser Ala Glu Asn Gly Ile Asp
            100                 105                 110

Val Phe Arg Ile Phe Asp Ala Leu Asn Asp Leu Arg Asn Leu Glu Arg
        115                 120                 125

Ser Val Gln Ala Val Lys Gln Cys Gly Lys His Ala Gln Val Ala Ile
    130                 135                 140

Ser Tyr Thr Ile Ser Pro Ile His Thr Thr Ala Lys Phe Val Glu Gln
145                 150                 155                 160

Ala Lys Arg Leu Val Asp Met Gly Cys Asp Ser Ile Cys Ile Lys Asp
                165                 170                 175

Met Ala Ala Leu Ile Lys Pro His Ala Thr Tyr Asp Leu Val Arg Gly
            180                 185                 190

Ile Lys Glu Ala Cys Gly Asp Arg Ile Arg Ile Gln Leu His Ala His
        195                 200                 205

Ala Thr Ser Gly Val Thr Met Val Ser Tyr Met Lys Ala Val Glu Ala
    210                 215                 220

Gly Val Asp Gly Val Asp Thr Ala Val Ser Ser Met Ser Leu Gly Pro
225                 230                 235                 240

Gly His Asn Pro Thr Glu Ser Phe Ala Glu Met Leu Glu Asn Thr Gly
                245                 250                 255

Tyr Thr Thr Arg Ile Asp Leu Gly Arg Val Asn Lys Val Lys Glu His
            260                 265                 270

Phe Ala Lys Val Leu Pro Arg Tyr Ser Glu Phe Leu Ser Thr Ile Thr
        275                 280                 285

Gly Ala Glu Thr Glu Ile Phe Arg Ser Gln Ile Pro Gly Gly Met Leu
    290                 295                 300

Ser Asn Met Glu Ser Gln Leu Lys Gln Gln Gly Ala Gly Asp Arg Met
305                 310                 315                 320

Arg Asp Val Leu Glu Glu Ile Pro Leu Val Arg Lys Asp Thr Gly Tyr
                325                 330                 335

Val Pro Leu Val Thr Pro Thr Ser Gln Ile Val Gly Thr Gln Ala Val
            340                 345                 350

Leu Asn Val Leu Met Gly Arg Tyr Lys Val Leu Thr Gly Glu Phe Ala
        355                 360                 365

Asp Leu Met Leu Gly Tyr Tyr Gly Leu Thr Pro Gly Glu Arg Asn Pro
    370                 375                 380

Glu Val Val Glu Gln Ala Arg Arg His Ala Asn Lys Glu Pro Ile Glu
385                 390                 395                 400

Cys Arg Pro Ala Asp Leu Leu Glu Pro Glu Trp Gly Lys Leu Arg Ala
                405                 410                 415

Ala Ala Leu Pro Leu Glu Gly Cys Asp Gly Ser Asp Glu Asp Val Leu
            420                 425                 430

Thr Tyr Ala Leu Phe Pro Gln Val Ala Pro Lys Phe Phe Ala Thr Arg
        435                 440                 445

Ser Glu Gly Pro Arg Asn Leu Gly Arg Asp Pro Val Thr Gly Ala Ser
    450                 455                 460

Glu Thr Ser Ile Pro Glu Gly His Pro Gly Lys Ile Thr Gly Pro Val
465                 470                 475                 480
```

```
Thr Tyr Thr Val Thr Leu Ser Gly Gln Pro His Lys Val Thr Val Ala
                485                 490                 495

Pro Tyr Gly Gln Glu
            500


<210> SEQ ID NO 64
<211> LENGTH: 195
<212> TYPE: DNA
<213> ORGANISM: G. bemidjiensis

<400> SEQUENCE: 64

gtggacgaag agatggagca ggaacacgat ccggaaatca cgcccgaact gctgatggtg     60

atgtccgccg cgatagccgc gtatctgggc aagaccgtga ggataaggcg ggccaggttc    120

gtcgacccga atctgatcaa cgcctgggga cagtcgagcc gcgtggtgct gcaggcgtcg    180

cacaacttga ggaga                                                     195


<210> SEQ ID NO 65
<211> LENGTH: 65
<212> TYPE: PRT
<213> ORGANISM: G. bemidjiensis

<400> SEQUENCE: 65

Val Asp Glu Glu Met Glu Gln Glu His Asp Pro Glu Ile Thr Pro Glu
1               5                   10                  15

Leu Leu Met Val Met Ser Ala Ala Ile Ala Ala Tyr Leu Gly Lys Thr
            20                  25                  30

Val Arg Ile Arg Arg Ala Arg Phe Val Asp Pro Asn Leu Ile Asn Ala
        35                  40                  45

Trp Gly Gln Ser Ser Arg Val Val Leu Gln Ala Ser His Asn Leu Arg
    50                  55                  60

Arg
65


<210> SEQ ID NO 66
<211> LENGTH: 1548
<212> TYPE: DNA
<213> ORGANISM: D. propionicus

<400> SEQUENCE: 66

atgagcacaa aggaaaaatt agagcagcta aagcaaaaaa gggccaaagc cttgctgggc     60

ggcggtcagg ataaaatcga caagatccac tcccagggca aatataccgc ccgtgagcgt    120

attcaactcc tcctcgaccc aggcaccttc gaggaatacg atgctttcaa gctccatcgc    180

tgctacaact tcggcatgga aaaaatcaag tttttcggcg acggtatcgt caccggatat    240

ggcaagctgg ccggccggcc ggtttatatt tacgcgcagg acttttcggt cctcgccggt    300

tctctttccg gaaccttggc tgaaaaaata tgcaaaatca tggatctggg catgaaaaac    360

ggcattccgg tcatcggatt gaacgactcc ggtggcgccc gtatccagga aggtatcgag    420

gccctggcag gatataccga aatcttcacc cgtaatgttc tcgcttcggg tgttgttccc    480

cagatttccg gtgttttcgg accctgcgcc ggtggcgccg tttactctcc tgccctgacc    540

gacttcatca tccaggtcaa gatccagtcc tacatgttcc tgacaggtcc caaggtcgtt    600

aagactgtgt taaacgagga cgtcaccacc gagcagttgg gtggtgcggc catgcatacc    660

accaagtccg gcgtcaccga ctatgctgcc gagaacgagg acgacgccat tcagtacatc    720

aaggatctga tgagctattt gccgcagaac aatctggaga atcctccgga tgccccctgc    780
```

```
gacgatccga tcacccgccg ctccgaactg ctcaacgaca tcattccgga caacccgaat    840

gccgcctacg acatgaaaaa ggtcatcacc gagacggcag acaacggtat cttctttgaa    900

atcaagaaga atttcgctcc gaacatcgtc atcggttttg cccgttatgg tggcaaggct    960

attggcatcg ttgccaacca gccgtcctac tacgccggtg ttctcgacat cgattcctcg   1020

atcaaaggtg cccgcttcat ccgcttctgc gactgcttca acattccgat ccttaccttc   1080

gtcgacgtcc ctggcttcct gcccggcact gcacaggaat tcggcggcgt tatccgcaac   1140

ggcgccaaga tgctgtatgc ctacgccgaa tcgacagtgc caaaggtaac gattattacc   1200

cgtaaatcct atggcggcgc ctactgcgct atgtcgtcca agcacctgcg aaccgatatc   1260

aactactcct ggccgaccgg tgaaatcgcc gttatgggct ccaaaggcgc ggtcgaagtc   1320

ctgcacgcca agggcgctaa agcagcagaa gatcccagag cgttcctggc cgaaaaagaa   1380

aacgagtaca acgagcagtt ctccaatcca tattgtgcgg ccgagcgtgg ctatatcgac   1440

gatgtcattg aaccggccga aaccaggtac cgtatcatca acgcgtttga gtcgatctct   1500

ggaaagcgtg acacgatccc gatgaagaaa cacggcaata tcccgctg                1548
```

<210> SEQ ID NO 67
<211> LENGTH: 516
<212> TYPE: PRT
<213> ORGANISM: D. propionicus

<400> SEQUENCE: 67

```
Met Ser Thr Lys Glu Lys Leu Glu Gln Leu Lys Gln Lys Arg Ala Lys
1               5                   10                  15

Ala Leu Leu Gly Gly Gly Gln Asp Lys Ile Asp Lys Ile His Ser Gln
            20                  25                  30

Gly Lys Tyr Thr Ala Arg Glu Arg Ile Gln Leu Leu Leu Asp Pro Gly
        35                  40                  45

Thr Phe Glu Glu Tyr Asp Ala Phe Lys Leu His Arg Cys Tyr Asn Phe
    50                  55                  60

Gly Met Glu Lys Ile Lys Phe Phe Gly Asp Gly Ile Val Thr Gly Tyr
65                  70                  75                  80

Gly Lys Leu Ala Gly Arg Pro Val Tyr Ile Tyr Ala Gln Asp Phe Ser
                85                  90                  95

Val Leu Ala Gly Ser Leu Ser Gly Thr Leu Ala Glu Lys Ile Cys Lys
            100                 105                 110

Ile Met Asp Leu Gly Met Lys Asn Gly Ile Pro Val Ile Gly Leu Asn
        115                 120                 125

Asp Ser Gly Gly Ala Arg Ile Gln Glu Gly Ile Glu Ala Leu Ala Gly
    130                 135                 140

Tyr Thr Glu Ile Phe Thr Arg Asn Val Leu Ala Ser Gly Val Val Pro
145                 150                 155                 160

Gln Ile Ser Gly Val Phe Gly Pro Cys Ala Gly Gly Ala Val Tyr Ser
                165                 170                 175

Pro Ala Leu Thr Asp Phe Ile Ile Gln Val Lys Ile Gln Ser Tyr Met
            180                 185                 190

Phe Leu Thr Gly Pro Lys Val Val Lys Thr Val Leu Asn Glu Asp Val
        195                 200                 205

Thr Thr Glu Gln Leu Gly Gly Ala Ala Met His Thr Thr Lys Ser Gly
    210                 215                 220

Val Thr Asp Tyr Ala Ala Glu Asn Glu Asp Asp Ala Ile Gln Tyr Ile
225                 230                 235                 240
```

-continued

```
Lys Asp Leu Met Ser Tyr Leu Pro Gln Asn Asn Leu Glu Asn Pro Pro
                245                 250                 255

Asp Ala Pro Cys Asp Asp Pro Ile Thr Arg Arg Ser Glu Leu Leu Asn
            260                 265                 270

Asp Ile Ile Pro Asp Asn Pro Asn Ala Ala Tyr Asp Met Lys Lys Val
        275                 280                 285

Ile Thr Glu Thr Ala Asp Asn Gly Ile Phe Phe Glu Ile Lys Lys Asn
    290                 295                 300

Phe Ala Pro Asn Ile Val Ile Gly Phe Ala Arg Tyr Gly Gly Lys Ala
305                 310                 315                 320

Ile Gly Ile Val Ala Asn Gln Pro Ser Tyr Tyr Ala Gly Val Leu Asp
                325                 330                 335

Ile Asp Ser Ser Ile Lys Gly Ala Arg Phe Ile Arg Phe Cys Asp Cys
            340                 345                 350

Phe Asn Ile Pro Ile Leu Thr Phe Val Asp Val Pro Gly Phe Leu Pro
        355                 360                 365

Gly Thr Ala Gln Glu Phe Gly Gly Val Ile Arg Asn Gly Ala Lys Met
    370                 375                 380

Leu Tyr Ala Tyr Ala Glu Ser Thr Val Pro Lys Val Thr Ile Ile Thr
385                 390                 395                 400

Arg Lys Ser Tyr Gly Gly Ala Tyr Cys Ala Met Ser Ser Lys His Leu
                405                 410                 415

Arg Thr Asp Ile Asn Tyr Ser Trp Pro Thr Gly Glu Ile Ala Val Met
            420                 425                 430

Gly Ser Lys Gly Ala Val Glu Val Leu His Ala Lys Gly Ala Lys Ala
        435                 440                 445

Ala Glu Asp Pro Arg Ala Phe Leu Ala Glu Lys Glu Asn Glu Tyr Asn
    450                 455                 460

Glu Gln Phe Ser Asn Pro Tyr Cys Ala Ala Glu Arg Gly Tyr Ile Asp
465                 470                 475                 480

Asp Val Ile Glu Pro Ala Glu Thr Arg Tyr Arg Ile Ile Asn Ala Phe
                485                 490                 495

Glu Ser Ile Ser Gly Lys Arg Asp Thr Ile Pro Met Lys Lys His Gly
            500                 505                 510

Asn Ile Pro Leu
        515
```

<210> SEQ ID NO 68
<211> LENGTH: 195
<212> TYPE: DNA
<213> ORGANISM: D. propionicus

<400> SEQUENCE: 68

```
atggcaaaaa tgaacaaaaa aatggctgcg gcccttgcag ccgttaatgc ctacctgatg      60

caggaagagg aggcggcata ccaggcccag ttgctggctg ccaaatctgt tgcaccagcc     120

gggccaagct tatgggcaat tgccggccgt caggatatca tgaatttccg caggctgatt     180

caaatgaaag ccttc                                                      195
```

<210> SEQ ID NO 69
<211> LENGTH: 65
<212> TYPE: PRT
<213> ORGANISM: D. propionicus

<400> SEQUENCE: 69

-continued

```
Met Ala Lys Met Asn Lys Lys Met Ala Ala Ala Leu Ala Ala Val Asn
1               5                   10                  15

Ala Tyr Leu Met Gln Glu Glu Glu Ala Ala Tyr Gln Ala Gln Leu Leu
            20                  25                  30

Ala Ala Lys Ser Val Ala Pro Ala Gly Pro Ser Leu Trp Ala Ile Ala
        35                  40                  45

Gly Arg Gln Asp Ile Met Asn Phe Arg Arg Leu Ile Gln Met Lys Ala
    50                  55                  60

Phe
65


<210> SEQ ID NO 70
<211> LENGTH: 1989
<212> TYPE: DNA
<213> ORGANISM: D. propionicus

<400> SEQUENCE: 70

atgagcgacc aagtgaaaat gaccgccatg aattatgcaa ctgaccggcc tgctgcagaa     60

aatccggtca aagttatgga cttgagcctt cgtgacggcc accagtctct gttcgccacc    120

cgcgggcgca ccgaggacat gattccgatc gcggaaatga tggacgagat cggcttctgg    180

gcagttgaga cctggggtgg cgccaccttt gacaccatgc accgcttcct caacgaggac    240

ccgtgggagc gtctccgcac cctgaaacgt tacatcaaga agaccccctt ctccatgttg    300

ctgcgcgcgc agaacctggt tggataccgt aactatgccg atgacttggc caccgccttt    360

gttgagcgcg ctgccgagaa cggtatggat atcttccgga cctttgacgc cctcaacgat    420

taccgtaact tcgagaccgt tgttaaacag atcaagaaga gcggcaagca cttccagggt    480

tgtatttgct attcgctgac cgaaccgcgt ctgggcgggg atgtttatga cctgaagtac    540

tatgtcgacc gcgccaaagc gcttgacgac atgggcgctg actccatctg catcaaggac    600

atggccggtc tgatcgcccc atacgacgcc tacgccatcg tcaaggctat caaggaagtc    660

accaagaccc cgatccacct gcacagccac ttcacctctg gtatggcgtc catgagtcat    720

ctgaaggcca ttgaggctgg cgtagatatc gttgacacct gcatgacccc gtacgctttc    780

cgtaccgccc atccggccat cgagccgttg gtcatggccc tgctcggcac caaccgcgac    840

accggtttcg acatcaagaa actggccgcc atcaacgagg tgctagagaa agaggttatg    900

ccgaaataca agcacctcat ggatgactcc aagtgctcaa tcatcgatat caacgttctt    960

ctccatcaga ccccgggcgg catgctctcc aacctggtca accagttgcg tgagatggat   1020

gctctggaca agatcgatca ggtctacaaa gagctgccga aagttcggaa agacctcggc   1080

cagattccgc tggttacccc gaccagccag atcgttggca tccagaccgt gaacaacgtg   1140

ctgtttgaca ctcctgatga gcgctacaag atgatcaccg cccaggtcaa agacctgtgc   1200

tacggtctct atggtaaaac cgctgtgccg atcaaccctg aactgcagaa gaaggctctg   1260

aaaggctatc cgcgcggtga agagccgatc acctgccgtc cggcagaggt gcttgagccc   1320

gagttggaaa aggccaagaa agagattggc gatctcgcca aggatatcga tgacttggta   1380

ctctacgcca tctacccggt caccgggaag aagttccttg agtggaagta tggcattacc   1440

ccggcaccgc ccgaagtcaa gccgctcacc cttgaggatg tcaagaagcg tgatgaactg   1500

gtggccaagg ccaaggctgg caagctcatc gagcccaagc ccgctgctcc ggagaagacc   1560

gctaacgttc ggaccttcaa cgtcttcgtc gacggtgagt atttcaacgt tgaggtcgac   1620

ccgaccggtg acttccagcc gatggtcgcc gctgctccgc ggcctgccgc acctgccgct   1680
```

-continued

```
gcaccgaaag ctgctgcacc tgccgctgct gcacctgctg ccgcgccgaa ggctgctgca   1740

cctgccgccg ccgctccggc tccagccgct gttgagggag gaaccccgct gttggccccc   1800

atgcccggca tgatcgtcaa gaatctggtc aatgttggtg atgcggtcaa agctggcgac   1860

cccatcctcg ttcttgaggc catgaagatg gagaacaatc tcggttctcc gtgcgatggt   1920

actgtgaagg cgcttaattt tggcagcggt gactcggttg ccaaggatac cgtcctggca   1980

atcatcgga                                                           1989
```

<210> SEQ ID NO 71
<211> LENGTH: 663
<212> TYPE: PRT
<213> ORGANISM: D. propionicus

<400> SEQUENCE: 71

```
Met Ser Asp Gln Val Lys Met Thr Ala Met Asn Tyr Ala Thr Asp Arg
1               5                   10                  15

Pro Ala Ala Glu Asn Pro Val Lys Val Met Asp Leu Ser Leu Arg Asp
            20                  25                  30

Gly His Gln Ser Leu Phe Ala Thr Arg Gly Arg Thr Glu Asp Met Ile
        35                  40                  45

Pro Ile Ala Glu Met Met Asp Glu Ile Gly Phe Trp Ala Val Glu Thr
    50                  55                  60

Trp Gly Gly Ala Thr Phe Asp Thr Met His Arg Phe Leu Asn Glu Asp
65                  70                  75                  80

Pro Trp Glu Arg Leu Arg Thr Leu Lys Arg Tyr Ile Lys Lys Thr Pro
                85                  90                  95

Phe Ser Met Leu Leu Arg Ala Gln Asn Leu Val Gly Tyr Arg Asn Tyr
            100                 105                 110

Ala Asp Asp Leu Ala Thr Ala Phe Val Glu Arg Ala Ala Glu Asn Gly
        115                 120                 125

Met Asp Ile Phe Arg Thr Phe Asp Ala Leu Asn Asp Tyr Arg Asn Phe
    130                 135                 140

Glu Thr Val Val Lys Gln Ile Lys Lys Ser Gly Lys His Phe Gln Gly
145                 150                 155                 160

Cys Ile Cys Tyr Ser Leu Thr Glu Pro Arg Leu Gly Gly Asp Val Tyr
                165                 170                 175

Asp Leu Lys Tyr Tyr Val Asp Arg Ala Lys Ala Leu Asp Asp Met Gly
            180                 185                 190

Ala Asp Ser Ile Cys Ile Lys Asp Met Ala Gly Leu Ile Ala Pro Tyr
        195                 200                 205

Asp Ala Tyr Ala Ile Val Lys Ala Ile Lys Glu Val Thr Lys Thr Pro
    210                 215                 220

Ile His Leu His Ser His Phe Thr Ser Gly Met Ala Ser Met Ser His
225                 230                 235                 240

Leu Lys Ala Ile Glu Ala Gly Val Asp Ile Val Asp Thr Cys Met Thr
                245                 250                 255

Pro Tyr Ala Phe Arg Thr Ala His Pro Ala Ile Glu Pro Leu Val Met
            260                 265                 270

Ala Leu Leu Gly Thr Asn Arg Asp Thr Gly Phe Asp Ile Lys Lys Leu
        275                 280                 285

Ala Ala Ile Asn Glu Val Leu Glu Lys Glu Val Met Pro Lys Tyr Lys
    290                 295                 300

His Leu Met Asp Asp Ser Lys Cys Ser Ile Ile Asp Ile Asn Val Leu
305                 310                 315                 320
```

-continued

```
Leu His Gln Thr Pro Gly Gly Met Leu Ser Asn Leu Val Asn Gln Leu
                325                 330                 335

Arg Glu Met Asp Ala Leu Asp Lys Ile Asp Gln Val Tyr Lys Glu Leu
            340                 345                 350

Pro Lys Val Arg Lys Asp Leu Gly Gln Ile Pro Leu Val Thr Pro Thr
        355                 360                 365

Ser Gln Ile Val Gly Ile Gln Thr Val Asn Asn Val Leu Phe Asp Thr
    370                 375                 380

Pro Asp Glu Arg Tyr Lys Met Ile Thr Ala Gln Val Lys Asp Leu Cys
385                 390                 395                 400

Tyr Gly Leu Tyr Gly Lys Thr Ala Val Pro Ile Asn Pro Glu Leu Gln
                405                 410                 415

Lys Lys Ala Leu Lys Gly Tyr Pro Arg Gly Glu Glu Pro Ile Thr Cys
            420                 425                 430

Arg Pro Ala Glu Val Leu Glu Pro Glu Leu Glu Lys Ala Lys Lys Glu
        435                 440                 445

Ile Gly Asp Leu Ala Lys Asp Ile Asp Asp Leu Val Leu Tyr Ala Ile
    450                 455                 460

Tyr Pro Val Thr Gly Lys Lys Phe Leu Glu Trp Lys Tyr Gly Ile Thr
465                 470                 475                 480

Pro Ala Pro Pro Glu Val Lys Pro Leu Thr Leu Glu Asp Val Lys Lys
                485                 490                 495

Arg Asp Glu Leu Val Ala Lys Ala Lys Ala Gly Lys Leu Ile Glu Pro
            500                 505                 510

Lys Pro Ala Ala Pro Glu Lys Thr Ala Asn Val Arg Thr Phe Asn Val
        515                 520                 525

Phe Val Asp Gly Glu Tyr Phe Asn Val Glu Val Asp Pro Thr Gly Asp
    530                 535                 540

Phe Gln Pro Met Val Ala Ala Ala Pro Arg Pro Ala Ala Pro Ala Ala
545                 550                 555                 560

Ala Pro Lys Ala Ala Ala Pro Ala Ala Ala Ala Pro Ala Ala Ala Pro
                565                 570                 575

Lys Ala Ala Ala Pro Ala Ala Ala Ala Pro Ala Pro Ala Ala Val Glu
            580                 585                 590

Gly Gly Thr Pro Leu Leu Ala Pro Met Pro Gly Met Ile Val Lys Asn
        595                 600                 605

Leu Val Asn Val Gly Asp Ala Val Lys Ala Gly Asp Pro Ile Leu Val
    610                 615                 620

Leu Glu Ala Met Lys Met Glu Asn Asn Leu Gly Ser Pro Cys Asp Gly
625                 630                 635                 640

Thr Val Lys Ala Leu Asn Phe Gly Ser Gly Asp Ser Val Ala Lys Asp
                645                 650                 655

Thr Val Leu Ala Ile Ile Gly
            660
```

<210> SEQ ID NO 72
<211> LENGTH: 933
<212> TYPE: DNA
<213> ORGANISM: T. saccharolyticum

<400> SEQUENCE: 72

```
atgagcaagg tagcaataat aggatctggt tttgtaggtg caacatcggc atttacgctg     60

gcattaagtg ggactgtgac agatatcgtg ctggtggatt taaacaagga caaggctata    120
```

-continued

```
ggcgatgcac tggacataag ccatggcata ccgctaatac agcctgtaaa tgtgtatgca    180

ggtgactaca aagatgtgaa aggcgcagat gtaatagttg tgacagcagg tgctgctcaa    240

aagccgggag agacacggct tgaccttgta aagaaaaata cagccatatt taagtccatg    300

atacctgagc ttttaaagta caatgacaag gccatatatt tgattgtgac aaatcccgta    360

gatatactga cgtacgttac atacaagatt tctggacttc catggggcag agtttttggt    420

tctggcaccg ttcttgacag ctcaaggttt agataccttt taagcaagca ctgcaatata    480

gatccgagaa atgtccacgg aaggataatc ggcgagcatg gtgacacaga gtttgcagca    540

tggagcataa caaacatatc gggtatatca tttaatgagt actgcagcat atgcggacgc    600

gtctgcaaca caaatttcag aaaggaagta gaagaagaag tcgtaaatgc tgcttacaag    660

ataatagaca aaaaaggtgc tacatactat gctgtggcag ttgcagtaag aaggattgtg    720

gagtgcatct taagagatga aaattccatc ctcacagtat catctccatt aaatggacag    780

tacggcgtga aagatgtttc attaagcttg ccatctatcg taggcaggaa tggcgttgcc    840

aggattttgg acttgccttt atctgacgaa gaagtggaga agtttaggca ttcagcaagt    900

gtcatggcag atgtcataaa acaattagat ata                                 933
```

<210> SEQ ID NO 73
<211> LENGTH: 2577
<212> TYPE: DNA
<213> ORGANISM: T. saccharolyticum

<400> SEQUENCE: 73

```
atggcaacga caaaaacgga attagacgtt cagaagcaga tagatctact tgtgtcaaga     60

gcacaagagg ctcagaaaaa attcatgtct tacacgcaag agcaaatcga cgcaatagtt    120

aaggcaatgg ctttagcagg cgttgacaaa cacgtagagc tggcaaagat ggcgtacgaa    180

gagacaaaaa tgggtgtata cgaagataag ataacaaaaa atctcttcgc aacagagtac    240

gtgtaccacg acataaaaaa tgaaaagact gtaggaatca taaacgagaa catagaagaa    300

aactacatgg aagtggcaga accgataggc gtaattgccg gtgtcacacc tgtcacaaac    360

ccaacatcta ccacgatgtt taaatgctta atatccataa agacgcgaaa tcctataata    420

ttcagcttcc atccaaaggc aataaagtgc agcatcgcag cagccaaagt gatgtatgaa    480

gctgcactaa aggcaggcgc acctgaagga tgcataggat ggatagaaac gccatcaatt    540

gaggccacac agcttctcat gacacatcca ggcgtatcgc tgatccttgc aacgggcggt    600

gcaggaatgg taaaagcggc atacagctca ggaaaaccgg cattaggcgt aggtcctggc    660

aatgtgccat gctacatcga aaaatcagca aacataaaga gggctgtatc ggatctcata    720

ctaagcaaga catttgacaa tggagtaata tgcgcatcag agcaggccgt aataatagac    780

gaggaaatag cagatgaagt caaaaagctt atgaaagaat acggctgcta cttcttaaac    840

aaagatgaaa taaagaagct tgagaaattt gcaattgatg agcaaagctg cgccatgagc    900

cctgcagtgg taggtcagcc agcggcgaag attgctgaaa tggcaggctt caaagtcccc    960

gaaggcacaa agatattagt ggcagagtac gaaggagtag gtccaaaata tcctctatca   1020

agggagaaac taagcccgat tcttgcttgc tacaccgtca aagactacaa tgaaggaatc   1080

aaaaagtgcg aggaaatgac tgaattcgga ggtttaggcc actctgctgt aatacactct   1140

gaaaatcaaa acgtcataaa tgaatttgca aggcgagtcc gcacaggaag acttatcgta   1200

aattcaccat catcacaggg agcaatagga gatatataca atacaaacac gccatcactt   1260

acattaggct gtggttctat gggaagaaac tcaacgacag acaatgtaag cgtcaagaac   1320
```

ctttttgaata ttaagcgtgt cgtgataagg aatgatagaa tgaaatggtt caagattcca 1380
ccgaagattt actttgaaag cgggtcactc cagtacctgt gcaaagtcaa aagaaaaaaa 1440
gcgtttatcg tcacagatcc attcatggtt aagcttggct tcgtagacaa agtgacatat 1500
caattagaca aagcaaacat cgaatacgaa atattctcag aagtagagcc agatccatct 1560
gttgacacag tcatgaacgg cgtaaaaata atgaattcgt acaatcctga cttaataatc 1620
gctgtaggcg gtggctctgc aatagacgca gcaaagggaa tgtggctttt ctacgaatat 1680
cctgatacag agtttgaaac attgaggctt aaatttgcag acatcagaaa aagggcattt 1740
aagttcccag aacttggcaa aaaagcgcta ttcatcgcaa taccgacaac aagcggcaca 1800
ggctcagaag tgacagcatt tgccgtaata accgacaaaa agagaaacat caagtatcca 1860
ctggcagact acgaacttac acctgacata gccataatag atcctgacct tacaaagact 1920
gtaccgccat ctgtaacagc agacacaggc atggatgtgc tgacacacgc catagaagca 1980
tacgtatcag taatggcatc agactacaca gatgcactgg cggaaaaggc tataaagatc 2040
gtatttgaat acctgccaag ggcttataaa aacggcaatg atgaagaagc ccgcgaaaag 2100
atgcacaatg cttcctgcat ggctggtatg gcattcacaa atgcattctt aggaataaac 2160
cacagcatgg cacacatact gggcggaaag ttccacatac cacacggaag agcaaatgca 2220
atacttctgc cgtatgtaat aaggtacaat gcagaaaaac ctacaaagtt tgtggcattc 2280
ccacaatacg aatatccaaa agcagcagaa agatatgcgg aaatcgccaa attcttagga 2340
ctgcctgctt caactgttga agaaggcgta gaaagcttaa tagaagctat aaagaacctc 2400
atgaaagagc ttaacattcc gcttacactt aaagacgccg gcatcaacaa agaacagttt 2460
gaaaaagaaa tagaggaaat gtcagacatc gccttcaacg atcagtgcac agggacaaac 2520
ccgagaatgc ctctcacaaa agaaattgca gagatctaca gaaaagcata cggtgca 2577

<210> SEQ ID NO 74
<211> LENGTH: 1752
<212> TYPE: DNA
<213> ORGANISM: T. saccharolyticum

<400> SEQUENCE: 74
atgcgtagaa ctaagataat atgcacgatt ggtcctgcca gtgaaaaata tgagatattg 60
aaagagctta tagaaagcgg tcttaatatt tgcaggttga atttttcaca tggggatcat 120
gaagagcatg gaagcagaat agacaatatt ataaagatta gagaagaact taagctgcct 180
attgcaatta tgcttgatac aaaagggcct gaaataagga ctggcagatt taaaggcggt 240
gttgcagagc ttaaagaagg ccagacattt acgataacat caagggaaat tgaaggagat 300
aacactattt gttctgtttc atacaagggg cttcctcaag atgtggagag aggttctcgc 360
atattgattg atgacggatt agtatcattg aaagtcaatg acgtaaaagg tgaagatata 420
gtatgcactg tggagaattc tggtacaata ggtgatcaca aaggtgtaaa tgtacctggt 480
acaaagctta atttgcctgc cataacgcaa aaagacgtgg atgatataga gtttggaata 540
aaaaaaggaa tcgacatgat tgcagcgtct tttgtcagaa aagcagcaga tgtaattgcc 600
ataaggagat tgttagaaga caatgacgct ggccatatac ttatcatatc aaaaattgaa 660
aatcgcgaag gcgtagaaaa tattgacgaa ataatcaaag tctctgatgg cataatggta 720
gcccgcggcg atttgggtgt cgaaattcct atagaggaaa tacctatcgt tcagaaaagg 780
ataattgaaa aatgcaacaa agcaggtaaa ccagtagtta ctgctacaca gatgcttgac 840

```
tctatgataa gaaatccaag gccaacaagg gcagaagtaa cagatgtagc caatgctata    900

ttggatggca ctgatgcgat aatgttgtct ggtgaaacag cgcaaggcaa atatcctgta    960

gaggctttta agacgatgtc aaagatagct gaaaagattg agacgtatat aaattacaaa   1020

gaaaatttag ataaaaatgt ggattacaat atttctatga caaatgccat aagccatgct   1080

acgtgcacta ccgcgagaga tataggcgca actgccatta ttacatctac aatatcaggt   1140

tatactgcga gaatggtgtc taagtataga ccgtcagcac ctataatagc agtgacgcca   1200

aacaaagatg ttgcaagaag gcttagcatc gtgtggggtg tacatccatt gatatcacag   1260

gaagtcaatt ctacagatga aatgatagaa gtatcagtaa atacggcttt aaatgaagga   1320

ttaattcgaa atggcgatat tgtagtaata tcggcaggaa tacctgtcgc gactacaggc   1380

acaacaaata tgttgaaggt tcatattgtg ggagatgtaa tagtaaaagg cacaggcata   1440

ggcactaaat ccataagtgg tgttgtttcc atcataagag atccatacaa ggacaaagat   1500

aagttcagag aaggagatat catcgttgct caaaaaactg aaagggatta tatgcctata   1560

attgagaagg cttcagctat cataacagaa gaaggtggac taacgtccca tgctgcaata   1620

gttggattga actatggatt acctgtcatt gtaggctgtg aaggagtaac ttcaaagctt   1680

aaagatggaa tgacggtaac tctcgatact gccagaggat tggtctacaa aggtatagtg   1740

aatataaaat ag                                                       1752
```

<210> SEQ ID NO 75
<211> LENGTH: 2226
<212> TYPE: DNA
<213> ORGANISM: T. saccharolyticum

<400> SEQUENCE: 75

```
atgatcaatg aatggcgcgg gtttcaggag ggcaaatggc aaaagactat tgacgttcaa     60

gattttatcc agaaaaatta cacattatac gaaggcgatg atagtttttt agaagggcct    120

acagaaaaga ctattaagct ttggaacaaa gttcttgagc taatgaagga agaactgaaa    180

aaaggtgtgt tagatattga tacaaaaact gtatcgtcta taacatccca tgatgcgggg    240

tatatagaca aagatcttga ggaaatagtt ggattgcaga cagacaaacc tcttaaaaga    300

gctataatgc cttacggtgg cataagaatg gtcaaaaaag cttgcgaagc ttatggatat    360

aaagtggacc caaaagtaga agagatattt acgaagtaca gaaagaccca caatgatggt    420

gtatttgatg catatactcc agaaataaga gcagcaagac atgccggcat aataacaggt    480

cttccagatg catatggcag aggaagaatc ataggtgatt acagaagagt tgctctttat    540

ggaattgata gactcatcga agaaaaggaa aaagaaaaac ttgagcttga ttacgatgaa    600

tttgatgaag caactattcg cttgagagaa gaattgacag aacagataaa agcattaaac    660

gaaatgaaag agatggcttt aaagtacggt tatgacatat caaagcctgc aaaaaatgca    720

aaagaagctg tgcagtggac ttactttgcc ttccttgctg ctataaagga acaaaatggt    780

gccgctatgt cgctgggcag agtatctact tttttagata tatacattga aagagatctt    840

aaagaaggaa cattgacaga gaaacaagca caagagttaa tggatcactt tgtcatgaag    900

cttagaatgg tgaggttctt aaggactcct gattacaatg aactatttag tggcgatcct    960

gtttgggtga ctgaatcaat tggcggtgta ggcgtagacg gaagacctct tgtcactaaa   1020

aattcattca ggatattaaa tactttatat aacttaggtc ctgcacctga gccaaacttg   1080

acggttttat ggtccaaaaa ccttcctgaa aactttaaaa gattctgtgc caaggtatca   1140

atagatacaa gttctattca atatgaaaat gacgacttaa tgaggccaat atacaatgac   1200
```

gactatagca tcgcctgctg tgtgtcagct atgaagacgg gagaacagat gcaatttttt 1260
ggagcaaggg caaatctcgc gaaggcgcta ctgtatgcta taaacggcgg tatcgatgaa 1320
aggtataaaa cgcaagtggc accaaaattt aatcctataa cgtctgagta tttagactac 1380
gatgaggtaa tggcagcata tgacaatatg ttagagtggc ttgcaaaagt gtatgttaaa 1440
gctatgaata taatacacta catgcacgat aaatacgctt atgaaagatc ccttatggct 1500
ttgcatgata gagacatcgt aaggacgatg gcttttggaa tcgcaggtct ttctgttgcg 1560
gcagattcgt taagcgccat aaagtatgct aaagtaaaag ccataagaga tgaaaatggc 1620
atagcaatag attatgaagt ggaaggagat ttccctaagt ttggcaatga tgatgacagg 1680
gttgactcaa tagcagttga cattgtagaa agattcatga ataagcttaa aaagcacaag 1740
acttacagaa actctatacc aacactgtct gttttgacaa taacgtcaaa tgtggtgtac 1800
ggcaaaaaga cgggtgctac acctgacgga agaaaagcgg gagaaccttt tgcgccaggc 1860
gcaaatccga tgcacggcag agatacaaaa ggtgccatag catcaatgaa ttcagtatca 1920
aaaatacctt atgacagttc attggatggt atatcataca catttacgat tgtaccaaat 1980
gcgcttggca aggatgacga agataaaatt aataatcttg taggactatt agatggatat 2040
gcatttaatg cggggcacca cataaacatc aatgttttaa acagagatat gttgcttgat 2100
gctatggagc atcctgaaaa atatccgcag cttactataa gggtttcagg gtatgctgtc 2160
aatttcaata aattaacgag agagcaacag ttggaggtta tatcccgcac ttttcacgaa 2220
tctatg 2226

<210> SEQ ID NO 76
<211> LENGTH: 2285
<212> TYPE: DNA
<213> ORGANISM: T. saccharolyticum

<400> SEQUENCE: 76
gtgtatacaa tatatttctt cttagtaaga ggaatgtata aaaataaata ttttaaagga 60
agggacgatc ttatgagcat tattcaaaac atcattgaaa aagctaaaag cgataaaaag 120
aaaattgttc tgccagaagg tgcagaaccc aggacattaa aagctgctga aatagtttta 180
aaagaaggga ttgcagattt agtgcttctt ggaaatgaag atgagataag aaatgctgca 240
aaagacttgg acatatccaa agctgaaatc attgaccctg taaagtctga aatgtttgat 300
aggtatgcta atgatttcta tgagttaagg aagaacaaag gaatcacgtt ggaaaaagcc 360
agagaaacaa tcaaggataa tatctatttt ggatgtatga tggttaaaga aggttatgct 420
gatggattgg tatctggcgc tattcatgct actgcagatt tattaagacc tgcatttcag 480
ataattaaaa cggctccagg agcaaagata gtatcaagct tttttataat ggaagtgcct 540
aattgtgaat atggtgaaaa tggtgtattc ttgtttgctg attgtgcggt caacccatcg 600
cctaatgcag aagaacttgc ttctattgcc gtacaatctg ctaatactgc aaagaatttg 660
ttgggctttg aaccaaaagt tgccatgcta tcattttcta caaaaggtag tgcatcacat 720
gaattagtag ataaagtaag aaaagcgaca gagatagcaa aagaattgat gccagatgtt 780
gctatcgacg gtgaattgca attggatgct gctcttgtta aagaagttgc agagctaaaa 840
gcgccgggaa gcaaagttgc gggatgtgca aatgtgctta tattccctga tttacaagct 900
ggtaatatag gatataagct tgtacagagg ttagctaagg caaatgcaat tggacctata 960
acacaaggaa tgggtgcacc ggttaatgat ttatcaagag gatgcagcta tagagatatt 1020
gttgacgtaa tagcaacaac agctgtgcag gctcaataaa atgtaaagta tggaggatga 1080
aaattatgaa aatactggtt attaattgcg gaagttcttc gctaaaatat caactgattg 1140
aatcaactga tggaaatgtg ttggcaaaag gccttgctga aagaatcggc ataaatgatt 1200
ccatgttgac acataatgct aacggagaaa aaatcaagat aaaaaaagac atgaaagatc 1260
acaaagacgc aataaaattg gttttagatg ctttggtaaa cagtgactac ggcgttataa 1320
aagatatgtc tgagatagat gctgtaggac atagagttgt tcacggagga gaatctttta 1380
catcatcagt tctcataaat gatgaagtgt taaaagcgat aacagattgc atagaattag 1440
ctccactgca caatcctgct aatatagaag gaattaaagc ttgccagcaa atcatgccaa 1500
acgttccaat ggtggcggta tttgatacag cctttcatca gacaatgcct gattatgcat 1560
atctttatcc aataccttat gaatactaca caaagtacag gattagaaga tatggatttc 1620
atggcacatc gcataaatat gtttcaaata gggctgcaga gattttgaat aaacctattg 1680
aagatttgaa aatcataact tgtcatcttg gaaatggctc cagcattgct gctgtcaaat 1740
atggtaaatc aattgacaca agcatgggat ttacaccatt agaaggtttg gctatgggta 1800
cacgatctgg aagcatagac ccatccatca tttcgtatct tatggaaaaa gaaaatataa 1860
gcgctgaaga agtagtaaat atattaaata aaaaatctgg tgtttacggt atttcaggaa 1920
taagcagcga ttttagagac ttagaagatg ccgcctttaa aaatggagat gaaagagctc 1980
agttggcttt aaatgtgttt gcatatcgag taaagaagac gattggcgct tatgcagcag 2040
ctatgggagg cgtcgatgtc attgtattta cagcaggtgt tggtgaaaat ggtcctgaga 2100
tacgagaatt tatacttgat ggattagagt ttttagggtt cagcttggat aaagaaaaaa 2160
ataaagtcag aggaaaagaa actattatat ctacgccgaa ttcaaaagtt agcgtgatgg 2220
ttgtgcctac taatgaagaa tacatgattg ctaaagatac tgaaaagatt gtaaagagta 2280
taaaa 2285

<210> SEQ ID NO 77
<211> LENGTH: 38
<212> TYPE: DNA
<213> ORGANISM: Artificial
<220> FEATURE:
<223> OTHER INFORMATION: pMU433 construction; X01648

<400> SEQUENCE: 77
gtctttcgac tgagcctttc gttttatttg atgcctgg 38

<210> SEQ ID NO 78
<211> LENGTH: 35
<212> TYPE: DNA
<213> ORGANISM: Artificial
<220> FEATURE:
<223> OTHER INFORMATION: pMU433 construction; X01649

<400> SEQUENCE: 78
aattgtagaa tacaatccac ttcacaatgg gcacg 35

<210> SEQ ID NO 79
<211> LENGTH: 34
<212> TYPE: DNA
<213> ORGANISM: Artificial
<220> FEATURE:
<223> OTHER INFORMATION: pMU433 construction; X01654

<400> SEQUENCE: 79
aggggtcccg agcgcctacg aggaatttgt atcg 34

<210> SEQ ID NO 80
<211> LENGTH: 35
<212> TYPE: DNA
<213> ORGANISM: Artificial
<220> FEATURE:
<223> OTHER INFORMATION: pMU433 construction; X01655

<400> SEQUENCE: 80
ccgtcagtag ctgaacagga gggacagctg ataga 35

<210> SEQ ID NO 81
<211> LENGTH: 169
<212> TYPE: DNA
<213> ORGANISM: Artificial
<220> FEATURE:
<223> OTHER INFORMATION: adhE promoter

<400> SEQUENCE: 81
tcatataagt gtaaggtgat tgttaaatga ataacaaaaa ttatttacat cacacagtcc 60
aaaattcaat tcattcaagc gaatttcctg ttgaaatgct tgaaaaactg atacaatcac 120
ctgaaatgta gagatttatt gttaataaat taacacggag gtgtttatt 169

<210> SEQ ID NO 82
<211> LENGTH: 621
<212> TYPE: DNA
<213> ORGANISM: Artificial
<220> FEATURE:
<223> OTHER INFORMATION: cbp promoter

<400> SEQUENCE: 82
gagtcgtgac taagaacgtc aaagtaatta acaatacagc tatttttctc atgcttttac 60
ccctttcata aaatttaatt ttatcgttat cataaaaaat tatagacgtt atattgcttg 120
ccgggatata gtgctgggca ttcgttggtg caaaatgttc ggagtaaggt ggatattgat 180
ttgcatgttg atctattgca ttgaaatgat tagttatccg taaatattaa ttaatcatat 240
cataaattaa ttatatcata attgttttga cgaatgaagg tttttggata aattatcaag 300
taaaggaacg ctaaaaattt tggcgtaaaa tatcaaaatg accacttgaa ttaatatggt 360
aaagtagata taatattttg gtaaacatgc cttcagcaag gttagattag ctgtttccgt 420
ataaattaac cgtatggtaa aacggcagtc agaaaaataa gtcataagat tccgttatga 480
aaatatactt cggtagttaa taataagaga tatgaggtaa gagatacaag ataagagata 540
taaggtacga atgtataaga tggtgctttt aggcacacta aataaaaaac aaataaacga 600
aaattttaag gaggacgaaa g 621

<210> SEQ ID NO 83
<211> LENGTH: 172
<212> TYPE: DNA
<213> ORGANISM: Artificial
<220> FEATURE:
<223> OTHER INFORMATION: pta promoter

<400> SEQUENCE: 83
gtattctaca attaaaccta atacgctcat aatatgcgcc tttctaaaaa attattaatt 60
gtacttatta ttttataaaa aatatgttaa aatgtaaaat gtgtatacaa tatatttctt 120
cttagtaaga ggaatgtata aaaataaata ttttaaagga agggacgatc tt 172

<210> SEQ ID NO 84

<211> LENGTH: 214
<212> TYPE: DNA
<213> ORGANISM: Artificial
<220> FEATURE:
<223> OTHER INFORMATION: hyd promoter

<400> SEQUENCE: 84

```
ataagcgaaa gggtaaattg ctttgattta gatgatttga atatggtagt cgactggatg     60

tgcaagtaaa gaaaacatat caaattagtc gggattatca gaaaataaaa aaatttttat    120

ttttaactgt taaaaaaata attaacatat ggtataataa ttatgtccta ttttgcaatt    180

ttaaagatta attttttaa aaggagggta ttag                                 214
```

<210> SEQ ID NO 85
<211> LENGTH: 251
<212> TYPE: DNA
<213> ORGANISM: Artificial
<220> FEATURE:
<223> OTHER INFORMATION: hfs promoter

<400> SEQUENCE: 85

```
gctgtaattg tccttgatga cgataggaag ataaacattc caacaaaata tcttcccagc     60

aatattgctg aagaagatgc catagatatt tcattggatg tcaatgaaag aggacgaaaa    120

ttaaaaaagt tgattgaaga atcaagggag gaagactaat tttttaattt ttttaacgtt    180

aattgttaat aaattaacta ttgtttacac actttctttt atgtaataaa ataattgtat    240

acagtatacg g                                                         251
```

<210> SEQ ID NO 86
<211> LENGTH: 237
<212> TYPE: DNA
<213> ORGANISM: Artificial
<220> FEATURE:
<223> OTHER INFORMATION: ech promoter

<400> SEQUENCE: 86

```
tactgaatgg agaaactgca caaaaagctt gttgacggca gcagaggaga ttattcctct     60

gctatttttg tgggaaaaac tgcaaaattc attgaaatat tgttaaataa taaacaaaat    120

taattaatat taaatacaat tgacttatca tttaattaga tttataatca aaatgggtat    180

ttaaaaatgt atacaatata taatattcat taaatgaaat aaagaaggag tgaaaaa       237
```

<210> SEQ ID NO 87
<211> LENGTH: 1670
<212> TYPE: DNA
<213> ORGANISM: Acinetobacter sp.

<400> SEQUENCE: 87

```
cagaagatat ggttcggtta tcggttggga ttgaacatat tgatgatttg attgcagatc     60

tggaacaagc attggccaca gtttgagcgt aaattttata aaaaacctct gcaatttcag    120

aggttttttt atatttgctt tattatcgta tgatgttcat aattgatcta gcaaataata    180

aaaattagag caattactct aaaaacattt gtaatttcag atacttaaca ctagattttt    240

taaccaaatc actttagatt aactttagtt ctggaaattt tatttccctt taaccgtctt    300

caatccaaat acaataatga cagcctttac agtttgatat caatcaggga aaaacgcgtg    360

aacaaaaaac ttgaagctct cttccgagag aatgtaaaag gtaaagtggc tttgatcact    420

ggtgcatcta gtggaatcgg tttgacgatt gcaaaaagaa ttgctgcggc aggtgctcat    480

gtattattgg ttgcccgaac ccaagaaaca ctggaagaag tgaaagctgc aattgaacag    540
```

caagggggac aggcctctat ttttccttgt gacctgactg acatgaatgc gattgaccag 600
ttatcacaac aaattatggc cagtgtcgat catgtcgatt tcctgatcaa taatgcaggg 660
cgttcgattc gccgtgccgt acacgagtcg tttgatcgct tccatgattt tgaacgcacc 720
atgcagctga attactttgg tgcggtacgt ttagtgttaa atttactgcc acatatgatt 780
aagcgtaaaa atggccagat catcaatatc agctctattg gtgtattggc caatgcgacc 840
cgtttttctg cttatgtcgc gtctaaagct gcgctggatg ccttcagtcg ctgtctttca 900
gccgaggtac tcaagcataa aatctcaatt acctcgattt atatgccatt ggtgcgtacc 960
ccaatgatcg cacccaccaa aatttataaa tacgtgccca cgctttcccc agaagaagcc 1020
gcagatctca ttgtctacgc cattgtgaaa cgtccaacac gtattgcgac gcacttgggt 1080
cgtctggcgt caattaccta tgccatcgca ccagacatca ataatattct gatgtcgatt 1140
ggatttaacc tattcccaag ctcaacggct gcactgggtg aacaggaaaa attgaatctg 1200
ctacaacgtg cctatgcccg cttgttccca ggcgaacact ggtaaaattt ataaaagaag 1260
cctctcatac cgagaggctt ttttatggtt acgaccatca gccagattta gaggaaattg 1320
acttttcctg tttttacatc ataaatcgca ccaacaatat caatttcttt gcgatccagc 1380
atatctttaa gtacagaact atgctgaata atgtattgaa tattatagtg aacattcata 1440
gcagtcacct gatcaataaa tgctttgctt aattcacgcg gttgcataat atcaaataca 1500
ctgccaaccg aatgcatgag tggcccaagc acgtattgga tgtgtggcat ttcctgaata 1560
tcggaaatct gcttatgttg caatcttaac tggcatgcgc tggtgaccgc accacagtcg 1620
gtatgtccca aaaccagaat cactttggaa cctttggctt gacaggcaaa 1670

<210> SEQ ID NO 88
<211> LENGTH: 1188
<212> TYPE: DNA
<213> ORGANISM: Geobacillus thermodenitrificans

<400> SEQUENCE: 88
ttacgccttg tgcggctcta cgatcgtccc ggcaaacgcg gcttcgtaaa tcgcacggat 60
gtcggcttcc aacagcggca acggactgcg ggcaagcaaa cgtttctgtt ggacagcatc 120
tttcgtcaag ctttctagcg cgctttcggg gatgccaaat ccccccaatg ttttcggaat 180
gccgacatcg gcgacgaacc gttctagttc ctcgacgcac cgataagacg cttccacttc 240
ggacaaaaaa cttgagttgc cgccaagcgc gttgaaaata tcggccattc tcttcgtaca 300
gctttgacgg atgtagccca tcacatacgg caacagcaca gcattcgatt caccatgagc 360
gatatgaaac tgaccaccga gcggataagc gagcgcatgc acaccggcta ccccggcgtt 420
gaaaaatgcc aagccggcca aataactgcc gttcgccata tcaatgcgcg cctgtttgtc 480
cgaaccgttg gccaccgctt tgcgcagtga gcgtgaaatc agccgaatag cggcaacggc 540
caatccatcc gatgttgggc tcgcattgac cgacacatac gcctcaactg catgggtgag 600
tgcatcaatt cccgttgcgg ccgttacccg cggtggaacg gaaacggtca gctgcggatc 660
aacgatcgcg acgtcggcca ataagtaatc gtgcgtcacg acatctttcg tcgtttccaa 720
agacaagaca gagatgtttg tcacttccga cccggtgccc gatgtcgtgg gaatcaaaat 780
tttcggcaac ccttttttct caagtgttcg cgttcctgtc aaatttaaat agtcagcgac 840
cgagccatca tgcaccgcca aaacagccgc cagtttcgcc aaatccagcg cgctgccacc 900
accaacaccg atgacaaggt caaactttcc gtcgcgggca aacgccactg ccttttcccc 960

-continued

```
tgtctcaagc ggcggctctg gcacaacatc cgtatacaca tgcacgctat acccttcttg   1020

acggagcggg gacgtcactt gatcgactag gccgatcttc acaagcatcg ggtcggtaat   1080

caccaaaata tgttttgctc ccaaccgctt cacttcagga actaactggt caagcgctcc   1140

ccagccgaca tggctgagcg gcggaaagac aatgcgggct acactcat                1188


<210> SEQ ID NO 89
<211> LENGTH: 1164
<212> TYPE: DNA
<213> ORGANISM: Geobacillus thermodenitrificans

<400> SEQUENCE: 89

ttataaagac gcacgcaaaa tggcgagcac atcatcacga tttaacgttt tgaaacggcc     60

aaactcacca aacgccatcg ctttatccgc catcagctcg agattttcct cgccgatgcc    120

ataatcagcc aatcgagacg gcgccccgag gctcgaccaa aacgcgcgca accgctcgat    180

gccctcaagc gccacgtcgc gctccgtttt gcccgtcgga tcgacgtcaa agacgcgcac    240

cgccagttgg gcgaaacggc tgacattttc atcaagcaca tgtttcatcc aattcgggaa    300

caaaatggcc aatcccccgg cgtgcgggat atcgtataca gcagagaccg catgctcgat    360

atcatgcgtc gcccaatcac cgcgcacgcc catttgcaaa aagccgttta aggcgatcgt    420

gcccgagtac atgatcgtct cgcgcagctc gtagttctct aagtcgtcaa ccaattttgg    480

cgccgcctca atgaccgttt ttaacactgc ctcgcacatc cggtcttgca gcggcgtgtt    540

cggcgtatga tggaaatatt gctcaaacac atgggacatc atatcgacga tgccgtaaac    600

ggtatggtct ttcggcaccg tcatcgtgta cgtcggatcc aaaatcgaaa attgcgggaa    660

tgtcaccggg ctgccccagc cgtatttttc tttcgtctcc caattggtga tcaccgatcc    720

ggcgttcatt tccgagccgg tcgctgccag cgtcaggacc gtcccaaacg gcaacgcctc    780

agtgacagtc gctttttttcg taatgaactc ccacggatcg ccatcaaact tcgcgccggc    840

tgcaatcgct ttcgtacagt cgatcacact gccgccgcca acggcaagca aaaattcaat    900

tccttcccgt ctgcaaatgt ctaccccttt tttgacggtc gaaaggcgcg ggttcggttc    960

gacgcctggc agttcaacga cttcggcgcc aatgtccgtc aataggctca tgacttcatc   1020

atatagtccg tttcgtttaa tgctgccgcc cccatagaca agcagcactt ttttgccata   1080

tttcggcact tcttctttga gctgctcaat ttgtcctctc ccaaaaaatga gtttggtcgg   1140

attgcgaaac gtaaaatttt gcat                                          1164


<210> SEQ ID NO 90
<211> LENGTH: 59
<212> TYPE: DNA
<213> ORGANISM: Artificial
<220> FEATURE:
<223> OTHER INFORMATION: X12312 primer

<400> SEQUENCE: 90

ttttgtctgt cttaattttt ggtatcatta taggatctat gtaacccagg aagcggcaa      59


<210> SEQ ID NO 91
<211> LENGTH: 48
<212> TYPE: DNA
<213> ORGANISM: Artificial
<220> FEATURE:
<223> OTHER INFORMATION: X12313 primer

<400> SEQUENCE: 91

acgagattac tgctgctgtg cagactttgc gttccattgc acggatca                  48
```

<210> SEQ ID NO 92
<211> LENGTH: 48
<212> TYPE: DNA
<213> ORGANISM: Artificial
<220> FEATURE:
<223> OTHER INFORMATION: X12314 primer

<400> SEQUENCE: 92
tgatccgtgc aatggaacgc aaagtctgca cagcagcagt aatctcgt 48

<210> SEQ ID NO 93
<211> LENGTH: 59
<212> TYPE: DNA
<213> ORGANISM: Artificial
<220> FEATURE:
<223> OTHER INFORMATION: X12315 primer

<400> SEQUENCE: 93
gataacaatt tcacacagga aacagctatg accatacggc ctcttctccc ataccaaat 59

<210> SEQ ID NO 94
<211> LENGTH: 59
<212> TYPE: DNA
<213> ORGANISM: Artificial
<220> FEATURE:
<223> OTHER INFORMATION: X12316 primer

<400> SEQUENCE: 94
ttttgtctgt cttaattttt ggtatcatta taggaacgca gttgctggat atcagaggt 59

<210> SEQ ID NO 95
<211> LENGTH: 48
<212> TYPE: DNA
<213> ORGANISM: Artificial
<220> FEATURE:
<223> OTHER INFORMATION: X12317 primer

<400> SEQUENCE: 95
tactggtcag agcttctgct gtcaactcgt tcacctgttg caggtact 48

<210> SEQ ID NO 96
<211> LENGTH: 48
<212> TYPE: DNA
<213> ORGANISM: Artificial
<220> FEATURE:
<223> OTHER INFORMATION: X12318 primer

<400> SEQUENCE: 96
agtacctgca acaggtgaac gagttgacag cagaagctct gaccagta 48

<210> SEQ ID NO 97
<211> LENGTH: 59
<212> TYPE: DNA
<213> ORGANISM: Artificial
<220> FEATURE:
<223> OTHER INFORMATION: X12319 primer

<400> SEQUENCE: 97
gataacaatt tcacacagga aacagctatg accatttggg atgtgtgcat tacccaacg 59

<210> SEQ ID NO 98
<211> LENGTH: 59
<212> TYPE: DNA
<213> ORGANISM: Artificial
<220> FEATURE:

<223> OTHER INFORMATION: X12320 primer

<400> SEQUENCE: 98
ttttgtctgt cttaattttt ggtatcatta taggatactg gtaaacgtct gccgaccaa 59

<210> SEQ ID NO 99
<211> LENGTH: 48
<212> TYPE: DNA
<213> ORGANISM: Artificial
<220> FEATURE:
<223> OTHER INFORMATION: X12321 primer

<400> SEQUENCE: 99
acagcttagc gccttctaca gcttcgcgcg aacgttcaat gattcgat 48

<210> SEQ ID NO 100
<211> LENGTH: 48
<212> TYPE: DNA
<213> ORGANISM: Artificial
<220> FEATURE:
<223> OTHER INFORMATION: X12322 primer

<400> SEQUENCE: 100
atcgaatcat tgaacgttcg cgcgaagctg tagaaggcgc taagctgt 48

<210> SEQ ID NO 101
<211> LENGTH: 59
<212> TYPE: DNA
<213> ORGANISM: Artificial
<220> FEATURE:
<223> OTHER INFORMATION: X12323 primer

<400> SEQUENCE: 101
gataacaatt tcacacagga aacagctatg accatgctga cattggctat ccctgcatt 59

<210> SEQ ID NO 102
<211> LENGTH: 59
<212> TYPE: DNA
<213> ORGANISM: Artificial
<220> FEATURE:
<223> OTHER INFORMATION: X12324 primer

<400> SEQUENCE: 102
ttttgtctgt cttaattttt ggtatcatta taggagcggg tcaatttcca gataacgca 59

<210> SEQ ID NO 103
<211> LENGTH: 48
<212> TYPE: DNA
<213> ORGANISM: Artificial
<220> FEATURE:
<223> OTHER INFORMATION: X12325 primer

<400> SEQUENCE: 103
tcaggaacag gaatacgcga ccaagatcgg cttgaaaggt ttgcacga 48

<210> SEQ ID NO 104
<211> LENGTH: 48
<212> TYPE: DNA
<213> ORGANISM: Artificial
<220> FEATURE:
<223> OTHER INFORMATION: X12326 primer

<400> SEQUENCE: 104
tcgtgcaaac ctttcaagcc gatcttggtc gcgtattcct gttcctga 48

<210> SEQ ID NO 105
<211> LENGTH: 59
<212> TYPE: DNA
<213> ORGANISM: Artificial
<220> FEATURE:
<223> OTHER INFORMATION: X12327 primer

<400> SEQUENCE: 105
gataacaatt tcacacagga aacagctatg accatgcgaa acatgcactg ccttacctt 59

<210> SEQ ID NO 106
<211> LENGTH: 59
<212> TYPE: DNA
<213> ORGANISM: Artificial
<220> FEATURE:
<223> OTHER INFORMATION: X12328 primer

<400> SEQUENCE: 106
ttttgtctgt cttaattttt ggtatcatta taggatggac cgaatggacg atggagttt 59

<210> SEQ ID NO 107
<211> LENGTH: 48
<212> TYPE: DNA
<213> ORGANISM: Artificial
<220> FEATURE:
<223> OTHER INFORMATION: X12329 primer

<400> SEQUENCE: 107
agaatgcctt tcacgcgttc catgtcgttg ctttatagac acccgcct 48

<210> SEQ ID NO 108
<211> LENGTH: 48
<212> TYPE: DNA
<213> ORGANISM: Artificial
<220> FEATURE:
<223> OTHER INFORMATION: X12330 primer

<400> SEQUENCE: 108
aggcgggtgt ctataaagca acgacatgga acgcgtgaaa ggcattct 48

<210> SEQ ID NO 109
<211> LENGTH: 59
<212> TYPE: DNA
<213> ORGANISM: Artificial
<220> FEATURE:
<223> OTHER INFORMATION: X12331 primer

<400> SEQUENCE: 109
gataacaatt tcacacagga aacagctatg accatttccg ttaacgatac gcttcgggt 59

<210> SEQ ID NO 110
<211> LENGTH: 59
<212> TYPE: DNA
<213> ORGANISM: Artificial
<220> FEATURE:
<223> OTHER INFORMATION: X12332 primer

<400> SEQUENCE: 110
ttttgtctgt cttaattttt ggtatcatta taggaattca aacgttatgc ccgacgctg 59

<210> SEQ ID NO 111
<211> LENGTH: 48
<212> TYPE: DNA
<213> ORGANISM: Artificial
<220> FEATURE:
<223> OTHER INFORMATION: X12333 primer

<400> SEQUENCE: 111
agcgggtcgg tgtaaatatt ccgttccttg atggtttctc ccagcact 48

<210> SEQ ID NO 112
<211> LENGTH: 48
<212> TYPE: DNA
<213> ORGANISM: Artificial
<220> FEATURE:
<223> OTHER INFORMATION: X12334 primer

<400> SEQUENCE: 112
agtgctggga gaaaccatca aggaacggaa tatttacacc gacccgct 48

<210> SEQ ID NO 113
<211> LENGTH: 59
<212> TYPE: DNA
<213> ORGANISM: Artificial
<220> FEATURE:
<223> OTHER INFORMATION: X12335 primer

<400> SEQUENCE: 113
gataacaatt tcacacagga aacagctatg accatttgaa attagccagt ggcggcaag 59

<210> SEQ ID NO 114
<211> LENGTH: 59
<212> TYPE: DNA
<213> ORGANISM: Artificial
<220> FEATURE:
<223> OTHER INFORMATION: X12336 primer

<400> SEQUENCE: 114
ttttgtctgt cttaattttt ggtatcatta taggacagcc gctacattaa aggcaccaa 59

<210> SEQ ID NO 115
<211> LENGTH: 48
<212> TYPE: DNA
<213> ORGANISM: Artificial
<220> FEATURE:
<223> OTHER INFORMATION: X12337 primer

<400> SEQUENCE: 115
ccagcagcgg cagatcaaat tcaatggcgg ttcgacttta gcctgtat 48

<210> SEQ ID NO 116
<211> LENGTH: 48
<212> TYPE: DNA
<213> ORGANISM: Artificial
<220> FEATURE:
<223> OTHER INFORMATION: X12338 primer

<400> SEQUENCE: 116
atacaggcta aagtcgaacc gccattgaat ttgatctgcc gctgctgg 48

<210> SEQ ID NO 117
<211> LENGTH: 59
<212> TYPE: DNA
<213> ORGANISM: Artificial
<220> FEATURE:
<223> OTHER INFORMATION: X12339 primer

<400> SEQUENCE: 117
gataacaatt tcacacagga aacagctatg accatatggt ttagcggcta tttgcgtgc 59

<210> SEQ ID NO 118
<211> LENGTH: 59

<212> TYPE: DNA
<213> ORGANISM: Artificial
<220> FEATURE:
<223> OTHER INFORMATION: X12340 primer

<400> SEQUENCE: 118
ttttgtctgt cttaattttt ggtatcatta taggatggcg aatggcactc cctatgtta 59

<210> SEQ ID NO 119
<211> LENGTH: 48
<212> TYPE: DNA
<213> ORGANISM: Artificial
<220> FEATURE:
<223> OTHER INFORMATION: X12341 primer

<400> SEQUENCE: 119
tgacaatcac caggtcacca gacatccgaa tgaaataacg ccgcgatg 48

<210> SEQ ID NO 120
<211> LENGTH: 48
<212> TYPE: DNA
<213> ORGANISM: Artificial
<220> FEATURE:
<223> OTHER INFORMATION: X12342 primer

<400> SEQUENCE: 120
catcgcggcg ttatttcatt cggatgtctg gtgacctggt gattgtca 48

<210> SEQ ID NO 121
<211> LENGTH: 59
<212> TYPE: DNA
<213> ORGANISM: Artificial
<220> FEATURE:
<223> OTHER INFORMATION: X12343 primer

<400> SEQUENCE: 121
gataacaatt tcacacagga aacagctatg accattgttg atgagatgtt tgccaccgc 59

<210> SEQ ID NO 122
<211> LENGTH: 59
<212> TYPE: DNA
<213> ORGANISM: Artificial
<220> FEATURE:
<223> OTHER INFORMATION: X12344 primer

<400> SEQUENCE: 122
ttttgtctgt cttaattttt ggtatcatta taggaatgct gtacgtaata cgcctgcga 59

<210> SEQ ID NO 123
<211> LENGTH: 48
<212> TYPE: DNA
<213> ORGANISM: Artificial
<220> FEATURE:
<223> OTHER INFORMATION: X12345 primer

<400> SEQUENCE: 123
tctttaacaa gctgcggcac aacgatggga gaaacttgct ttctgggc 48

<210> SEQ ID NO 124
<211> LENGTH: 48
<212> TYPE: DNA
<213> ORGANISM: Artificial
<220> FEATURE:
<223> OTHER INFORMATION: X12346 primer

<400> SEQUENCE: 124

-continued gcccagaaag caagtttctc ccatcgttgt gccgcagctt gttaaaga 48

<210> SEQ ID NO 125
<211> LENGTH: 59
<212> TYPE: DNA
<213> ORGANISM: Artificial
<220> FEATURE:
<223> OTHER INFORMATION: X12347 primer

<400> SEQUENCE: 125
gataacaatt tcacacagga aacagctatg accatatctt tagcagcctg aacgtcgga 59

<210> SEQ ID NO 126
<211> LENGTH: 58
<212> TYPE: DNA
<213> ORGANISM: Artificial
<220> FEATURE:
<223> OTHER INFORMATION: X13802 primer

<400> SEQUENCE: 126
ttataggtta atgtcatgat aataatggtt tcttccgtca aagggcaaat caccgaaa 58

<210> SEQ ID NO 127
<211> LENGTH: 58
<212> TYPE: DNA
<213> ORGANISM: Artificial
<220> FEATURE:
<223> OTHER INFORMATION: X13803 primer

<400> SEQUENCE: 127
gggttccgcg cacatttccc cgaaaagtgc caccactcgg aataaccggt tcgggaaa 58

<210> SEQ ID NO 128
<211> LENGTH: 58
<212> TYPE: DNA
<213> ORGANISM: Artificial
<220> FEATURE:
<223> OTHER INFORMATION: X13804 primer

<400> SEQUENCE: 128
cgccttctat cgccttcttg acgagttctt ctgatacgac aaagcgttcg tcgcttca 58

<210> SEQ ID NO 129
<211> LENGTH: 58
<212> TYPE: DNA
<213> ORGANISM: Artificial
<220> FEATURE:
<223> OTHER INFORMATION: X13805 primer

<400> SEQUENCE: 129
actgttggga agggcgatcg gtgcgggcct cttcgaatga agcccagttc gcccattt 58

<210> SEQ ID NO 130
<211> LENGTH: 58
<212> TYPE: DNA
<213> ORGANISM: Artificial
<220> FEATURE:
<223> OTHER INFORMATION: X14576 primer

<400> SEQUENCE: 130
ttataggtta atgtcatgat aataatggtt tcttgcggat gcgaaggctt tgttgtat 58

<210> SEQ ID NO 131
<211> LENGTH: 48
<212> TYPE: DNA
<213> ORGANISM: Artificial

<220> FEATURE:
<223> OTHER INFORMATION: X14577 primer

<400> SEQUENCE: 131
tgggtagaaa aaataaacgg ctcagattcc tgtcacgaaa cggttgct 48

<210> SEQ ID NO 132
<211> LENGTH: 48
<212> TYPE: DNA
<213> ORGANISM: Artificial
<220> FEATURE:
<223> OTHER INFORMATION: X14578 primer

<400> SEQUENCE: 132
agcaaccgtt tcgtgacagg aatctgagcc gtttattttt tctaccca 48

<210> SEQ ID NO 133
<211> LENGTH: 48
<212> TYPE: DNA
<213> ORGANISM: Artificial
<220> FEATURE:
<223> OTHER INFORMATION: X14579 primer

<400> SEQUENCE: 133
ggtcaaacca ttgttaacgc gcattttagt gctccgctaa tgtcaact 48

<210> SEQ ID NO 134
<211> LENGTH: 48
<212> TYPE: DNA
<213> ORGANISM: Artificial
<220> FEATURE:
<223> OTHER INFORMATION: X14580 primer

<400> SEQUENCE: 134
agttgacatt agcggagcac taaaatgcgc gttaacaatg gtttgacc 48

<210> SEQ ID NO 135
<211> LENGTH: 58
<212> TYPE: DNA
<213> ORGANISM: Artificial
<220> FEATURE:
<223> OTHER INFORMATION: X14581 primer

<400> SEQUENCE: 135
gggttccgcg cacatttccc cgaaaagtgc cacctagaag cgataccttt cagcggca 58

<210> SEQ ID NO 136
<211> LENGTH: 58
<212> TYPE: DNA
<213> ORGANISM: Artificial
<220> FEATURE:
<223> OTHER INFORMATION: X14588 primer

<400> SEQUENCE: 136
ttataggtta atgtcatgat aataatggtt tctttctatg taacccagga agcggcaa 58

<210> SEQ ID NO 137
<211> LENGTH: 48
<212> TYPE: DNA
<213> ORGANISM: Artificial
<220> FEATURE:
<223> OTHER INFORMATION: X14589 primer

<400> SEQUENCE: 137
tgggtagaaa aaataaacgg ctcactttgc gttccattgc acggatca 48

<210> SEQ ID NO 138
<211> LENGTH: 48
<212> TYPE: DNA
<213> ORGANISM: Artificial
<220> FEATURE:
<223> OTHER INFORMATION: X14590 primer

<400> SEQUENCE: 138
tgatccgtgc aatggaacgc aaagtgagcc gtttattttt tctaccca 48

<210> SEQ ID NO 139
<211> LENGTH: 48
<212> TYPE: DNA
<213> ORGANISM: Artificial
<220> FEATURE:
<223> OTHER INFORMATION: X14591 primer

<400> SEQUENCE: 139
ataaagaact aagacaatct tcattttagt gctccgctaa tgtcaact 48

<210> SEQ ID NO 140
<211> LENGTH: 48
<212> TYPE: DNA
<213> ORGANISM: Artificial
<220> FEATURE:
<223> OTHER INFORMATION: X14592 primer

<400> SEQUENCE: 140
agttgacatt agcggagcac taaaatgaag attgtcttag ttctttat 48

<210> SEQ ID NO 141
<211> LENGTH: 48
<212> TYPE: DNA
<213> ORGANISM: Artificial
<220> FEATURE:
<223> OTHER INFORMATION: X14593 primer

<400> SEQUENCE: 141
acgagattac tgctgctgtg cagactattt cttatcgtgt ttaccgta 48

<210> SEQ ID NO 142
<211> LENGTH: 48
<212> TYPE: DNA
<213> ORGANISM: Artificial
<220> FEATURE:
<223> OTHER INFORMATION: X14594 primer

<400> SEQUENCE: 142
tacggtaaac acgataagaa atagtctgca cagcagcagt aatctcgt 48

<210> SEQ ID NO 143
<211> LENGTH: 58
<212> TYPE: DNA
<213> ORGANISM: Artificial
<220> FEATURE:
<223> OTHER INFORMATION: X14595 primer

<400> SEQUENCE: 143
gggttccgcg cacatttccc cgaaaagtgc caccacggcc tcttctccca taccaaat 58

<210> SEQ ID NO 144
<211> LENGTH: 58
<212> TYPE: DNA
<213> ORGANISM: Artificial
<220> FEATURE:
<223> OTHER INFORMATION: X15570 primer

<400> SEQUENCE: 144
ttataggtta atgtcatgat aataatggtt tctttgcgat ccgtagcaga caccataa 58

<210> SEQ ID NO 145
<211> LENGTH: 48
<212> TYPE: DNA
<213> ORGANISM: Artificial
<220> FEATURE:
<223> OTHER INFORMATION: X15571 primer

<400> SEQUENCE: 145
gaatactgcg ccagcgtttc acttcgttcc gcttgttctt cgatggtt 48

<210> SEQ ID NO 146
<211> LENGTH: 48
<212> TYPE: DNA
<213> ORGANISM: Artificial
<220> FEATURE:
<223> OTHER INFORMATION: X15572 primer

<400> SEQUENCE: 146
aaccatcgaa gaacaagcgg aacgaagtga aacgctggcg cagtattc 48

<210> SEQ ID NO 147
<211> LENGTH: 58
<212> TYPE: DNA
<213> ORGANISM: Artificial
<220> FEATURE:
<223> OTHER INFORMATION: X15573 primer

<400> SEQUENCE: 147
gggttccgcg cacatttccc cgaaaagtgc cacccatcaa tggcgatcac tttggcgt 58

<210> SEQ ID NO 148
<211> LENGTH: 58
<212> TYPE: DNA
<213> ORGANISM: Artificial
<220> FEATURE:
<223> OTHER INFORMATION: X15574 primer

<400> SEQUENCE: 148
ttataggtta atgtcatgat aataatggtt tcttaattga ccgccagttt gtcacacg 58

<210> SEQ ID NO 149
<211> LENGTH: 48
<212> TYPE: DNA
<213> ORGANISM: Artificial
<220> FEATURE:
<223> OTHER INFORMATION: X15575 primer

<400> SEQUENCE: 149
tcgccgtgca tttcaccatc aatcgagcgc ggcgacaact tcaataaa 48

<210> SEQ ID NO 150
<211> LENGTH: 48
<212> TYPE: DNA
<213> ORGANISM: Artificial
<220> FEATURE:
<223> OTHER INFORMATION: X15576 primer

<400> SEQUENCE: 150
tttattgaag ttgtcgccgc gctcgattga tggtgaaatg cacggcga 48

<210> SEQ ID NO 151

<211> LENGTH: 58
<212> TYPE: DNA
<213> ORGANISM: Artificial
<220> FEATURE:
<223> OTHER INFORMATION: X15577 primer

<400> SEQUENCE: 151
gggttccgcg cacatttccc cgaaaagtgc caccgccata aatcaccaat gcaccgct 58

<210> SEQ ID NO 152
<211> LENGTH: 58
<212> TYPE: DNA
<213> ORGANISM: Artificial
<220> FEATURE:
<223> OTHER INFORMATION: X15578 primer

<400> SEQUENCE: 152
ttataggtta atgtcatgat aataatggtt tcttcagctg gcaggcagta aaccattt 58

<210> SEQ ID NO 153
<211> LENGTH: 48
<212> TYPE: DNA
<213> ORGANISM: Artificial
<220> FEATURE:
<223> OTHER INFORMATION: X15579 primer

<400> SEQUENCE: 153
tcaaatgcgc tcagggtacc gatattctga acctgaaggc agttgggt 48

<210> SEQ ID NO 154
<211> LENGTH: 48
<212> TYPE: DNA
<213> ORGANISM: Artificial
<220> FEATURE:
<223> OTHER INFORMATION: X15580 primer

<400> SEQUENCE: 154
acccaactgc cttcaggttc agaatatcgg taccctgagc gcatttga 48

<210> SEQ ID NO 155
<211> LENGTH: 58
<212> TYPE: DNA
<213> ORGANISM: Artificial
<220> FEATURE:
<223> OTHER INFORMATION: X15581 primer

<400> SEQUENCE: 155
gggttccgcg cacatttccc cgaaaagtgc caccactggc ggtttaccta ccattcca 58

<210> SEQ ID NO 156
<211> LENGTH: 58
<212> TYPE: DNA
<213> ORGANISM: Artificial
<220> FEATURE:
<223> OTHER INFORMATION: X15586 primer

<400> SEQUENCE: 156
ttataggtta atgtcatgat aataatggtt tctttcgaca tcgctattgt caccacca 58

<210> SEQ ID NO 157
<211> LENGTH: 48
<212> TYPE: DNA
<213> ORGANISM: Artificial
<220> FEATURE:
<223> OTHER INFORMATION: X15587 primer

<400> SEQUENCE: 157

-continued

```
tttcggaagt ttgtgccaca acataatgct ctcctgataa tgttaaac                48


<210> SEQ ID NO 158
<211> LENGTH: 48
<212> TYPE: DNA
<213> ORGANISM: Artificial
<220> FEATURE:
<223> OTHER INFORMATION: X15588 primer

<400> SEQUENCE: 158

gtttaacatt atcaggagag cattatgttg tggcacaaac ttccgaaa                48


<210> SEQ ID NO 159
<211> LENGTH: 58
<212> TYPE: DNA
<213> ORGANISM: Artificial
<220> FEATURE:
<223> OTHER INFORMATION: X15589 primer

<400> SEQUENCE: 159

gggttccgcg cacatttccc cgaaaagtgc caccccaagt ggtcggcaat ttcagcat      58


<210> SEQ ID NO 160
<211> LENGTH: 24
<212> TYPE: DNA
<213> ORGANISM: Artificial
<220> FEATURE:
<223> OTHER INFORMATION: X12354 primer

<400> SEQUENCE: 160

ttgctgtatt tgacaccgcg ttcc                                          24


<210> SEQ ID NO 161
<211> LENGTH: 24
<212> TYPE: DNA
<213> ORGANISM: Artificial
<220> FEATURE:
<223> OTHER INFORMATION: X12355 primer

<400> SEQUENCE: 161

tttcacgaaa gaagcggtcg gact                                          24


<210> SEQ ID NO 162
<211> LENGTH: 24
<212> TYPE: DNA
<213> ORGANISM: Artificial
<220> FEATURE:
<223> OTHER INFORMATION: X12356 primer

<400> SEQUENCE: 162

ggcaagttta acgtcgcagt agca                                          24


<210> SEQ ID NO 163
<211> LENGTH: 24
<212> TYPE: DNA
<213> ORGANISM: Artificial
<220> FEATURE:
<223> OTHER INFORMATION: X12357 primer

<400> SEQUENCE: 163

tttatggcgg tgtcgtttgg cttg                                          24


<210> SEQ ID NO 164
<211> LENGTH: 24
<212> TYPE: DNA
```

<213> ORGANISM: Artificial
<220> FEATURE:
<223> OTHER INFORMATION: X12358 primer

<400> SEQUENCE: 164
atatctggaa gaagagggcg cgaa 24

<210> SEQ ID NO 165
<211> LENGTH: 24
<212> TYPE: DNA
<213> ORGANISM: Artificial
<220> FEATURE:
<223> OTHER INFORMATION: X12359 primer

<400> SEQUENCE: 165
gatgcattac gccgtgtggt tgaa 24

<210> SEQ ID NO 166
<211> LENGTH: 24
<212> TYPE: DNA
<213> ORGANISM: Artificial
<220> FEATURE:
<223> OTHER INFORMATION: X12360 primer

<400> SEQUENCE: 166
aacagcaatt gtagcagcgt gtcg 24

<210> SEQ ID NO 167
<211> LENGTH: 24
<212> TYPE: DNA
<213> ORGANISM: Artificial
<220> FEATURE:
<223> OTHER INFORMATION: X12361 primer

<400> SEQUENCE: 167
ttgtttgcca gcatcacgat accc 24

<210> SEQ ID NO 168
<211> LENGTH: 24
<212> TYPE: DNA
<213> ORGANISM: Artificial
<220> FEATURE:
<223> OTHER INFORMATION: X12362 primer

<400> SEQUENCE: 168
ctgggcgttt atgcttgccg tatt 24

<210> SEQ ID NO 169
<211> LENGTH: 24
<212> TYPE: DNA
<213> ORGANISM: Artificial
<220> FEATURE:
<223> OTHER INFORMATION: X12363 primer

<400> SEQUENCE: 169
agtcgtcagt tgtgagctcg actt 24

<210> SEQ ID NO 170
<211> LENGTH: 24
<212> TYPE: DNA
<213> ORGANISM: Artificial
<220> FEATURE:
<223> OTHER INFORMATION: X12364 project

<400> SEQUENCE: 170
tattcacggt ggcgacgctt ctaa 24

-continued

<210> SEQ ID NO 171
<211> LENGTH: 24
<212> TYPE: DNA
<213> ORGANISM: Artificial
<220> FEATURE:
<223> OTHER INFORMATION: X12365 primer

<400> SEQUENCE: 171
cgcctgttgc aggatttcaa tggt 24

<210> SEQ ID NO 172
<211> LENGTH: 24
<212> TYPE: DNA
<213> ORGANISM: Artificial
<220> FEATURE:
<223> OTHER INFORMATION: X12366 primer

<400> SEQUENCE: 172
aaagcgttag gtgcaaacct ggtg 24

<210> SEQ ID NO 173
<211> LENGTH: 24
<212> TYPE: DNA
<213> ORGANISM: Artificial
<220> FEATURE:
<223> OTHER INFORMATION: X12367 primer

<400> SEQUENCE: 173
attgccgtgc ctgctatcaa acag 24

<210> SEQ ID NO 174
<211> LENGTH: 24
<212> TYPE: DNA
<213> ORGANISM: Artificial
<220> FEATURE:
<223> OTHER INFORMATION: X12368

<400> SEQUENCE: 174
gctatggcac tggaagccaa tgtt 24

<210> SEQ ID NO 175
<211> LENGTH: 24
<212> TYPE: DNA
<213> ORGANISM: Artificial
<220> FEATURE:
<223> OTHER INFORMATION: X12369

<400> SEQUENCE: 175
agaacgtagt gaagctgaac gcga 24

<210> SEQ ID NO 176
<211> LENGTH: 24
<212> TYPE: DNA
<213> ORGANISM: Artificial
<220> FEATURE:
<223> OTHER INFORMATION: X12370

<400> SEQUENCE: 176
tgaagcttac cgcctcatcc tgaa 24

<210> SEQ ID NO 177
<211> LENGTH: 24
<212> TYPE: DNA
<213> ORGANISM: Artificial
<220> FEATURE:

<223> OTHER INFORMATION: X12371

<400> SEQUENCE: 177
agaatggtga accagagcaa ggga 24

<210> SEQ ID NO 178
<211> LENGTH: 24
<212> TYPE: DNA
<213> ORGANISM: Artificial
<220> FEATURE:
<223> OTHER INFORMATION: X12801

<400> SEQUENCE: 178
gattgattac gcggtgaaag cgca 24

<210> SEQ ID NO 179
<211> LENGTH: 24
<212> TYPE: DNA
<213> ORGANISM: Artificial
<220> FEATURE:
<223> OTHER INFORMATION: X12802

<400> SEQUENCE: 179
acacccggta tcaaaccctt ccat 24

<210> SEQ ID NO 180
<211> LENGTH: 24
<212> TYPE: DNA
<213> ORGANISM: Artificial
<220> FEATURE:
<223> OTHER INFORMATION: X14574

<400> SEQUENCE: 180
ccgtggcgat taacgtgaac aact 24

<210> SEQ ID NO 181
<211> LENGTH: 24
<212> TYPE: DNA
<213> ORGANISM: Artificial
<220> FEATURE:
<223> OTHER INFORMATION: X14575

<400> SEQUENCE: 181
agtcgatagt gccatcttca cgca 24

<210> SEQ ID NO 182
<211> LENGTH: 24
<212> TYPE: DNA
<213> ORGANISM: Artificial
<220> FEATURE:
<223> OTHER INFORMATION: X15590

<400> SEQUENCE: 182
actgttccct tcccgcgttt gata 24

<210> SEQ ID NO 183
<211> LENGTH: 24
<212> TYPE: DNA
<213> ORGANISM: Artificial
<220> FEATURE:
<223> OTHER INFORMATION: X15591

<400> SEQUENCE: 183
gcatcaactg ccgagttaaa cgca 24

<210> SEQ ID NO 184
<211> LENGTH: 24
<212> TYPE: DNA
<213> ORGANISM: Artificial
<220> FEATURE:
<223> OTHER INFORMATION: X15592

<400> SEQUENCE: 184
aggtcgaagc cagcttgatc agaa 24

<210> SEQ ID NO 185
<211> LENGTH: 24
<212> TYPE: DNA
<213> ORGANISM: Artificial
<220> FEATURE:
<223> OTHER INFORMATION: X15593

<400> SEQUENCE: 185
cgctgacggt ttgtgataac gctt 24

<210> SEQ ID NO 186
<211> LENGTH: 24
<212> TYPE: DNA
<213> ORGANISM: Artificial
<220> FEATURE:
<223> OTHER INFORMATION: X15594

<400> SEQUENCE: 186
taccttctgc tttgcccagt gagt 24

<210> SEQ ID NO 187
<211> LENGTH: 24
<212> TYPE: DNA
<213> ORGANISM: Artificial
<220> FEATURE:
<223> OTHER INFORMATION: X15595

<400> SEQUENCE: 187
tgaagcattg ctggtgggat ctga 24

<210> SEQ ID NO 188
<211> LENGTH: 24
<212> TYPE: DNA
<213> ORGANISM: Artificial
<220> FEATURE:
<223> OTHER INFORMATION: X15596

<400> SEQUENCE: 188
agtggcacca caccaatgct ttca 24

<210> SEQ ID NO 189
<211> LENGTH: 24
<212> TYPE: DNA
<213> ORGANISM: Artificial
<220> FEATURE:
<223> OTHER INFORMATION: X15597

<400> SEQUENCE: 189
tgaacgccag cttcacggat agat 24

<210> SEQ ID NO 190
<211> LENGTH: 58
<212> TYPE: DNA
<213> ORGANISM: Artificial
<220> FEATURE:
<223> OTHER INFORMATION: X16072

<400> SEQUENCE: 190
tctcagtagt agttgacatt agcggagcac taaaatgaag attgtcttag ttctttat 58

<210> SEQ ID NO 191
<211> LENGTH: 58
<212> TYPE: DNA
<213> ORGANISM: Artificial
<220> FEATURE:
<223> OTHER INFORMATION: X16073

<400> SEQUENCE: 191
cagtctttcg actgagcctt tcgttttacg gccgctattt cttatcgtgt ttaccgta 58

<210> SEQ ID NO 192
<211> LENGTH: 58
<212> TYPE: DNA
<213> ORGANISM: Artificial
<220> FEATURE:
<223> OTHER INFORMATION: X16082

<400> SEQUENCE: 192
tctcagtagt agttgacatt agcggagcac taaaatggca accgttctgt gtgttctg 58

<210> SEQ ID NO 193
<211> LENGTH: 58
<212> TYPE: DNA
<213> ORGANISM: Artificial
<220> FEATURE:
<223> OTHER INFORMATION: X16083

<400> SEQUENCE: 193
cagtctttcg actgagcctt tcgttttacg gccgttaggt cagacgatag ctctgtgc 58

<210> SEQ ID NO 194
<211> LENGTH: 59
<212> TYPE: DNA
<213> ORGANISM: Artificial
<220> FEATURE:
<223> OTHER INFORMATION: X16829

<400> SEQUENCE: 194
tgtgagcgga taacaatttc acacaggaaa cagctatgtc gaaggttatg aaaaccatg 59

<210> SEQ ID NO 195
<211> LENGTH: 48
<212> TYPE: DNA
<213> ORGANISM: Artificial
<220> FEATURE:
<223> OTHER INFORMATION: X16064

<400> SEQUENCE: 195
gctttcacac ctccaagatt tcgtctaatt ttgttcagca agcttctt 48

<210> SEQ ID NO 196
<211> LENGTH: 48
<212> TYPE: DNA
<213> ORGANISM: Artificial
<220> FEATURE:
<223> OTHER INFORMATION: X16065

<400> SEQUENCE: 196
aagaagcttg ctgaacaaaa ttagacgaaa tcttggaggt gtgaaagc 48

<210> SEQ ID NO 197
<211> LENGTH: 59

<212> TYPE: DNA
<213> ORGANISM: Artificial
<220> FEATURE:
<223> OTHER INFORMATION: X16830

<400> SEQUENCE: 197
cctcgaggtc gacggtatcg ataagcttga tatcttattc agccttaata gctcctgtt 59

<210> SEQ ID NO 198
<211> LENGTH: 59
<212> TYPE: DNA
<213> ORGANISM: Artificial
<220> FEATURE:
<223> OTHER INFORMATION: X16831

<400> SEQUENCE: 198
tgtgagcgga taacaatttc acacaggaaa cagctatggg aaagaaaatg atgacgact 59

<210> SEQ ID NO 199
<211> LENGTH: 50
<212> TYPE: DNA
<213> ORGANISM: Artificial
<220> FEATURE:
<223> OTHER INFORMATION: X16075

<400> SEQUENCE: 199
tacacctcct tatcttaata ggcgttctac ttcttcgtcc gcttgctgag 50

<210> SEQ ID NO 200
<211> LENGTH: 50
<212> TYPE: DNA
<213> ORGANISM: Artificial
<220> FEATURE:
<223> OTHER INFORMATION: X16076

<400> SEQUENCE: 200
ctcagcaagc ggacgaagaa gtagaacgcc tattaagata aggaggtgta 50

<210> SEQ ID NO 201
<211> LENGTH: 51
<212> TYPE: DNA
<213> ORGANISM: Artificial
<220> FEATURE:
<223> OTHER INFORMATION: X16077

<400> SEQUENCE: 201
cccgtctgat atttatggtt ctacgactta ctcttgaact ggagctccta c 51

<210> SEQ ID NO 202
<211> LENGTH: 51
<212> TYPE: DNA
<213> ORGANISM: Artificial
<220> FEATURE:
<223> OTHER INFORMATION: X16078

<400> SEQUENCE: 202
gtaggagctc cagttcaaga gtaagtcgta gaaccataaa tatcagacgg g 51

<210> SEQ ID NO 203
<211> LENGTH: 59
<212> TYPE: DNA
<213> ORGANISM: Artificial
<220> FEATURE:
<223> OTHER INFORMATION: X16832

<400> SEQUENCE: 203
ccctcgaggt cgacggtatc gataagcttg atatcctatt ggttctgccg gatatatat 59

<210> SEQ ID NO 204
<211> LENGTH: 59
<212> TYPE: DNA
<213> ORGANISM: Artificial
<220> FEATURE:
<223> OTHER INFORMATION: X16981

<400> SEQUENCE: 204
tgtgagcgga taacaatttc acacaggaaa cagctatgcc cgatatgaca aacgaatct 59

<210> SEQ ID NO 205
<211> LENGTH: 59
<212> TYPE: DNA
<213> ORGANISM: Artificial
<220> FEATURE:
<223> OTHER INFORMATION: X16982

<400> SEQUENCE: 205
ccctcgaggt cgacggtatc gataagcttg atatcttaaa caccagcttc gaagtcctt 59

<210> SEQ ID NO 206
<211> LENGTH: 5568
<212> TYPE: DNA
<213> ORGANISM: Artificial
<220> FEATURE:
<223> OTHER INFORMATION: Sequence of the PNO gene and flanking regions
used to create FP66

<400> SEQUENCE: 206
tgagccgttt attttttcta cccatatcct tgaagcggtg ttataatgcc gcgccctcga 60
tatggggatt tttaacgacc tgattttcgg gtctcagtag tagttgacat tagcggagca 120
ctaaaatgaa acagagcgtt cgtccgatta ttagcaatgt tctgcgtaaa gaagttgccc 180
tgtatagcac cattattggt caggataaag gtaaagaacc gacaggtcgt acctatacca 240
gcggtccgaa accggcaagc catattgaag ttccgcatca tgttaccgtt ccggcaaccg 300
atcgtacccc gaatccggat gcacagtttt ttcagagcgt tgatggtagc caggcaacca 360
gccatgttgc atatgccctg agcgataccg catttatcta tccgattacc ccgagcagcg 420
ttatgggtga actggcagat gtttggatgg cacagggtcg taaaaatgcc tttggtcagg 480
ttgttgatgt tcgtgaaatg cagagcgaag ccggtgcagc gggtgcactg catggtgcac 540
tggcagccgg tgcgattgca accaccttta ccgcaagcca gggtctgctg ctgatgattc 600
cgaatatgta taaaatcgca ggcgaactga tgccgagcgt tattcatgtt gcagcacgtg 660
agctggcagg tcatgcactg agcatttttg gtggtcatgc agatgttatg gcagttcgtc 720
agaccggttg ggcaatgctg tgtagccata ccgttcagca gagccatgat atggcactga 780
ttagccatgt ggcaaccctg aaaagcagca ttccgtttgt tcattttttt gatggttttc 840
gcaccagcca cgaagtgaac aaaatcaaaa tgctgccgta tgccgaactg aaaaaactgg 900
ttccgcctgg caccatggaa cagcattggg cacgtagcct gaatccgatg catccgacca 960
ttcgtggcac caatcagagc gcagatatct attttcagaa tatggaaagc gccaaccagt 1020
attataccga tctggcagaa gttgttcaag aaaccatgga tgaagttgca ccgtatattg 1080
gtcgtcatta caaaatcttt gagtatgttg gtgcaccgga tgcagaagag gtgaccgttc 1140
tgatgggtag cggtgccacc accgttaatg aagcagttga tctgctggtt aaacgcggta 1200
aaaaagttgg tgcagttctg gttcatctgt atcgtccgtg gtcaaccaaa gcatttgaaa 1260

-continued

```
aagttctgcc gaaaaccgtg aaacgtattg cagcactgga tcgttgcaaa gaagttaccg   1320
cactgggcga accgctgtat ctggatgtta gcgccaccct gaacctgttt ccggaacgtc   1380
agaatgttaa agttattggt ggtcgttatg gtctgggtag caaagatttc attccggaac   1440
atgcactggc catttatgca aatctggcaa gcgaaaatcc gattcagcgt tttaccgttg   1500
gtattaccga tgatgttacc ggcaccagcg tgccgtttgt taatgaacgt gttgataccc   1560
tgccggaagg cacccgtcag tgtgtttttt ggggtattgg tagtgatggc accgttggtg   1620
caaatcgtag cgcagttcgt attattggtg ataatagcga tctgatggtg caggcgtatt   1680
ttcagtttga tgcatttaaa agcggtggtg ttaccagcag ccatctgcgt tttggtccta   1740
aaccgattac cgcacagtat ctggttacca atgcagatta tattgcctgc cactttcaag   1800
agtatgtgaa acgttttgat atgctggatg caattcgtga aggtggcacc tttgttctga   1860
atagccgttg gaccaccgaa gatatggaaa aagaaattcc ggcagatttt cgtcgtaatg   1920
tggcacagaa aaaagtgcgc ttttataacg ttgatgcccg taaaatttgc gatagctttg   1980
gtctgggcaa acgcattaac atgctgatgc aggcatgttt tttcaaactg agcggtgttc   2040
tgccgctggc cgaagcacag cgtctgctga atgaaagcat tgttcatgag tatggcaaaa   2100
aaggtggtaa agtggtggaa atgaatcagg cagttgttaa tgcagtgttt gccggtgatc   2160
tgcctcaaga agttcaggtt ccggcagcat gggcaaatgc agttgatacc agcacccgca   2220
ccccgaccgg tattgaattt gttgataaaa tcatgcgtcc gctgatggat ttcaaaggtg   2280
atcagctgcc ggttagcgtt atgacaccgg gtggtacatt tccggttggc accacccagt   2340
atgcaaaacg tgcaattgcg gcatttattc cgcagtggat tccggcaaat tgtacccagt   2400
gtaattattg cagctatgtt tgtccgcatg caaccattcg tccgtttgtg ctgaccgatc   2460
aagaagtgca gctggcaccg gaaagctttg ttacccgtaa agcaaaaggt gattatcagg   2520
gtatgaactt tcgtattcag gttgcaccgg aagattgtac cggttgtcag gtttgtgttg   2580
aaacctgtcc ggatgatgca ctggaaatga ccgatgcgtt taccgccaca ccggttcagc   2640
gtaccaattg ggaatttgca attaaagttc cgaatcgtgg tacgatgacc gatcgctata   2700
gcctgaaagg tagccagttt cagcaaccgc tgctggaatt tagcggtgca tgtgaaggtt   2760
gtggtgaaac cccgtatgtt aaactgctga cccagctgtt tggtgaacgt accgttattg   2820
caaatgccac cggttgtagc agcatttggg gtggtacggc aggtctggct ccgtatacca   2880
ccaatgcaaa aggtcagggt ccggcatggg gtaatagcct gtttgaagat aatgccgaat   2940
ttggttttgg tattgcagtt gccaatgcac agaaacgtag ccgtgttcgt gattgtattc   3000
tgcaggccgt tgaaaaaaaa gtggccgatg aaggtctgac caccctgctg gcacagtggc   3060
tgcaggattg gaataccggt gataaaacac tgaaatatca ggaccagatt attgccggtc   3120
tggcacagca gcgtagtaaa gatcctctgc tggaacaaat ttatggcatg aaagatatgc   3180
tgccgaatat cagccagtgg attattggcg gtgatggttg ggccaatgat attggctttg   3240
gtggcctgga tcatgttctg gcgagcggtc agaatctgaa tgttctggtg ctggataccg   3300
aaatgtatag caatacaggt ggtcaggcaa gcaaaagcac ccatatggca agcgttgcaa   3360
aatttgccct gggtggtaaa cgtaccaaca aaaaaaacct gaccgaaatg gccatgagct   3420
atggtaatgt ttatgttgca accgttagcc atggtaatat ggcccagtgt gttaaagcct   3480
ttgttgaagc agaaagctat gatggtccga gcctgattgt tggttatgca ccgtgcattg   3540
aacatggtct gcgtgcaggt atggcacgta tggttcaaga atcagaagca gcaattgcaa   3600
ccggttattg gccactgtat cgttttgatc cgcgtctggc aaccgaaggt aaaaacccgt   3660
```

ttcagctgga tagcaaacgt attaaaggta acctgcaaga atatctggat cgccagaatc 3720
gttatgtgaa cctgaaaaaa aacaatccga aaggtgccga tctgctgaaa agccagatgg 3780
cagataacat tacagcacgc tttaatcgtt atcgtcgtat gctggaaggt ccgaatacca 3840
aagcagcagc accgagcggt aatcatgtga ccattctgta tggtagtgaa accggtaata 3900
gcgaaggtct ggcaaaagaa ctggccaccg attttgaacg tcgtgaatat agcgttgcag 3960
ttcaggccct ggatgatatt gatgttgcgg atctggaaaa tatgggcttt gttgttattg 4020
ccgtttcaac ctgtggtcag ggccagtttc cgcgtaatag tcagctgttt tggcgtgaac 4080
tgcagcgtga taaaccggaa ggttggctga aaaatctgaa atacaccgtt tttggcctgg 4140
gtgatagcac ctattacttt tattgtcata ccgccaaaca aatcgatgca cgtctggcag 4200
cgctgggtgc acagcgtgtt gttccgattg gtttcggtga tgatggtgat gaagatatgt 4260
ttcataccgg cttcaataat tggattccga gcgtttggaa tgagctgaaa accaaaactc 4320
cggaagaagc actgtttacc ccgtcaattg ccgttcagct gaccccgaat gcaacaccgc 4380
aggattttca ttttgccaaa agcacaccgg tgctgagcat taccggtgca gaacgtatta 4440
caccggcaga tcatacccgc aattttgtta ccattcgttg gaaaaccgat ctgagctatc 4500
aggttggtga tagcctgggt gtttttccag aaaatacccg tagcgttgtt gaagaattcc 4560
tgcagtatta tggcctgaac ccgaaagatg ttattaccat tgaaaataaa ggctcacgcg 4620
aactgccgca ttgtatggcc gttggtgacc tgtttaccaa agttctggat attctgggta 4680
aaccgaataa ccgcttctat aaaaccctga gctatttcgc cgttgataaa gcagaaaaag 4740
aacgcctgct gaaaattgca gaaatgggtc cggaatatag caacattctg tcagagatgt 4800
atcattatgc cgacatcttt catatgtttc cgagcgcacg tccgacactg cagtatctga 4860
ttgaaatgat cccgaacatt aaaccgcgtt attatagcat tagtagcgca ccgattcata 4920
ctccgggtga agtgcatagc ctggttctga ttgatacctg gattaccctg agcggtaaac 4980
atcgtacggg tctgacctgt accatgctgg aacatctgca ggcaggtcag gtggtggatg 5040
gttgtattca tccgaccgca atggaatttc cggatcatga aaaaccggtt gttatgtgtg 5100
caatgggttc aggtctggca ccttttgttg catttctgcg tgaacgtagc accctgcgta 5160
aacagggtaa aaaaacgggc aatatggcgc tgtattttgg caatcgttac gaaaaaaccg 5220
aatttctgat gaaagaggaa ctgaaaggcc atatcaatga tggtctgctg acactgcgtt 5280
gtgcatttag ccgtgatgat ccgaaaaaaa aagtctatgt gcaggatctg atcaaaatgg 5340
atgaaaaaat gatgtatgat tacctggtgg ttcagaaagg cagcatgtat tgttgtggta 5400
gccgtagttt tatcaaaccg gtgcaagaaa gcctgaaaca ttgttttatg aaagcgggtg 5460
gtctgaccgc agaacaggca gaaaatgaag ttattgatat gtttaccacg ggtcgctata 5520
acattgaagc gtggcggccg taaaacgaaa ggctcagtcg aaagactg 5568

<210> SEQ ID NO 207
<211> LENGTH: 14039
<212> TYPE: DNA
<213> ORGANISM: Artificial
<220> FEATURE:
<223> OTHER INFORMATION: pMU2924

<400> SEQUENCE: 207
ctgacgggct tgtctgctcc cggcatccgc ttacagacaa gctgtgaccg tctccgggag 60
ctgcatgtgt cagaggtttt caccgtcatc accgaaacgc gcgagacgaa agggcctcgt 120

```
gatacgccta tttttatagg ttaatgtcat gataataatg gtttcttacg cagttgctgg    180
atatcagagg ttaatgcgag agagagtttt ccctgccatt cctgccaggg agaaaaaatc    240
agtttatcga tattgatcca ggtgttaggc agcatggcct gccactgcgc gagtgttttt    300
ggagcggctg gcgattgctc cgtctgcggc aatttcgcca gacaagcaga atcaagttct    360
accgtgccga cgttcaataa ccagcggctg ggatgtgaaa ggctggcgtt ggtgatatgc    420
gcaagctgac aatctcccac cagataacgg agatcgggaa tgattaaacc tttacgcgta    480
atgcgtgggc tttcatctaa tgcaatacgt gtcccgagcg gtagccagat gcccgccagc    540
gtgggaaccc acagcccgag cgtcatcagc agcgtcaacg gcacaagaat aatcagtaat    600
aacagcgcga gaacggcttt atatttaccc agcatgggta gttaatatcc tgatttagcg    660
aaaaattaag cattcaatac gggtattgtg gcatgtttaa ccgttcagtt gaaggttgcg    720
cctacactaa gcatagttgt tgatgaattt ttcaatatcg ccatagcttt caattaaatt    780
tgaaattttg taaaatattt ttagtagctt aaatgtgatt caacatcact ggagaaagtc    840
ttatgaaact cgccgtttat agcacaaaac agtacgacaa gaagtacctg caacaggtga    900
acgagttgag ccgtttattt tttctaccca tatccttgaa gcggtgttat aatgccgcgc    960
cctcgatatg ggattttta acgacctgat tttcgggtct cagtagtagt tgacattagc    1020
ggagcactaa aatgtcaata gatgatagga ttgaagacct tcttagaaga agagagatgg   1080
ttttagaagg cggtggttta gataaagtag agaaacaaca ccaaaaggga aagcttaccg   1140
caagagagag gatatacaag cttttagatg aagatagctt tgtggaaata gatgcgtatg   1200
ttgagcacag gtgtattgac tttggcatgg aaaagcaaag gatacctggc gaaggcgtag   1260
tgacagggta tgggacgata gatggaaggc ttgtctacgt ttatgcacag gattttacgg   1320
ttttaggagg atcattaggc gagtatcatg caaagaaaat cacaaaaatc atggatatgg   1380
ctttaaagat gggagcaccg ctcattggat taaatgattc cggaggtgcc agaatacagg   1440
aaggcgtcga tgctttatcg ggatatggca acatattttt cagaaacacg ctggcatcag   1500
gcgtaatacc gcaaatatcg gtgataatgg ggcccagcgc tggaggtgca gtttattcgc   1560
ctgctcttac tgactttata ttcatggtag acaagacaag tcagatgttt ataactggac   1620
cgcaggtcat aaaagccgtc acaggtgaag atgtttcggc agaggagctt ggtggatcga   1680
ttactcacag cacgaaaagc ggtgtggcgc attttagggc tgaaaacgac gaagagtgtt   1740
tgaagatggt gaggaagcta ttaagttacc ttccatcaaa caatttggaa gatccgccac   1800
agttggcgac agatgacgac ataaacagat tttccgatag gcttattgag ataatcccag   1860
atagtcctaa taagccatac gatatgaaag aagtaatttc ggaaatagtg gatgaaggcg   1920
tgtattttga atcacaggca atgtatgcgc aaaacataat aacggcattt gcaaggctta   1980
atggaaggac ggtagggata atagcaaatc agcctaaagt tttggctgga tgtctcgaca   2040
tcaatgcgtc tgataaggca tcgaggttta taaggttttg cgatgcattt aacatcccgc   2100
ttctcaatat agtagatgtt ccaggatttt tgcctggaac gaatcaagag tacggtggaa   2160
taatacgcca tggggcaaag atgttgtacg cttactctga ggctacagtg ccaaaagtga   2220
ctctcattgt gaggaaagct tatggcggtg cttaccttgc catgtgcagc aaagacttag   2280
gagctgattt tgttttggca tggcctactg ctgaaatagc ggtcatggga cctgatgggg   2340
cagcaaacat cgtgtttaaa aatgaaataa aatcgtctga tgatcctgtg gctgcaagaa   2400
atgaaaagat aaatgagtac agggagaatt tcgcaaatcc atacagggca gcagcgagag   2460
gatatgtaga tgatgtagtt ctgccgcaag agacgagacc tcgcctcatc tcggcgttcg   2520
```

atatgcttat gagcaaaagg gagtcaaggc ccagcaaaaa gcatggcaat tttcctgttt 2580
aaaatcgatt taaggggaag tgaaagaatg gaagagataa atgaagaaat agttgctgtc 2640
attgaagctg cgatttacgc ggcatttggt cagtacgaaa agaatttccg catcaaggta 2700
ataaagagag tggactcaaa tatgccggaa tggagaaaag ctggccttta caatcagatg 2760
agatagatga ggaggatgga aatgaaaaaa tttatagtaa ctgtcaatgg aaaaaaatac 2820
gatgtggaag tagaagaagt aaaagtcgac gtggcaagtg agaaaaaagc aaaagaagat 2880
actgctgcta aaaatgcgtc agatgcaagt gtaaaaagca aacaggttga agtaaaaaac 2940
gaagtcaaag acggtttctc aatcaatgca ccgatgccgg gaactatatt ggatgtcaaa 3000
ataagccaag gccagactgt cagacgaggc gatgtgcttt taatactgga agccatgaag 3060
atggaaaatg aaatcacgtc accttacgat ggcacaataa tatccataaa tgtttcaaaa 3120
ggtgcctctg taaatacagg cgatgtgctt ttgtacttaa aatgagagta aaggaggagt 3180
tttaatgtct aagataaaaa taacggagac tgttttaaga gatgcacatc aatcgttgct 3240
ggcaaccaga atgacaaccg atgaaatgct tcctatagca gaaaaattag atgaagttgg 3300
ttttttctcg ctggaagcat ggggcggtgc tacatttgat gcatgtatga gatttttgaa 3360
tgaagaccca tgggaaagat taagactttt aaagaaggcg attaagaaga cacctcttca 3420
aatgctttta agaggtcaaa atttactcgg atataaacac tatcccgatg atgtcgtaaa 3480
tgaatttata ataaaatctg ttgaaaatgg tatagatata ataagaattt ttgatgcgtt 3540
aaatgatgtg agaaatttag aagtgccaat aaaatctgca aaaagtgcag gtgctcatgt 3600
acaggcagct attgtatata cagttagtcc tgtacataat acagatcatt atttgaaagt 3660
ggcaaagtct cttcaagata tgggtgcgga ttccatatgc attaaggata tgtctggaat 3720
attatcaccc tatgttgcat acgatttgat taaatctctg aaaagagcac tttacacgcc 3780
aattcaactg catagccatt atacagcagg actggcttca atgacttatt taaaagccat 3840
agaagctggt gtagacgggg ttgatacagc tatttcttcg cttgccttag gaacatcaca 3900
accagctaca gaatcaatcg tggctgcatt gaaagataca gaatatgata cagggctaga 3960
tttaaaattg cttgctgaga tagctcagca ttttaatgta gtcaaacaga atcacaaaaa 4020
tgacagcgat atgtctttgc ttatgtctgt tgatgttaaa gcattagaaa gtcaaatacc 4080
agggggaatg ttatcaaatt tggtttcaca gctaaagcag cagaatgcat taaacaaata 4140
tcaagacgtc ttgaaagaag ttccaagggt acgcgaagat ttgggatatc ctcctcttgt 4200
tactccaatg agccagatgg ttggaaccca ggctgtttta aatgttatta caggggagag 4260
atataaaatc gttcctaaag aaattaaaga ttatgtcaaa ggtttatatg ggatgccacc 4320
agctccaatt tcagattcta tacgaaagaa aataatcggc gatgaagaag taatttcaaa 4380
gaggccagca gatttactaa gtcctcaatt ggatgaattt aaaaatgaga taaaggaatt 4440
tatagagcaa gatgaagatg ttttatcata tgcattattt cctcaagtag caagaagatt 4500
tttcgagtat aggcaagcca aaaaatacag aattgattca acattattaa atatcgaaga 4560
aagggttcat ccgatataac ggccgtaaaa cgaaaggctc agtcgaaaga ctgggccttt 4620
cgttttatct gttgtttgtc ggtgaacgct ctcctgagta ggacaaatcc gccgggagcg 4680
gatttgaacg ttgcgaagca acggcccgga gggtggcggg caggacgccc gccataaact 4740
gccaggcatc aaattaagca gaaggccatc ctgacggatg gcctttttgc gtttctacaa 4800
actcttcctg tcgtcatatc tacaagccat ccccccacag atacggtaaa ctagcctcgt 4860
ttttgcatca ggaaagcagc tatgaaccac tcctccagcc aggacagaaa tgcctcgact 4920
tcgctgctgc ccaaggttgc cgggtgacgc acaccgtgga aacggatgaa ggcacgaacc 4980
cagtggacat aagcctgttc ggttcgtaag ctgtaatgca agtagcgtat gcgctcacgc 5040
aactggtcca gaaccttgac cgaacgcagc ggtggtaacg gcgcagtggc ggttttcatg 5100
gcttgttatg actgtttttt tggggtacag tctatgcctc gggcatccaa gcagcaagcg 5160
cgttacgccg tgggtcgatg tttgatgtta tggagcagca acgatgttac gcagcagggc 5220
agtcgcccta aaacaaagtt aaacatcatg agggaagcgg tgatcgccga agtatcgact 5280
caactatcag aggtagttgg cgtcatcgag cgccatctcg aaccgacgtt gctggccgta 5340
catttgtacg gctccgcagt ggatggcggc ctgaagccac acagtgatat tgatttgctg 5400
gttacggtga ccgtaaggct tgatgaaaca acgcggcgag ctttgatcaa cgaccttttg 5460
gaaacttcgg cttcccctgg agagagcgag attctccgcg ctgtagaagt caccattgtt 5520
gtgcacgacg acatcattcc gtggcgttat ccagctaagc gcgaactgca atttggagaa 5580
tggcagcgca atgacattct tgcaggtatc ttcgagccag ccacgatcga cattgatctg 5640
gctatcttgc tgacaaaagc aagagaacat agcgttgcct tggtaggtcc agcggcggag 5700
gaactctttg atccggttcc tgaacaggat ctatttgagg cgctaaatga aaccttaacg 5760
ctatggaact cgccgcccga ctgggctggc gatgagcgaa atgtagtgct tacgttgtcc 5820
cgcatttggt acagcgcagt aaccggcaaa atcgcgccga aggatgtcgc tgccgactgg 5880
gcaatggagc gcctgccggc ccagtatcag cccgtcatac ttgaagctag acaggcttat 5940
cttggacaag aagaagatcg cttggcctcg cgcgcagatc agttggaaga atttgtccac 6000
tacgtgaaag gcgagatcac caaggtagtc ggcaaataac cctcgagcca cccatgacca 6060
aaatccctta acgtgagtta cgcgtcgttc cactgtgaca gcagaagctc tgaccagtat 6120
ttctcagact acgctgcaaa acttaagcaa tctggaaaaa ggcgaaacct gcccgaacga 6180
actggtttaa tcttgccgct cccctgcatt ccaggggagc tgattcagat aatccccaat 6240
gacctttcat cctctattct taaaatagtc ctgagtcaga aactgtaatt gagaaccaca 6300
atgaagaaag tagccgcgtt tgttgcgcta agcctgctga tggcgggatg tgtaagtaat 6360
gacaaaattg ctgttacgcc agaacagcta cagcatcatc gctttgtgct ggaaagcgta 6420
aacggtaagc ccgtgaccag cgataaaaat ccgccagaaa tcagctttgg tgaaaaaatg 6480
atgatttccg gcagcatgtg taaccgcttt agcggtgaag gcaaactgtc taatggtgaa 6540
ctgacagcca aagggctggc aatgacccgt atgatgtgcg ctaacccgca gcttaatgaa 6600
ctcgataaca ccattagcga aatgctgaaa gaaggtgcac aagtggatct gaccgcgaac 6660
cagttaacgc tggcgaccgc aaaacagaca ttaacttata agctggcgga tttaatgaat 6720
taatagctgc cacagctccc ggcggcaagt gactgttcgc tacagcgttt gccgttgggt 6780
aatgcacaca tcccaaggtg gcacttttcg gggaaatgtg cgcggaaccc ctatttgttt 6840
atttttctaa atacattcaa atatgtatcc gctcatgaga caataaccct gataaatgct 6900
tcaataatat tgaaaaagga agagtatgag tattcaacat ttccgtgtcg cccttattcc 6960
cttttttgcg gcattttgcc ttcctgtttt tgctcaccca gaaacgctgg tgaaagtaaa 7020
agatgctgaa gatcagttgg gtgcacgagt gggttacatc gaactggatc tcaacagcgg 7080
taagatcctt gagagttttc gccccgaaga acgttttcca atgatgagca cttttaaagt 7140
tctgctatgt ggcgcggtat tatcccgtat tgacgccggg caagagcaac tcggtcgccg 7200
catacactat tctcagaatg acttggttga gtactcacca gtcacagaaa agcatcttac 7260

```
ggatggcatg acagtaagag aattatgcag tgctgccata accatgagtg ataacactgc   7320
ggccaactta cttctgacaa cgatcggagg accgaaggag ctaaccgctt ttttgcacaa   7380
catgggggat catgtaactc gccttgatcg ttgggaaccg gagctgaatg aagccatacc   7440
aaacgacgag cgtgacacca cgatgcctgt agcaatggca acaacgttgc gcaaactatt   7500
aactggcgaa ctacttactc tagcttcccg gcaacaatta atagactgga tggaggcgga   7560
taaagttgca ggaccacttc tgcgctcggc ccttccggct ggctggttta ttgctgataa   7620
atctggagcc ggtgagcgtg ggtctcgcgg tatcattgca gcactggggc cagatggtaa   7680
gccctcccgt atcgtagtta tctacacgac ggggagtcag gcaactatgg atgaacgaaa   7740
tagacagatc gctgagatag gtgcctcact gattaagcat tggtaagcga tgaaatgtga   7800
ggtgaatcag ggttttcacc cgattttgtg ctgatcagaa tttttttct ttttccccct   7860
tgaaggggcg aagcctcatc cccatttctc tggtcaccag ccgggaaacc acgtaagctc   7920
cggcgtcacc cataacagat acggactttc tcaaaggaga gttatcaatg aacatcaaaa   7980
agtttgcaaa acaagcaaca gtattaacct ttactaccgc actgctggca ggaggcgcaa   8040
ctcaagcgtt tgcgaaagaa acgaaccaaa agccatataa ggaaacatac ggcatttccc   8100
atattacacg ccatgatatg ctgcaaatcc ctgaacagca aaaaaatgaa aaatatcaag   8160
ttcctgagtt cgattcgtcc acaattaaaa atatctcttc tgcaaaaggc ctggacgttt   8220
gggacagctg gccattacaa aacgctgacg gcactgtcgc aaactatcac ggctaccaca   8280
tcgtctttgc attagccgga gatcctaaaa atgcggatga cacatcgatt tacatgttct   8340
atcaaaaagt cggcgaaact tctattgaca gctggaaaaa cgctggccgc gtctttaaag   8400
acagcgacaa attcgatgca aatgattcta tcctaaaaga ccaaacacaa gaatggtcag   8460
gttcagccac atttacatct gacggaaaaa tccgtttatt ctacactgat ttctccggta   8520
aacattacgg caaacaaaca ctgacaactg cacaagttaa cgtatcagca tcagacagct   8580
ctttgaacat caacggtgta gaggattata aatcaatctt tgacggtgac ggaaaaacgt   8640
atcaaaatgt acagcagttc atcgatgaag gcaactacag ctcaggcgac aaccatacgc   8700
tgagagatcc tcactacgta gaagataaag gccacaaata cttagtattt gaagcaaaca   8760
ctggaactga agatggctac caaggcgaag aatctttatt taacaaagca tactatggca   8820
aaagcacatc attcttccgt caagaaagtc aaaaacttct gcaaagcgat aaaaaacgca   8880
cggctgagtt agcaaacggc gctctcggta tgattgagct aaacgatgat tacacactga   8940
aaaaagtgat gaaaccgctg attgcatcta acacagtaac agatgaaatt gaacgcgcga   9000
acgtctttaa aatgaacggc aaatggtatc tgttcactga ctcccgcgga tcaaaaatga   9060
cgattgacgg cattacgtct aacgatattt acatgcttgg ttatgtttct aattctttaa   9120
ctggcccata caagccgctg aacaaaactg gccttgtgtt aaaaatggat cttgatccta   9180
acgatgtaac ctttacttac tcacacttcg ctgtacctca agcgaaagga aacaatgtcg   9240
tgattacaag ctatatgaca aacagaggat tctacgcaga caaacaatca acgtttgcgc   9300
ctagcttcct gctgaacatc aaaggcaaga aaacatctgt tgtcaaagac agcatccttg   9360
aacaaggaca attaacagtt aacaaataac caggagctat ttaatggcaa cagttaacca   9420
gctggtacgc aaaccacgtg ctcgcaaagt tgcgaaaagc aacgtgcctg cgctggaagc   9480
atgcccgcaa aaacgtggcg tatgtactcg tgtatatact accactccta aaaaaccgaa   9540
ctccgcgctg cgtaaagtat gccgtgttcg tctgactaac ggtttcgaag tgacttccta   9600
```

catcggtggt gaaggtcaca acctgcagga gcactccgtg atcctgatcc gtggcggtcg 9660
tgttaaagac ctcccgggtg ttcgttacca caccgtacgt ggtgcgcttg actgctccgg 9720
cgttaaagac cgtaagcagg ctcgttccaa gtatggcgtg aagcgtccta aggcttaatg 9780
gttctccgtt aagtaaggcc aaatagagga tctgaagatc agcagttcaa cctgttgata 9840
gtacgtacta agctctcatg tttcacgtac taagctctca tgtttaacgt actaagctct 9900
catgtttaac gaactaaacc ctcatggcta acgtactaag ctctcatggc taacgtacta 9960
agctctcatg tttcacgtac taagctctca tgtttgaaca ataaaattaa tataaatcag 10020
caacttaaat agcctctaag gttttaagtt ttataagaaa aaaaagaata tataaggctt 10080
ttaaagcttt taaggtttaa cggttgtgga caacaagcca gggatgtaac gcactgagaa 10140
gcccttagag cctctcaaag caattttcag tgacacagga acacttaacg gctgacagac 10200
gctgccgcaa gcactcaggg cgcaagggct gctaaaggaa gcggaacacg tagaaagcca 10260
gtccgcagaa acggtgctga ccccggatga atgtcagcta ctgggctatc tggacaaggg 10320
aaaacgcaag cgcaaagaga aagcaggtag cttgcagtgg gcttacatgg cgatagctag 10380
actgggcggt tttatggaca gcaagcgaac cggaattgcc agctggggcg ccctctggta 10440
aggttgggaa gccctgcaaa gtaaactgga tggctttctt gccgccaagg atctgatggc 10500
gcaggggatc aagatctgat caagagacag gatgaggatc gtttcgcatg attgaacaag 10560
atggattgca cgcaggttct ccggccgctt gggtggagag gctattcggc tatgactggg 10620
cacaacagac aatcggctgc tctgatgccg ccgtgttccg gctgtcagcg caggggcgcc 10680
cggttctttt tgtcaagacc gacctgtccg gtgccctgaa tgaactccaa gacgaggcag 10740
cgcggctatc gtggctggcc acgacgggcg ttccttgcgc agctgtgctc gacgttgtca 10800
ctgaagcggg aagggactgg ctgctattgg gcgaagtgcc ggggcaggat ctcctgtcat 10860
ctcaccttgc tcctgccgag aaagtatcca tcatggctga tgcaatgcgg cggctgcata 10920
cgcttgatcc ggctacctgc ccattcgacc accaagcgaa acatcgcatc gagcgagcac 10980
gtactcggat ggaagccggt cttgtcgatc aggatgatct ggacgaagag catcaggggc 11040
tcgcgccagc cgaactgttc gccaggctca aggcgcggat gcccgacggc gaggatctcg 11100
tcgtgaccca tggcgatgcc tgcttgccga atatcatggt ggaaaatggc cgcttttctg 11160
gattcatcga ctgtggccgg ctgggtgtgg cggaccgcta tcaggacata gcgttggcta 11220
cccgtgatat tgctgaagag cttggcggcg aatgggctga ccgcttcctc gtgctttacg 11280
gtatcgccgc tcccgattcg cagcgcatcg ccttctatcg ccttcttgac gagttcttct 11340
gaattccgga tccgaagagg cccgcaccga tcgcccttcc caacagttgc gcagcctgaa 11400
tggcgaatgg cgcctgatgc ggtattttct ccttacgcat ctgtgcggta tttcacaccg 11460
catagggtaa taactgatat aattaaattg aagctctaat ttgtgagttt agtatacatg 11520
catttactta taatacagtt ttttagtttt gctggccgca tcttctcaaa tatgcttccc 11580
agcctgcttt tctgtaacgt tcaccctcta ccttagcatc ccttcccttt gcaaatagtc 11640
ctcttccaac aataataatg tcagatcctg tagagaccac atcatccacg gttctatact 11700
gttgacccaa tgcgtctccc ttgtcatcta aacccacacc gggtgtcata atcaaccaat 11760
cgtaaccttc atctcttcca cccatgtctc tttgagcaat aaagccgata acaaaatctt 11820
tgtcgctctt cgcaatgtca acagtaccct tagtatattc tccagtagat agggagccct 11880
tgcatgacaa ttctgctaac atcaaaaggc ctctaggttc ctttgttact tcttctgccg 11940
cctgcttcaa accgctaaca atacctgggc ccaccacacc gtgtgcattc gtaatgtctg 12000

```
cccattctgc tattctgtat acacccgcag agtactgcaa tttgactgta ttaccaatgt  12060
cagcaaattt tctgtcttcg aagagtaaaa aattgtactt ggcggataat gcctttagcg  12120
gcttaactgt gccctccatg gaaaaatcag tcaagatatc cacatgtgtt tttagtaaac  12180
aaattttggg acctaatgct tcaactaact ccagtaattc cttggtggta cgaacatcca  12240
atgaagcaca caagtttgtt tgcttttcgt gcatgatatt aaatagcttg gcagcaacag  12300
gactaggatg agtagcagca cgttccttat atgtagcttt cgacatgatt tatcttcgtt  12360
tcggtttttg ttctgtgcag ttgggttaag aatactgggc aatttcatgt ttcttcaaca  12420
ctacatatgc gtatatatac caatctaagt ctgtgctcct tccttcgttc ttccttctgt  12480
tcggagatta ccgaatcaaa aaaatttcaa agaaaccgaa atcaaaaaaa agaataaaaa  12540
aaaaatgatg aattgaaaag ctcttgttac ccatcattga attttgaaca tccgaacctg  12600
ggagttttcc ctgaaacaga tagtatattt gaacctgtat aataatatat agtctagcgc  12660
tttacggaag acaatgtatg tatttcggtt cctggagaaa ctattgcatc tattgcatag  12720
gtaatcttgc acgtcgcatc cccggttcat tttctgcgtt tccatcttgc acttcaatag  12780
catatctttg ttaacgaagc atctgtgctt catttttgtag aacaaaaatg caacgcgaga  12840
gcgctaattt ttcaaacaaa gaatctgagc tgcattttta cagaacagaa atgcaacgcg  12900
aaagcgctat tttaccaacg aagaatctgt gcttcatttt tgtaaaacaa aaatgcaacg  12960
cgagagcgct aatttttcaa acaaagaatc tgagctgcat ttttacagaa cagaaatgca  13020
acgcgagagc gctattttac caacaaagaa tctatacttc ttttttgttc tacaaaaatg  13080
catcccgaga gcgctatttt tctaacaaag catcttagat tacttttttt ctcctttgtg  13140
cgctctataa tgcagtctct tgataacttt ttgcactgta ggtccgttaa ggttagaaga  13200
aggctacttt ggtgtctatt ttctcttcca taaaaaaagc ctgactccac ttcccgcgtt  13260
tactgattac tagcgaagct gcgggtgcat tttttcaaga taaaggcatc cccgattata  13320
ttctataccg atgtggattg cgcatacttt gtgaacagaa agtgatagcg ttgatgattc  13380
ttcattggtc agaaaattat gaacggtttc ttctattttg tctctatata ctacgtatag  13440
gaaatgttta cattttcgta ttgttttcga ttcactctat gaatagttct tactacaatt  13500
tttttgtcta aagagtaata ctagagataa acataaaaaa tgtagaggtc gagtttagat  13560
gcaagttcaa ggagcgaaag gtggatgggt aggttatata gggatatagc acagagatat  13620
atagcaaaga gatacttttg agcaatgttt gtggaagcgg tattcgcaat attttagtag  13680
ctcgttacag tccggtgcgt tttggttttt ttgaaagtgc gtcttcagag cgcttttggt  13740
tttcaaaagc gctctgaagt tcctatactt tctagctaga gaataggaac ttcggaatag  13800
gaacttcaaa gcgtttccga aaacgagcgc ttccgaaaat gcaacgcgag ctgcgcacat  13860
acagctcact gttcacgtcg cacctatatc tgcgtgttgc ctgtatatat atatacatga  13920
gaagaacggc atagtgcgtg tttatgctta aatgcgttat ggtgcactct cagtacaatc  13980
tgctctgatg ccgcatagtt aagccagccc cgacacccgc caacacccgc tgacgcgcc   14039
```

<210> SEQ ID NO 208
<211> LENGTH: 14251
<212> TYPE: DNA
<213> ORGANISM: Artificial
<220> FEATURE:
<223> OTHER INFORMATION: pMU2969

<400> SEQUENCE: 208

-continued

```
agccccgaca cccgccaaca cccgctgacg cgccctgacg ggcttgtctg ctcccggcat     60
ccgcttacag acaagctgtg accgtctccg ggagctgcat gtgtcagagg ttttcaccgt    120
catcaccgaa acgcgcgaga cgaaagggcc tcgtgatacg cctattttta taggttaatg    180
tcatgataat aatggtttct tacgcagttg ctggatatca gaggttaatg cgagagagag    240
ttttccctgc cattcctgcc agggagaaaa aatcagttta tcgatattga tccaggtgtt    300
aggcagcatg gcctgccact gcgcgagtgt ttttggagcg gctggcgatt gctccgtctg    360
cggcaatttc gccagacaag cagaatcaag ttctaccgtg ccgacgttca ataaccagcg    420
gctgggatgt gaaaggctgg cgttggtgat atgcgcaagc tgacaatctc ccaccagata    480
acggagatcg ggaatgatta aacctttacg cgtaatgcgt gggctttcat ctaatgcaat    540
acgtgtcccg agcggtagcc agatgcccgc cagcgtggga acccacagcc cgagcgtcat    600
cagcagcgtc aacggcacaa gaataatcag taataacagc gcgagaacgg ctttatattt    660
acccagcatg ggtagttaat atcctgattt agcgaaaaat taagcattca atacgggtat    720
tgtggcatgt ttaaccgttc agttgaaggt tgcgcctaca ctaagcatag ttgttgatga    780
atttttcaat atcgccatag ctttcaatta aatttgaaat tttgtaaaat atttttagta    840
gcttaaatgt gattcaacat cactggagaa agtcttatga aactcgccgt ttatagcaca    900
aaacagtacg acaagaagta cctgcaacag gtgaacgagt tgagccgttt atttttttcta    960
cccatatcct tgaagcggtg ttataatgcc gcgccctcga tatggggatt tttaacgacc   1020
tgattttcgg gtctcagtag tagttgacat tagcggagca ctaaaatgag tccgcgagaa   1080
attgaggttt ccgagccgcg cgaggttggt atcaccgagc tcgtgctgcg cgatgcccat   1140
cagagcctga tggccacacg aatggcaatg gaagacatgg tcggcgcctg tgcagacatt   1200
gatgctgccg ggtactggtc agtggagtgt tggggtggtg ccacgtatga ctcgtgtatc   1260
cgcttcctca acgaggatcc ttgggagcgt ctgcgcacgt tccgcaagct gatgcccaac   1320
agccgtctcc agatgctgct gcgtggccag aacctgctgg gttaccgcca ctacaacgac   1380
gaggtcgtcg atcgcttcgt cgacaagtcc gctgagaacg gcatggacgt gttccgtgtc   1440
ttcgacgcca tgaatgatcc ccgcaacatg gcgcacgcca tggctgccgt caagaaggcc   1500
ggcaagcacg cgcagggcac catttgctac acgatcagcc cggtccacac cgttgagggc   1560
tatgtcaagc ttgctggtca gctgctcgac atgggtgctg attccatcgc cctgaaggac   1620
atggccgccc tgctcaagcc gcagccggcc tacgacatca tcaaggccat caaggacacc   1680
tacggccaga agacgcagat caacctgcac tgccactcca ccacgggtgt caccgaggtc   1740
tccctcatga aggccatcga ggccggcgtc gacgtcgtcg acaccgccat ctcgtccatg   1800
tcgctcggcc cgggccacaa ccccaccgag tcggttgccg agatgctcga gggcaccggg   1860
tacaccacca accttgacta cgatcgcctg cacaagatcc gcgatcactt caaggccatc   1920
cgcccgaagt acaagaagtt cgagtcgaag acgcttgtcg acacctcgat cttcaagtcg   1980
cagatccccg gcggcatgct ctccaacatg gagtcgcagc tgcgcgccca gggcgccgag   2040
gacaagatgg acgaggtcat ggcagaggtg ccgcgcgtcc gcaaggccgc cggcttcccg   2100
cccctggtca ccccgtccag ccagatcgtc ggcacgcagg ccgtgttcaa cgtgatgatg   2160
ggcgagtaca agaggatgac cggcgagttc gccgacatca tgctcggcta ctacggcgcc   2220
agcccggccg atcgcgatcc gaaggtggtc aagttggccg aggagcagtc cggcaagaag   2280
ccgatcaccc agcgcccggc cgatctgctg ccccccgagt gggaggagca gtccaaggag   2340
gccgcggccc tcaagggctt caacggcacc gacgaggacg tgctcaccta tgcactgttc   2400
```

ccgcaggtcg ctccggtctt cttcgagcat cgcgccgagg gcccgcacag cgtggctctc 2460
accgatgccc agctgaaggc cgaggccgag ggcgacgaga agtcgctcgc cgtggccggt 2520
cccgtcacct acaacgtgaa cgtgggcgga accgtccgcg aagtcaccgt tcagcaggcg 2580
tgaggatgat tgccaatcat ggctgaaaac aacaatttga agctcgccag caccatggaa 2640
ggtcgcgtgg agcagctcgc agagcagcgc caggtgatcg aagccggtgg cggcgaacgt 2700
cgcgtcgaga agcaacattc ccagggtaag cagaccgctc gtgagcgcct gaacaacctg 2760
ctcgatcccc attcgttcga cgaggtcggc gctttccgca agcaccgcac cacgttgttc 2820
ggcatggaca aggccgtcgt cccggcagat ggcgtggtca ccggccgtgg caccatcctt 2880
ggtcgtcccg tgcacgccgc gtcccaggac ttcacggtca tgggtggttc ggctggcgag 2940
acgcagtcca cgaaggtcgt cgagacgatg gaacaggcgc tgctcaccgg cacgcccttc 3000
ctgttcttct acgattcggg cggcgcccgg atccaggagg gcatcgactc gctgagcggt 3060
tacggcaaga tgttcttcgc caacgtgaag ctgtcgggcg tcgtgccgca gatcgccatc 3120
attgccggcc cctgtgccgg tggcgcctcg tattcgccgg cactgactga cttcatcatc 3180
atgaccaaga aggcccatat gttcatcacg ggcccccagg tcatcaagtc ggtcaccggc 3240
gaggatgtca ccgctgacga actcggtggc gctgaggccc atatggccat ctcgggcaat 3300
atccacttcg tggccgagga cgacgacgcc gcggagctca ttgccaagaa gctgctgagc 3360
ttccttccgc agaacaacac tgaggaagca tccttcgtca acccgaacaa tgacgtcagc 3420
cccaataccg agctgcgcga catcgttccg attgacggca agaagggcta tgacgtgcgc 3480
gatgtcattg ccaagatcgt cgactggggt gactacctcg aggtcaaggc cggctatgcc 3540
accaacctcg tgaccgcctt cgcccgggtc aatggtcgtt cggtgggcat cgtggccaat 3600
cagccgtcgg tgatgtcggg ttgcctcgac atcaacgcct ctgacaaggc cgccgaattc 3660
gtgaatttct gcgattcgtt caacatcccg ctggtgcagc tggtcgacgt gccgggcttc 3720
ctgcccggcg tgcagcagga gtacggcggc atcattcgcc atggcgcgaa gatgctgtac 3780
gcctactccg aggccaccgt gccgaagatc accgtggtgc tccgcaaggc ctacggcggc 3840
tcctacctgg ccatgtgcaa ccgtgacctt ggtgccgacg ccgtgtacgc ctggcccagc 3900
gccgagattg cggtgatggg cgccgagggt gcggcaaatg tgatcttccg caaggagatc 3960
aaggctgccg acgatcccga cgccatgcgc gccgagaaga tcgaggagta ccagaacgcg 4020
ttcaacacgc cgtacgtggc cgccgcccgc ggtcaggtcg acgacgtgat tgacccggct 4080
gatacccgtc gaaagattgc ttccgccctg gagatgtacg ccaccaagcg tcagacccgc 4140
ccggcgaaga agcatggaaa cttcccctgc tgagcgagga gagaaattat ggctgatgag 4200
gaagagaagg acctgatgat cgccacgctc aacaagcgcg tcgcgtcatt ggagtctgag 4260
ttgggttcac tccagagcga tacccagggt gtcaccgagg acgtactgac ggccatttcg 4320
gccgccgttg cggcctatct cggcaacgat ggatcggctg aggtcgtcca tttcgccccg 4380
agcccgaact gggtccgcga gggtcgtcgg gctctgcaga accattccat tcgttgatcc 4440
gggagtaact cacatgaaac tgaaggtaac agtcaacggc actgcgtatg acgttgacgt 4500
tgacgtcgac aagtcacacg aaaacccgat gggcaccatc ctgttcggcg gcggcaccgg 4560
cggcgcgccg gcaccgcgcg cagcaggtgg cgcaggcgcc ggtaaggccg gagagggcga 4620
gattcccgct ccgctggccg gcaccgtctc caagatcctc gtgaaggagg gtgacacggt 4680
caaggctggt cagaccgtgc tcgttctcga ggccatgaag atggagaccg agatcaacgc 4740
tcccaccgac ggcaaggtcg agaaggtcct tgtcaaggag cgtgacgccg tgcagggcgg 4800
tcagggtctc atcaagatcg gctgacggcc gtaaaacgaa aggctcagtc gaaagactgg 4860
gcctttcgtt ttatctgttg tttgtcggtg aacgctctcc tgagtaggac aaatccgccg 4920
ggagcggatt tgaacgttgc gaagcaacgg cccggagggt ggcgggcagg acgcccgcca 4980
taaactgcca ggcatcaaat taagcagaag gccatcctga cggatggcct ttttgcgttt 5040
ctacaaactc ttcctgtcgt catatctaca agccatcccc ccacagatac ggtaaactag 5100
cctcgttttt gcatcaggaa agcagctatg aaccactcct ccagccagga cagaaatgcc 5160
tcgacttcgc tgctgcccaa ggttgccggg tgacgcacac cgtggaaacg gatgaaggca 5220
cgaacccagt ggacataagc ctgttcggtt cgtaagctgt aatgcaagta gcgtatgcgc 5280
tcacgcaact ggtccagaac cttgaccgaa cgcagcggtg gtaacggcgc agtggcggtt 5340
ttcatggctt gttatgactg tttttttggg gtacagtcta tgcctcgggc atccaagcag 5400
caagcgcgtt acgccgtggg tcgatgtttg atgttatgga gcagcaacga tgttacgcag 5460
cagggcagtc gccctaaaac aaagttaaac atcatgaggg aagcggtgat cgccgaagta 5520
tcgactcaac tatcagaggt agttggcgtc atcgagcgcc atctcgaacc gacgttgctg 5580
gccgtacatt tgtacggctc cgcagtggat ggcggcctga agccacacag tgatattgat 5640
ttgctggtta cggtgaccgt aaggcttgat gaaacaacgc ggcgagcttt gatcaacgac 5700
cttttggaaa cttcggcttc ccctggagag agcgagattc tccgcgctgt agaagtcacc 5760
attgttgtgc acgacgacat cattccgtgg cgttatccag ctaagcgcga actgcaattt 5820
ggagaatggc agcgcaatga cattcttgca ggtatcttcg agccagccac gatcgacatt 5880
gatctggcta tcttgctgac aaaagcaaga gaacatagcg ttgccttggt aggtccagcg 5940
gcggaggaac tctttgatcc ggttcctgaa caggatctat ttgaggcgct aaatgaaacc 6000
ttaacgctat ggaactcgcc gcccgactgg gctggcgatg agcgaaatgt agtgcttacg 6060
ttgtcccgca tttggtacag cgcagtaacc ggcaaaatcg cgccgaagga tgtcgctgcc 6120
gactgggcaa tggagcgcct gccggcccag tatcagcccg tcatacttga agctagacag 6180
gcttatcttg gacaagaaga agatcgcttg gcctcgcgcg cagatcagtt ggaagaattt 6240
gtccactacg tgaaaggcga gatcaccaag gtagtcggca aataaccctc gagccaccca 6300
tgaccaaaat cccttaacgt gagttacgcg tcgttccact gtgacagcag aagctctgac 6360
cagtatttct cagactacgc tgcaaaactt aagcaatctg gaaaaaggcg aaacctgccc 6420
gaacgaactg gtttaatctt gccgctcccc tgcattccag gggagctgat tcagataatc 6480
cccaatgacc tttcatcctc tattcttaaa atagtcctga gtcagaaact gtaattgaga 6540
accacaatga agaaagtagc cgcgtttgtt gcgctaagcc tgctgatggc gggatgtgta 6600
agtaatgaca aaattgctgt tacgccagaa cagctacagc atcatcgctt tgtgctggaa 6660
agcgtaaacg gtaagcccgt gaccagcgat aaaaatccgc cagaaatcag ctttggtgaa 6720
aaaatgatga tttccggcag catgtgtaac cgctttagcg gtgaaggcaa actgtctaat 6780
ggtgaactga cagccaaagg gctggcaatg acccgtatga tgtgcgctaa cccgcagctt 6840
aatgaactcg ataacaccat tagcgaaatg ctgaaagaag gtgcacaagt ggatctgacc 6900
gcgaaccagt taacgctggc gaccgcaaaa cagacattaa cttataagct ggcggattta 6960
atgaattaat agctgccaca gctcccggcg gcaagtgact gttcgctaca gcgtttgccg 7020
ttgggtaatg cacacatccc aaggtggcac ttttcgggga aatgtgcgcg gaacccctat 7080
ttgtttattt ttctaaatac attcaaatat gtatccgctc atgagacaat aaccctgata 7140
aatgcttcaa taatattgaa aaaggaagag tatgagtatt caacatttcc gtgtcgccct 7200
tattcccttt tttgcggcat tttgccttcc tgtttttgct cacccagaaa cgctggtgaa 7260
agtaaaagat gctgaagatc agttgggtgc acgagtgggt tacatcgaac tggatctcaa 7320
cagcggtaag atccttgaga gttttcgccc cgaagaacgt tttccaatga tgagcacttt 7380
taaagttctg ctatgtggcg cggtattatc ccgtattgac gccgggcaag agcaactcgg 7440
tcgccgcata cactattctc agaatgactt ggttgagtac tcaccagtca cagaaaagca 7500
tcttacggat ggcatgacag taagagaatt atgcagtgct gccataacca tgagtgataa 7560
cactgcggcc aacttacttc tgacaacgat cggaggaccg aaggagctaa ccgctttttt 7620
gcacaacatg ggggatcatg taactcgcct tgatcgttgg gaaccggagc tgaatgaagc 7680
cataccaaac gacgagcgtg acaccacgat gcctgtagca atggcaacaa cgttgcgcaa 7740
actattaact ggcgaactac ttactctagc ttcccggcaa caattaatag actggatgga 7800
ggcggataaa gttgcaggac cacttctgcg ctcggccctt ccggctggct ggtttattgc 7860
tgataaatct ggagccggtg agcgtgggtc tcgcggtatc attgcagcac tggggccaga 7920
tggtaagccc tcccgtatcg tagttatcta cacgacgggg agtcaggcaa ctatggatga 7980
acgaaataga cagatcgctg agataggtgc ctcactgatt aagcattggt aagcgatgaa 8040
atgtgaggtg aatcagggtt ttcacccgat tttgtgctga tcagaatttt ttttcttttt 8100
ccccccttgaa ggggcgaagc ctcatcccca tttctctggt caccagccgg gaaaccacgt 8160
aagctccggc gtcacccata acagatacgg actttctcaa aggagagtta tcaatgaaca 8220
tcaaaaagtt tgcaaaacaa gcaacagtat taacctttac taccgcactg ctggcaggag 8280
gcgcaactca agcgtttgcg aaagaaacga accaaaagcc atataaggaa acatacggca 8340
tttcccatat tacacgccat gatatgctgc aaatccctga acagcaaaaa aatgaaaaat 8400
atcaagttcc tgagttcgat tcgtccacaa ttaaaaatat ctcttctgca aaaggcctgg 8460
acgtttggga cagctggcca ttacaaaacg ctgacggcac tgtcgcaaac tatcacggct 8520
accacatcgt ctttgcatta gccggagatc ctaaaaatgc ggatgacaca tcgatttaca 8580
tgttctatca aaaagtcggc gaaacttcta ttgacagctg gaaaaacgct ggccgcgtct 8640
ttaaagacag cgacaaattc gatgcaaatg attctatcct aaaagaccaa acacaagaat 8700
ggtcaggttc agccacattt acatctgacg gaaaaatccg tttattctac actgatttct 8760
ccggtaaaca ttacggcaaa caaacactga caactgcaca agttaacgta tcagcatcag 8820
acagctcttt gaacatcaac ggtgtagagg attataaatc aatctttgac ggtgacggaa 8880
aaacgtatca aaatgtacag cagttcatcg atgaaggcaa ctacagctca ggcgacaacc 8940
atacgctgag agatcctcac tacgtagaag ataaaggcca caaatactta gtatttgaag 9000
caaacactgg aactgaagat ggctaccaag gcgaagaatc tttatttaac aaagcatact 9060
atggcaaaag cacatcattc ttccgtcaag aaagtcaaaa acttctgcaa agcgataaaa 9120
aacgcacggc tgagttagca aacggcgctc tcggtatgat tgagctaaac gatgattaca 9180
cactgaaaaa agtgatgaaa ccgctgattg catctaacac agtaacagat gaaattgaac 9240
gcgcgaacgt ctttaaaatg aacggcaaat ggtatctgtt cactgactcc cgcggatcaa 9300
aaatgacgat tgacggcatt acgtctaacg atatttacat gcttggttat gtttctaatt 9360
ctttaactgg cccatacaag ccgctgaaca aaactggcct tgtgttaaaa atggatcttg 9420
atcctaacga tgtaaccttt acttactcac acttcgctgt acctcaagcg aaaggaaaca 9480

-continued

```
atgtcgtgat tacaagctat atgacaaaca gaggattcta cgcagacaaa caatcaacgt   9540
ttgcgcctag cttcctgctg aacatcaaag gcaagaaaac atctgttgtc aaagacagca   9600
tccttgaaca aggacaatta acagttaaca aataaccagg agctatttaa tggcaacagt   9660
taaccagctg gtacgcaaac cacgtgctcg caaagttgcg aaaagcaacg tgcctgcgct   9720
ggaagcatgc ccgcaaaaac gtggcgtatg tactcgtgta tatactacca ctcctaaaaa   9780
accgaactcc gcgctgcgta aagtatgccg tgttcgtctg actaacggtt tcgaagtgac   9840
ttcctacatc ggtggtgaag gtcacaacct gcaggagcac tccgtgatcc tgatccgtgg   9900
cggtcgtgtt aaagacctcc cgggtgttcg ttaccacacc gtacgtggtg cgcttgactg   9960
ctccggcgtt aaagaccgta agcaggctcg ttccaagtat ggcgtgaagc gtcctaaggc  10020
ttaatggttc tccgttaagt aaggccaaat agaggatctg aagatcagca gttcaacctg  10080
ttgatagtac gtactaagct ctcatgtttc acgtactaag ctctcatgtt taacgtacta  10140
agctctcatg tttaacgaac taaaccctca tggctaacgt actaagctct catggctaac  10200
gtactaagct ctcatgtttc acgtactaag ctctcatgtt tgaacaataa aattaatata  10260
aatcagcaac ttaaatagcc tctaaggttt taagttttat aagaaaaaaa agaatatata  10320
aggcttttaa agcttttaag gtttaacggt tgtggacaac aagccaggga tgtaacgcac  10380
tgagaagccc ttagagcctc tcaaagcaat tttcagtgac acaggaacac ttaacggctg  10440
acagacgctg ccgcaagcac tcagggcgca agggctgcta aaggaagcgg aacacgtaga  10500
aagccagtcc gcagaaacgg tgctgacccc ggatgaatgt cagctactgg gctatctgga  10560
caagggaaaa cgcaagcgca aagagaaagc aggtagcttg cagtgggctt acatggcgat  10620
agctagactg ggcggtttta tggacagcaa gcgaaccgga attgccagct ggggcgccct  10680
ctggtaaggt tgggaagccc tgcaaagtaa actggatggc tttcttgccg ccaaggatct  10740
gatggcgcag gggatcaaga tctgatcaag agacaggatg aggatcgttt cgcatgattg  10800
aacaagatgg attgcacgca ggttctccgg ccgcttgggt ggagaggcta ttcggctatg  10860
actgggcaca acagacaatc ggctgctctg atgccgccgt gttccggctg tcagcgcagg  10920
ggcgcccggt tctttttgtc aagaccgacc tgtccggtgc cctgaatgaa ctccaagacg  10980
aggcagcgcg gctatcgtgg ctggccacga cgggcgttcc ttgcgcagct gtgctcgacg  11040
ttgtcactga agcgggaagg gactggctgc tattgggcga agtgccgggg caggatctcc  11100
tgtcatctca ccttgctcct gccgagaaag tatccatcat ggctgatgca atgcggcggc  11160
tgcatacgct tgatccggct acctgcccat tcgaccacca agcgaaacat cgcatcgagc  11220
gagcacgtac tcggatggaa gccggtcttg tcgatcagga tgatctggac gaagagcatc  11280
aggggctcgc gccagccgaa ctgttcgcca ggctcaaggc gcggatgccc gacggcgagg  11340
atctcgtcgt gacccatggc gatgcctgct tgccgaatat catggtggaa aatggccgct  11400
tttctggatt catcgactgt ggccggctgg gtgtggcgga ccgctatcag gacatagcgt  11460
tggctacccg tgatattgct gaagagcttg gcggcgaatg ggctgaccgc ttcctcgtgc  11520
tttacggtat cgccgctccc gattcgcagc gcatcgcctt ctatcgcctt cttgacgagt  11580
tcttctgaat tccggatccg aagaggcccg caccgatcgc ccttcccaac agttgcgcag  11640
cctgaatggc gaatggcgcc tgatgcggta ttttctcctt acgcatctgt gcggtatttc  11700
acaccgcata gggtaataac tgatataatt aaattgaagc tctaatttgt gagtttagta  11760
tacatgcatt tacttataat acagtttttt agttttgctg gccgcatctt ctcaaatatg  11820
cttcccagcc tgcttttctg taacgttcac cctctacctt agcatccctt ccctttgcaa  11880
```

atagtcctct tccaacaata ataatgtcag atcctgtaga gaccacatca tccacggttc 11940
tatactgttg acccaatgcg tctcccttgt catctaaacc cacaccgggt gtcataatca 12000
accaatcgta accttcatct cttccaccca tgtctctttg agcaataaag ccgataacaa 12060
aatctttgtc gctcttcgca atgtcaacag tacccttagt atattctcca gtagataggg 12120
agcccttgca tgacaattct gctaacatca aaaggcctct aggttccttt gttacttctt 12180
ctgccgcctg cttcaaaccg ctaacaatac ctgggcccac cacaccgtgt gcattcgtaa 12240
tgtctgccca ttctgctatt ctgtatacac ccgcagagta ctgcaatttg actgtattac 12300
caatgtcagc aaattttctg tcttcgaaga gtaaaaaatt gtacttggcg gataatgcct 12360
ttagcggctt aactgtgccc tccatggaaa aatcagtcaa gatatccaca tgtgttttta 12420
gtaaacaaat tttgggacct aatgcttcaa ctaactccag taattccttg gtggtacgaa 12480
catccaatga agcacacaag tttgtttgct tttcgtgcat gatattaaat agcttggcag 12540
caacaggact aggatgagta gcagcacgtt ccttatatgt agctttcgac atgatttatc 12600
ttcgtttcgg tttttgttct gtgcagttgg gttaagaata ctgggcaatt tcatgtttct 12660
tcaacactac atatgcgtat atataccaat ctaagtctgt gctccttcct tcgttcttcc 12720
ttctgttcgg agattaccga atcaaaaaaa tttcaaagaa accgaaatca aaaaaaagaa 12780
taaaaaaaaa atgatgaatt gaaaagctct tgttacccat cattgaattt tgaacatccg 12840
aacctgggag ttttccctga aacagatagt atatttgaac ctgtataata atatatagtc 12900
tagcgcttta cggaagacaa tgtatgtatt tcggttcctg gagaaactat tgcatctatt 12960
gcataggtaa tcttgcacgt cgcatccccg gttcattttc tgcgtttcca tcttgcactt 13020
caatagcata tctttgttaa cgaagcatct gtgcttcatt ttgtagaaca aaaatgcaac 13080
gcgagagcgc taatttttca aacaaagaat ctgagctgca tttttacaga acagaaatgc 13140
aacgcgaaag cgctatttta ccaacgaaga atctgtgctt catttttgta aaacaaaaat 13200
gcaacgcgag agcgctaatt tttcaaacaa agaatctgag ctgcattttt acagaacaga 13260
aatgcaacgc gagagcgcta ttttaccaac aaagaatcta tacttctttt ttgttctaca 13320
aaaatgcatc ccgagagcgc tatttttcta acaaagcatc ttagattact tttttctcc 13380
tttgtgcgct ctataatgca gtctcttgat aactttttgc actgtaggtc cgttaaggtt 13440
agaagaaggc tactttggtg tctattttct cttccataaa aaaagcctga ctccacttcc 13500
cgcgtttact gattactagc gaagctgcgg gtgcattttt tcaagataaa ggcatccccg 13560
attatattct ataccgatgt ggattgcgca tactttgtga acagaaagtg atagcgttga 13620
tgattcttca ttggtcagaa aattatgaac ggtttcttct attttgtctc tatatactac 13680
gtataggaaa tgtttacatt ttcgtattgt tttcgattca ctctatgaat agttcttact 13740
acaatttttt tgtctaaaga gtaatactag agataaacat aaaaaatgta gaggtcgagt 13800
ttagatgcaa gttcaaggag cgaaaggtgg atgggtaggt tatataggga tatagcacag 13860
agatatatag caaagagata cttttgagca atgtttgtgg aagcggtatt cgcaatattt 13920
tagtagctcg ttacagtccg gtgcgttttt ggtttttga aagtgcgtct tcagagcgct 13980
tttggttttc aaaagcgctc tgaagttcct atactttcta gctagagaat aggaacttcg 14040
gaataggaac ttcaaagcgt ttccgaaaac gagcgcttcc gaaaatgcaa cgcgagctgc 14100
gcacatacag ctcactgttc acgtcgcacc tatatctgcg tgttgcctgt atatatatat 14160
acatgagaag aacggcatag tgcgtgttta tgcttaaatg cgttatggtg cactctcagt 14220
acaatctgct ctgatgccgc atagttaagc c 14251

<210> SEQ ID NO 209
<211> LENGTH: 910
<212> TYPE: PRT
<213> ORGANISM: B. adolescentis

<400> SEQUENCE: 209

Met Ala Asp Ala Lys Lys Lys Glu Glu Pro Thr Lys Pro Thr Pro Glu
1 5 10 15

Glu Lys Leu Ala Ala Ala Glu Ala Glu Val Asp Ala Leu Val Lys Lys
20 25 30

Gly Leu Lys Ala Leu Asp Glu Phe Glu Lys Leu Asp Gln Lys Gln Val
35 40 45

Asp His Ile Val Ala Lys Ala Ser Val Ala Ala Leu Asn Lys His Leu
50 55 60

Val Leu Ala Lys Met Ala Val Glu Glu Thr His Arg Gly Leu Val Glu
65 70 75 80

Asp Lys Ala Thr Lys Asn Ile Phe Ala Cys Glu His Val Thr Asn Tyr
85 90 95

Leu Ala Gly Gln Lys Thr Val Gly Ile Ile Arg Glu Asp Asp Val Leu
100 105 110

Gly Ile Asp Glu Ile Ala Glu Pro Val Gly Val Val Ala Gly Val Thr
115 120 125

Pro Val Thr Asn Pro Thr Ser Thr Ala Ile Phe Lys Ser Leu Ile Ala
130 135 140

Leu Lys Thr Arg Cys Pro Ile Ile Phe Gly Phe His Pro Gly Ala Gln
145 150 155 160

Asn Cys Ser Val Ala Ala Ala Lys Ile Val Arg Asp Ala Ala Ile Ala
165 170 175

Ala Gly Ala Pro Glu Asn Cys Ile Gln Trp Ile Glu His Pro Ser Ile
180 185 190

Glu Ala Thr Gly Ala Leu Met Lys His Asp Gly Val Ala Thr Ile Leu
195 200 205

Ala Thr Gly Gly Pro Gly Met Val Lys Ala Ala Tyr Ser Ser Gly Lys
210 215 220

Pro Ala Leu Gly Val Gly Ala Gly Asn Ala Pro Ala Tyr Val Asp Lys
225 230 235 240

Asn Val Asp Val Val Arg Ala Ala Asn Asp Leu Ile Leu Ser Lys His
245 250 255

Phe Asp Tyr Gly Met Ile Cys Ala Thr Glu Gln Ala Ile Ile Ala Asp
260 265 270

Lys Asp Ile Tyr Ala Pro Leu Val Lys Glu Leu Lys Arg Arg Lys Ala
275 280 285

Tyr Phe Val Asn Ala Asp Glu Lys Ala Lys Leu Glu Gln Tyr Met Phe
290 295 300

Gly Cys Thr Ala Tyr Ser Gly Gln Thr Pro Lys Leu Asn Ser Val Val
305 310 315 320

Pro Gly Lys Ser Pro Gln Tyr Ile Ala Lys Ala Ala Gly Phe Glu Ile
325 330 335

Pro Glu Asp Ala Thr Ile Leu Ala Ala Glu Cys Lys Glu Val Gly Glu
340 345 350

Asn Glu Pro Leu Thr Met Glu Lys Leu Ala Pro Val Gln Ala Val Leu
355 360 365

-continued

```
Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu
    530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
    690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
    770                 775                 780

Lys Tyr Asn Lys Tyr Ile Ala Pro Glu Arg Tyr Gln Glu Ile Ala Lys
```

785 790 795 800

Asn Leu Gly Val Asn Pro Gly Lys Thr Pro Glu Glu Gly Val Glu Asn
805 810 815

Leu Ala Lys Ala Val Glu Asp Tyr Arg Asp Asn Lys Leu Gly Met Asn
820 825 830

Lys Ser Phe Gln Glu Cys Gly Val Asp Glu Asp Tyr Tyr Trp Ser Ile
835 840 845

Ile Asp Gln Ile Gly Met Arg Ala Tyr Glu Asp Gln Cys Ala Pro Ala
850 855 860

Asn Pro Arg Ile Pro Gln Ile Glu Asp Met Lys Asp Ile Ala Ile Ala
865 870 875 880

Ala Tyr Tyr Gly Val Ser Gln Ala Glu Gly His Lys Leu Arg Val Gln
885 890 895

Arg Gln Gly Glu Ala Ala Thr Glu Glu Ala Ser Glu Arg Ala
900 905 910

<210> SEQ ID NO 210
<211> LENGTH: 292
<212> TYPE: PRT
<213> ORGANISM: B. adolescentis

<400> SEQUENCE: 210

Met Ser Glu His Ile Phe Arg Ser Thr Thr Arg His Met Leu Arg Asp
1 5 10 15

Ser Lys Asp Tyr Val Asn Gln Thr Leu Met Gly Gly Leu Ser Gly Phe
20 25 30

Glu Ser Pro Ile Gly Leu Asp Arg Leu Asp Arg Ile Lys Ala Leu Lys
35 40 45

Ser Gly Asp Ile Gly Phe Val His Ser Trp Asp Ile Asn Thr Ser Val
50 55 60

Asp Gly Pro Gly Thr Arg Met Thr Val Phe Met Ser Gly Cys Pro Leu
65 70 75 80

Arg Cys Gln Tyr Cys Gln Asn Pro Asp Thr Trp Lys Met Arg Asp Gly
85 90 95

Lys Pro Val Tyr Tyr Glu Ala Met Val Lys Lys Ile Glu Arg Tyr Ala
100 105 110

Asp Leu Phe Lys Ala Thr Gly Gly Gly Ile Thr Phe Ser Gly Gly Glu
115 120 125

Ser Met Met Gln Pro Ala Phe Val Ser Arg Val Phe His Ala Ala Lys
130 135 140

Gln Met Gly Val His Thr Cys Leu Asp Thr Ser Gly Phe Leu Gly Ala
145 150 155 160

Ser Tyr Thr Asp Asp Met Val Asp Asp Ile Asp Leu Cys Leu Leu Asp
165 170 175

Val Lys Ser Gly Asp Glu Glu Thr Tyr His Lys Val Thr Gly Gly Ile
180 185 190

Leu Gln Pro Thr Ile Asp Phe Gly Gln Arg Leu Ala Lys Ala Gly Lys
195 200 205

Lys Ile Trp Val Arg Phe Val Leu Val Pro Gly Leu Thr Ser Ser Glu
210 215 220

Glu Asn Val Glu Asn Val Ala Lys Ile Cys Glu Thr Phe Gly Asp Ala
225 230 235 240

Leu Glu His Ile Asp Val Leu Pro Phe His Gln Leu Gly Arg Pro Lys
245 250 255

-continued

```
Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
        275                 280                 285

Phe Thr Val Tyr
    290


<210> SEQ ID NO 211
<211> LENGTH: 791
<212> TYPE: PRT
<213> ORGANISM: B. adolescentis

<400> SEQUENCE: 211

Met Ala Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335
```

```
Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
                485                 490                 495

Glu Lys Ala Leu Glu Trp Leu Ser Glu Thr Tyr Val Met Ala Leu Asn
            500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
    530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
                565                 570                 575

Asn Glu Tyr Val Glu Gly Ala Asp Asp Asp Leu Ile Val Gly Tyr Arg
            580                 585                 590

Thr Glu Gly Asp Phe Pro Leu Tyr Gly Asn Asp Asp Asp Arg Ala Asp
        595                 600                 605

Asp Ile Ala Lys Trp Val Val Ser Thr Val Met Gly Gln Val Lys Arg
    610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
                645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
    690                 695                 700

Pro Asp Gly Leu Gly Arg Asp Glu Glu Glu Arg Ile Gly Asn Leu Val
705                 710                 715                 720

Gly Ile Leu Asp Ala Gly Asn Gly His Gly Leu Tyr His Ala Asn Ile
                725                 730                 735

Asn Val Leu Arg Lys Glu Gln Leu Glu Asp Ala Val Glu His Pro Glu
            740                 745                 750
```

```
Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe
    770                 775                 780

His Gln Gly Ala Val Val Asp
785                 790


<210> SEQ ID NO 212
<211> LENGTH: 26
<212> TYPE: DNA
<213> ORGANISM: Artificial
<220> FEATURE:
<223> OTHER INFORMATION: X11316

<400> SEQUENCE: 212

gtaatacatc acctcgatga aagaga                                          26


<210> SEQ ID NO 213
<211> LENGTH: 29
<212> TYPE: DNA
<213> ORGANISM: Artificial
<220> FEATURE:
<223> OTHER INFORMATION: X11816

<400> SEQUENCE: 213

gcagtcatca ggatcgtagg agataagca                                       29


<210> SEQ ID NO 214
<211> LENGTH: 30
<212> TYPE: DNA
<213> ORGANISM: Artificial
<220> FEATURE:
<223> OTHER INFORMATION: X11821

<400> SEQUENCE: 214

tcacaagagt gtgcagaaat aggaggtgga                                      30


<210> SEQ ID NO 215
<211> LENGTH: 59
<212> TYPE: DNA
<213> ORGANISM: Artificial
<220> FEATURE:
<223> OTHER INFORMATION: X11822

<400> SEQUENCE: 215

gttgggggaa aaagaggcaa caggaaagat cagagacagc aagcattgat aaggaaggg      59


<210> SEQ ID NO 216
<211> LENGTH: 59
<212> TYPE: DNA
<213> ORGANISM: Artificial
<220> FEATURE:
<223> OTHER INFORMATION: X11823

<400> SEQUENCE: 216

cccttcctta tcaatgcttg ctgtctctga tctttcctgt tgcctctttt tcccccaac      59


<210> SEQ ID NO 217
<211> LENGTH: 29
<212> TYPE: DNA
<213> ORGANISM: Artificial
<220> FEATURE:
<223> OTHER INFORMATION: X11824

<400> SEQUENCE: 217
```

-continued aagcctacag gcgcaagata acacatcac 29

<210> SEQ ID NO 218
<211> LENGTH: 35
<212> TYPE: DNA
<213> ORGANISM: Artificial
<220> FEATURE:
<223> OTHER INFORMATION: X11829

<400> SEQUENCE: 218
ctcagcattg atcttagcag attcaggatc taggt 35

<210> SEQ ID NO 219
<211> LENGTH: 59
<212> TYPE: DNA
<213> ORGANISM: Artificial
<220> FEATURE:
<223> OTHER INFORMATION: X11830

<400> SEQUENCE: 219
tatgttatct ttctccaata aatctaatct tcatgtagac tatcagcagc agcagacat 59

<210> SEQ ID NO 220
<211> LENGTH: 59
<212> TYPE: DNA
<213> ORGANISM: Artificial
<220> FEATURE:
<223> OTHER INFORMATION: X11831

<400> SEQUENCE: 220
gataatataa agatgtctgc tgctgctgat agtctacatg aagattagat ttattggag 59

<210> SEQ ID NO 221
<211> LENGTH: 30
<212> TYPE: DNA
<213> ORGANISM: Artificial
<220> FEATURE:
<223> OTHER INFORMATION: X11845

<400> SEQUENCE: 221
ttacttgtga aactgtctcc gctatgtcag 30

<210> SEQ ID NO 222
<211> LENGTH: 59
<212> TYPE: DNA
<213> ORGANISM: Artificial
<220> FEATURE:
<223> OTHER INFORMATION: X14775

<400> SEQUENCE: 222
ccccctccac aaacacaaat attgataata taaagatggc agacgcaaag aagaaggaa 59

<210> SEQ ID NO 223
<211> LENGTH: 34
<212> TYPE: DNA
<213> ORGANISM: Artificial
<220> FEATURE:
<223> OTHER INFORMATION: X14778

<400> SEQUENCE: 223
atttattgga gaaagataac atatcatact ttcc 34

<210> SEQ ID NO 224
<211> LENGTH: 59
<212> TYPE: DNA
<213> ORGANISM: Artificial

<220> FEATURE:
<223> OTHER INFORMATION: X14829

<400> SEQUENCE: 224
gaaagtatga tatgttatct ttctccaata aatctagtct tctaggcggg ttatctact 59

<210> SEQ ID NO 225
<211> LENGTH: 59
<212> TYPE: DNA
<213> ORGANISM: Artificial
<220> FEATURE:
<223> OTHER INFORMATION: X14835

<400> SEQUENCE: 225
caaattctaa ccaacttcaa aatgacatag tacctcatct ataattttta ccctgatct 59

<210> SEQ ID NO 226
<211> LENGTH: 59
<212> TYPE: DNA
<213> ORGANISM: Artificial
<220> FEATURE:
<223> OTHER INFORMATION: X14836

<400> SEQUENCE: 226
agttagatca gggtaaaaat tatagatgag gtactatgtc attttgaagt tggttagaa 59

<210> SEQ ID NO 227
<211> LENGTH: 59
<212> TYPE: DNA
<213> ORGANISM: Artificial
<220> FEATURE:
<223> OTHER INFORMATION: X14837

<400> SEQUENCE: 227
ggtccatgta aaatgattgc tccaatgatt gaaattgatt caggtcaaaa tggattcag 59

<210> SEQ ID NO 228
<211> LENGTH: 59
<212> TYPE: DNA
<213> ORGANISM: Artificial
<220> FEATURE:
<223> OTHER INFORMATION: X14838

<400> SEQUENCE: 228
acgtccctga atccattttg acctgaatca atttcaatca ttggagcaat cattttaca 59

<210> SEQ ID NO 229
<211> LENGTH: 59
<212> TYPE: DNA
<213> ORGANISM: Artificial
<220> FEATURE:
<223> OTHER INFORMATION: X14843

<400> SEQUENCE: 229
ggtggaacca tttactgtat tttcaatgta acgctagaga ataaattcaa gttaaaaga 59

<210> SEQ ID NO 230
<211> LENGTH: 59
<212> TYPE: DNA
<213> ORGANISM: Artificial
<220> FEATURE:
<223> OTHER INFORMATION: X14844

<400> SEQUENCE: 230
catcatcttt taacttgaat ttattctcta gcgttacatt gaaaatacag taaatggtt 59

-continued

<210> SEQ ID NO 231
<211> LENGTH: 26
<212> TYPE: DNA
<213> ORGANISM: Artificial
<220> FEATURE:
<223> OTHER INFORMATION: X15380

<400> SEQUENCE: 231
taggtctaga gatctgttta gcttgc 26

<210> SEQ ID NO 232
<211> LENGTH: 23
<212> TYPE: DNA
<213> ORGANISM: Artificial
<220> FEATURE:
<223> OTHER INFORMATION: X15382

<400> SEQUENCE: 232
gagactacat gatagtccaa aga 23

<210> SEQ ID NO 233
<211> LENGTH: 59
<212> TYPE: DNA
<213> ORGANISM: Artificial
<220> FEATURE:
<223> OTHER INFORMATION: X15546

<400> SEQUENCE: 233
ggacgaggca agctaaacag atctctagac ctactttata ttatcaatat ttgtgtttg 59

<210> SEQ ID NO 234
<211> LENGTH: 59
<212> TYPE: DNA
<213> ORGANISM: Artificial
<220> FEATURE:
<223> OTHER INFORMATION: X15547

<400> SEQUENCE: 234
ccgtttcttt tctttggact atcatgtagt ctcatttatt ggagaaagat aacatatca 59

<210> SEQ ID NO 235
<211> LENGTH: 59
<212> TYPE: DNA
<213> ORGANISM: Artificial
<220> FEATURE:
<223> OTHER INFORMATION: X15548

<400> SEQUENCE: 235
ggacgaggca agctaaacag atctctagac ctatgataag gaaggggagc gaaggaaaa 59

<210> SEQ ID NO 236
<211> LENGTH: 59
<212> TYPE: DNA
<213> ORGANISM: Artificial
<220> FEATURE:
<223> OTHER INFORMATION: X15549

<400> SEQUENCE: 236
ccgtttcttt tctttggact atcatgtagt ctcctctgat ctttcctgtt gcctctttt 59

<210> SEQ ID NO 237
<211> LENGTH: 59
<212> TYPE: DNA
<213> ORGANISM: Artificial
<220> FEATURE:
<223> OTHER INFORMATION: X15552

<400> SEQUENCE: 237
ccgtttcttt tctttggact atcatgtagt ctcgagtgat tatgagtatt tgtgagcag 59

<210> SEQ ID NO 238
<211> LENGTH: 31
<212> TYPE: DNA
<213> ORGANISM: Artificial
<220> FEATURE:
<223> OTHER INFORMATION: X15553

<400> SEQUENCE: 238
accagcgtct ggtggacaaa cggccttcaa c 31

<210> SEQ ID NO 239
<211> LENGTH: 59
<212> TYPE: DNA
<213> ORGANISM: Artificial
<220> FEATURE:
<223> OTHER INFORMATION: X15554

<400> SEQUENCE: 239
ggacgaggca agctaaacag atctctagac ctaattaatt ttcagctgtt atttcgatt 59

<210> SEQ ID NO 240
<211> LENGTH: 59
<212> TYPE: DNA
<213> ORGANISM: Artificial
<220> FEATURE:
<223> OTHER INFORMATION: X15555

<400> SEQUENCE: 240
ccgtttcttt tctttggact atcatgtagt ctcgagtgat tatgagtatt tgtgagcag 59

<210> SEQ ID NO 241
<211> LENGTH: 25
<212> TYPE: DNA
<213> ORGANISM: Artificial
<220> FEATURE:
<223> OTHER INFORMATION: X15559

<400> SEQUENCE: 241
ggaaggcacc gatactagaa ctccg 25

<210> SEQ ID NO 242
<211> LENGTH: 59
<212> TYPE: DNA
<213> ORGANISM: Artificial
<220> FEATURE:
<223> OTHER INFORMATION: X15564

<400> SEQUENCE: 242
ctaatcaaat caaaataaca gctgaaaatt aatctactta ttcccttcga gattatatc 59

<210> SEQ ID NO 243
<211> LENGTH: 59
<212> TYPE: DNA
<213> ORGANISM: Artificial
<220> FEATURE:
<223> OTHER INFORMATION: X15565

<400> SEQUENCE: 243
gttcctagat ataatctcga agggaataag tagattaatt ttcagctgtt attttgatt 59

<210> SEQ ID NO 244

<211> LENGTH: 59
<212> TYPE: DNA
<213> ORGANISM: Artificial
<220> FEATURE:
<223> OTHER INFORMATION: X15566

<400> SEQUENCE: 244
tcggatcagt agataacccg cctagaagac taggagtgat tatgagtatt tgtgagcag 59

<210> SEQ ID NO 245
<211> LENGTH: 59
<212> TYPE: DNA
<213> ORGANISM: Artificial
<220> FEATURE:
<223> OTHER INFORMATION: X15567

<400> SEQUENCE: 245
aaaacttctg ctcacaaata ctcataatca ctcctagtct tctaggcggg ttatctact 59

<210> SEQ ID NO 246
<211> LENGTH: 59
<212> TYPE: DNA
<213> ORGANISM: Artificial
<220> FEATURE:
<223> OTHER INFORMATION: X15870

<400> SEQUENCE: 246
ctaatcaaat caaaataaca gctgaaaatt aatgagtgat tatgagtatt tgtgagcag 59

<210> SEQ ID NO 247
<211> LENGTH: 59
<212> TYPE: DNA
<213> ORGANISM: Artificial
<220> FEATURE:
<223> OTHER INFORMATION: X15871

<400> SEQUENCE: 247
aaaacttctg ctcacaaata ctcataatca ctcattaatt ttcagctgtt attttgatt 59

<210> SEQ ID NO 248
<211> LENGTH: 30
<212> TYPE: DNA
<213> ORGANISM: Artificial
<220> FEATURE:
<223> OTHER INFORMATION: X16096

<400> SEQUENCE: 248
catggtgctt agcagcagat gaaagtgtca 30

<210> SEQ ID NO 249
<211> LENGTH: 59
<212> TYPE: DNA
<213> ORGANISM: Artificial
<220> FEATURE:
<223> OTHER INFORMATION: X16097

<400> SEQUENCE: 249
gttcctagat ataatctcga agggaataag tagattaatt ttcagctgtt atttcgatt 59

<210> SEQ ID NO 250
<211> LENGTH: 59
<212> TYPE: DNA
<213> ORGANISM: Artificial
<220> FEATURE:
<223> OTHER INFORMATION: X16098

<400> SEQUENCE: 250
ctaatcaaat cgaaataaca gctgaaaatt aatctactta ttcccttcga gattatatc 59

<210> SEQ ID NO 251
<211> LENGTH: 59
<212> TYPE: DNA
<213> ORGANISM: Artificial
<220> FEATURE:
<223> OTHER INFORMATION: X16099

<400> SEQUENCE: 251
aaaacttctg ctcacaaata ctcataatca ctcctagtct tctaggcggg ttatctact 59

<210> SEQ ID NO 252
<211> LENGTH: 59
<212> TYPE: DNA
<213> ORGANISM: Artificial
<220> FEATURE:
<223> OTHER INFORMATION: X16100

<400> SEQUENCE: 252
tcggatcagt agataacccg cctagaagac taggagtgat tatgagtatt tgtgagcag 59

<210> SEQ ID NO 253
<211> LENGTH: 25
<212> TYPE: DNA
<213> ORGANISM: Artificial
<220> FEATURE:
<223> OTHER INFORMATION: X16463

<400> SEQUENCE: 253
cagagtttga agatatccaa atggt 25

<210> SEQ ID NO 254
<211> LENGTH: 29
<212> TYPE: DNA
<213> ORGANISM: Artificial
<220> FEATURE:
<223> OTHER INFORMATION: X16464

<400> SEQUENCE: 254
tttgttcttc ttgttattgt attgtgttg 29

<210> SEQ ID NO 255
<211> LENGTH: 30
<212> TYPE: DNA
<213> ORGANISM: Artificial
<220> FEATURE:
<223> OTHER INFORMATION: X16465

<400> SEQUENCE: 255
gctaattaac ataaaactca tgattcaacg 30

<210> SEQ ID NO 256
<211> LENGTH: 27
<212> TYPE: DNA
<213> ORGANISM: Artificial
<220> FEATURE:
<223> OTHER INFORMATION: X16466

<400> SEQUENCE: 256
acataggttt gcaagcttta taatctg 27

<210> SEQ ID NO 257
<211> LENGTH: 59
<212> TYPE: DNA

<213> ORGANISM: Artificial
<220> FEATURE:
<223> OTHER INFORMATION: X16467

<400> SEQUENCE: 257
agaacaacac aatacaataa caagaagaac aaataggtct agagatctgt ttagcttgc 59

<210> SEQ ID NO 258
<211> LENGTH: 59
<212> TYPE: DNA
<213> ORGANISM: Artificial
<220> FEATURE:
<223> OTHER INFORMATION: X16468

<400> SEQUENCE: 258
aaacgttgaa tcatgagttt tatgttaatt agcgagacta catgatagtc caaagaaaa 59

<210> SEQ ID NO 259
<211> LENGTH: 59
<212> TYPE: DNA
<213> ORGANISM: Artificial
<220> FEATURE:
<223> OTHER INFORMATION: X16469

<400> SEQUENCE: 259
agaacaacac aatacaataa caagaagaac aaactactta ttcccttcga gattatatc 59

<210> SEQ ID NO 260
<211> LENGTH: 59
<212> TYPE: DNA
<213> ORGANISM: Artificial
<220> FEATURE:
<223> OTHER INFORMATION: X16470

<400> SEQUENCE: 260
aaacgttgaa tcatgagttt tatgttaatt agcctagtct tctaggcggg ttatctact 59

<210> SEQ ID NO 261
<211> LENGTH: 25
<212> TYPE: DNA
<213> ORGANISM: Artificial
<220> FEATURE:
<223> OTHER INFORMATION: X16471

<400> SEQUENCE: 261
aagaatctgt tagttcgaac tccag 25

<210> SEQ ID NO 262
<211> LENGTH: 30
<212> TYPE: DNA
<213> ORGANISM: Artificial
<220> FEATURE:
<223> OTHER INFORMATION: X16472

<400> SEQUENCE: 262
tttgttggca atatgttttt gctatattac 30

<210> SEQ ID NO 263
<211> LENGTH: 25
<212> TYPE: DNA
<213> ORGANISM: Artificial
<220> FEATURE:
<223> OTHER INFORMATION: X16473

<400> SEQUENCE: 263
gccattagta gtgtactcaa acgaa 25

<210> SEQ ID NO 264
<211> LENGTH: 24
<212> TYPE: DNA
<213> ORGANISM: Artificial
<220> FEATURE:
<223> OTHER INFORMATION: X16474

<400> SEQUENCE: 264
acgactcaac atatgtatgt tgct 24

<210> SEQ ID NO 265
<211> LENGTH: 59
<212> TYPE: DNA
<213> ORGANISM: Artificial
<220> FEATURE:
<223> OTHER INFORMATION: X16475

<400> SEQUENCE: 265
cacgtaatat agcaaaaaca tattgccaac aaataggtct agagatctgt ttagcttgc 59

<210> SEQ ID NO 266
<211> LENGTH: 59
<212> TYPE: DNA
<213> ORGANISM: Artificial
<220> FEATURE:
<223> OTHER INFORMATION: X16476

<400> SEQUENCE: 266
aacaataatt cgtttgagta cactactaat ggcgagacta catgatagtc caaagaaaa 59

<210> SEQ ID NO 267
<211> LENGTH: 59
<212> TYPE: DNA
<213> ORGANISM: Artificial
<220> FEATURE:
<223> OTHER INFORMATION: X16477

<400> SEQUENCE: 267
cacgtaatat agcaaaaaca tattgccaac aaactactta ttcccttcga gattatatc 59

<210> SEQ ID NO 268
<211> LENGTH: 59
<212> TYPE: DNA
<213> ORGANISM: Artificial
<220> FEATURE:
<223> OTHER INFORMATION: X16478

<400> SEQUENCE: 268
aacaataatt cgtttgagta cactactaat ggcctagtct tctaggcggg ttatctact 59

<210> SEQ ID NO 269
<211> LENGTH: 31
<212> TYPE: DNA
<213> ORGANISM: Artificial
<220> FEATURE:
<223> OTHER INFORMATION: X16951

<400> SEQUENCE: 269
atgttccgct gatgtgatgt gcaagataaa c 31

<210> SEQ ID NO 270
<211> LENGTH: 59
<212> TYPE: DNA
<213> ORGANISM: Artificial
<220> FEATURE:

<223> OTHER INFORMATION: X16952

<400> SEQUENCE: 270
gaggcaagct aaacagatct ctagacctat ttgattgatt tgactgtgtt attttgcgt 59

<210> SEQ ID NO 271
<211> LENGTH: 59
<212> TYPE: DNA
<213> ORGANISM: Artificial
<220> FEATURE:
<223> OTHER INFORMATION: X16953

<400> SEQUENCE: 271
ataacctcac gcaaaataac acagtcaaat caatcaaata ggtctagaga tctgtttag 59

<210> SEQ ID NO 272
<211> LENGTH: 59
<212> TYPE: DNA
<213> ORGANISM: Artificial
<220> FEATURE:
<223> OTHER INFORMATION: X16954

<400> SEQUENCE: 272
aaaactttaa ctaataatta gagattaaat cgcttagaga ctacatgata gtccaaaga 59

<210> SEQ ID NO 273
<211> LENGTH: 59
<212> TYPE: DNA
<213> ORGANISM: Artificial
<220> FEATURE:
<223> OTHER INFORMATION: X16955

<400> SEQUENCE: 273
gtccccccgt ttcttttctt tggactatca tgtagtctct aagcgattta atctctaat 59

<210> SEQ ID NO 274
<211> LENGTH: 36
<212> TYPE: DNA
<213> ORGANISM: Artificial
<220> FEATURE:
<223> OTHER INFORMATION: X16956

<400> SEQUENCE: 274
tcggtcattg ggtgagttta agcattagca gcaatg 36

<210> SEQ ID NO 275
<211> LENGTH: 59
<212> TYPE: DNA
<213> ORGANISM: Artificial
<220> FEATURE:
<223> OTHER INFORMATION: X16957

<400> SEQUENCE: 275
taaaacttta actaataatt agagattaaa tcgcttattt gattgatttg actgtgtta 59

<210> SEQ ID NO 276
<211> LENGTH: 59
<212> TYPE: DNA
<213> ORGANISM: Artificial
<220> FEATURE:
<223> OTHER INFORMATION: X16958

<400> SEQUENCE: 276
cacgcaaaat aacacagtca aatcaatcaa ataagcgatt taatctctaa ttattagtt 59

<210> SEQ ID NO 277
<211> LENGTH: 1128
<212> TYPE: DNA
<213> ORGANISM: S. cerevisiae

<400> SEQUENCE: 277
atgtcgaagg gaaaggtttt gctggttctt tacgaaggtg gtaagcatgc tgaagagcag 60
gaaaagttat tggggtgtat tgaaaatgaa cttggtatca gaaatttcat tgaagaacag 120
ggatacgagt tggttactac cattgacaag gaccctgagc caacctcaac ggtagacagg 180
gagttgaaag acgctgaaat tgtcattact acgccctttt tccccgccta catctcgaga 240
aacaggattg cagaagctcc taacctgaag ctctgtgtaa ccgctggcgt cggttcagac 300
catgtcgatt tagaagctgc aaatgaacgg aaaatcacgg tcaccgaagt tactggttct 360
aacgtcgttt ctgtcgcaga gcacgttatg gccacaattt tggttttgat aagaaactat 420
aatggtggtc atcaacaagc aattaatggt gagtgggata ttgccggcgt ggctaaaaat 480
gagtatgatc tggaagacaa aataatttca acggtaggtg ccggtagaat tggatatagg 540
gttctggaaa gattggtcgc atttaatccg aagaagttac tgtactacga ctaccaggaa 600
ctacctgcgg aagcaatcaa tagattgaac gaggccagca agcttttcaa tggcagaggt 660
gatattgttc agagagtaga gaaattggag gatatggttg ctcagtcaga tgttgttacc 720
atcaactgtc cattgcacaa ggactcaagg ggtttattca ataaaaagct tatttcccac 780
atgaaagatg gtgcatactt ggtgaatacc gctagaggtg ctatttgtgt cgcagaagat 840
gttgccgagg cagtcaagtc tggtaaattg gctggctatg gtggtgatgt ctgggataag 900
caaccagcac caaaagacca tccctggagg actatggaca ataaggacca cgtgggaaac 960
gcaatgactg ttcatatcag tggcacatct ctggatgctc aaaagaggta cgctcaggga 1020
gtaaagaaca tcctaaatag ttacttttcc aaaaagtttg attaccgtcc acaggatatt 1080
attgtgcaga atggttctta tgccaccaga gcttatggac agaagaaa 1128

<210> SEQ ID NO 278
<211> LENGTH: 376
<212> TYPE: PRT
<213> ORGANISM: S. cerevisiae

<400> SEQUENCE: 278

Met Ser Lys Gly Lys Val Leu Leu Val Leu Tyr Glu Gly Gly Lys His
1 5 10 15

Ala Glu Glu Gln Glu Lys Leu Leu Gly Cys Ile Glu Asn Glu Leu Gly
20 25 30

Ile Arg Asn Phe Ile Glu Glu Gln Gly Tyr Glu Leu Val Thr Thr Ile
35 40 45

Asp Lys Asp Pro Glu Pro Thr Ser Thr Val Asp Arg Glu Leu Lys Asp
50 55 60

Ala Glu Ile Val Ile Thr Thr Pro Phe Phe Pro Ala Tyr Ile Ser Arg
65 70 75 80

Asn Arg Ile Ala Glu Ala Pro Asn Leu Lys Leu Cys Val Thr Ala Gly
85 90 95

Val Gly Ser Asp His Val Asp Leu Glu Ala Ala Asn Glu Arg Lys Ile
100 105 110

Thr Val Thr Glu Val Thr Gly Ser Asn Val Val Ser Val Ala Glu His
115 120 125

Val Met Ala Thr Ile Leu Val Leu Ile Arg Asn Tyr Asn Gly Gly His
130 135 140

Gln Gln Ala Ile Asn Gly Glu Trp Asp Ile Ala Gly Val Ala Lys Asn
145 150 155 160

Glu Tyr Asp Leu Glu Asp Lys Ile Ile Ser Thr Val Gly Ala Gly Arg
165 170 175

Ile Gly Tyr Arg Val Leu Glu Arg Leu Val Ala Phe Asn Pro Lys Lys
180 185 190

Leu Leu Tyr Tyr Asp Tyr Gln Glu Leu Pro Ala Glu Ala Ile Asn Arg
195 200 205

Leu Asn Glu Ala Ser Lys Leu Phe Asn Gly Arg Gly Asp Ile Val Gln
210 215 220

Arg Val Glu Lys Leu Glu Asp Met Val Ala Gln Ser Asp Val Val Thr
225 230 235 240

Ile Asn Cys Pro Leu His Lys Asp Ser Arg Gly Leu Phe Asn Lys Lys
245 250 255

Leu Ile Ser His Met Lys Asp Gly Ala Tyr Leu Val Asn Thr Ala Arg
260 265 270

Gly Ala Ile Cys Val Ala Glu Asp Val Ala Glu Ala Val Lys Ser Gly
275 280 285

Lys Leu Ala Gly Tyr Gly Gly Asp Val Trp Asp Lys Gln Pro Ala Pro
290 295 300

Lys Asp His Pro Trp Arg Thr Met Asp Asn Lys Asp His Val Gly Asn
305 310 315 320

Ala Met Thr Val His Ile Ser Gly Thr Ser Leu Asp Ala Gln Lys Arg
325 330 335

Tyr Ala Gln Gly Val Lys Asn Ile Leu Asn Ser Tyr Phe Ser Lys Lys
340 345 350

Phe Asp Tyr Arg Pro Gln Asp Ile Ile Val Gln Asn Gly Ser Tyr Ala
355 360 365

Thr Arg Ala Tyr Gly Gln Lys Lys
370 375

<210> SEQ ID NO 279
<211> LENGTH: 1158
<212> TYPE: DNA
<213> ORGANISM: B. stabilis

<400> SEQUENCE: 279
atggctaccg ttttgtgtgt cttgtatcca gatccagttg atggttatcc accacattat 60
gttagagata ccattccagt tattaccaga tacgctgatg gtcaaactgc tccaactcca 120
gctggtccac caggttttag accaggtgaa ttggttggtt ctgtttctgg tgctttgggt 180
ttgagaggtt atttggaagc tcatggtcat actttgatcg ttacctctga taaggatggt 240
ccagattctg aattcgaaag aagattgcca gacgccgatg ttgttatttc tcaaccattt 300
tggccagctt acttgaccgc tgaaagaatt gctagagcac caaaattgag attggctttg 360
actgctggta ttggttctga tcatgttgat ttggatgctg ctgctagagc ccatattact 420
gttgctgaag ttactggttc caactctatt tcagttgccg aacacgttgt tatgactact 480
ttggctttgg tcagaaacta cttgccatct catgctattg ctcaacaagg tggttggaat 540
attgctgatt gtgtctctag atcctacgat gttgaaggta tgcattttgg tactgttggt 600
gctggtagaa ttggtttggc tgttttgaga agattgaagc catttggttt acacttgcac 660
tacacccaaa gacatagatt ggatgcagct atcgaacaag aattgggttt aacttatcat 720
gctgatccag cttcattggc tgctgctgtt gatatagtta acttgcaaat cccattatac 780

```
ccatccaccg aacatttgtt tgatgctgct atgattgcta gaatgaagag aggtgcatac    840

ttgattaaca ccgctagagc taaattggtt gatagagatg ctgttgttag agctgttact    900

tctggtcatt tggctggtta tggtggtgat gtttggtttc cacaaccagc tccagctgat    960

catccttgga gagctatgcc ttttaatggt atgactccac atatctccgg tacatctttg   1020

tctgctcaag ctagatatgc tgctggtact ttggaaatat tgcaatgttg gtttgacggt   1080

agaccaatca gaaacgaata tttgattgtc gacggtggta ctttagctgg tactggtgct   1140

caatcttaca gattaact                                                 1158
```

<210> SEQ ID NO 280
<211> LENGTH: 386
<212> TYPE: PRT
<213> ORGANISM: B. stabilis

<400> SEQUENCE: 280

```
Met Ala Thr Val Leu Cys Val Leu Tyr Pro Asp Pro Val Asp Gly Tyr
1               5                   10                  15

Pro Pro His Tyr Val Arg Asp Thr Ile Pro Val Ile Thr Arg Tyr Ala
            20                  25                  30

Asp Gly Gln Thr Ala Pro Thr Pro Ala Gly Pro Pro Gly Phe Arg Pro
        35                  40                  45

Gly Glu Leu Val Gly Ser Val Ser Gly Ala Leu Gly Leu Arg Gly Tyr
    50                  55                  60

Leu Glu Ala His Gly His Thr Leu Ile Val Thr Ser Asp Lys Asp Gly
65                  70                  75                  80

Pro Asp Ser Glu Phe Glu Arg Arg Leu Pro Asp Ala Asp Val Val Ile
                85                  90                  95

Ser Gln Pro Phe Trp Pro Ala Tyr Leu Thr Ala Glu Arg Ile Ala Arg
            100                 105                 110

Ala Pro Lys Leu Arg Leu Ala Leu Thr Ala Gly Ile Gly Ser Asp His
        115                 120                 125

Val Asp Leu Asp Ala Ala Ala Arg Ala His Ile Thr Val Ala Glu Val
    130                 135                 140

Thr Gly Ser Asn Ser Ile Ser Val Ala Glu His Val Val Met Thr Thr
145                 150                 155                 160

Leu Ala Leu Val Arg Asn Tyr Leu Pro Ser His Ala Ile Ala Gln Gln
                165                 170                 175

Gly Gly Trp Asn Ile Ala Asp Cys Val Ser Arg Ser Tyr Asp Val Glu
            180                 185                 190

Gly Met His Phe Gly Thr Val Gly Ala Gly Arg Ile Gly Leu Ala Val
        195                 200                 205

Leu Arg Arg Leu Lys Pro Phe Gly Leu His Leu His Tyr Thr Gln Arg
    210                 215                 220

His Arg Leu Asp Ala Ala Ile Glu Gln Glu Leu Gly Leu Thr Tyr His
225                 230                 235                 240

Ala Asp Pro Ala Ser Leu Ala Ala Ala Val Asp Ile Val Asn Leu Gln
                245                 250                 255

Ile Pro Leu Tyr Pro Ser Thr Glu His Leu Phe Asp Ala Ala Met Ile
            260                 265                 270

Ala Arg Met Lys Arg Gly Ala Tyr Leu Ile Asn Thr Ala Arg Ala Lys
        275                 280                 285

Leu Val Asp Arg Asp Ala Val Val Arg Ala Val Thr Ser Gly His Leu
    290                 295                 300
```

```
Ala Gly Tyr Gly Gly Asp Val Trp Phe Pro Gln Pro Ala Pro Ala Asp
305                 310                 315                 320

His Pro Trp Arg Ala Met Pro Phe Asn Gly Met Thr Pro His Ile Ser
                325                 330                 335

Gly Thr Ser Leu Ser Ala Gln Ala Arg Tyr Ala Ala Gly Thr Leu Glu
            340                 345                 350

Ile Leu Gln Cys Trp Phe Asp Gly Arg Pro Ile Arg Asn Glu Tyr Leu
        355                 360                 365

Ile Val Asp Gly Gly Thr Leu Ala Gly Thr Gly Ala Gln Ser Tyr Arg
    370                 375                 380

Leu Thr
385


<210> SEQ ID NO 281
<211> LENGTH: 1647
<212> TYPE: DNA
<213> ORGANISM: S. cerevisiae

<400> SEQUENCE: 281

atgtcccctt ctaaaatgaa tgctacagta ggatctactt ccgaagttga acaaaaaatc      60

agacaagaat tggctcttag tgacgaagtc accaccatca gacgcaatgc tccagctgcc     120

gttttgtatg aagatggtct aaaagaaaat aaaactgtca tttcatcaag cggtgcattg     180

atcgcttatt ccggtgttaa aaccggaaga tctccaaagg acaaacgtat tgttgaagaa     240

cctacctcga aagacgaaat ttggtggggt ccggtcaata aaccatgttc tgaaagaaca     300

tggtctatca accgtgaaag agctgcagat tacttgagaa caagagacca catttatatt     360

gtcgatgcat ttgcaggatg ggatccaaaa tacagaatca aagtccgcgt tgtttgtgcc     420

agggcttacc acgctttatt catgacaaat atgcttatta gacctacaga agaagaatta     480

gcccattttg gagaacctga ttttactgtc tggaacgctg gtcagttccc agccaattta     540

cacacccagg atatgtcttc aaagagtact atagaaatta acttcaaagc aatggaaatg     600

atcattttag gtaccgaata cgccggtgaa atgaaaaaag gtattttcac agttatgttt     660

tacttgatgc ctgtgcacca taacgtttta actttgcact cttccgccaa ccagggtatt     720

caaaacggtg acgttacttt attctttggc ctaagtggta ccgggaaaac cactttatcc     780

gcagacccac atagattgtt gatcggcgat gatgaacatt gttggtccga ccatggtgtc     840

ttcaatatcg aaggtggttg ttacgccaag tgtattaatt tatctgccga aaaggagcct     900

gaaattttcg acgctatcaa gtttggttct gtattagaaa acgttatcta tgacgagaag     960

tcgcatgtag tcgactatga cgactcttct attactgaaa atactagatg tgcctaccca    1020

attgactaca ttccaagtgc caagattcca tgtttggcgg actctcatcc aaagaacatt    1080

atcctgctaa cttgtgatgc ttcgggtgtt ttaccaccag tatctaaatt gactcctgaa    1140

caagtcatgt accatttcat ctctggttac acttctaaaa tggctggtac tgagcaaggt    1200

gtcactgaac ctgaaccaac attttcatct tgtttcggac aacccttcct agccttgcac    1260

cctattagat acgcaaccat gttagctaca aagatgtctc aacataaagc taatgcgtac    1320

ttaatcaaca ccggctggac tggttcttcc tacgtatctg gtggtaaacg ttgcccattg    1380

aagtacacaa gggccattct ggattctatt catgatggtt cgttagccaa tgaaacgtac    1440

gaaactttac cgattttcaa tcttcaagta cctaccaagg ttaacggtgt tccagctgag    1500

cttttgaatc ctgctaaaaa ctggtctcaa ggtgaatcca aatacagagg tgcagttacc    1560
```

-continued

```
aacttggcca acttgtttgt tcaaaatttc aagatttatc aagacagagc cacaccagat   1620

gtattagccg ctggtcctca attcgag                                       1647


<210> SEQ ID NO 282
<211> LENGTH: 549
<212> TYPE: PRT
<213> ORGANISM: S. cerevisiae

<400> SEQUENCE: 282

Met Ser Pro Ser Lys Met Asn Ala Thr Val Gly Ser Thr Ser Glu Val
1               5                   10                  15

Glu Gln Lys Ile Arg Gln Glu Leu Ala Leu Ser Asp Glu Val Thr Thr
            20                  25                  30

Ile Arg Arg Asn Ala Pro Ala Ala Val Leu Tyr Glu Asp Gly Leu Lys
        35                  40                  45

Glu Asn Lys Thr Val Ile Ser Ser Ser Gly Ala Leu Ile Ala Tyr Ser
    50                  55                  60

Gly Val Lys Thr Gly Arg Ser Pro Lys Asp Lys Arg Ile Val Glu Glu
65                  70                  75                  80

Pro Thr Ser Lys Asp Glu Ile Trp Trp Gly Pro Val Asn Lys Pro Cys
                85                  90                  95

Ser Glu Arg Thr Trp Ser Ile Asn Arg Glu Arg Ala Ala Asp Tyr Leu
            100                 105                 110

Arg Thr Arg Asp His Ile Tyr Ile Val Asp Ala Phe Ala Gly Trp Asp
        115                 120                 125

Pro Lys Tyr Arg Ile Lys Val Arg Val Val Cys Ala Arg Ala Tyr His
    130                 135                 140

Ala Leu Phe Met Thr Asn Met Leu Ile Arg Pro Thr Glu Glu Glu Leu
145                 150                 155                 160

Ala His Phe Gly Glu Pro Asp Phe Thr Val Trp Asn Ala Gly Gln Phe
                165                 170                 175

Pro Ala Asn Leu His Thr Gln Asp Met Ser Ser Lys Ser Thr Ile Glu
            180                 185                 190

Ile Asn Phe Lys Ala Met Glu Met Ile Ile Leu Gly Thr Glu Tyr Ala
        195                 200                 205

Gly Glu Met Lys Lys Gly Ile Phe Thr Val Met Phe Tyr Leu Met Pro
    210                 215                 220

Val His His Asn Val Leu Thr Leu His Ser Ser Ala Asn Gln Gly Ile
225                 230                 235                 240

Gln Asn Gly Asp Val Thr Leu Phe Phe Gly Leu Ser Gly Thr Gly Lys
                245                 250                 255

Thr Thr Leu Ser Ala Asp Pro His Arg Leu Leu Ile Gly Asp Asp Glu
            260                 265                 270

His Cys Trp Ser Asp His Gly Val Phe Asn Ile Glu Gly Gly Cys Tyr
        275                 280                 285

Ala Lys Cys Ile Asn Leu Ser Ala Glu Lys Glu Pro Glu Ile Phe Asp
    290                 295                 300

Ala Ile Lys Phe Gly Ser Val Leu Glu Asn Val Ile Tyr Asp Glu Lys
305                 310                 315                 320

Ser His Val Val Asp Tyr Asp Asp Ser Ser Ile Thr Glu Asn Thr Arg
                325                 330                 335

Cys Ala Tyr Pro Ile Asp Tyr Ile Pro Ser Ala Lys Ile Pro Cys Leu
            340                 345                 350

Ala Asp Ser His Pro Lys Asn Ile Ile Leu Leu Thr Cys Asp Ala Ser
```

```
        355                 360                 365

Gly Val Leu Pro Pro Val Ser Lys Leu Thr Pro Glu Gln Val Met Tyr
    370                 375                 380

His Phe Ile Ser Gly Tyr Thr Ser Lys Met Ala Gly Thr Glu Gln Gly
385                 390                 395                 400

Val Thr Glu Pro Glu Pro Thr Phe Ser Ser Cys Phe Gly Gln Pro Phe
                405                 410                 415

Leu Ala Leu His Pro Ile Arg Tyr Ala Thr Met Leu Ala Thr Lys Met
            420                 425                 430

Ser Gln His Lys Ala Asn Ala Tyr Leu Ile Asn Thr Gly Trp Thr Gly
        435                 440                 445

Ser Ser Tyr Val Ser Gly Gly Lys Arg Cys Pro Leu Lys Tyr Thr Arg
    450                 455                 460

Ala Ile Leu Asp Ser Ile His Asp Gly Ser Leu Ala Asn Glu Thr Tyr
465                 470                 475                 480

Glu Thr Leu Pro Ile Phe Asn Leu Gln Val Pro Thr Lys Val Asn Gly
                485                 490                 495

Val Pro Ala Glu Leu Leu Asn Pro Ala Lys Asn Trp Ser Gln Gly Glu
            500                 505                 510

Ser Lys Tyr Arg Gly Ala Val Thr Asn Leu Ala Asn Leu Phe Val Gln
        515                 520                 525

Asn Phe Lys Ile Tyr Gln Asp Arg Ala Thr Pro Asp Val Leu Ala Ala
    530                 535                 540

Gly Pro Gln Phe Glu
545


<210> SEQ ID NO 283
<211> LENGTH: 903
<212> TYPE: DNA
<213> ORGANISM: A. thaliana

<400> SEQUENCE: 283

atgcttgatt ggaaacctag gcgttctgac atgctggtgg atccttttgg tatagggaga     60

attgttcagg atggccttgt gttccgtcag aatttttcta ttaggtcata tgaaataggt    120

gctgatcgct ctgcatctat agaaaccgtc atgaatcatc tgcaggaaac ggcgcttaat    180

catgttaaga ctgctggatt gcttggagat gggtttggct ctacacctga gatgtttaag    240

aagaacttga tatgggttgt cactcgtatg caggttgtgg ttgataaata tcctacttgg    300

ggagatgttg ttgaagtaga cacctgggtc agtcaatctg gaaagaatgg tatgcgtcgt    360

gattggctag ttcgggattg taatactgga gaaaccttaa cacgagcatc aagtgtgtgg    420

gtgatgatga ataaactgac aaggagattg tcaaagattc ctgaagaggt tcgaggggaa    480

atagagcctt attttgtgaa ttctgatcct gtccttgccg aggacagcag aaagttaaca    540

aaaattgatg acaagactgc tgactatgtt cgatctggtc tcactcctcg atggagtgac    600

ctagatgtta accagcatgt gaataatgta aagtacattg ggtggatcct ggagagtgct    660

ccagtgggaa taatggagag gcagaagctg aaaagcatga ctctggagta tcggagggaa    720

tgcgggagag acagtgtgct tcagtccctc actgcagtta cgggttgcga tatcggtaac    780

ctggcaacag cgggggatgt ggaatgtcag catttgctcc gactccagga tggagcggaa    840

gtggtgagag gaagaacaga gtggagtagt aaaacaccaa caacaacttg gggaactgca    900

ccg                                                                  903
```

<210> SEQ ID NO 284
<211> LENGTH: 301
<212> TYPE: PRT
<213> ORGANISM: A. thaliana

<400> SEQUENCE: 284

```
Met Leu Asp Trp Lys Pro Arg Arg Ser Asp Met Leu Val Asp Pro Phe
1               5                   10                  15

Gly Ile Gly Arg Ile Val Gln Asp Gly Leu Val Phe Arg Gln Asn Phe
            20                  25                  30

Ser Ile Arg Ser Tyr Glu Ile Gly Ala Asp Arg Ser Ala Ser Ile Glu
        35                  40                  45

Thr Val Met Asn His Leu Gln Glu Thr Ala Leu Asn His Val Lys Thr
    50                  55                  60

Ala Gly Leu Leu Gly Asp Gly Phe Gly Ser Thr Pro Glu Met Phe Lys
65                  70                  75                  80

Lys Asn Leu Ile Trp Val Val Thr Arg Met Gln Val Val Val Asp Lys
                85                  90                  95

Tyr Pro Thr Trp Gly Asp Val Val Glu Val Asp Thr Trp Val Ser Gln
            100                 105                 110

Ser Gly Lys Asn Gly Met Arg Arg Asp Trp Leu Val Arg Asp Cys Asn
        115                 120                 125

Thr Gly Glu Thr Leu Thr Arg Ala Ser Ser Val Trp Val Met Met Asn
    130                 135                 140

Lys Leu Thr Arg Arg Leu Ser Lys Ile Pro Glu Glu Val Arg Gly Glu
145                 150                 155                 160

Ile Glu Pro Tyr Phe Val Asn Ser Asp Pro Val Leu Ala Glu Asp Ser
                165                 170                 175

Arg Lys Leu Thr Lys Ile Asp Asp Lys Thr Ala Asp Tyr Val Arg Ser
            180                 185                 190

Gly Leu Thr Pro Arg Trp Ser Asp Leu Asp Val Asn Gln His Val Asn
        195                 200                 205

Asn Val Lys Tyr Ile Gly Trp Ile Leu Glu Ser Ala Pro Val Gly Ile
    210                 215                 220

Met Glu Arg Gln Lys Leu Lys Ser Met Thr Leu Glu Tyr Arg Arg Glu
225                 230                 235                 240

Cys Gly Arg Asp Ser Val Leu Gln Ser Leu Thr Ala Val Thr Gly Cys
                245                 250                 255

Asp Ile Gly Asn Leu Ala Thr Ala Gly Asp Val Glu Cys Gln His Leu
            260                 265                 270

Leu Arg Leu Gln Asp Gly Ala Glu Val Val Arg Gly Arg Thr Glu Trp
        275                 280                 285

Ser Ser Lys Thr Pro Thr Thr Thr Trp Gly Thr Ala Pro
    290                 295                 300
```

<210> SEQ ID NO 285
<211> LENGTH: 12309
<212> TYPE: DNA
<213> ORGANISM: Artificial
<220> FEATURE:
<223> OTHER INFORMATION: pMU2737

<400> SEQUENCE: 285

```
tctccgggag ctgcatgtgt cagaggtttt caccgtcatc accgaaacgc gcgagacgaa     60

agggcctcgt gatacgccta tttttatagg ttaatgtcat gataataatg gtttcttgtg    120

acattggcgc aacgaaggta tattttgttt tttgccggag gatagcagca gatcgctgca    180
```

-continued

```
caatgtccgt caagtctaac attgacactc tggggcaaaa tagaccggcg tcccggcctg    240
ctggaattta tcgctatgca tacagctgtc ggggcatacg ctttacagac ggcggtgaaa    300
cgcctgtcac aatcacacta aacaaagagt acggaaccca ctcatggata ttcgtaagat    360
taaaaaactg atcgagctgg ttgaagaatc aggcatctcc gaactggaaa tttctgaagg    420
cgaagagtca gtacgcatta gccgtgcagc tcctgccgca agtttccctg tgatgcaaca    480
agcttacgct gcaccaatga tgcagcagcc agctcaatct aacgcagccg ctccggcgac    540
cgttccttcc atggaagcgc cagcagcagc ggaaatcagt ggtcacatcg tacgttcccc    600
gatggttggt actttctacc gcaccccaag cccggacgca aaagcgttca tcgaagtggg    660
tcagaaagtc aacgtgggcg ataccctgtg catcgttgaa gccatgaaaa tgatgaacca    720
gatcgaagcg gacaaatccg gtaccgtgaa agcaattctg gtcgaaagtg gacaaccggt    780
agaatttgac gagccgctgg tcgtcatcga gtaacgaggc gaacacggcc tgatggtcaa    840
ctatctctac aagctcgacg acatcgtggc caaccacgag gctctggcgc agcgcggcga    900
agtgattgcc tcgcctgctg tcaaaagcct gctcaaccag aacgacgaag gccgcagtgg    960
cggcaatggc cagcaaggct cccggccatt cgcacagata gtgaattcaa cgcttggagg   1020
agggcgaaag tgagcaacca tcttttcgac gccatgcggg ccgccgcgcc cggtaacgca   1080
ccattcatcc ggatcgataa cacgcgcaca tggacctatg acgacgcctt cgctctttcc   1140
ggccgcattg ccagcgcgat ggacgcgctc ggcattcgcc ccggcgaccg cgttgcggtg   1200
caggtcgaga aaagtgccga ggcattgatc ctctatctcg cctgtcttcg aagcggcgcc   1260
gtctacctgc cgctcaacac cgcctatacg ctggctgagc tcgattattt tatcggcgat   1320
gcggagccgc gtttggtggt tgtcgcatcg tcggctcgag cgggcgtgga gacaatcgcc   1380
aagccccgcg gtgcgatcgt cgaaactctc gacgctgctg gcagcggctc gttgctggat   1440
ctcgccccgcg acgagccggc cgactttgtc gatgcctcgc gctccgccga tgatctggcg   1500
gcgatcctct acacgtccgg aacgacggga cgctccaagg gggcgatgct cacgcatggg   1560
aacctgctct cgaacgccct gaccttgcga gatttttggc gcgtcaccgc cggcgatcga   1620
ctgatccatg ccttgccgat cttccacacg catggactgt tcgtcgccac gaacgtcaca   1680
ctgctcgccg gcgcctcgat gttcctgctg tcgaagttcg acccggagga gatcctgtcg   1740
ctgatgccgc aggcaacgat gctgatgggc gtgccgacct tctacgtgcg cctcctgcag   1800
agcccgcgcc tcgacaagca agcggtcgcc aacatccgcc tcttcatttc cggttcggct   1860
ccactgcttg cagaaacaca taccgagttc caggcacgta ccggtcacgc cattctcgag   1920
cgctacggca tgacggaaac caatatgaac acgtccaacc cttatgaggg gaaacggatt   1980
gccggaacgg tcggcttccc gctgcctgat gtgacggtgc gcgtcaccga tcccgccacc   2040
gggctcgcgc tgccgcccga acaaaccggc atgatcgaga tcaaggggcc gaacgttttc   2100
aagggctatt ggcgcatgcc cgaaaaaacc gcggccgaat tcaccgccga cggtttcttc   2160
atcagcggcg atctcggcaa gatcgaccgc gacggttatg tccacatcgt cggccgcggc   2220
aaggatctgg tgatttcggg tggatacaac atctatccga aagaggttga gggcgagatc   2280
gaccagatcg agggtgtggt tgagagcgct gtgatcggcg tgccgcatcc cgatttcgga   2340
gaaggcgtaa cggccgtcgt cgtgcgcaag cccggcgctg ccctcgatga aaaggccatc   2400
gtcagcgccc tccaggaccg gctcgcgcgc tacaaacaac ccaagcgcat catctttgca   2460
gaggacttgc cgcgcaacac gatgggtaag gttcagaaaa acatcctgcg gcagcaatac   2520
```

-continued

```
gccgatcttt ataccaggac gtaaggcgac cgcgctctct gggaggagag tgcgtcgaca   2580
tcccgcatca atcttgaaaa cagcaactgc gacgcggagg cgtcggaggg aggggaatca   2640
tgggtattga attactgtcc ataggcctgc tgatcgccat gttcatcatt gcgacgatcc   2700
agccaatcaa catgggtgcg ctcgcctttg ccggcgcctt cgtgctcggc tcgatgatca   2760
tcgggatgaa aaccaacgaa atatttgccg gctttccgag tgatctgttc ctgacgctcg   2820
tcgccgtcac ctacctcttc gccatagcgc agatcaacgg cacgatcgac tggctcgtcg   2880
aatgtgccgt ccgcctggta cgcgggcgga tcggcttgat tccctgggtg atgttccttg   2940
tcgccgccat cattactggc ttcggtgcac ttgggcctgc tgcggtcgcc attctcgcac   3000
ccgtcgcgtt gagctttgcc gtgcagtacc gcattcatcc ggtgatgatg ggtctgatgg   3060
tgatccacgg cgcgcaggca ggcggcttct cgccgatcag catctatggc ggaatcacca   3120
accagatcgt tgcgaaggcc ggcctgcctt tcgctccgac ctcgctgttt ctttccagct   3180
tcttctttaa cctggcgatc gcggtgctgg tgttcttcgt gttcggcggc gcgagggtga   3240
tgaagcacga tcccgcatca cttggcccct tgcccgaact ccatcccgag ggcgtatcgg   3300
cgtcgatcag aggccacggc ggcacgccgg caaaaccgat cagagagcat gcctatggta   3360
cggcggccga taccgcgacg acgttgcgtc tgaacaatga gagaattacc accttgatcg   3420
gcctgacggc gctcggcatc ggcgccctgg ttttcaagtt caatgttggc ctcgtcgcca   3480
tgaccgtcgc cgtcgtcctc gcgctgctgt caccgaagac ccagaaggcc gcaatcgaca   3540
aggtcagttg gtcgaccgtg ctgctgattg ccggcatcat cacctatgtc ggcgtcatgg   3600
agaaggccgg tacggtcgac tacgtggcga atggcatatc cagtctcggc atgccgctac   3660
tggtagcgct cctgctttgc tttacgggcg ccatcgtctc ggcctttgct tcctcgaccg   3720
cgctgctcgg cgcgatcatc ccgcttgccg ttccattcct cctgcaaggg cacatcagcg   3780
ccatcggtgt ggtcgcggcg atcgccatct cgacgacgat cgtcgacacc agcccattct   3840
ccaccaacgg cgcccttgtc gtcgccaatg cgccggacga cagccgtgag caggtgttgc   3900
gacagctact gatctacagc gccttgatcg ctatcatcgg tccgatcgtt gcctggttgg   3960
tgttcgtcgt gcccgggctg gtttgacgac gggctgctcc cagcgaaaag tgtgccgagc   4020
cctgttcggc acacttggag accgtggatg tcccaattac ggaactcggt cttcaggaaa   4080
aataagactg ctaaagcgtc aaaaggccgg attttccggc ctttttttatt actggggatc   4140
gacaaccccc ataaggtaca atccccgctt tcttcaccca tcagggacaa aaaatggaca   4200
ctcgttttgt tcaggcccat aaagaggcgc gctgggcgct ggggctgacc cttttgtatc   4260
tggcagtttg gttagtagcc gcttacttat ctggcgttgc cccccggtttt accggctttc   4320
cgcgctggtt tgagatggcc tgcatcctga cgccgctgct gtttattgga ctgtgctggg   4380
cgatggtgaa atttatctat cgcgatatcc cactggagga tgacgatgca gcttgaagta   4440
attctaccgc tggtcgccta tctggtggtg gtgttcggta tctcggttta tgcgatgcgt   4500
aaacggagca ccggcacctt ccttaatgag tatttcctcg gcagccgctc tatgggcggt   4560
attgtgctgg cgatgacgct caccgcgacc tatatcagtg ccagttcgtt tatcggcggg   4620
ccaggagctg cttataaata cgggctgggc tgggtattgc tggcgatgat tcagcttcct   4680
gcagtctggc tttcactcgg tattctcggc aagaagtttg cgattcttgc gcgccgctac   4740
aatgcagtga cgctgaacga tatgctgttt gcccgctacc agagtcgtct tctggtgtgg   4800
ctggcgagtt tgagtttgct ggttgcgttc gttggtgcga tgaccgtgca gtttatcggc   4860
ggtgcgcgcc tgctggaaac cgcggcgggt attccttatg aaaccgggct gctgattttt   4920
```

ggtatcagca ttgcgttata taccgccttt ggtggctttc gcgccagcgt gctgaacgac 4980
accatgcaag ggcttgtgat gctgattggc accgttggtg gcacttttcg gggaaatgtg 5040
cgcggaaccc ctatttgttt atttttctaa atacattcaa atatgtatcc gctcatgaga 5100
caataaccct gataaatgct tcaataatat tgaaaaagga agagtatgag tattcaacat 5160
ttccgtgtcg cccttattcc cttttttgcg gcattttgcc ttcctgtttt tgctcaccca 5220
gaaacgctgg tgaaagtaaa agatgctgaa gatcagttgg gtgcacgagt gggttacatc 5280
gaactggatc tcaacagcgg taagatcctt gagagttttc gccccgaaga acgttttcca 5340
atgatgagca cttttaaagt tctgctatgt ggcgcggtat tatcccgtat tgacgccggg 5400
caagagcaac tcggtcgccg catacactat tctcagaatg acttggttga gtactcacca 5460
gtcacagaaa agcatcttac ggatggcatg acagtaagag aattatgcag tgctgccata 5520
accatgagtg ataacactgc ggccaactta cttctgacaa cgatcggagg accgaaggag 5580
ctaaccgctt ttttgcacaa catgggggat catgtaactc gccttgatcg ttgggaaccg 5640
gagctgaatg aagccatacc aaacgacgag cgtgacacca cgatgcctgt agcaatggca 5700
acaacgttgc gcaaactatt aactggcgaa ctacttactc tagcttcccg gcaacaatta 5760
atagactgga tggaggcgga taaagttgca ggaccacttc tgcgctcggc ccttccggct 5820
ggctggttta ttgctgataa atctggagcc ggtgagcgtg ggtctcgcgg tatcattgca 5880
gcactggggc cagatggtaa gccctcccgt atcgtagtta tctacacgac ggggagtcag 5940
gcaactatgg atgaacgaaa tagacagatc gctgagatag gtgcctcact gattaagcat 6000
tggtaagcga tgaaatgtga ggtgaatcag ggttttcacc cgattttgtg ctgatcagaa 6060
tttttttct ttttccccct tgaaggggcg aagcctcatc cccatttctc tggtcaccag 6120
ccgggaaacc acgtaagctc cggcgtcacc cataacagat acggactttc tcaaaggaga 6180
gttatcaatg aacatcaaaa agtttgcaaa acaagcaaca gtattaacct ttactaccgc 6240
actgctggca ggaggcgcaa ctcaagcgtt tgcgaaagaa acgaaccaaa agccatataa 6300
ggaaacatac ggcatttccc atattacacg ccatgatatg ctgcaaatcc ctgaacagca 6360
aaaaaatgaa aaatatcaag ttcctgagtt cgattcgtcc acaattaaaa atatctcttc 6420
tgcaaaaggc ctggacgttt gggacagctg gccattacaa aacgctgacg gcactgtcgc 6480
aaactatcac ggctaccaca tcgtctttgc attagccgga gatcctaaaa atgcggatga 6540
cacatcgatt tacatgttct atcaaaaagt cggcgaaact tctattgaca gctggaaaaa 6600
cgctggccgc gtctttaaag acagcgacaa attcgatgca aatgattcta tcctaaaaga 6660
ccaaacacaa gaatggtcag gttcagccac atttacatct gacggaaaaa tccgtttatt 6720
ctacactgat ttctccggta aacattacgg caaacaaaca ctgacaactg cacaagttaa 6780
cgtatcagca tcagacagct ctttgaacat caacggtgta gaggattata aatcaatctt 6840
tgacggtgac ggaaaaacgt atcaaaatgt acagcagttc atcgatgaag gcaactacag 6900
ctcaggcgac aaccatacgc tgagagatcc tcactacgta gaagataaag gccacaaata 6960
cttagtattt gaagcaaaca ctggaactga agatggctac caaggcgaag aatctttatt 7020
taacaaagca tactatggca aaagcacatc attcttccgt caagaaagtc aaaaacttct 7080
gcaaagcgat aaaaaacgca cggctgagtt agcaaacggc gctctcggta tgattgagct 7140
aaacgatgat tacacactga aaaaagtgat gaaaccgctg attgcatcta acacagtaac 7200
agatgaaatt gaacgcgcga acgtctttaa aatgaacggc aaatggtatc tgttcactga 7260
ctcccgcgga tcaaaaatga cgattgacgg cattacgtct aacgatattt acatgcttgg 7320
ttatgtttct aattctttaa ctggcccata caagccgctg aacaaaactg gccttgtgtt 7380
aaaaatggat cttgatccta acgatgtaac ctttacttac tcacacttcg ctgtacctca 7440
agcgaaagga aacaatgtcg tgattacaag ctatatgaca aacagaggat tctacgcaga 7500
caaacaatca acgtttgcgc ctagcttcct gctgaacatc aaaggcaaga aaacatctgt 7560
tgtcaaagac agcatccttg aacaaggaca attaacagtt aacaaataac caggagctat 7620
ttaatggcaa cagttaacca gctggtacgc aaaccacgtg ctcgcaaagt tgcgaaaagc 7680
aacgtgcctg cgctggaagc atgcccgcaa aaacgtggcg tatgtactcg tgtatatact 7740
accactccta aaaaaccgaa ctccgcgctg cgtaaagtat gccgtgttcg tctgactaac 7800
ggtttcgaag tgacttccta catcggtggt gaaggtcaca acctgcagga gcactccgtg 7860
atcctgatcc gtggcggtcg tgttaaagac ctcccgggtg ttcgttacca caccgtacgt 7920
ggtgcgcttg actgctccgg cgttaaagac cgtaagcagg ctcgttccaa gtatggcgtg 7980
aagcgtccta aggcttaatg gttctccgtt aagtaaggcc aaatagagga tctgaagatc 8040
agcagttcaa cctgttgata gtacgtacta agctctcatg tttcacgtac taagctctca 8100
tgtttaacgt actaagctct catgtttaac gaactaaacc ctcatggcta acgtactaag 8160
ctctcatggc taacgtacta agctctcatg tttcacgtac taagctctca tgtttgaaca 8220
ataaaattaa tataaatcag caacttaaat agcctctaag gttttaagtt ttataagaaa 8280
aaaaagaata tataaggctt ttaaagcttt taaggtttaa cggttgtgga caacaagcca 8340
gggatgtaac gcactgagaa gcccttagag cctctcaaag caattttcag tgacacagga 8400
acacttaacg gctgacagac gctgccgcaa gcactcaggg cgcaagggct gctaaaggaa 8460
gcggaacacg tagaaagcca gtccgcagaa acggtgctga ccccggatga atgtcagcta 8520
ctgggctatc tggacaaggg aaaacgcaag cgcaaagaga aagcaggtag cttgcagtgg 8580
gcttacatgg cgatagctag actgggcggt tttatggaca gcaagcgaac cggaattgcc 8640
agctggggcg ccctctggta aggttgggaa gccctgcaaa gtaaactgga tggctttctt 8700
gccgccaagg atctgatggc gcaggggatc aagatctgat caagagacag gatgaggatc 8760
gtttcgcatg attgaacaag atggattgca cgcaggttct ccggccgctt gggtggagag 8820
gctattcggc tatgactggg cacaacagac aatcggctgc tctgatgccg ccgtgttccg 8880
gctgtcagcg caggggcgcc cggttctttt tgtcaagacc gacctgtccg gtgccctgaa 8940
tgaactccaa gacgaggcag cgcggctatc gtggctggcc acgacgggcg ttccttgcgc 9000
agctgtgctc gacgttgtca ctgaagcggg aagggactgg ctgctattgg gcgaagtgcc 9060
ggggcaggat ctcctgtcat ctcaccttgc tcctgccgag aaagtatcca tcatggctga 9120
tgcaatgcgg cggctgcata cgcttgatcc ggctacctgc ccattcgacc accaagcgaa 9180
acatcgcatc gagcgagcac gtactcggat ggaagccggt cttgtcgatc aggatgatct 9240
ggacgaagag catcaggggc tcgcgccagc cgaactgttc gccaggctca aggcgcggat 9300
gcccgacggc gaggatctcg tcgtgaccca tggcgatgcc tgcttgccga atatcatggt 9360
ggaaaatggc cgcttttctg gattcatcga ctgtggccgg ctgggtgtgg cggaccgcta 9420
tcaggacata gcgttggcta cccgtgatat tgctgaagag cttggcggcg aatgggctga 9480
ccgcttcctc gtgctttacg gtatcgccgc tcccgattcg cagcgcatcg ccttctatcg 9540
ccttcttgac gagttcttct gaattccgga tccgaagagg cccgcaccga tcgcccttcc 9600
caacagttgc gcagcctgaa tggcgaatgg cgcctgatgc ggtattttct ccttacgcat 9660

```
ctgtgcggta tttcacaccg catagggtaa taactgatat aattaaattg aagctctaat   9720
ttgtgagttt agtatacatg catttactta taatacagtt ttttagtttt gctggccgca   9780
tcttctcaaa tatgcttccc agcctgcttt tctgtaacgt tcaccctcta ccttagcatc   9840
ccttcccttt gcaaatagtc ctcttccaac aataataatg tcagatcctg tagagaccac   9900
atcatccacg gttctatact gttgacccaa tgcgtctccc ttgtcatcta aacccacacc   9960
gggtgtcata atcaaccaat cgtaaccttc atctcttcca cccatgtctc tttgagcaat  10020
aaagccgata acaaaatctt tgtcgctctt cgcaatgtca acagtaccct tagtatattc  10080
tccagtagat agggagccct tgcatgacaa ttctgctaac atcaaaaggc ctctaggttc  10140
ctttgttact tcttctgccg cctgcttcaa accgctaaca atacctgggc ccaccacacc  10200
gtgtgcattc gtaatgtctg cccattctgc tattctgtat acacccgcag agtactgcaa  10260
tttgactgta ttaccaatgt cagcaaattt tctgtcttcg aagagtaaaa aattgtactt  10320
ggcggataat gcctttagcg gcttaactgt gccctccatg gaaaaatcag tcaagatatc  10380
cacatgtgtt tttagtaaac aaattttggg acctaatgct tcaactaact ccagtaattc  10440
cttggtggta cgaacatcca atgaagcaca caagtttgtt tgcttttcgt gcatgatatt  10500
aaatagcttg gcagcaacag gactaggatg agtagcagca cgttccttat atgtagcttt  10560
cgacatgatt tatcttcgtt tcggtttttg ttctgtgcag ttgggttaag aatactgggc  10620
aatttcatgt ttcttcaaca ctacatatgc gtatatatac caatctaagt ctgtgctcct  10680
tccttcgttc ttccttctgt tcggagatta ccgaatcaaa aaaatttcaa agaaaccgaa  10740
atcaaaaaaa agaataaaaa aaaaatgatg aattgaaaag ctcttgttac ccatcattga  10800
attttgaaca tccgaacctg ggagttttcc ctgaaacaga tagtatattt gaacctgtat  10860
aataatatat agtctagcgc tttacggaag acaatgtatg tatttcggtt cctggagaaa  10920
ctattgcatc tattgcatag gtaatcttgc acgtcgcatc cccggttcat tttctgcgtt  10980
tccatcttgc acttcaatag catatctttg ttaacgaagc atctgtgctt cattttgtag  11040
aacaaaaatg caacgcgaga gcgctaattt ttcaaacaaa gaatctgagc tgcattttta  11100
cagaacagaa atgcaacgcg aaagcgctat tttaccaacg aagaatctgt gcttcatttt  11160
tgtaaaacaa aaatgcaacg cgagagcgct aatttttcaa acaaagaatc tgagctgcat  11220
ttttacagaa cagaaatgca acgcgagagc gctattttac caacaaagaa tctatacttc  11280
tttttgttc tacaaaaatg catcccgaga gcgctatttt tctaacaaag catcttagat  11340
tactttttt ctcctttgtg cgctctataa tgcagtctct tgataacttt ttgcactgta  11400
ggtccgttaa ggttagaaga aggctacttt ggtgtctatt ttctcttcca taaaaaaagc  11460
ctgactccac ttcccgcgtt tactgattac tagcgaagct gcgggtgcat tttttcaaga  11520
taaaggcatc cccgattata ttctataccg atgtggattg cgcatacttt gtgaacagaa  11580
agtgatagcg ttgatgattc ttcattggtc agaaaattat gaacggtttc ttctattttg  11640
tctctatata ctacgtatag gaaatgttta cattttcgta ttgttttcga ttcactctat  11700
gaatagttct tactacaatt tttttgtcta aagagtaata ctagagataa acataaaaaa  11760
tgtagaggtc gagtttagat gcaagttcaa ggagcgaaag gtggatgggt aggttatata  11820
gggatatagc acagagatat atagcaaaga gatacttttg agcaatgttt gtggaagcgg  11880
tattcgcaat attttagtag ctcgttacag tccggtgcgt ttttggtttt ttgaaagtgc  11940
gtcttcagag cgcttttggt tttcaaaagc gctctgaagt tcctatactt tctagctaga  12000
```

gaataggaac ttcggaatag gaacttcaaa gcgtttccga aaacgagcgc ttccgaaaat 12060
gcaacgcgag ctgcgcacat acagctcact gttcacgtcg cacctatatc tgcgtgttgc 12120
ctgtatatat atatacatga gaagaacggc atagtgcgtg tttatgctta aatgcgttat 12180
ggtgcactct cagtacaatc tgctctgatg ccgcatagtt aagccagccc cgacacccgc 12240
caacacccgc tgacgcgccc tgacgggctt gtctgctccc ggcatccgct tacagacaag 12300
ctgtgaccg 12309

<210> SEQ ID NO 286
<211> LENGTH: 8500
<212> TYPE: DNA
<213> ORGANISM: Artificial
<220> FEATURE:
<223> OTHER INFORMATION: pMU2898

<400> SEQUENCE: 286
caggggggcg gagcctatgg aaaaacgcca gcaacgcggc ctttttacgg ttcctggcct 60
tttgctggcc ttttgtgagc cgtttatttt ttctacccat atccttgaag cggtgttata 120
atgccgcgcc ctcgatatgg ggatttttaa cgacctgatt ttcgggtctc agtagtagtt 180
gacattagcg gagcactaaa atgtcacaaa ttgaaaagat acaaaattta aaaaacatga 240
aaaaaactat agctaaaggc ggcggagaag agaaaatagc aaaaagacac gcagatggaa 300
agctttctgc cagagaaaga atccatttgt tgtttgatga aaacagtttt gttgaggtag 360
atgcattcat agaatccaga tgctttgact ttggtatgca gaagaagaaa cttccaggtg 420
acggggttgt taccggttac ggaacagtta atggcagaaa ggtctttgtt tcatcacagg 480
actttactgt tataggcggt tcattgggag agatgcacgc aaagaaaatt acaaaggtta 540
tggatatggc tctgaaaatg ggagcaccgt tcatagccat taatgattcc ggcggagctc 600
gtattgagga aggtctggat gctctttcag gttacggaga tatttttac aggaatactc 660 ttgcatcagg cgttattccg cagatatcag taataatggg gccatgtgca ggtggtgcgg 720
tatattcccc ggccataact gattttatat tcatggtgga aaaaacaagt cagatgttta 780
ttacaggccc acaggtaata aagtctgtta cgggtgaaga tgtatcagtt gaaaatctgg 840
gaggtgcaga tgttcatact gctacaagcg gtgtagcaca tttcaaatct tcaagcgaag 900
aagagtgtat agaagatata aagaggcttt taagttttat tcccgataat aatgtatcag 960
atactatgta ctacggagtg tctgatgctg ccgacagatt agccgaaagc ctcaacagca 1020
ttattccaga agagtcaaac aagccatatg acatgtttga cgtaatagca gaagtagtag 1080
atgatggaga tttctttgaa gttcagagtt atttctctca gaatataata atcggatttg 1140
caagaatgaa tggcagaagt gttggtattg ttgcaaacca gcctaagata atggcagggt 1200
cactagatat gaacgcggct gataaggcgg cacgtttcgt tcgtttctgt gatgcattta 1260
atattcctgt cgtttcatta accgatgtac ctgcattcct gcccggggta gcccaggagc 1320
ataacggcat aatacgtcac ggtgcaaaac tcctatatgc tttctctgaa gcaacagtac 1380
caaagataaa tgttattctt agaaaggcat atggaggagc atatattgct atgaacagta 1440
aaacaatagg tgccgatatg gttttggcat ggccatcagc tgaaattgca gttatgggac 1500
ctgacggagc agcaaatatt atatttaaaa aggatattgc tgcgtcggaa gatccagcag 1560
aaaccagaaa ggaaaagatt gcggaatata gagataaatt ctcaaatcct tatgtagcag 1620
catcaagagg gtatattgat gatgttatcg agccttctga aaccagagta aaaattataa 1680
ctgctctgga aatgctggat acaaagaggg aaaacaggcc ttcaaaaaaa catggaaaca 1740

```
ttccgctata atatagtata ggaaacaaaa tatctggagg atgagtgtaa tgagtaaata   1800
tataataaag gtaaacggaa ctccttatga agtagaggtt gaagaagtgg gcgggggaag   1860
gcccatttca gctgctccaa agctaagagc taccaagccg ggacatacct ctgctgcaaa   1920
agcagcacag ccgcaggcag gtaaagcagg tgatgttgct gctccaatgc cgggaactgt   1980
tttaaaggta aaggttgcta tcggtgatga agtaaagaag gggcaggtac ttttaatact   2040
tgaagctatg aaaatggaga atgaaatagt tgctccggct gacggtaaag ttacggcgtt   2100
aaacgtcgag gccggaaagt ctgttactgc tggagaacta atggtgtcta tagcctaaaa   2160
ggctgactta ccgcaaagga gatggaaaaa tgccaggcgt aagaattacg gaaacagttt   2220
taagagatgc tcaccagtcc cttatagcaa ccagaatgaa gaccgaagaa atgcttccaa   2280
ttgttgagaa gcttgacaat attggttacc attcactgga agcttggggc ggagctactt   2340
ttgactcatg tatgagattt ttgaatgaag atccatggat gagacttaga aaaataaaag   2400
atgttgcaaa gaaaacacct ctgcaaatgc ttcttagggg ccagaacctt ttaggataca   2460
aacactatgc cgatgatata gttgagtact ttgttcagaa ggctgttgca aacggcatgg   2520
acattatgag aatattcgat gcactaaatg atgccaggaa tatcgagacg gcaattaagg   2580
catgtaaaaa ggaaggcggc catgctcagg gctgtatttg ctatactata agtcctgttc   2640
acaatcttga gctttttgta aaagatgcaa agcagttgga gagcatggga gcagattcta   2700
tctgtataaa agacatggcc ggacttctgg tgccgtatca ggcttatgaa ctggtaaagg   2760
ctttgaaaga aagtgtaaag ataccgatac aattgcacac tcactatact agcggtgtag   2820
catctatgac gtatttgaag gctatagaag caggtataga tattgttgac tgtgcaattt   2880
cacctatgtc aatgggaacg tcacagccgc ctacagagcc tttggtggca actttaaagg   2940
gaactgattt cgatactgga ctggatttgg aaaaactcag tgaaattgca gactatttca   3000
gacccottaa agaaaaatat attgagagcg gactattaga cgttaaggta atgggtgttg   3060
acgttaacac tcttatttat caggtacctg gtggaatgct ttcaaatctt gtttcacaat   3120
tgaagcagtc aaatgctttg gataaatatg aagaggttct caaggaagtt cccagagtaa   3180
gagccgattt cggctatcct ccgcttgtaa caccatcaag tcagatagtt ggtacccaag   3240
cggtacttaa tgtattgact ggtgagagat acaagatggt accaaaggaa tcaaaaggcg   3300
ttgtaaaggg ggaatacggt aaaacccctg cacctattag tgatgaaata aaagctaaga   3360
ttctgggcga tgaaaagcct ataacatgca gacctgctga ccttattgaa cctgagcttg   3420
aaaagattag agaagctgtt aaggattata tagagcagga tgaagatgta ctttcatacg   3480
caatgcttcc tcaggttgcc gagaagttct ttaaacagcg tattgaggat agaaataagg   3540
ctactgcacc cgcatcagac gaaataaaac ccgaagttgt agcggcaata tcagccgtag   3600
taaacgaaat gggcgaaaga gacggcacac agtacagaat cggaaatatc tctaagttga   3660
accagaatca gaacagatgg agtctgtatg gtatgcttga tagattcaga acaaaaattt   3720
aacggccgta aaacgaaagg ctcagtcgaa agactgggcc tttcgtttta tctgttgttt   3780
gtcggtgaac gctctcctga gtaggacaaa tccgccggga gcggatttga acgttgcgaa   3840
gcaacggccc ggagggtggc gggcaggacg cccgccataa actgccaggc atcaaattaa   3900
gcagaaggcc atcctgacgg atggcctttt tgcgtttcta caaactcttc ctgtcgtcat   3960
atctacaagc catcccccca cagatacggt aaactagcct cgtttttgca tcaggaaagc   4020
agctatgaac cactccttat aattaaattg aagctctaat ttgtgagttt agtatacatg   4080
```

-continued

```
catttactta taatacagtt ttttagtttt gctggccgca tcttctcaaa tatgcttccc   4140
agcctgcttt tctgtaacgt tcaccctcta ccttagcatc ccttcccttt gcaaatagtc   4200
ctcttccaac aataataatg tcagatcctg tagagaccac atcatccacg gttctatact   4260
gttgacccaa tgcgtctccc ttgtcatcta aacccacacc gggtgtcata atcaaccaat   4320
cgtaaccttc atctcttcca cccatgtctc tttgagcaat aaagccgata acaaaatctt   4380
tgtcgctctt cgcaatgtca acagtaccct tagtatattc tccagtagat agggagccct   4440
tgcatgacaa ttctgctaac atcaaaaggc ctctaggttc ctttgttact tcttctgccg   4500
cctgcttcaa accgctaaca atacctgggc ccaccacacc gtgtgcattc gtaatgtctg   4560
cccattctgc tattctgtat acacccgcag agtactgcaa tttgactgta ttaccaatgt   4620
cagcaaattt tctgtcttcg aagagtaaaa aattgtactt ggcggataat gcctttagcg   4680
gcttaactgt gccctccatg gaaaaatcag tcaagatatc cacatgtgtt tttagtaaac   4740
aaattttggg acctaatgct tcaactaact ccagtaattc cttggtggta cgaacatcca   4800
atgaagcaca caagtttgtt tgcttttcgt gcatgatatt aaatagcttg gcagcaacag   4860
gactaggatg agtagcagca cgttccttat atgtagcttt cgacatgatt tatcttcgtt   4920
tcggtttttg ttctgtgcag ttgggttaag aatactgggc aatttcatgt ttcttcaaca   4980
ctacatatgc gtatatatac caatctaagt ctgtgctcct tccttcgttc ttccttctgt   5040
tcggagatta ccgaatcaaa aaaatttcaa agaaaccgaa atcaaaaaaa agaataaaaa   5100
aaaaatgatg aattgaaaag ctcttgttac ccatcattga attttgaaca tccgaacctg   5160
ggagttttcc ctgaaacaga tagtatattt gaacctgtat aataatatat agtctagcgc   5220
tttacggaag acaatgtatg tatttcggtt cctggagaaa ctattgcatc tattgcatag   5280
gtaatcttgc acgtcgcatc cccggttcat tttctgcgtt tccatcttgc acttcaatag   5340
catatctttg ttaacgaagc atctgtgctt cattttgtag aacaaaaatg caacgcgaga   5400
gcgctaattt ttcaaacaaa gaatctgagc tgcattttta cagaacagaa atgcaacgcg   5460
aaagcgctat tttaccaacg aagaatctgt gcttcatttt tgtaaaacaa aaatgcaacg   5520
cgagagcgct aatttttcaa acaaagaatc tgagctgcat tttacagaa cagaaatgca   5580
acgcgagagc gctattttac caacaaagaa tctatacttc ttttttgttc tacaaaaatg   5640
catcccgaga gcgctatttt tctaacaaag catcttagat tacttttttt ctcctttgtg   5700
cgctctataa tgcagtctct tgataacttt ttgcactgta ggtccgttaa ggttagaaga   5760
aggctacttt ggtgtctatt ttctcttcca taaaaaaagc ctgactccac ttcccgcgtt   5820
tactgattac tagcgaagct gcgggtgcat tttttcaaga taaaggcatc cccgattata   5880
ttctataccg atgtggattg cgcatacttt gtgaacagaa agtgatagcg ttgatgattc   5940
ttcattggtc agaaaattat gaacggtttc ttctattttg tctctatata ctacgtatag   6000
gaaatgttta cattttcgta ttgttttcga ttcactctat gaatagttct tactacaatt   6060
tttttgtcta aagagtaata ctagagataa acataaaaaa tgtagaggtc gagtttagat   6120
gcaagttcaa ggagcgaaag gtggatgggt aggttatata gggatatagc acagagatat   6180
atagcaaaga gatacttttg agcaatgttt gtggaagcgg tattcgcaat attttagtag   6240
ctcgttacag tccggtgcgt ttttggtttt ttgaaagtgc gtcttcagag cgcttttggt   6300
tttcaaaagc gctctgaagt tcctatactt tctagctaga gaataggaac ttcggaatag   6360
gaacttcaaa gcgtttccga aaacgagcgc ttccgaaaat gcaacgcgag ctgcgcacat   6420
acagctcact gttcacgtcg cacctatatc tgcgtgttgc ctgtatatat atatacatga   6480
```

gaagaacggc atagtgcgtg tttatgctta aatgcgttat ggtgcactct cagtacaatc 6540
tgctctgatg ccgcatagtt aagccagccc cgacacccgc caacacccgc tgacgcgccc 6600
tgacgggctt gtctgctccc ggcatccgct tacagacaag ctgtgaccgt ctccgggagc 6660
tgcatgtgtc agaggttttc accgtcatca ccgaaacgcg cgagacgaaa gggcctcgtg 6720
atacgcctat ttttataggt taatgtcatg ataataatgg tttcttagac gtcaggtggc 6780
acttttcggg gaaatgtgcg cggaacccct atttgtttat ttttctaaat acattcaaat 6840
atgtatccgc tcatgagaca ataaccctga taaatgcttc aataatattg aaaaaggaag 6900
agtatgagta ttcaacattt ccgtgtcgcc cttattccct tttttgcggc attttgcctt 6960
cctgtttttg ctcacccaga aacgctggtg aaagtaaaag atgctgaaga tcagttgggt 7020
gcacgagtgg gttacatcga actggatctc aacagcggta agatccttga gagttttcgc 7080
cccgaagaac gttttccaat gatgagcact tttaaagttc tgctatgtgg cgcggtatta 7140
tcccgtattg acgccgggca agagcaactc ggtcgccgca tacactattc tcagaatgac 7200
ttggttgagt actcaccagt cacagaaaag catcttacgg atggcatgac agtaagagaa 7260
ttatgcagtg ctgccataac catgagtgat aacactgcgg ccaacttact tctgacaacg 7320
atcggaggac cgaaggagct aaccgctttt ttgcacaaca tgggggatca tgtaactcgc 7380
cttgatcgtt gggaaccgga gctgaatgaa gccataccaa acgacgagcg tgacaccacg 7440
atgcctgtag caatggcaac aacgttgcgc aaactattaa ctggcgaact acttactcta 7500
gcttcccggc aacaattaat agactggatg gaggcggata aagttgcagg accacttctg 7560
cgctcggccc ttccggctgg ctggtttatt gctgataaat ctggagccgg tgagcgtggg 7620
tctcgcggta tcattgcagc actggggcca gatggtaagc cctcccgtat cgtagttatc 7680
tacacgacgg ggagtcaggc aactatggat gaacgaaata gacagatcgc tgagataggt 7740
gcctcactga ttaagcattg gtaactgtca gaccaagttt actcatatat actttagatt 7800
gatttaaaac ttcattttta atttaaaagg atctaggtga agatcctttt tgataatctc 7860
atgaccaaaa tcccttaacg tgagttttcg ttccactgag cgtcagaccc cgtagaaaag 7920
atcaaaggat cttcttgaga tccttttttt ctgcgcgtaa tctgctgctt gcaaacaaaa 7980
aaaccaccgc taccagcggt ggtttgtttg ccggatcaag agctaccaac tctttttccg 8040
aaggtaactg gcttcagcag agcgcagata ccaaatactg tccttctagt gtagccgtag 8100
ttaggccacc acttcaagaa ctctgtagca ccgcctacat acctcgctct gctaatcctg 8160
ttaccagtgg ctgctgccag tggcgataag tcgtgtctta ccgggttgga ctcaagacga 8220
tagttaccgg ataaggcgca gcggtcgggc tgaacggggg gttcgtgcac acagcccagc 8280
ttggagcgaa cgacctacac cgaactgaga tacctacagc gtgagcattg agaaagcgcc 8340
acgcttcccg aagggagaaa ggcggacagg tatccggtaa gcggcagggt cggaacagga 8400
gagcgcacga gggagcttcc agggggaaac gcctggtatc tttatagtcc tgtcgggttt 8460
cgccacctct gacttgagcg tcgatttttg tgatgctcgt 8500

<210> SEQ ID NO 287
<211> LENGTH: 8563
<212> TYPE: DNA
<213> ORGANISM: Artificial
<220> FEATURE:
<223> OTHER INFORMATION: pMU2899

<400> SEQUENCE: 287

-continued

```
ttgagcgtcg atttttgtga tgctcgtcag gggggcggag cctatggaaa aacgccagca     60
acgcggcctt tttacggttc ctggcctttt gctggccttt tgtgagccgt ttattttttc    120
tacccatatc cttgaagcgg tgttataatg ccgcgccctc gatatgggga tttttaacga    180
cctgattttc gggtctcagt agtagttgac attagcggag cactaaaatg acaaacaagc    240
tcagagagct caagcaaaag agagaaagaa tactaaagct tggtggagaa gataaaataa    300
aaaaacagca tgatagcaaa aaacttactt gtagagagag aatagaatat ttacttgacc    360
ctggaagctt caatgaaata gatatgtttg ttgaacacag atgtcaagaa tttgatatga    420
aagatacatt tgtcccctgt gatggtgttg taacgggtta tggaacaatc aatggcagaa    480
aagtttttgt ttatgctcaa gattttactt cgataggcgg ttctcttggc gagatgcatg    540
caaaaaagat ttgtaaagtt ttggacttag cattaaaata tggttgtcca gtgataggta    600
taaatgattc tggtggtgca agaattcaag aaggtgttga tgcattagca ggatatggtg    660
aaatcttcta tagaaatacc atggcatcag gtgtaattcc acaaattgca gctataatgg    720
gaccttgtgc aggtggagct gtatactctc ctgctattat ggattttatt tttatggtgg    780
acaaaaccag ccaaatgttt gttacaggac ctcaggttat aaaagctgtg actggagagg    840
agatatcctt tgaagagctt ggtggcgctt acactcacag ctcaaagagt ggagttgctc    900
attttattgc agaggatgag tatcacctac ttgatatgat aaagtattta ttgtcgttta    960
taccttcaaa taacatggaa gacccacctt ttataatgtc atctgattca gaaaaaagat   1020
ttgttcccga gctcgaaaat ataattccgc aagagccaaa caaagcttat gatgtaaaag   1080
aaataattta taaagtagta gacaaccaag aatttttaga agtacaacct tattttgctc   1140
aaaatgctgt tgtaggattt ggtagaatag gggctttag cgtaggaatt gtagcaaatc    1200
agcccaaagt gaacgctgga gtgcttgatt atgattcgtc tgacaagata gcacgatttg   1260
taagattttg tgatgctttt aatattccca taataacatt tacagacgtg cctggatttt   1320
tgccaggtgt taaccaagag cacaatggaa taattcgtca tggggctaag gttttgtatg   1380
catactcaga ggcaacagtt ccaaagataa atgtaatttt gagaaaagca tatggtgggg   1440
cttacattgc aatgagcagc aaacacattg gtgcagactt tgtgtttgca tggccaactg   1500
ccgagatagc tgttatggga ccagatggcg cagcaaatat tatatttaga aaagagatac   1560
aaagcgctca aaatcccgaa gaggaaagaa aaagaaggat agaagagtat actcaaaagt   1620
ttgcaaatcc atacattgca gctgcccgtg ggtatgttga cgatgtgatt gagccacagc   1680
ttacccgtaa caaaatcatt gaggcgctca aaatttccat tacaaaaaga gagcaaaggc   1740
ccccaaaaaa gcatggcaat attccattat aaaatgtatt tttgtaaaaa aaggagagtg   1800
ttttaaaaat gtatgctcag gtcagtacta tttcaaccat tacaaaagaa gaacttgctt   1860
gtatttgtgc atgtctgcac attgtgatgg gtgaaggtca atataaaatt accaacataa   1920
ctaaacagca aaacaagtgg gtcaaaggtg caagagaaat gatgctcaat cagtcacaga   1980
tgttttatag atggaggtaa agcttgtgat gagaaagttc aaggtgaaga tcaatagcca   2040
agaatttgtt gtagaagtgg aagaaatagg agttgaaaat gctacttctg tcgtgccaag   2100
gcctaagatt ggccattttg agccaaaaca ggaaaaacat gaggataaaa caaaacaaag   2160
ccctgtactt tcttctgata aaaattcggt tgttgcccag cttccgggta ctattgtaag   2220
gctgctaaaa agtgaaggtg atgttgttga tgcaaatgaa cctgttttaa ttcttgaagc   2280
catgaaaatg gaaaatgaaa taactgcacc tgtcaaagga aaaattaaaa gaatacatgt   2340
aaaggaaggg cagaaggtag caaaaggaga tttgctattt gaaatagagt aagaaaaatt   2400
```

ttctggaggt tttaaaaata atgggggtaa aaataacaga aacaatactc agagatgctc 2460
atcagtcact cattgcaacc cgcatgacaa ctgaacagat gcttgagatt gctcctgtgc 2520
ttgaccaagt tggttattat tcggttgagt gctggggcgg tgctacattt gatgcgtgtc 2580
tgaggttttt caatgaagac ccatgggaaa gattaaaaag actgagaact gcttttaaaa 2640
agacaaagct ccagatgctt cttcgaggac aaaatcttgt tgggtataga cattattctg 2700
atgatgttgt tgaagagttt gtaaaaaagg ccatatacta tggcattgat attataagaa 2760
tatttgatgc acttaatgac atccggaata ttgaaatggc tctaaaaata acaaaaaaag 2820
aaaaaggaca tgcccaggtt gccatatcat acactgtctc accttatcat actattgaaa 2880
actatgtaaa tttggcaaaa caaatagaag aacttggggc agactcaatt tgtataaaag 2940
acatggctgg gcttctctct ccatttgatg cttataaact tgtaaaagcg ttaaaagagc 3000
aggtaaaact tcctattcat cttcatacac actacaccac aggatttgga tcaatgacat 3060
atttgaaagc tgtcgaagca ggtgtggatg gtattgacac ggctttatct ccgcttgcac 3120
tgggcacatc ccagcctcca accgaaacaa ttgtatatgc acttgaaaat acagaatatg 3180
ctccaaaact tgatttagaa aagatcaacg aggcaagcga atattttaaa gtactcagag 3240
aagaatatat aagaaaaggg cttcttgacc cgaaagtatt aagtgttgat ataaacgctc 3300
ttcattatca aatacctggt ggaatgctat caaatcttat ttctcagcta aaagaacaag 3360
ggcaggaaga caagttagat gaggttttaa aagaggtacc tgaggttcga aaagattttg 3420
gatatccgcc acttgtaact cctacgagtc aaattgtggg aacacaagct gttttgaatg 3480
ttatagcagg tgagagatac aaacttgtca caaaagaaac aaaagcatat tttaaaggtg 3540
agtatgggaa acctccagct cctgtgaatg aagaggtaaa aagaaaaatc ttgaaagacg 3600
aaaaagagat aacctgcaga cctgcagatt tgattttgcc agagcttgaa aatgcaaaag 3660
aaaagattaa ggagtatatt gaaaatgata ctgatgtggt aacttactgt ttattccctc 3720
aacttgcaga aaattttttc aaattaaggt tcgcaaaaaa atacaaggtt gacgctgatc 3780
ttgttcaggg taacaaagtg tatcctgtgt aacggccgta aaacgaaagg ctcagtcgaa 3840
agactgggcc tttcgtttta tctgttgttt gtcggtgaac gctctcctga gtaggacaaa 3900
tccgccggga gcggatttga acgttgcgaa gcaacggccc ggagggtggc gggcaggacg 3960
cccgccataa actgccaggc atcaaattaa gcagaaggcc atcctgacgg atggcctttt 4020
tgcgtttcta caaactcttc ctgtcgtcat atctacaagc catcccccca cagatacggt 4080
aaactagcct cgtttttgca tcaggaaagc agctatgaac cactccttat aattaaattg 4140
aagctctaat ttgtgagttt agtatacatg catttactta taatacagtt ttttagtttt 4200
gctggccgca tcttctcaaa tatgcttccc agcctgcttt tctgtaacgt tcaccctcta 4260
ccttagcatc ccttcccttt gcaaatagtc ctcttccaac aataataatg tcagatcctg 4320
tagagaccac atcatccacg gttctatact gttgacccaa tgcgtctccc ttgtcatcta 4380
aacccacacc gggtgtcata atcaaccaat cgtaaccttc atctcttcca cccatgtctc 4440
tttgagcaat aaagccgata acaaaatctt tgtcgctctt cgcaatgtca acagtaccct 4500
tagtatattc tccagtagat agggagccct tgcatgacaa ttctgctaac atcaaaaggc 4560
ctctaggttc ctttgttact tcttctgccg cctgcttcaa accgctaaca atacctgggc 4620
ccaccacacc gtgtgcattc gtaatgtctg cccattctgc tattctgtat acacccgcag 4680
agtactgcaa tttgactgta ttaccaatgt cagcaaattt tctgtcttcg aagagtaaaa 4740

-continued

```
aattgtactt ggcggataat gcctttagcg gcttaactgt gccctccatg gaaaaatcag   4800
tcaagatatc cacatgtgtt tttagtaaac aaattttggg acctaatgct tcaactaact   4860
ccagtaattc cttggtggta cgaacatcca atgaagcaca caagtttgtt tgcttttcgt   4920
gcatgatatt aaatagcttg gcagcaacag gactaggatg agtagcagca cgttccttat   4980
atgtagcttt cgacatgatt tatcttcgtt tcggtttttg ttctgtgcag ttgggttaag   5040
aatactgggc aatttcatgt ttcttcaaca ctacatatgc gtatatatac caatctaagt   5100
ctgtgctcct tccttcgttc ttccttctgt tcggagatta ccgaatcaaa aaaatttcaa   5160
agaaaccgaa atcaaaaaaa agaataaaaa aaaaatgatg aattgaaaag ctcttgttac   5220
ccatcattga attttgaaca tccgaacctg ggagttttcc ctgaaacaga tagtatattt   5280
gaacctgtat aataatatat agtctagcgc tttacggaag acaatgtatg tatttcggtt   5340
cctggagaaa ctattgcatc tattgcatag gtaatcttgc acgtcgcatc cccggttcat   5400
tttctgcgtt tccatcttgc acttcaatag catatctttg ttaacgaagc atctgtgctt   5460
cattttgtag aacaaaaatg caacgcgaga gcgctaattt ttcaaacaaa gaatctgagc   5520
tgcattttta cagaacagaa atgcaacgcg aaagcgctat tttaccaacg aagaatctgt   5580
gcttcatttt tgtaaaacaa aaatgcaacg cgagagcgct aatttttcaa acaaagaatc   5640
tgagctgcat ttttacagaa cagaaatgca acgcgagagc gctattttac caacaaagaa   5700
tctatacttc tttttgttc tacaaaaatg catcccgaga gcgctatttt tctaacaaag   5760
catcttagat tacttttttt ctcctttgtg cgctctataa tgcagtctct tgataacttt   5820
ttgcactgta ggtccgttaa ggttagaaga aggctacttt ggtgtctatt ttctcttcca   5880
taaaaaaagc ctgactccac ttcccgcgtt tactgattac tagcgaagct gcgggtgcat   5940
tttttcaaga taaaggcatc cccgattata ttctataccg atgtggattg cgcatacttt   6000
gtgaacagaa agtgatagcg ttgatgattc ttcattggtc agaaaattat gaacggtttc   6060
ttctattttg tctctatata ctacgtatag gaaatgttta cattttcgta ttgttttcga   6120
ttcactctat gaatagttct tactacaatt tttttgtcta aagagtaata ctagagataa   6180
acataaaaaa tgtagaggtc gagtttagat gcaagttcaa ggagcgaaag gtggatgggt   6240
aggttatata gggatatagc acagagatat atagcaaaga gatacttttg agcaatgttt   6300
gtggaagcgg tattcgcaat attttagtag ctcgttacag tccggtgcgt ttttggtttt   6360
ttgaaagtgc gtcttcagag cgcttttggt tttcaaaagc gctctgaagt tcctatactt   6420
tctagctaga gaataggaac ttcggaatag gaacttcaaa gcgtttccga aaacgagcgc   6480
ttccgaaaat gcaacgcgag ctgcgcacat acagctcact gttcacgtcg cacctatatc   6540
tgcgtgttgc ctgtatatat atatacatga gaagaacggc atagtgcgtg tttatgctta   6600
aatgcgttat ggtgcactct cagtacaatc tgctctgatg ccgcatagtt aagccagccc   6660
cgacacccgc caacacccgc tgacgcgccc tgacgggctt gtctgctccc ggcatccgct   6720
tacagacaag ctgtgaccgt ctccgggagc tgcatgtgtc agaggttttc accgtcatca   6780
ccgaaacgcg cgagacgaaa gggcctcgtg atacgcctat ttttataggt taatgtcatg   6840
ataataatgg tttcttagac gtcaggtggc acttttcggg gaaatgtgcg cggaacccct   6900
atttgtttat ttttctaaat acattcaaat atgtatccgc tcatgagaca ataaccctga   6960
taaatgcttc aataatattg aaaaaggaag agtatgagta ttcaacattt ccgtgtcgcc   7020
cttattccct tttttgcggc attttgcctt cctgtttttg ctcacccaga aacgctggtg   7080
aaagtaaaag atgctgaaga tcagttgggt gcacgagtgg gttacatcga actggatctc   7140
```

```
aacagcggta agatccttga gagttttcgc cccgaagaac gttttccaat gatgagcact   7200
tttaaagttc tgctatgtgg cgcggtatta tcccgtattg acgccgggca agagcaactc   7260
ggtcgccgca tacactattc tcagaatgac ttggttgagt actcaccagt cacagaaaag   7320
catcttacgg atggcatgac agtaagagaa ttatgcagtg ctgccataac catgagtgat   7380
aacactgcgg ccaacttact tctgacaacg atcggaggac cgaaggagct aaccgctttt   7440
ttgcacaaca tgggggatca tgtaactcgc cttgatcgtt gggaaccgga gctgaatgaa   7500
gccataccaa acgacgagcg tgacaccacg atgcctgtag caatggcaac aacgttgcgc   7560
aaactattaa ctggcgaact acttactcta gcttcccggc aacaattaat agactggatg   7620
gaggcggata aagttgcagg accacttctg cgctcggccc ttccggctgg ctggtttatt   7680
gctgataaat ctggagccgg tgagcgtggg tctcgcggta tcattgcagc actggggcca   7740
gatggtaagc cctcccgtat cgtagttatc tacacgacgg ggagtcaggc aactatggat   7800
gaacgaaata gacagatcgc tgagataggt gcctcactga ttaagcattg gtaactgtca   7860
gaccaagttt actcatatat actttagatt gatttaaaac ttcattttta atttaaaagg   7920
atctaggtga agatcctttt tgataatctc atgaccaaaa tcccttaacg tgagttttcg   7980
ttccactgag cgtcagaccc cgtagaaaag atcaaaggat cttcttgaga tccttttttt   8040
ctgcgcgtaa tctgctgctt gcaaacaaaa aaaccaccgc taccagcggt ggtttgtttg   8100
ccggatcaag agctaccaac tctttttccg aaggtaactg gcttcagcag agcgcagata   8160
ccaaatactg tccttctagt gtagccgtag ttaggccacc acttcaagaa ctctgtagca   8220
ccgcctacat acctcgctct gctaatcctg ttaccagtgg ctgctgccag tggcgataag   8280
tcgtgtctta ccgggttgga ctcaagacga tagttaccgg ataaggcgca gcggtcgggc   8340
tgaacggggg gttcgtgcac acagcccagc ttggagcgaa cgacctacac cgaactgaga   8400
tacctacagc gtgagcattg agaaagcgcc acgcttcccg aagggagaaa ggcggacagg   8460
tatccggtaa gcggcagggt cggaacagga gagcgcacga gggagcttcc agggggaaac   8520
gcctggtatc tttatagtcc tgtcgggttt cgccacctct gac                      8563
```

<210> SEQ ID NO 288
<211> LENGTH: 8652
<212> TYPE: DNA
<213> ORGANISM: Artificial
<220> FEATURE:
<223> OTHER INFORMATION: pMU2900

<400> SEQUENCE: 288

```
tttgtgatgc tcgtcagggg ggcggagcct atggaaaaac gccagcaacg cggccttttt     60
acggttcctg gccttttgct ggccttttgt gagccgttta ttttttctac ccatatcctt    120
gaagcggtgt tataatgccg cgccctcgat atggggattt ttaacgacct gattttcggg    180
tctcagtagt agttgacatt agcggagcac taaaatgtca atagatgata ggattgaaga    240
ccttcttaga agaagagaga tggttttaga aggcggtggt ttagataaag tagagaaaca    300
acaccaaaag ggaaagctta ccgcaagaga gaggatatac aagcttttag atgaagatag    360
ctttgtggaa atagatgcgt atgttgagca caggtgtatt gactttggca tggaaaagca    420
aaggatacct ggcgaaggcg tagtgacagg gtatgggacg atagatggaa ggcttgtcta    480
cgtttatgca caggatttta cggttttagg aggatcatta ggcgagtatc atgcaaagaa    540
aatcacaaaa atcatggata tggctttaaa gatgggagca ccgctcattg gattaaatga    600
```

-continued

```
ttccggaggt gccagaatac aggaaggcgt cgatgcttta tcgggatatg gcaacatatt    660
tttcagaaac acgctggcat caggcgtaat accgcaaata tcggtgataa tggggcccag    720
cgctggaggt gcagtttatt cgcctgctct tactgacttt atattcatgg tagacaagac    780
aagtcagatg tttataactg gaccgcaggt cataaaagcc gtcacaggtg aagatgtttc    840
ggcagaggag cttggtggat cgattactca cagcacgaaa agcggtgtgg cgcattttag    900
ggctgaaaac gacgaagagt gtttgaagat ggtgaggaag ctattaagtt accttccatc    960
aaacaatttg gaagatccgc cacagttggc gacagatgac gacataaaca gattttccga   1020
taggcttatt gagataatcc cagatagtcc taataagcca tacgatatga aagaagtaat   1080
ttcggaaata gtggatgaag gcgtgtattt tgaatcacag gcaatgtatg cgcaaaacat   1140
aataacggca tttgcaaggc ttaatggaag gacggtaggg ataatagcaa atcagcctaa   1200
agttttggct ggatgtctcg acatcaatgc gtctgataag gcatcgaggt ttataaggtt   1260
ttgcgatgca tttaacatcc cgcttctcaa tatagtagat gttccaggat tttgcctgg   1320
aacgaatcaa gagtacggtg gaataatacg ccatggggca aagatgttgt acgcttactc   1380
tgaggctaca gtgccaaaag tgactctcat tgtgaggaaa gcttatggcg gtgcttacct   1440
tgccatgtgc agcaaagact taggagctga ttttgttttg gcatggccta ctgctgaaat   1500
agcggtcatg ggacctgatg gggcagcaaa catcgtgttt aaaaatgaaa taaaatcgtc   1560
tgatgatcct gtggctgcaa gaaatgaaaa gataaatgag tacagggaga atttcgcaaa   1620
tccatacagg gcagcagcga gaggatatgt agatgatgta gttctgccgc aagagacgag   1680
acctcgcctc atctcggcgt tcgatatgct tatgagcaaa agggagtcaa ggcccagcaa   1740
aaagcatggc aatttcctg tttaaaatcg atttaagggg aagtgaaaga atggaagaga   1800
taaatgaaga aatagttgct gtcattgaag ctgcgattta cgcggcattt ggtcagtacg   1860
aaaagaattt ccgcatcaag gtaataaaga gagtggactc aaatatgccg gaatggagaa   1920
aagctggcct ttacaatcag atgagataga tgaggaggat ggaaatgaaa aaatttatag   1980
taactgtcaa tggaaaaaaa tacgatgtgg aagtagaaga agtaaaagtc gacgtggcaa   2040
gtgagaaaaa agcaaaagaa gatactgctg ctaaaaatgc gtcagatgca agtgtaaaaa   2100
gcaaacaggt tgaagtaaaa aacgaagtca aagacggttt ctcaatcaat gcaccgatgc   2160
cgggaactat attggatgtc aaaataagcc aaggccagac tgtcagacga ggcgatgtgc   2220
ttttaatact ggaagccatg aagatggaaa atgaaatcac gtcaccttac gatggcacaa   2280
taatatccat aaatgtttca aaaggtgcct ctgtaaatac aggcgatgtg cttttgtact   2340
taaaatgaga gtaaaggagg agttttaatg tctaagataa aaataacgga gactgtttta   2400
agagatgcac atcaatcgtt gctggcaacc agaatgacaa ccgatgaaat gcttcctata   2460
gcagaaaaat tagatgaagt tggtttttttc tcgctggaag catggggcgg tgctacattt   2520
gatgcatgta tgagattttt gaatgaagac ccatgggaaa gattaagact tttaaagaag   2580
gcgattaaga agacacctct tcaaatgctt ttaagaggtc aaaatttact cggatataaa   2640
cactatcccg atgatgtcgt aaatgaattt ataataaaat ctgttgaaaa tggtatagat   2700
ataataagaa tttttgatgc gttaaatgat gtgagaaatt tagaagtgcc aataaaatct   2760
gcaaaaaagtg caggtgctca tgtacaggca gctattgtat atacagttag tcctgtacat   2820
aatacagatc attatttgaa agtggcaaag tctcttcaag atatgggtgc ggattccata   2880
tgcattaagg atatgtctgg aatattatca ccctatgttg catacgattt gattaaatct   2940
ctgaaaagag cactttacac gccaattcaa ctgcatagcc attatacagc aggactggct   3000
```

tcaatgactt atttaaaagc catagaagct ggtgtagacg gggttgatac agctatttct 3060
tcgcttgcct taggaacatc acaaccagct acagaatcaa tcgtggctgc attgaaagat 3120
acagaatatg atacagggct agatttaaaa ttgcttgctg agatagctca gcattttaat 3180
gtagtcaaac agaatcacaa aaatgacagc gatatgtctt tgcttatgtc tgttgatgtt 3240
aaagcattag aaagtcaaat accaggggga atgttatcaa atttggtttc acagctaaag 3300
cagcagaatg cattaaacaa atatcaagac gtcttgaaag aagttccaag ggtacgcgaa 3360
gatttgggat atcctcctct tgttactcca atgagccaga tggttggaac ccaggctgtt 3420
ttaaatgtta ttacagggga gagatataaa atcgttccta aagaaattaa agattatgtc 3480
aaaggtttat atgggatgcc accagctcca atttcagatt ctatacgaaa gaaaataatc 3540
ggcgatgaag aagtaatttc aaagaggcca gcagatttac taagtcctca attggatgaa 3600
tttaaaaatg agataaagga atttatagag caagatgaag atgttttatc atatgcatta 3660
tttcctcaag tagcaagaag atttttcgag tataggcaag ccaaaaaata cagaattgat 3720
tcaacattat taaatatcga agaaagggtt catccgatat aacggccgta aaacgaaagg 3780
ctcagtcgaa agactgggcc tttcgtttta tctgttgttt gtcggtgaac gctctcctga 3840
gtaggacaaa tccgccggga gcggatttga acgttgcgaa gcaacggccc ggagggtggc 3900
gggcaggacg cccgccataa actgccaggc atcaaattaa gcagaaggcc atcctgacgg 3960
atggcctttt tgcgtttcta caaactcttc ctgtcgtcat atctacaagc catcccccca 4020
cagatacggt aaactagcct cgtttttgca tcaggaaagc agctatgaac cactcctgcg 4080
aagaggcccg caccgatcgc ccttcccaac agttgcgcag cctgaatggc gaatggcgcc 4140
tgatgcggta ttttctcctt acgcatctgt gcggtatttc acaccgcata gggtaataac 4200
tgatataatt aaattgaagc tctaatttgt gagtttagta tacatgcatt tacttataat 4260
acagtttttt agttttgctg gccgcatctt ctcaaatatg cttcccagcc tgcttttctg 4320
taacgttcac cctctacctt agcatccctt ccctttgcaa atagtcctct tccaacaata 4380
ataatgtcag atcctgtaga gaccacatca tccacggttc tatactgttg acccaatgcg 4440
tctcccttgt catctaaacc cacaccgggt gtcataatca accaatcgta accttcatct 4500
cttccaccca tgtctctttg agcaataaag ccgataacaa aatctttgtc gctcttcgca 4560
atgtcaacag tacccttagt atattctcca gtagataggg agcccttgca tgacaattct 4620
gctaacatca aaaggcctct aggttccttt gttacttctt ctgccgcctg cttcaaaccg 4680
ctaacaatac ctgggcccac cacaccgtgt gcattcgtaa tgtctgccca ttctgctatt 4740
ctgtatacac ccgcagagta ctgcaatttg actgtattac caatgtcagc aaattttctg 4800
tcttcgaaga gtaaaaaatt gtacttggcg gataatgcct ttagcggctt aactgtgccc 4860
tccatggaaa aatcagtcaa gatatccaca tgtgttttta gtaaacaaat tttgggacct 4920
aatgcttcaa ctaactccag taattccttg gtggtacgaa catccaatga agcacacaag 4980
tttgtttgct tttcgtgcat gatattaaat agcttggcag caacaggact aggatgagta 5040
gcagcacgtt ccttatatgt agctttcgac atgatttatc ttcgtttcgg tttttgttct 5100
gtgcagttgg gttaagaata ctgggcaatt tcatgtttct tcaacactac atatgcgtat 5160
atataccaat ctaagtctgt gctccttcct tcgttcttcc ttctgttcgg agattaccga 5220
atcaaaaaaa tttcaaagaa accgaaatca aaaaaaagaa taaaaaaaaa atgatgaatt 5280
gaaaagctct tgttacccat cattgaattt tgaacatccg aacctgggag ttttccctga 5340
aacagatagt atatttgaac ctgtataata atatatagtc tagcgcttta cggaagacaa 5400
tgtatgtatt tcggttcctg gagaaactat tgcatctatt gcataggtaa tcttgcacgt 5460
cgcatccccg gttcattttc tgcgtttcca tcttgcactt caatagcata tctttgttaa 5520
cgaagcatct gtgcttcatt ttgtagaaca aaaatgcaac gcgagagcgc taatttttca 5580
aacaaagaat ctgagctgca tttttacaga acagaaatgc aacgcgaaag cgctatttta 5640
ccaacgaaga atctgtgctt catttttgta aaacaaaaat gcaacgcgag agcgctaatt 5700
tttcaaacaa agaatctgag ctgcattttt acagaacaga aatgcaacgc gagagcgcta 5760
ttttaccaac aaagaatcta tacttctttt ttgttctaca aaaatgcatc ccgagagcgc 5820
tatttttcta acaaagcatc ttagattact ttttttctcc tttgtgcgct ctataatgca 5880
gtctcttgat aactttttgc actgtaggtc cgttaaggtt agaagaaggc tactttggtg 5940
tctattttct cttccataaa aaaagcctga ctccacttcc cgcgtttact gattactagc 6000
gaagctgcgg gtgcattttt tcaagataaa ggcatccccg attatattct ataccgatgt 6060
ggattgcgca tactttgtga acagaaagtg atagcgttga tgattcttca ttggtcagaa 6120
aattatgaac ggtttcttct attttgtctc tatatactac gtataggaaa tgtttacatt 6180
ttcgtattgt tttcgattca ctctatgaat agttcttact acaatttttt tgtctaaaga 6240
gtaatactag agataaacat aaaaaatgta gaggtcgagt ttagatgcaa gttcaaggag 6300
cgaaaggtgg atgggtaggt tatataggga tatagcacag agatatatag caaagagata 6360
cttttgagca atgtttgtgg aagcggtatt cgcaatattt tagtagctcg ttacagtccg 6420
gtgcgttttt ggtttttga aagtgcgtct tcagagcgct tttggttttc aaaagcgctc 6480
tgaagttcct atactttcta gctagagaat aggaacttcg gaataggaac ttcaaagcgt 6540
ttccgaaaac gagcgcttcc gaaaatgcaa cgcgagctgc gcacatacag ctcactgttc 6600
acgtcgcacc tatatctgcg tgttgcctgt atatatatat acatgagaag aacggcatag 6660
tgcgtgttta tgcttaaatg cgttatggtg cactctcagt acaatctgct ctgatgccgc 6720
atagttaagc cagccccgac acccgccaac acccgctgac gcgccctgac gggcttgtct 6780
gctcccggca tccgcttaca gacaagctgt gaccgtctcc gggagctgca tgtgtcagag 6840
gttttcaccg tcatcaccga aacgcgcgag acgaaagggc ctcgtgatac gcctattttt 6900
ataggttaat gtcatgataa taatggtttc ttagacgtca ggtggcactt ttcggggaaa 6960
tgtgcgcgga acccctattt gtttattttt ctaaatacat tcaaatatgt atccgctcat 7020
gagacaataa ccctgataaa tgcttcaata atattgaaaa aggaagagta tgagtattca 7080
acatttccgt gtcgccctta ttcccttttt tgcggcattt tgccttcctg tttttgctca 7140
cccagaaacg ctggtgaaag taaaagatgc tgaagatcag ttgggtgcac gagtgggtta 7200
catcgaactg gatctcaaca gcggtaagat ccttgagagt tttcgccccg aagaacgttt 7260
tccaatgatg agcactttta aagttctgct atgtggcgcg gtattatccc gtattgacgc 7320
cgggcaagag caactcggtc gccgcataca ctattctcag aatgacttgg ttgagtactc 7380
accagtcaca gaaaagcatc ttacggatgg catgacagta agagaattat gcagtgctgc 7440
cataaccatg agtgataaca ctgcggccaa cttacttctg acaacgatcg gaggaccgaa 7500
ggagctaacc gcttttttgc acaacatggg ggatcatgta actcgccttg atcgttggga 7560
accggagctg aatgaagcca taccaaacga cgagcgtgac accacgatgc ctgtagcaat 7620
ggcaacaacg ttgcgcaaac tattaactgg cgaactactt actctagctt cccggcaaca 7680
attaatagac tggatggagg cggataaagt tgcaggacca cttctgcgct cggcccttcc 7740

```
ggctggctgg tttattgctg ataaatctgg agccggtgag cgtgggtctc gcggtatcat   7800
tgcagcactg gggccagatg gtaagccctc ccgtatcgta gttatctaca cgacggggag   7860
tcaggcaact atggatgaac gaaatagaca gatcgctgag ataggtgcct cactgattaa   7920
gcattggtaa ctgtcagacc aagtttactc atatatactt tagattgatt taaaacttca   7980
tttttaattt aaaaggatct aggtgaagat cctttttgat aatctcatga ccaaaatccc   8040
ttaacgtgag ttttcgttcc actgagcgtc agaccccgta gaaaagatca aaggatcttc   8100
ttgagatcct ttttttctgc gcgtaatctg ctgcttgcaa acaaaaaaac caccgctacc   8160
agcggtggtt tgtttgccgg atcaagagct accaactctt tttccgaagg taactggctt   8220
cagcagagcg cagataccaa atactgtcct tctagtgtag ccgtagttag gccaccactt   8280
caagaactct gtagcaccgc ctacatacct cgctctgcta atcctgttac cagtggctgc   8340
tgccagtggc gataagtcgt gtcttaccgg gttggactca agacgatagt taccggataa   8400
ggcgcagcgg tcgggctgaa cggggggttc gtgcacacag cccagcttgg agcgaacgac   8460
ctacaccgaa ctgagatacc tacagcgtga gcattgagaa agcgccacgc ttcccgaagg   8520
gagaaaggcg gacaggtatc cggtaagcgg cagggtcgga acaggagagc gcacgaggga   8580
gcttccaggg ggaaacgcct ggtatcttta tagtcctgtc gggtttcgcc acctctgact   8640
tgagcgtcga tt                                                       8652
```

```
<210> SEQ ID NO 289
<211> LENGTH: 8864
<212> TYPE: DNA
<213> ORGANISM: Artificial
<220> FEATURE:
<223> OTHER INFORMATION: pMU2901

<400> SEQUENCE: 289
```

```
ctcgtcaggg gggcggagcc tatggaaaaa cgccagcaac gcggcctttt tacggttcct     60
ggccttttgc tggccttttg tgagccgttt atttttctta cccatatcct tgaagcggtg    120
ttataatgcc gcgccctcga tatggggatt tttaacgacc tgattttcgg gtctcagtag    180
tagttgacat tagcggagca ctaaaatgag tccgcgagaa attgaggttt ccgagccgcg    240
cgaggttggt atcaccgagc tcgtgctgcg cgatgcccat cagagcctga tggccacacg    300
aatggcaatg gaagacatgg tcggcgcctg tgcagacatt gatgctgccg ggtactggtc    360
agtggagtgt tggggtggtg ccacgtatga ctcgtgtatc cgcttcctca acgaggatcc    420
ttgggagcgt ctgcgcacgt tccgcaagct gatgcccaac agccgtctcc agatgctgct    480
gcgtggccag aacctgctgg gttaccgcca ctacaacgac gaggtcgtcg atcgcttcgt    540
cgacaagtcc gctgagaacg gcatggacgt gttccgtgtc ttcgacgcca tgaatgatcc    600
ccgcaacatg gcgcacgcca tggctgccgt caagaaggcc ggcaagcacg cgcagggcac    660
catttgctac acgatcagcc cggtccacac cgttgagggc tatgtcaagc ttgctggtca    720
gctgctcgac atgggtgctg attccatcgc cctgaaggac atggccgccc tgctcaagcc    780
gcagccggcc tacgacatca tcaaggccat caaggacacc tacggccaga agacgcagat    840
caacctgcac tgccactcca ccacgggtgt caccgaggtc tccctcatga aggccatcga    900
ggccggcgtc gacgtcgtcg acaccgccat ctcgtccatg tcgctcggcc cgggccacaa    960
ccccaccgag tcggttgccg agatgctcga gggcaccggg tacaccacca accttgacta   1020
cgatcgcctg cacaagatcc gcgatcactt caaggccatc cgcccgaagt acaagaagtt   1080
```

-continued cgagtcgaag acgcttgtcg acacctcgat cttcaagtcg cagatccccg gcggcatgct 1140
ctccaacatg gagtcgcagc tgcgcgccca gggcgccgag gacaagatgg acgaggtcat 1200
ggcagaggtg ccgcgcgtcc gcaaggccgc cggcttcccg cccctggtca ccccgtccag 1260
ccagatcgtc ggcacgcagg ccgtgttcaa cgtgatgatg ggcgagtaca agaggatgac 1320
cggcgagttc gccgacatca tgctcggcta ctacggcgcc agcccggccg atcgcgatcc 1380
gaaggtggtc aagttggccg aggagcagtc cggcaagaag ccgatcaccc agcgcccggc 1440
cgatctgctg ccccccgagt gggaggagca gtccaaggag gccgcggccc tcaagggctt 1500
caacggcacc gacgaggacg tgctcaccta tgcactgttc ccgcaggtcg ctccggtctt 1560
cttcgagcat cgcgccgagg gcccgcacag cgtggctctc accgatgccc agctgaaggc 1620
cgaggccgag ggcgacgaga agtcgctcgc cgtggccggt cccgtcacct acaacgtgaa 1680
cgtgggcgga accgtccgcg aagtcaccgt tcagcaggcg tgaggatgat tgccaatcat 1740
ggctgaaaac aacaatttga agctcgccag caccatggaa ggtcgcgtgg agcagctcgc 1800
agagcagcgc caggtgatcg aagccggtgg cggcgaacgt cgcgtcgaga agcaacattc 1860
ccagggtaag cagaccgctc gtgagcgcct gaacaacctg ctcgatcccc attcgttcga 1920
cgaggtcggc gctttccgca agcaccgcac cacgttgttc ggcatggaca aggccgtcgt 1980
cccggcagat ggcgtggtca ccggccgtgg caccatcctt ggtcgtcccg tgcacgccgc 2040
gtcccaggac ttcacggtca tgggtggttc ggctggcgag acgcagtcca cgaaggtcgt 2100
cgagacgatg gaacaggcgc tgctcaccgg cacgcccttc ctgttcttct acgattcggg 2160
cggcgcccgg atccaggagg gcatcgactc gctgagcggt tacggcaaga tgttcttcgc 2220
caacgtgaag ctgtcgggcg tcgtgccgca gatcgccatc attgccggcc cctgtgccgg 2280
tggcgcctcg tattcgccgg cactgactga cttcatcatc atgaccaaga aggcccatat 2340
gttcatcacg ggcccccagg tcatcaagtc ggtcaccggc gaggatgtca ccgctgacga 2400
actcggtggc gctgaggccc atatggccat ctcgggcaat atccacttcg tggccgagga 2460
cgacgacgcc gcggagctca ttgccaagaa gctgctgagc ttccttccgc agaacaacac 2520
tgaggaagca tccttcgtca acccgaacaa tgacgtcagc cccaataccg agctgcgcga 2580
catcgttccg attgacggca agaagggcta tgacgtgcgc gatgtcattg ccaagatcgt 2640
cgactggggt gactacctcg aggtcaaggc cggctatgcc accaacctcg tgaccgcctt 2700
cgcccgggtc aatggtcgtt cggtgggcat cgtggccaat cagccgtcgg tgatgtcggg 2760
ttgcctcgac atcaacgcct ctgacaaggc cgccgaattc gtgaatttct gcgattcgtt 2820
caacatcccg ctggtgcagc tggtcgacgt gccgggcttc ctgcccggcg tgcagcagga 2880
gtacggcggc atcattcgcc atggcgcgaa gatgctgtac gcctactccg aggccaccgt 2940
gccgaagatc accgtggtgc tccgcaaggc ctacggcggc tcctacctgg ccatgtgcaa 3000
ccgtgacctt ggtgccgacg ccgtgtacgc ctggcccagc gccgagattg cggtgatggg 3060
cgccgagggt gcggcaaatg tgatcttccg caaggagatc aaggctgccg acgatcccga 3120
cgccatgcgc gccgagaaga tcgaggagta ccagaacgcg ttcaacacgc cgtacgtggc 3180
cgccgcccgc ggtcaggtcg acgacgtgat tgacccggct gatacccgtc gaaagattgc 3240
ttccgccctg gagatgtacg ccaccaagcg tcagacccgc ccggcgaaga agcatggaaa 3300
cttcccctgc tgagcgagga gagaaattat ggctgatgag gaagagaagg acctgatgat 3360
cgccacgctc aacaagcgcg tcgcgtcatt ggagtctgag ttgggttcac tccagagcga 3420
tacccagggt gtcaccgagg acgtactgac ggccatttcg gccgccgttg cggcctatct 3480

```
cggcaacgat ggatcggctg aggtcgtcca tttcgccccg agcccgaact gggtccgcga   3540
gggtcgtcgg gctctgcaga accattccat tcgttgatcc gggagtaact cacatgaaac   3600
tgaaggtaac agtcaacggc actgcgtatg acgttgacgt tgacgtcgac aagtcacacg   3660
aaaacccgat gggcaccatc ctgttcggcg gcggcaccgg cggcgcgccg gcaccgcgcg   3720
cagcaggtgg cgcaggcgcc ggtaaggccg gagagggcga gattcccgct ccgctggccg   3780
gcaccgtctc caagatcctc gtgaaggagg gtgacacggt caaggctggt cagaccgtgc   3840
tcgttctcga ggccatgaag atggagaccg agatcaacgc tcccaccgac ggcaaggtcg   3900
agaaggtcct tgtcaaggag cgtgacgccg tgcagggcgg tcagggtctc atcaagatcg   3960
gctgacggcc gtaaaacgaa aggctcagtc gaaagactgg gcctttcgtt ttatctgttg   4020
tttgtcggtg aacgctctcc tgagtaggac aaatccgccg ggagcggatt tgaacgttgc   4080
gaagcaacgg cccggagggt ggcgggcagg acgcccgcca taaactgcca ggcatcaaat   4140
taagcagaag gccatcctga cggatggcct ttttgcgttt ctacaaactc ttcctgtcgt   4200
catatctaca agccatcccc ccacagatac ggtaaactag cctcgttttt gcatcaggaa   4260
agcagctatg aaccactcct gcgaagaggc ccgcaccgat cgcccttccc aacagttgcg   4320
cagcctgaat ggcgaatggc gcctgatgcg gtattttctc cttacgcatc tgtgcggtat   4380
ttcacaccgc atagggtaat aactgatata attaaattga agctctaatt tgtgagttta   4440
gtatacatgc atttacttat aatacagttt tttagttttg ctggccgcat cttctcaaat   4500
atgcttccca gcctgctttt ctgtaacgtt caccctctac cttagcatcc cttccctttg   4560
caaatagtcc tcttccaaca ataataatgt cagatcctgt agagaccaca tcatccacgg   4620
ttctatactg ttgacccaat gcgtctccct tgtcatctaa acccacaccg ggtgtcataa   4680
tcaaccaatc gtaaccttca tctcttccac ccatgtctct ttgagcaata aagccgataa   4740
caaaatcttt gtcgctcttc gcaatgtcaa cagtaccctt agtatattct ccagtagata   4800
gggagccctt gcatgacaat tctgctaaca tcaaaaggcc tctaggttcc tttgttactt   4860
cttctgccgc ctgcttcaaa ccgctaacaa tacctgggcc caccacaccg tgtgcattcg   4920
taatgtctgc ccattctgct attctgtata cacccgcaga gtactgcaat ttgactgtat   4980
taccaatgtc agcaaatttt ctgtcttcga agagtaaaaa attgtacttg gcggataatg   5040
cctttagcgg cttaactgtg ccctccatgg aaaaatcagt caagatatcc acatgtgttt   5100
ttagtaaaca aattttggga cctaatgctt caactaactc cagtaattcc ttggtggtac   5160
gaacatccaa tgaagcacac aagtttgttt gcttttcgtg catgatatta aatagcttgg   5220
cagcaacagg actaggatga gtagcagcac gttccttata tgtagctttc gacatgattt   5280
atcttcgttt cggtttttgt tctgtgcagt tgggttaaga atactgggca atttcatgtt   5340
tcttcaacac tacatatgcg tatatatacc aatctaagtc tgtgctcctt ccttcgttct   5400
tccttctgtt cggagattac cgaatcaaaa aaatttcaaa gaaaccgaaa tcaaaaaaaa   5460
gaataaaaaa aaaatgatga attgaaaagc tcttgttacc catcattgaa ttttgaacat   5520
ccgaacctgg gagttttccc tgaaacagat agtatatttg aacctgtata ataatatata   5580
gtctagcgct ttacggaaga caatgtatgt atttcggttc ctggagaaac tattgcatct   5640
attgcatagg taatcttgca cgtcgcatcc ccggttcatt ttctgcgttt ccatcttgca   5700
cttcaatagc atatctttgt taacgaagca tctgtgcttc attttgtaga acaaaaatgc   5760
aacgcgagag cgctaatttt tcaaacaaag aatctgagct gcatttttac agaacagaaa   5820
```

tgcaacgcga aagcgctatt ttaccaacga agaatctgtg cttcattttt gtaaaacaaa 5880
aatgcaacgc gagagcgcta atttttcaaa caaagaatct gagctgcatt tttacagaac 5940
agaaatgcaa cgcgagagcg ctattttacc aacaaagaat ctatacttct tttttgttct 6000
acaaaaatgc atcccgagag cgctattttt ctaacaaagc atcttagatt actttttttc 6060
tcctttgtgc gctctataat gcagtctctt gataactttt tgcactgtag gtccgttaag 6120
gttagaagaa ggctactttg gtgtctattt tctcttccat aaaaaaagcc tgactccact 6180
tcccgcgttt actgattact agcgaagctg cgggtgcatt ttttcaagat aaaggcatcc 6240
ccgattatat tctataccga tgtggattgc gcatactttg tgaacagaaa gtgatagcgt 6300
tgatgattct tcattggtca gaaaattatg aacggtttct tctattttgt ctctatatac 6360
tacgtatagg aaatgtttac attttcgtat tgttttcgat tcactctatg aatagttctt 6420
actacaattt ttttgtctaa agagtaatac tagagataaa cataaaaaat gtagaggtcg 6480
agtttagatg caagttcaag gagcgaaagg tggatgggta ggttatatag ggatatagca 6540
cagagatata tagcaaagag atacttttga gcaatgtttg tggaagcggt attcgcaata 6600
ttttagtagc tcgttacagt ccggtgcgtt tttggttttt tgaaagtgcg tcttcagagc 6660
gcttttggtt ttcaaaagcg ctctgaagtt cctatacttt ctagctagag aataggaact 6720
tcggaatagg aacttcaaag cgtttccgaa aacgagcgct tccgaaaatg caacgcgagc 6780
tgcgcacata cagctcactg ttcacgtcgc acctatatct gcgtgttgcc tgtatatata 6840
tatacatgag aagaacggca tagtgcgtgt ttatgcttaa atgcgttatg gtgcactctc 6900
agtacaatct gctctgatgc cgcatagtta agccagcccc gacacccgcc aacacccgct 6960
gacgcgccct gacgggcttg tctgctcccg gcatccgctt acagacaagc tgtgaccgtc 7020
tccgggagct gcatgtgtca gaggttttca ccgtcatcac cgaaacgcgc gagacgaaag 7080
ggcctcgtga tacgcctatt tttataggtt aatgtcatga taataatggt ttcttagacg 7140
tcaggtggca cttttcgggg aaatgtgcgc ggaaccccta tttgtttatt tttctaaata 7200
cattcaaata tgtatccgct catgagacaa taaccctgat aaatgcttca ataatattga 7260
aaaaggaaga gtatgagtat tcaacatttc cgtgtcgccc ttattccctt ttttgcggca 7320
ttttgccttc ctgtttttgc tcacccagaa acgctggtga aagtaaaaga tgctgaagat 7380
cagttgggtg cacgagtggg ttacatcgaa ctggatctca acagcggtaa gatccttgag 7440
agttttcgcc ccgaagaacg ttttccaatg atgagcactt ttaaagttct gctatgtggc 7500
gcggtattat cccgtattga cgccgggcaa gagcaactcg gtcgccgcat acactattct 7560
cagaatgact tggttgagta ctcaccagtc acagaaaagc atcttacgga tggcatgaca 7620
gtaagagaat tatgcagtgc tgccataacc atgagtgata acactgcggc caacttactt 7680
ctgacaacga tcggaggacc gaaggagcta accgcttttt tgcacaacat gggggatcat 7740
gtaactcgcc ttgatcgttg ggaaccggag ctgaatgaag ccataccaaa cgacgagcgt 7800
gacaccacga tgcctgtagc aatggcaaca acgttgcgca aactattaac tggcgaacta 7860
cttactctag cttcccggca acaattaata gactggatgg aggcggataa agttgcagga 7920
ccacttctgc gctcggccct tccggctggc tggtttattg ctgataaatc tggagccggt 7980
gagcgtgggt ctcgcggtat cattgcagca ctggggccag atggtaagcc ctcccgtatc 8040
gtagttatct acacgacggg gagtcaggca actatggatg aacgaaatag acagatcgct 8100
gagataggtg cctcactgat taagcattgg taactgtcag accaagttta ctcatatata 8160
ctttagattg atttaaaact tcatttttaa tttaaaagga tctaggtgaa gatccttttt 8220

```
gataatctca tgaccaaaat cccttaacgt gagttttcgt tccactgagc gtcagacccc   8280

gtagaaaaga tcaaaggatc ttcttgagat cctttttttc tgcgcgtaat ctgctgcttg   8340

caaacaaaaa aaccaccgct accagcggtg gtttgtttgc cggatcaaga gctaccaact   8400

ctttttccga aggtaactgg cttcagcaga gcgcagatac caaatactgt ccttctagtg   8460

tagccgtagt taggccacca cttcaagaac tctgtagcac cgcctacata cctcgctctg   8520

ctaatcctgt taccagtggc tgctgccagt ggcgataagt cgtgtcttac cgggttggac   8580

tcaagacgat agttaccgga taaggcgcag cggtcgggct gaacgggggg ttcgtgcaca   8640

cagcccagct tggagcgaac gacctacacc gaactgagat acctacagcg tgagcattga   8700

gaaagcgcca cgcttcccga agggagaaag gcggacaggt atccggtaag cggcagggtc   8760

ggaacaggag agcgcacgag ggagcttcca gggggaaacg cctggtatct ttatagtcct   8820

gtcgggtttc gccacctctg acttgagcgt cgatttttgt gatg                    8864
```

```
<210> SEQ ID NO 290
<211> LENGTH: 1220
<212> TYPE: PRT
<213> ORGANISM: C. aurantiacus

<400> SEQUENCE: 290

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255
```

-continued

```
Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Gly
    370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
        435                 440                 445

Arg Ala Arg Gly Pro Arg Val Ile Phe Leu Ser Asn Gly Ala Asp Gln
    450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
```

-continued

```
        675                 680                 685

Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
    770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Ala Arg Thr Asp Glu Arg Ser Met
                805                 810                 815

His Glu Leu Val Glu Leu Leu Leu Pro Asn Asp Val Ala Ala Leu Glu
            820                 825                 830

Gln Asn Pro Ala Ala Pro Thr Ala Leu Arg Glu Leu Ala Arg Arg Phe
        835                 840                 845

Arg Ser Glu Gly Asp Pro Ala Ala Ser Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
        915                 920                 925

Val Ala Met Ala Thr Val Tyr Tyr Leu Ala Asp Arg Asn Val Ser Gly
    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu  Glu Arg Tyr Gly Ala  Arg Gln Val
        995                 1000                1005

Val Met  Ile Val Glu Thr Glu  Thr Gly Ala Glu Thr  Met Arg Arg
    1010                1015                1020

Leu Leu  His Asp His Val Glu  Ala Gly Arg Leu Met  Thr Ile Val
    1025                1030                1035

Ala Gly  Asp Gln Ile Glu Ala  Ala Ile Asp Gln Ala  Ile Thr Arg
    1040                1045                1050

Tyr Gly  Arg Pro Gly Pro Val  Val Cys Thr Pro Phe  Arg Pro Leu
    1055                1060                1065

Pro Thr  Val Pro Leu Val Gly  Arg Lys Asp Ser Asp  Trp Ser Thr
    1070                1075                1080

Val Leu  Ser Glu Ala Glu Phe  Ala Glu Leu Cys Glu  His Gln Leu
    1085                1090                1095
```

```
Thr His  His Phe Arg Val Ala  Arg Lys Ile Ala Leu  Ser Asp Gly
    1100                 1105                 1110

Ala Ser  Leu Ala Leu Val Thr  Pro Glu Thr Thr Ala  Thr Ser Thr
    1115                 1120                 1125

Thr Glu  Gln Phe Ala Leu Ala  Asn Phe Ile Lys Thr  Thr Leu His
    1130                 1135                 1140

Ala Phe  Thr Ala Thr Ile Gly  Val Glu Ser Glu Arg  Thr Ala Gln
    1145                 1150                 1155

Arg Ile  Leu Ile Asn Gln Val  Asp Leu Thr Arg Arg  Ala Arg Ala
    1160                 1165                 1170

Glu Glu  Pro Arg Asp Pro His  Glu Arg Gln Gln Glu  Leu Glu Arg
    1175                 1180                 1185

Phe Ile  Glu Ala Val Leu Leu  Val Thr Ala Pro Leu  Pro Pro Glu
    1190                 1195                 1200

Ala Asp  Thr Arg Tyr Ala Gly  Arg Ile His Arg Gly  Arg Ala Ile
    1205                 1210                 1215

Thr Val
    1220


<210> SEQ ID NO 291
<211> LENGTH: 1219
<212> TYPE: PRT
<213> ORGANISM: C. aurantiacus

<400> SEQUENCE: 291

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
```

-continued

```
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Ala
    370                 375                 380

Gly Glu Asn Thr Gly Gly Ile His Ala Ala Val Ile Leu Pro Ala Thr
385                 390                 395                 400

Ser His Glu Pro Ala Pro Cys Val Ile Glu Val Asp Asp Glu Arg Val
                405                 410                 415

Leu Asn Phe Leu Ala Asp Glu Ile Thr Gly Thr Ile Val Ile Ala Ser
            420                 425                 430

Arg Leu Ala Arg Tyr Trp Gln Ser Gln Arg Leu Thr Pro Gly Ala Arg
        435                 440                 445

Ala Arg Gly Pro Arg Val Ile Phe Leu Ser Asn Gly Ala Asp Gln Asn
    450                 455                 460

Gly Asn Val Tyr Gly Arg Ile Gln Ser Ala Ala Ile Gly Gln Leu Ile
465                 470                 475                 480

Arg Val Trp Arg His Glu Ala Glu Leu Asp Tyr Gln Arg Ala Ser Ala
                485                 490                 495

Ala Gly Asp His Val Leu Pro Pro Val Trp Ala Asn Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg His Ile Asn Glu Ile Thr Leu Asn
    530                 535                 540

Ile Pro Ala Asn Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
                565                 570                 575

Ile Thr Gly Gly Ser Ala Gly Ile Gly Gly Gln Ile Gly Arg Leu Leu
            580                 585                 590

Ala Leu Ser Gly Ala Arg Val Met Leu Ala Ala Arg Asp Arg His Lys
        595                 600                 605

Leu Glu Gln Met Gln Ala Met Ile Gln Ser Glu Leu Ala Glu Val Gly
    610                 615                 620

Tyr Thr Asp Val Glu Asp Arg Val His Ile Ala Pro Gly Cys Asp Val
625                 630                 635                 640

Ser Ser Glu Ala Gln Leu Ala Asp Leu Val Glu Arg Thr Leu Ser Ala
                645                 650                 655
```

```
Phe Gly Thr Val Asp Tyr Leu Ile Asn Asn Ala Gly Ile Ala Gly Val
            660                 665                 670

Glu Glu Met Val Ile Asp Met Pro Val Glu Gly Trp Arg His Thr Leu
        675                 680                 685

Phe Ala Asn Leu Ile Ser Asn Tyr Ser Leu Met Arg Lys Leu Ala Pro
    690                 695                 700

Leu Met Lys Lys Gln Gly Ser Gly Tyr Ile Leu Asn Val Ser Ser Tyr
705                 710                 715                 720

Phe Gly Gly Glu Lys Asp Ala Ala Ile Pro Tyr Pro Asn Arg Ala Asp
                725                 730                 735

Tyr Ala Val Ser Lys Ala Gly Gln Arg Ala Met Ala Glu Val Phe Ala
            740                 745                 750

Arg Phe Leu Gly Pro Glu Ile Gln Ile Asn Ala Ile Ala Pro Gly Pro
        755                 760                 765

Val Glu Gly Asp Arg Leu Arg Gly Thr Gly Glu Arg Pro Gly Leu Phe
    770                 775                 780

Ala Arg Arg Ala Arg Leu Ile Leu Glu Asn Lys Arg Leu Asn Glu Leu
785                 790                 795                 800

His Ala Ala Leu Ile Ala Ala Ala Arg Thr Asp Glu Arg Ser Met His
                805                 810                 815

Glu Leu Val Glu Leu Leu Leu Pro Asn Asp Val Ala Ala Leu Glu Gln
            820                 825                 830

Asn Pro Ala Ala Pro Thr Ala Leu Arg Glu Leu Ala Arg Arg Phe Arg
        835                 840                 845

Ser Glu Gly Asp Pro Ala Ala Ser Ser Ser Ser Ala Leu Leu Asn Arg
    850                 855                 860

Ser Ile Ala Ala Lys Leu Leu Ala Arg Leu His Asn Gly Gly Tyr Val
865                 870                 875                 880

Leu Pro Ala Asp Ile Phe Ala Asn Leu Pro Asn Pro Pro Asp Pro Phe
                885                 890                 895

Phe Thr Arg Ala Gln Ile Asp Arg Glu Ala Arg Lys Val Arg Asp Gly
            900                 905                 910

Ile Met Gly Met Leu Tyr Leu Gln Arg Met Pro Thr Glu Phe Asp Val
        915                 920                 925

Ala Met Ala Thr Val Tyr Tyr Leu Ala Asp Arg Asn Val Ser Gly Glu
    930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ser Pro Glu Arg Leu Ala Glu Leu Val
                965                 970                 975

Gly Ser Thr Val Tyr Leu Ile Gly Glu His Leu Thr Glu His Leu Asn
            980                 985                 990

Leu Leu Ala Arg Ala Tyr Leu Glu  Arg Tyr Gly Ala Arg  Gln Val Val
        995                 1000                1005

Met Ile  Val Glu Thr Glu Thr  Gly Ala Glu Thr Met  Arg Arg Leu
    1010                1015                1020

Leu His  Asp His Val Glu Ala  Gly Arg Leu Met Thr  Ile Val Ala
    1025                1030                1035

Gly Asp  Gln Ile Glu Ala Ala  Ile Asp Gln Ala Ile  Thr Arg Tyr
    1040                1045                1050

Gly Arg  Pro Gly Pro Val Val  Cys Thr Pro Phe Arg  Pro Leu Pro
    1055                1060                1065
```

```
Thr Val  Pro Leu Val Gly Arg  Lys Asp Ser Asp Trp  Ser Thr Val
    1070                 1075                 1080

Leu Ser  Glu Ala Glu Phe Ala  Glu Leu Cys Glu His  Gln Leu Thr
    1085                 1090                 1095

His His  Phe Arg Val Ala Arg  Lys Ile Ala Leu Ser  Asp Gly Ala
    1100                 1105                 1110

Ser Leu  Ala Leu Val Thr Pro  Glu Thr Thr Ala Thr  Ser Thr Thr
    1115                 1120                 1125

Glu Gln  Phe Ala Leu Ala Asn  Phe Ile Lys Thr Thr  Leu His Ala
    1130                 1135                 1140

Phe Thr  Ala Thr Ile Gly Val  Glu Ser Glu Arg Thr  Ala Gln Arg
    1145                 1150                 1155

Ile Leu  Ile Asn Gln Val Asp  Leu Thr Arg Arg Ala  Arg Ala Glu
    1160                 1165                 1170

Glu Pro  Arg Asp Pro His Glu  Arg Gln Gln Glu Leu  Glu Arg Phe
    1175                 1180                 1185

Ile Glu  Ala Val Leu Leu Val  Thr Ala Pro Leu Pro  Pro Glu Ala
    1190                 1195                 1200

Asp Thr  Arg Tyr Ala Gly Arg  Ile His Arg Gly Arg  Ala Ile Thr
    1205                 1210                 1215

Val


<210> SEQ ID NO 292
<211> LENGTH: 1219
<212> TYPE: PRT
<213> ORGANISM: Chloroflexus sp.

<400> SEQUENCE: 292

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205
```

-continued

```
Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Ala
    370                 375                 380

Gly Glu Asn Thr Gly Gly Ile His Ala Ala Val Ile Leu Pro Ala Thr
385                 390                 395                 400

Ser His Glu Pro Ala Pro Cys Val Ile Glu Val Asp Asp Glu Arg Val
                405                 410                 415

Leu Asn Phe Leu Ala Asp Glu Ile Thr Gly Thr Ile Val Ile Ala Ser
            420                 425                 430

Arg Leu Ala Arg Tyr Trp Gln Ser Gln Arg Leu Thr Pro Gly Ala Arg
        435                 440                 445

Ala Arg Gly Pro Arg Val Ile Phe Leu Ser Asn Gly Ala Asp Gln Asn
    450                 455                 460

Gly Asn Val Tyr Gly Arg Ile Gln Ser Ala Ala Ile Gly Gln Leu Ile
465                 470                 475                 480

Arg Val Trp Arg His Glu Ala Glu Leu Asp Tyr Gln Arg Ala Ser Ala
                485                 490                 495

Ala Gly Asp His Val Leu Pro Pro Val Trp Ala Asn Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg His Ile Asn Glu Ile Thr Leu Asn
    530                 535                 540

Ile Pro Ala Asn Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
                565                 570                 575

Ile Thr Gly Gly Ser Ala Gly Ile Gly Gly Gln Ile Gly Arg Leu Leu
            580                 585                 590

Ala Leu Ser Gly Ala Arg Val Met Leu Ala Ala Arg Asp Arg His Lys
        595                 600                 605

Leu Glu Gln Met Gln Ala Met Ile Gln Ser Glu Leu Ala Glu Val Gly
    610                 615                 620

Tyr Thr Asp Val Glu Asp Arg Val His Ile Ala Pro Gly Cys Asp Val
```

-continued

```
625                 630                 635                 640

Ser Ser Glu Ala Gln Leu Ala Asp Leu Val Glu Arg Thr Leu Ser Ala
                645                 650                 655

Phe Gly Thr Val Asp Tyr Leu Ile Asn Asn Ala Gly Ile Ala Gly Val
            660                 665                 670

Glu Glu Met Val Ile Asp Met Pro Val Glu Gly Trp Arg His Thr Leu
        675                 680                 685

Phe Ala Asn Leu Ile Ser Asn Tyr Ser Leu Met Arg Lys Leu Ala Pro
    690                 695                 700

Leu Met Lys Lys Gln Gly Ser Gly Tyr Ile Leu Asn Val Ser Ser Tyr
705                 710                 715                 720

Phe Gly Gly Glu Lys Asp Ala Ala Ile Pro Tyr Pro Asn Arg Ala Asp
                725                 730                 735

Tyr Ala Val Ser Lys Ala Gly Gln Arg Ala Met Ala Glu Val Phe Ala
            740                 745                 750

Arg Phe Leu Gly Pro Glu Ile Gln Ile Asn Ala Ile Ala Pro Gly Pro
        755                 760                 765

Val Glu Gly Asp Arg Leu Arg Gly Thr Gly Glu Arg Pro Gly Leu Phe
    770                 775                 780

Ala Arg Arg Ala Arg Leu Ile Leu Glu Asn Lys Arg Leu Asn Glu Leu
785                 790                 795                 800

His Ala Ala Leu Ile Ala Ala Ala Arg Thr Asp Glu Arg Ser Met His
                805                 810                 815

Glu Leu Val Glu Leu Leu Leu Pro Asn Asp Val Ala Ala Leu Glu Gln
            820                 825                 830

Asn Pro Ala Ala Pro Thr Ala Leu Arg Glu Leu Ala Arg Arg Phe Arg
        835                 840                 845

Ser Glu Gly Asp Pro Ala Ala Ser Ser Ser Ser Ala Leu Leu Asn Arg
    850                 855                 860

Ser Ile Ala Ala Lys Leu Leu Ala Arg Leu His Asn Gly Gly Tyr Val
865                 870                 875                 880

Leu Pro Ala Asp Ile Phe Ala Asn Leu Pro Asn Pro Pro Asp Pro Phe
                885                 890                 895

Phe Thr Arg Ala Gln Ile Asp Arg Glu Ala Arg Lys Val Arg Asp Gly
            900                 905                 910

Ile Met Gly Met Leu Tyr Leu Gln Arg Met Pro Thr Glu Phe Asp Val
        915                 920                 925

Ala Met Ala Thr Val Tyr Tyr Leu Ala Asp Arg Asn Val Ser Gly Glu
    930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ser Pro Glu Arg Leu Ala Glu Leu Val
                965                 970                 975

Gly Ser Thr Val Tyr Leu Ile Gly Glu His Leu Thr Glu His Leu Asn
            980                 985                 990

Leu Leu Ala Arg Ala Tyr Leu Glu  Arg Tyr Gly Ala Arg  Gln Val Val
        995                 1000                1005

Met Ile  Val Glu Thr Glu Thr  Gly Ala Glu Thr Met  Arg Arg Leu
    1010                1015                1020

Leu His  Asp His Val Glu Ala  Gly Arg Leu Met Thr  Ile Val Ala
    1025                1030                1035

Gly Asp  Gln Ile Glu Ala Ala  Ile Asp Gln Ala Ile  Thr Arg Tyr
    1040                1045                1050
```

Gly Arg Pro Gly Pro Val Val Cys Thr Pro Phe Arg Pro Leu Pro
1055 1060 1065

Thr Val Pro Leu Val Gly Arg Lys Asp Ser Asp Trp Ser Thr Val
1070 1075 1080

Leu Ser Glu Ala Glu Phe Ala Glu Leu Cys Glu His Gln Leu Thr
1085 1090 1095

His His Phe Arg Val Ala Arg Lys Ile Ala Leu Ser Asp Gly Ala
1100 1105 1110

Ser Leu Ala Leu Val Thr Pro Glu Thr Thr Ala Thr Ser Thr Thr
1115 1120 1125

Glu Gln Phe Ala Leu Ala Asn Phe Ile Lys Thr Thr Leu His Ala
1130 1135 1140

Phe Thr Ala Thr Ile Gly Val Glu Ser Glu Arg Thr Ala Gln Arg
1145 1150 1155

Ile Leu Ile Asn Gln Val Asp Leu Thr Arg Arg Ala Arg Ala Glu
1160 1165 1170

Glu Pro Arg Asp Pro His Glu Arg Gln Gln Glu Leu Glu Arg Phe
1175 1180 1185

Ile Glu Ala Val Leu Leu Val Thr Ala Pro Leu Pro Pro Glu Ala
1190 1195 1200

Asp Thr Arg Tyr Ala Gly Arg Ile His Arg Gly Arg Ala Ile Thr
1205 1210 1215

Val

<210> SEQ ID NO 293
<211> LENGTH: 1219
<212> TYPE: PRT
<213> ORGANISM: C. aggregans

<400> SEQUENCE: 293

Met Ser Val Thr Gly Arg Leu Ala Gly Lys Ile Ala Leu Ile Thr Gly
1 5 10 15

Gly Ala Gly Asn Ile Gly Ser Glu Met Thr Arg Arg Phe Leu Ala Glu
20 25 30

Gly Ala Thr Val Ile Ile Ser Gly Arg Asn Ser Ala Lys Leu Ala Ala
35 40 45

Leu Ala Glu Arg Leu Arg Ser Glu Ala Gly Val Pro Ala Lys Arg Ile
50 55 60

Asp Leu Glu Val Met Asp Gly Ser Asp Pro Ala Ala Val Arg Ala Gly
65 70 75 80

Val Ala Ala Ile Ile Gly Arg His Gly His Ile Asp Ile Leu Val Asn
85 90 95

Asn Ala Gly Ser Thr Gly Ala Gln Arg Arg Leu Ala Glu Ile Pro Leu
100 105 110

Asn Glu Thr Asp Arg Asp Leu Asp Asp Glu Glu Ala Leu Ser Thr Ser
115 120 125

Val Ala Asn Leu Leu Gly Met Ala Trp His Leu Met Arg Ile Leu Ser
130 135 140

Pro His Met Pro Pro Gly Ser Ala Ile Ile Asn Ile Ser Thr Ile Phe
145 150 155 160

Ser Arg Ala Glu Tyr Tyr Gly Arg Ile Pro Tyr Val Val Pro Lys Ala
165 170 175

Ala Leu Asn Thr Leu Thr Gln Ile Ala Ala Arg Glu Leu Gly Ile Arg
180 185 190

```
Gly Ile Arg Val Asn Thr Ile Phe Pro Gly Pro Ile Glu Ser Glu Arg
        195                 200                 205

Ile Gln Thr Val Phe Gln Arg Met Asp Gln Leu Lys Gly Arg Pro Glu
    210                 215                 220

Gly Asp Thr Ala Ser Gln Phe Leu Ala Thr Met Arg Leu Tyr Arg Ala
225                 230                 235                 240

Asn Asp Gln Gly Gln Leu Glu Arg Arg Phe Pro Thr Ile Cys Asp Val
                245                 250                 255

Ala Asp Ala Ala Val Phe Leu Ala Ser Asp Glu Ala Ala Ala Leu Thr
            260                 265                 270

Gly Glu Thr Ile Glu Val Thr His Gly Met Glu Leu Pro Thr Ser Ser
        275                 280                 285

Glu Thr Ser Leu Leu Ala Arg Thr Asp Leu Arg Thr Ile Asp Ala Asn
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Glu Ala Ala Leu Ala Gln Phe Glu Gln Ala Ile Gly Glu
            340                 345                 350

Ser Arg Arg Leu Ala Gly Glu Ser Phe Ile Pro Pro Ile Ala Leu Pro
        355                 360                 365

Ile Asp Leu Arg Asn Pro Ser Thr Ile Asp Ala Leu Phe Asp Trp Ala
    370                 375                 380

Gly Glu Asn Thr Gly Gly Ile His Ala Ala Val Ile Leu Pro Ala Ser
385                 390                 395                 400

Gly Arg Glu Pro Ala Thr Gln Val Ile Asp Ile Asp Asp Ala His Val
                405                 410                 415

Gln Ala Phe Leu Asn Asp Glu Ile Val Gly Ser Ile Ile Ile Ala Ser
            420                 425                 430

Arg Leu Ala Arg Tyr Trp Gln Ala Gln Arg Ile Ala Pro Gly Ala Arg
        435                 440                 445

Ala Arg Glu Pro Arg Val Ile Phe Leu Ser Asn Gly Ala Ser Thr Ala
    450                 455                 460

Gly Asn Pro Tyr Gly Arg Ile Gln Ser Ala Ala Ile Glu Gln Leu Ile
465                 470                 475                 480

Arg Val Trp Arg His Glu Ala Ala Leu Asp Tyr Glu Arg Ala Thr Ala
                485                 490                 495

Ala Gly Glu Arg Val Leu Pro Ala Val Trp Ala Ser Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg Arg Ile Asn Glu Ile Thr Leu Thr
    530                 535                 540

Ile Pro Ala Asp Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
                565                 570                 575

Ile Thr Gly Gly Ser Ala Gly Ile Gly Gly Gln Ile Gly Arg Leu Leu
            580                 585                 590

Ala Leu Ser Gly Ala Arg Val Met Leu Ala Ala Arg Asp Pro His Lys
        595                 600                 605
```

```
Leu Glu Gln Ile Gln Ala Thr Ile Arg Ala Glu Leu Ala Glu Val Gly
    610                 615                 620

Tyr Thr Asp Val Glu Glu Arg Val Gln Ile Ala Pro Gly Cys Asp Val
625                 630                 635                 640

Ser Ser Glu Glu Gln Leu Val Asp Leu Val Glu Arg Thr Leu Ala Ala
                645                 650                 655

Phe Gly Thr Val Asp Tyr Leu Ile Asn Asn Ala Gly Ile Ala Gly Val
            660                 665                 670

Glu Glu Met Val Ile Asp Met Pro Val Glu Gly Trp Arg Asn Thr Leu
        675                 680                 685

Tyr Ala Asn Leu Ile Ser Asn Tyr Ser Leu Met Arg Lys Leu Ala Pro
    690                 695                 700

Leu Met Lys Lys Gln Gly Ser Gly Tyr Val Leu Asn Val Ser Ser Tyr
705                 710                 715                 720

Phe Gly Gly Glu Lys Asp Ala Ala Ile Pro Tyr Pro Asn Arg Ala Asp
                725                 730                 735

Tyr Ala Val Ser Lys Ala Gly Gln Arg Ala Met Ala Glu Val Phe Ala
            740                 745                 750

Arg Phe Leu Gly Pro Glu Ile Gln Ile Asn Ala Ile Ala Pro Gly Pro
        755                 760                 765

Val Glu Gly Asp Arg Leu Arg Gly Thr Gly Glu Arg Pro Gly Leu Phe
    770                 775                 780

Ala Arg Arg Ala Arg Leu Ile Leu Glu Asn Lys Arg Leu Asn Glu Leu
785                 790                 795                 800

His Ala Ala Leu Ile Thr Ala Ala Arg Thr Asp Asn Arg Pro Met Arg
                805                 810                 815

Glu Leu Val Glu Leu Leu Leu Pro Asn Asp Val Ala Ala Leu Ala Gln
            820                 825                 830

His Pro Ala Ala Pro Asp Val Leu Arg Thr Leu Ala Lys Arg Phe Gln
        835                 840                 845

Ser Glu Gly Asp Pro Ala Ala Ser Ser Ser Ser Phe Leu Leu Asn Arg
    850                 855                 860

Ser Ile Ala Ala Lys Leu Leu Ala Arg Leu Ile Asn Gly Gly Tyr Asp
865                 870                 875                 880

Leu Pro Ala Asp Ile Phe Ala Asn Leu Ala Val Pro Pro Asp Pro Phe
                885                 890                 895

Phe Thr Arg Ala Gln Ile Asp Arg Glu Ala Arg Lys Val Arg Asp Gly
            900                 905                 910

Ile Met Gly Met Leu Tyr Leu Gln Arg Met Pro Thr Glu Phe Asp Val
        915                 920                 925

Ala Met Ala Thr Val Tyr Tyr Leu Ala Asp Arg Asn Val Ser Gly Glu
    930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ala Pro Glu Arg Leu Ala Glu Leu Val
                965                 970                 975

Gly Ser Thr Val Tyr Leu Ile Gly Glu His Leu Thr Glu His Leu Asn
            980                 985                 990

Leu Leu Ala Arg Ala Tyr Leu Glu  Arg Tyr Gly Ala Arg  Gln Val Val
        995                 1000                1005

Met Ile  Val Glu Thr Glu Ala  Gly Ala Glu Lys Met  Arg His Leu
    1010                1015                1020

Leu His  Asp His Val Glu Ala  Gly Arg Leu Pro Ile  Ile Val Ala
```

```
    1025                1030                1035

Gly Asp  Gln Ile Glu Ala Ala  Ile Asp Gln Ala Ile  Ala Asn Tyr
    1040                1045                1050

Gly Arg  Pro Gly Pro Val Val  Cys Thr Pro Phe Arg  Pro Leu Pro
    1055                1060                1065

Ser Ala  Pro Leu Val Gly Arg  Lys Asp Ser Asp Trp  Ser Thr Val
    1070                1075                1080

Leu Ser  Glu Ala Glu Phe Ala  Glu Leu Cys Glu His  Gln Leu Thr
    1085                1090                1095

His His  Phe Arg Val Ala Arg  Lys Ile Ala Leu Ser  Asp Gly Ala
    1100                1105                1110

Ser Leu  Ala Leu Val Thr Pro  Glu Thr Thr Ala Thr  Ser Ser Thr
    1115                1120                1125

Glu Gln  Phe Ala Leu Ala Asn  Phe Val Lys Thr Thr  Leu His Ala
    1130                1135                1140

Phe Thr  Ala Thr Ile Gly Val  Glu Ser Glu Arg Thr  Ala Gln Arg
    1145                1150                1155

Ile Leu  Ile Asn Gln Val Asp  Leu Thr Arg Arg Ala  Arg Ala Glu
    1160                1165                1170

Glu Pro  Arg Asp Pro Arg Glu  Arg Gln Gln Glu Leu  Glu Arg Phe
    1175                1180                1185

Ile Glu  Ala Val Leu Leu Val  Thr Ala Pro Leu Pro  Pro Glu Ala
    1190                1195                1200

Asp Thr  Arg Tyr Ala Gly Arg  Ile His Arg Gly Arg  Ala Ile Thr
    1205                1210                1215

Val
```

<210> SEQ ID NO 294
<211> LENGTH: 1221
<212> TYPE: PRT
<213> ORGANISM: O. trichoides

<400> SEQUENCE: 294

```
Met Phe Met Thr Arg Leu Asn Asp Lys Ile Ala Leu Ile Thr Gly Gly
1               5                   10                  15

Ala Gly Thr Ile Gly Glu Val Ile Thr Arg Arg Tyr Leu Glu Glu Gly
            20                  25                  30

Ala Thr Val Val Met Ala Gly Arg Asn Arg Asp Lys Leu Asp Arg Tyr
        35                  40                  45

Arg Glu Arg Leu Ile Thr Glu Phe His Ala Leu Pro Glu Arg Val Met
    50                  55                  60

Val Val Arg Met Asp Gly Ser Ser Asn Ala Glu Val Arg Met Gly Ile
65                  70                  75                  80

Ala Ala Val Val Ala His Phe Gly Arg Ile Asp Ile Leu Val Asn Asn
                85                  90                  95

Ala Gly Ser Ala Gly Ala Arg Gln Arg Leu Pro Ala Ile Pro Leu Leu
            100                 105                 110

Arg Ser Glu Leu Gln Ala Asp Glu Thr Glu Thr Leu Ala Asp Ser Ile
        115                 120                 125

Gly Asn Leu Ile Gly Ile Thr Trp Asn Leu Ile Arg Ala Ala Ala Pro
    130                 135                 140

Phe Met Pro Ala Gly Ser Ser Val Ile Asn Ile Ser Thr Ile Phe Ala
145                 150                 155                 160

Arg Thr Asp Tyr Tyr Gly Arg Ile Pro Tyr Val Val Pro Lys Ala Ala
```

-continued

```
                165                 170                 175

Leu His Ala Leu Thr Leu Ala Ala Ala Thr Glu Leu Gly Glu Arg Gly
            180                 185                 190

Ile Arg Val Asn Gln Ile Asn Pro Gly Pro Ile Asp Ser Asp Arg Ile
        195                 200                 205

Arg Thr Val Phe Arg Arg Met Asp Glu Leu Lys Gly Val Pro Glu Gln
    210                 215                 220

Ser Thr Ala Asp Gly Phe Phe Gln Met Met Arg Leu Arg Arg Pro Asn
225                 230                 235                 240

Ala Glu Gly Asp Leu Val Lys Gly Phe Pro Lys Thr Leu Asp Val Ala
                245                 250                 255

Asn Val Ala Val Phe Leu Gly Ser Ala Glu Ser Ala Ala Leu Ser Gly
            260                 265                 270

Glu Thr Leu Asp Val Thr His Gly Met Ala Val Pro Thr Glu Ser Arg
        275                 280                 285

Thr Thr Leu Thr Ser Arg Pro Gly Leu Arg Ala Val Asp Gly Ser Gly
    290                 295                 300

His Thr Thr Leu Ile Cys Val Gly Asp Gln Ile Glu Glu Ala Ala Ala
305                 310                 315                 320

Leu Thr Gly Val Leu Arg Ala Cys Gly Ala Glu Val Val Ile Gly Phe
                325                 330                 335

Arg Ser Arg Ala Ala Ile Ala Arg Phe Asp His Leu Ile Glu Arg Gly
            340                 345                 350

Arg His Leu Pro Ser Gln Glu His Val Ala Pro Val Leu Leu Tyr Leu
        355                 360                 365

Asn Pro Thr Glu Pro Glu Ser Ile Asp Gln Ala Leu Arg Trp Met Ala
    370                 375                 380

Thr Asn Leu Asp Leu Pro Thr Ser Val Ile Ile Leu Pro Ala Gln Arg
385                 390                 395                 400

Gln Pro Leu Pro Pro Ser Val Val Arg Ala Ser Asp Glu Glu Val Ala
                405                 410                 415

Tyr Phe Leu Arg Asp Glu Leu Ser Gly Met Ile Val Leu Ala Ser Arg
            420                 425                 430

Leu Ala Arg Phe Trp Gln Gln Ala Thr Leu Ala Pro Gly Asn Ala Pro
        435                 440                 445

Ile Gln Pro Arg Val Leu Phe Met Thr Asn Pro Asp Asp Gly Gln Gly
    450                 455                 460

Asn Leu Tyr Ala Glu Ile Leu Arg Ala Gly Val Glu Gln Leu Cys Arg
465                 470                 475                 480

Val Trp Arg His Glu Ser Gln Leu Asp Tyr Thr Arg Leu Ala Gln Met
                485                 490                 495

Asp Ala His Pro Pro His Ile Arg Pro Val Trp Ala Asn Gln Leu Val
            500                 505                 510

Arg Phe Ala Asn Asn Glu Gln Glu Asn Leu Glu Tyr Cys Cys Ala Trp
        515                 520                 525

Val Ala Lys Ile Leu Leu Ser Glu Arg Thr Ile Glu Glu Leu Asn Leu
    530                 535                 540

Tyr Leu Pro Arg Gln Ile Gly Ser Thr Thr Gly Ser Arg Gln Pro Ser
545                 550                 555                 560

Phe Gly Trp Ala Glu Asn Leu Ile Gly Leu His Leu Gly Lys Thr Ala
                565                 570                 575

Leu Ile Thr Gly Gly Ser Ala Gly Ile Gly Ser Gln Ile Ala Arg Leu
            580                 585                 590
```

```
Leu Ala Leu Ser Gly Ala Arg Val Met Leu Cys Ala Arg Asp Glu Arg
        595                 600                 605

Lys Leu Ile Gln Met Arg Asp Met Ile Ile Ala Glu Leu Thr Glu Val
    610                 615                 620

Gly Tyr Asn Gln Val Glu Ser Arg Val Gln Ile Cys Ala Gly Cys Asp
625                 630                 635                 640

Val Gly Glu Glu Glu Gln Leu Glu Ile Ala Val Gln Arg Thr Leu Asp
                645                 650                 655

Leu Phe Gly His Val Asp Tyr Leu Ile Asn Asn Ala Gly Ile Ala Gly
            660                 665                 670

Ala Glu Glu Met Val Leu Asp Leu Pro Leu Glu Ala Trp Gln Arg Thr
        675                 680                 685

Leu Arg Thr Asn Leu Ile Ser Asn Tyr Ser Leu Ile Arg Lys Leu Ala
    690                 695                 700

Pro Gln Met Lys Ser Arg Gly Ser Gly Tyr Ile Leu Asn Val Ser Ser
705                 710                 715                 720

Tyr Phe Gly Gly Glu Lys Tyr Ala Ala Ile Pro Tyr Pro Asn Arg Ala
                725                 730                 735

Asp Tyr Ala Val Ser Lys Ala Gly Gln Arg Ala Leu Gly Glu Ala Leu
            740                 745                 750

Ala Arg Leu Leu Gly Pro Glu Val Gln Ile Asn Ala Met Ala Pro Gly
        755                 760                 765

Pro Val Glu Gly Glu Arg Leu Arg Gly Ser Gly Asp Arg Pro Gly Leu
    770                 775                 780

Phe Leu Arg Arg Gly Arg Leu Ile Leu Glu Asn Lys Arg Leu Asn Asp
785                 790                 795                 800

Leu His Ala Thr Leu Ile Ala Ala Glu Arg Glu Thr Gln Val Gly Met
                805                 810                 815

Arg Asp Leu Leu Ala Arg Leu Leu His Asn Asp Val Cys Ala Leu Ile
            820                 825                 830

Asp Asp Pro Ala Ala Pro Thr His Leu Arg Ala Leu Ala Glu Arg Ile
        835                 840                 845

Trp Glu Gln Ser Asp Pro Asn Ser Tyr Ala Arg Ala Phe Phe Met Asn
    850                 855                 860

Ala Asn Ile Ala Thr Lys Leu Leu Ala Arg Leu Phe Asn Ala Asp Gln
865                 870                 875                 880

Ile Asp Ala Gln Thr Phe His Thr Ser Gln Pro Asn Leu Pro Pro Glu
                885                 890                 895

Pro Phe Phe Ala Arg Thr Gln Ile Asp Arg Glu Ala Arg Arg Val Arg
            900                 905                 910

Asp Gly Val Met Ser Met Leu Tyr Leu Gln Arg Met Pro Thr Glu Phe
        915                 920                 925

Asp Val Ala Leu Ala Thr Val Tyr Tyr Leu Asn Asp Arg Ser Val Ser
    930                 935                 940

Gly Glu Thr Phe His Pro Ser Gly Gly Leu Arg His Glu Arg Thr Pro
945                 950                 955                 960

Thr Gly Ala Glu Leu Tyr Gly Ser Pro Ala Pro Gln Arg Leu Ala Ser
                965                 970                 975

Leu Ala Gly Ser Thr Val Tyr Leu Ile Gly Glu Ser Met Ala Ala His
            980                 985                 990

Leu Glu Ala Leu Ala Arg Ala Tyr  Ile Glu Arg Tyr Ala  Ala Thr Arg
        995                 1000                1005
```

Val Val Leu Ile Cys Ala Thr Pro Ala Gly Val Glu Arg Phe Ser
1010 1015 1020

His His Leu Ala Asp His Leu Ala Ser Gly Ala Leu Ala Ile Leu
1025 1030 1035

Ser Ala Glu Glu Gly Ile Glu Ala Ala Leu Ser Glu Ala Leu Arg
1040 1045 1050

Arg Phe Gly Pro Pro Gly Pro Val Val Ser Thr Pro Phe Gln Pro
1055 1060 1065

Leu Pro Ser Gln Pro Leu Ile Gly Arg Asn Asp Ser Asp Trp Ser
1070 1075 1080

Thr Val Leu Asp Val Ala Gly Phe Ser Ala Met Cys Glu Gln Gln
1085 1090 1095

Leu Thr His His Phe Arg Val Thr Arg Lys Leu Ser Leu Val Ala
1100 1105 1110

Gly Val Ser Leu Val Leu Val Thr Pro Glu Thr Asp Ser His Ser
1115 1120 1125

Ser Thr Glu Gln Phe Ala Leu Ala Asn Phe Val Lys Thr Thr Leu
1130 1135 1140

His Ala Phe Thr Ala Thr Val Gly Val Glu Cys Glu Arg Thr Ala
1145 1150 1155

His Arg Ile Leu Val Asn Gln Val Asp Leu Gly Arg Gln Ala Arg
1160 1165 1170

Ala Glu Glu Pro Arg Ser Pro Ala Glu Gln Ala Gln Glu Met Glu
1175 1180 1185

Arg Phe Ile Asp Ala Ile Met Leu Thr Thr Ala Pro Ile Pro Ala
1190 1195 1200

Glu Glu Asp Asn Arg Tyr Thr Gly Arg Ile Tyr Arg Gly Arg Ala
1205 1210 1215

Ile Thr Val
1220

<210> SEQ ID NO 295
<211> LENGTH: 1229
<212> TYPE: PRT
<213> ORGANISM: R. castenholzii

<400> SEQUENCE: 295

Met Ser Thr Val Arg Arg Leu Glu Gly Lys Val Ala Leu Ile Thr Gly
1 5 10 15

Gly Ala Gly Asn Ile Gly Glu Val Ile Thr Arg Arg Phe Leu Ala Glu
20 25 30

Gly Ala Thr Val Val Ile Thr Gly Arg Asn Ala Glu Lys Leu Ala Val
35 40 45

Tyr Arg Arg Arg Leu Ile Asp Glu Glu Arg Val Ala Pro Glu Arg Val
50 55 60

Val Ala Leu Arg Met Asp Gly Ser Asp Ile Ala Gln Val Arg Ala Gly
65 70 75 80

Val Ala Gln Ile Val His Gly Gly Thr Asp Val Pro Ile Pro Leu His
85 90 95

Arg Ile Asp Ile Leu Val Asn Asn Ala Gly Ser Ala Gly Pro Arg Arg
100 105 110

Arg Leu Val Asp Ile Pro Leu Glu Pro Ser Glu Val Gln Pro Pro Asp
115 120 125

Ser Glu Thr Leu Ala Gln Ala Val Gly Asn Leu Val Gly Ile Thr Trp
130 135 140

-continued

```
Asn Leu Thr Arg Ala Ala Ala Pro His Met Pro Ser Gly Ser Ser Val
145                 150                 155                 160

Ile Asn Ile Ser Thr Ile Phe Ser Arg Thr Asp Tyr Tyr Gly Arg Ile
                165                 170                 175

Ala Tyr Val Ala Pro Lys Ala Ala Leu Asn Ala Leu Ser Asp Gly Leu
            180                 185                 190

Ala Arg Glu Leu Gly Val Arg Gly Ile Arg Val Asn Thr Ile Tyr Pro
        195                 200                 205

Gly Pro Ile Glu Ser Glu Arg Ile Tyr Thr Met Phe Gln Ala Met Asp
    210                 215                 220

Ala Leu Lys Gly Gln Pro Glu Gly Asp Thr Ala Ser Gly Phe Leu Arg
225                 230                 235                 240

Met Met Arg Leu Ser Arg Ile Asp Gln Asn Gly Glu Val Val Lys Arg
                245                 250                 255

Phe Pro Ser Pro Val Asp Val Ala Asn Thr Ala Val Phe Leu Ala Ser
            260                 265                 270

Asp Glu Ser Ala Ala Phe Thr Gly His Ala Phe Glu Val Thr His Gly
        275                 280                 285

Met Glu Val Pro Thr Glu Ser Arg Thr Thr Phe Val Ser Arg Pro Gly
    290                 295                 300

Leu Arg Ser Val Asp Ala Thr Gly Lys Val Ile Leu Ile Cys Ala Gly
305                 310                 315                 320

Asp Gln Val Asp Asp Ala Val Ala Leu Ala Asp Thr Leu Arg Ser Cys
                325                 330                 335

Arg Ala Thr Val Val Ile Gly Phe Arg Asp Pro Arg Ala Leu Glu Lys
            340                 345                 350

Ala Ser Val Leu Leu Arg Glu Pro Arg His Ala Leu Ala Ala Asp Met
        355                 360                 365

Tyr Gly Arg Pro Thr Met Thr Ala Glu Ala Arg Leu Val Arg Leu Asp
    370                 375                 380

Pro Leu Asp Pro Arg Ala Ala Ala Gln Thr Leu Glu Gln Ile His Ala
385                 390                 395                 400

Glu Leu Gly Ala Ile His His Ala Val Val Leu Pro Gly Gln Ser Arg
                405                 410                 415

His Ala Pro Ser Ala Ser Leu Ile Glu Val Asp Asp Gln Val Val Glu
            420                 425                 430

Arg Phe Leu His Gln Glu Leu Val Gly Thr Ile Ala Leu Ala Arg Glu
        435                 440                 445

Leu Ala Arg Phe Trp Glu Glu Tyr Pro Ser Gly Ser Ser Met His Arg
    450                 455                 460

Val Leu Phe Val Ser Asn Pro Asp Asp Gln Gln Gly Asn Gln Tyr Ser
465                 470                 475                 480

His Ile Leu Arg Ala Ala Val Glu Gln Leu Val Arg Val Trp Arg His
                485                 490                 495

Glu Ser Glu Tyr Asp Ser Val Asn Pro Ala His Gln Gln Glu Gly Gln
            500                 505                 510

Ser Ser Ala Ala Val Trp Ala Asn Gln Leu Ile Arg Tyr Val Asn Asn
        515                 520                 525

Glu Met Ala Asn Leu Asp Phe Thr Cys Ala Trp Val Ala Lys Leu Leu
    530                 535                 540

Gly Ser Asp Arg Arg Ile Ala Glu Ile Asn Leu Tyr Leu Pro Glu Glu
545                 550                 555                 560
```

-continued

```
Ile Val Gly Thr Ile Gly Val His Asn Pro Gly Phe Gly Trp Ala Glu
                565                 570                 575

Ser Leu Phe Gly Leu His Met Gly Lys Val Ala Leu Ile Thr Gly Gly
            580                 585                 590

Ser Ala Gly Ile Gly Gly Gln Ile Gly Arg Leu Leu Ala Leu Ser Gly
        595                 600                 605

Ala His Val Met Leu Ala Ala Arg Asn Ala Asp Gln Leu Glu Gln Met
    610                 615                 620

Arg Ala Ser Ile Val Arg Glu Val Arg Asp Ala Ser Tyr Pro Asp Ala
625                 630                 635                 640

Glu Ser Arg Val Ala Ile Phe Pro Gly Ser Asp Val Ser Asp Ile Asp
                645                 650                 655

Gly Leu Glu Arg Leu Val Asn His Thr Val Arg Val Phe Gly Lys Val
            660                 665                 670

Asp Tyr Leu Ile Asn Asn Ala Gly Ile Ala Gly Ala Glu Glu Met Val
        675                 680                 685

Ile Asp Met Pro Val Asp Ala Trp Arg His Thr Leu Arg Ala Asn Leu
    690                 695                 700

Ile Ser Asn Tyr Ala Leu Leu Arg Arg Leu Ala Pro Gln Met Lys Ala
705                 710                 715                 720

Ala Gly Gly Ala Tyr Val Leu Asn Val Ser Ser Tyr Phe Gly Gly Glu
                725                 730                 735

Lys Tyr Val Ala Ile Pro Tyr Pro Asn Arg Ser Asp Tyr Ala Val Ser
            740                 745                 750

Lys Ala Gly Gln Arg Ala Met Val Glu Ser Leu Ala Arg Phe Leu Gly
        755                 760                 765

Pro Glu Ile Gln Ile Asn Ala Ile Ala Pro Gly Pro Val Glu Gly Glu
    770                 775                 780

Arg Leu Lys Gly Ala Gly Ser Arg Pro Gly Leu Phe Met Arg Arg Ala
785                 790                 795                 800

Arg Leu Ile Leu Glu Asn Lys Arg Leu Asn Glu Val Phe Ala Ala Leu
                805                 810                 815

Leu Ala Ala Arg His Glu Gly Ala Thr Ile Ala Asp Leu Leu Pro Asp
            820                 825                 830

Leu Phe Ala Asn Asp Ile Gln Ser Ile Ala Asn Ser Ala Ala Met Pro
        835                 840                 845

Ala Pro Leu Arg Arg Leu Ala Thr Met Leu Arg Glu Thr Ser Asp Ala
    850                 855                 860

Gly Gly Ser Ala Gln Ser Tyr Leu Met Asn Ala Thr Ile Ala Arg Lys
865                 870                 875                 880

Leu Leu Asn Arg Leu Glu Asn Gly Gly Tyr Ile Thr Leu His Asp Arg
                885                 890                 895

Arg Ala Leu Thr Val Glu Pro Pro Glu Pro Phe Phe Thr Glu Ala Gln
            900                 905                 910

Ile Glu Arg Glu Ala Ile Lys Val Arg Asp Gly Ile Leu Gly Met Leu
        915                 920                 925

His Leu Gln Arg Met Pro Thr Glu Phe Asp Val Ala Leu Ala Thr Val
    930                 935                 940

Phe Tyr Leu Ala Asp Arg Asn Val Thr Gly Glu Thr Phe His Pro Ser
945                 950                 955                 960

Gly Gly Leu Arg Phe Glu Arg Thr Val Thr Glu Gly Glu Leu Phe Gly
                965                 970                 975

Lys Pro Gly Gln Gln Arg Leu Glu Arg Leu Lys Gly Ser Val Val Tyr
```

```
            980                 985                 990

Leu Ile Gly Glu His Leu Arg Gln  His Leu Val Leu Leu  Ala Arg Thr
        995                 1000                1005

Phe Leu  Asp Glu Ile His Val  Ala Arg Val Val Leu  Leu Thr Glu
    1010                 1015                1020

Thr Thr  Gln Ala Ala Thr Asp  Leu Ala Ala Glu Leu  Ser Asp Tyr
    1025                 1030                1035

Glu Ala  Ala Gly Arg Phe Val  Val Ile Pro Thr Cys  Gly Asp Ile
    1040                 1045                1050

Glu Gly  Gly Ile Asp Arg Ala  Met Ala Glu Tyr Gly  Arg Pro Gly
    1055                 1060                1065

Pro Val  Ile Ser Thr Pro Phe  Arg Pro Leu Pro Asp  Arg Ala Leu
    1070                 1075                1080

Ser Ala  Arg Asn Gly Asp Trp  Ser Ser Val Leu Thr  Thr Ala Glu
    1085                 1090                1095

Phe Glu  Glu Leu Val Glu Gln  Gln Ile Thr His His  Phe Arg Val
    1100                 1105                1110

Ala Arg  Lys Ala Gly Leu Ile  Glu Gly Ala Asn Val  Thr Leu Val
    1115                 1120                1125

Thr Pro  Pro Thr Ser Ala Arg  Ser Thr Ser Glu Glu  Phe Ala Leu
    1130                 1135                1140

Ala Asn  Phe Val Lys Thr Thr  Leu His Ala Leu Thr  Ala Thr Ala
    1145                 1150                1155

Gly Ala  Glu Ser Glu Arg Thr  Val Pro His Val Pro  Val Asn Gln
    1160                 1165                1170

Val Asp  Leu Thr Arg Arg Ala  Arg Ser Glu Glu Pro  Arg Thr Pro
    1175                 1180                1185

Ser Glu  Glu Glu Glu Glu Leu  Gln Arg Phe Val Asn  Ala Val Leu
    1190                 1195                1200

Leu Thr  Ser Ala Pro Leu Pro  Thr Pro Leu Glu Ser  Arg Tyr Arg
    1205                 1210                1215

Ala Arg  Ile Tyr Arg Gly Asn  Ala Ile Thr Val
    1220                 1225


<210> SEQ ID NO 296
<211> LENGTH: 1232
<212> TYPE: PRT
<213> ORGANISM: Roseiflexus sp.

<400> SEQUENCE: 296

Met Ser Thr Thr Arg Arg His Asp Arg Leu Glu Gly Lys Val Ala Leu
1               5                   10                  15

Ile Thr Gly Gly Ala Gly Asn Ile Gly Glu Val Ile Thr Arg Arg Phe
            20                  25                  30

Leu Ala Glu Gly Ala Thr Val Val Ile Thr Gly Arg Asn Val Glu Lys
        35                  40                  45

Leu Ala Ala Tyr Arg Arg Arg Leu Ile Asp Glu Glu Arg Ile Ala Pro
    50                  55                  60

Asp Arg Val Val Ala Leu Arg Met Asp Gly Ser Asp Met Ala Gln Val
65                  70                  75                  80

Arg Ala Ala Ile Ala Gln Ile Val His Gly Gly Ala Asp Val Pro Thr
                85                  90                  95

Pro Leu Lys Arg Ile Asp Ile Leu Val Asn Asn Ala Gly Ser Ala Gly
            100                 105                 110
```

-continued

```
Pro Arg Arg Arg Leu Val Asp Ile Pro Leu Glu Pro Ser Glu Val His
        115                 120                 125

Pro Pro Asp Thr Glu Thr Leu Ala Gln Ala Val Gly Asn Leu Val Gly
    130                 135                 140

Val Ala Trp Asn Leu Thr Arg Ala Ala Ala Pro Tyr Met Pro Pro Gly
145                 150                 155                 160

Ser Ser Ile Ile Asn Val Ser Thr Ile Phe Ser Arg Thr Asp Tyr Tyr
                165                 170                 175

Gly Arg Ile Ala Tyr Val Val Pro Lys Ala Ala Leu Asn Ala Leu Ser
            180                 185                 190

Gln Gly Leu Ala Arg Glu Leu Gly Val Arg Gly Ile Arg Val Asn Thr
        195                 200                 205

Ile Tyr Pro Gly Pro Ile Glu Ser Glu Arg Ile His Thr Val Phe Gln
    210                 215                 220

Ala Met Asp Ala Leu Lys Gly Gln Pro Glu Gly Glu Thr Ala Arg Ser
225                 230                 235                 240

Phe Leu Arg Leu Met Arg Leu Ser Arg Ala Asp Thr Gln Gly Glu Val
                245                 250                 255

Thr Lys Arg Phe Pro Leu Pro Val Asp Val Ala Asn Thr Ala Val Phe
            260                 265                 270

Leu Ala Ser Glu Glu Ser Ala Ala Phe Thr Gly His Ala Phe Glu Val
        275                 280                 285

Thr His Gly Met Glu Ala Pro Val Glu Ser Arg Thr Thr Phe Val Ser
    290                 295                 300

Arg Pro Gly Leu Arg Ser Val Asp Ala Thr Gly Asn Val Ile Leu Ile
305                 310                 315                 320

Cys Ala Gly Asp Gln Val Asp Asp Ala Ile Ala Leu Ser Asp Thr Leu
                325                 330                 335

Arg Ser Cys Arg Ala Thr Val Val Val Gly Phe Arg Asp Val Gln Ala
            340                 345                 350

Leu Glu Lys Ala Ser Ala Leu Leu Arg Glu Pro Arg His Val Ala Pro
        355                 360                 365

Ala Asp Met Tyr Gly Arg Pro Thr Met Val Ala Glu Thr Arg Leu Val
    370                 375                 380

His Leu Asp Pro Leu Asp Ser Arg Ala Ala Ala Gln Thr Leu Glu Arg
385                 390                 395                 400

Ile Arg Ala Glu Leu Gly Thr Leu His His Ala Val Ile Leu Pro Ala
                405                 410                 415

Ser Leu Arg His Ala Pro Thr Glu Ser Leu Ile Asp Val Asp Asp Arg
            420                 425                 430

Ile Ile Asp Arg Phe Leu Glu Gln Glu Leu Val Gly Ala Ile Ala Leu
        435                 440                 445

Ala Arg Glu Leu Ala Arg Phe Trp Glu Glu His Pro Ala Gly Ser Arg
    450                 455                 460

Ala His Arg Val Leu Phe Val Ser Asn Pro Asp Asp Gln Gln Gly Asn
465                 470                 475                 480

Arg Tyr Ala Asp Ile Leu Arg Ala Ala Val Glu Gln Leu Ala Arg Val
                485                 490                 495

Trp Arg His Glu Ser Glu Tyr Asp Ala Ala Asn Pro Ala His Arg His
            500                 505                 510

Glu Asp Gln Pro Gly Ala Ala Val Trp Ala Asn Gln Leu Ile Arg Tyr
        515                 520                 525

Val Asn Ser Glu Ser Ala Asn Leu Asp Phe Thr Cys Ala Trp Val Ala
```

```
    530                 535                 540

Lys Leu Leu Gly Ser Asp Arg Arg Ile Ala Glu Ile Asn Leu Tyr Leu
545                 550                 555                 560

Pro Glu Gln Ile Val Ser Thr Ile Gly Val His Asn Pro Gly Phe Gly
                565                 570                 575

Trp Ala Glu Ser Leu Phe Gly Leu His Met Gly Lys Val Ala Leu Ile
            580                 585                 590

Thr Gly Gly Ser Ala Gly Ile Gly Ala Gln Ile Gly Arg Leu Leu Ala
        595                 600                 605

Leu Ser Gly Ala His Val Met Leu Ala Ala Arg Asn Ala Glu Gln Leu
    610                 615                 620

Glu Gln Met Arg Ala Leu Ile Val Arg Glu Val Arg Asp Ala Ser Tyr
625                 630                 635                 640

Pro Asp Ala Glu Ser Arg Val Ala Ile Phe Pro Asn Ser Asp Val Ser
                645                 650                 655

Asp Ile Asp Gly Leu Glu Arg Leu Val Asn His Thr Leu Arg Val Phe
            660                 665                 670

Gly Lys Val Asp Tyr Leu Ile Asn Asn Ala Gly Ile Ala Gly Ala Glu
        675                 680                 685

Glu Met Val Ile Asp Met Pro Val Asp Ala Trp Arg His Thr Leu Arg
    690                 695                 700

Ala Asn Leu Ile Ser Asn Tyr Ala Leu Leu Arg Arg Leu Ala Pro Gln
705                 710                 715                 720

Met Lys Ala Ala Gly Gly Ala Tyr Val Leu Asn Val Ser Ser Tyr Phe
                725                 730                 735

Gly Gly Glu Lys Tyr Val Ala Ile Pro Tyr Pro Asn Arg Ala Asp Tyr
            740                 745                 750

Ala Val Ser Lys Ala Gly Gln Arg Ala Met Val Glu Ser Leu Ala Arg
        755                 760                 765

Phe Leu Gly Pro Glu Ile Gln Ile Asn Ala Ile Ala Pro Gly Pro Val
    770                 775                 780

Glu Gly Glu Arg Leu Lys Gly Ala Ala Asn Arg Pro Gly Leu Phe Met
785                 790                 795                 800

Arg Arg Ala Arg Leu Ile Leu Glu Asn Lys Arg Leu Asn Glu Val Phe
                805                 810                 815

Ala Ala Leu Leu Ala Ala Arg His Glu Gly Ala Val Ile Ala Ala Leu
            820                 825                 830

Leu Pro Asp Leu Phe Val Asn Asp Leu Gln Thr Ile Ala Asp Asn Pro
        835                 840                 845

Ala Met Pro Ala Pro Val Arg Arg Leu Ala Thr Met Leu Arg Glu Thr
    850                 855                 860

Thr Asp Ala Gly Gly Ser Ala Gln Ser Tyr Leu Met Asn Ala Thr Ile
865                 870                 875                 880

Ala Arg Lys Leu Leu Asn Arg Leu Glu Asn Gly Gly Tyr Ile Thr Ala
                885                 890                 895

Gly Asp Arg Arg Ala Leu Thr Asn Glu Pro Pro Asp Pro Phe Phe Thr
            900                 905                 910

Glu Ala Gln Ile Glu Arg Glu Ala Ile Lys Val Arg Asp Gly Ile Leu
        915                 920                 925

Gly Met Leu His Leu Gln Arg Met Pro Thr Glu Phe Asp Val Ala Leu
    930                 935                 940

Ala Thr Val Phe Tyr Leu Ala Asp Arg Asn Val Thr Gly Glu Thr Phe
945                 950                 955                 960
```

-continued

His Pro Ser Gly Gly Leu Arg Phe Glu Arg Thr Val Thr Glu Gly Glu
965 970 975

Leu Phe Gly Lys Pro Gly Arg Gln Arg Leu Glu Arg Met Ala Gly Ser
980 985 990

Val Val Tyr Leu Ile Gly Glu His Leu Arg Gln His Leu Leu Leu Leu
995 1000 1005

Ala Arg Thr Phe Leu Asp Glu Ile His Val Ala Arg Val Val Leu
1010 1015 1020

Leu Thr Glu Thr Glu Gln Ala Ala Ala Glu Leu Ala Thr Val Phe
1025 1030 1035

Ala Asp Glu Glu Ala Ala Gly Arg Phe Val Ile Ile Pro Thr Gly
1040 1045 1050

Gly Asp Ile Glu Gly Gly Ile Asp Arg Ala Met Ala Glu Tyr Gly
1055 1060 1065

Arg Pro Gly Pro Val Ile Ser Thr Pro Phe Arg Pro Leu Pro Ser
1070 1075 1080

Arg Ala Leu Ser Ala Gln Asn Gly Asp Trp Ser Asn Val Leu Thr
1085 1090 1095

Thr Pro Glu Phe Glu Glu Leu Val Glu Gln His Ile Thr His His
1100 1105 1110

Phe Arg Val Val Arg Lys Ala Gly Leu Ile Glu Gly Ala Asn Val
1115 1120 1125

Thr Leu Val Thr Pro Pro Thr Ser Ala Arg Ser Thr Ala Glu Glu
1130 1135 1140

Phe Ala Leu Ala Asn Phe Ile Lys Thr Thr Leu His Ala Leu Thr
1145 1150 1155

Ala Thr Ala Gly Ala Glu Ser Glu Arg Thr Met Pro His Val Pro
1160 1165 1170

Val Asn Gln Val Asp Leu Thr Arg Arg Ala Arg Ser Glu Glu Pro
1175 1180 1185

Arg Thr Pro Ala Glu Glu Glu Glu Glu Leu Gln Arg Phe Val Asn
1190 1195 1200

Ala Val Leu Leu Thr Ser Ala Pro Leu Pro Thr Pro Leu Glu Ser
1205 1210 1215

Arg Tyr Arg Ala Arg Ile Tyr Arg Gly Asn Ala Ile Thr Val
1220 1225 1230

<210> SEQ ID NO 297
<211> LENGTH: 1217
<212> TYPE: PRT
<213> ORGANISM: Erythrobacter sp

<400> SEQUENCE: 297

Met Ser Lys Glu Gly Asn Ala Ala Lys Gly Arg Leu Glu Gly Lys Val
1 5 10 15

Ala Leu Ile Thr Gly Ala Ala Gly Asn Leu Gly Asn Glu Ile Ser Arg
20 25 30

Ala Phe Ala Arg Glu Gly Ala Phe Val Val Met Thr Gly Arg Thr Glu
35 40 45

Glu Arg Ile Ser Ala Ala Arg Glu Gln Leu Ile Ala Asp Thr Gly Val
50 55 60

Ala Pro Glu Arg Ile Asp Thr Ala Val Leu Asp Gly Gly Asn Pro Asp
65 70 75 80

Ser Ile Arg Ala Ala Met Ala Lys Leu Arg Lys Glu Tyr Gly Arg Ile

-continued

```
                85                  90                  95

Asp Ile Leu Ile Asn Asn Ala Gly Ser Ala Gly Pro Lys Gln Pro Leu
            100                 105                 110

His Asn Val Pro Leu Ser Pro Gln Glu Met Glu Ala Cys Gly Asp Thr
        115                 120                 125

Glu Thr Val Arg Asp Ala Met Leu Asn Ile Leu Gly Val Thr Trp Asn
    130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
                165                 170                 175

Tyr Val Val Pro Lys Ala Ala Leu Asn Ala Leu Ser Asn Gln Leu Ala
            180                 185                 190

Ser Glu Leu Gly Pro Arg Gly Ile Arg Val Asn Thr Val Phe Pro Gly
        195                 200                 205

Pro Ile Glu Ser Asp Arg Ile Arg Thr Val Phe Ala Ala Met Asp Glu
    210                 215                 220

Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
                245                 250                 255

Pro Asn Pro Lys Asp Ile Ala Gly Thr Cys Leu Phe Leu Ala Ser Glu
            260                 265                 270

Glu Ala Ala Gly Ile Ala Gly Glu Glu Val Asp Val Thr His Gly Leu
        275                 280                 285

Ser Ala Asn Arg Thr Ser Ala Ser Thr Tyr Met Thr Arg Pro Ser Met
    290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
                325                 330                 335

Ala Lys Val Arg Leu Gly Leu Ala Arg Asn Ala Asp Val Ala Gln Ala
            340                 345                 350

Asn Ala Arg Leu Lys Ala Gln Gly Ile Gly Glu Glu Leu Thr Val Thr
        355                 360                 365

Arg Phe Asn Arg Ala Glu Pro Asp Ala Met Glu Asp Ala Leu Ala Ala
    370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
                405                 410                 415

Asp Thr Val Thr Lys Phe Met Asp Thr Glu Leu Val Gly Ala Ile Ala
            420                 425                 430

Val Ser Arg Ser Leu Ala Arg Tyr Trp His Gly Arg Glu Asp Leu Gln
        435                 440                 445

Ser Pro Pro Arg Cys Val Phe Met Thr Asn Pro Gly Asp Pro Leu Gly
    450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
                485                 490                 495

His Ala Val Trp Ser Asn Gln Ile Val Arg His Thr Asn Thr Glu Asp
            500                 505                 510
```

-continued

```
Glu Asn Thr Arg Phe Ala Ser Gly His Ala Thr Arg Val Leu Phe Arg
        515                 520                 525

Glu Gln His Ile Ala Glu Ile Asp Leu Lys Leu Pro Ala Asn Ile Ser
    530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
                565                 570                 575

Gly Ile Gly Gly Gln Val Ala Arg Leu Leu Ala Leu Ala Gly Ala Lys
            580                 585                 590

Val Met Met Val Ala Arg Arg Glu Ser Glu Leu Val Ala Ala Arg Asp
        595                 600                 605

Arg Ile Val Gly Glu Leu Gln Asp Ile Gly Phe Ala Gly Val Glu Arg
    610                 615                 620

Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
                645                 650                 655

Leu Ile Asn Asn Ala Gly Val Ala Gly Ala Glu Asp Met Val Ile Asp
            660                 665                 670

Met Glu Pro Glu Ala Trp Arg Phe Thr Leu Asp Ala Asn Leu Ile Ser
        675                 680                 685

Asn Tyr His Leu Met Gln Arg Val Val Pro Leu Met Lys Glu Gln Gly
    690                 695                 700

Ser Gly Tyr Val Leu Asn Val Ser Ser Tyr Phe Gly Gly Glu Lys Phe
705                 710                 715                 720

Leu Ala Val Ala Tyr Pro Asn Arg Ala Asp Tyr Gly Leu Ser Lys Ala
                725                 730                 735

Gly Gln Arg Ala Met Val Glu Ala Phe Ser Pro Phe Leu Gly Pro Glu
            740                 745                 750

Val Gln Cys Asn Ala Ile Ala Pro Gly Pro Val Asp Gly Asp Arg Leu
        755                 760                 765

Ser Gly Thr Gly Gly Lys Pro Gly Leu Phe Gln Arg Arg Ala Lys Leu
    770                 775                 780

Ile Leu Glu Asn Lys Arg Leu Asn Ala Val Tyr Ser Ala Val Ile His
785                 790                 795                 800

Ala Ile Arg Glu Gly Gly Asp Ala Ala Lys Ile Leu Thr Arg Leu Ser
                805                 810                 815

Arg Asn Ser Thr Ser Thr Leu Ser His Asp Ala Glu Ala Pro Glu Glu
            820                 825                 830

Leu Arg Lys Leu Ala Leu Asp Phe Ala Ser Gln Gly Asp Gly Leu Cys
        835                 840                 845

Thr Trp Asp Gln Tyr Leu Leu Thr Asp Ala Met Ala Gln Arg Leu Leu
    850                 855                 860

Val Arg Leu Gln Leu Gly Gly Phe Leu Leu Gly Ser Asn Glu Trp Ala
865                 870                 875                 880

Ser Leu Ser Ser Ser Glu Gln Thr Trp Leu Lys Leu Ser Pro Pro Asp
                885                 890                 895

Asp Lys Pro Phe Leu Pro Ala Ala Gln Val Asp Lys Val Ala Asn Gly
            900                 905                 910

Val Gly Lys Gly Val Ile Ser Gln Leu His Leu Gly Ala Met Pro Thr
        915                 920                 925
```

```
Glu Ala Glu Val Ala Gln Ala Thr Val Phe Phe Leu Ala Asp Arg Ala
    930                 935                 940

Val Ser Gly Glu Thr Phe Met Pro Ser Gly Gly Leu Arg Val Glu Arg
945                 950                 955                 960

Ser Asn Thr Glu Arg Glu Met Phe Gly Ser Pro Lys Gln Glu Arg Ile
                965                 970                 975

Asp Lys Met Lys Gly Lys Thr Val Trp Ile Ile Gly Glu His Leu Ser
            980                 985                 990

Asp Tyr Val Ala Ala Thr Ile Glu  Glu Leu Val Ser Gly  Cys Gly Val
        995                 1000                 1005

Ala Lys  Val Val Leu Ile Ala  Lys Asp Lys Ser Gly  Glu Lys Ala
    1010                 1015                 1020

Val Arg  Asp Gln Leu Pro Asn  Asp Leu Ser Lys Asp  Ala Leu Glu
    1025                 1030                 1035

Val Leu  Ile Ala Gly Asp Gly  Leu Glu Glu Ala Met  Asp Glu Ala
    1040                 1045                 1050

Leu Gly  His Trp Gly Lys Pro  Thr Thr Val Leu Ser  Met Pro Gly
    1055                 1060                 1065

Glu Pro  Leu Pro Asp His Leu  Phe Glu Gly Gly Asn  Pro Leu Ser
    1070                 1075                 1080

Thr Lys  Asp Phe Ala His Met  Val Glu Ala Asn Ile  Thr Arg His
    1085                 1090                 1095

Tyr Arg  Val Thr Arg Lys Ala  Ser Leu Tyr Asp Gly  Cys Gln Val
    1100                 1105                 1110

Val Leu  Val Ser Pro Asp Val  Pro Tyr Gly Ser Asp  Gly Pro Gly
    1115                 1120                 1125

Val Ala  Leu Ala Asn Phe Val  Lys Thr Ser Leu His  Ala Phe Thr
    1130                 1135                 1140

Ala Thr  Val Ala Val Glu Asn  Glu Arg Leu Val His  Asp Val Pro
    1145                 1150                 1155

Val Asn  Gln Ile Asn Leu Thr  Arg Arg Val Ser Ser  Glu Glu Pro
    1160                 1165                 1170

Arg Asp  Ala Asp Glu His Ala  Glu Glu Leu Arg Arg  Phe Thr Arg
    1175                 1180                 1185

Ala Val  Leu Leu Val Gly Ala  Pro Leu Pro Asp Ala  Gln Asp Ser
    1190                 1195                 1200

Arg Tyr  Arg Ser Lys Ile Tyr  Arg Gly Thr Ser Met  Thr Val
    1205                 1210                 1215


<210> SEQ ID NO 298
<211> LENGTH: 1210
<212> TYPE: PRT
<213> ORGANISM: Artificial
<220> FEATURE:
<223> OTHER INFORMATION: gamma proteobacterium NOR51-B

<400> SEQUENCE: 298

Met Asn Thr Glu Thr Arg Thr Thr Ser Gly Gly Arg Leu His Asp Lys
1               5                   10                  15

Val Val Ile Leu Thr Gly Ala Ala Gly Asn Ile Gly Ser Tyr Ile Ser
            20                  25                  30

Arg Ser Leu Leu Arg Glu Gly Ala Asn Leu Val Met Thr Gly Arg Asn
        35                  40                  45

Glu Pro Lys Leu Gln Ala Phe Val Glu Gly Leu Val Glu Glu Gly Phe
    50                  55                  60
```

-continued

Asp Arg Asp Asn Ile Leu Ile Ala Ile Gly Asp Ser Ala Lys Ala Asp
65 70 75 80

Ile Cys Arg Glu Ile Val Lys Ala Thr Val Asn His Phe Gly Asn Ile
85 90 95

Asp Val Leu Val Asn Asn Ala Gly Gly Ala Gly Pro Arg Arg Thr Leu
100 105 110

Arg Asp Ile Pro Phe Ser Glu Ser Glu Arg Leu Ala Arg Gly Asp Asp
115 120 125

Glu Thr Met Leu Asp Ala Ala Met Asn Leu Leu Ala Gly Ala Trp Asn
130 135 140

Met Thr Arg Ala Ala Val Pro His Met Ser Glu Gly Gly Ser Ile Val
145 150 155 160

Asn Val Ser Thr Ile Phe Ser Arg Thr His Tyr Tyr Gly Arg Ile Pro
165 170 175

Tyr Val Val Pro Lys Ser Gly Leu Asn Ala Leu Ser Ile Gly Leu Ala
180 185 190

Lys Glu Leu Gly Glu Glu His Gly Ile Arg Val Asn Thr Leu Phe Pro
195 200 205

Gly Pro Ile Glu Ser Glu Arg Ile Asp Thr Val Phe Gly Asn Met Asp
210 215 220

Ala Leu Gln Ser Ala Pro Ala Gly Ala Thr Ser Gln Glu Phe Arg Asp
225 230 235 240

Leu Met Ile Thr Arg Arg Glu Asn Pro Asp Gly Glu Tyr Glu Tyr Arg
245 250 255

Tyr Pro Thr Pro Asn Asp Val Ala Ser Thr Val Thr Trp Leu Ala Ser
260 265 270

Glu Glu Ser Ala Ala Leu Ser Gly His His Ile Glu Val Thr Asn Gly
275 280 285

Met Gln Val Pro Ala Gln Ser Arg Ser Lys Leu Val Ser Trp Pro Asp
290 295 300

Lys Arg Leu Glu Asp Leu Ser Gly Gln Val Val Phe Leu Leu Ala Gly
305 310 315 320

Ser Asp Tyr Glu Asp Ala Leu Ala Phe Ala Glu Arg His Met Val Ser
325 330 335

Gly Ala Lys Val Val Leu Ala Phe Arg Ser Leu Glu Ser Leu Gly Leu
340 345 350

Ala Arg Ser Leu Cys Ala Ser Arg Asp Leu Glu Ser Ile His Leu Leu
355 360 365

His Leu Glu Pro Leu Arg Arg Glu Ser Ala Asp Arg Cys Phe Asp Tyr
370 375 380

Ile Arg Asp His Phe Gly Arg Leu Asp Gly Ile Val Val Leu Pro Arg
385 390 395 400

Ser Gly Asn Gly Glu His Gly Tyr Ser Leu Ser Thr Ala Gly Asp Asp
405 410 415

Asp Val Glu Ala Phe Val Arg Asp Glu Ile Ile Ser Pro Val Ala Phe
420 425 430

Ala Ala Ala Leu Ala Ile Asn Leu Asp Arg Trp Gly Ile Leu Glu Glu
435 440 445

Ala Pro Ala Leu Thr Tyr Val Thr Asn Pro Thr Asp Gly His Gly Asp
450 455 460

Tyr Leu Asn Glu Val Lys Arg Ala Ala Ile Glu Ala Leu Ile Arg Ile
465 470 475 480

Trp Arg His Glu Asp Arg Gln Met Arg Lys Lys Gly Glu Arg Glu Trp

-continued

```
                485                 490                 495

Ala Met Leu Pro Asn Gln Leu Val Arg Tyr Asp Asn Asn Glu Glu Asp
            500                 505                 510

Asn Leu Thr Phe Thr Ala Asp Trp Ala Ala Thr Leu Thr Asn Arg Val
        515                 520                 525

Arg Arg Met Asp Pro Ile Asn Leu Trp Val Pro Glu Ser Ile Met Arg
    530                 535                 540

Ala Thr Gly Lys Ser Gly Met Pro Gln Ser Ile Gln Arg Val Leu Pro
545                 550                 555                 560

Gly Leu His Lys Gly Arg Thr Ala Val Ile Thr Gly Gly Ser Leu Gly
                565                 570                 575

Ile Gly Leu Gln Leu Gly Arg Phe Leu Ala Ile Ala Gly Ala Arg Val
            580                 585                 590

Leu Leu Ser Ala Arg Ser Lys Glu Lys Leu Glu Glu Ala Arg His Glu
        595                 600                 605

Ile Val Glu Glu Leu Arg Gly Val Gly Tyr Pro Asn Ala His Gln Arg
    610                 615                 620

Val His Ile Leu Pro Asp Ile Asp Val Gly Asp Glu Glu Ala Leu Glu
625                 630                 635                 640

Arg Leu Tyr Asn His Ser Ile Glu Leu Phe Gly Asn Val Asp Phe Leu
                645                 650                 655

Ile Asn Asn Ala Gly Ile Ser Gly Ala Glu Glu Met Val Val Asp Met
            660                 665                 670

Ser Leu Glu Ala Trp Asn Arg Thr Met Tyr Ala Asn Leu Ile Ser Asn
        675                 680                 685

Tyr Ser Leu Ile Arg Lys Tyr Ala Pro Lys Met Lys Ala Asn Gly Tyr
    690                 695                 700

Gly Val Val Leu Asn Val Ser Ser Tyr Phe Gly Gly Glu Lys Tyr Val
705                 710                 715                 720

Ala Val Ala Tyr Pro Asn Arg Ala Asp Tyr Ala Val Ser Lys Ala Gly
                725                 730                 735

Gln Arg Val Leu Ala Glu Ile Leu Ser Arg His Leu Gly Pro Glu Ile
            740                 745                 750

Arg Ile Asn Ala Leu Ala Pro Gly Pro Val Asp Gly Ala Arg Leu Arg
        755                 760                 765

Gly Leu Gly Gly Ala Pro Gly Leu Phe Glu Arg Arg Gly Arg Leu Val
    770                 775                 780

Leu Glu Asn Lys Arg Leu Asn Ser Val His Lys Ala Val Leu Ala Ala
785                 790                 795                 800

Leu Arg Glu Gly Ala Thr Pro Glu Val Ile Met Ala Leu Ser Arg Asn
                805                 810                 815

Ala Leu Gly Asp Ala Lys Pro Thr Ala Gly Gln Ser Lys Ala Leu Asp
            820                 825                 830

Lys Leu Phe Ala Gln Val Glu Asp Ser Pro Glu Gly Gly Asn Ser Thr
        835                 840                 845

Ala Phe Leu Leu Asn Arg Asp Leu Ala Glu Lys Leu Met Asn Arg Leu
    850                 855                 860

Val Thr Gly Gly Leu Phe Thr Pro Glu Ser Ala Thr Gln Phe Met Glu
865                 870                 875                 880

Gly Phe Val Asp Ala Pro Ala Ile Phe Phe Asp Glu Lys Ser Val Asn
                885                 890                 895

Lys Ala Ala Ala Gly Ile Glu Ala Gly Ile Leu Asn Arg Leu His Leu
            900                 905                 910
```

His Lys Met Pro Thr Asp Glu Gln Ile Gly Leu Ser Thr Val Phe His
915 920 925

Leu Ala Asp Asp Ile Ala Ser Gly Glu Thr Phe His Pro Ser Gly Gly
930 935 940

Leu Lys Phe Asp Arg Ser Val Thr Glu Gly Glu Leu Leu Leu Pro Pro
945 950 955 960

Asp Arg Asp Ser Leu Ala Lys Leu Lys Gly Lys Arg Val Val Leu Ile
965 970 975

Gly Asp Ser Met Arg Glu Glu Leu Ser Ala Ile Gly Asn Gly Phe Ile
980 985 990

Asn Gln Gly Val Ala Ser Leu Thr Val Leu Thr Arg Ser Pro Glu Ala
995 1000 1005

Cys Glu Glu Val Gln His Ser Leu Gln Lys Ser Asn Ser Val Thr
1010 1015 1020

Leu Asp Val Arg Cys Ile Glu Asp Asn Ile Glu Asp Ala Leu Asp
1025 1030 1035

Asp Leu Leu Gln Asn Gln Gly Gly Phe Asp Val Val Val Ser Ala
1040 1045 1050

Pro Phe Ser Arg Leu Pro Tyr Asn Pro Leu Ala Ala Glu Arg Glu
1055 1060 1065

Gly Ser Trp Asn Arg Val Leu Ser His Thr Asp Phe Ala Arg Leu
1070 1075 1080

Ile Asp Glu Gln Leu Thr His His Phe Arg Val Ala Arg Arg Ala
1085 1090 1095

Ala Leu Val Pro Asn Cys Gln Ile Val Leu Leu Thr Pro Asp Thr
1100 1105 1110

Ser Phe Val Ser Ser Arg Glu Glu Phe Ala Leu Ala Leu Phe Val
1115 1120 1125

Lys Asn Ser Leu His Ala Phe Thr Val Thr Leu Gly Val Glu Thr
1130 1135 1140

Glu Arg Leu Pro Thr Val Pro Ala Val Asn Gln Val Gln Leu Thr
1145 1150 1155

Arg Arg Ala Arg Ala Glu Glu Pro Ala Thr Glu Ser Glu Leu Gln
1160 1165 1170

Glu Glu Met Glu Arg Leu Val Ser Ala Val Leu Gln Cys Ala Val
1175 1180 1185

Pro Ala Pro Ser Pro Ser Glu Ser Arg Tyr Leu Ala Arg Ile Phe
1190 1195 1200

Arg Gly Asn Ala Val Thr Val
1205 1210

<210> SEQ ID NO 299
<211> LENGTH: 10
<212> TYPE: PRT
<213> ORGANISM: T. saccharolyticum

<400> SEQUENCE: 299

Met Lys Lys Phe Ile Val Thr Val Asn Gly
1 5 10

<210> SEQ ID NO 300
<211> LENGTH: 24
<212> TYPE: DNA
<213> ORGANISM: Artificial
<220> FEATURE:
<223> OTHER INFORMATION: X13673 primer -continued

```
<400> SEQUENCE: 300

atacgggata ataccgcgcc acat                                           24


<210> SEQ ID NO 301
<211> LENGTH: 24
<212> TYPE: DNA
<213> ORGANISM: Artificial
<220> FEATURE:
<223> OTHER INFORMATION: X13674 primer

<400> SEQUENCE: 301

ccattcgacc accaagcgaa acat                                           24
```